US011021523B2

(12) United States Patent
Lagarias et al.

(10) Patent No.: US 11,021,523 B2
(45) Date of Patent: Jun. 1, 2021

(54) CYANOBACTERIOCHROMES ACTIVE IN THE FAR-RED TO NEAR-INFRARED

(71) Applicant: The Regents of the University of California, Oakland, CA (US)

(72) Inventors: John Clark Lagarias, Davis, CA (US); Nathan Clarke Rockwell, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 43 days.

(21) Appl. No.: 16/109,613

(22) Filed: Aug. 22, 2018

(65) Prior Publication Data

US 2018/0354998 A1 Dec. 13, 2018

Related U.S. Application Data

(63) Continuation of application No. PCT/US2017/018976, filed on Feb. 22, 2017.

(60) Provisional application No. 62/298,946, filed on Feb. 23, 2016.

(51) Int. Cl.

| | |
|---|---|
| ***C07K 14/36*** | (2006.01) |
| ***A61K 49/00*** | (2006.01) |
| ***C07K 14/195*** | (2006.01) |
| ***C12N 15/62*** | (2006.01) |

(52) U.S. Cl.

CPC .......... *C07K 14/36* (2013.01); *A61K 49/0045* (2013.01); *A61K 49/0056* (2013.01); *C07K 14/195* (2013.01); *C12N 15/62* (2013.01); *C07K 2319/60* (2013.01)

(58) Field of Classification Search

CPC .. C07K 14/195; C07K 2319/60; C07K 14/36; C12N 15/62; A61K 49/0056; A61K 49/0045

See application file for complete search history.

(56) References Cited

U.S. PATENT DOCUMENTS

2015/0056646 A1 2/2015 Ulijasz et al.

FOREIGN PATENT DOCUMENTS

WO 2017/147204 A1 8/2017

OTHER PUBLICATIONS

Rockwell (I) et al., (Biochemistry 2012, 51, 9667-9677). (Year: 2012).*

Rockwell (II) et al., (Biochemistry 2014, 53, 3118-3130). (Year: 2014).*

Rockwell (III) et al., (Biochemistry 2016, 55, 28, 3907-3919). (Year: 2016).*

(Continued)

*Primary Examiner* — Jana A Hines

(74) *Attorney, Agent, or Firm* — Kilpatrick Townsend & Stockton LLP

(57) ABSTRACT

The present invention provides a protein fusion construct comprising a far-red cyanobacteriochrome (CBCR) domain linked to a heterologous domain, wherein the far-red CBCR domain comprises a CBCR polypeptide and a tetrapyrrole chromophore. The invention also provides nucleic acids, expression cassettes, vectors, and host cells for expression of the far-red CBCR protein fusion constructs. Methods for detecting cellular components, methods for imaging biological structures, and method for modulating cellular processes using the protein fusion constructs are also provided.

12 Claims, 24 Drawing Sheets

Specification includes a Sequence Listing.

phycocyanobilin (PCB)

phytochromobilin (PΦB)

phycoerythrobilin (PEB)

biliverdin IXα (BV)

(56) References Cited

OTHER PUBLICATIONS

PET-28a-c(+) Vectors, Novagen, Available online at: https://www.helmholtz-muenchen.de/fileadmin/PEPF /pET_ vectors/pET -28a-c_map.pdf, 1998, 2 pages.
Synechococcus PCC7942 ORF327, ORF249, ORF376, Elongation Factor P (efp), Biotin Carboxyl Carrier Protein (accB), ORF1000, and ORF409 Genes, Complete cds, Genbank: U59235.1, 4 pages.
UniProtKB/TrEMBL Submission EOU6T9_CYAP2, Available online at: http://www.uniprot.org/uniprot/E0U6T9.txt?version=39, in entirety; amino acids 946-1056, 100% identity to SEQ ID N0:5; amino acids 978-983, 100% identity to) SEQ ID N0:1, wherein X9 is Asp, X6 is Asp, X1 is Thr, X5 is Trp, Dec. 9, 2015, 3 pages.
Alvey et al., Attachment of Noncognate Chromophores to CpcA of *Synechocystis* sp. PCC 6803 and *Synechococcus* sp. PCC 7002 by Heterologous Expression in *Escherichia coli*, Biochemistry, vol. 50, Jun. 7, 2011, pp. 4890-4902.
Anders et al., The Family of Phytochrome-Like Photoreceptors: Diverse, Complex and Multi-Colored, but very Useful, Current Opinion in Structural Biology, vol. 35, Dec. 2015, pp. 7-16.
Aravind et al., The Gaf Domain: an Evolutionary Link Between Diverse Phototransducing Proteins, Trends Biochem Sci., vol. 12, Dec. 1997, pp. 458-459.
Auldridge et al., Bacterial Phytochromes: More than Meets the Light, Critical Reviews in Biochemistry and Molecular Biology, vol. 46, No. 1, Feb. 2011, pp. 67-68.
Auldridge et al., Structure-guided Engineering Enhances a Phytochrome-Based Infrared Fluorescent Protein, The Journal of Biological Chemistry, vol. 287, No. 10, Mar. 2, 2012, pp. 7000-7009.
Berkelman et al., Visualization of Bilin-Linked Peptides and Proteins in Polyacrylamide Gels, Analytical Biochemistry, vol. 156, Jul. 1986, pp. 194-201.
Bhattacharya et al., Origins of Fluorescence in Evolved Bacteriophytochromes, The Journal of Biological Chemistry, vol. 289, No. 46, Nov. 14, 2014, pp. 32144-32152.
Bick et al., How to Switch Off a Histidine Kinase: Crystal Structure of Geobacillus Stearothermophilus KinB with the Inhibitor Sda, J Mol Biol., vol. 386, No. 1, Feb. 13, 2009, pp. 163-177.
Blot et al., Phycourobilin in Trichromatic Phycocyanin from Oceanic Cyanobacteria is Formed Post-Translationally by a Phycoerythrobilin Lyase-Isomerase, the Journal of Biological Chemistry, vol. 284, No. 14, Apr. 3, 2009, pp. 9290-9298.
Briggs et al., Phototropins 1 and 2: Versatile Plant Blue-Light Receptors, TRENDS in Plant Science, vol. 7, No. 5, May 2002, pp. 204-210.
Buckley et al., Reversible Optogenetic Control of Subcellular Protein Localization in a Live Vertebrate Embryo, Developmental Cell, vol. 36, Jan. 11, 2016, pp. 117-126.
Burgie et al., A Photo-Labile Thioether Linkage to Phycoviolobilin Provides the Foundation for the Blue/Green Photocycles in DXCF-Cyanobacteriochromes, Structure, vol. 21, Jan. 8, 2013, pp. 88-97.
Casino et al., Structural Insight into Partner Specificity and Phosphoryl Transfer in Two-Component Signal Transduction, Cell, vol. 139, Oct. 16, 2009, pp. 325-336.
Cornejo et al., Phytochrome Assembly. The Structure and Biological Activity of 2(R),3(E)-Phytochromobilind Erived from Phycobiliproteins, The Journal of Biological Chemistry, vol. 267, No. 21, Jul. 25, 1992, pp. 14790-14796.
Cornilescu et al., Dynamic Structural Changes Underpin Photoconversion of a Blue/Green Cyanobacteriochrome between Its Dark and Photoactivated States, The Journal of Biological Chemistry, vol. 289, No. 5, Jan. 31, 2014, pp. 3055-3065.
Enomoto et al., Thiol-Based Photocycle of the Blue and Teal Light-Sensing Cyanobacteriochrome Tlr1999, Biochemistry, vol. 51, Apr. 10, 2012, pp. 3050-3058.
Velazquez Escobar et al., Photoconversion Mechanism of the Second GAF Domain of Cyanobacteriochrome AnPixJ and the Cofactor Structure of Its Green-Absorbing State, Biochemistry, vol. 52, Jul. 23, 2013, pp. 4871-4880.
Falk, The Chemistry of Linear Oligopyrroles and Bile Pigments, vol. 102, Issue 3, 1989, pp. 355-399.
Fischer et al., Harnessing Phytochrome's Glowing Potential, PNAS, vol. 101, No. 50, Dec. 14, 2014, pp. 17334-17339.
Fischer et al., Multiple Roles of a Conserved Gaf Domain Tyrosine Residue in Cyanobacterial and Plant Phytochromes, Biochemistry, vol. 44, No. 46, Nov. 2005, pp. 15203-15215.
Gaidukov, über den Einflufs farbigen Lichts auf die Farbunglebender Oscillarien, Phys. Abh. nicht zur Akad. gehör. Gelehrter, 1902, 44 pages.
Gan et al., Adaptive and Acclimative Responses of Cyanobacteria to Far-Red Light, Environmental Microbiology, vol. 17, No. 10, Oct. 2015, pp. 3450-3465.
Gan et al., Extensive Remodeling of a Cyanobacterial Photosynthetic Apparatus in Far-Red Light, Research, Science Article, vol. 345, Issue 6202, Sep. 12, 2014, pp. 1312-1317.
Gan et al., Occurrence of Far-Red Light Photoacclimation (FaRLiP) in Diverse Cyanobacteria, Life (Basel), vol. 5, No. 1, Dec. 29, 2014, pp. 4-24.
Gasser et al., Engineering of a Red-Light-Activated Human cAMP/cGMP-Specific Phosphodiesterase, PNAS, vol. 111, No. 24, Jun. 17, 2014, pp. 8803-8808.
Giraud et al., Bacteriophytochrome Controls Photosystem Synthesis in Anoxygenic Bacteria, Nature, vol. 417, May 9, 2002, pp. 202-205.
Gomelsky et al., Light helps Bacteria make Important Lifestyle Decisions, Trends in Microbiology, vol. 19, No. 9, Sep. 2011, pp. 441-448.
Gornicki et al., Genes for Two Subunits of Acetyl Coenzyme A Carboxylase of *Anabaena* sp. Strain PCC 7120: Biotin Carboxylase and Biotin Carboxyl Carrier Protein, Journal of Bacteriology, vol. 175, No. 16, Aug. 1993, pp. 5268-5272.
Hahn et al., Solution-State 15N NMR Spectroscopic Studyof a-C-Phycocyanin: Implications for the Structure of the Chromophore-Binding Pocket of the Cyanobacterial Phytochrome Cph1, ChemBioChem, vol. 8, Dec. 5, 2007, pp. 2249-2255.
Heyne et al., Ultrafast Dynamics of Phytochrome from the Cyanobacterium Synechocystis, Reconstituted with Phycocyanobilin and Phycoerythrobilin, Biophysical Journal, vol. 82, Feb. 2002, pp. 1004-1016.
Hirose et al., Cyanobacteriochrome Ccas is the Green Light Receptor that Induces the Expression of Phycobilisome Linker Protein, PNAS, vol. 105, No. 28, Jul. 15, 2008, pp. 9528-9533.
Hirose et al., Green/Red Cyanobacteriochromes Regulate Complementary Chromatic Acclimation via a Protochromic Photocycle, PNAS, vol. 110, No. 13, Mar. 26, 2013, pp. 4974-4979.
Hirose et al., Cyanobacteriochrome CcaS Regulates Phycoerythrin Accumulation in Nostoc Punctiforme, a Group II Chromatic Adapter, PNAS, vol. 107, No. 19, May 11, 2010, pp. 8854-8859.
Ho et al., Structure of the GAF Domain, a Ubiquitous Signaling Motif and a New Class of Cyclic GMP Receptor, The EMBO Journal, vol. 19, No. 20, Oct. 16, 2000, pp. 5288-5299.
Hughes, Phytochrome Three-Dimensional Structures and Functions, Biochemical Society Transactions, vol. 38, Part 2, Apr. 2010, pp. 710-716.
Ikeuchi et al., Cyanobacteriochromes: A New Superfamily of Tetrapyrrole-Binding Photoreceptors in Cyanobacteria, Photochem. Photobiol. Sci., vol. 7, Oct. 2008, pp. 1159-1167.
Ishizuka et al., Cyanobacteriochrome TePixJ of Thermosynechococcus elongatus Harbors Phycoviolobilin as a Chromophore, Plant Cell Physiol., vol. 48, No. 9, Sep. 2007, pp. 1385-1390.
Ishizuka et al., The Cyanobacteriochrome, TePixJ, Isomerizes Its Own Chromophore by Converting Phycocyanobilin to Phycoviolobilin, Biochemistry, vol. 50, Feb. 2011, pp. 953-961.
Kehoe et al., Responding to Color: The Regulation of Complementary Chromatic Adaptation, Annu. Rev. Plant Biol., vol. 27, Feb. 2006, pp. 127-150.
Kehoe et al., Similarity of a Chromatic Adaptation Sensor to Phytochrome and Ethylene Receptors, Science, New Series, vol. 273, No. 5280, Sep. 6, 1996, pp. 1409-1412.
Kim et al., Femtosecond Photodynamics of the Red/Green Cyanobacteriochrome NpR6012g4 from Nostoc punctiforme. 1. Forward Dynamics, Biochemistry, vol. 51, 2012, pp. 608-618.

(56) References Cited

OTHER PUBLICATIONS

Kim et al., Heterogeneous Photodynamics of the Pfr State in the Cyanobacterial Phytochrome Cph1, Biochemistry, vol. 53, Jun. 18, 2014, pp. 4601-4611.
Le et al., Accounting for Solvent Accessibility and Secondary Structure in Protein Phylogenetics is Clearly Beneficial, Syst. Biol., vol. 59, No. 3, Mar. 10, 2010, pp. 277-287.
Leung et al., Genetically Encoded Photoswitching of Actin Assembly through the Cdc42-WASP-Arp2/3 Complex Pathway, PNAS, vol. 105, No. 35, Sep. 2, 2008, pp. 12797-12802.
Lim et al., Photoconversion Changes Bilin Chromophore Conjugation and Protein Secondary Structure in the Violet/Orange C87yanobacteriochrome NpF2163g3, Photochem. Photobiol. Sci., vol. 13, No. 6, Jun. 2014, pp. 951-962.
Marina et al., Structure of the Entire Cytoplasmic Portion of a Sensor Histidine-Kinase Protein, The EMBO Journal, vol. 24, Dec. 21, 2005, pp. 4247-4529.
Micura et al., Long-Wavelength Absorbing Derivatives of Phycocyanobilin: New Structural Aspects on Phytochrome, Bioorgnic & Medicinal Chemistry Letters, vol. 4, No. 21, Nov. 10, 1994, pp. 2517-2522.
Mukougawa et al., Metabolic Engineering to Produce Phytochromes with Phytochromobilin, Phycocyanobilin, or Phycoerythrobilin Chromophore in *Escherichia coli*, FEBS Letters, vol. 580, Feb. 20, 2006, pp. 1333-1338.
Murphy et al., The Phytofluors: a New Class of Fluorescent Protein Probes, Current Biology, vol. 7, No. 11, Nov. 1, 997, pp. 870-876.
Nakamura et al., CyanoBase, a www Database Containing the Complete Nucleotide Sequence of the Genome of *Synechocystis* sp. strain PCC6803, Nucleic Acids Research, vol. 26, No. 1, Jan. 1, 1998, pp. 63-67.
Narikawa et al., A Biliverdin-Binding Cyanobacteriochrome from the Chlorophyll d-bearing Cyanobacterium Acaryochloris Marina, Scientific Reports, vol. 5, No. 7950, Jan. 22, 2015, 10 pages.
Narikawa et al., A New Type of Dual-Cys Cyanobacteriochrome GAF Domain Found in Cyanobacterium Acaryochloris marina, Which Has an Unusual Red/ Blue Reversible Photoconversion Cycle, Biochemistry, vol. 53, Jul. 14, 2014, pp. 5051-5059.
Narikawa et al., A Novel Photoactive GAF Domain of Cyanobacteriochrome AnPixJ that Shows Reversible Green/Red Photoconversion, J. Mol. Biol., vol. 380, Jul. 25, 2008, pp. 844-855.
Narikawa et al., Red-Shifted Red/Green-Type Cyanobacteriochrome AM1_1870g3 from the Chlorophyll d-bearing Cyanobacterium Acaryochloris Marina, Biochemical and Biophysical Research Communications, vol. 461, Apr. 16, 2015, pp. 390-395.
Narikawa et al., Structures of Cyanobacteriochromes from Phototaxis Regulators AnPixJ and TePixJ Reveal General and Specific Photoconversion Mechanism, PNAS, vol. 110, No. 3, Jan. 15, 2013, pp. 918-923.
Reiner et al., The Brain Prize 2013: The Optogenetics Revolution, Trends Neurosci., vol. 36, No. 10, Oct. 2013, pp. 557-560.
Rivera-Cancel et al., Full-Length Structure of a Monomeric Histidine Kinase Reveals Basis for Sensory Regulation, PNAS, vol. 111, No. 50, Dec. 16, 2014, pp. 17839-17844.
Rockwell et al., A Brief History of Phytochromes, Chemphyschem., vol. 11, No. 6, Apr. 26, 2010, pp. 1172-1180.
Rockwell et al., A Second Conserved Gaf Domain Cysteine is Required for the Blue/ Green Photoreversibility of Cyanobacteriochrome Tlr0924 from Thermosynechococcus Elongatus, Biochemistry, vol. 47, No. 27, Jul. 8, 2008, pp. 7304-7316.
Rockwell et al., Characterization of Red/Green Cyanobacteriochrome NpR6012g4 by Solution Nuclear Magnetic Resonance Spectroscopy: A Hydrophobic Pocket for the C15-E,anti Chromophore in the Photoproduct, Biochemistry, vol. 54, Jun. 23, 2015, pp. 3772-3783.
Rockwell et al., Characterization of Red/Green Cyanobacteriochrome NpR6012g4 by Solution Nuclear Magnetic Resonance Spectroscopy: A Protonated Bilin Ring System in Both Photostates, Biochemistry, vol. 54, Apr. 6, 2015, pp. 2581-2600.
Rockwell et al., Conserved Phenylalanine Residues are Required for Blue-Shifting of Cyanobacteriochrome Photoproducts, Biochemistry, vol. 53, May 20, 2014, pp. 3118-3130.
Rockwell et al., Distinct Classes of Red/Far-Red Photochemistry Within the Phytochrome Superfamily, PNAS, vol. 106, No. 15, Apr. 14, 2009, pp. 6123-6127.
Rockwell et al., Diverse Two-Cysteine Photocycles in Phytochromes and Cyanobacteriochromes, PNAS, vol. 108, No. 29, Jul. 19, 2011, pp. 11854-11859.
Rockwell et al., Eukaryotic Algal Phytochromes Span the Visible Spectrum, PNAS, vol. 111, No. 10, Mar. 11, 2014, pp. 3871-3876.
Rockwell et al., Identification of DXCF Cyanobacteriochrome Lineages with Predictable Photocycles, Photochem. Photobiol. Sci., vol. 14, May 2015, pp. 929-941.
Rockwell et al., Mechanistic Insight into the Photosensory Versatility of DXCF Cyanobacteriochromes, Biochemistry, vol. 51, May 1, 2012, pp. 3576-3585.
Rockwell et al., NpR3784 is the Prototype for a Distinctive Group of Red/Green Cyanobacteriochromes using Alternative Phe Residues for Photoproduct Tuning, Photochem. Photobiol. Sci., vol. 14, No. 258, Feb. 2015, pp. 258-269.
Rockwell et al., Phycoviolobilin Formation and Spectral Tuning in the DXCF Cyanobacteriochrome Subfamily, Biochemistry, vol. 51, Feb. 21, 2012, pp. 1449-1463.
Rockwell et al., Phytochome Structure and Signaling Mechanisms, Annu Rev Plant Biol., vol. 57, Feb. 2006, pp. 837-858.
Rockwell et al., Red/Green Cyanobacteriochromes: Sensors of Color and Power, Biochemistry, vol. 51, Dec. 4, 2012, pp. 9667-9677.
Rockwell et al., The Structure of Phytochrome: A Picture Is Worth a Thousand Spectra, The Plant Cell, vol. 18, Jan. 2006, pp. 4-14.
Ryu et al., Near-Infrared Light Responsive Synthetic c-di-GMP Module for Optogenetic Applications, ACS Synth. Biol., vol. 3, Nov. 21, 2014, pp. 802-810.
Sadaie et al., Quantitative in Vivo Fluorescence Cross-Correlation Analyses Highlight the Importance of Competitive Effects in the Regulation of Protein-Protein Interactions, Molecular and Cellular Biology, vol. 34, No. 17, Sep. 2014, pp. 3272-3290.
Samols et al., Evolutionary Conservation among Biotin Enzymes, The Journal of Biological Chemistry, vol. 263, No. 14, May 15, 1988, pp. 6461-6464.
Schatz, Use of Peptide Libraries to Map the Substrate Specificity of a Peptide-Modifying Enzyme: A 13 Residue Consensus Peptide Specifies Biotinylation in *Escherichia coli*, Bio/Technology, vol. 11, Oct. 11, 1993, 6 pages.
Scheer et al., Studies on Plant Bile Pigments: Characterization of a Model for the Phytochrome Pr Chromophor, Institut für Botanik, Universität München, vol. 358, No. 2, 1976, pp. 413-417.
Scherbakova et al., Near-Infrared Fluorescent Proteins Engineered from Bacterial Phytochromes, Current Opinion in Chemical Biology, vol. 27, Aug. 2015, pp. 52-63.
Shang et al., Biliverdin Amides Reveal Roles for Propionate Side Chains in Bilin Reductase Recognition and in Holophytochrome Assembly and Photoconversion, Biochemistry, vol. 49, No. 29, Jul. 27, 2010, pp. 6070-6082.
Shu et al., Mammalian Expression of Infrared Fluorescent Proteins Engineered from a Bacterial Phytochrome, Science, vol. 324, No. 5928, May 8, 2009, pp. 804-807.
Sineshchekov, Photobiophysics and Photobiochemistry of the Heterogeneous Phytochrome System, Biochimica et Biophysica Acta., vol. 1228, Mar. 14, 1995, pp. 125-164.
Solov'yov et al., Decrypting Cryptochrome: Revealing the Molecular Identity of the Photoactivation Reaction, J Am Chem Soc., vol. 134, No. 43, Oct. 31, 2012, pp. 18046-180582.
Solov'yov et al., Separation of Photo-Induced Radical Pair in Cryptochrome to a Functionally Critical Distance, Scientific Reports, vol. 4, No. 3845, Jan. 24, 2014, 8 pages.
Song et al., The D-Ring, not the A-Ring, Rotates in Synechococcus OS-B' Phytochrome, The Journal of Biological Chemistry, vol. 289, No. 5, Jan. 31, 2014, pp. 2552-2562.
Song et al., Two Ground State Isoforms and a Chromophore D-Ring Photoflip Triggering Extensive Intramolecular Changes in a Canonical Phytochrome, PNAS, vol. 108, No. 10, Mar. 8, 2011, pp. 3842-3847.

(56) References Cited

OTHER PUBLICATIONS

Stanek et al., Deprotonated 2,3-DihydrobilindionesÐModels for the Chromophore of the Far-Red-Absorbing Form of Phytochrome, Chem. Eur. J., vol. 4, No. 9, Dec. 14, 1998, 6 pages.
Tabor et al., Multichromatic Control of Gene Expression in *Escherichia coli*, J Mol Biol., vol. 405, No. 2, Jan. 14, 2011, pp. 315-324.
Tang et al., The Terminal Phycobilisome Emitter, Lcm: A Lightharvesting Pigment with a Phytochrome Chromophore, PNAS, vol. 112, No. 52, Dec. 29, 2015, pp. 15880-15885.
Tatsumi et al., Construction of Biotinylated Firefly Luciferases Using Biotin Acceptor Peptides, Analytical Biochemistry, vol. 243, Dec. 1, 1996, pp. 176-180.
Terry et al., Inactivation of Phytochrome- and Phycobiliprotein-Chromophore Precursors by Rat Liver Biliverdin Reductase, The Journal of Biological Chemistry, vol. 268, No. 35, Dec. 15, 1993, pp. 26099-26106.
Tsien, Constructing and Exploiting the Fluorescent Protein Paintbox (Nobel Lecture), Angew. Chem. Int., vol. 48, Jul. 15, 2009, pp. 5612-5626.
Ulijasz et al., Characterization of Two Thermostable Cyanobacterial Phytochromes Reveals Global Movements in the Chromophore-Binding Domain during Photoconversion, The Journal of Biological Chemistry, vol. 283, No. 30, Jul. 25, 2008, pp. 21251-21266.
Van Der Horst et al., Photosensing in Chemotrophic, Non-Phototrophic Bacteria: Let there be Light Sensing Too, TRENDS in Microbiology, vol. 15, No. 12, Dec. 2007, pp. 554-562.
Wagner et al., A Light-Sensing Knot Revealed by the Structure of the Chromophore-Binding Domain of Phytochrome, Nature, vol. 438, Nov. 2005, pp. 325-331.
Weissleder, A Clearer Vision for in vivo Imaging, Nature Biotechnology, vol. 19, Available Online at: http://biotech.nature.com, Apr. 2001, pp. 316-317.
Whippo et al., Phototropism: Bending towards Enlightenment, The Plant Cell, vol. 18, No. 5, Available online at: www.plantcell.org, May 2006, pp. 1110-1119.
Wilde et al., Disruption of a *Synechocystis* sp. PCC 6803 Gene with Partial Similarity to Phytochrome Genes Alters Growth Under Changing Light Qualities, FEBS Letters, vol. 406, Apr. 7, 1997, pp. 89-92.
Wu et al., Defining the Bilin Lyase Domain: Lessons from the Extended Phytochrome Superfamily, Biochemistry, vol. 39, Dec. 2000, pp. 13487-13495.
Wu et al., Phycocyanobilin is the Natural Precursor of the Phytochrome Chromophore in the Green Alga Mesotaenium Caldariorum, The Journal of Biological Chemistry, vol. 272, No. 41, Oct. 10, 1997, pp. 25700-25705.
Xu et al., Combined Mutagenesis and Kinetics Characterization of the Bilin-Binding GAF Domain of the Protein Slr1393 from the Cyanobacterium Synechocystis PCC6803, ChemBioChem, vol. 15, May 26, 2014, pp. 1190-1199.
Yang et al., Temperature-Scan Cryocrystallography Reveals Reaction Intermediates in Bacteriophytochrome, Nature, vol. 479, Nov. 17, 2011, 6 pages.
Yao et al., Multi-Scale Photoacoustic Tomography Using Reversibly Switchable Bacterial Phytochrome as a Near-Infrared Photochromic Probe, Nat Methods., vol. 13, No. 1, Jan. 2016, pp. 67-73.
Yeh et al., A Cyanobacterial Phytochrome Two-Component Light Sensory System, Science, vol. 277, Sep. 5, 1997, pp. 1505-1508.
Yoshihara et al., Cyanobacterial Phytochrome-like PixJ1 Holoprotein Shows Novel Reversible Photoconversion Between Blue- and Green-absorbing Forms, Plant Cell Physiol., vol. 45, No. 12, Dec. 2004, pp. 1729-1737.
Yoshihara et al., Reconstitution of Blue-Green Reversible Photoconversion of a3 Cyanobacterial Photoreceptor, PixJ1, in Phycocyanobilin-Producing *Escherichia coli*, Biochemistry, vol. 45, Mar. 21, 2006, pp. 3775-3784.
Zhang et al., Biochemical Validation of the Glyoxylate Cycle in the Cyanobacterium Chlorogloeopsis fritschii Strain PCC 9212, Journal of Biological Chemistry, vol. 290, No. 22, May 29, 2015, pp. 14019-14030.
Zhao et al., RfpA,RfpB, and RfpC are the Master Control Elements of Far-Red Light Photoacclimation (FaRLip), Original Research, vol. 6, Article 1303, Nov. 25, 2015, 13 pages.
Zhao et al., Type I and Type II Reversible Photochemistry of Phycoerythrocyanin A-Subunit from Mastigocladus Laminosus both Involve Z, E Isomerization of Phycoviolobilin Chromophore and are Controlled by Sulfhydryls in Apoprotein, Biochimica et Biophysica Acta, vol. 1228, Mar. 14, 1995, pp. 244-253.
Zhao et al., Type I Reversible Photochemistry of Phycoerythrocyanin involves Z/E-Isomerization of α-84 Phycoviolobilin Chromophore, Biochimica et Biophysica Acta, vol. 1228, Mar. 14, 1995, pp. 235-243.

* cited by examiner phytochromobilin (PΦB)

biliverdin IXα (BV)

phycocyanobilin (PCB)

phycoerythrobilin (PEB)

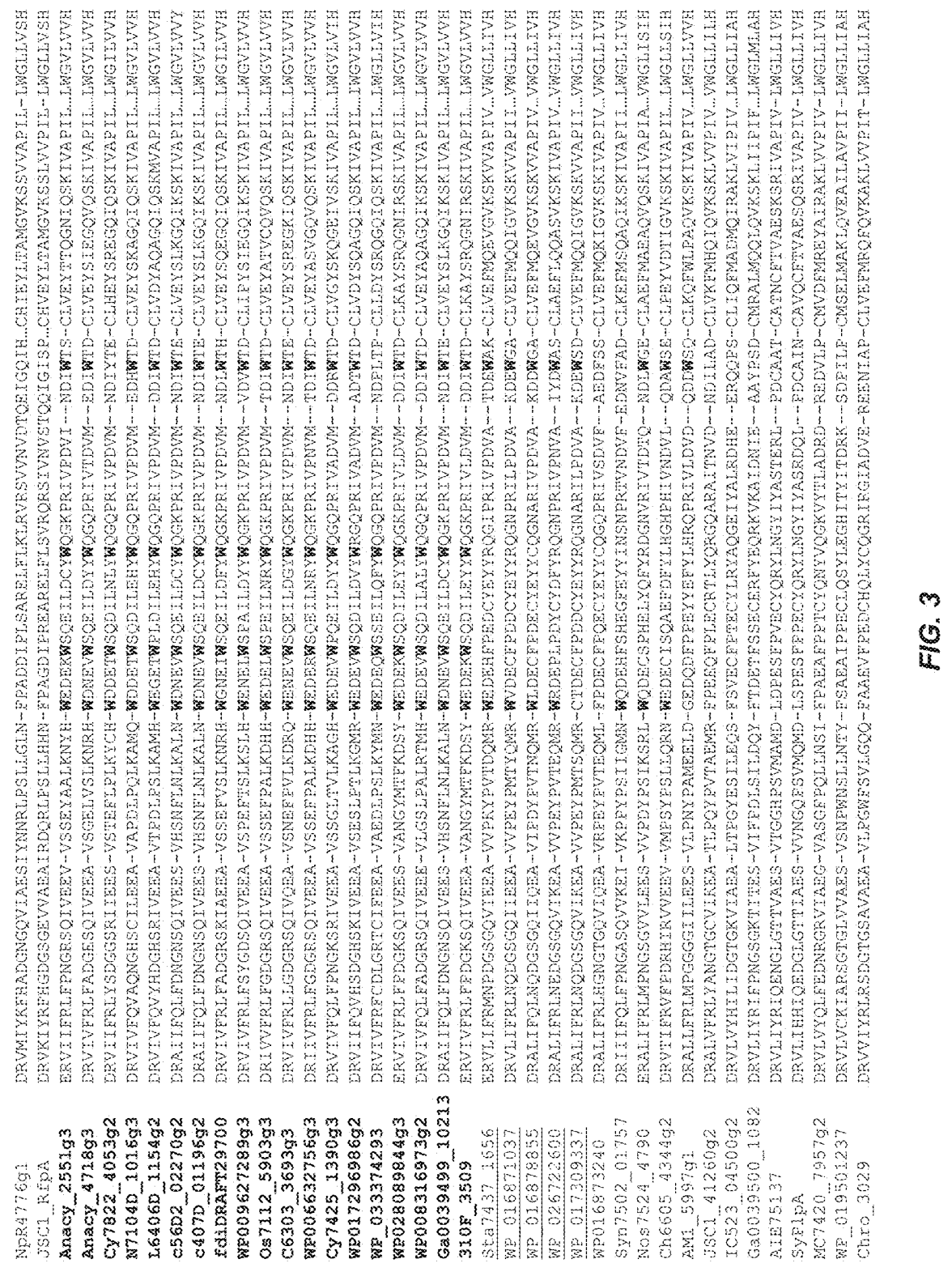

```
NpR4776g1          DRVMIYKFHADGNGQVIAESIYNNRLPSLLGLN-FPADDIPLSARELFLKLRVRSVVNVDTQEIGQIH...CHIEYLTAMGVKSSVVAPIL-LWGLLVSH
JSC1_RfpA          DRVKIYRFHGDGSGEVVAEAIRDQRLPSLLHHN-FPAGDIPREARELFLSVRQRSIVNVSTQQIGISP...CHVEYLTAMGVKSSLVVPIL-LWGLLVSH
Anacy_2551g3       ERVIIFRLFPNGRSQIVEEV-VSSEYAALKNYH-WEDEKWSQEILDCYWQGKPRIVPDVI---NDIWTS-CLVEYTTQGNIQSKIVAPIL...LWGVLVVH
Anacy_4718g3       DRVIVFRLFADGESQIVEEA-VSGELVSLKNRH-WDNEVWSQEILDYYWQGQPRIVTDVM--EDIWTD-CLVEYSIEGQVQSKIVAPIL...LWGVLVVH
Cy7822_4053g2      DRVIIFRLYSDGGSRIIEES-VSTEFLPLKYCH-WDDETWSQDILNLYWQGQPRIVPDVM--NDIYTE-CLHEYSREGQIQSKIVAPIL...LWGILVVH
N7104D_1016g3      DRVIVFQVAQNGHSCILEEA-VAPDLPQLKAMQ-WDDETWSQDILEHYWQGQPRIVPDVM--EDHWTD-CLVEYSKAGQIQSKIVAPIL...LWGVLVVH
L6406D_1154g2      DRVIVFQVYHDGHSRIVEEA-VTPDLPSLKAMH-WEGETWPLDILEHYWQGQPRIVPDVM--DDIWTD-CLVDYAQAGQIQSKMVAPIL...LWGVLVVH
c56D2_02270g2      DRAIIFQLFDNGNSQIVEES-VHSNFLNLKALN-WDNEVWSQEILDCYWQGKPRIVPDVM--NDIWTE-CLVEYSLKGQIKSKIVAPIL...LWGVLVVY
c407D_01196g2      DRAIIFQLFDNGNSQIVEES-VHSNFLNLKALN-WDNEVWSQEILDCYWQGKPRIVPDVM--NDIWTE-CLVEYSLKGQIKSKIVAPIL...LWGVLVVH
fdiDRAFT29700      DRVIVFRLFADGRSKIAEEA-VSSEFVSLKNRH-WGNEIWSQEILDFYWQGKPRIVPDVM--NDLWTH-CLVEYSQEGQIQSKIVAPIL...LWGILVVH
WP009627289g3      DRVIVFRLFSYGDSQIVEEA-VSPEFTSLKSLH-WENELWSPAILDYYWQGKPRIVPDVM--VDVWTD-CLIPYSIEGQIKSKIVAPIL...LWGVLVVH
Os7112_5903g3      DRIVVFRLFGDGRSQIVEEA-VSSEFPALKDHH-WEDELWSPEILNRYWQGKPRIVPDVM--TDIWTD-CLVEYATVCQVQSKIVAPIL...LWGVLVVH
C6303_3693g3       DRVIVFRLLGDGRSQIVQEA-VSNEFPVLKDRQ-WENEVWSQEILDGYWQGKPRIVPDVM--NDIWTE-CLVEYSREGKIQSKIVAPIL...LWGVLVVH
WP006632756g3      DRIIVFRLFGDGRSQIVEEA-VSSEFPALKDHH-WEDERWSQEILNRYWQGKPRIVPNVM--TDIWTD-CLVEYASVGQVQSKIVAPIL...LWGVLVVH
Cy7425_1390g3      DRVIVFQLFPNGKSRIVEEA-VSSGLTVLKAGH-WEDEVWPQEILDYYWQGQPRIVADVM--DDRWTD-CLVGYSKQGEIVSKIVAPIL...LWGVLVIH
WP017296986g2      DRVIIFQVHSDGHSKIVEEA-VSESLPTLKGMR-WEDEVWSQDILDVYWRGQPRIVADVM--ADTWTD-CLVDYSQAGQIQSKIVAPIL...IWGVLVVH
WP_033374293       DRVIVFRFCDLGRTCIFEEA-VAEDLPSLKYMN-WEDEQWSSEILQFYWQGQPRIVPDVM--NDPLTP-CLLDYSRQGQIQSKIVAPIL...LWGLLVIH
WP028089844g3      ERVIVFRLFPDGKSQIVEES-VANGYMTFKDSY-WEDEKWSQDILEYYWQGKPRIVLDVM--DDIWTD-CLKAYSRQGNIRSKIVAPIL...LWGVLVVH
WP008316973g2      DRVIVFQLFADGRSQIVEEE-VLGSLPALRTMH-WEDEVWSQDILALYWQGQPRIVPDVM--DDIWTD-CLVEYAQAGQIKSKIVAPIL...LWGVLVVH
Ga0039499_10213    DRAIIFQLFDNGNSQIVEES-VHSNFLNLKALN-WDNEVWSQEILDCYWQGKPRIVPDVM--NDIWTE-CLVEYSLKGQIKSKIVAPIL...LWGVLVVH
310F_3509          ERVIVFRLFPDGKSQIVEEA-VANGYMTFKDSY-WEDEKWSQDILEYYWQGKPRIVLDVM--DDIWTD-CLKAYSRQGNIRSKIVAPIL...LWGVLVVH
Sta7437_1656       ERVLIFRMNPDGSGQVIEEA-VVPKYPVTDQMR-WEDEHFPEDCYEYYRQGIPRIVPDVA--TDEWAK-CLVEFMQEVGVKSKVVAPIV...VWGLLIVH
WP_016871037       DRVLIFRLNQDGSGQIIEEA-VVPEYPMTYQMR-WVDECFPDDCYEYYRQGNPRILPDVA--KDEWGA-CLVEFMQQIGVKSKVVAPII...VWGLLIVH
WP_016878855       DRALIFQLNQDGSGQIIQEA-VIPDYPVTNQMR-WLDECFPDECYEYYCQGNARIVPDVA--KDDWGA-CLVEFMQEVGVKSKVVAPIV...VWGLLIVH
WP_026722600       DRALIFRLNEDGSGQVIKEA-VVPEYPVTEQMR-WRDEPLPDYCYDFYRQGNPRIVPNVA--IYDWAS-CLAEFLQQASVKSKIVAPIV...VWGLLIVH
WP_017309337       DRALIFRLNQDGSGQVIKEA-VVPEYPMTSQMR-CTDECFPDDCYEYYRQGNARILPDVA--KDEWSD-CLVEFMQQIGVKSKVVAPII...VWGLLIVH
WP016873240        DRALIFRLHGNGTGQVIQEA-VRPEYPVTEQML-FPDECFPQECYEYYCQGQPRIVSDVF--AEDFSS-CLVEFMQKIGVKSKIVAPIV...VWGLLIVH
Syn7502_01757      DRIIIFQLFPNGASQVVKEI-VKPPYPSIIGMN-WQDEHFSHEGFEYYINSNPRTVNDVF-EDNVFAD-CLKEFMSQAQIKSKIVAPII...LWGLLIVH
Nos7524_4790       ERALIFRLMPNGSGVVLEES-VVPDYPSIKSRL-WQDECSPHELYQFYRDGNVRIVTDTQ--NDLWGE-CLAEFMAEAQVQSKIVAPIA...VWGLISIH
Ch6605_4344g2      DRVTIFRVFPDRHIRVVEEV-VMPSYPSLLQRN-WEDECISQAEFDFYLHGHPHIVNDVL--QDAWSE-CLPEYVDTIGVKSKIVAPIL...LWGLLSIH
AM1_5997g1         DRALLFRLMPGGGGIILEES-VLPNYPAMEELD-GEDQDFPPEYYEFYLHRQPRIVLDVD--QDDWSQ-CLKQFWLPAQVKSKIVAPIV...LWGLLVVH
JSC1_41260g2       DRALVFRLYANGTGCVIKEA-TLPQYPVTAEMR-FPEEQFPLECRTLYQRGQARAITNVD--NDILAD-CLVKFMHQIQVKSKLVVPIV...VWGLLILH
IC523_04500g2      DRVLVYHILIDGTGKVIAEA-LTPGYESILEQS-FSVECFPTECYLRYAQGEIYALRDHE--ERQQPS-CLIQFMADMQIRAKLVIPIV...LWGLLIAH
Ga0039500_1082     DRVLIYRIFPNGSGKTITES-VIFPDLSILDQY-FTDETFSSECERFYEQRKVKAIDNIE--AAYPSD-CMRALMQQLQVKSKLIIPIF...LWGLMLAH
AIE75137           DRVLIYRIQENGLGTTVAES-VTGGHPSVMAMD-LDPESFPVECYQRYLNGYIYASTERL--PDCAAT-CATNCFTVAESKSRIVAPIV-LWGLLIVH
SyPlpA             DRVLIHHIQEDGLGTTIAES-VVNGQPSVMQMD-LSPESFPPECYQRYLNGYIYASRDQL--PDCAIN-CAVQCFTVAESQSRIVAPIV-LWGLLIVH
MC7420_7957g2      DRVLVYQLFEDNRGRVIAEG-VASGFPQLLNSI-FPAEAFPPTCYQNYVQGKVYTLADRD--REDVLP-CMVDFMREYAIRAKLVVPIV-LWGLLIVH
WP_019501237       DRVLVCKIARSGTGLVVAES-VSNPWNSLLNTY-FSAEAIPPECLQSYLEGHITYITDRK--SDPILP-CMSELMAKLQVEAILAVPII-LWGLLIAH
Chro_3029          DRVVIYRLRSDGTGSAVAEA-VLPGWFSVLGQQ-FAAEVFPEDCHQLYCQGRIRGIADVE-REENIAP-CLVEFMRQFQVKAKLVVPIT-LWGLLIAH
```

FIG. 3

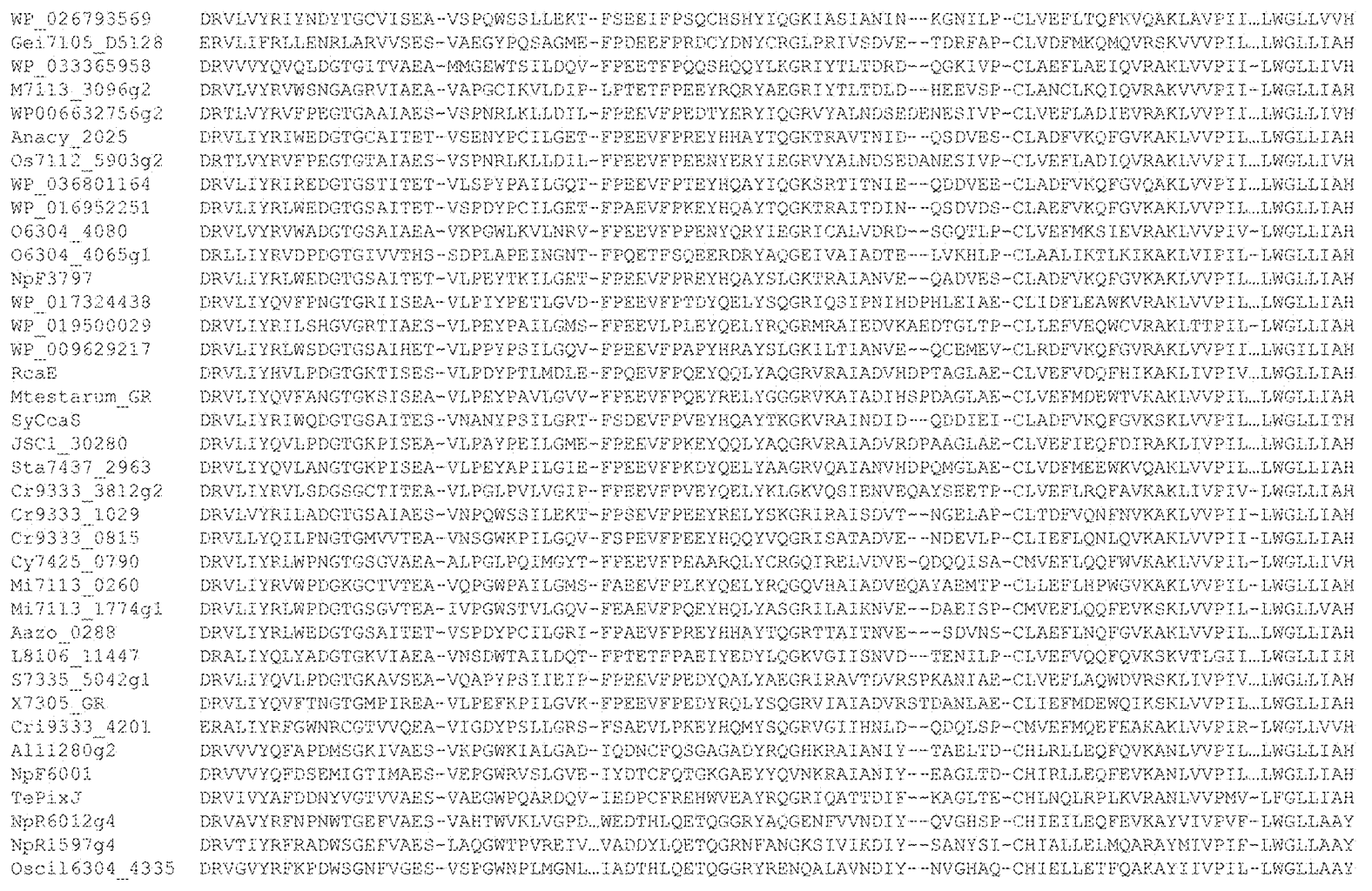

| | |
|---|---|
| WP_026793569 | DRVLVYRIYNDYTGCVISEA-VSPQWSSLLEKT-FSEEIFPSQCHSHYIQGKIASIANIN---KGNILP-CLVEFLTQFKVQAKLAVPII...LWGLLVVH |
| Gei7105_D5128 | ERVLIFRLLENRLARVVSES-VAEGYPQSAGME-FPDEEFPRDCYDNYCRGLPRIVSDVE--TDRFAP-CLVDFMKQMQVRSKVVVPIL...LWGLLIAH |
| WP_033365958 | DRVVVYQVQLDGTGITVAEA-MMGEWTSILDQV-FPEETFPQQSHQQYLKGRIYTLTDRD--QGKIVP-CLAEFLAEIQVRAKLVVPII-LWGLLIVH |
| M7113_3096g2 | DRVLVYRVWSNGAGRVIAEA-VAPGCIKVLDIP-LPTETFPEEYRQRYAEGRIYTLTDLD--HEEVSP-CLANCLKQIQVRAKVVVPII-LWGLLIAH |
| WP006632756g2 | DRTLVYRVFPEGTGAAIAES-VSPNRLKLLDIL-FPEEVFPEDTYERYIQGRVYALNDSEDENESIVP-CLVEFLADIEVRAKLVVPII...LWGLLIVH |
| Anacy_2025 | DRVLIYRIWEDGTGCAITET-VSENYPCILGET-FPEEVFPREYHHAYTQGKTRAVTNID--QSDVES-CLADFVKQFGVKAKLVVPIL...LWGLLIAH |
| Os7112_5903g2 | DRTLVYRVFPEGTGTAIAES-VSPNRLKLLDIL-FPEEVFPEENYERYIEGRVYALNDSEDANESIVP-CLVEFLADIQVRAKLVVPII...LWGLLIVH |
| WP_036801164 | DRVLIYRIREDGTGSTITET-VLSPYPAILGQT-FPEEVFPTEYHQAYIQGKSRTITNIE--QDDVEE-CLADFVKQFGVQAKLVVPII...LWGLLIAH |
| WP_016952251 | DRVLIYRLWEDGTGSAITET-VSPDYPCILGET-FPAEVFPKEYHQAYTQGKTRAITDIN--QSDVDS-CLAEFVKQFGVKAKLVVPIL...LWGLLIAH |
| O6304_4080 | DRVLVYRVWADGTGSAIAEA-VKPGWLKVLNRV-FPEEVFPPENYQRYIEGRICALVDRD--SGQTLP-CLVEFMKSIEVRAKLVVPIV-LWGLLIAH |
| O6304_4065g1 | DRLLIYRVDPDGTGIVVTHS-SDPLAPEINGNT-FPQETFSQEERDRYAQGEIVAIADTE--LVKHLP-CLAALIKTLKIKAKLVIPIL-LWGLLIAH |
| NpF3797 | DRVLIYRLWEDGTGSAITET-VLPEYTKILGET-FPEEVFPREYHQAYSLGKTRAIANVE--QADVES-CLADFVKQFGVKAKLVVPIL...LWGLLIAH |
| WP_017324438 | DRVLIYQVFPNGTGRIISEA-VLPIYPETLGVD-FPEEVFPTDYQELYSQGRIQSIPNIHDPHLEIAE-CLIDFLEAWKVRAKLVVPIL...LWGLLIAH |
| WP_019500029 | DRVLIYRILSHGVGRTIAES-VLPEYPAILGMS-FPEEVLPLEYQELYRQGRMRAIEDVKAEDTGLTP-CLLEFVEQWCVRAKLTTPIL-LWGLLIAH |
| WP_009629217 | DRVLIYRLWSDGTGSAIHET-VLPPYPSILGQV-FPEEVFPAPYHRAYSLGKILTIANVE--QCEMEV-CLRDFVKQFGVRAKLVVPII...LWGILIAH |
| RcaE | DRVLIYHVLPDGTGKTISES-VLPDYPTLMDLE-FPQEVFPQEYQQLYAQGRVRAIADVHDPTAGLAE-CLVEFVDQFHIKAKLIVPIV...LWGLLIAH |
| Mtestarum_GR | DRVLIYQVFANGTGKSISEA-VLPEYPAVLGVV-FPEEVFPQEYRELYGGGRVKAIADIHSPDAGLAE-CLVEFMDEWTVKAKLVVPIL...LWGLLIAH |
| SyCcaS | DRVLIYRIWQDGTGSAITES-VNANYPSILGRT-FSDEVFPVEYHQAYTKGKVRAINDID--QDDIEI-CLADFVKQFGVKSKLVVPIL...LWGLLITH |
| JSC1_30280 | DRVLIYQVLPDGTGKPISEA-VLPAYPEILGME-FPEEVFPKEYQQLYAQGRVRAIADVRDPAAGLAE-CLVEFIEQFDIRAKLIVPIL...LWGLLIAH |
| Sta7437_2963 | DRVLIYQVLANGTGKPISEA-VLPEYAPILGIE-FPEEVFPKDYQELYAAGRVQAIANVHDPQMGLAE-CLVDFMEEWKVQAKLVVPIL...LWGLLIAH |
| Cr9333_3812g2 | DRVLIYRVLSDGSGCTITEA-VLPGLPVLVGIP-FPEEVFPVEYQELYKLGKVQSIENVEQAYSEETP-CLVEFLRQFAVKAKLIVPIV-LWGLLIAH |
| Cr9333_1029 | DRVLVYRILADGTGSAIAES-VNPQWSSILEKT-FPSEVFPEEYRELYSKGRIRAISDVT--NGELAP-CLTDFVQNFNVKAKLVVPII-LWGLLIAH |
| Cr9333_0815 | DRVLLYQILPNGTGMVVTEA-VNSGWKPILGQV-FSPEVFPEEYHQQYVQGRISATADVE--NDEVLP-CLIEFLQNLQVKAKLVVPII-LWGLLIAH |
| Cy7425_0790 | DRVLIYRLWPNGTGSGVAEA-ALPGLPQIMGYT-FPEEVFPEAARQLYCRGQIRELVDVE-QDQQISA-CMVEFLQQFWVKAKLVVPIL-LWGLLIVH |
| Mi7113_0260 | DRVLIYRVWPDGKGCTVTEA-VQPGWPAILGMS-FAEEVFPLKYQELYRQGQVHAIADVEQAYAEMTP-CLLEFLHPWGVKAKLVVPIL-LWGLLIAH |
| Mi7113_1774g1 | DRVLIYRLWPDGTGSGVTEA-IVPGWSTVLGQV-FEAEVFPQEYHQLYASGRILAIKNVE--DAEISP-CMVEFLQQFEVKSKLVVPIL-LWGLLVAH |
| Aazo_0288 | DRVLIYRLWEDGTGSAITET-VSPDYPCILGRI-FPAEVFPREYHHAYTQGRTTAITNVE---SDVNS-CLAEFLNQFGVKAKLVVPIL...LWGLLIAH |
| L8106_11447 | DRALIYQLYADGTGKVIAEA-VNSDWTAILDQT-FPTETFPAEIYEDYLQGKVGIISNVD--TENILP-CLVEFVQQFQVKSKVTLGII...LWGLLIIH |
| S7335_5042g1 | DRVLIYQVLPDGTGKAVSEA-VQAPYPSIIEIP-FPEEVFPEDYQALYAEGRIRAVTDVRSPKANIAE-CLVEFLAQWDVRSKLIVPIV...LWGLLIAH |
| X7305_GR | DRVLIYQVFTNGTGMPIREA-VLPEFKPILGVK-FPEEVFPEDYRQLYSQGRVIAIADVRSTDANLAE-CLIEFMDEWQIKSKLVVPIL...LWGLLIAH |
| Cri9333_4201 | ERALIYRFGWNRCGTVVQEA-VIGDYPSLLGRS-FSAEVLPKEYHQMYSQGRVGIIHNLD--QDQLSP-CMVEFMQEFEAKAKLVVPIR-LWGLLVVH |
| A11i280g2 | DRVVVYQFAPDMSGKIVAES-VKPGWKIALGAD-IQDNCFQSGAGADYRQGHKRAIANIY--TAELTD-CHLRLLEQFQVKANLVVPIL...LWGLLIAH |
| NpF6001 | DRVVVYQFDSEMIGTIMAES-VEPGWRVSLGVE-IYDTCFQTGKGAEYYQVNKRAIANIY--EAGLTD-CHIRLLEQFEVKANLVVPIL...LWGLLIAH |
| TePixJ | DRVIVYAFDDNYVGTVVAES-VAEGWPQARDQV-IEDPCFREHWVEAYRQGRIQATTDIF--KAGLTE-CHLNQLRPLKVRANLVVPMV-LFGLLIAH |
| NpR6012g4 | DRVAVYRFNPNWTGEFVAES-VAHTWVKLVGPD...WEDTHLQETQGGRYAQGENFVVNDIY--QVGHSP-CHIEILEQFEVKAYVIVPVF-LWGLLAAY |
| NpR1597g4 | DRVTIYRFRADWSGEFVAES-LAQGWTPVREIV...VADDYLQETQGRNFANGKSIVIKDIY--SANYSI-CHIALLELMQARAYMIVPIF-LWGLLAAY |
| Oscil6304_4335 | DRVGVYRFKPDWSGNFVGES-VSPGWNPLMGNL...IADTHLQETQGGRYRENQALAVNDIY--NVGHAQ-CHIELLETFQAKAYIIVPIL-LWGLLAAY |

FIG. 3 (cont'd)

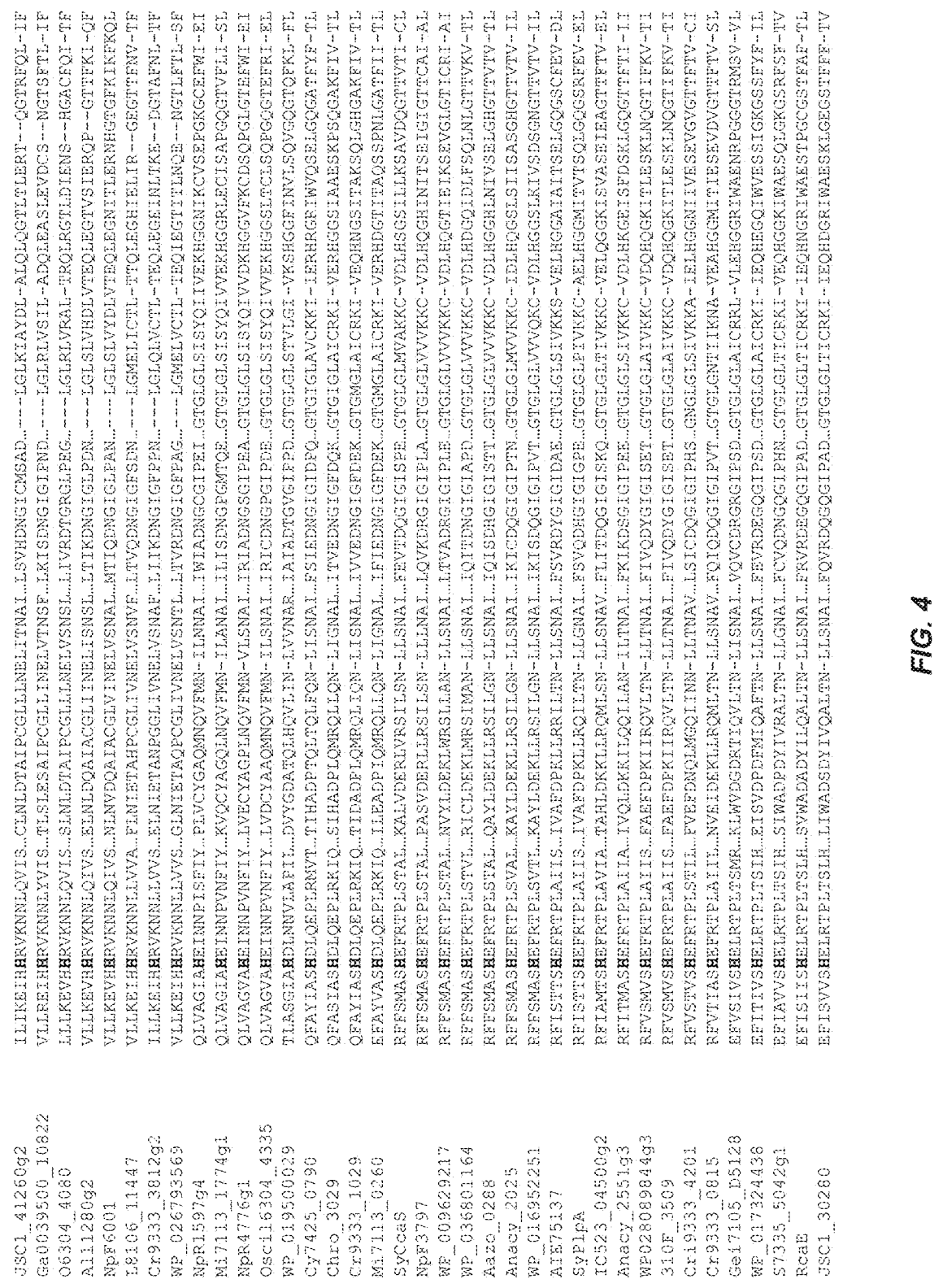

| | |
|---|---|
| JSC1_41260g2 | ILIKEIH**H**RVKNNLQVIS...CLNLDTAIPCGLLLNELITNAI...LSVHDNGICMSAD...---LGLKIAYDL-ALQLQGTLTLERT--QGTRFQL-IF |
| Ga0039500_10822 | VLLREIH**H**RVKNNLYVIS...TLSLESAIPCGLLINELVTNSF...LKISDNGIGIPND...---LGLRLVSIL-ADQLEASLEVDCS--NGTSFTL-IF |
| O6304_4080 | LLLKEVH**H**RVKNNLQVIS...SLNLDTAIPCGLLLNELVSNSL...LIVRDTGRGLPEG...---LGLRLVRAL-TRQLRGTLDIENS--HGACFQI-TF |
| All1280g2 | VLLKEVH**H**RVKNNLQIVS...ELNLDQAIACGLIINELISNSL...LTIKDNGIGLPDN...---LGLSLVHDLVTEQLEGTVSIERQP--GTTFKI-QF |
| NpF6001 | VLLKEVH**H**RVKNNLQIVS...NLNVDQAIACGLVINELVSNAL...MTIQDNGIGLPAN...---LGLSLVYDLVTEQLEGNITLERNHGTGFKIKFKQL |
| L8106_11447 | VLLKEIH**H**RVKNNLLVVA...FLNIETAHPCGLIVNELVSNVF...LTVQDNGIGFSDN...---LGMELICTL-TTQLEGHIELIR--GEGTTFNV-TF |
| Cr9333_3812g2 | ILLKEIH**H**RVKNNLLVVS...ELNIETANPGGLIVNELVSNAF...LIIKDNGIGFPPN...---LGLQLVCTL-TEQLEGEINLTKE--DGTAFNL-TF |
| WP_026793569 | VLLKEIH**H**RVKNNLLVVS...GLNIETAQPCGLIVNELVSNTL...LTVRDNGIGFPAG...---LGMELVCTL-TEQIEGTITLNQE--NGTLFTL-SF |
| NpR1597g4 | QLVAGIA**H**EINNPISFIY...PLVCYGAQMNQVFMN-ILNNAI...IWIADNGCGIPEI...GTGLGLSISYQIIVEKHGGNIKCVSEPGKGCEFWI-EI |
| Mi7113_1774g1 | QLVAGIA**H**EINNPVNFIY...KVQCYAGQLNQVFMN-ILANAI...ILISDNGPGMTQE...GTGLGLSISYQIVVEKHGGRLECISAPGQGTVFLI-SL |
| NpR4776g1 | QLVAGVA**H**EINNPVNFIY...LVECYAGPLNQVFMN-VLSNAI...IRIADNGSGIPEA...GTGLGLSISYQIVVDKHGGVFKCDSQPGLGTEFWI-EI |
| Oscil6304_4335 | QLVAGVA**H**EINNPVNFIY...LVDCYAAQMNQVFMN-ILSNAI...IRICDNGPGIPDE...GTGLGLSISYQIVVEKHGGSLTCLSQPGQGTEFRI-EL |
| WP_019500029 | TLASGIA**H**DLNNVLAPIL...DVYGDATQLHQVLIN-LVVNAR...IAIADTGVGIPPD...GTGLGLSTVLGI-VKSHGGFINVLSQVGQGTQFKL-FL |
| Cy7425_0790 | QFAYIAS**H**DLQEPLRMVT...TIHADPTQLTQLFQN-LISNAI...FSIEDNGIGIDPQ...GTGIGLAVCKKI-IERHRGRIWVQSELGQGATFYF-TL |
| Chro_3029 | QFASIAS**H**DLQEPLRKIQ...SIHADPLQMRQLLQN-LIGNAL...ITVEDNGIGFDQK...GTGIGLAICRKI-VERHGGSIAAESKPSQGAKFIV-TL |
| Cr9333_1029 | QFAYIAS**H**DLQEPLRKIQ...TIDADPLQMRQLIQN-LISNAL...IVVEDNGIGFDEK...GTGMGLAICRKI-VEQHNGSITAKSQLGHGAKFIV-TL |
| Mi7113_0260 | EFAYVAS**H**DLQEPLRKIQ...ILEADPIQMRQLLQN-LIGNAL...IFIEDNGIGFDEK...GTGMGLAICRKI-VERHDGTITAQSSPNLGATFII-TL |
| SyCcaS | RFFSMAS**H**EFRTPLSTAL...KALVDERLVRSILSN-LLSNAI...FEVTDQGIGISPE...GTGLGLMVAKKC-VDLHSGSILLKSAVDQGTTVTI-CL |
| NpF3797 | RFFSMAS**H**EFRTPLSTAL...PASVDERLLRSILSN-LLLNAI...LQVKDRGIGIPLA...GTGLGLVVVKKC-VDLHQGHINITSEIGIGTTCAI-AL |
| WP_009629217 | RFFSMAS**H**EFRTPLSTAL...NVYLDEKLWRSLLAN-LLSNAI...LTVADRGIGIPLE...GTGLGLVVVKKC-VDLHQGTIEIKSEVGLGTICRI-AI |
| WP_036801164 | RFFSMAS**H**EFRTPLSTVL...RICLDEKLMRSIMAN-LLSNAI...IQITDNGIGIAPD...GTGLGLVVVKKC-VDLHDGQIDLFSQLNLGTTVKV-TL |
| Aazo_0288 | RFFSMAS**H**EFRTPLSTAL...QAYLDEKLLRSILGN-LLSNAI...IQISDHGIGISTT...GTGLGLVVVKKC-VDLHGGHLNIVSELGHGTTVTV-TL |
| Anacy_2025 | RFFSMAS**H**EFRTPLSVAL...KAYLDEKLLRSILGN-LLSNAI...IKICDQGIGIPTN...GTGLGLMVVKKC-IDLHQGSLSIISASGHGTTVTV-IL |
| WP_016952251 | RFFSMAS**H**EFRTPLSVTL...KAYLDEKLLRSILGN-LLSNAI...IKISDQGIGIPVT...GTGLGLVVVQKC-VDLHGGSLKIVSDSGNGTTVTV-IL |
| AIE75137 | RFISTTS**H**EFRTPLAIIS...IVAFDPKLLRRILTN-LLSNAI...FSVRDYGIGIDAE...GTGLGLSIVKKS-VELHGGAIAITSELGQGSCFEV-DL |
| SyPlpA | RFISTTS**H**EFRTPLAIIS...IVAFDPKLLRQILTN-LLGNAI...FSVQDHGIGIGPE...GTGLGLPIVKKC-AELHGGMITVTSQLGQGSRFEV-EL |
| IC523_04500g2 | RFIAMTS**H**EFRTPLAVIA...TAHLDKKLLRQMLSN-LLSNAV...FLITDQGIGISKQ...GTGLGLTIVKKC-VELQGGKISVASEIEAGTTFTV-EL |
| Anacy_2551g3 | RFITMAS**H**EFRTPLAIIA...IVQLDKKILQQILAN-ILTNAI...FKIKDSGIGIPEE...GTGLGLSIVKKC-VDLHKGEISFDSKLGQGTTFTI-II |
| WP028089844g3 | RFVSMVS**H**EFRTPLAIIS...FAEFDPKIIRQVLTN-LLTNAI...FIVQDYGIGISET...GTGLGLAIVKKC-VDQHQGKITLESKLNQGTIFKV-TI |
| 310F_3509 | RFVSMVS**H**EFRTPLAIIS...FAEFDPKIIRQVLTN-LLTNAI...FIVQDYGIGISET...GTGLGLAIVKKC-VDQHQGKITLESKLNQGTIFKV-TI |
| Cri9333_4201 | RFVSTVS**H**EFRTPLSTIL...FVEFDNQLMGQIINN-LLTNAV...LSICDQGIGIPHS...GNGLGLSIVKKA-IELHGGNIIVESEVGVGTTFTV-CI |
| Cr9333_0815 | RFVTIAS**H**EFRTPLAIIL...NVEIDEKLLRQMLTN-LLSNAV...FQIQDQGIGIPVT...GTGLGNTIIKNA-VEAHGGMITIESEVDVGTTFTV-SL |
| Gei7105_D5128 | EFVSIVS**H**ELRTPLTSMR...KLWVDGDRTIQVLTN-LISNAI...VQVCDRGRGIPSD...GTGLGLAICRRL-VLEHGGRIWAENRPGGGTRMSV-VL |
| WP_017324438 | EFITIVS**H**ELRTPLTSIH...EISVDPDFMIQAFTN-LLSNAI...FEVRDEGQGIPSD...GTGLGLAICRKI-IEQHEGQIWVESSIGKGSSFYF-IL |
| S7335_5042g1 | EFIAVVS**H**ELRTPLTSIH...SIWADPDYIVRALTN-LLGNAI...FCVQDNGQGIPHN...GTGLGLTICRKI-VEQHGGKIWAESQLGKGSRFSF-TV |
| RcaE | EFISIIS**H**ELRTPLTSLH...SVWADADYILQALTN-LLSNAI...FRVRDEGQGIPAD...GTGLGLTICRKI-IEQHNGRIWAESTPGCGSTFAF-TL |
| JSC1_30280 | EFISVVS**H**ELRTPLTSLH...LIWADSDYIVQALTN-LLSNAI...FQVRDQGQGIPAD...GTGLGLTICRKI-IEQHDGRIWAESKLGEGSTFFF-TV |

FIG. 4

```
X7305_GR            EFISVVSHELRTPLTSIH…IVWADRDYIVQALTN-LLSNAI…FAVQDQGQGIPED…GTGLGLAICRQI-VEGHGGQIWVESCLDKGSTFYF-TL
Mtestarum_GR        EFISVVSHELRTPLTSIH…VVWADRDYIVQTLTN-LLSNAI…FEVKDRGQGIPTS…GTGLGLAICRQI-IEGHGGKIWAESCLEEGSTFYF-TL
Sta7437_2963        EFISVVSHELRTPLTSIH…VVWADRDYIVQTLTN-LLSNAI…FEVKDQGQGIPAN…GTGLGLAICRHI-IEEHGGKIWAESSLGGGSTFYF-TL
JSC1_RfpA           EFVSIVSHELRTPLTSIR…TLWADPDRIIQTFTN-LLNNAI…FRIKDQGVGIPAD…GTGLGLTICRGI-VQQHQGQIWVESKLGEGSTFCF-SL
WP_033365958        EFISVVSHELRTPLAAIH…QVWADPDRIIQTLVN-LVSNAI…FKVQDQGRGIPYD…GTGLGLPICRSI-VEQHGGKIWAESVLGKGSVFYF-TL
M7113_3096g2        EFISIVSHELRTPLSSIR…QVWADRDRILQTLVN-LVSNAI…FQVKDQGRGIPAD…GTGLGLAICKSI-VQQHGGKIWVESVVGEGSNFYF-TL
Sta7437_1656        EFISVVSHELRTPLTSIR…TLWAAPDAIIQTLTN-LLSNAI…FTVKDRGRGIPED…GTGLGLSICKRI-VQQHGGRIWVESSLGEGSTFYF-TL
WP_026722600        EFISIVSHELRTPLTAIR…QISAEADSIIRALTN-LLSNAI…FKIRDQGRGIPPD…GTGLGLAICKNI-VQQHGGHIWVESVLGEGSTFYF-TL
WP_017309337        EFISIVSHELRTPLTAIR…QISAAADSIIQTLIN-LLSNAI…FKVRDQGRGIPPE…GTGLGLAICKNI-VQQHGGCIWVESVLGEGSTFYF-TL
WP_016871037        EFISIVSHELRTPLTAIR…QIWAAPDAIVQTLIN-LLSNAI…FAVKDQGRGIPPE…GTGLGLSICKSI-VDQHGGRIWVESLLGEGSTFYF-IL
Syn7502_01757       EFISIVSHELRTPLTAIR…QIWAAPDAIVQTLIN-LLSNAI…FAVKDQGRGIPPE…GTGLGLSICKSI-VDQHGGRIWVESLLGEGSTFYF-IL
WP016873240         EFVSIVSHELRTPLTAIR…QIWVAPDAIVQTLIN-LLSNAI…FTVRDQGRGIPSD…GTGLGLAICKSI-VKQHGGKIWVESRVGEGSTFYF-TL
WP_016878855        EFISIVSHELRTPLTAIR…QIWAAPDAITQTLIN-LLGNAI…FFVRDNGRGIPSD…GTGLGLAICKTI-IRQHGGKIWVESVLGEGSTFYF-TL
Ch6605_4344g2       EFLASMSHELRTPLNAIL…NIRVDDLRIRQVLIN-LLSNAV…LSIVDTGIGIAPE…GTGLGLALVKRI-VELHGGTVTVESQVDRGSCFRV-CL
Nos7524_4790        EFLASMSHELRTPLNAIL…DIAVDERRMRQVLIN-LLNNAV…FAVIDTGIGIAPE…GTGLGLALVRQI-AELHGGNVTVSSEVGKGSCFTV-RL
WP009627289g3       EFLANMSHELRTPLNAIL…DLKIDERRIRQVLIN-LLNNAV…FAVIDTGIGITPH…GTGLGLALVKRI-VEMHGGQVKATSDFGVGSCFTI-EL
Cy7425_1390g3       EFLANMSHELRTPLNAIL…DVWVDERRIRQVLIN-LLNNAV…IAVTDTGIGIPSH…GTGLGLALVKRI-VELHGGEVGVTSTEGAGSCFTI-DL
Cy7822_4053g2       EFLANMSHELRTPLNAIL…MLTLDERRIRQVIIN-LLNNAV…FAVKDTGIGIAAE…GTGLGLALVKRL-VDLHGGEVSVTSELGVGSCFSV-DL
c56D2_02270g2       EFLANMSHELRTPLNSIL…KIMLDERRIRQVLIN-LLNNAV…IAVIDTGIGISAE…GTGLGLALVKRL-VEIHGGTVELTSELGVGSCFAI-NL
Ga0039499_10213     EFLANMSHELRTPLNSIL…KIMLDERRIRQVLIN-LLNNAV…IAVIDTGIGISAE…GTGLGLALVKRL-VEIHGGTVELTSELGVGSCFAI-NL
c407D_01196g2       EFLANMSHELRTPLNSIL…EIMLDERRIRQVLIN-LLNNAV…IAVIDTGIGISAE…GTGLGLALVKRL-VEIHGGTVELTSELGVGSCFAI-NL
WP_033374293        EFLANMSHELRTPLNAIL…DIVLDERRIRQVLIN-LLNNAV…FSVIDTGIGITPE…GTGLGLAVTKRI-VELHGGQVGVSSEEGKGSCFMI-DL
N7104D_1016g3       EFLANMSHELRTPLNAIL…EITLDERRIRQVLIN-LLSNAV…FAVTDTGIGITPE…GTGLGLALVKRI-VELHRGQVGLTSDVGVGSCFTV-EL
L6406D_1154g2       EFLANMSHELRTPLNTIL…EITLDERRIRQVLIN-LLNNAV…FAVTDTGIGITPE…GTGLGLALVKRI-VELHGGQVGLTSAVGVGSCFTF-DL
Os7112_5903g3       EFLANMSHELRTPLNAIL…DLLIDERRMRQVLIN-LLNNAV…ISVIDTGIGIAPE…GTGLGLALVKRI-VELHGGQVLLTSTVGVGSCFTI-DL
Os7112_5903g2       EFLANMSHELRTPLNAIL…DLLIDERRMRQVLIN-LLNNAV…ISVIDTGIGIAPE…GTGLGLALVKRI-VELHGGQVLLTSTVGVGSCFTI-DL
WP006632756g2       EFLANMSHELRTPLNAIL…DLLIDERRMRQVLIN-LLNNAV…IAVIDTGIGIAPE…GTGLGLALVKRI-VELHGGQVGLTSTVGVGSCFTI-DL
WP006632756g3       EFLANMSHELRTPLNAIL…DLLIDERRMRQVLIN-LLNNAV…IAVIDTGIGIAPE…GTGLGLALVKRI-VELHGGQVGLTSTVGVGSCFTI-DL
Anacy_4718g3        EFLANMSHELRTPLNAIL…DLFVDERRIRQVLIN-LLNNGV…ITVIDTGIGISPE…GTGLGLALVKQI-VELHGGQVGLTSELGVGSCFMI-DL
C6303_3693g3        EFLANMSHELRTPLNAIL…DLFVDERRIRQVLIN-LLNNAV…FAVRDTGIGISPE…GTGLGLALVKRI-IELHGGLVGLTSELGVGSCFTI-DL
fdiDRAFT29700       EFLANMSHELRTPLNAIL…HLLVDERRIRQVLIN-LLNNAV…IAVKDTGIGIAPE…GTGLGLALVKRI-VELHGGRVGLSSELGVGSCFTI-EL
MC7420_7957g2       EFLANMSHELRTPLNAIL…TILGDERRLQQVLIN-LLSNAV…ISVSDTGIGIAKE…GTGLGLALVRRI-VELHGGWVTVESEIGKGSCFTV-RL
WP_019501237        EFLANMSHELRTPLNAIL…PVFMDERRMRQVLIN-LLSNAV…FNVIDTGIGIASK…GTGLGLALVRRI-VEMHGGKVSVESEVGQGSKFQV-NI
WP017296986g2       EFLANMSHELRTPLNVIL…YIVADPNKLRQVLIN-LLGNAI…FAVEDTGTGIAPA…GTGLGLAISRSL-VQLMGGSLTVSSRLGQGSTFCF-SL
WP008316973g2       EFLANMSHELRTPLNVIL…YIVADPNKLRQVLIN-LLNNAI…FQVIDTGVGIPSE…STGLGLAISRSL-VKLMGGELTVNSAPDQGSTFQF-AI
O6304_4065g1        EFLANMSHELRTPLNAIL…MIMSDESKLRQVLIN-ILGNAI…IEIADTGSGIAPE…GTGLGLPISRKF-IQLMGGDIHVSSTVGVGTVFSF-EI
AM1_5997g1          IFLANMSHELRTPLNAIL…YIRTDPGKLRQVLMN-LLSNAI…FTVSDTGSGIAPE…GTGLGLAISRQF-VQIMGGNLTAHSIHNQGTTLTF-NI
```

FIG. 4 (cont'd)

FIG. 13A
FIG. 13B
FIG. 13C
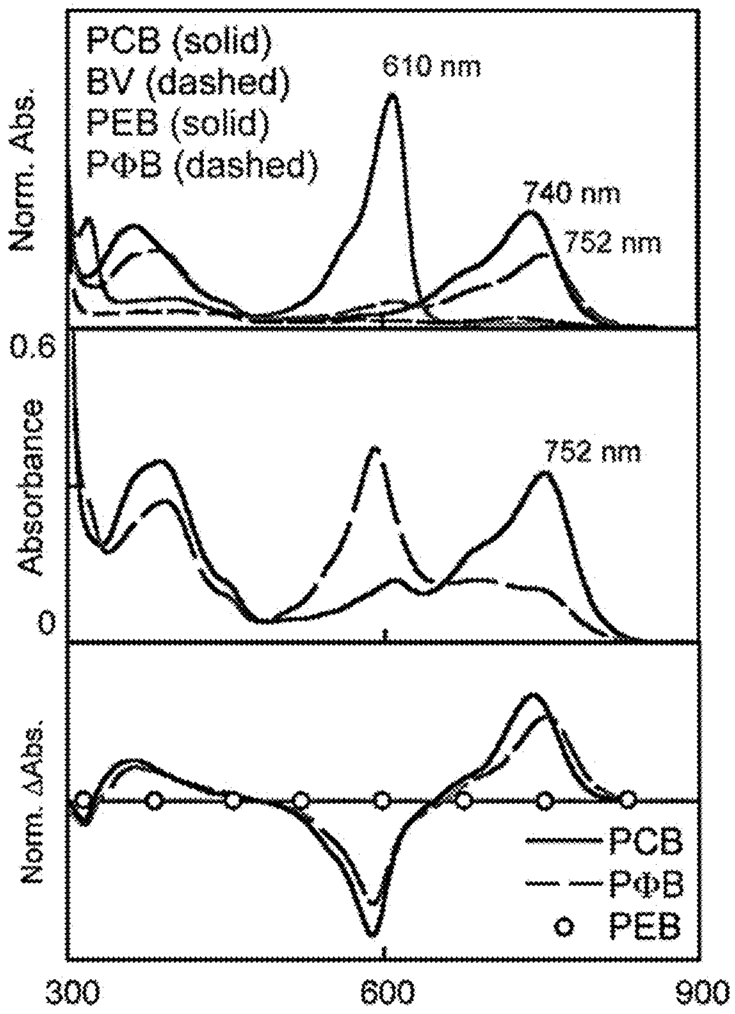
FIG. 13D
FIG. 13E
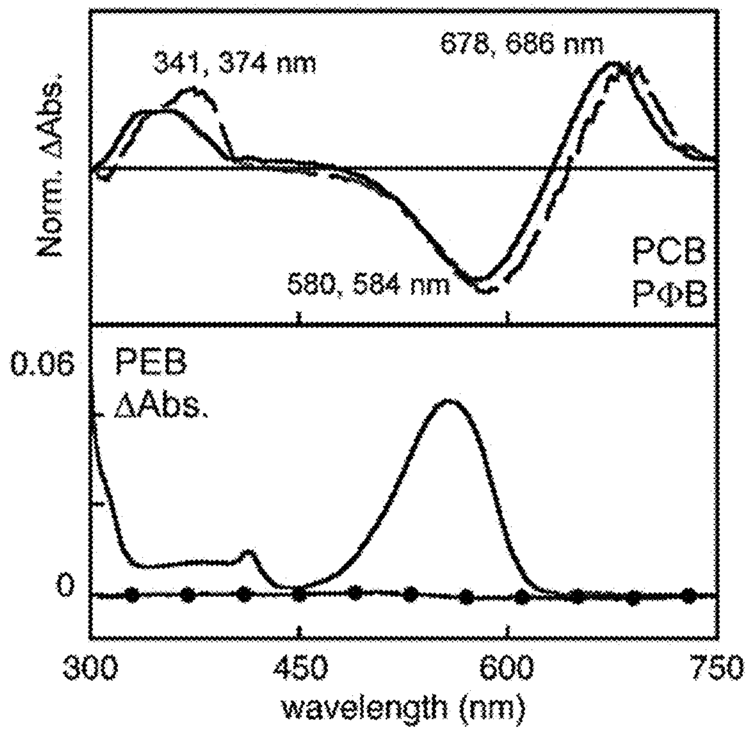

CYANOBACTERIOCHROMES ACTIVE IN THE FAR-RED TO NEAR-INFRARED

CROSS-REFERENCES TO RELATED APPLICATIONS

The present application is continuation of International Application No. PCT/US2017/018976 filed Feb. 22, 2017, which claims priority to U.S. Provisional Application No. 62/298,946, filed on Feb. 23, 2016, the disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. DE-FG02-09ER16117, awarded by the U.S. Department of Energy. The Government has certain rights in this invention.

BACKGROUND OF THE INVENTION

Almost all organisms at the surface of the earth use photosensory proteins to sense the ambient light environment and to tune their metabolism and behavior. Animal photoreceptors provide a basis for diverse biological responses including the entrainment of circadian rhythms and visual navigation.[1, 2] Photosynthetic organisms also utilize diverse photosensors.[3] For example, flavin-based phototropins control plant phototropism, a photobiological response first noted in antiquity and studied by Charles Darwin.[4-6] Plants also contain phytochromes, linear tetrapyrrole (bilin)-containing sensors which measure red and far-red light to control every aspect of plant biology, from seed germination and light-dependent growth and development (photomorphogenesis) to shade avoidance and flowering.[7-10] Photosynthetic and nonphotosynthetic bacteria also contain photoreceptors.[11-13] Indeed, the first photobiological response discovered in cyanobacteria, complementary chromatic acclimation (CCA), was reported within 25 years of Darwin's studies on phototropism[14] and is now known to leverage bilin-based photoreceptors to optimize light harvesting under green or red light.[15-17]

More recently, photoproteins have become critical research tools. Cell biology has been profoundly altered by the discovery and development of green fluorescent protein,[18] and light-dependent channelrhodopsins have proven equally transformational in the development of optogenetic approaches to neurobiology.[19] Phytochromes have also attracted attention as fluorescent probes,[20-26] as reagents for controlling protein-protein interactions with light,[27] in systems for light-controlled gene expression and subcellular localization,[28, 28A] and as tools for regulation of second messenger metabolism with light.[29, 30] Phytochromes are particularly appealing for application in multicellular animals due to their peak absorption in the red to far-red, partially overlapping the far-red/near-infrared (near-IR) window of optimum transparency in animal tissues.[31] Moreover, metazoans lack phytochromes, so there is no endogenous phytochrome photobiology in animals. However, counterbalancing points limit such applications of phytochromes. The minimal size for photochemically and biologically functional phytochromes is relatively large (300-500 amino acids), phytochromes are often dimeric, and many phytochromes utilize reduced linear tetrapyrrole (bilin) chromophores not present in animal cells.[32-34] Moreover, most phytochromes exhibit an unusual knotted architecture [35] that can constrain their application in fusion constructs.

Cyanobacteriochromes (CBCRs) present a possible alternative. Like the distantly related phytochromes, CBCRs use 15,16-photoisomerization of bilin chromophores (FIG. 1) to reversibly photoconvert between two states with distinct spectral and biochemical properties.[34, 36] In both CBCRs and phytochromes, the bilin is covalently attached to a conserved Cys residue via a thioether linkage (FIG. 1). However, the minimal CBCR domain is much smaller than that of phytochromes (<200 amino acids), and the three CBCRs examined to date are monomeric in solution.[37-39] Several examples have shown that chromophore assembly, peak absorption, and photoconversion are properties of isolated CBCR domains rather than of the diverse cyanobacterial signaling proteins in which such domains are found.[40-45] CBCR domains often occur in the middle of these signaling proteins and hence allow more flexible design of fusion constructs.[34, 36, 46, 47] Moreover, like phytochromes, some CBCRs can utilize biliverdin IXα (BV), a bilin chromophore present in animal cells.[48, 49] CBCRs described to date exhibit a broad range of photocycles, providing responses ranging from the near ultraviolet to the red region of the visible spectrum.[36, 47, 50] Several CBCR subfamilies are recognized,[36, 43, 45, 47, 51-54] including the green/red RcaE and CcaS CBCRs regulating CCA.[17] However, the most significant disadvantage limiting their application in large animals is the absence to date of CBCRs detecting far-red and near infrared light.[55]

BRIEF SUMMARY OF THE INVENTION

In a first aspect, the invention provides a protein fusion construct comprising a far-red cyanobacteriochrome (CBCR) domain linked to a heterologous domain, wherein the far-red CBCR domain comprises a CBCR polypeptide and a tetrapyrrole chromophore. In addition, the invention provides nucleic acids, expression cassettes, vectors, and host cells for expression of the far-red CBCR protein fusion constructs.

In another aspect, the invention provides a method for detecting a cellular component. The method includes: providing a protein fusion construct in a sample, the fusion construct comprising a far-red CBCR domain and a heterologous domain specifically detecting a cellular component; exposing the protein fusion construct to far-red light or near-IR light, wherein the exposing causes fluorescence of the far-red CBCR domain; and detecting the fluorescence of the far-red CBCR domain, thereby detecting the cellular component.

In a related aspect, the invention provides a method for imaging a biological structure in a subject. The method includes: providing a protein fusion construct in or near the biological structure, the fusion construct comprising a far-red CBCR domain and a heterologous domain; exposing the protein fusion construct to far-red light or near-IR light, wherein the exposing causes absorbance by, or release of an acoustic signal or fluorescence from, the far-red CBCR domain; detecting the absorbance, acoustic signal, or fluorescence of the far-red CBCR domain; and constructing an image of the biological structure; thereby imaging the biological structure.

In another aspect, the invention provides a method for modulating a cellular process. The method includes: expressing a protein fusion construct in a cell, the fusion construct comprising a far-red CBCR domain and a heterologous signaling domain; exposing the protein fusion construct to far-red light or near-IR light; wherein the exposing increases or decreases the activity of the heterologous signaling domain, thereby modulating the cellular process.

Other objects, features, and advantages of the present invention will be apparent to one of skill in the art from the following detailed description and figures.

BRIEF DESCRIPTION OF THE DRAWINGS

FIG. 3. (SEQ ID NO: 55-130) Sequence alignment of CBCR domains. Trp (W) residues conserved in far-red CBCRs are in bold. The far-red/orange CBCR cluster is in bold, and the far-red/red cluster is underlined.

FIG. 4. (SEQ ID NO: 131-204) Sequence alignment of His kinase bidomains. The presumptive phosphoacceptor His residue is in bold.

FIG. 13A. Characterization of Anacy_4718g3 incorporating different bilins. Absorption spectra are shown for Anacy_4718g3 incorporating PCB (solid black trace, 740 nm peak), BV (dashed black trace, no significant chromophore bound), PEB (solid grey trace, 610 nm peak), or PΦB (dashed grey trace, 752 nm peak). PCB and PΦB are in the 15Z configuration. Spectra were normalized to the protein absorption band at 280 nm to assess relative chromophore incorporation.

FIG. 13B. Characterization of Anacy_4718g3 incorporating different bilins. Absorption spectra are shown for Anacy_4718g3-PΦB in the far-red-absorbing 15Z dark state (solid black trace) and orange-absorbing 15E photoproduct (dashed grey trace).

FIG. 13C. Characterization of Anacy_4718g3 incorporating different bilins. Photochemical difference spectra are shown for native Anacy_4718g3 incorporating PCB (solid black trace), PΦB (dashed grey trace), or PEB (circles, no photoconversion) in the color scheme of panel A. Difference spectra were normalized for chromophore content.

FIG. 13D. Characterization of Anacy_4718g3 incorporating different bilins. Normalized photochemical difference spectra are shown for denatured Anacy4718g3-PΦB (dashed grey trace) and Anacy4718g3-PCB (solid black trace).

FIG. 13E. Characterization of Anacy_4718g3 incorporating different bilins. The absorption spectrum is shown for denatured Anacy_4718g3-PEB as the solid grey trace (556 nm peak). The photochemical difference spectrum resulting from 1 min illumination with white light is shown as the black trace with circles.

FIG. 18 B. Imaging Anacy_2551g3 in phantom mouse. Image was acquired at 18.1 mm depth with 710 nm excitation and 760 nm emission. A Perkin-Elmer IVIS system was used to acquire the image with purified Anacy_2551g3.

FIG. 18 C. Imaging Anacy_2551g3 in phantom mouse. Image was acquired at 7 mm depth with 745 nm excitation and 800 nm emission. A Perkin-Elmer IVIS system was used to acquire the image with purified Anacy_2551g3.

DETAILED DESCRIPTION OF THE INVENTION

I. General

Figure 1:
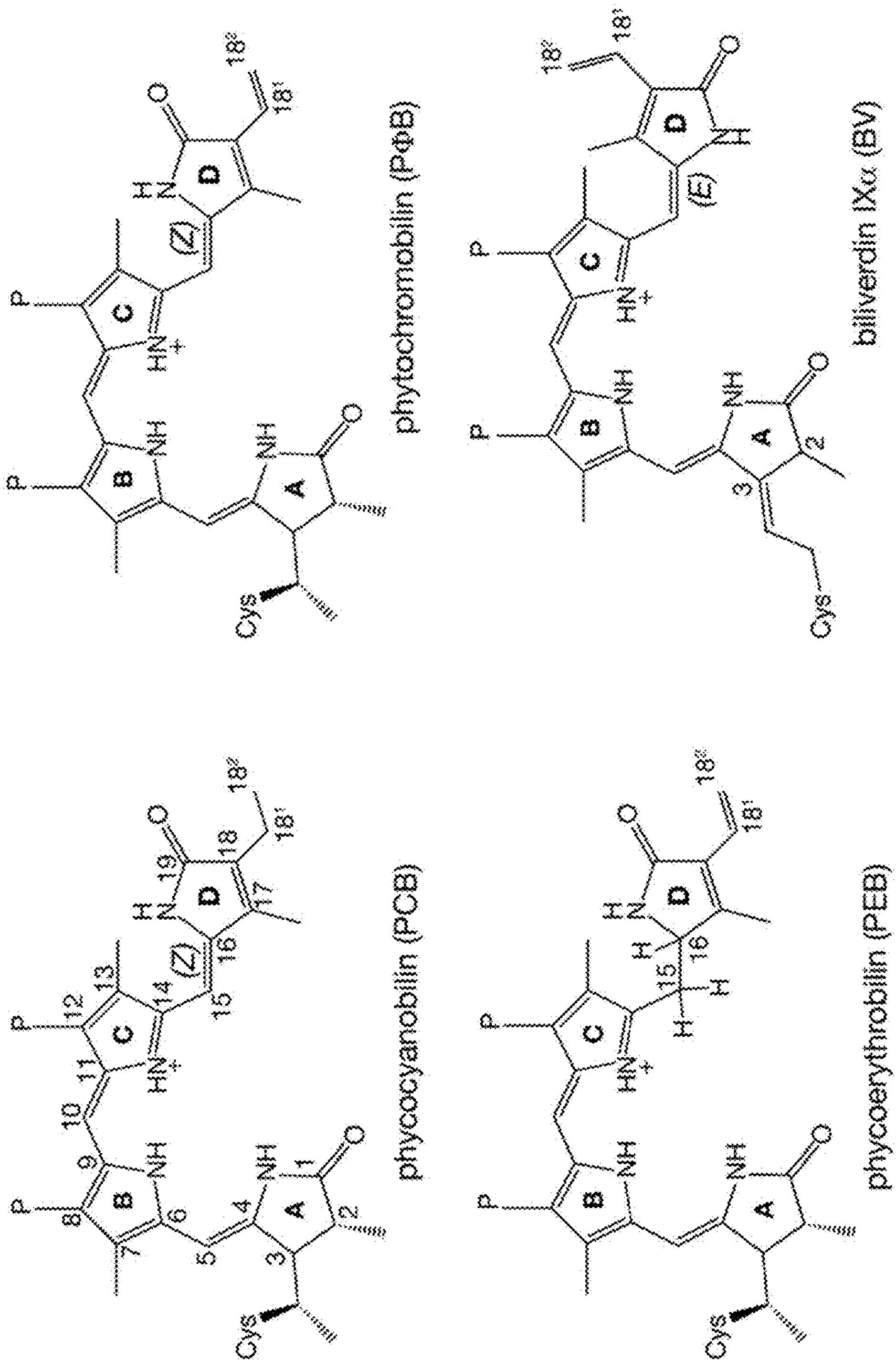
FIG. 1. Structures of bilin adducts. The indicated bilins are shown as covalent adducts, with rings designated. The numbering system is shown for the covalent adduct formed by incorporation of PCB. For other adducts, positions differing from the PCB adduct are indicated. PCB, PΦB and PVB are shown in the 15Z configuration. BV is shown in the 15E configuration. PEB lacks the 15,16-double bond. P, propionate.

The opacity of mammalian tissue to visible light and the strong attenuation of infrared light by water have contributed to growing interest in the development of far-red and near-infrared absorbing tools for visualizing and actuating responses within live cells. Disclosed herein is the discovery of cyanobacteriochromes (CBCRs) responsive to light in this far-red window. CBCRs are linear tetrapyrrole (bilin)-based light sensors from cyanobacteria distantly related to plant phytochrome sensors. These studies reveal far-red ($\lambda_{max}$ 725-755 nm)/orange ($\lambda_{max}$ 590-600 nm) and far-red/red ($\lambda_{max}$ 590-600 nm) photoswitches that are small (<200 amino acids) and can be genetically reconstituted in other living cells. Phylogenetic analysis and characterization of additional CBCRs establish that far-red/orange CBCRs evolved after a complex transition from green/red CBCRs known for regulating complementary chromatic acclimation (CCA). Incorporation of different bilin chromophores demonstrates that the tuning mechanisms responsible for red-shifted chromophore absorption act on the A-, B-, and/or C-ring system, whereas photoisomerization occurs at the D-ring. Two such proteins exhibited detectable fluorescence extending well into the near infrared. This work extends the spectral window of CBCRs to the edge of the infrared, raising the possibility of using CBCRs in synthetic biology applications in the far-red region of the spectrum.

Photoreceptors provide cells with the ability to sense the light environment. Such proteins also provide valuable tools for imaging of living tissues in research or clinical settings, because non-ionizing visible and near-infrared light is much safer than UV or x-ray irradiation. Human or animal tissues are maximally transparent to far-red and near-infrared light. Therefore, photoreceptors able to detect this spectral window are optimal for such applications. Very few photoreceptors detect light in this region of the spectrum. As such, a new group of photoreceptors with peak absorption in the far-red and with detectable fluorescence well into the near infrared has now been identified. These new photoreceptors can be developed for a range of applications, including fluorescent reporters, optical contrast agents, and optical tomography.

II. Definitions

As used herein, the terms "nucleic acid," "nucleotide," and "polynucleotide" refer to deoxyribonucleic acids (DNA) or ribonucleic acids (RNA) and polymers. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "nucleotide sequence encoding a peptide" and "gene" refer to the segment of DNA involved in producing a peptide chain. In addition, a gene will generally include regions preceding and following the coding region (leader and trailer) involved in the transcription/translation of the gene product and the regulation of the transcription/translation. A gene can also include intervening sequences (introns) between individual coding segments (exons). Leaders, trailers, and introns can include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms with manual adjustment informed by structural parameters. These definitions also refer to the complement of a nucleic acid test sequence.

"Similarity" and "percent similarity," in the context of two or more polypeptide sequences, refer to two or more sequences or subsequences that have a specified percentage of amino acid residues that are either the same or similar as defined by conservative amino acid substitutions (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% similar over a specified region), when compared and aligned for maximum correspondence over a comparison window, or designated region as measured using one of the following sequence comparison algorithms with manual adjustment informed by structural parameters. Sequences are "substantially similar" to each other if, for example, they are at least 20%, at least 25%, at least 30%, at least 35%, at least 40%, at least 45%, at least 50%, or at least 55% similar to each other.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins,* 1993).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or with manual adjustment informed by structural parameters (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative amino acid substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "transfection" and "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The terms "expression" and "expressed" in the context of a gene refer to the transcriptional and/or translational product of the gene. The level of expression of a DNA molecule in a cell may be determined on the basis of either the amount of corresponding mRNA that is present within the cell or the amount of protein encoded by that DNA produced by the cell.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

As used herein, the term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gin), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, as described herein, may also be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

The terms "amino acid modification" and "amino acid alteration" refer to a substitution, a deletion, or an insertion of one or more amino acids. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1993)).

As used herein, the term "expression cassette" refers to a nucleic acid construct, which when introduced into a host cell, results in transcription and/or translation of an RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

As used herein, the term "promoter" refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types without a need for a particular stimulus or condition, whereas a "tissue-specific promoter" initiates transcription only in one or a few particular tissue types. An "inducible promoter" is one that initiates transcription only under particular environmental conditions or developmental conditions.

As used herein, the term "vector" refers to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

A polynucleotide/polypeptide sequence is "heterologous" to an organism or a second polynucleotide/polypeptide sequence if it is synthetic or originates from a different species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

As used herein, the terms "cyanobacteriochrome" and "CBCR" refer to sensory photoreceptor proteins that mediate one or more processes including, but not limited to, photochromic responses, phototactic responses, development, and nitrogen metabolism in cyanobacteria. CBCRs typically include at least one GAF domain and at least one bilin chromophore as described herein. Among other characteristics, CBCRs exhibit a variety of photocycles spanning the entire visible and near-UV spectrum. At least six subfamilies of CBCRs have been identified based on photochemistry and primary structure. Examples of previously known CBCRs include Tlr0924, AnPixJg2, TePixJg, NpR6012g4, CikA, CcaS, and RcaE.

As used herein, the terms "far-red cyanobacteriochrome" and "near-IR cyanobacteriochrome" refer to CBCRs having at least one local absorbance maximum and/or at least one local emission maximum in the far-red portion or the near-IR portion of the electromagnetic spectrum. "Far-red" refers to light having an emission spectrum where there is an emission peak or emission maximum at a wavelength ranging from about 720 nm to about 760 nm. "Near infra-red" and "NIR" refer to light having an emission spectrum where there is an emission peak or emission maximum at a wavelength ranging from about 761 nm to about 1000 nm.

The "bilin" components of the adducts of the present invention are linear oligopyrroles (e.g., di-, tri-, or tetrapyrroles) capable of fluorescing, or photointerconverting between spectrophotometrically distinct forms, when associated with an apoprotein. Typically, the bilin components of the invention are isolated from vascular plants, algae, or cyanobacteria according to standard techniques or are synthesized in the same cell in which a CBCR is expressed. The bilin components can also be synthesized de novo. For a general discussion of bilins useful in the present invention, see, e.g., Falk (1989) Pp. 355-399 In: *The Chemistry of Linear Oligopyrroles and Bile Pigments*, Springer-Verlag, Vienna. Examples of bilins include, but are not limited to, phycocyanobilin (PCB), phytochromobilin (PΦB), phycoerythrobilin (PEB), and any of the four biliverdin IX (BV) isomers: BV IXα, IXβ, IXγ or IXδ.

As used herein, the term "GAF domain" refers to a polypeptide having a characteristic tertiary structure present in a number of cGMP phosphodiesterases, certain adenyl cyclases, and the bacterial transcription factor FhlA first described by Aravind and Pontig (*Tr. Biochem. Sci.* 22(12): 458-459. 1997). The structure of GAF domains is described, for example, by Hurley et al. (*EMBO J.*, 19(20): 5288-5299. 2000) and Narikawa et al. (*Proc. Nat. Acad. Sci. USA*, 110(3): 918-923. 2013). Characteristic features of GAF domains of the invention include a central 5-stranded anti-parallel β-sheet, one or more α-helices on the chromophore-binding side of the domain, and two or more α-helices opposite the chromophore-binding side of the domain.

As used herein, the term "acidic motif" refers to a region in the chromophore-binding side of the domain containing at least one acidic amino acid residue that contributes to chromophore binding.

As used herein, the term "signaling protein" refers to a protein that is part of a cellular signal transduction pathway. Examples of signaling pathways include, but are not limited to, MAP kinase signaling, PI3K/Akt signaling, protein kinase C signaling, and phospholipase signaling. Examples of signaling proteins include, but are not limited to, kinases, phosphatases, phosphodiesterases, proteases, phopholipases, cyclase, G-proteins, and channel proteins. A "signaling polypeptide" refers to a polypeptide exhibiting signaling activity by itself or as part of a protein fusion construct.

As used herein, the term "structural protein" refers to a protein that provides structural support to cells and other biological structures. Structural proteins often assemble to form structures such as filaments, cables, and sheets to provide biomechanical properties necessary for maintenance of cell shape and function. Non-limiting examples of structural proteins include actin, tubulin, myosin, keratin, fibroin, collagen, elastin, and proteoglycans. A "structural polypeptide" refers to a polypeptide exhibiting the structural properties and/or assembly properties of a structural protein by itself or as part of a protein fusion construct.

As used herein, the term "transport protein" refers to a polypeptide which functions to convey molecules or inorganic ions (e.g., $H^+$, $K^+$, $Na^+$, $Ca^{2+}$, $Mg^{2+}$, $Cl^-$, $Br^-$, etc.) into (e.g., uptake proteins) and out of (e.g., efflux proteins) a cell, as well as transportation of molecules intracellularly (e.g., translocation proteins) and other related transport activity. Examples of transport proteins include, but are not limited to, annexins, clathrin, caveolins, SNARE proteins, glucose transporter proteins, and aquaporins. A "transport polypeptide" refers to a polypeptide exhibiting the activity of a transport protein by itself or as part of a protein fusion construct.

As used herein, the terms "targeting protein" and "targeting polypeptide" refer to a protein that can selectively interact with a target feature such as a cellular receptor or another cell surface protein. Examples of targeting proteins include, but are not limited to, annexins, antibodies, antibody fragments such as synthetic $F_{ab}$'s, aptamers, and subcellular targeting signals, such as, e.g., mitochondrial or chloroplast targeting sequences, signal sequences, ER retention sequences, nuclear localization/export sequences, and the like.

As used herein, the term "hormone protein" refers to a protein that serves as an extracellular signal to elicit a response from a target cell or tissue. Examples of hormone proteins include, but are not limited to, insulin, luteinizing hormone, and platelet-derived growth factor. A "hormone polypeptide" refers to a polypeptide that exhibits the activity of a hormone protein by itself or as part of protein fusion construct.

As used herein, the term "regulatory protein" refers to a protein that contributes to the control of cellular processes and/or physiological activity. Examples of regulatory proteins include, but are not limited to, transcription factors, corepressors, coactivators, and the like. A "regulatory polypeptide" refers to a polypeptide that exhibits the activity of a regulatory protein by itself or as part of protein fusion construct.

III. Far-Red CBCR Constructs

The present invention is directed to fluorescent protein adducts, referred to herein as far-red CBCR labels, and their use as fluorescent markers/labels in a variety of contexts. The far-red CBCR labels comprise an apoprotein component (i.e., a far-red cyanobacteriochrome) and a tetrapyrrole component (e.g., a bilin such as phycoerythrobilin (PEB)). The far-red CBCR labels (fluorescent adducts) can be chemically conjugated or fused (i.e., recombinantly expressed as a fusion protein) to a heterologous subject moiety that is to be so labeled. For example, the labeled moiety can be a member of a biological binding pair for use in a number of techniques involving fluorescent labeling of analytes or other moieties.

A. CBCR Polypeptides

Accordingly, a first aspect of the invention provides a protein fusion construct comprising a far-red cyanobacteriochrome (CBCR) domain linked to a heterologous domain, wherein the far-red CBCR domain comprises a CBCR polypeptide and a tetrapyrrole chromophore. The CBCR polypeptide generally includes at least one GAF domain, named for the presence of domain in various cGMP phosphodiesterases (G), certain adenyl cyclases (A), and the bacterial transcription factor FhlA (F).

In some embodiments, the CBCR polypeptide comprises a GAF domain having an acidic motif comprising:
  a conserved tryptophan residue; followed by
  two acidic amino acid residues, wherein at least one of the amino acid residues is an acidic amino acid residue; followed by
  a conserved glutamic acid residue; followed by
  a further amino acid residue; followed by
  an aromatic amino acid residue.

In some embodiments, the acidic motif comprises an amino acid sequence set forth in SEQ ID NO: 1:

$$W-X^9-X^6-E-X^1-X^5 \tag{1}$$

wherein:
  W is a tryptophan residue;
  E is a glutamic acid residue;
  $X^1$ is an independently selected amino acid residue;
  $X^5$ is independently selected from the group consisting of a phenylalanine residue, a tyrosine residue, and a tryptophan residue;
  $X^6$ is independently selected from the group consisting of an aspartic acid residue and an asparagine residue; and
  $X^9$ is independently selected from the group consisting of an aspartic acid residue and a glutamate residue.

In other embodiments, the acidic motif comprises an amino acid sequence set forth in SEQ ID NO: 2:

$$X^2-X^1-D-E-X^1-X^2-P \tag{2}$$

wherein:

each $X^1$ is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

$X^1$ is an independently selected amino acid residue;

D is an aspartic acid residue;

E is a glutamic acid residue; and

P is a proline residue.

When complexed with the CBCR polypeptides of the invention, tetrapyrrole chromophores (e.g., bilins) exhibit large red shifts in their absorbance and fluorescence spectra as described in more detail below. Without wishing to be bound by any particular theory, it is believed that the presence of multiple conserved Trp residues in the CBCR polypeptides could promote a charge-transfer process that generates a labile, red-shifted species.

In some embodiments, the CBCR polypeptide comprises an amino acid sequence as set forth in SEQ ID NO: 3:

(3)

$X^9$-R-$X^1$-$X^3$-$X^4$-F-$X^1$-$X^3$-$(X^1)_2$-$X^6$-G-$(X^1)_3$-$X^4$-

$X^2$-E-E-$X^1$-V-$(X^1)_3$-$X^2$-$(X^1)_2$-$X^2$-$(X^1)_4$-W-$X^8$-$X^6$-

E-$X^1$-$X^5$-$X^1$-$X^7$-$X^9$-$(X^2)_2$-$X^8$-$X^2$-Y-$X^1$-Q-G-$X^1$-P-R-I-V-

$X^1$-$X^6$-V-$X^2$-$X^{10}$-$X^1$-D-$X^1$-$X^5$-$X^2$-$X^1$-C-L-$X^1$-E-$X^5$-

$(X^1)_5$-$X^4$-$X^1$-S-K-$X^4$-V-A-P-I-$X^2$;

wherein each A is an alanine residue, each C is a cysteine residue, each D is an aspartic acid residue, each E is a glutamic acid residue, each F is a phenylalanine residue, each G is a glycine residue, each I is an isoleucine residue, each K is a lysine residue, each L is a leucine residue, each P is a proline residue, each Q is a glutamine residue, each R is an arginine residue, each S is a serine residue, each V is a valine residue, each W is a tryptophan residue, and each Y is a tyrosine residue;

and wherein:

each $X^1$ is an independently selected amino acid residue;

each $X^2$ is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

each $X^3$ is independently selected from the group consisting of a valine residue, a leucine residue, an isoleucine residue, and a methionine residue;

each $X^4$ is independently selected from the group consisting of a valine residue, an isoleucine residue, and a threonine residue;

each $X^5$ is independently selected from the group consisting of a phenylalanine residue, a tyrosine residue, and a tryptophan residue;

each $X^6$ is independently selected from the group consisting of an aspartic acid residue and an asparagine residue;

each $X^7$ is independently selected from the group consisting of a glutamic acid residue and a glutamine residue;

each $X^8$ is independently selected from the group consisting of an aspartic acid residue, an asparagine residue, a glutamic acid residue, and a glutamine residue;

each $X^9$ is independently selected from the group consisting of an aspartic acid residue and a glutamate residue; and $X^{10}$ is absent or $X^{10}$ is one or more independently selected amino acid residues.

In some embodiments, $X^{10}$ is absent.

In some embodiments, the CBCR polypeptide comprises an amino acid sequence set forth in:

SEQ ID NO: 4 (Sta7437_1656),
SEQ ID NO: 5 (Cyan7822_4053g2),
SEQ ID NO: 6 (Anacy_2551g3), or
SEQ ID NO: 7 (Anacy_4718g3).

In some embodiments, the CBCR polypeptide comprises an amino acid sequence set forth in:

SEQ ID NO: 4 (Sta7437_1656),
SEQ ID NO: 5 (Cy7822_4053g2);
SEQ ID NO: 6 (Anacy_2551g3);
SEQ ID NO: 7 (Anacy_4718g3);
SEQ ID NO: 8 (N7104D_1016g3);
SEQ ID NO: 9 (L6406D_1154g2);
SEQ ID NO: 10 (c56D2_02270g2);
SEQ ID NO: 11 (c407D_01196g2);
SEQ ID NO: 12 (fdiDRAFT29700);
SEQ ID NO: 13 (WP009627289g3);
SEQ ID NO: 14 (Os7112_5903g3);
SEQ ID NO: 15 (C6303_3693g3);
SEQ ID NO: 16 (WP006632756g3);
SEQ ID NO: 17 (Cy7425_1390g3);
SEQ ID NO: 18 (WP017296986g2);
SEQ ID NO: 19 (WP_033374293);
SEQ ID NO: 20 (WP028089844g3);
SEQ ID NO: 21 (WP008316973g2);
SEQ ID NO: 22 (Ga0039499_10213);
SEQ ID NO: 23 (310F_3509)
SEQ ID NO: 24 (WP_016871037);
SEQ ID NO: 25 (WP_016878855);
SEQ ID NO: 26 (WP_026722600);
SEQ ID NO: 27 (WP_017309337); or
SEQ ID NO: 28 (WP_016873240).

In some embodiments, the CBCR polypeptide in the far-red CBCR domain has at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth in SEQ ID NOS: 1-28 (e.g., SEQ ID NO: 4, SEQ ID NO: 5, SEQ ID NO: 6, or SEQ ID NO: 7). In some embodiments, the CBCR polypeptide comprises the amino acid sequence set forth in SEQ ID NO: 4, SEQ ID NO: 5, SEQ ID NO: 6, or SEQ ID NO: 7. In some embodiments, the CBCR polypeptide comprises the amino acid sequence set forth in SEQ ID NO: 4. In some embodiments, the CBCR polypeptide comprises the amino acid sequence set forth in SEQ ID NO: 5. In some embodiments, the CBCR polypeptide comprises the amino acid sequence set forth in SEQ ID NO: 6. In some embodiments, the CBCR polypeptide comprises the amino acid sequence set forth in SEQ ID NO: 7.

B. Chromophores for Far-Red CBCR Domains

As described above, the far-red CBCR domain in the protein fusion construct of the invention includes a tetrapyrrole chromophore. The far-red CBCR domain can contain any natural or synthetic tetrapyrrole capable of binding to the CBCR polypeptide in the domain. In some embodiments, the invention provides protein fusion constructs as described above wherein the tetrapyrrole chromophore is a bilin.

The far-red CBCR domain can contain one bilin, which is generally covalently coupled to the domain through one or more cysteine thioether linkages. As such, the far-red CBCR domain of the protein fusion construct provides a substrate for autocatalytic bilin addition.

Bilins and other tetrapyrrole chromophores can be isolated from natural sources or synthesized according to techniques known in the art. Methods for synthesis of the dimethyl ester of phytochromobilin are described, for example, by Weller et al. (*Chem. Ber.* 113:1603-1611 (1980)). Conversion of the dimethyl ester to the free acid can be accomplished according to known techniques (see, e.g., Greene and Wuts, *Protective Groups in Organic Synthesis,* 4th Ed. 2007, Wiley-Interscience, New York). Bilins including phytochromobilin, phycocyanobilin (PCB), and phycoerythrobilin (PEB) can be isolated from natural sources according to known methods. For instance, crude phycocyanobilin can be prepared from *Spirulina platensis* as described by Terry et al. (1993) *J. Biol. Chem.* 268:26099-26106. Crude phytochromobilin and PEB can be prepared by methanolysis of *Porphyridium cruentum* cells as described by Cornejo et al. (1992) J. Biol. Chem. 267: 14790-14798. The structures of phytochromobilin, PCB, and PEB are shown below. As described herein, the protein fusion constructs can also be co-expressed with enzymes that are capable of forming bilin chromophores.

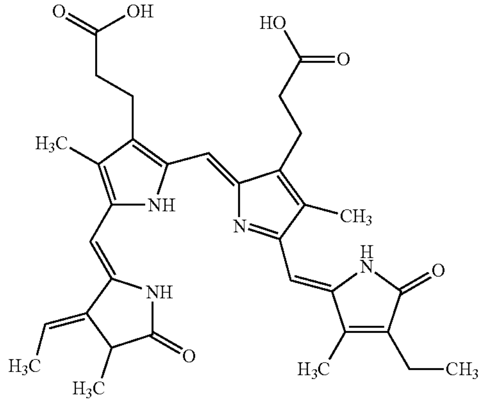

phycocyanobilin

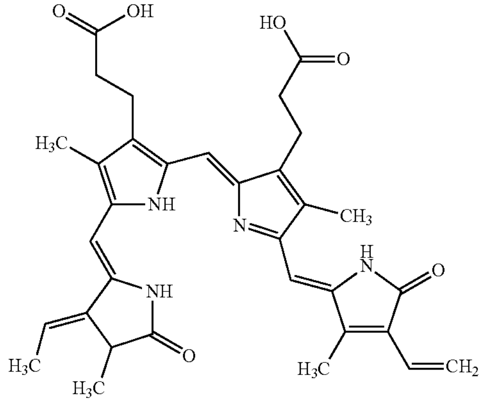

phytochromobilin

-continued

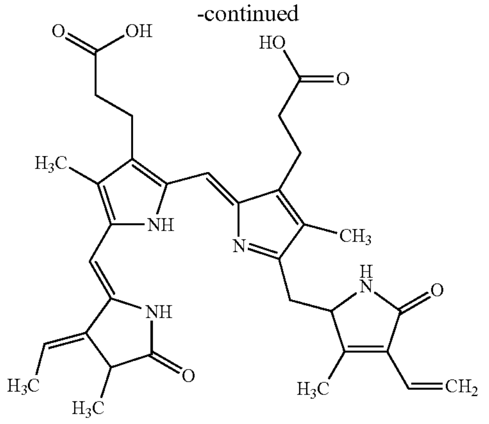

phycoerythrobilin

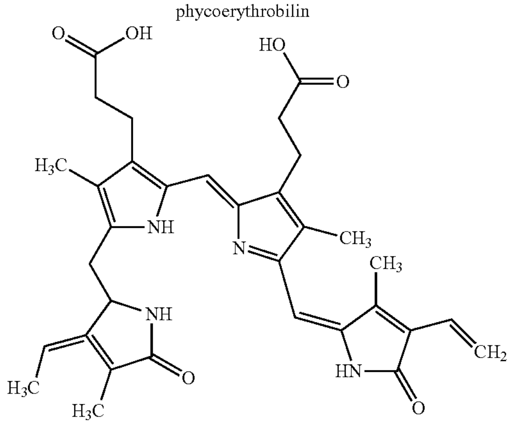

biliverdin

Accordingly, some embodiments of the invention provide protein fusion constructs as described above, wherein the bilin is selected from the group consisting of phycocyanobilin (PCB), phytochromobilin (PΦB), phycoerythrobilin (PEB), and biliverdin (BV).

The far-red CBCR domain confers fluorescence on the fusion protein, preferably providing fluorescence quantum yield and molar extinction coefficients of at least 1%, e.g., at least 10%, 50%, 75%, 90% of a corresponding unfused far-red CBCR domain, or substantially equivalent to a corresponding unfused far-red CBCR domain, measured as described herein. Certain domains provide extinction coefficients of at least 40,000 and/or quantum yields of at least 0.01. In certain instances, the fluorescence emission spectrum of the far-red CBCR protein fusion construct is substantially equivalent to that of a corresponding unfused CBCR.

In some embodiments, the C-terminus of the CBCR polypeptide is linked to the heterologous domain. In some embodiments, the N-terminus of the CBCR polypeptide is linked to the heterologous domain.

In some embodiments, the protein fusion construct further comprises one or more ancillary amino acid sequences located at the N-terminus and/or the C-terminus of the CBCR polypeptide or the heterologous polypeptide. These ancillary sequences can be useful for expressing, purifying, and/or using the protein fusion construct. The protein fusion construct can contain, for example, a poly-histidine tag (e.g., a His6 tag); a calmodulin-binding peptide (CBP) tag; a NorpA peptide tag; a Strep tag (e.g., Trp-Ser-His-Pro-Gln-Phe-Glu-Lys) for recognition by/binding to streptavidin or a variant thereof; a FLAG peptide (i.e., Asp-Tyr-Lys-Asp-Asp-Asp-Asp-Lys) for recognition by/binding to anti-FLAG antibodies (e.g., M1, M2, M5); a glutathione S-transferase (GST); a chitin-binding domain (CBP) or a maltose binding protein (MBP) polypeptide.

Various spacers or flexible linker peptides providing a variety of functionalities, such as a specific endopeptidase recognition and/or cleavage site, an affinity-purification tag, etc., can be used between the heterologous domain and the far-red CBCR domain. For example, when displayed C-terminally to the far-red CBCR domain, a specific protease recognition and cleavage site can be engineered immediately upstream from the heterologous domain so, upon cleavage with the protease, the heterologous domain can be cleanly released from the protein fusion construct. This strategy also works for most proteins displayed on the N-terminus of the fusion protein because the functions of most heterologous proteins are not affected by C-terminal extensions several residues long. In situations where such C-terminal extension is highly undesirable, an intein domain (Perler (2000), Nucleic Acids Res 28:344-345) can be engineered immediately downstream from the heterologous protein domain. Subsequent excision of intein cleanly releases the displayed domain from the fusion protein.

The length and amino acid sequence requirements of such linkers are readily determined empirically for a given fusion construct. Generally, the linkers are preferably from at least 5, preferably at least 10 residues in length, typically requiring no more than 50, and more often no more than 30 residues. To facilitate an unintrusive orientation, small, flexible residues such as Ala, Gly and Ser are particularly convenient components.

C. Heterologous Domains

A number of heterologous domains are suitable for use in the protein fusion constructs of the invention. In general, the heterologous domain will contain a polypeptide, some of which will be recognized by particular antibodies, receptors, enzymes, for use in particular applications. For example, the fusion protein construct can contain a specific binding moiety comprising at least one of a specific binding pair, such as a receptor-ligand pair, e.g., an immunoglobulin antigen-binding domain or antigenic domain, a lectin saccharide-binding domain, or an avidin or streptavidin domain. In a particular embodiment, the fusion protein comprises a biotinylated or biotinylatable domain, which is preferably biotinylated in the expression system (e.g., cell) selected for expression of the fusion protein. A wide variety of synthetic, semi-synthetic and natural such domains are known in the art, including homologs in phycobiliprotein producing cyanobacteria (see, e.g., Schatz et al. 1993, Bio/Technology 11, 1138-1143; Tatsumi et al., 1996, Anal Biochem 243, 176-180; Samols et al. 1988, J Biol Chem 263, 6461-6464; Gomicki et al. 1993, J Bacteriol 175, 5268-5272; Phung et al., GenBank Accession No. U59235; Nakamura et al. 1998 Nucl Acids Res 26, 63-67). In fact, enzymes sufficient to biotinylate biotinylatable domains have been characterized, permitting in vitro biotinylation. These biotinylated domains permit especially convenient affinity purification tags and are useful in the many well developed biotin/avidin applications (see, e.g., Beckett et al. 1999, Protein Sci 8, 921-929; Buoncristiani et al. 1988, J Biol Chem 263, 1013-1016; Li et al., 1992, J Biol Chem 267, 855-863; Cronan 1990, J Biol Chem 265, 10327-10333; Wilchek and Bayer (ed) 1990, Methods Enzymol 184).

In some embodiments, the invention provides far-red CBCR protein fusion constructs as described above, wherein the heterologous domain comprises a heterologous polypeptide selected from the group consisting of a signaling polypeptide, a structural polypeptide, a transport polypeptide, a targeting peptide, a hormone polypeptide, and a regulatory peptide.

In some embodiments, the signaling polypeptide is selected from the group consisting of a kinase polypeptide, a phosphatase polypeptide, a phosphodiesterase polypeptide, a nucleotide cyclase polypeptide, a protease, a phopholipase, a G-protein polypeptide, and a channel protein polypeptide.

In some embodiments, the structural polypeptide is selected from the group consisting of an actin polypeptide, a tubulin polypeptide, a myosin polypeptide, and a collagen polypeptide.

In some embodiments, the transport polypeptide is selected from the group consisting of an annexin polypeptide and a clathrin polypeptide.

In some embodiments, the targeting polypeptide is selected from the group consisting of an antibody, an antibody fragment, an aptamer, and a subcellular targeting signal.

In some embodiments, the heterologous domain comprises a streptavidin polypeptide.

The far-red CBCR label labels of this invention can be attached to a variety of other non-protein heterologous groups, including nucleic acids (e.g., single or double stranded DNA, cDNA, mRNA, cRNA, rRNA, tRNA) various sugars and polysaccharides, lectins, and the like. Uses of the various labeled biomolecules will be readily apparent to one of skill in the art. For example, labeled nucleic acids can be used as probes to specifically detect and/or quantify the presence of the complementary nucleic acid in, for example, fluorescence in situ hybridization or a Southern blot.

The far-red CBCR labels of this invention can be attached to non-biological molecules and various articles of manufacture. Thus, for example where it is desired to associate an article of manufacture with a particular manufacturer, distributor, or supplier, the far-red CBCR label, or simply one component of the far-red CBCR label can be attached to the subject article. Later development (e.g., by addition of the second component such as bilin or apoprotein) and exposure to an appropriate light source will provide a fluorescent signal identifying the article as one from a source of such labeled articles.

D. Recombinant Nucleic Acids and Host Cells for Expression

In a related aspect, the invention provides nucleic acids encoding the CBCR polypeptides and far-red CBCR protein fusion constructs as described herein. The nucleic acids can be generated from a nucleic acid template encoding CBCRs, using a number of recombinant DNA techniques that are known to those of skill in the art. Accordingly, certain embodiments of the invention provide an isolated nucleic acid comprising a polynucleotide sequence encoding a polypeptide comprising the amino acid sequence set forth in any one of SEQ ID NOS: 1-28 (e.g., SEQ ID NO: 4, SEQ ID NO: 5, SEQ ID NO: 6, or SEQ ID NO: 7).

In some embodiments, the invention provides an isolated far-red CBCR nucleic acid having at least about 50%, e.g., at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to a nucleic acid sequence encoding an amino acid sequence set forth in any one of SEQ ID NOS: 1-28 (e.g., SEQ ID NO: 4, SEQ ID NO: 5, SEQ ID NO: 6, or SEQ ID NO: 7). In certain embodiments, the isolated far-red CBCR nucleic acid is a synthetic gene that uses alternative codons for encoding an amino acid sequence set forth in any one of SEQ ID NOS: 1-28.

Using a far-red CBCR nucleic acid of the invention, a variety of expression constructs and vectors can be made. Generally, expression vectors include transcriptional and translational regulatory nucleic acid regions operably linked to the nucleic acid encoding the far-red CBCR. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retro-regulatory Element (PRE) to enhance the half-life of the transcribed mRNA (see, Gelfand et al. U.S. Pat. No. 4,666,848). The transcriptional and translational regulatory nucleic acid regions will generally be appropriate to the host cell used to express the far-red CBCR. Numerous types of appropriate expression vectors and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. Typically, the regulatory sequences will include a promoter and/or transcriptional start and stop sequences. Vectors also typically include a polylinker region containing several restriction sites for insertion of foreign DNA. As described above, heterologous sequences (e.g., a fusion tag such as a His tag) can be used to facilitate purification and, if desired, removed after purification. The construction of suitable vectors containing DNA encoding replication sequences, regulatory sequences, phenotypic selection genes, and the far-red CBCR of interest are prepared using standard recombinant DNA procedures. In some instances, isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)). In other instances, topo cloning or cloning by gap repair in yeast can be used.

Accordingly, some embodiments of the invention provide an expression cassette comprising a far-red CBCR nucleic acid as described herein operably linked to a promoter. In some embodiments, the invention provides a vector comprising a far-red CBCR nucleic acid as described herein. In some embodiments, the far-red CBCR nucleic acid in the expression cassette or vector encodes a polypeptide comprising an amino acid sequence set forth in any one of SEQ ID NOS: 1-28 (e.g., SEQ ID NO: 4, SEQ ID NO: 5, SEQ ID NO: 6, or SEQ ID NO: 7).

Cassettes for expression of the CBCR polypeptides can further include one or more nucleic acids encoding enzymes that synthesize the tetrapyrrole chromophores (e.g., a heme oxygenase for forming a bilin such as biliverdin). The heme oxygenase can be native or recombinant, such as a recombinantly expressed HO1 from *Synechocystis* sp. PCC6803. A bilin is generally further subject to a bilin reductase and may be further subject to additional enzymes of the cell such as additional reductases, to form the particular bilin. Nucleic acids encoding a number of recombinant reductases can be included in the expression cassette and in various combinations to obtain the far-red CBCR protein fusion constructs. For example, the expression cassettes can include nucleic acids encoding 3Z-phycocyanobilin:ferredoxin oxidoreductase (PcyA), which converts biliverdin to PCB; 3Z-phycoerythrobilin:ferredoxin oxidoreductase (PebS), which converts biliverdin to 3Z-phycoerythrobilin; and/or HY2, which converts biliverdin to phytochromobilin.

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a far-red CBCR of the invention is introduced into a cell, either alone or in combination with a vector. By "introduced into," it is meant that the nucleic acids enter the cells in a manner suitable for subsequent integration, amplification, and/or expression of the nucleic acid. The method of introduction or transfection is largely dictated by the targeted cell type. Exemplary methods include $CaPO_4$ precipitation, liposome fusion, LIPOFECTIN®, electroporation, heat shock, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, *Escherichia coli, Saccharomyces cerevisiae, Pichia pastoris*, Sf9 insect cells, and CHO cells. They are particularly useful for rapid production of large amounts of DNA, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; and other strains of *E. coli*, such as LMG194, HB101, JM101, NM522, NM538, and NM539. Many other species and genera of prokaryotes including bacilli such as *Bacillus subtilis*, other enterobacteriaceae such as *Salmonella typhimurium* or *Serratia marcescens*, and various *Pseudomonas* species can all be used as hosts. Prokaryotic host cells or other host cells with rigid cell walls are typically transformed using the calcium chloride method as described in Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.,* 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many new expression vectors are available as well.

Accordingly, some embodiments of the invention provide a host cell comprising a far-red CBCR nucleic acid, expression cassette, or vector, as described herein. In some embodiments, the far-red CBCR nucleic acid, expression cassette, or vector in the host cell encodes a polypeptide comprising the amino acid sequence set forth in any one of SEQ ID NOS: 1-28 (e.g., SEQ ID NO: 4, SEQ ID NO: 5, SEQ ID NO: 6, or SEQ ID NO: 7).

In some embodiments, the far-red CBCR protein fusion constructs of the present invention are produced by culturing a host cell transformed with an expression vector containing a nucleic acid encoding the far-red CBCR, under the appropriate conditions to induce or cause expression of the far-red CBCR. Methods of culturing transformed host cells under conditions suitable for protein expression are well known in the art (see, e.g., Sambrook et al., supra). Suitable host cells for production of the far-red CBCR protein fusion constructs from T7 promoter-containing plasmid vectors include *E. coli* strain BL21 (DE3) and related lysogens (see, e.g., U.S. Pat. No. 5,693,489). Following expression, a far-red CBCR protein fusion construct can be harvested and isolated.

IV. Methods

The far-red CBCR protein fusion constructs of the invention are useful as fluorescent markers in the many ways fluorescent markers already are used. This includes, for example, coupling far-red CBCR domains to antibodies, nucleic acids, or other receptors for use in detection assays, such as immunoassays or hybridization assays. Such constructs are particularly useful in applications involving the monitoring of gene expression and protein localization. Far-red CBCRs are ideal for such applications as they are readily detectable, can be detected on irradiation using standard long-wave light sources; offer the possibility of real-time detection in vivo; do not require introduction of a substrate to produce a signal; and allow manageable protein fusions due to their relatively small size and monomeric nature.

Accordingly, another aspect of the invention provides a method for detecting a cellular component, the method comprising:

providing a protein fusion construct in a sample, the fusion construct comprising a far-red CBCR domain and a heterologous domain detecting a cellular component;

exposing the protein fusion construct to far-red light or near-IR light, wherein the exposing causes fluorescence of the far-red CBCR domain; and detecting the fluorescence of the far-red CBCR domain, thereby detecting the cellular component.

In some embodiments, the sample is a cell or tissue and wherein providing the protein fusion construct comprises expressing the protein fusion construct in the cell or tissue.

As a non-limiting example, the invention provides for antibodies or antibody fragments to which the far-red CBCR labels of the invention are joined. The antibodies are capable of specifically binding to the antigen to which they are directed. Detection of the presence, absence, or particular amount of far-red/near-IR fluorescence provides an indication of presence, absence, or amount of analyte to which the antibody is directed.

Similarly, far-red CBCR label labeled antibodies, or other ligands, can be used in immunohistochemical applications. In this context, far-red CBCR antibody constructs are used to probe cells, tissues, and sections thereof. When the subject sample is contacted with the antibody construct, the antibody binds and localizes to specific regions of the sample in which the target molecule (the molecule or moiety recognized by the antibody) is located. Localization and/or quantification of the far-red/near-IR fluorescence provides information concerning the location and/or quantity of the target molecule in the sample. One of skill in the art will appreciate that the far-red CBCR constructs are also well suited for in situ and in vivo labeling of molecules, cells, and cellular components.

As another non-limiting example, the far-red CBCR constructs can be used for probing protein-protein interactions. In certain embodiments, two apoprotein cDNA constructs are used. The first construct will encode an apoprotein species whose assembly with a given bilin emits at a well-defined wavelength (donor). The second construct will encode an apoprotein species whose assembly with the same, or different, bilin produces a fluorescent species that both absorbs and emits light at longer wavelengths (acceptor). Protein-protein interaction between two proteins of interest (e.g., protein X and protein Y) is identified following their co-expression as translational fusions with apoprotein in constructs 1 (donor) and 2 (acceptor) using fluorescence energy transfer from the shorter wavelength-absorbing donor species to the longer wavelength-absorbing acceptor species.

In another application, chimeric apoprotein-protein X cDNA (where protein X is any protein of interest) are expressed in transgenic eukaryotes (yeast, plants, *Drosophila*, etc.) in order to study the subcellular localization of protein X in situ. Following feeding of exogenous bilin or engineering bilin biosynthesis in target tissues, subcellular localization can be performed using fluorescence microscopy (e.g., laser confocal microscopy).

In some embodiments, the far-red CBCR protein fusion constructs of the invention are used as in vitro or in vivo labels in a manner analogous to the use of Green Fluorescent Protein (GFP). This typically involves transfecting a cell with a nucleic acid encoding an apoprotein in such an manner that the cell expresses the apoprotein (e.g., the nucleic acid is a component of an expression cassette). When the apoprotein is provided with the appropriate bilin, supplied either exogenously or produced endogenously, the far-red CBCR label (fluorescent adduct) self assembles and thereby produces a fluorescent marker. Uses of such markers are well known to those of skill in the art (see, e.g., U.S. Pat. No. 5,491,084 which describes uses of GFP).

In a related aspect, the invention provides a method for imaging a biological structure in a subject, the method comprising:

providing a protein fusion construct in or near the biological structure, the fusion construct comprising a far-red CBCR domain and a heterologous domain;

exposing the protein fusion construct to far-red light or near-IR light, wherein the exposing causes absorbance by, or release of an acoustic signal or fluorescence from, the far-red CBCR domain;

detecting the absorbance, acoustic signal, or fluorescence of the far-red CBCR domain; and constructing an image of the biological structure;

thereby imaging the biological structure.

In some embodiments, the biological structure is selected from the group consisting of a tissue, an organ, or a tumor. In the imaging methods, the far-red CBCR domain can be used in the manner of other infrared dyes (e.g., phthalocyanine dyes, naphthalocyanine dyes, polymethine dyes, quinone dyes, and azo dyes) as described, for example, in U.S. Pat. Nos. 6,083,485; 9,089,603; 8,463,365; and 9,201,014. Examples of imaging techniques include, but are not limited to, optical coherence tomography and photoacoustic tomography (see, Matcher, *Methods Mol Biol.* 2011; 695: 261-80; Yao et al. *Nat Methods.* 2016 (1):67-73).

In some embodiments, the protein fusion construct is expressed in a cell or organism prior to imaging. Expression can be transient or permanent. With respect to expression in organisms, expression can be limited to specific cell types, tissue types, or developmental stages, or the protein fusion construct can be expressed throughout the entire organism. Suitable cells include bacterial cells, insect cells, fungal cells, yeast cells, plant cells, animal cells, mammalian cells, human cells, cancer cells, and stem cells.

In particular embodiments, the organism is a transgenic animal. Non-limiting examples of animals suitable for transgenesis include mice, rats, guinea pigs, rabbits, livestock (e.g., cattle, sheep, chickens, goats, pigs, salmon, trout, carp, catfish, silkworms), zebrafish, tilapia, frogs, and fruit flies. Methods for introducing recombinant nucleic acids for achieving transgenesis and inducing expression are described herein and will be known to one of skill in the art.

In another aspect, the invention provides a method for modulating a cellular process, the method comprising:

expressing a protein fusion construct in a cell, the fusion construct comprising a far-red CBCR domain and a heterologous signaling domain;

exposing the protein fusion construct to far-red light or near-IR light;

wherein the exposing increases or decreases the activity of the heterologous signaling domain, thereby modulating the cellular process.

In some embodiments, the heterologous signaling domain is selected from the group consisting of a kinase polypeptide, a phosphatase polypeptide, a phosphodiesterase polypeptide, a nucleotide cyclase polypeptide, a protease, a phopholipase, a G-protein polypeptide, and a channel protein polypeptide. Methods for control of output domains (e.g., adenylyl cyclases, phosphodiesterases, caspases, etc.) using light-activated sensors (e.g., phytochrome domains, bacteriophytochrome domains, and the like) can be applied to the methods for controlling cellular processes. See, for example, U.S. Pat. Nos. 8,828,658 and 8,835,399.

Genes encoding the far-red CBCR protein fusion constructs can be introduced into live animals, plants or microbes, where their activities can be turned on (or off) by far-red/near-IR light, controlled by the duration and/or intensity of light, and turned off (or on) by light of a different wavelength than the activating light. Diverse cellular processes can be regulated with high spatial and temporal precision in a nontoxic manner, often using external light sources. For example, far-red CBCR protein fusion constructs possessing nucleotidyl cyclase, protein kinase, protease, DNA-binding and RNA-binding activities can be used to control metabolic enzymes, signal transduction, cell apoptosis, proliferation, adhesion, differentiation and other processes.

In some embodiments, the protein fusion construct is expressed in a transgenic animal. Non-limiting examples of animals suitable for transgenesis include mice, rats, guinea pigs, rabbits, livestock (e.g., cattle, sheep, chickens, goats, pigs, salmon, trout, carp, catfish, silkworms), zebrafish, tilapia, frogs, and fruit flies.

In other embodiments, the protein fusion construct is expressed in a transgenic plant. Non-limiting examples of plants suitable for transgenesis include tobacco, maize, rice, potato, apple, tomato, wheat, sunflower, soybean, carrot, radish, spinach, and alfalfa.

In some other embodiments, the protein fusion construct is expressed in a transgenic microbe. Non-limiting examples of microbes suitable for transgenesis include BL21 *E. coli*, DE3 strain *E. coli, E. coli* M15, DH5α, DH10β, HB101, T7 Express Competent *E. coli* (NEB), *B. subtilis* cells, *Pseudomonas fluorescens* cells, *Chlamydomonas reinhardtii* cells, *Synechococcus elongatus* cells, *Pyrococcus furiosus, Metallosphera sedula, Thermococcus litoralis, Methanobacterium thermoautotrophicum, Methanococcus jannaschii, Pyrococcus abyssi, Sulfolobus solfataricus, Pyrococcus woesei, Sulfolobus shibatae*, and variants thereof.

A far-red/near-IR light-activated executor (effector) caspase can be introduced into tumors (or other kinds of disease-causing cells, e.g., cells carrying viruses) to induce an apoptotic cell death pathway, thus providing a noninvasive gene therapy of cancer (or viral diseases). Human cells expressing hormones (e.g., insulin) can be regulated by far-red CBCR protein fusion constructs (e.g., due to the light-regulated gene expression or hormone-synthesizing activity) and can be used to treat hormone deficiencies (e.g., diabetes). Far-red CBCR protein fusion constructs can be used to photoactivate immune cells at desired locations (e.g., tumor or infection sites). Far-red CBCR protein fusion constructs can also be used to convert prodrugs into active drugs in irradiated tissues and/or organs. Far-red CBCR protein fusion constructs expressed in bacteria (e.g., *E. coli* or *Lactobacillus*) that belong to normal human or animal microflora can be used to photoactivate organ-localized (e.g., colon, vagina) synthesis of bacteriophages, antibiotics, and other drugs to target pathogenic microorganisms, polyps and tumors or to produce probiotics. Some far-red CBCR protein fusion constructs can be used as protein-based drugs directly (e.g., by light-activated binding and control of cellular receptors).

The output module can be selected from enzymes and other proteins that have a desired biological activity, e.g., enzymatic activity, or ability to bind DNA, RNA or other proteins. In some embodiments, the output modules can include protein kinases, proteases (including caspases), nucleotidyl cyclases, nucleases (including recombinases), DNA-binding and RNA-binding protein modules, and others that are activated by homodimerization.

In certain instances, the far-red CBCR protein fusion constructs can be activated or their activity can be enhanced by the application of light of an activating wavelength. They can be inactivated, or their activity can be reduced by the absence of light or by the application of light of an inactivating wavelength. Some far-red CBCR protein fusion constructs can be active or show enhanced activity in the dark or reduced light, and be inactivated or show reduced activity when light of an inactivating wavelength is applied. The "absence of light" can mean the absence of all light (i.e., darkness), or can mean the absence of light in a selected wavelength range that causes a change in the conformation of the CBCR protein module.

Thus, in some embodiments the desired activity is increased by the application of far-red/near-IR light of a selected wavelength. In some embodiments, the desired activity is decreased by the application of far-red/near-IR light of a selected wavelength. In some embodiments, the desired activity is gradually decreased or gradually increased by ceasing to apply far-red/near-IR light of a selected wavelength. In some embodiments, the desired activity is immediately increased or decreased by the application of NIR light of a selected wavelength. Suitable selected wavelengths are determined by the spectral properties of the CBCR domain.

It is to be understood that the terms "active" and "inactive" in the foregoing explanation are relative and include complete activity of the protein to complete inactivity of the protein (complete "on/off" modes) as well as relative activity or inactivity of the proteins, i.e., the fusion protein constructs can have high activation ratios, low activation ratios, or activation ratios between high and low. In some embodiments, the fusion protein constructs can be controlled by light so as to have relatively high ratios (e.g., about 2:1 or greater, about 5:1, or about 10:1 or greater) of activity to inactivity or of inactivity to activity under the control of light of appropriate wavelengths.

V. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Disclosed herein is the discovery of CBCRs with peak absorption in the far-red window. Phylogenetic analysis identified a small CBCR cluster related to green/red CBCRs but exhibiting differences in a key sequence motif. In vitro characterization of five such proteins after recombinant expression in *Escherichia coli* revealed three with a conserved far-red/orange photocycle and two with a conserved far-red/red photocycle. The far-red-absorbing chromophore adopts a reversed chemical configuration relative to that of the far-red-absorbing $P_{fr}$ state of phytochromes and is a covalent PCB adduct similar to those of many other CBCR lineages (FIG. 1), but with a remarkable red shift of 70-80 nm in the native protein. Moreover, some far-red/orange CBCRs exhibit detectable far-red and near-infrared fluorescence. These studies establish far-red CBCRs as promising compounds for diverse applications in live cells and provide new insight into detection of far-red and near-IR light by bilin chromophores.

Example 1. Materials and Methods for Discovery and Characterization of Far-Red and Near-IR CBCRs Bioinformatics. CBCR sequences were identified using BLAST searches[56] against the Genbank and DOE-IMG databases. Locus tags from DOE-IMG are reported in Tables 1 and 3. All phylogenies were calculated using maximum-likelihood methods with structural information in PhyML-structure.[57] To generate the final alignment used for calculating the CBCR phylogeny shown in FIG. 2, new CBCR sequences were manually added to a pre-existing alignment.[54] The resulting alignment was pruned, and the region encompassing the Asp-motif was manually adjusted to optimize conservation of hydrophobic residues. Key regions are presented in FIG. 3. Structural information was projected onto the sequence alignment using an in-house script as described[54] using CBCR crystal structures for TePixJ and AnPixJ (PDB accession codes 3W2Z, 4FOF, and 4GLQ).[58, 59] TePixJ and AnPixJ themselves are not associated with histidine kinases and hence were removed for final phylogeny calculation, because the encoding of the structural information in PhyML-structure is not tied to the individual sequences. [57] C-terminal His kinase regions were initially aligned to sequences from histidine kinases for which crystal structures were available (PDB accession codes: 2C2A, 3DGE, 4U7N, 4U70, 3D36, 4R39) [60-63] using MUSCLE.[64] The resulting alignment was adjusted manually and structural information was added to the alignment using the in-house script as described above to yield the alignment used for calculating the maximum-likelihood phylogeny shown in FIG. 2. Key regions are presented in FIG. 4. Sequences for the crystal structures were again removed prior to calculation of the phylogeny, because those sequences were not associated with His kinase domains and hence would not be matched in the 'tanglegram' representation of FIG. 2.

Both phylogenies were calculated in PhyML-structure using the six-matrix EX_EHO model in partitioning mode, using the LG substitution matrix for positions with no structural information. [57] Maximum likelihood estimates were used for the proportion of invariable sites and for the distribution of the gamma shape parameter, with four substitution categories and optimization of tree topology, branch length, and rate parameters. The resulting tree was processed using FigTree (available online) and graphics editing software.

Cloning, Expression, and Purification of CBCRs.

Anacy_4718g3 (amino acids 1274-1466 of the Anacy_4718 locus in *Anabaena cylindrica* PCC 7122), Anacy_2551g3 (amino acids 835-1026) of Anacy_2551), and Oscil6304_4080 (amino acids 341-515 of Oscil6304_4080 in *Oscillatoria acuminata* PCC 6304) were cloned from genomic DNA prepared from *Anabaena* sp. PCC 7938 and *Oscillatoria acuminata* PCC 6304 using PCR with appropriate primers and with addition of one to two amino acids at the N terminus to create a start codon with an NcoI restriction site. For *Anabaena* sp. PCC 7938, amplified DNA sequences were identical to those of *A. cylindrica* PCC 7122.

Cyan7822_4053g2 (amino acids 903-1091 of Cyan7822_4053 in *Cyanothece* sp. PCC 7822), Nos7524_4790 (amino acids 932-1105 of Nos7524_4790 in *Nostoc* sp. PCC 7524), Sta7437_1656 (amino acids 696-871 of Sta7437_1656 from *Staniera cyanosphaera* PCC 7437), and WP_016871037 (amino acids 1246-1419 of UYKDRAFT_01008 from *Fischerella thermalis* PCC 7521) were obtained as synthetic genes (Genscript, Piscataway, N.J.) codon-optimized for expression in *E. coli.*

Anacy_4718g3, Cyan7822_4053g2, Nos7524_4790, and Oscil6304_4080 were cloned into pBAD-Cph1-CBD[65] using unique NcoI and SmaI sites, generating in-frame fusions to a C-terminal intein-CBD tag. Expression in *E. coli* strain LMG194 with co-production of PCB using pPL-PCB followed published procedures.[66] Co-production of PΦB and PEB was performed in the same way, but used pPL-PΦB and pAT-PebS, respectively.[22, 45] Proteins were purified on chitin resin (NEB) as previously described, with final dialysis into TKKG buffer (25 mM TES-KOH pH 7.8, 100 mM KCl, 10% (v/v) glycerol). [54, 65]

Anacy_2551g3, Anacy_4718g3, Sta7437_1656, and WP_016871037 were cloned into pET28-RcaE[17] using unique NcoI and BamHI sites, thereby cloning each CBCR as an in-frame fusion to a C-terminal His tag. His-tagged proteins were expressed in *E. coli* strain C41[67] with co-production of PCB using pKT271[68] and were purified on purified on His-bind $Ni^{2+}$-NTA resin (Novagen) using an imidazole gradient.[17, 42] His-tagged proteins were dialyzed into 20 mM sodium phosphate (pH 7.5), 50 mM NaCl, 10% (v/v) glycerol and 1 mM EDTA.

Figure 5:
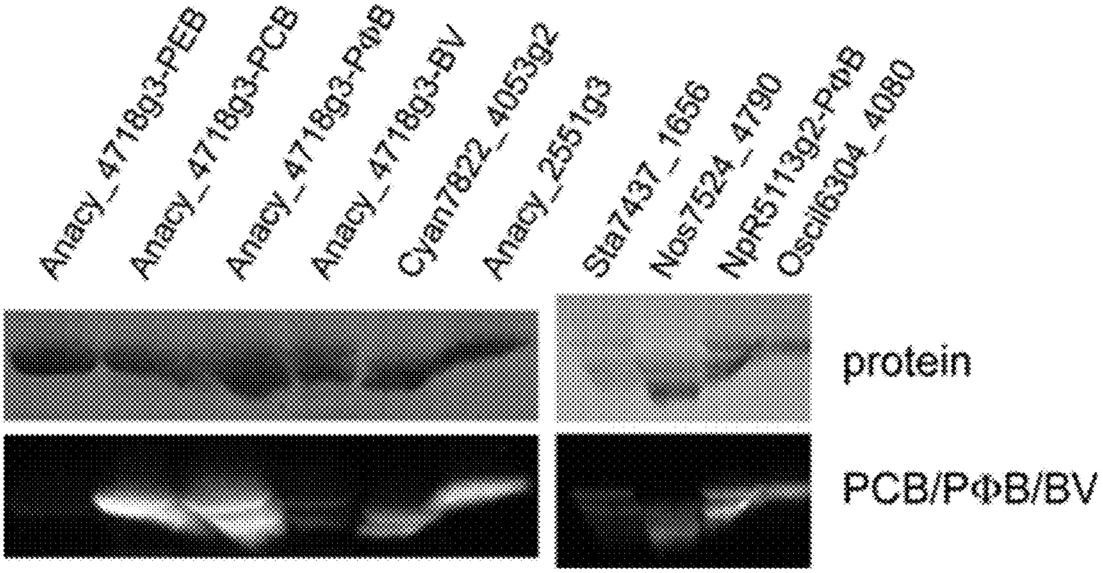
FIG. 5. Characterization of purified proteins. The indicated proteins were subjected to SDS-PAGE followed by semi-dry transfer to PVDF. Transferred proteins were visualized by Amido Black (top) and by zinc blotting (bottom; PEB is not detected).

Purified proteins were analyzed by SDS-PAGE using standard procedures and apparatus (Bio-Rad) followed by semi-dry transfer to PVDF membranes, staining with amido black for visualizing total protein, and zinc blotting (FIG. 5).[69]

Spectroscopic Characterization of CBCRs.

Absorption spectra were acquired on a Cary 50 spectrophotometer at 25° C. Photoconversion was triggered in the absorption cuvette using 728 nm LEDs (Sanyo) or using a xenon source equipped with band-pass interference filters (400±35 nm, 550±35 nm, 600±20 nm, 650±20 nm).[65] For WP_016871037, a red laser pointer (632.8 nm, 2 mW) was used as well. Fluorescence spectra were acquired on a QM-6/2005SE fluorimeter equipped with red-enhanced photomultiplier tubes (Photon Technology International). For denaturation assays, a 100 µl aliquot of protein was added to 1 ml of 7 M guanidinium chloride/1% HCl (v/v). Denatured samples were illuminated using the xenon lamp equipped with a 320 nm long-pass filter, and extinction coefficients were estimated from the denatured spectra as described previously[51] using the known extinction cofficients for PCB under acid denaturation conditions.[70] The fluorescence quantum yield of Anacy_2551g3 was estimated using the ratio method with Alexa 750 (Thermo Fisher) as the reference standard. [22]

Example 2. Discovery of Conserved Far-Red/Orange and Far-Red/Red CBCR Lineages Previous phylogenetic analyses clustered CBCR domains Anacy_4718g3 and Anacy_2551g3 from the filamentous cyanobacterium *Anabaena cylindrica* PCC 7122 with green/red CBCRs.[54] These sequences diverge from those of canonical green/red CBCRs, particularly in the Asp-motif region associated with spectral tuning in many CBCR lineages.[17, 43, 54, 59, 71] These sequences were therefore assessed to determine if they might be part of a previously uncharacterized CBCR lineage by using them as queries in BLAST [56] searches. This approach identified additional CBCR sequences containing similar variant Asp-motifs (Table 1).

TABLE 1

Accession information for far-red CBCRs

| Sequence | Domain architecture | DOE-IMG accession | Organism |
|---|---|---|---|
| WP008316973g2 | HAMP-PAS$_{10}$-CBCR-**CBCR**-HK-REC | LEP6406DRAFT_2712 | *Leptolyngbya* PCC 6406 |
| C56DFT2_02270g2 | PAS$_2$-CBCR-**CBCR**-HK-REC | cya56DRAFT2_02270 | *Planktothrix agardhii* NIVA-CYA 56/3 |
| c407DFT_01196g2 | PAS$_4$-CBCR-**CBCR**-HK-REC | Ga0039498_104087 | *Planktothrix rubescens* NIVA-CYA 407 |
| Ga0039499_10213 | PAS$_4$-CBCR-**CBCR**-HK-REC | Ga0039499_10213 | *Planktothrix prolifica* NIVA-CYA 406 |
| WP017296986g2 | PAS$_7$-CBCR-**CBCR**-HK-REC | Lepto7104DRAFT_1307 | *Leptolyngbya* PCC 7104 (*Nodosilinea nodulosa*) |
| Cy7822_4053g2 | CBS$_2$-PAS$_3$-CBCR-**CBCR**-HK-REC | Cyan7822_4053 | *Cyanothece* sp. PCC 7822 |
| C6303_3693g3 | CBS$_4$-GAF-**CBCR**-HK-REC | Cal6303_3693 | *Calothrix parietina* PCC 6303 |
| L6406D_1154g2 | CBS$_4$-GAF-PAS$_{10}$-CBCR-**CBCR**-HK-REC | LEP6406DRAFT_1154 | *Leptolyngbya* PCC 6406 |
| Anacy_2551g3 | CBS$_4$-CBCR-PAS-CBCR-**CBCR**-HK | Anacy_2551 | *Anabaena cylindrica* PCC 7122, PCC 7938 |
| WP028089844g3 | CBS$_3$-CBCR-PAS$_3$-CBCR-**CBCR**-HK | 131C_1565 | *Anabaena circinalis* AWQC131C |
| 310F_3509 | CBS$_3$-CBCR-PAS$_3$-CBCR-**CBCR**-HK | 310F_3509 | *Anabaena circinalis* AWQC310F |
| WP006632756g3 | CBS$_4$-CBCR-PAS$_{11}$-CBCR-**CBCR**-HK | MicvaDRAFT_3059 | *Microcoleus vaginatus* FGP-2 |
| N7104D_1016g3 | CBS$_2$-CBCR-PAS$_7$-CBCR-**CBCR**-HK-REC | Lepto7104DRAFT_1016 | *Leptolyngbya* PCC 7104 (*Nodosilinea nodulosa*) |
| fdiDRAFT29700 | CBS$_3$-CBCR-PAS$_2$-CBCR-**CBCR**-HK-REC | fdiDRAFT29700 | *Tolypothrix* sp. PCC 7601 |
| Anacy_4718g3 | CBS$_4$-CBCR-PAS$_3$-CBCR-**CBCR**-HK-REC | Anacy_4718 | *Anabaena cylindrica* PCC 7122, PCC 7938 |
| WP009627289g3 | CBS$_2$-CBCR-PAS$_3$-CBCR-**CBCR**-HK-REC | Pse7429DRAFT_2072 | *Pseudanabaena* sp. PCC 7429 |
| Os7112_5903g3 | CBS$_4$-CBCR-PAS$_{11}$-CBCR-**CBCR**-HK-REC | Osc7112_5903 | *Oscillatoria nigro-viridis* PCC 7112 |
| WP_033374293 | CBS$_4$-CBCR-PAS$_5$-GAF-CBCR-HK-REC | Spi9445_1327 | *Spirulina subsalsa* PCC 9445 |
| Cy7425_1390g3 | CBS-CBCR-PAS-GAF-PAS$_4$-CBCR-**CBCR**-HK-REC | Cyan7425_1390 | *Cyanothece* sp. PCC 7425 |
| Sta7437_1656 | XXX-HAMP-PAS$_2$-**CBCR**-PAS-HK | Sta7437_1656 | *Staniera cyanosphaera* PCC 7437 |

In Table 1, abbreviations for domains are as follows. CBS: cystathionine-β-synthase; CBCR: cyanobacteriochrome domain; PAS: Per-ARNT-Sim; GAF: cGMP-specific phosphodiesterases, cyanobacterial adenylate cyclases, and formate hydrogen lyase transcription activator FhlA; HAMP: Histidine kinases, Adenylate cyclases, Methyl-accepting proteins and Phosphatases; HK, histidine kinase bidomain; REC, response regulator receiver domain. Numbers indicate multiple domains of a given type in tandem, and CBCRs belonging to the far-red cluster are indicated in bold.

Figure 2:
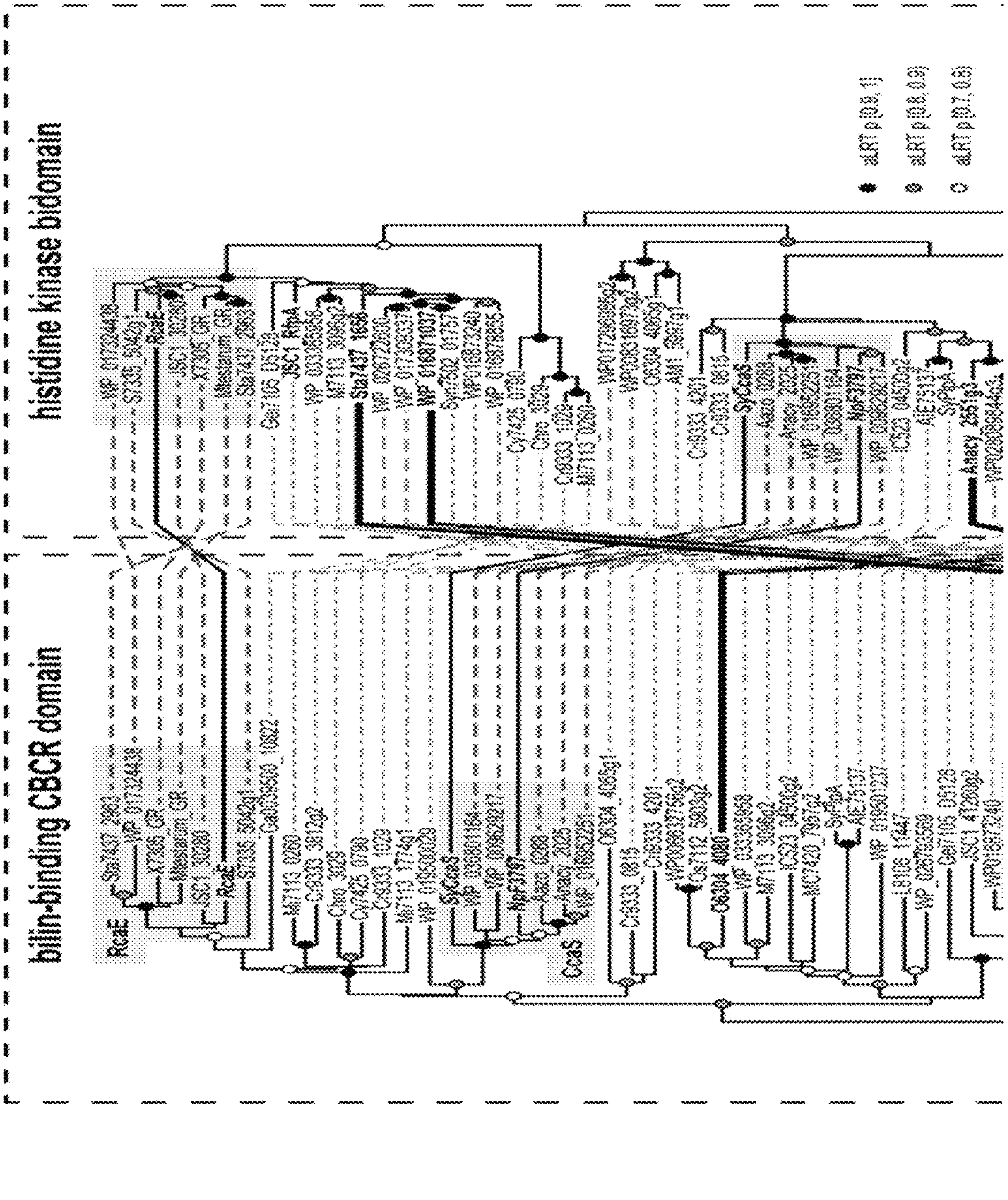
FIG. 2. Phylogenetic analysis of far-red CBCRs. Maximum-likelihood phylogenetic trees are shown for bilin-binding CBCR domains (left) and their associated histidine kinase bidomains (right). Far-red CBCRs, RcaE CBCRs regulating type III CCA,[16, 17] and CcaS CBCRs regulating type II CCA[42, 44] are indicated, with experimentally characterized examples matched to their kinases with solid lines and CBCRs characterized in this work in bold solid lines. Both RcaE and CcaS exhibit protochromic green/red photocycles.[17] Key regions of the underlying sequence alignments for CBCRs and histidine kinases are presented in FIG. 3 & FIG. 4.
Figure 2:
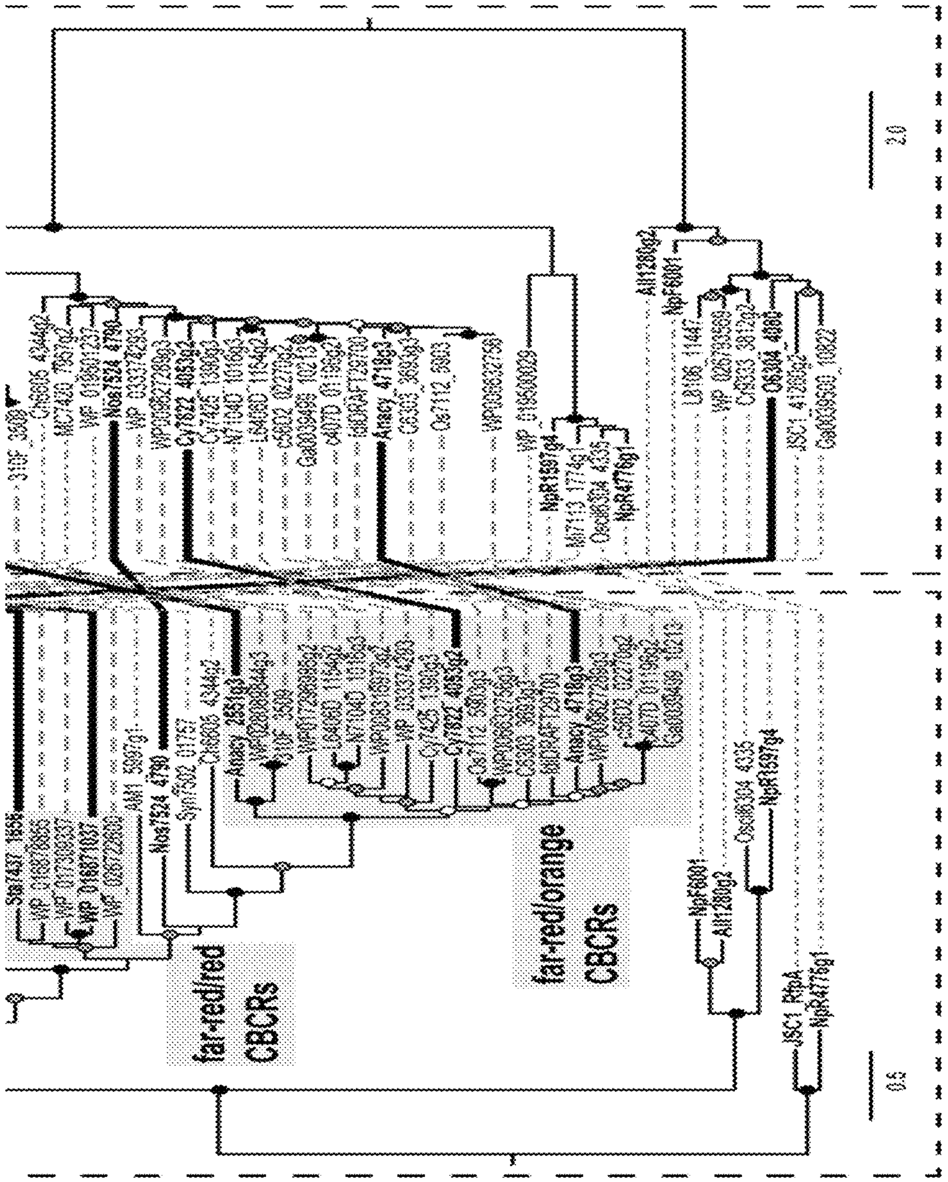

These CBCRs could readily be aligned with those of known green/red CBCRs (FIG. 3). Maximum-likelihood phylogenetic analysis demonstrated that these sequences, including Anacy_4718g3 and Anacy_2551g3, formed part of a distinct cluster (FIG. 2). CBCR domains in this cluster were part of larger signaling molecules with C-terminal histidine kinases (Table 1 & FIG. 4) and possessed diverse full-length domain architectures associated with at least three different subfamilies of C-terminal histidine kinase "output" domains (FIG. 2). By contrast, coherent CBCR/kinase pairings were observed for the green/red CBCRs RcaE and CcaS associated with CCA (FIG. 2). Taken together, these studies establish Anacy_4718g3 and Anacy_2551g3 as members of a new subfamily of CBCR photosensors associated with evolutionarily diverged signaling proteins.

Figures 6A, 6B, 6C, 6D, 6E:
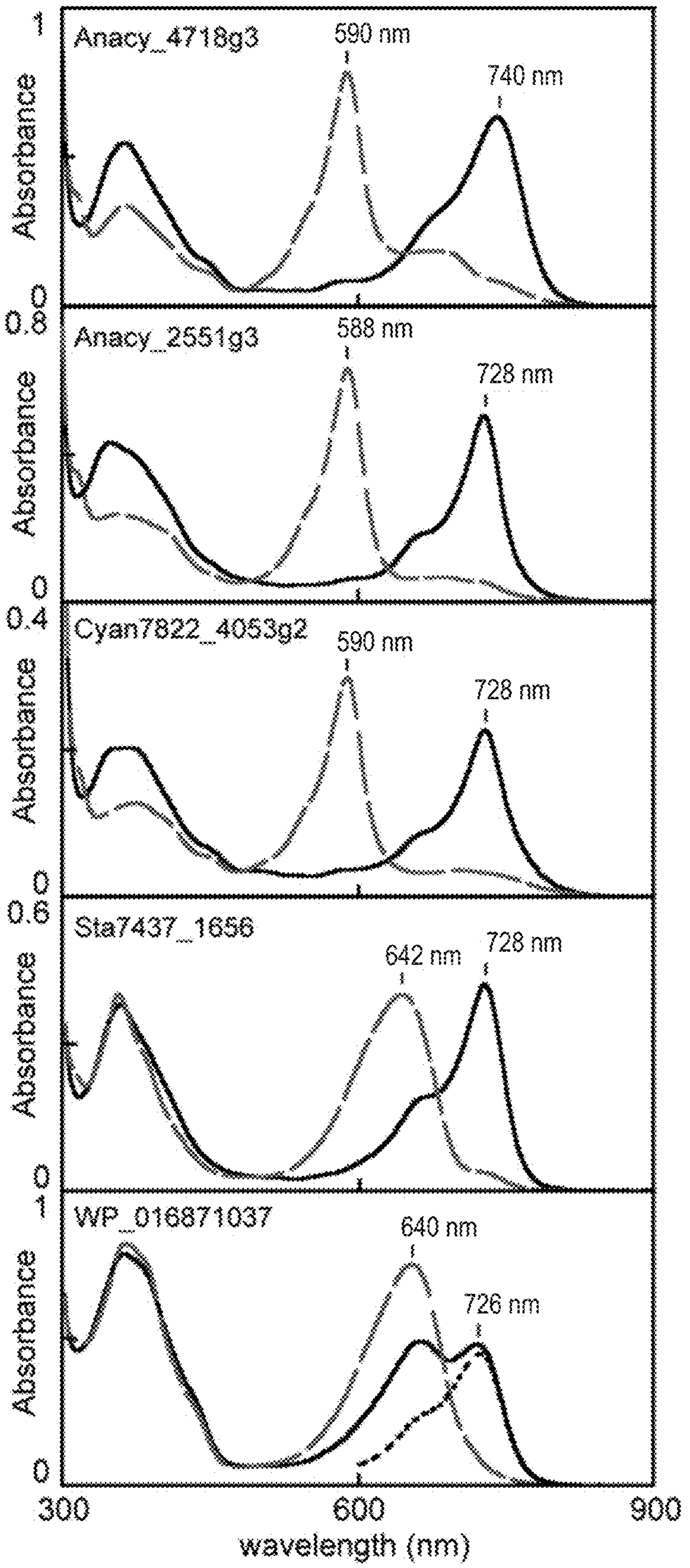
FIG. 6A. Characterization of far-red CBCRs. Absorption spectra are shown for Anacy_4718g3 in the far-red-absorbing 15Z dark state (solid black trace) and orange-absorbing 15E photoproduct (dashed grey trace). Anacy_4718g3 was purified as an intein-CBD fusion protein. Photoconversion was reversibly triggered using far-red LEDs (728 nm) or orange light (600±20 nm).
FIG. 6B. Characterization of far-red CBCRs. Absorption spectra are shown for Anacy_2551g3 using the color scheme and light sources of panel A.
FIG. 6C. Characterization of far-red CBCRs. Absorption spectra are shown for Cyan7822_4053g2 using the color scheme and light sources of panel A.
FIG. 6D. Characterization of far-red CBCRs. Absorption spectra are shown for Sta7437_1656 using the color scheme and light sources of panel A.
FIG. 6E. Characterization of far-red CBCRs. Absorption spectra are shown for WP_016871037 as initially purified (solid black trace) and after illumination with far-red light (dashed grey trace). Estimated bilin content in the two photostates was used to calculate a spectrum for the 15Z photostate (dotted black) as described in the Results.
Figures 7A, 7B, 7C, 7D, 7E, 7F, 7G, 7H:
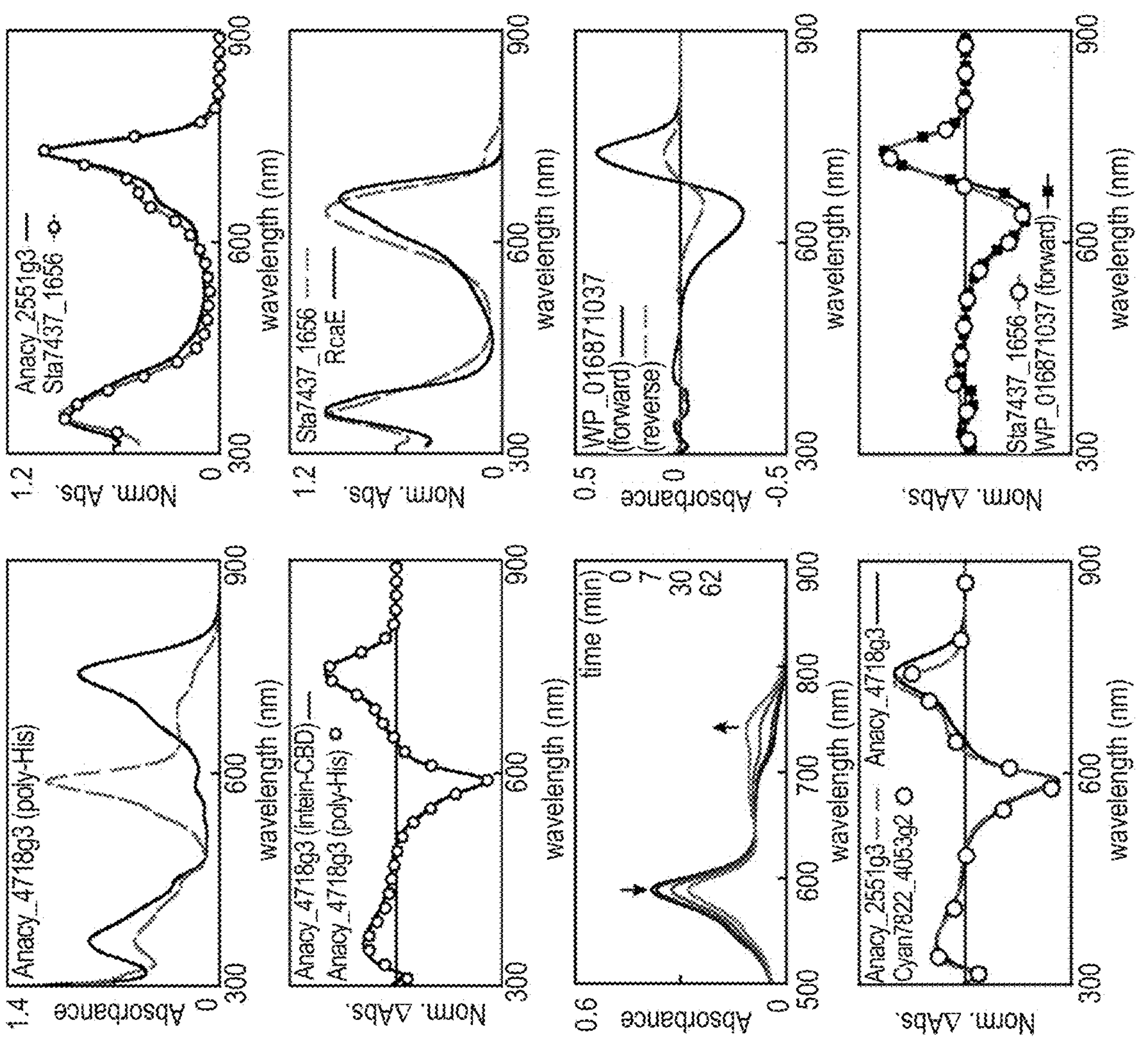
FIG. 7A. Additional characterization of far-red/orange CBCRs. Absorption spectra are shown for His-tagged Anacy_4718g3 in the far-red-absorbing state (solid black trace) and orange-absorbing state (dashed grey trace).
FIG. 7B. Additional characterization of far-red/orange CBCRs. Normalized photochemical difference spectra are shown for intein-CBD (solid black trace) and His-tagged (circles) constructs of Anacy_4718g3.
FIG. 7C. Additional characterization of far-red/orange CBCRs. Absorption spectra are shown for Anacy_4718g3 during incubation in darkness.
FIG. 7D. Additional characterization of far-red/orange CBCRs. Normalized photochemical difference spectra are shown for Anacy4718g3 (solid black trace), Anacy2551g3 (dashed grey trace), and Cyan7822_4053g2 (circles).
FIG. 7E. Additional characterization of far-red/orange CBCRs. Normalized absorption spectra are shown for Anacy_2551g3 (solid black trace) and Sta7437_1656 (grey trace with circles) in the far-red-absorbing state.
FIG. 7F. Additional characterization of far-red/orange CBCRs. Normalized absorption spectra are shown for Sta7437_1656 (dashed grey trace) and RcaE (solid black trace) in the red-absorbing state.
FIG. 7G. Additional characterization of far-red/orange CBCRs. Forward (solid black) and reverse (dashed grey) photochemical difference spectra are shown for WP_016871037. The reverse difference spectrum was acquired after extensive illumination, whereas the forward reaction readily proceeded to completion.
FIG. 7H. Additional characterization of far-red/orange CBCRs. Normalized photochemical difference spectra are shown for Sta7437_1656 (grey trace with circles) and WP_016871037 (black trace with squares, forward reaction).

Next, Anacy_4718g3 was characterized in vitro after recombinant expression in *E. coli* engineered to produce PCB.[66] This protein exhibited photoconversion between far-red-absorbing and orange-absorbing states exhibiting peak absorption at 740 nm and 590 nm, respectively (FIG. 6A & Table 2). Similar photocycles were observed for two constructs with different affinity tags (FIG. 7A-B), indicating that the different reagents employed in purifying His-tagged proteins or intein-CBD fusion proteins did not affect the far-red/orange photocycle. Slow dark reversion from the orange-absorbing state to the far-red-absorbing state was observed, indicating that the far-red-absorbing state is dark-adapted and the orange-absorbing state is the photoproduct (FIG. 7C). Anacy_2551g3 exhibited a similar photocycle (FIG. 6B), with the far-red-absorbing maximum at a slightly shorter wavelength (728 nm: Table 1). A third member of this cluster, Cyan7822_4053g2 from the unicellular cyanobacterium *Cyanothece* sp. PCC 7822, exhibited almost identical behavior to Anacy_2551g3 (FIG. 6C & FIG. 7D; Table 2). These results establish the existence of a cluster of CBCRs related to green/red CBCRs but exhibiting conserved far-red/orange photocycles.

TABLE 2

Spectral properties of CBCRs

| Protein | Construct | Bilin | 15Z $\lambda_{max}$ | 15E $\lambda_{max}$ | SAR |
|---|---|---|---|---|---|
| Anacy_4718g3 | intein-CBD | PCB | 740 | 590 | 0.16 |
| Anacy_4718g3 | intein-CBD | PΦB | 752 | 590 | 0.12 |
| Anacy_4718g3 | intein-CBD | PEB | 610 | — | 0.37 |
| Anacy_4718g3 | intein-CBD | BV | — | — | <0.02 |
| Anacy_4718g3 | poly-His | PCB | 740 | 590 | 0.17 |
| Anacy_2551g3 | poly-His | PCB | 728 | 588 | 0.13 |
| Cyan7822_4053g2 | poly-His | PCB | 728 | 590 | 0.07 |
| Sta7437_1656 | poly-His | PCB | 728 | 642 | 0.35 |
| WP_016871037 | poly-His | PCB | 726 | 640 | 0.34 |
| Oscil_6304_4080 | intein-CBD | PCB | 544 | — | 0.63 |
| Nos7524_4790 | intein-CBD | PCB | 418 | 658 | 0.17 |

In Table 2, all peak wavelengths are reported in nm. Specific Absorbance Ratio (SAR) was calculated as the ratio of the peak absorbance of the longest-wavelength chromophore band for the 15Z photostate to the peak absorbance of the aromatic amino acid band at 280 nm and serves as a relative measure of chromophore loading for a given protein/chromophore combination. The 15Z value for Anacy_4718g3 is for the dark-adapted state. The SAR value for WP_016871037 was estimated after subtraction of 15E signals Phylogenetic analysis tentatively placed far-red/orange CBCRs as part of a larger lineage that is sister to the CCA photoreceptors CcaS and RcaE (FIG. 2). Within this lineage, one branch of CBCRs includes proteins with Asp-motifs very similar to those of CcaS and RcaE, such as PlpA from *Synechocystis* sp. PCC 6803[72] and Oscil6304_4080 from *Oscillatoria acuminata* PCC 6304 (FIG. 3). The other branch includes both the far-red/orange CBCRs and other sequences. Some of these other sequences have Cys residues in or near the Asp-motif (FIG. 3), including Nos7524_4790 and Sta7437_1656. Such Cys residues can form a second covalent linkage to the chromophore, resulting in absorption of blue to ultraviolet light.[43, 45, 73] Additional CBCRs were therefore characterized to explore the transition from green/red photocycles to far-red/orange photocycles.

Figure 8A:
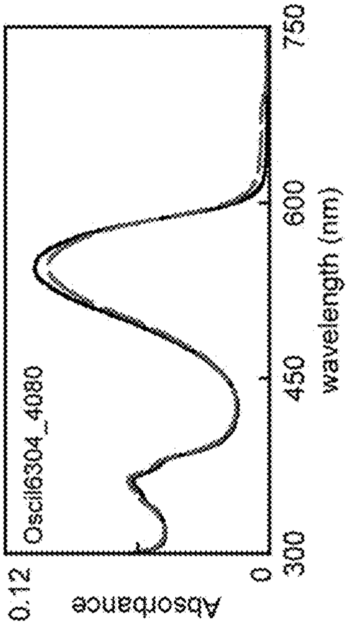
FIG. 8A. Characterization of additional CBCRs. Absorption spectra are shown for Oscil6304_4080 before (solid black) and after (dashed grey) illumination with green light (550±35 nm).
Figure 8B:
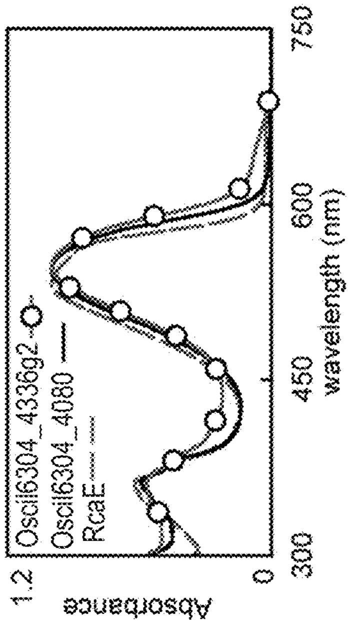
FIG. 8B. Characterization of additional CBCRs. Normalized absorption spectra are shown for the green-absorbing states of Oscil6304_4080 (solid black), green/red CBCR RcaE (dashed grey), and green/blue CBCR Oscil6304_4336g2 (solid grey with circles).
Figure 8C:
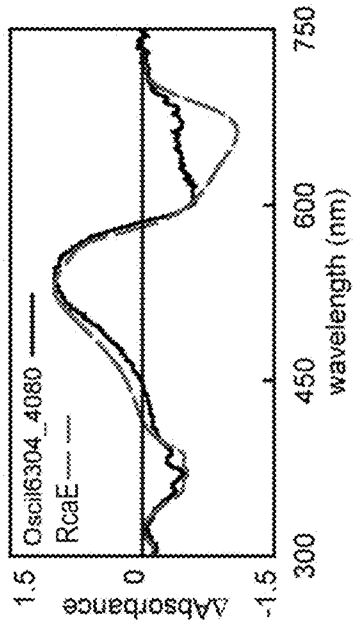
FIG. 8C. Characterization of additional CBCRs. Normalized photochemical difference spectra are shown for Oscil6304_4080 (solid black) and RcaE (dashed grey).
Figure 8D:
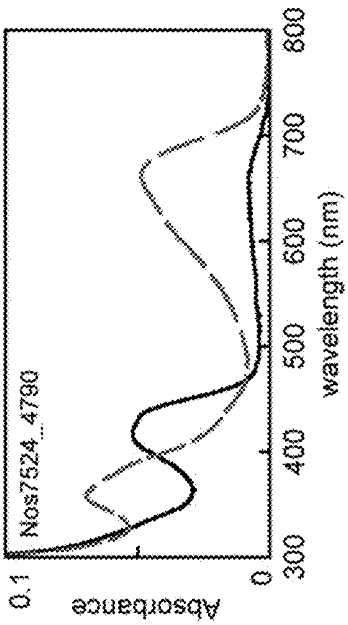
FIG. 8D. Characterization of additional CBCRs. Absorption spectra are shown for Nos7524_4790 in the 15Z (solid black) and 15E (dashed grey) configurations. Photoconversion was triggered using violet and red light (400±35 nm and 650±20 nm, respectively).
Figure 8E:
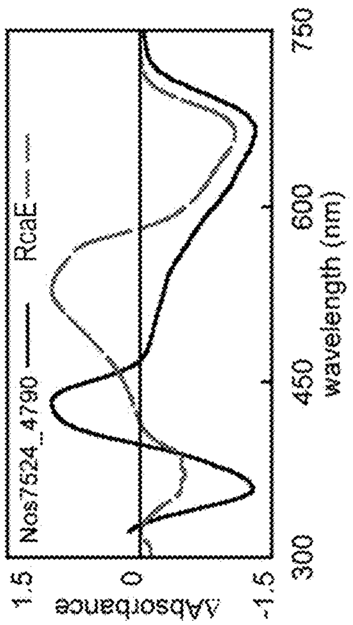
FIG. 8E. Characterization of additional CBCRs. Normalized absorption spectra are shown for the red-absorbing states of Nos7524_4790 (solid black) and RcaE (dashed grey).

Oscil6304_4080 exhibited a dark-adapted state with peak absorption in the green region of the spectrum (FIG. 8A). Illumination with green light (550±35 nm) produced only minimal photoconversion. The peak wavelength and lineshape of the green-absorbing state were similar to those of the green-absorbing states previously reported for the CCA regulator RcaE from *Fremyella diplosiphon* [17] and the green/blue CBCR Oscil6304_4336g2 from *O. acuminata* (FIG. 8B). Comparison of the normalized difference spectra for Oscil6304_4080 and RcaE shows similar depletion of the green state, but Oscil6304_4080 fails to form the red-absorbing photoproduct state (FIG. 8C). Nos7524_4790 exhibited photoconversion between two photostates with peak absorption in the blue and red regions of the visible spectrum (FIG. 8D & Table 2). The red-absorbing state was again similar to that of RcaE (FIG. 8E). Neither Oscil6304_4080 nor Nos7254_4790 exhibited detectable species with far-red absorption.

Sta7437_1656 exhibited photoconversion between states with far-red and red peak absorption (FIG. 6D). The far-red state was very similar to that of Anacy_2551g3, whereas the red-absorbing state was blue-shifted relative to those of RcaE and Nos7524_4790 (FIG. 7E-F). As purified, WP_016871037 exhibited a mix of red- and far-red-absorbing species (FIG. 6E), with ready conversion of the far-red state to the red state but poor reversibility even after laser illumination (FIG. 7G). The far-red/red photochemical difference spectrum for WP_016871037 was similar to that of Sta7437_1656 (FIG. 7H). Sta7437_1656 and WP_016871037 are part of a small cluster of CBCR domains associated with clustered histidine kinase output domains (FIG. 2) but having diverse domain architectures (Table 3). These results implicate a second cluster of far-red CBCRs with far-red/red photocycles (FIG. 2).

TABLE 3

Accession information for far-red/red CBCRs

| Sequence | Domain architecture | DOE-IMG accession | Organism |
|---|---|---|---|
| Sta7437_1656 | CACHE-HAMP-$PAS_2$-**CBCR**-PAS-HK | Sta7437_1656 | *Stanieria cyanosphaera* PCC 7437 |
| WP_016871037 | TPR-GAF-$PAS_7$-**CBCR**-$PAS_3$-HK | UYKDRAFT_01008 | *Fischerella thermalis* PCC 7521 |
| WP_026722600 | GAF-$PAS_6$-**CBCR**-$PAS_2$-HK | Fis9431DRAFT_3998 | *Fischerella* sp. PCC 9431 |
| WP_017309337 | GAF-$PAS_4$-**CBCR**-$PAS_2$-HK | PCC9339DRAFT_00524 | *Fischerella* sp. PCC 9339 |

TABLE 3-continued

| Accession information for far-red/red CBCRs | | | |
|---|---|---|---|
| Sequence | Domain architecture | DOE-IMG accession | Organism |
| WP_016878855 | REC-PAS$_6$-**CBCR**-PAS-HK | UYEDRAFT_06529 | *Chlorogloeopsis fritschii* PCC 9212 |
| WP016873240 | CACHE-HAMP-PAS$_4$-GAF-**CBCR**-PAS-HK | UYEDRAFT_00976 | *Chlorogloeopsis fritschii* PCC 9212 |

In Table 3, abbreviations for domains follow those of Table S1. Additonal domains: TPR, tetratricopeptide repeat domain; CACHE: $Ca^{2+}$ channels, chemotaxis protein.

Spatial Separation of Photoconversion and Spectral Tuning in the Far-Red-Absorbing Chromophore.

Figure 9B:
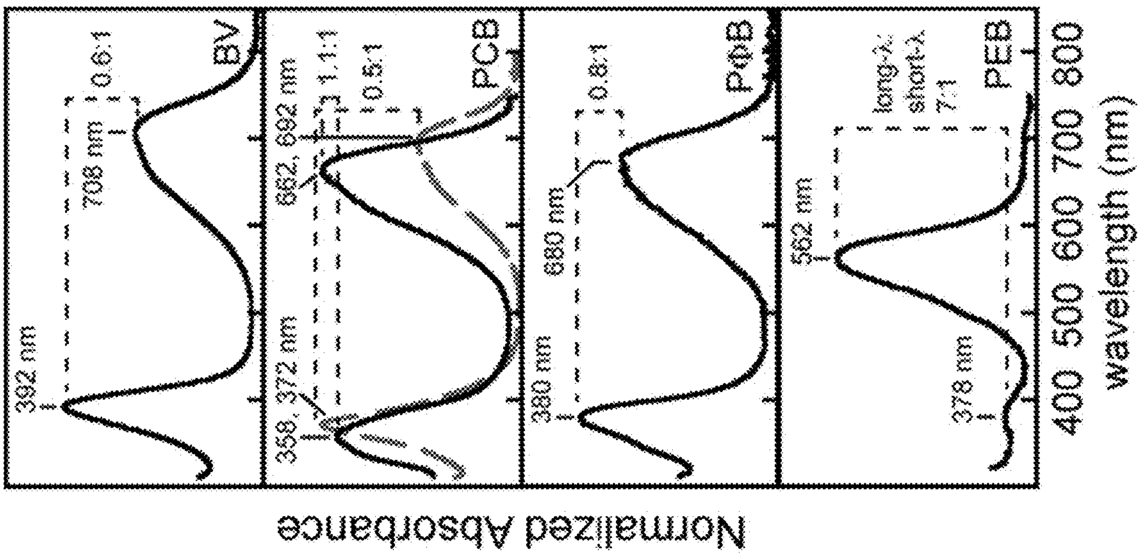
FIG. 9B. Assignment of biliprotein chromophore structure using acidic denaturation. Examples of denatured spectra are shown for the indicated bilins under denaturing conditions (corresponding to the lower left-hand corner in panel A). Peak wavelengths for the two chromophore bands are shown for each, along with the ratio of intensities for the two bands. Where the 15,16-double bond is present, bilin spectra are for the 15Z configuration. Covalent adducts are in solid black, and noncovalent species (PCB only) are in dashed grey.
Figure 9A:
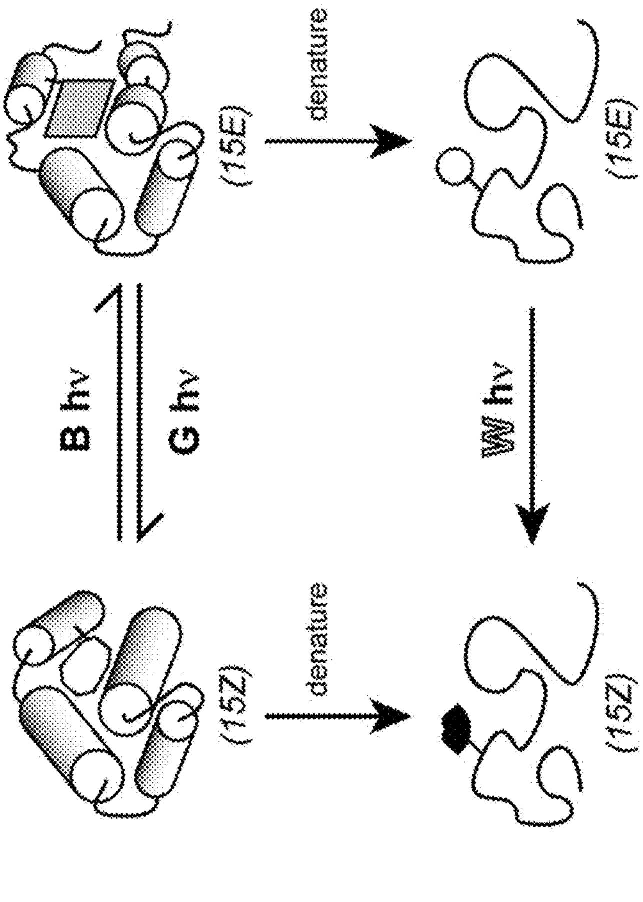
FIG. 9A. Assignment of biliprotein chromophore structure using acidic denaturation. Assignment of biliprotein chromophore structure using acidic denaturation. A cartoon schematic shows effects of denaturation on protein structure and reversibility of photoconversion. Denatured 15E bilin can be photoconverted to the 15Z configuration by white light in the absence of protein structure.

The far-red-absorbing states of these newly described CBCRs exhibited remarkable red shifts relative to previously known CBCRs (ca. 650-710 nm)[17, 42, 46, 48, 49, 51-53]. Therefore, an acid denaturation assay[73-77] was used to examine chromophore structure in far-red CBCRs. In this assay (FIG. 9A), samples in either photostate are denatured by dilution into concentrated guanidinium chloride. In the absence of native protein structure, 15E bilins can be unidirectionally photoconverted to the 15Z configuration by white light, allowing assignment of the chemical configuration of the photostates. Different bilins have characteristic spectra under denaturing conditions, with different peak wavelengths and with different relative intensities for the long- and short-wavelength chromophore absorption bands in the ultraviolet to visible spectrum (FIG. 9B). Although it is possible for labile structural changes to be lost upon denaturation, this assay can provide tentative identification of bilin species. [45, 47, 73]

Figure 8F:
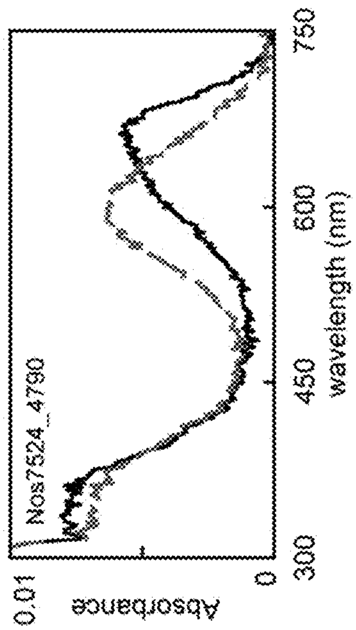
FIG. 8F. Characterization of additional CBCRs. Absorption spectra are shown for Nos7524_4790 in the red-absorbing state after dilution into acidic guanidinium chloride. Spectra are shown before (dashed grey) and after (solid black) illumination with white light.
Figures 10A, 10B, 10C, 10D:
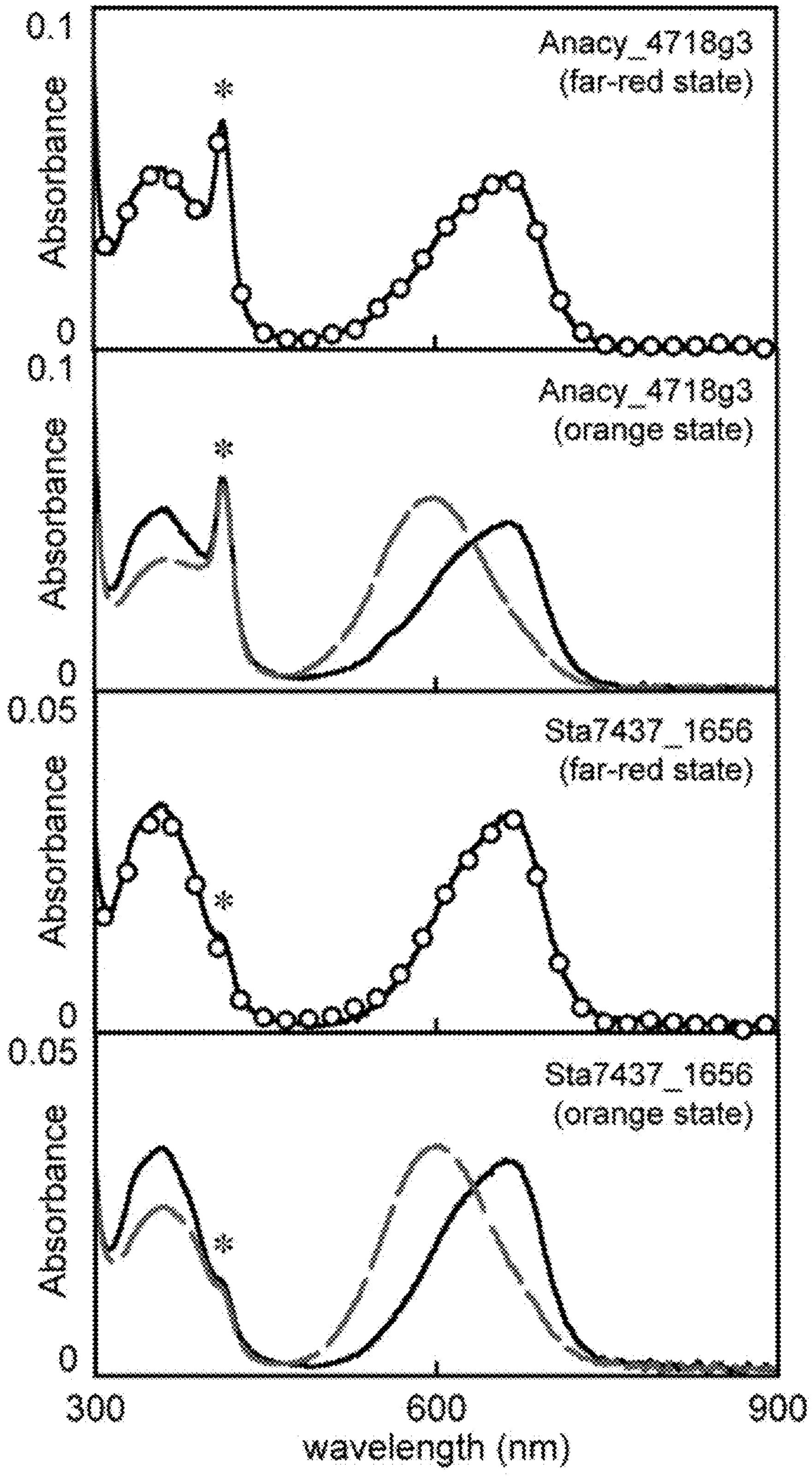
FIG. 10A. Assignment of chemical configuration in far-red CBCRs. Absorption spectra are shown for Anacy_4718g3 in the far-red-absorbing state after dilution into acidic guanidinium chloride. Spectra are shown before (circles) and after (solid black trace) illumination with white light. Asterisk, porphyrin contaminant.
FIG. 10B. Assignment of chemical configuration in far-red CBCRs. Absorption spectra are shown for Anacy_4718g3 in the orange-absorbing state using the same assay. Spectra are shown before (dashed gray trace) and after (solid black trace) illumination with white light. Asterisk, porphyrin contaminant.
FIG. 10C. Assignment of chemical configuration in far-red CBCRs. Absorption spectra are shown for Sta7437_1656 in the far-red-absorbing state using the same assay. Spectra are shown before (circles) and after (solid black trace) illumination with white light. Asterisk, porphyrin contaminant.
FIG. 10D. Assignment of chemical configuration in far-red CBCRs. Absorption spectra are shown for Sta7437_1656 in the red-absorbing state using the same assay. Spectra are shown before (dashed gray trace) and after (solid black trace) illumination with white light. Asterisk, porphyrin contaminant.
Figure 11A:
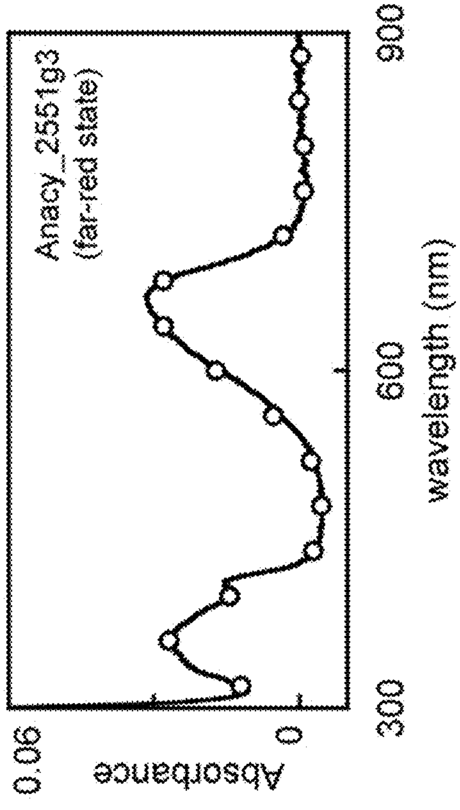
FIG. 11A. Characterization of far-red CBCRs under denaturing conditions. Absorption spectra are shown for Anacy_2551g3 in the far-red-absorbing photostate after acid denaturation before (circles) and after (solid black trace) 1 min illumination with white light.
Figure 11B:
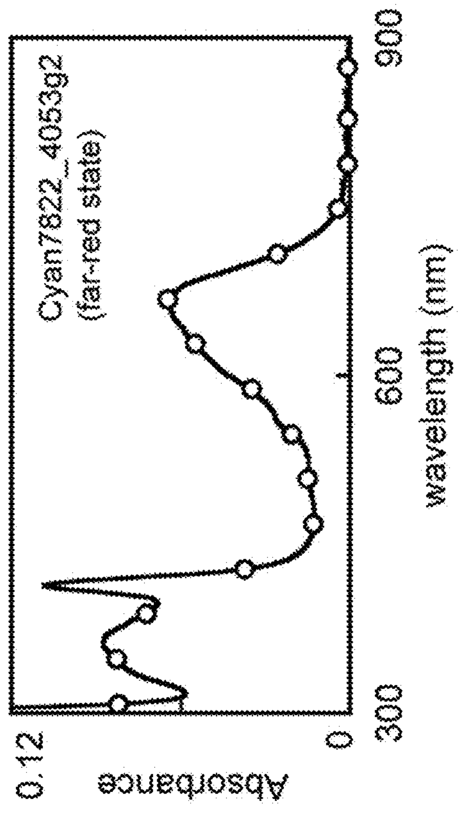
FIG. 11B. Characterization of far-red CBCRs under denaturing conditions. Absorption spectra are shown for Cyan7822_4053g2 in the far-red-absorbing photostate after acid denaturation before (circles) and after (solid black trace) 1 min illumination with white light.
Figure 11C:
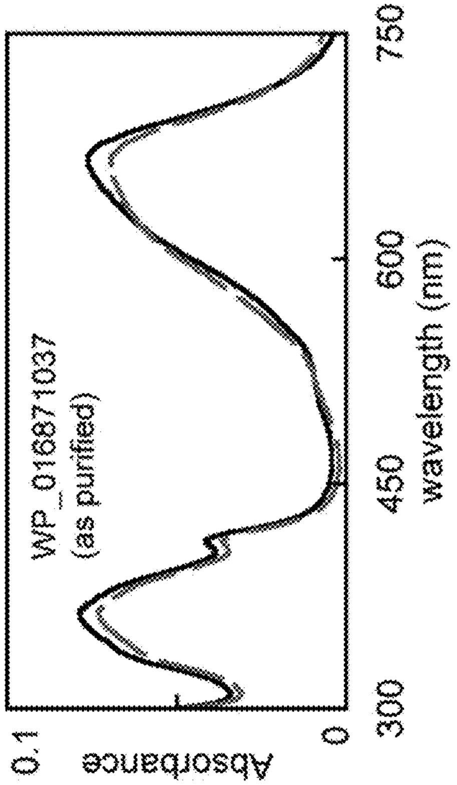
FIG. 11C. Characterization of far-red CBCRs under denaturing conditions. A detail view is shown for WP_016871037 as purified after acid denaturation before (dashed grey trace) and after (solid black trace) 1 min illumination with white light.
Figure 11D:
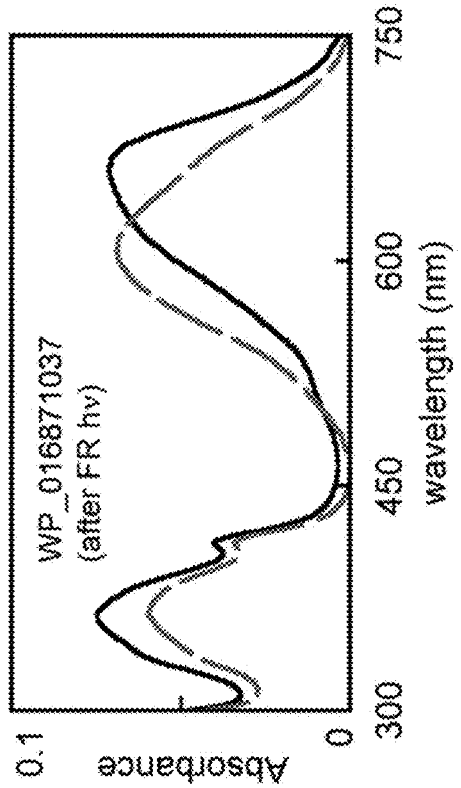
FIG. 11D. Characterization of far-red CBCRs under denaturing conditions. A detail view is shown for WP_016871037 after far-red illumination and subsequent acid denaturation before (dashed grey trace) and after (solid black trace) 1 min illumination with white light.

Acid denaturation of Anacy_4718g3 resulted in the expected spectral changes and also revealed the presence of a porphyrin side population. Photoconversion of denatured samples established the far-red-absorbing state as having the 15Z configuration and the orange-absorbing state as having the 15E configuration (FIG. 10A-B). Denaturation analysis of Anacy_2551g3 and Cyan7822_4053g2 confirmed that the far-red-absorbing states of all three far-red/orange CBCRs adopted the 15Z configuration (FIG. 11A-B), albeit with varying amounts of porphyrin. The far-red/red CBCR Sta7437_1656 exhibited a 15Z far-red-absorbing photostate and 15E red-absorbing photoproduct, with notably less contaminating porphyrin (FIG. 10C-D). Nos7524_4790 exhibited a similar red-absorbing 15E photoproduct, in this case with a blue-absorbing 15Z dark state (FIG. 8F). As purified, WP_016871037 exhibited both far-red- and red-absorbing species, confirmed as a mix of 15Z and 15E bilin by acid denaturation (FIG. 11C). Photoconversion of this protein with far-red light resulted in incomplete formation of 15E bilin (FIG. 11D), assigning the red-absorbing state as the 15E photoproduct. The presence of 15E photoproduct in this preparation arose due to the combination of light exposure during purification and poor reverse photoconversion in this protein (see above). Estimation of the extent of photoconversion in both samples by comparison to reference spectra[17] allowed for the subtraction of a scaled photoproduct spectrum from the initial spectrum, resulting in a spectrum similar to that of Sta7437_1656 in the far-red-absorbing photostate (FIG. 6E). These results demonstrate that far-red CBCRs exhibit a conserved 15Z photostate with peak absorption in the far-red and with blue-shifted 15E photoproducts absorbing orange or red light. Far-red CBCRs thus are reversed relative to phytochromes, in which the red-absorbing 15Z Pr state is blue-shifted relative to the far-red-absorbing 15E $P_{fr}$ state. [34, 78, 79]

Figure 12A:
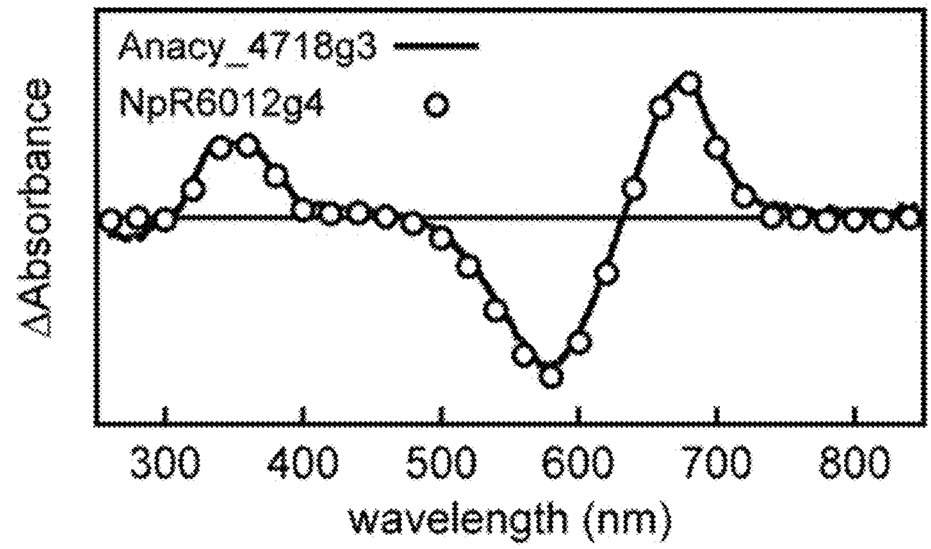
FIG. 12A. The far-red-absorbing state contains a covalent PCB adduct. The photochemical difference spectrum for denatured Anacy_4718g3 from FIG. 4B (black line) is compared to that of NpR6012g4 (circles). [107]
Figure 12B:
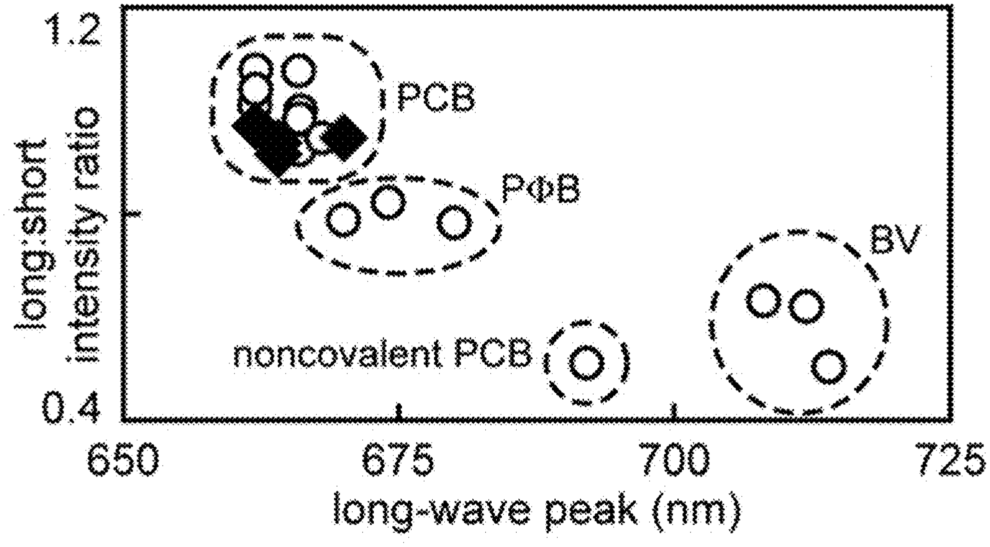
FIG. 12B. The far-red-absorbing state contains a covalent PCB adduct. The 15Z peak wavelength and intensity ratio of the long-wavelength and short-wavelength (Soret) chromophore absorption bands for denatured far-red CBCRs in the 15Z configuration (black diamonds) are compared to those of CBCRs and phytochromes in the same configuration containing the indicated chromophores (circles).[53]

The photochemical difference spectrum for denatured Anacy_4718g3 was superimposable on that of the red/green CBCR NpR6012g4 (FIG. 12A). Recent characterization of NpR6012g4 using solution NMR spectroscopy confirmed the presence of a covalent PCB adduct in both photostates, with intramolecular nuclear Overhauser effect cross-peaks confirming photoisomerization at the 15,16-double bond. [39, 80] The peak wavelength and relative bilin band intensities of denatured 15Z Anacy_4718g3 in the far-red state were also consistent with a 15Z covalent PCB adduct (FIG. 12B). Therefore, both photostates of Anacy_4718g3 contain a covalent PCB adduct, despite the fact that 15Z PCB adducts typically absorb at 530-670 nm rather than 720-740 nm.[17, 22, 34, 42, 44, 46, 51, 52, 55, 81-83]

Example 3. Chromophore Structure in the Far-Red State

Figure 14A:
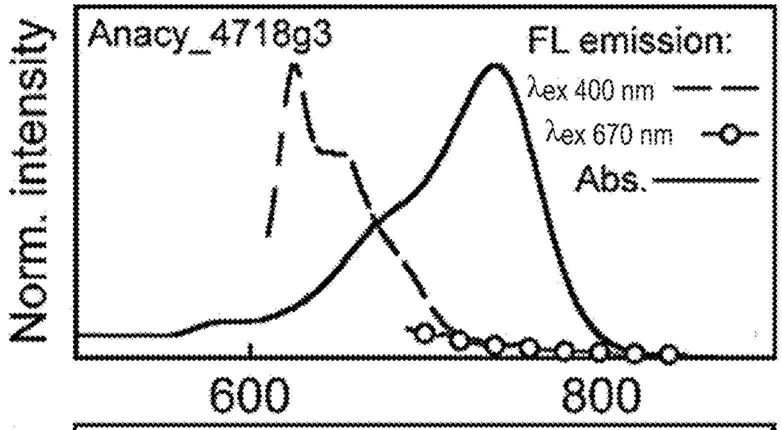
FIG. 14A. Characterization of far-red CBCRs using fluorescence spectroscopy. Absorption (solid black trace) and emission spectra are shown for 15Z Anacy_4718g3. The emission spectrum with 400 nm excitation (dashed dark grey) exhibits a sharp peak at 626 nm with decay at longer wavelengths, consistent with fluorescence from contaminating porphyrin. The emission spectrum with 670 nm excitation (solid grey trace with circles) exhibits similar decay, without additional peaks.
Figure 14B:
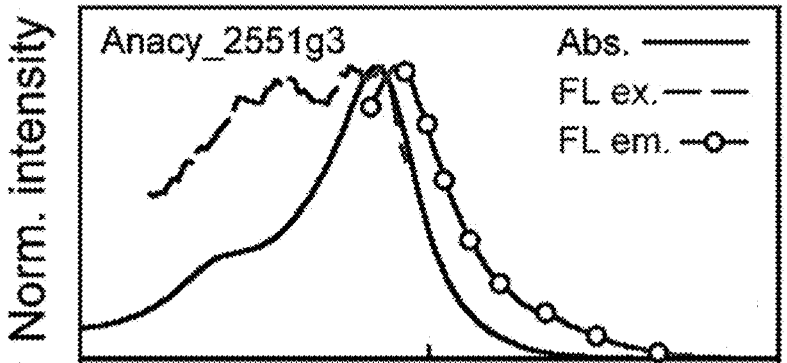
FIG. 14B. Characterization of far-red CBCRs using fluorescence spectroscopy. Absorption (solid black trace), excitation (dashed grey trace, 755 nm emission), and emission (solid grey trace with circles, 710 nm excitation) spectra are shown for Anacy_2551g3 in the 15Z far-red-absorbing state.
Figure 14C:
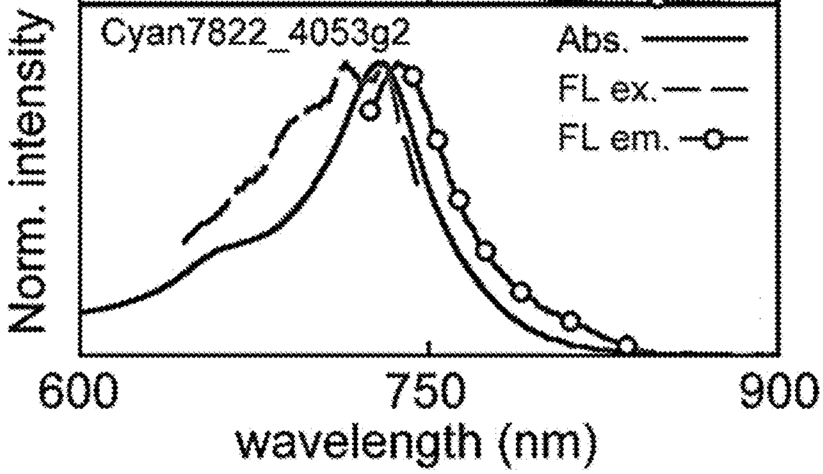
FIG. 14C. Characterization of far-red CBCRs using fluorescence spectroscopy. Absorption (solid black trace), excitation (dashed grey trace, 755 nm emission), and emission (solid grey trace with circles, 715 nm excitation) spectra are shown for Cyan7822_4053g2 in the 15Z far-red-absorbing state.
Figure 14D:
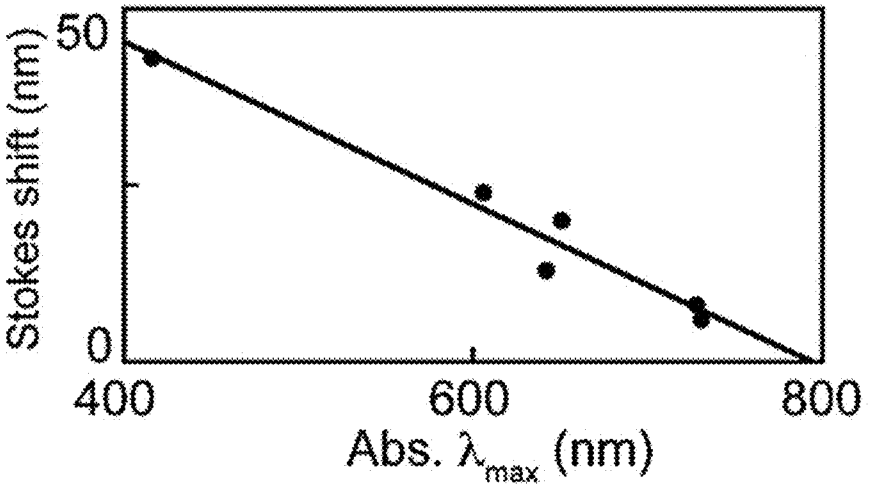
FIG. 14D. Characterization of far-red CBCRs using fluorescence spectroscopy. The Stokes shift for fluorescence emission is plotted versus peak wavelength for various CBCRs. Data were fit by linear regression ($r^2$=0.96).
Figure 15A:
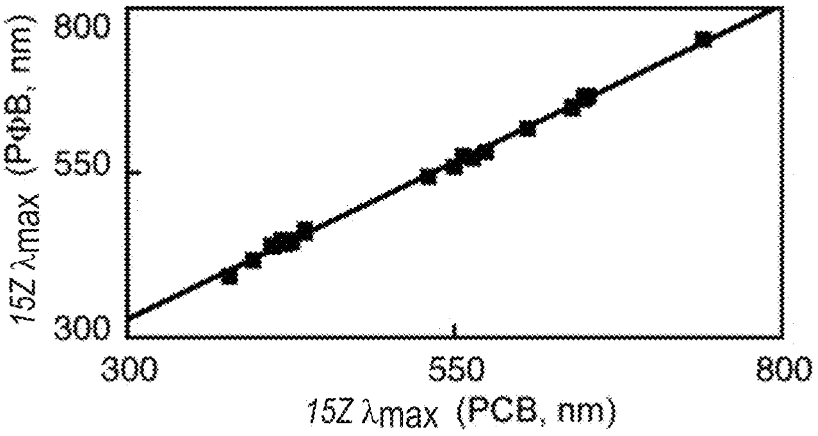
FIG. 15A. Correlations between CBCR spectral properties. Native 15Z peak wavelengths for PΦB adducts are plotted versus the equivalent PCB adducts for various CBCRs. Data were fit using linear regression ($r^2$=0.998).
Figure 15B:
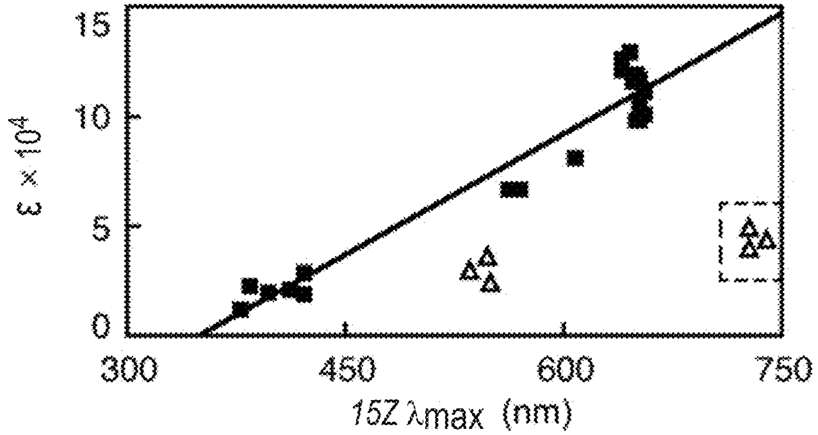
FIG. 15B. Correlations between CBCR spectral properties. Extinction coefficients are plotted versus peak wavelengths for various CBCRs in the 15Z photostate. Most CBCRs follow the same general trend (black squares; data fit by linear regression with $r^2$=0.93). Far-red CBCRs (dashed box), green/red CBCRs,[44] and green/blue CBCRs [54] do not follow this trend and are omitted from the regression analysis (triangles). Far-red CBCRs are boxed.

Next, Anacy_4718g3 was characterized after co-expression with other bilins (FIG. 1). BV did not bind efficiently, but Anacy_4718g3 adducts with phytochromobilin (PΦB) and phycoerythrobilin (PEB) were obtained (FIG. 13A). Anacy_4718g3-PΦB exhibited a red shift of the far-red-absorbing state to 752 nm relative to Anacy_4718g3-PCB, but photoconversion with far-red light resulted in formation of a photoproduct having similar photoproduct effect peak absorption to that of Anacy_4718g3-PCB (FIGS. 13B-C & Table 2). Denaturation analysis confirmed the presence of PΦB (FIG. 14D). The 18-ethyl moiety of PCB is instead an 18-vinyl in PΦB (FIG. 1), providing one extra double bond in the conjugated π-electron system of PΦB. PΦB adducts of biliproteins are thus red-shifted relative to PCB adducts. [22, 47, 51, 81, 84] Indeed, the red shift observed for Anacy_4718g3-PΦB relative to Anacy_4718g3-PCB is consistent with those observed for a broad range of CBCRs upon introduction of the 18-vinyl moiety (FIG. 15A). By contrast, the extinction coefficient of the PCB adduct did not follow the general correlation between peak wavelength and extinction coefficient observed for PCB and phycoviolobilin adducts of most other CBCRs (FIG. 15B & Table 4).

TABLE 4

| Estimated extinction coefficients for far-red CBCRs in this study. | |
|---|---|
| Protein | 15Z ε ($M^{-1}$ $cm^{-1}$) |
| Anacy_4718g3 (intein-CBD) | 40,800 |
| Anacy_4718g3 (His tag) | 44,400 |
| Anacy_2551g3 (His tag) | 49,200 |
| Cyan7822_4053g2 (intein-CBD) | 39,900 |
| Sta7437_1656 (His tag) | 43,600 |

In Table 4, all values are for PCB adducts. Comparison of values for different Anacy_4718g3 constructs suggests an error range of ±10%. WP_016871037 was excluded because a native 15Z spectrum could not be obtained in the absence of 15E bilin.

Figure 15C:
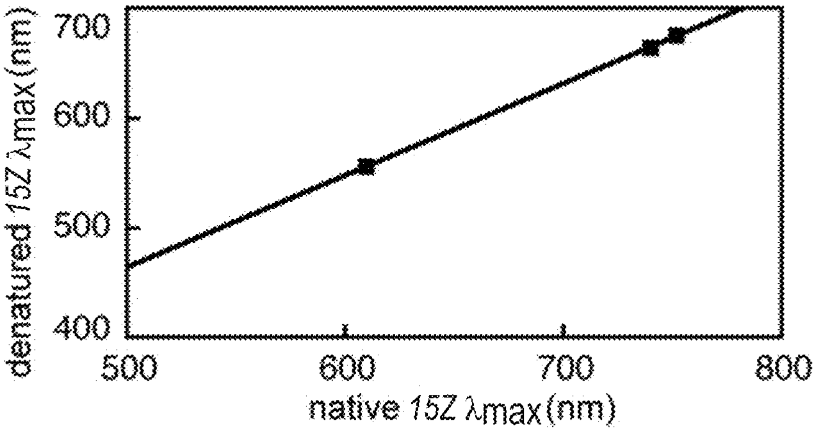
FIG. 15C. Correlations between CBCR spectral properties. Native and denatured peak wavelengths are plotted for Anacy_4718g3 containing PCB, PΦB, and PEB in the dark-adapted state (15Z for photoactive chromophores). Data were fit by linear regression ($r^2$>0.999).

PEB differs from PCB and PΦB in having a saturated 15,16-bond that results in loss of conjugation from the bilin D-ring (FIG. 1). PEB adducts of phytochromes are therefore blue-shifted and cannot undergo photoconversion.[20] Anacy_4718g3-PEB exhibited peak absorption at 610 nm (FIG. 13A), blue-shifted relative to the PCB adduct, and was also photoinactive (FIG. 13C). The absorption maximum of Anacy4718g3-PEB is red-shifted ca. 50 nm relative to PEB adducts of other CBCRs (550-560 nm),[50] but denaturation analysis confirmed the presence of PEB (FIG. 13E). A linear relationship was observed between the peak wavelengths of native and denatured Anacy_4718g3 assembled with PEB, PCB, or PΦB chromophores for the 15Z configuration of PCB and PΦB (FIG. 15C). This correlation implies that spectral tuning of all three chromophores by Anacy_4718g3 is comparable, despite the lack of a conjugated D-ring in PEB. Therefore, these results establish the D-ring as the site of primary photochemistry and the A-, B-, and/or C-rings as the site of the pronounced red shift induced by Anacy_4718g3. Spectral tuning and photoconversion of the far-red-absorbing photostate thus occur at different locations within the bilin chromophore.

Example 4. Fluorescence Properties of Far-Red/Orange CBCRs

The peak absorption observed for far-red CBCRs is well into the far-red/near-IR window of maximum penetrance in animal tissues.[31] The only biliproteins known to absorb at longer wavelengths are BV-containing bacteriophytochromes in the 15E $P_{fr}$ state.[79] Unfortunately, known phytochromes exhibit little to no fluorescence from the $P_{fr}$ state, with extremely short-lived excited states.[85-87] The 15Z far-red states of these newly characterized CBCRs might therefore exhibit higher near-IR fluorescence, because the bilin chromophore is in the same 15Z configuration found in phytochromes engineered for higher fluorescence quantum yield.[21-24, 88] The far-red/orange CBCRs were the focus of subsequent studies because the two photostates in such proteins have greater spectral separation.

Figure 16A:
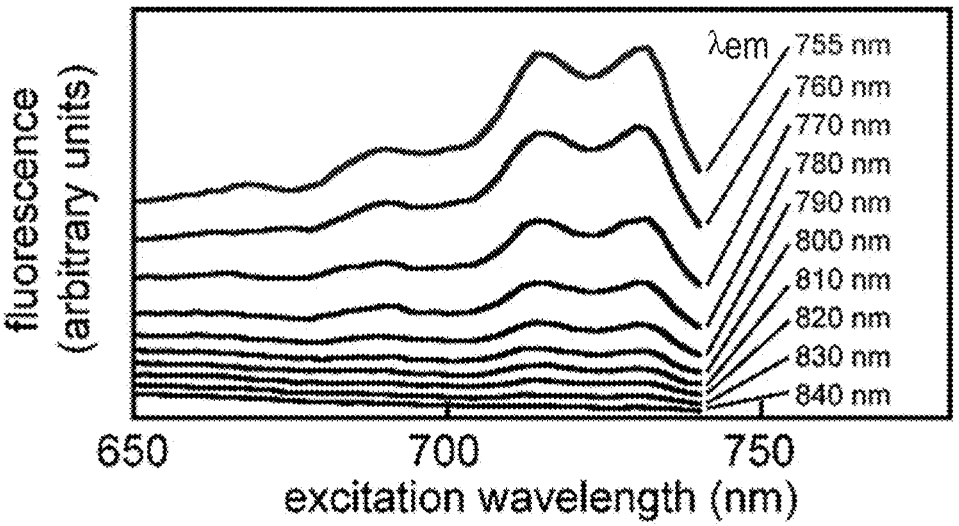
FIG. 16A. Characterization of Anacy_2551g3 using fluorescence spectroscopy. Excitation scans were performed at the indicated emission wavelengths.
Figure 16B:
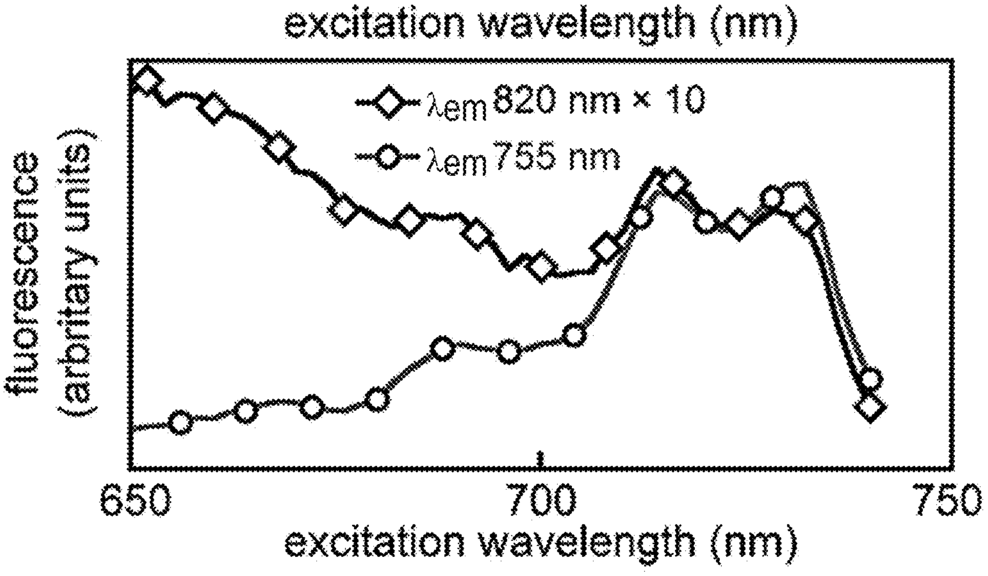
FIG. 16B. Characterization of Anacy_2551g3 using fluorescence spectroscopy. Excitation scans at 755 nm (grey trace with circles) and 820 nm (black trace with diamonds) from FIG. 16A are shown in detail, with the 820 nm trace magnified 10-fold.
Figure 16C:
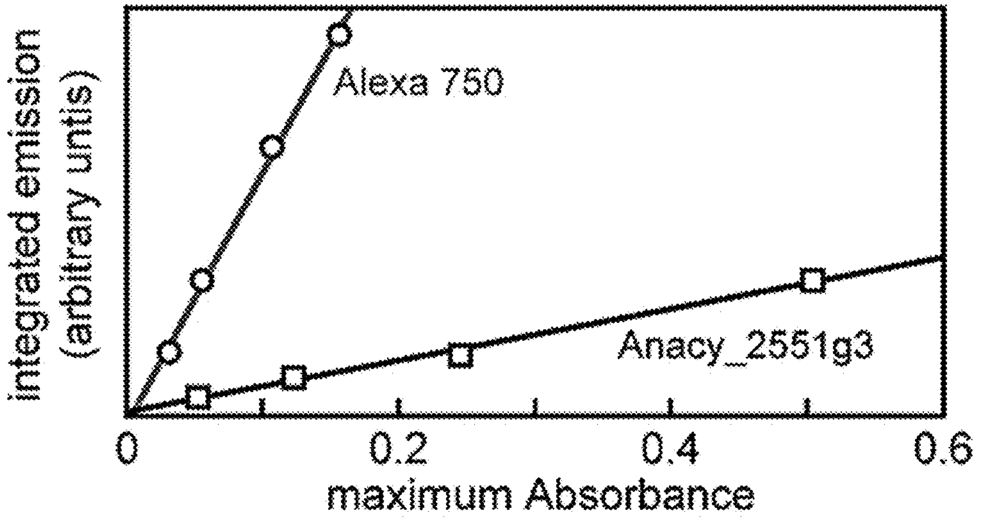
FIG. 16C. Characterization of Anacy_2551g3 using fluorescence spectroscopy. A plot of integrated fluorescence emission versus peak absorbance is shown for dilution series of Alexa750 dye (grey trace with circles) and Anacy_2551g3 (black trace with squares). The relative slopes and known quantum yield of Alexa 750 imply a fluorescence quantum yield of 0.012 for Anacy_2551g3.

All three far-red/orange CBCRs were characterized by fluorescence spectroscopy. These measurements were complicated by the presence of porphyrin (FIG. 10A, asterisk), and fluorescence from the far-red state of Anacy_4718g3 could not be detected against this background (FIG. 14A). Far-red and near-infrared fluorescence could be detected for both Anacy_2551g3 and Cyan7822_4053g2 (FIG. 14B-C). Interestingly, the excitation spectrum of Anacy_2551g3 contained multiple peaks (FIG. 16A) that were ascribed to heterogeneity of the far-red state. Fluorescence emission of Anacy_2551g3 extended well into the near-IR (FIG. 16A-B). The observed Stokes shift for the far-red/near-IR state was small, with fluorescence emission peaking at approximately 740 nm for both Anacy_2551g3 and Cyan7822_4053g2. This Stokes shift followed the general trend seen for other CBCRs (FIG. 14D). The fluorescence quantum yield for Anacy_2551g3 was estimated at 1.2% using the ratio method,[22] plotting integrated emission versus absorbance for a dilution series with Alexa 750 as standard (FIG. 16C). These results establish far-red CBCRs as fluorescent, with some examples exhibiting modest near-IR fluorescence detectable at very long wavelengths.

The work described herein reveals two conserved clusters of far-red CBCRs. Three such proteins belong to the first cluster and exhibited similar far-red/orange photocycles. Two of these proteins also exhibited detectable near-infrared fluorescence from the far-red-absorbing state. Two other proteins belong to the second cluster and exhibited similar far-red/red photocycles. Denaturation analysis demonstrated that far-red sensing at 728-740 nm utilized a covalent 15Z PCB chromophore similar to that found in other CBCRs and in cyanobacterial and algal phytochromes.[42, 46, 47, 51, 54, 81, 82, 89] Remarkably, this indicates that the same chromophore precursor provides CBCRs with the ability to detect light ranging from 330 to 740 nm through diverse tuning mechanisms. CBCR tuning mechanisms characterized to date provide strategies for blue shifting peak absorption relative to a protonated, cationic bilin 7C system.[17, 43, 47, 71, 73] The extreme red shift reported here therefore implies the existence of a previously unrecognized tuning mechanism.

Figure 17:
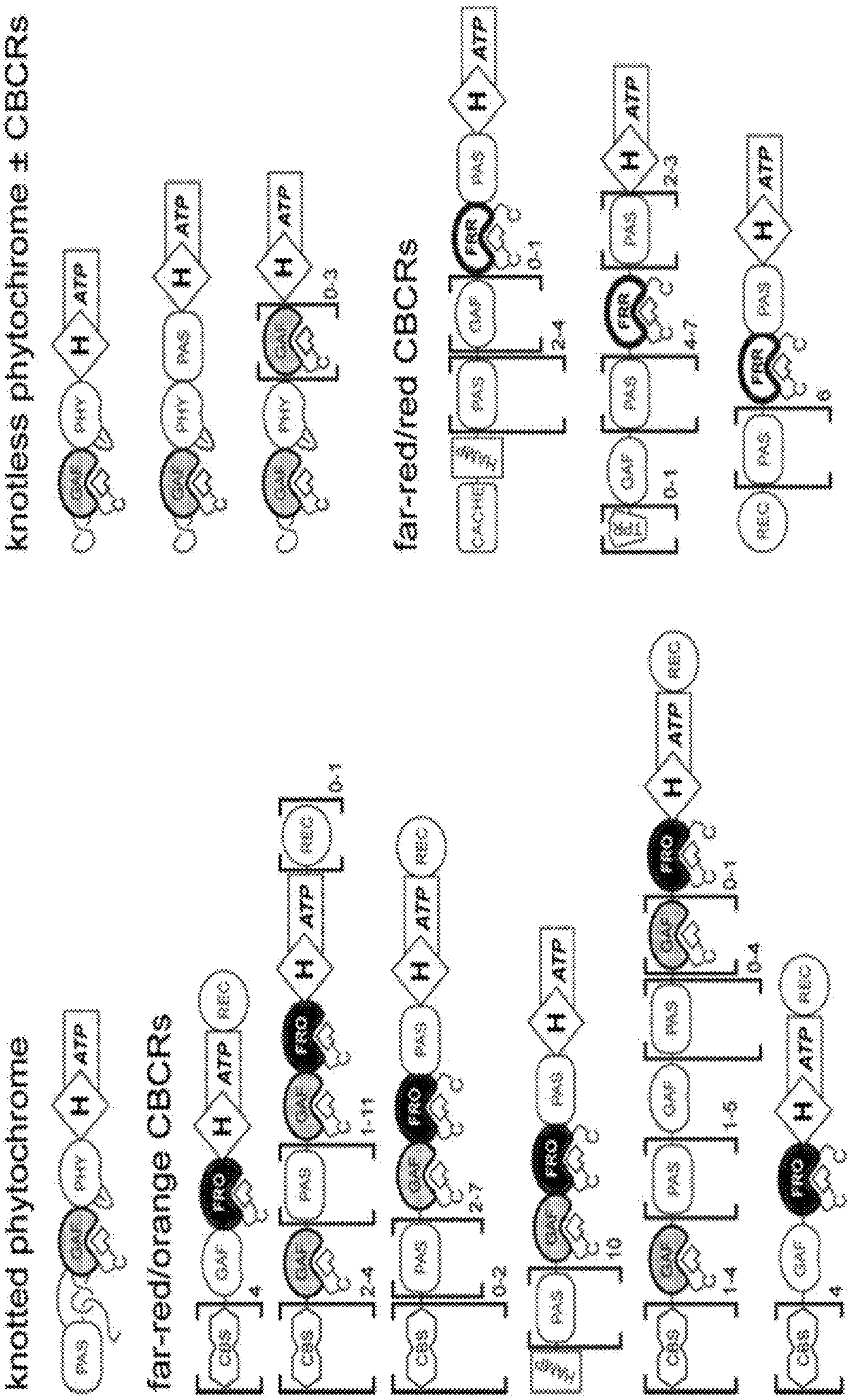
FIG. 17. Domain architectures of cyanobacterial far-red-responsive histidine kinases. Jellybean domain-architecture cartoons are shown for the three known classes of cyanobacterial far-red histidine kinases: knotted phytochromes, knotless phytochromes, and two classes of far-red CBCRs. [93,108-110] For variable or repeated domains in far-red CBCRs, the range present for a given type of architecture is indicated by subscript.
Figure 17:

Although there are parallels between far-red CBCRs and the far-red-absorbing $P_{fr}$ states of phytochromes, there are also striking differences. It is therefore unclear whether the same tuning mechanisms are responsible for far-red peak absorption in phytochromes and CBCRs. Far-red CBCRs absorb far-red light in the 15Z chromophore configuration rather than the 15E configuration of the phytochrome $P_{fr}$ state.[90, 91] Moreover, most phytochromes require both the bilin-binding GAF domain and the adjacent PHY domain for $P_{fr}$ formation,[22, 32, 92, 93] whereas far-red CBCRs lack PHY domains altogether (FIG. 17). Previous studies indicate that different phytochromes generate the $P_{fr}$ state in different ways,[65] and no model explaining far-red absorption of PCB or PΦB in the phytochrome $P_{fr}$ state is generally accepted at present.[94] A variety of models for the 15Z far-red-absorbing state of these newly described CBCRs should therefore be considered.

Denaturation analysis confirms that far-red CBCRs employ 15,16-photoisomerization as in other CBCRs,[37, 39, 58, 59] establishing D-ring rotation as the site of photochemistry. However, the photochemically inactive PEB adduct of Anacy4718g3 exhibits a red-shifted 15Z state comparable to those seen for the other two bilin adducts (FIG. 15C). The D-ring in PEB is not conjugated with the rest of the chromophore (FIG. 1), so the red shift of the PEB adduct must be due to protein-dependent perturbations of the conjugated ABC-ring system. By contrast, the red shift of the PΦB adduct of Anacy4718g3 relative to that of its PCB adduct is comparable to those seen in other CBCRs (FIG. 15A). Therefore, the tuning mechanism generating far-red absorption in Anacy_4718g3 and related proteins is independent of conjugation between the C- and D-ring.

Far-red CBCRs could use a tuning mechanism that does not occur in phytochromes. For example, the far-red state could arise due to formation of the lactim tautomer at the A-ring, consistent with the known red shift of O-alkylated bilins and inconsistent with the known protonation state of $P_{fr}$ phytochrome.[90, 95, 96] Anionic bilin 7C systems also exhibit substantial red shifts[97, 98] but are again incompatible with the known $P_{fr}$ protonation state. Without wishing to be bound by any particularly theory, it is believed that an anionic bilin could be stabilized by a bound metal ion, but the presence of such a cation in far-red CBCRs has not yet been directly observed. The presence of multiple conserved Trp residues in far-red/orange CBCRs (FIG. 3) is consistent with the role of Trp residues in red-shifting phycobiliprotein chromophores,[99] although the red shift observed in phycobiliproteins is much smaller than that observed in this work. The presence of Trp residues proximal to the chromophore also raises the possibility of a previously unknown charge-transfer process generating a labile species not observed in the denaturation assay, a situation somewhat analogous to charge-transfer processes in the blue light receptor cryptochrome.[100, 101] Any of these mechanisms could explain the anomalously low extinction coefficients observed for far-red states described in this study (FIG. 15B), because the resulting chromophore structures would chemically differ from the protonated PCB and phycoviolobilin chromophores that establish the observed trend. Consistent with this point, the other exception for the general correlation between extinction coefficient and peak wavelength observed in 15Z PCB adducts is green-absorbing states such as that of RcaE, which is known to have a deprotonated bilin ring system.[17] Elucidating the basis for far-red sensing in these proteins will thus require further studies.

The far-red/orange and far-red/red CBCR photocycles described here imply that members of the far-red/orange cluster have a distinct mechanism for spectral tuning of the orange-absorbing photoproduct. The orange-absorbing photoproducts observed in Anacy_4718g3, Anacy_2551g3, and Cyan7822_4053g2 are very similar, exhibiting a slight blue shift relative to denatured 15E PCB adducts and a characteristic lineshape (FIG. 6). Moreover, no red shift is observed in the Anacy_4718g3-PΦB photoproduct relative to the Anacy_4718g3-PCB photoproduct (Table 2). The absence of such a PΦB blue shift has also been observed in the teal-DXCF CBCR lineage, in which the photoproduct D-ring is trapped in a twisted geometry reducing conjugation to yield a blue-shifted chromophore with a similar lineshape.[71]

Figure 15D:
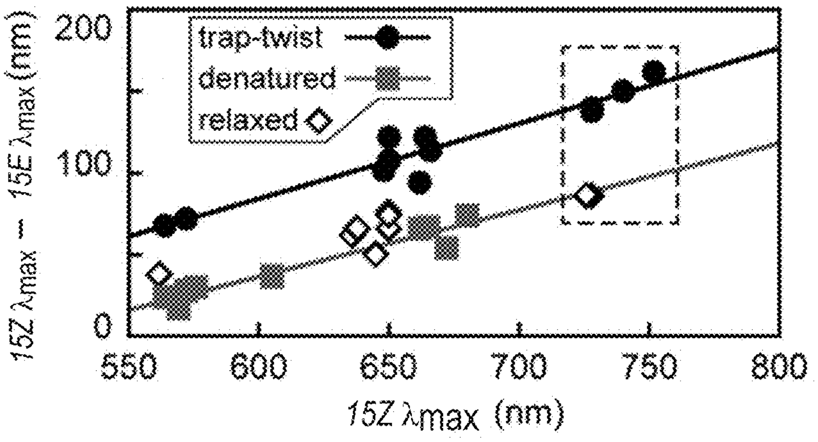
FIG. 15D. Correlations between CBCR spectral properties. Photoconversion-induced blue shift was plotted versus 15Z peak wavelength for a range of CBCRs exhibiting trapped-twist, blue-shifted photoproducts with no second linkages in either photostate[45, 51, 53] (black circles). A linear correlation was observed (solid black trace; $r^2$=0.92). These CBCRs were distinct from denatured samples (grey squares; linear fit, solid grey trace; $r^2$=0.93) and CBCRs lacking key residues for trapped-twist photoproduct tuning (diamonds).[53, 71] Far-red CBCRs are boxed.

It is thus possible that a similar trapped-twist mechanism acts to tune the orange-absorbing photoproduct. To examine this hypothesis, 15E photoproduct blue shift was plotted versus 15Z peak wavelength for a range of trapped-twist CBCRs, for a range of CBCRs lacking residues required for trapped-twist photoproducts and hence having 'relaxed' photoproducts, and for denatured samples.[51, 53, 71] CBCRs with trapped-twist photoproducts exhibited a linear relationship between these spectral parameters (FIG. 15D), and far-red/orange CBCRs followed this correlation. Relaxed CBCRs were more similar to denatured samples, and both far-red/red CBCRs examined in this study followed the relaxed trend (FIG. 15D). This analysis implicates some type of trapped-twist tuning in the orange-absorbing photoproducts of far-red CBCRs. Interestingly, comparison of the Asp-motifs of far-red/red CBCRs to those of far-red/orange CBCRs reveals that far-red/red CBCRs lack one of the Trp residues found in far-red/orange CBCRs (FIG. 3). This Trp residue may thus constrain chromophore motions during photoconversion. Aromatic residues are similarly implicated in spectral tuning in other CBCR lineages,[53, 71, 102] and recent work also implicates Trp residues in spectral tuning of phycobiliproteins.[99] It is thus possible that a similar effect provides spectral tuning in far-red/orange CBCRs.

The work described herein also implicates additional unknown far-red to near-IR photobiology in cyanobacteria. The newly recognized far-red CBCRs do not correlate with known far-red photobiological responses. For example, the filamentous cyanobacterium *Leptolyngbya* sp. JSC-1 is known to exhibit far-red light-induced photoacclimation (FaRLiP), but this organism lacks a far-red CBCR (Tables 1 and 3) and FaRLiP is controlled by a different photosensor.[93, 103-105] The more recently described low-light-induced photoacclimation (LoLiP) response also does not correlate with FR CBCRs, as shown by the presence of a far-red CBCR (Table 1) but absence of LoLiP in *Leptolyngbya* sp. PCC 7104.[104] Far-red CBCRs are present in both unicellular and filamentous cyanobacteria and are associated with multiple histidine kinase lineages and domain architectures (FIG. 2 & Tables 1 and 3). By contrast, the two known classes of CCA regulator are associated with coherent phylogenetic clusters in both the CBCR and histidine kinase trees (FIG. 2), and the RcaE cluster correlates well with the presence of type III CCA in the host organisms (Table 5). Far-red CBCRs are therefore likely to be associated with multiple physiological responses.

TABLE 5

CCA properties for cyanobacteria hosting RcaE-type CBCRs.

| cyanobacterium | green/red CBCR | CCA type |
|---|---|---|
| *Staniera cyanosphaera* PCC 7437 | Sta7437_2963 | III |
| *Synechococcus* sp. PCC 7336 | WP_017324438 (Syn7336_0672) | III |
| *Xenococcus* sp. PCC 7305 | X7305_GR (Xen7305DRAFT_00010580) | III |
| *Leptolyngbya* sp. JSC-1 | JSC1_30280 (CYJSC1_DRAFT_30280) | III |
| *Tolypothrix* sp. PCC 7601[2] | RcaE (fdiDRAFT24240) | III |
| *Synechococcus* sp. PCC 7335 | S7335_5042g1 (S7335_5042) | III |

In Table 5, strains hosting the RcaE cluster identified in FIG. 2 are reported where information about CCA is available. Both the protein tag used in FIG. 2 and the DOE-IMG locus tag are listed when they are different. Information about strains in the Pasteur Culture Collection (PCC) is taken from the PCC catalog, and information about *Leptolyngbya* sp. JSC-1 is taken from Gan & Bryant [104]. *Tolypothrix* sp. PCC 7601 in Table 5 is also known as *Fremyella diplosiphon.*

The far-red CBCRs characterized here can be used as fluorescent reporters, optical contrast agents, or synthetic biology reagents responding to far-red or near-infrared light. Far-red CBCRs exhibit a unique combination of far-red peak absorption and detectable near-infrared fluorescence not found in other phytochromes or CBCRs. These proteins thus hold great promise as fluorescent reporters and optical contrast agents in systems for which the far-red/near-IR window is critical for optimal performance. It should be possible to engineer far-red CBCRs with improved affinity for BV and/or higher fluorescence QY.[21, 23-25] It should also be possible to couple far-red CBCRs to alternative outputs for modulating various aspects of eukaryotic biology, as has been done for bacteriophytochromes.[29, 30] Far-red CBCRs thus extend a series of studies[40, 42, 45-49, 51-54, 106] establishing CBCRs as having the broadest light sensing range of known photoreceptor families. As modular light sensors ranging from ca. 330 nm to 750 nm, CBCRs span the full range of the electromagnetic spectrum amenable to oxygenic photosynthesis by cyanobacteria.

Example 5. Far-Red CBCR-Annexin Fusion Construct for In Vivo Detection of Apoptosis Apoptotic processes are studied in vivo by fusing the Anacy_2551g3 CBCR domain to annexin V, a well-established apoptotic reporter, using recombinant DNA technology. Annexin V binds to phosphatidylserine (PS), which is normally not present on the extracellular leaflet of the mammalian plasma membrane. Induction of apoptosis results in the loss of asymmetric lipid distribution and the appearance of extracellular PS. Fluorescent conjugates of annexin V are thus widely used as apoptotic markers in fluorescence microscopy and cell sorting, often being generated by derivatization with reagents such as fluorescein isothiocyanate (FITC). Application of FITC-annexin V to whole animals is more difficult, because fluorescein fluorescence is not in the window of optimal transmission for mammalian cells. The use of a far-red CBCR fused to annexin V alleviates this difficulty and also permits the use of annexin V markers in the presence of other fluorescent reagents that normally overlap with FITC fluorescence, such as green fluorescent protein (GFP).

Figure 20:
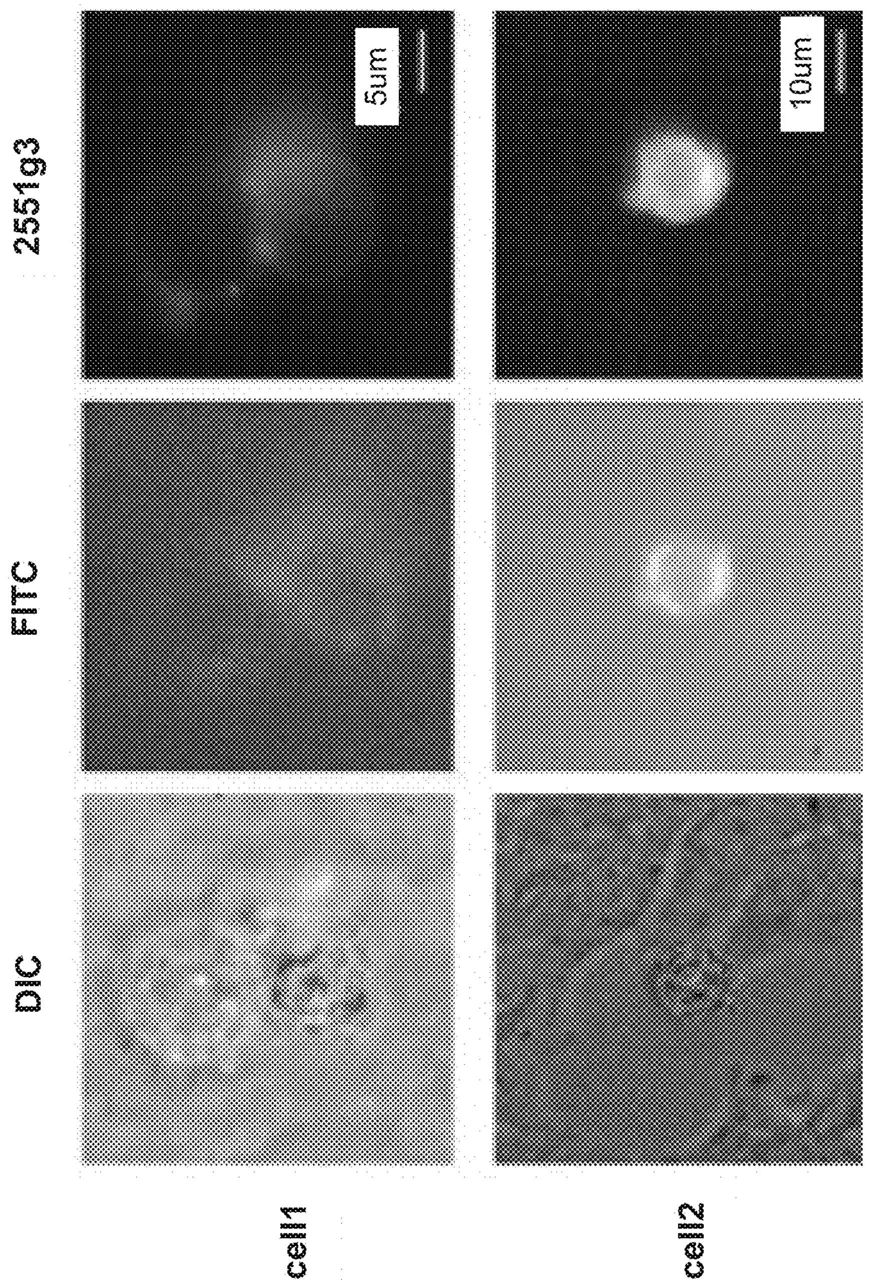
FIG. 20. Annexin-Anacy_2551g3 fluorescence imaging in HEK 293 cells.

DNA encoding Annexin V is procured from a commercially available pJM31 plasmid (Addgene) or by commercial gene synthesis. The annexin V sequence is then fused to the Anacy_2551g3 CBCR domain in either orientation (i.e., CBCR-annexin or annexin-CBCR) and the resulting fusion construct is purified after heterologous expression in *E. coli*. The fusion construct is then used as a reagent for imaging in tissue culture or whole animals. Examples of annexin-Anacy_2551g3 images of HEK cells are shown in FIG. 20 and discussed further in Example 6 below.

Example 6. Annexin-Anacy_2551g3 Fluorescence Imaging in HEK 293 Cells

In this example, an annexin-Anacy_2551g3 protein fusion construct was expressed and purified, and then the concentrated purified protein (25X) was used for imaging in HEK 293 cells.

HEK 293 cells were treated with camptothecin at a concentration of 5 μM for 4 hours to induce apoptosis. Then the cells were treated with 10 μL, 20 μL, or 30 μL of 25× stock protein fusion construct solution for 15 minutes. Cells were subsequently imaged with a 40× air objective, wide-field microscope (i.e. Zeiss observer) and excited with Xcite LED RDX (660-675 nm, filter set cy5.5). As a control, FITC-annexin was added for co-staining (i.e., added at 15 minutes post annexin-Anacy_2551g3 incubation). Representative images are shown in FIG. 20.

A GFP filter was usted to identify cells that were FITC-positive, and then imaging was performed using all three channels. The images in the top row (i.e. "cell1") are depicted using pseudo-color, while the images in the bottom row (i.e. "cell2") are depicted in original format. As a result of the apoptotic cells becoming detached, they were not entirely within the imaging focal plane, also demonstrating that the fluorescent signal was mostly localized at the cell surface.

Example 7. In Vivo Imaging in Phantom Mice Using Purified Anacy_2551g3

Figures 18A, 18B, 18C:
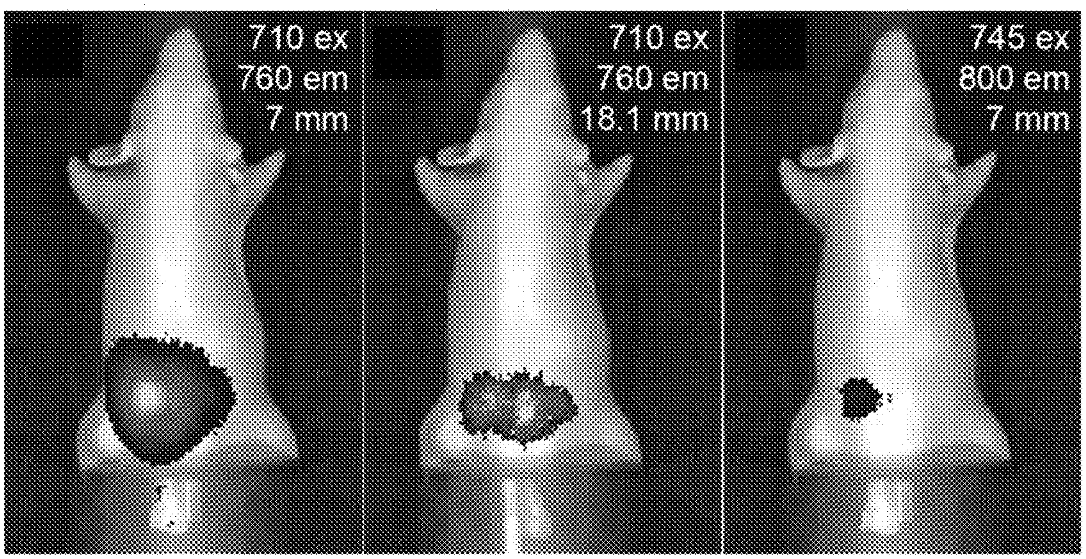
FIG. 18 A. Imaging Anacy_2551g3 in phantom mouse. Image was acquired at 7 mm depth with 710 nm excitation and 760 nm emission. A Perkin-Elmer IVIS system was used to acquire the image with purified Anacy_2551g3.
Figure 19C:
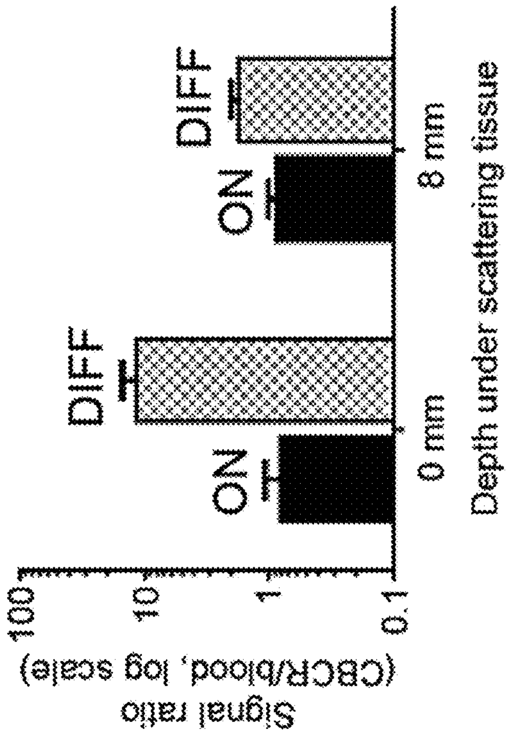
FIG. 19C. Characterization of purified Anacy_2551g3 phantom with PACT. The graph shows a comparison of the signal ratios quantified from the ON state images and the differential images (DIFF). Error bars represent standard deviations (n=4). The protein signal amplitude was normalized to 10 μM. The hemoglobin concentration was 2.3 mM.
Figure 19A:
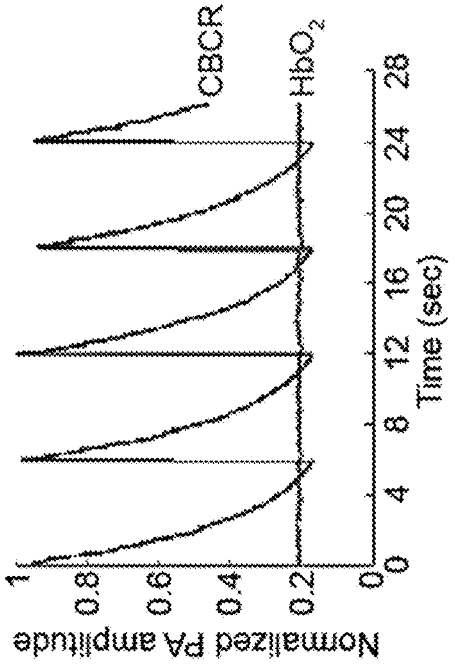
FIG. 19A. Characterization of purified Anacy_2551g3 phantom with PACT. PA signals of CBCR in clear medium with 728 nm illumination and 588 nm illumination during several switching cycles.
Figure 19B:
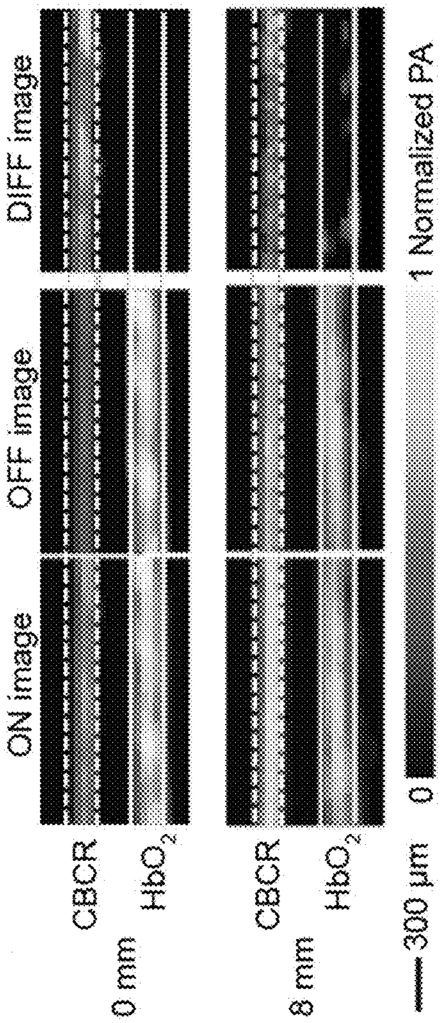
FIG. 19B. Characterization of purified Anacy_2551g3 phantom with PACT. PACT images of silicone tubes filled with purified protein solution in clear media (first row) and under 8 mm of chicken tissue (second row).

To demonstrate the utility of these new CBCRs for in vivo imaging techniques, purified Anacy_2551g3 was used in two systems that mimic real-world imaging modalities: fluorescence imaging in a widely used phantom mouse model (FIGS. 18A-18C) and photoacoustic (PA) imaging of silicone tubes mounted under chicken meat to mimic the scattering properties of animal tissue (FIGS. 19A-19C).

For the phantom mouse experiment, a commercial IVIS system (Perkin-Elmer) and its associated phantom mouse were used to demonstrate the potential of these proteins for fluorescence imaging in whole animals with off-the-shelf components. Using wavelengths of 710 nm for excitation and 760 nm for emission, Anacy_2551g3 could be detected at a depth of 18.1 mm in the phantom animal (FIG. 18B). Surprisingly, fluorescence could also be detected at a depth of 7 mm using wavelengths of 745 nm for excitation and 800 nm for emission (FIG. 18C), demonstrating the ability of near-infrared (NIR) CBCRs to function as reagents for in vivo fluorescence imaging.

For the PA experiment, data was obtained using a PA system with purified Anacy_2551g3 mounted in transparent silicone tubes that were either immersed in water or placed under 8 mm of highly scattering media (i.e., chicken tissue). For PA imaging and photoconversion of the far-red "ON" dark-adapted state to the orange-absorbing "OFF" photoproduct state, 728 nm laser illumination was used. 588 nm laser light was used to regenerate the ON state, matching photoproduct absorption. PA signals could readily be observed over multiple switching cycles (FIG. 19A) and even under 8 mm of tissue (FIG. 19B). The signal ratio was defined as the ratio of the mean protein signal to the mean blood signal. In the ON image, Anacy_2551g3 had a comparable signal ratio to that of blood. However, the signal ratio was above unity at both 0 mm (~11 fold) and 8 mm (~2 fold) depth in differential images (FIG. 19C), demonstrating the ability of NIR CBCRs to function as contrast agents for in vivo PA imaging.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

VI. References

1. Garm et al. (2011) *Curr. Biol.* 21(9):798-803.
2. Diaz et al. (2015) "Melanopsin and the Non-visual Photochemistry in the Inner Retina of Vertebrates." *Photochem. Photobiol. DOI* 10.1111/php.12545
3. Moglich et al. (2010) *Ann. Rev. Plant Biol.* 61:21-47.
4. Darwin and Darwin. *The Power of Movement in Plants.* 1880, London: John Murray
5. Briggs et al. (2002) *Tr. Plant Sci.* 7(5):204-210.
6. Whippo et al. (2006) *Plant Cell* 18(5):1110-1119.
7. Rockwell & Lagarias (2006) *Plant Cell* 18:4-14.
8. Franklin et al. (2010) *J. Exp. Bot.* 61(1):11-24.
9. Chen et al. (2011) *Trends Cell Biol.* 21(11):664-671.
10. Casal (2013) *Ann. Rev. Plant Biol.* 64:403-427.
11. Giraud, et al. (2002) *Nature* 417:202-205.
12. van der Horst et al. (2007) *Trends Microbiol.* 15(12):554-562.
13. Gomelsky et al. (2011) *Trends Microbiol.* 19(9):441-448.
14. Gaidukov (1902) *Abh. Königl. Akad. Wiss. Berlin* 5:1-36.
15. Kehoe et al. (1996) *Science* 273(5280):1409-1412.
16. Kehoe et al. (2006) *Ann. Rev. Plant Biol.* 57:127-150.
17. Hirose et al. (2013) *Proc. Natl. Acad. Sci. USA* 110(13):4974-4979.
18. Tsien (2009) *Angew. Chem. Intl. Ed.* 48(31):5612-5626.
19. Reiner et al. (2013) *Trends Neurosci.* 36(10):557-560.
20. Murphy & Lagarias (1997) *Curr. Biol.* 7(11):870-876.
21. Fischer & Lagarias (2004) *Proc. Natl. Acad. Sci. USA* 101(50):17334-17339.
22. Fischer et al. (2005) *Biochemistry* 44(46):15203-15215.

23. Shu et al. (2009) *Science* 324(5928):804-807.
24. Auldridge et al. (2012) *J Biol. Chem.* 287(10):7000-7009.
25. Shcherbakova et al. (2015) *Curr. Opin. Chem. Biol.* 27:52-63.
26. Yao et al. (2015) *Nat. Meth.* 13:67-73.
27. Leung et al. (2008) *Proc Natl Acad Sci USA* 105(35):12797-12802.
28. Tabor et al. (2011) *J Mol. Biol.* 405(2):315-324.
28A. Buckley et al (2016) *Devel. Cell* 36:117-126.
29. Gasser, et al. (2014) *Proc. Natl. Acad. Sci. USA* 111(24):8803-8808.
30. Ryu et al. (2014) *ACS Synth. Biol.* 3(11):802-810.
31. Weissleder (2001) *Nat. Biotech.* 19(4):316-317.
32. Wu & Lagarias (2000) *Biochemistry* 39(44):13487-13495.
33. Rockwell & Lagarias et al. (2006) *Ann. Rev. Plant Biol.* 57:837-858.
34. Rockwell & Lagarias (2010) *ChemPhysChem* 11(6):1172-1180.
35. Wagner et al. (2005) *Nature* 438(7066):325-331.
36. Ikeuchi et al. (2008) *Photochem. Photobiol. Sci.* 7(10):1159-1167.
37. Cornilescu et al. (2013) *J. Biol. Chem.* 289(5):3055-3065.
38. Lim et al. (2014) *Photochem. Photobiol. Sci.* 13(6):951-962.
39. Rockwell & Lagarias et al. (2015) *Biochemistry* 54(24):3772-3783.
40. Yoshihara et al. (2004) *Plant Cell Physiol.* 45(12):1729-1737.
41. Yoshihara et al. (2006) *Biochemistry* 45(11):3775-3784.
42. Hirose et al. (2008) *Proc. Natl. Acad. Sci. USA* 105(28):9528-9533.
43. Rockwell, et al. (2008) *Biochemistry* 47(27):7304-7316.
44. Hirose et al. (2010) *Proc. Natl. Acad. Sci. USA* 107(19):8854-8859.
45. Rockwell & Lagarias et al. (2012) *Biochemistry* 51:1449-1463.
46. Narikawa et al. (2008) *J. Mol. Biol.* 380(5):844-855.
47. Rockwell & Lagarias et al. (2011) *Proc. Natl. Acad. Sci. USA* 108(29):11854-11859.
48. Narikawa et al. (2015) *Biochem. Biophys. Res. Comm.* 461(2):390-395.
49. Narikawa et al. (2015) *Sci. Rep.* 5:7950.
50. Rockwell & Lagarias et al. (2012) *Biochemistry* 51(17):3576-3585.
51. Rockwell & Lagarias et al. (2012) *Biochemistry* 51(48):9667-9677.
52. Narikawa et al. (2014) *Biochemistry* 53(31):5051-5059.
53. Rockwell & Lagarias et al. (2015) *Photochem. Photobiol. Sci.* 14(2):258-269.
54. Rockwell & Lagarias et al. (2015) *Photochem. Photobiol. Sci.* 14(5):929-941.
55. Anders et al. (2015) *Curr. Opin. Struct. Biol.* 35:7-16.
56. Altschul et al. (1997) *Nucl. Acids Res.* 25(17):3389-3402.
57. Le et al. (2010) *Syst. Biol.,* 59: p. 277-87.
58. Burgie et al. (2013) *Structure,* 21: p. 88-97.
59. Narikawa et al. (2013) *Proc. Natl. Acad. Sci. USA* 110(3):918-923.
60. Marina et al. (2005) *EMBO* 1, 24: p. 4247-59.
61. Bick et al. (2009) *J Mol Biol,* 386: p. 163-77.
62. Casino et al. (2009) *Cell,* 139: p. 325-36.
63. Rivera-Cancel et al. (2014) *Proc Natl Acad Sci USA,* 111: p. 17839-44.
64. Edgar, R. C. (2004) *Nucl. Acids Res.,* 32: p. 1792-7.
65. Rockwell and Lagarias et al. (2009) *Proc. Natl. Acad. Sci. USA,* 106: p. 6123-7.
67. Miroux et al. (1996) *J Mol. Biol.,* 260: p. 289-298.
68. Mukougawa et al. (2006) *FEBS Lett.,* 580: p. 1333-8.
69. Berkelman and Lagarias (1986) *Anal. Biochem.,* 156: p. 194-201.
70. Blot et al. (2009) *J. Biol. Chem.,* 284: p. 9290-8.
71. Rockwell and Lagarias et al. (2014) *Biochemistry,* 53: p. 3118-30.
72. Wilde et al. (1997) *FEBS Lett,* 406: p. 89-92.
73. Ishizuka et al. (2011) *Biochemistry,* 50: p. 953-61.
74. Zhao et al. (1995) *Biochim. Biophys. Acta Bioenerg.,* 1228: p. 235-243.
75. Zhao et al. (1995) *Biochim. Biophys. Acta Bioenerg.,* 1228: p. 244-253.
76. Ishizuka et al. (2007) *Plant Cell Physiol.,* 48: p. 1385-90.
77. Shang, Rockwell, and Lagarias et al. (2010) *Biochemistry,* 49: p. 6070-82.
78. Hughes (2010) *Biochem. Soc. Trans.,* 38: p. 710-6.
79. Auldridge et al. (2011) *Crit. Rev. Biochem. Mol. Biol.,* 46: p. 67-88.
80. Rockwell and Lagarias et al. (2015) *Biochemistry,* 54: p. 2581-600.
81. Yeh and Lagarias et al. (1997) *Science,* 277: p. 1505-1508.
82. Rockwell and Lagarias et al. (2014) *Proc. Natl. Acad. Sci. USA,* 111: p. 3871-6.
83. Xu et al. (2014) *ChemBioChem,* 15: p. 1190-9.
84. Alvey et al. (2011) *Biochemistry,* 50: p. 4890-902.
85. Sineshchekov (1995) *Biochim. Biophys. Acta,* 1228: p. 125-164.
86. Heyne et al. (2002) *Biophys. Chem.,* 82: p. 1004-16.
87. Kim, Rockwell, and Lagarias et al. (2014) *Biochemistry,* 53: p. 4601-11.
88. Bhattacharya et al. (2014) *J. Biol. Chem.,* 289: p. 32144-52.
89. Wu and Lagarias et al. (1997) *J. Biol. Chem.,* 272: p. 25700-5.
90. Song et al. (2011) *Proc. Natl. Acad. Sci. USA,* 108: p. 3842-3847.
91. Yang et al. (2011) *Nature,* 479: p. 428-32.
92. Ulijasz et al. (2008) *J. Biol. Chem.,* 283: p. 21251-66.
93. Gan, Rockwell, and Lagarias et al. (2014) *Science,* 345: p. 1312-7.
94. Song et al. (2014) *J. Biol. Chem.,* 289: p. 2552-62.
95. Micura et al. (1994) *Bioorg. Med. Chem. Lett.,* 4: p. 2517-2522.
96. Hahn et al. (2007) *ChemBioChem,* 8: p. 2249-55.
97. Scheer. (1976) *Z. Naturforsch.,* 31*c: p.* 413-417.
98. Stanek et al. (1998) *Chem. Eur. J.,* 4: p. 1660-1666.
99. Tang et al. (2015) *Proc. Natl. Acad. Sci. USA,* 112: p. 15880-5.
100. Solov'yov et al. (2012) *J Am. Chem. Soc.,* 134: p. 18046-52.
101. Solov'yov et al. (2014) *Scientific Reports,* 4: p. 3845.
102. Velazquez Escobar et al. (2013) *Biochemistry,* 52: p. 4871-80.
103. Gan et al. (2014) *Life,* 5: p. 4-24.
104. Gan et al. (2015) *Environ. Microbiol.,* 17: p. 3450-65.
105. Zhao et al. (2015) *Front. Microbiol.,* 6: p. 1303.
106. Enomoto et al. (2012) *Biochemistry,* 51: p. 3050-8.
107. Kim, Rockwell, and Lagarias et al. (2012) *Biochemistry,* 51: p. 608-18.
108. Wu and Lagarias. (2000) *Biochemistry,* 39: p. 13487-13495.
109. Rockwell and Lagarias et al. (2006) *Ann. Rev. Plant Biol.,* 57: p. 837-858.

110. Rockwell and Lagarias. (2010) *ChemPhysChem,* 11: p. 1172-80.

111. Gan, Rockwell, and Lagarias et al. (2014). *Science,* 345: p. 1312-7.

VII. Exemplary Embodiments

Exemplary embodiments provided in accordance with the presently disclosed subject matter include, but are not limited to, the claims and the following embodiments:

1. A protein fusion construct comprising a far-red cyanobacteriochrome (CBCR) domain linked to a heterologous domain, wherein the far-red CBCR domain comprises a CBCR polypeptide and a tetrapyrrole chromophore.
2. The protein fusion construct of embodiment 1, wherein the CBCR polypeptide comprises a GAF domain having an acidic motif comprising:

a conserved tryptophan residue; followed by two acidic amino acid residues, wherein at least one of the amino acid residues is an acidic amino acid residue; followed by a conserved glutamic acid residue; followed by a further amino acid residue; followed by an aromatic amino acid residue.

3. The protein fusion construct of embodiment 2, wherein the acidic motif comprises an amino acid sequence set forth in SEQ ID NO: 1:

```
W-X9-X6-E-X1-X5                          (1)
```

wherein:

W is a tryptophan residue;

E is a glutamic acid residue;

X1 is an independently selected amino acid residue;

X5 is independently selected from the group consisting of a phenylalanine residue, a tyrosine residue, and a tryptophan residue;

X6 is independently selected from the group consisting of an aspartic acid residue and an asparagine residue; and X9 is independently selected from the group consisting of an aspartic acid residue and a glutamine residue.

4. The protein fusion construct of embodiment 1, wherein the CBCR polypeptide comprises a GAF domain having an acidic motif comprising:

a hydrophobic residue independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue; followed by a further amino acid residue; followed by a conserved aspartic acid residue; followed by a conserved glutamic acid residue; followed by a further amino acid residue; followed by a hydrophobic residue independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue; followed by a proline residue.

5. The protein fusion construct of embodiment 4, wherein the acidic motif comprises an amino acid sequence set forth in SEQ ID NO: 2:

```
X2-X1-D-E-X1-X2-P                        (2)
```

wherein:

each X2 is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

X1 is an independently selected amino acid residue;

D is an aspartic acid residue;

E is a glutamic acid residue; and

P is a proline residue.

6. The protein fusion construct of any one of embodiments 1-5, wherein the CBCR polypeptide comprises an amino acid sequence as set forth in SEQ ID NO: 3:

```
                                                   (3)
X9-R-X1-X3-X4-F-X1-X3-(X1)2-X6-G-(X1)3-X4-X2-E-E-
X1-V-(X1)3-X2-(X1)2-X2-(X1)4-W-X8-X6-E-X1-X5-X1-
X7-X9-(X2)2-X8-X2-Y-X1-Q-G-X1-P-R-I-V-X1-X6-V-X2-
X10-X1-D-X1-X5-X2-X1-C-L-X1-E-X5-(X1)5-X4-X1-S-K-
X4-V-A-P-I-X2;
```

wherein each A is an alanine residue, each C is a cysteine residue, each D is an aspartic acid residue, each E is a glutamic acid residue, each F is a phenylalanine residue, each G is a glycine residue, each I is an isoleucine residue, each K is a lysine residue, each L is a leucine residue, each P is a proline residue, each Q is a glutamine residue, each R is an arginine residue, each S is a serine residue, each V is a valine residue, each W is a tryptophan residue, and each Y is a tyrosine residue;

and wherein:

each X1 is an independently selected amino acid residue;

each X2 is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

each X3 is independently selected from the group consisting of a valine residue, a leucine residue, an isoleucine residue, and a methionine residue;

each X4 is independently selected from the group consisting of a valine residue, an isoleucine residue, and a threonine residue;

each X5 is independently selected from the group consisting of a phenylalanine residue, a tyrosine residue, and a tryptophan residue;

each X6 is independently selected from the group consisting of an aspartic acid residue and an asparagine residue;

each X7 is independently selected from the group consisting of a glutamic acid residue and a glutamine residue;

each X8 is independently selected from the group consisting of an aspartic acid residue, an asparagine residue, a glutamic acid residue, and a glutamine residue;

each X9 is independently selected from the group consisting of an aspartic acid residue and a glutamate residue; and X10 is absent or X10 is one or more independently selected amino acid residues.

7. The protein fusion construct of embodiment 6, wherein X10 is absent.

8. The protein fusion construct of any one of embodiments 1-7, wherein the CBCR polypeptide comprises an amino acid sequence set forth in:

SEQ ID NO: 4 (Sta7437_1656),
SEQ ID NO: 5 (Cyan7822_4053g2),
SEQ ID NO: 6 (Anacy_2551g3), or
SEQ ID NO: 7 (Anacy_4718g3).

9. The protein fusion construct of any one of embodiments 1-7, wherein the CBCR polypeptide comprises an amino acid sequence set forth in:

SEQ ID NO: 4 (Sta7437_1656),
SEQ ID NO: 5 (Cy7822_4053g2);
SEQ ID NO: 6 (Anacy_2551g3);
SEQ ID NO: 7 (Anacy_4718g3);
SEQ ID NO: 8 (N7104D_1016g3);
SEQ ID NO: 9 (L6406D_1154g2);
SEQ ID NO: 10 (c56D2_02270g2);
SEQ ID NO: 11 (c407D_01196g2);
SEQ ID NO: 12 (fdiDRAFT29700);
SEQ ID NO: 13 (WP009627289g3);
SEQ ID NO: 14 (Os7112_5903g3);
SEQ ID NO: 15 (C6303_3693g3);
SEQ ID NO: 16 (WP006632756g3);
SEQ ID NO: 17 (Cy7425_1390g3);
SEQ ID NO: 18 (WP017296986g2);
SEQ ID NO: 19 (WP_033374293);
SEQ ID NO: 20 (WP028089844g3);
SEQ ID NO: 21 (WP008316973g2);
SEQ ID NO: 22 (Ga0039499_10213);
SEQ ID NO: 23 (310F_3509);
SEQ ID NO: 24 (WP_016871037);
SEQ ID NO: 25 (WP_016878855);
SEQ ID NO: 26 (WP_026722600);
SEQ ID NO: 27 (WP_017309337); or
SEQ ID NO: 28 (WP_016873240).

10. The protein fusion construct of any one of embodiments 1-9, wherein the tetrapyrrole chromophore is a bilin.

11. The protein fusion construct of embodiment 10, wherein the bilin is selected from the group consisting of phycocyanobilin (PCB), phytochromobilin (PΦB), phycoerythrobilin (PEB), and biliverdin (BV).

12. The protein fusion construct of any one of embodiments 1-11, wherein the C-terminus of the CBCR polypeptide is linked to the heterologous domain.

13. The protein fusion construct of any one of embodiments 1-11, wherein the N-terminus of the CBCR polypeptide is linked to the heterologous domain.

14. The protein fusion construct of any one of embodiments 1-13, wherein the heterologous domain comprises a heterologous oligopeptide or a heterologous polypeptide.

15. The protein fusion construct of any one of embodiments 1-13, wherein the heterologous domain comprises a heterologous polypeptide selected from the group consisting of a signaling polypeptide, a structural polypeptide, a transport polypeptide, a targeting peptide, a hormone polypeptide, and a regulatory peptide.

16. The protein fusion construct of embodiment 15, wherein the signaling polypeptide is selected from the group consisting of a kinase polypeptide, a phosphatase polypeptide, a phosphodiesterase polypeptide, a nucleotide cyclase polypeptide, a protease, a phopholipase, a G-protein polypeptide, and a channel protein polypeptide.

17. The protein fusion construct of embodiment 15, wherein the structural polypeptide is selected from the group consisting of an actin polypeptide, a tubulin polypeptide, a myosin polypeptide, and a collagen polypeptide.

18. The protein fusion construct of embodiment 15, wherein the transport polypeptide is selected from the group consisting of an annexin polypeptide and a clathrin polypeptide.

19. The protein fusion construct of embodiment 15, wherein the targeting polypeptide is selected from the group consisting of an antibody, an antibody fragment, and an aptamer.

20. The protein fusion construct of any one of embodiments 1-13, wherein the heterologous domain comprises a streptavidin polypeptide.

21. A method for detecting a cellular component, the method comprising:

providing a protein fusion construct in a sample, the fusion construct comprising a far-red CBCR domain and a heterologous domain specifically detecting a cellular component;

exposing the protein fusion construct to far-red light or near-IR light, wherein the exposing causes fluorescence of the far-red CBCR domain; and detecting the fluorescence of the far-red CBCR domain, thereby detecting the cellular component.

22. The method of embodiment 21, wherein the sample is a cell or tissue and wherein providing the protein fusion construct comprises expressing the protein fusion construct in the cell or tissue.

23. A method for imaging a biological structure in a subject, the method comprising:

providing a protein fusion construct in or near the biological structure, the fusion construct comprising a far-red CBCR domain and a heterologous domain;

exposing the protein fusion construct to far-red light or near-IR light, wherein the exposing causes absorbance by, or release of an acoustic signal or fluorescence from, the far-red CBCR domain;

detecting the absorbance, acoustic signal, or fluorescence of the far-red CBCR domain; and constructing an image of the biological structure;

thereby imaging the biological structure.

24. The method of embodiment 23, wherein the biological structure is selected from the group consisting of a tissue, an organ, or a tumor.

25. A method for modulating a cellular process, the method comprising:

expressing a protein fusion construct in a cell, the fusion construct comprising a far-red CBCR domain and a heterologous signaling domain;

exposing the protein fusion construct to far-red light or near-IR light;

wherein the exposing increases or decreases the activity of the heterologous signaling domain, thereby modulating the cellular process.

26. The method of embodiment 25, wherein the heterologous signaling domain is selected from the group consisting of a kinase polypeptide, a phosphatase polypeptide, a phosphodiesterase polypeptide, a nucleotide cyclase polypeptide, a protease, a phopholipase, a G-protein polypeptide, and a channel protein polypeptide.

27. The method of any one of embodiments 21-26, wherein the far-red cyanobacteriochrome domain comprises a CBCR polypeptide and a tetrapyrrole chromophore.

28. The method of embodiment 27, wherein the CBCR polypeptide comprises an amino acid sequence set forth in any one of SEQ ID NOS: 1-28.

29. The method of embodiment 27 or 28, wherein the tetrapyrrole chromophore is selected from the group consisting of phycocyanobilin (PCB), phytochromobilin (PΦB), phycoerythrobilin (PEB), and biliverdin (BV).

30. An isolated nucleic acid comprising a polynucleotide sequence encoding the protein fusion construct of any one of embodiments 1-20.

31. An expression cassette comprising the nucleic acid of embodiment 30 operably linked to a promoter.

32. The expression cassette of embodiment 31, further comprising at least one nucleic acid encoding an enzyme for chromophore synthesis.

33. A vector comprising the nucleic acid of embodiment 30.

34. A host cell comprising the nucleic acid of embodiment 30, the expression cassette of embodiment 31, or the vector of embodiment 33.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

The following Informal Sequence Listing provides exemplary sequences of full-length proteins containing far-red CBCRs. Bold and underlined regions correspond to the core CBCR regions aligned in FIG. 3.

Anacy_4718
(Bold and underlined region = SEQ ID NO: 7)
(SEQ ID NO: 29)

MFSRSVILTPSELKSAIIRNPLIVKPETTVIDAIAMLAAGIGQMGGVGAI

SNTKIIDGQLDELHLETRPSCVLVMEDGKLLGIFTERDVVRLISQQHSLE

NLVIQDVMTYPVVTLYESAFSDLFSTINLLQQYHIRHIPILNEQDCVVGL

VTDESLRQISNPIYPLRSRLVSAAMTNEVICAALDSSIRTIVQLMAKNCI

SCVIIVQKRGSQAQPLQIPVGIITEQDIVKFQVLGLNLETSQAETVMSAP

IFSVKPNDSLEMVQQIMEQQLIRKLAVTNEEGNLLGIVTQNSLLQTLNPL

ELYKLAEVLEEKVLRLEAEKILLLETRTVELEKELADQNIALQTKTEQEK

LVAIIATQIRSSLNLQTILDTTVEQIRQLLNCDRVTIWQLEANGKLITVA

ESTGCTLSLLGQQSQDQCISQQLVEIYQQGKIRIVPDIYTTEMSDCHRNL

LISLDIRAKILMPLMCGDELWGFLNVTESQHPRQWQDSEIELLKLLTVQL

AIALQQATTHQKLQEELRERQRAESTLQKLVTGTAAVTGDDFFPALVQHI

AEALDVSYAIVTELVGDQLHTLGFWANGSLQPSVSYYAAHTPCKYALRDG

-continued

QFYCKSGIQEAFANDFDLVMMRADSYLGIALKDDLGNAIGNLCILDVQPL

HNSQLKEARDILQVFAARAAAELQRKIAKDALISLNHNLELRIEQRTTKL

QAREAQLRDLFDNATDLIQSISLNGRILFVNKSWKEALGYDDTDLEKLSI

FQVIHPDELVHCQTVMASLASGNPSMSMETRFLTKDGREIIVEGNVNCQF

AKGKPIATRGVFRDITQRKQAELALEEAQQFLYTVLDTFPLFIFWKNRES

VYLGCNQNFAISGGFASPAEVIGKTDDDFPWRNGEADIYRADDRQVIESG

IAKLGIIETQQQTNGSTIWLETNKLPLRNLKGEVIGILGTYQDITERKQA

ENALQNSELRFRRMFDSSVVGMIFADFQGRILDTNDRFLQMLGYTRDDFN

AGAINWLAITPSEYIPTDFAAIDHLMKYGEIDPWEKAYYRQDGSRIPVLI

GAAILPESKDQTICVVVDISEQKAALRERQEAELSLQQEAMYKQLLLTLS

QAIRESLEIEVILNTSVNEARSLLVVDRVAVYRFQPDWSGEFITEAVVPG

WVKLAAESDVKKVWQDTYLQETQGGRFRNYETLIVRDIYQAGLQPCHIEL

LEQFQARAYVITPIFVGESLWGLLGMYQNDQPYWWTTGEIELLQQIASQL

AIAIYQANLYQQVQAELIIRQKAELAISHQLQQQRTLGKIVQKIRDSLDI

KDILATVTQEIKNSLNCDRVIVFRLFADGESQIVEEAVSGELVSLKNRHW

DNEVWSQEILDYYWQGQPRIVTDVMEDIWTDCLVEYSIEGQVQSKIVAPI

LQEAQDGEKNRWVASGENNKLWGVLVVHACSEKRIWKDCEAQLLQQIANQ

LAIAIQQANLFEKLQQELTERQKTEIKLTHSNQQLAISNEELARATRLKD

EFLANMSHELRTPLNAILGMTEALQEQVFGGINERQLKALKTVENSGNHL

LELINDILDLAKIEAGQINLNCTSISVSHLCQSSLAFIKQQALKKRIKLN

IKLPQNLPDLFVDERRIRQVLINLLNNGVKFTPQGGSITLEVTQFHPDME

NADFFPQGFLRITVIDTGIGISPENINRLFHPFIQIDSSLSRQYNGTGLG

LALVKQIVELHGGQVGLTSELGVGSCFMIDLPCSPLLSEITTDDQSASTS

ELDFLTAEEAESQAPLILLAEDNEANIITFSSYLEAKGYQIILARDGHEA

VNLAKTHQPNLILMDIQMPGMDGLEAMTQIRLDPKLINIPIIALTALAMT

GDRERCLEAGANDYLTKPVMLKQLATTIQQLLNKDG

Anacy_2551
(Bold and underlined region = SEQ ID NO: 6)
(SEQ ID NO: 30)

MFVPAKAHTQAELRLAIVRDPLLVTPETTVVEAIAQMSGVRSVCSVSQNT

DSKQESLLAEARSSCVVVVENNQPIGIFTERDVVRLSAQRRKLNNLAIRD

VMAYPLVTLYESEFTDLFFAINLLQHHKIRHLPVIDEQNQLVGLLTHESL

RQKSRPVDLLRLRLVSEVMTTKVICAAPHISILMIARLMAENRISSVVIV

QTQASLIIPIGIVTERDIVQFQALDLNFETCLAEAVMSTPIFCVNADESL

WNVQQIMEQRLIQRLAVTGTNGELLGIVTQSSILQVLNPLELYKLTELLE

KKVSQLEAEKIELLENRTVELEEEVGERTIALRKKIVREQLITKIAAQIR

SSLNLQDILNTTVAEMRSLLQCDRVIIYQFRPDFSGTVIAESIVANGVSI

LHDEPQDPCITPEWLEPYRQGQIRVINDIHSESMSDCYQDMLIELDIRAK

LMVPIVIAEQLWGLILTSYRDQSHNWELEEIELVRQLSIQLSVAIQQAQT

HQQLYQLNQELENQIQERTKALQASEAKYRNLVEAATHVTWLCNTKGELI

YLSPQFQELFGWEVEKFYGQSFISLIHPDDRPYMISTSEELGKSDKNLVS

AEFRHLHQNGSYIWVESKASNLKDASGVIIGCQGVLLDISDRKQAEKIIK

-continued

QQAEREHLLYQTTQRIRQSLDLATIFNTATQEIRQFMNADRVVIFQLDPV
SNFNDSKFVSESVVEGFTSALATKINNKCFGEQYAAHYQQGRIQVVDDLD
NAGLTDCHRDVLAQFQVRANLVVPLLQGENLWGLLCIHQCSVPRHWQEFE
VELVQQIAHQLAIAIQQSILYEQVQSELIIRKQAEDAISLQLQRQKIIQD
ITQQIRSTLNVNHILATVTQQVKELMQVERVIIFRLFPNGRSQIVEEVVS
SEYAALKNYHWEDEKWSQEILDCYWQGKPRIVPDVINDIWTSCLVEYTTQ
GNIQSKIVAPILQELGENETGRWVSSEHKQKLWGVLVVHACSTKRVWEED
EAQLLQQIANQLAIAIQQAALFEQLQLSLVQEKEVSKMRSRFITMASHEF
RTPLAIIASSTGILQKFRERLSAEKQQEHLGTIQKTIKHIIQLLDDVLMI
NRTEAEKMEFKPEASDIIAFCHQITQQIEATSNKHVIEFSFTASKPILDN
SFIVQLDKKILQQILANILTNAIKYSPQTSLIKFDLTIEDDKLIFKIKDS
GIGIPEEYKINLFAPFHRASNVGTISGTGLGLSIVKKCVDLHKGEISFDS
KLGQGTTFTIIIPYSRIQESGVRSQE

310F_3509
(Bold and underlined region = SEQ ID NO: 23)

(SEQ ID NO: 31)

MLIPVNAISATELKSAITYNPLLATADTTVREAVVQMSGISANTLWLNVP
AVCYIPQTANNYLEHLQIQACCSCVLIVENNRPVGIFRQEDVVKISTQKP
NLEDLALRDVMTHPVITLEESKFTDLFSALNLLQHHRIRHLPLVDEENQL
VGLLTYESLRQILRPVDLLRLRLVHEVMTTNVLCAPANVSILEIARLMAE
NQVSSVMIVETQASLTIPLGMVTEHDIVQLKALSVNFDTCLAQTVMSTPV
FCVTVDESLWNVQQIMEQRFIQLLAVTGSKGELLGIVTHSSILEALNPWE
LYKLTAVLQEKVLQLETEKIQLLENRTLELEKQIEERTIKLRRKAEQEEL
INQIATQIHSSLDLQEILNNTVVGVRSLLNCDRVIVYQFSGDFRGQVIAE
AIITGESVLNQEVHDPCISPEWLELYRQGQIRVINDINTESITQCHQQML
KDLDIRGKLLSPLIVENQLWGLMLASYRDIPHNWELEEIELVQQISLRVA
IAIQQANIYQQTQIEIHQRQQAEELIKQQLAELKIWKNRYELASTVSGQI
MYEYNLLNDAPVWPANMEEILGYSYSECPRNLAEFMDIVHPEDRDRLYSL
IQKKLAHKSPLSTEYRLRRKDGNYIWVEDRNQVVLDDQGEIVVVIGAIVD
ITVRKNSEEKLSKLFQKSEKLQERLSLVLKGSNDAWWDWDLLEDTIYYSA
RWFSLLGYKHEELYLKSESFWQNFMHPEDIDPIRGNFNQALDDKNIEFIE
SKFRLRHKQEYYIFINCRSYILRDETGKAVRVSGANTDITQLVQKEEELQ
ATLNQLSQFNQKLETRVQKRTVQLQNLSSRLELAIKAAKIAIWEWDLDNN
HTIWDKKMYELYGVKPSEYKDGMEILQTVLHPEDAVRVNEILQHKLKDGE
EFEMDFRIVLPDGKIRVLQSYGIIKRDSQGKAERVIGVNKDITEWKQTEQ
KIKQQAEREYLLWETTQRIRQSLDLHTIFNTAAAEIRQLMNADRVGIFKF
DPDSNFNYGEFVSESVVPGFISALEMKVHDQCFGERFSSDYAAGRMQIVD
DIDNAGLADCHRDILAQFQVRANLVVPLIQGRILWGLLCIHQCSQPRHWE
DFEIELVQQIANQLAIAIQQSMLYEQVQSELIIRKQAEVEIYLQLQRQRA
IQDITQEIRSSLNLNHILTTITAKVQELTKAERVIVFRLFPDGKSQIVEE
AVANGYMTFKDSYWEDEKWSQDILEYYWQGKPRIVLDVMDDIWTDCLKAY
SRQGNIRSKIVAPILQDLVENENGRWVNHPHNKLWGVLVVHACGEKRIWE

-continued

ESEAELLQQIANQLAIAIQQADLFEKLQKSLKQEKEISAMRSRFVSMVSH
EFRTPLAIISSSTGILQTFGDRLNAEKKQGHLETIQKTIKYTVQLLDDVL
MINSVETEKIEFKPETLDIIDFCRRLIREIQGTSYSHVIDFSLNSTQLIL
DHTLFAEFDPKIIRQVLTNLLTNAIKYSPGSSTVSFSLNITDKQIVFIVQ
DYGIGISETDQVNLFASFYRGSNVGNISGTGLGLAIVKKCVDQHQGKITL
ESKLNQGTIFKVTIPRYNLIGNG

131C_1565
(Bold and underlined region = SEQ ID NO: 20)

(SEQ ID NO: 32)

MLIPVNAISATELKSAIIYNPLLATADTTVREAVVQMSGIAANPLWLTVP
AVCSIPHSANNYLEHLQIQACCSCVLIVENNRPVGIFTQQDVVEISAQRP
NLEDLALREVMTHPVITLQESKFTDLFFTLNLLQHHRIRHLPLVDEENQL
VGLLTYEILRQILRPVDLLRLRLVHEVMTTNVLCAPANVSILEIARLMTE
NQVSSVMIVETQASLTIPLGMVTEHDIVQLKALSVNFDTCLAQTVMSTPV
FCVTVDESLWNVQQIMEQRFIQRLAVTGSKGELVGIVTHSSILEALNPWE
LYKLTAVLQEKVLQLETEKIQLLGNRTLELEKQIEERTIKLRRKAEQEKL
INQIATQIYSSLDLQEILNNTVVGVRSLLNCDRVIVYQFSGDFRGQVIAE
AIVAGGHSVLHQEVHDPCISPEWLELYRQGQIRVINDINTESITQCHQQM
LKDLDIRGKLLSPLIVENQLWGLMLASYRDIPHNWELEEIELVQQISLRV
AIAIQQANIYQQTQIEIHQRQQAEELIKQQLAELKIWKNRYELASTASGQ
IMYEYNLLKDAPVWAANMEEVLGYSYSECPRNLAEFMDIVYPEDRDRLYS
LIQKNLAQKSPLSTEYRLRRKDGNYIWVEDRNQVVLDDQGEIVVVIGAIV
DITVRKNSEEKLSKLFQKSEKLQQRLSLVLKGSNDAWWDWDILDDTIYYS
ARWFSLLGYKHEELYLKSESFWENFMHPEDIDPIRGNFNQALDDKNIEFI
ESKFRLRHKQEYYIFINCRSYILRDETGKAVRVSGANTDITQLVRKEEEL
QATLNQLSQFNQKLEARVQKRTVQLQNLSSRLELAIKAAKIAIWEWDLDN
NHTIWDKKMYELYGVNPLEYKDGMEILQTALHPEDAVRVNEILQHKLKDG
EEFEMDFRIVLPDGKIRVLQSYGIIKRDSQGKAERVIGVNRDITEWKQAE
QKIKQQAEREHLLRETTQRIRQSLDLHTIFNTAAAEIRQLMNADRVGIFK
FDPVSNFNYGEFVSESVVPGFISALEMKVHDQCFGEKFSPDYAAGRMQIV
DDIDNAGLADCHRDILAQFQVKANLVVPLIQGKNLWGLLCIHQCSQPRHW
EDFEIELVQQIANQLAIAIKQSMLYEQVQSELIIRKQAEVEIYLQLQRQR
AIQDITQEIRSSLNLNHILTTITAKVQELTQAERVIVFRLFPDGKSQIVE
ESVANGYMTFKDSYWEDEKWSQDILEYYWQGKPRIVLDVMDDIWTDCLKA
YSRQGNIRSKIVAPILQDLVENENGRWVNHPHNKLWGVLVVHACGEKRIW
EESEAELLQQIANQLAIAIQQADLFEKLQKSLKQEKEISAMRSRFVSMVS
HEFRTPLAIISSSTGILQTFGDRLNAEKKQGHLETIQKTIKYTVQLLDDV
LMINSVETEKIEFKPETLDIIDFCRRLIREIQGTSYSHVIDFSLNSTQLI
LDHTLFAEFDPKIIRQVLTNLLTNAIKYSPGSSTVSFSLNITDKQIVFIV
QDYGIGISETDQVNLFASFYRGSNVGNISGTGLGLAIVKKCVDQHQGKIT
LESKLNQGTIFKVTIPRYNLIGNG

-continued

Pse7429DRAFT_2072
(Bold and underlined region = SEQ ID NO: 13)
(SEQ ID NO: 33)

MSVAKLNASELSSAIIRPPVVVAAHTTVMEAIAQMLGGGFDTSVQSAPND

RHNDRHNDCQESTSSYVIAIAEDGRAIGILTERDVMRLSFQQADFTRLQI

HEVMTCPLVTLYEADFCDISLAVQLFQQHSIRHLPILDYRDRPVGIVTAE

SLQHFLQQHQQNSAAELTAKNIAREQLIAQIADHIRLSFNLQEVLDSCVQ

EVRNFLQCDRVVVYQFQSDWSGFIISESVESPFVISLGNHIQDSCFQSQA

KQRYDHDQPIIVNNIYNAGYAPCHIEVLEQYQVKANIVIPLQVSGNLWGL

LIGHQCREHRDWQPEDASLLRNIAIHLAIAIQQLYAYEQAQKELTERQRS

EALIQQQLAELTEWYYRYEAAEKASGQMLYEYDLSSKSLIWGANIARVLG

FTVSESPKNLSDLLSAIHPEDRNHFFQTAEICRTNQTPFFCQYRLKHQEG

YYIWVEDRNQWLFDDRGEAKRLIGMIADISDRKNAEINLKISEAHHRALI

KAIPDLFMRIDRSGIYLEFVCIPSQHRIIGHLLDMNGVHVSETIPPELAQ

RRMEYIELALQTQSLQIYEQDFSTPEIDHIEEVRVVPYHENEVLLLVRDI

SDRKKAERELKHTEKLFREAQRIAKIGNWELNLTNQVLYWSDEIFRISEI

DPQQFSASYETFLNTVHPEDREMVDRAYQQSVSDRLPYNIVHRLLLPDGR

IKYIQNQGETIYAEDGSPKLSQGTIQDITSLKQTELELENLNDQLEARML

ERETRYWALMNGASDAIMLADLQGNILEVNMQAEQILGYSRAELTSMHFT

QLHPEEELTRTRDAFESLTHQQKIQVYDIIFITKNGQLIPFDVSASVIDI

QGEPILQGIFRDIRDRKQIESDLQESRDRSQQKASQETILRKITQRIRQS

LNLQVIFDTACHEIRQILQADRVGIFQFDADTNYSDGEFVAESTVEGFSS

VLAIRLQDYCFGDSYSFSYSQGRCQIVDDIYQTDLEKCHTCILEQFQVRA

NLVIPLLCGEALWGLLCIHQCSAPRHWQNFEIELSQQIANQLGIAIYQAS

LYQQAQSELLIRQKAEVAISQQLRQQQTIGAITQKIRESLDINAILSTVT

RQVKEVLNCDRVIVFRLFSYGDSQIVEEAVSPEFTSLKSLHWENELWSPA

ILDYYWQGKPRIVPDVMVDVWTDCLIPYSIEGQIKSKIVAPILQDLGNIE

RSRWISPLANNKLWGVLVVHACAEKRVWQDSEAQLLQQIANQLAIAIQQA

SLFAQVQQELSDRQQAQQQLTATNRKLALSNQELERATRLKDEFLANMSH

ELRTPLNAILGITEGLQEEVFGVLNAKQKQVLLAVERSGNHLLDLINDIL

DLAKIEAGKVTLDRSLTNIEQLSQSSLMFVMQQALQKNIQLHIQVEKSLP

DLKIDERRIRQVLINLLNNAVKFTLENGRVVLEVILHKVNDSNLQDVIHW

VRFAVIDTGIGITPHALQTLFQPFIQVDSALNRQYEGTGLGLALVKRIVE

MHGGQVKATSDFGVGSCFTIELPYNERDSSLLLKHSNSFPSDFVPEPDAK

DSQLGHPLILIAEDNEANIITFSSYLSANGYRVIVAKDGQTAVDLVQSEH

PDLVLMDIQMPGMDGLKAIEYIRQHQLSNAPIIAVTALAMVGDRERCLAA

GANDYLSKPVKLKKLAEVVQQFLHPPC

Lepto7104DRAFT_1016
(Bold and underlined region = SEQ ID NO: 8)
(SEQ ID NO: 34)

MATPRPADLTAAIIDKPLTVQPDVSAGTAIALMGGVSTPGPTGHDPAGED

GLHMEAGSCVVVVEQGRVVGLLTERDVVRLSAQQRSLDRLSVAEVMTQPV

ITRRLSDLTDLTSTIELLQQHRLRHLPLVDEQDCLVGLVTHDSLWQAFSP

-continued

LKYCNLTEALERKVTRLETERLALLENRAAELERQVAERTQMVQVQAERD

RLMAGLAAQILASLDVQVILDTTVQQVQQILGCDRASIWRFEADWTTVVV

AESNDADRSLIGERIADKCFLETQVEAYRQGRIRVVSDIDAIEMSDCHRN

MLIRLQTRAKILVPLLCGDELWGLLNVTEMQPRDWQPAEVEFVRSLSIQL

AIALNQASTHEQLRSELQERQQAERQLRQSTERLKKAQRIAHIGNWELDL

QHNTSYWSKEVFRIFEVDSQQFAASYEAFLDLVHPDDRTLIDTAYANHLR

DRQPFSLVHRLRLADGRIKYVREQCETIYSADGTPRISQGTVQDITPQQE

AEIRRDRAETTLRQLTEGTAAVTGEAFFPALVHHISEALGVRYVSISQAM

PDGFQVLAFFADGELSVPLFLPYDELPCCFEALQTGSCCHPTGVQALYPD

NALFTDLQVDSYLGVRLQNAAGDPIGNICILHDAPLADLDWAKTLLTIFA

ARAGAELERLMTAQALEQLNGELESRVVERTAELAERETLLQDFLDNAND

LIQMVDVSTGRFEFVNRAWQNVLGYTTAEVAQLTCFDVLAPDCLPHCQTV

FTQMQSGSITHVEQMELTFICKSGQRVVVEGNVNCRFAVGADGSQRPVST

RGIFRDITDRKTTEQELQRREARYRGLMEGAADAVLLIDLEGNILEANQN

AAAMFGYPLAELSTLHFTQLHPAETLPRAAAEFAEVAQGQRTQVLDMPCC

RRDGSVVPVDITASVISTGEGRLVHGALRDISDRKRYETALQESQQFLQT

VLDTVPLSVFWKDQNSRYLGANQRFLKDASLGSVSELVGKDDSAMPWGVT

EADAYRAADRVVMDSGEAKLGIIELQHQQDGAVIWLETNKLPLRNLAGEV

VGILGTYRDITERKNAEIALQRQLAAIEAAVNGIAILENERYLYFNSSHA

KMFGYEQAEELVGQSWRMLYSPEQLERFDREILPILSAEKSWQGEVTATR

KDGTTFPEQLSLTISTDNLLICVCQDISERARLDAERKQAEAALRESERR

YAMLAQAVPVAIFRFDLEGHCTYVNERWCEMTGKPIDFALDDRWLETIHP

DDRERTQTVIQQWLQTGAVAPFQNEARILRDDGSIIWYYCQMLLETDVNG

AMLGYVGTLTDISDRKQSEEALGESEEKFRQLAEVVDAVFWILHLNRTDR

VYVSPAYERIWGRPCTDLYITPDAWIDRIHADDREQVLAAIPKQLEGTFD

EEYRIVRPDGTQRWIHDRAFPIRNAQGQVYRLAGIAEDITERKNSEEIIC

QQAEREVVLREITQHIRESLDLQTIFNTACDEIRAFLRADRVGIFKFYPD

SGYDDGEFVAESVVNGFSSAMAIRIHDHCFGENYANLYAQGRYQVVDNIY

SNGLTPCHSDILAQFQVQANLVMPLLCNHELWGLLCIHQCDAPRHWQQSE

INLGQQLANQLAIAIQQASLYEQVQTELLERQQAEAKIARQLRQQTALEL

ILQQIRQSLDLPELLAIATQQVQELLQSDRVIVFQVAQNGHSCILEEAVA

PDLPQLKAMQWDDETWSQDILEHYWQGQPRIVPDVMEDHWTDCLVEYSKA

GQIQSKIVAPILQELCDIETHRWASPEGSSKLWGVLVVHACRTRRVWHQQ

EAQLLQQIANQLAIAIQQANLFEQLQQELQERQQAEAQLTLTNGELMRAT

RLKDEFLANMSHELRIPLNAILGMTEVLQDDDVFGPVNAQQLKALKTVER

SGTHLLELINDVLDVAKIEAGQLELDCHPTAIAPLCQSSLAFIKQPALKK

GLQLAVKLPPNLPEITLDERRIRQVLINLLSNAVKFTLEGGHITLDVSLL

PPTQSHPELSYLRFAVTDTGIGITPENMQRLFKPFVQVDSSLNRQYQGTG

LGLALVKRIVELHRGQVGLTSDVGVGSCFTVELPYGAGIPAPPVPAPPSA

IGPATPLPKVAATPTTTPLILLVEDNEANISTLRSYLQAKGCRVEVAHNG

-continued

EEAIDWAQHKTPDLILMDIQMPRMDGLEAIGHLRRIPSLANVPVIALTSL

AMAGDRDRCIAAGATDYLTKPVSLKQLNERIHALLTP

Lepto7104DRAFT_1307
(Bold and underlined region = SEQ ID NO: 18)
(SEQ ID NO: 35)
MRRFSWSRHLRQPFLLWWLLLPLGLQTVGTAVLIGVLLHGNAAQPAVESA

NPLPAANGYLTPAIALWGAVQVLAVGLGAAIARTVAAPKRPQGGLPNASA

SHDCRMIEAALQASEARFQTLMAHIPGMVYRYLPGSDGDGAFTYVSAGCY

ELFGLSPNQVLQNANAVWGLIHPDDWPSLQASVASAVARCADWHWEGRFT

TVTGQPRWLQGRARPQPTPAGAVWDGLLIDITALKQTETALNQEISYRRA

LLNASIDGVVIVDREGNVLEANHSFTAMLGYTPAEILSLNVADFDVDLGH

LKEDLKSEKTKLCLDRFERLHRRKDGSTYAVEISANAVDWNGQAVHLCVC

RDISDRVRAEAIRRESEARYLSILEEQTEFITRFQPDGKLIFVNNAYCRY

FSQSKAQLEGQNYQPVVYPADQPAIDRCLASLSPETPIRTVENRVYVRGE

LRWTTWTNKAIYDDCGNLIELQSVGQDIHDRKRAELALAESEARFQRLTA

ASPAIIYTVIESLQGIVRFEYLSPAAEEIHEIPIATLMQNGALISEQMHP

DDRERYLEAYAASLQSMTTFICEWRIITPSGKTKWLKANSRPEQRPSGEV

AWHGITLDITPRKQAEAALGNLQAALLEAQQVAHIGNWEFDLASQKITWS

PELFRMFGLDPAQGEPTYADYLELLQPDDRILLQQAVDRAIAEGTPYRLD

YRVLLPDGSLRYQEGRGKVERDRTGQWRLFGTALDITDRKHTEIALQAS

QLRLQLAINSTGTGTWDWNMQTNEVLFDQKLWRALLGYGADAAIDNSVAE

WESRIHPKDKPQVQADIARHIRGETEIYENTHRLRCHDGTYKWNLAQGKI

IERDDRGNPIRFVGIHRDVSEQVLLDAGRRLAEEALQASEARFRAIFEQA

AVGINQADASGRFIQANQYFCGLLGYTQAELLRLTVQDLTHPEDLERDRL

QILRLFQGKQKGFTTIKRYRHRHGSWIWTEVTLSAICNPAGEVISDLAIV

VDIRKLRQANAALKASEARLRAIFDQALAGINQIDSQGQFTEANQYFCDL

LGYSRDELLALKLEDLIHPDDMERCREPVDRILRGEIDNLRLERRQRHKN

GDWIWTEAMISLLRDEAGEVIGNLAVVVDIRERIRLEADRKRAEQTIRQQ

AERETMLRKLTQSIHRSLDLQTIFDTACREIRACLQADRVGIFKFRPGSS

YSTGELVAEAMVDGVTPVLAIPIHDHCFGERRAAFYAEGHCHIIDDIYAS

DLENCYIDFLAQLQVRANLVIPLLCGRDLWGLLCIHQCAGPRHWLRADID

LGCQLAHQLALAIKQALFVEQIQSELQVRQRAEAKIAHQLRQQTALGMIL

QQVRESLDLDQILATVTQNVQEILQSDRVIIFQVHSDGHSKIVEEAVSES

LPTLKGMRWEDEVWSQDILDVYWRGQPRIVADVMADTWTDCLVDYSQAGQ

IQSKIVAPILQEIRTSEGHRWVAPRAKNKIWGVLVVHACRQKRVWQDSEA

QLLQQIANQLAIAIQQSTLFEQLQQELSDRQLAQQQLTESNQELAVANQA

LSRATRLKDEFLANMSHELRTPLNVILGFAQILSSDLSLQAQQQEYIRIM

HRSGDHLLHLINDILDLSKIEANRITLEPESIDLLELLHDLQGMFQERAE

DKELRFTLALAPDLPQYIVADPNKLRQVLINLLGNAIKFTQEGSVALRVS

LALPEHPEPQPEPPQPYLSFAVEDTGTGIAPAELASIFDAFTQAKAGKVS

LEGTGLGLAISRSLVQLMGGSLTVSSRLGQGSTFCFSLPCHRGRAEDVAL

TNYPGAVTGLAPAQPNYRILVVDDQPENRQLLLAAFSQVGLAVREAAHGA

-continued

EAIAQWRQWQPHLIWMDLRMPTLDGCEATRRIRAESAAIANGDRPIIIAL

SAQASNDECSNALAAGCDDFVSKPVKLNLLWTKMSDYLGLRYVYAETPTP

AGLVNPTSAKAIRIDTSDLQVMPPEWIGALHQAALHCDSHDTAQLIQQIP

AEHGALTTSLNRLLDGYKFEVIMQLTQPYLEAAP

LEP6406DRAFT_1154
(Bold and underlined region = SEQ ID NO: 9)
(SEQ ID NO: 36)
MIRAMKVDLTAAIVPSPLTVTPETLVQDAIALMSSVRTLCSTDRNPTSND

NLHLEHRSSCVLVVVENDLVAGILTERDVVRLSAQQQPLDQLLVAEVMAQ

PVITHRQSDLTDLFSTIHLLKHHHIRHLPVVDDQNRLVGLLTHESLRQLT

RPVDLLRLRLVQEVMTADVLCAAPDSAMLEIAQLMADRRVSSVVITLPGG

STDAPFRRAVGLLTERDLVQFQALGLSLTTTTAQTVMSSPVFAVAPQDSL

WTVQQVMEQHRIRRVIVAGEQGELLGIVTQTSLLQAFNPIELYQLAEVLE

QKVVHLETERIALLQSQSAELEWHITESNQAIRMQAEIDRLLQGFALATT

HLMTLQDGHESVQAALDALGSALRVDRSYIFENHPHPKTGEMVLSQRWEW

VAEGVTRQIDNPELQNIPVDKVLPNWYQSLSQGQTVGGLTKDFPEEEQAH

LRPQGIVSILLVPIFIEDYFWGMVGFDDCHEERVWENSTQSALKSIAGTI

GSAIARRRAEANATLLAKRLQEAQRLAHVGNWEQDLQRHTFYWSEEVFRI

LEIDAQQISASYETFLGLVHPDDLTLVDEAYANHLRSRQPTSLVHRLQMP

DGRIKYMQEWWETTYSADGAPLISRGTAQDITQQQEAELCRERAEAALRQ

VIEGTAAVTGEAFFPALVRHISAALGVRYVSIDQAMPEGFQVLAFFADGE

LSPPLFLPYNELPCCFKSLQTGSCCHPSGVQALYPGNALFHDLQVDSYLG

VRLQNAAGDPIGNLCILHDAPLADPDWAQTLLSIFAARAGAELERLMTAQ

ALEQLNGELESRVAERTAALAEREALLQDFLDNANDLIQMVEIDTGRFEF

VNRAWQTVLGYTTDDVAQLTCFDVLAPDCHPHCQAIFAQMQSGDITHLDP

MELTFVGKSGQRVVVEGNVNCRFVTEADGRQRPVSTRGIFRDITARKAAE

LELERREARYRALMEGASDAILLANPEGYLIEVNPQAVDLMGYEHHELVG

MHFTQLHPPEALSTVSEAFGSLAQGGRIEVLNFEILRQDGQRVPVDITGS

VIEVGEETIIQGIFHDIRERLQAEQALRDSEIRFRRVFESNVVGMIFADF

SGHISDANDRFLDMLGYSRQELESGCCLNWADLTPSEYQAQDEAVIAHLQ

HHEAITPWEKAYRHKDGHLVPVLIGVAVLSREEGSCVGVVVDISDRKRYE

IALQESQQFLQTILDTVPLSVFWKDRTSKYLGANQRFLQDADLSSVSELV

GKTDLDLPWGATEAEAYRADDRAVIDSGEAKLGIVETLHQKDGAEIWLET

NKLPLRNLAGDVIGILGTYQDITERRNADIALQRQLVVIEAAINGIAILQ

NERYLYLNSSHVELFGYQSPQELIGQSWRVLYSPEELERFDQEIWPALYE

QMSWRGEVMATRKDGTTFPEHLSLTLSPDNLLICVCEDISDRKQTEAALK

ESEQRYAMLAQAAPVAIFRFDLQGQCTYVNERWSEMTGKPIASAMGDRWL

ETIHPDDRERSQTETQQWLQSGTVTMFQNEARILRDDGSIVWYYCQVLVE

TDANGTQTGYVGTLTDISDRMKAEQALRDSEIRFRRVFESNVVGMLFADL

SGHVTDANDRFLDLIGYSRADLEAHRINWAQITPPEYVEADQRAIDQLQR

YGEILPWEKEYLRPDGRRVAVLISVALLSAIDGRCVCVVVDISDRKRYET

ALQDSQQLLQTVLDTVPLSVFWKDRQSVILGCNQPFASASGFAEVADVLG

-continued

KNNFDLGFTQAEAESYTADDYEVMTSGIAKLGIEETVTPAGSQQRWIETN
KLPLRDGAGNAIGIVGTFQDITDRKQAEEALRESEEKFRQLAEVVDAVFW
ILHLNRTDRVYVSPAYERIWGRPCTELYVTPDAWVEMIHADDREQVLAAI
PKQIQGTFDEEYRIIRPDGTQRWIHDRAFPIRNAQGEIYRLAGIAEDITE
RKRSEEVIRQQAARETVLREISQRIRESLDLQTIFDTACEEIRTCLQADR
VGIFKFYPNTGYDDGEFVAESVVNGLSSVVAIRVHDHCFGENYSTLYAQG
RYQVVDDIYHPGLTSYHADILAQFQVRANLVMPLLCNHELWGLLCIHQCD
GPRHWHQSEVDLGQQLANQLAIAIQQAILYEQLQAELQERQRAESTITQQ
LRQQTALELILQQIRKSLDLPEILAIATQQVQELLHSDRVIVFQVYHDGH
SRIVEEAVTPDLPSLKAMHWEGETWPLDILEHYWQGQPRIVPDVMDDIWT
DCLVDYAQAGQIQSKMVAPILQELRSVEEHRWVCPEGSNKLWGVLVVHAC
QTQRVWQADEAQLLQQIANQLAIAIQQSNLFEQLQQELTERQQAQHQLTE
RNEELIRATRLKDEFLANMSHELRTPLNTILGMTESLQEEDVFGPVNPQQ
LKALKSVERSGLHLLELINDVLNVAKIEAGQMELDYTSTEIALLCRSSLT
FVKQPAFKKRIQLTVNMPPDLPEITLDERRIRQVLINLLNNAVKFTPEGG
HITLDVTPLTPSPPSKEPLYLRFAVTDTGIGITPEDQQRLFQPFVQVDSA
LNRQYQGTGLGLALVKRIVELHGGQVGLTSAVGVGSCFTFDLPYGVEIAL
LPTPLGPQPDLSATTPLQTEAAIPESKALILLAEDNEASISTMVSYLEAK
GYRVAIANNGQAAIEKAQRLRPDLILMDIQMPGMDGLEAISHIRRDPNLA
DIPVIALTALAMSGDRDRCLTAGATDYLSKPVRMKQLVKRIQTLLNP

LEP6406DRAFT_2712
(Bold and underlined region = SEQ ID NO: 21)
(SEQ ID NO: 37)

MRQFSDLNRPLGPISLQVLFRVSLGLQTVGTMALVGYLLYGLLGYGGGVG
AGLPPLLSPLGGSVPLAIALIILICGTWGVTIVLGFFTSRQITQGIDQVI
QASQTLAAGQMPPPLPRGSMIGDLDRLAQSFQQMATAVDLYQVQTQDNLA
ALEEKFTLLFHYSPIPTWIATLEEGRCLLVNDSFCQLMGYAQAEIIGQTC
RQLQFWDNLVDYQNFRHGLTTQGQVRDFECVFRTQSGGTKTLLLTAQVSC
LEGQDCILGIAHDISDRKQAELALRDSEMRLQALLANTPGMIYRYLPIDD
GGGTFLEVSAGAYELLGLEPEQVRQDVSTVWALIHPEDVLTLQDSVEIAV
RDCTDWHWEGRLTTPSGELKWLRGYSRPYVTPAGIVWDGLFTDITALKQT
EISLHQEVSRRRSLFETSIDGIVIVDRAGNVLESNARFANMLGYSLEEVK
TLNLVDFDVNLSSVEIEGKIDKDELCLDHFESRHRRKDGSIYAVEISANT
INWGDQSVSLCICRDITERKRNELALQTSQLRLELALDSSGTGTWDWNME
TNEVFFSEKSWRAMVGYGADDRFGNTITEWESRIHPEDKAQLEVDIAKHL
RGETETYESVHRIRCQDGTYKWNLAQGKVIEWDQAGNPVRFIGLYRDISD
RKQTEIALSNLRSQLERAQEIAHLGHWSFDLDTQKLTWSDEVFRIFDMTT
DQDEPTFREHLEQIHPDDQSSWLERVAEANQGIPQNFCFRILRPTGEVRY
VNSYLELEYEGEQIVRMFGVVMDITEQKQNELALQASEARFRAIFEQAAV
GINQADVSGQFIEANQYFCDLLGYTRDELLALTFQAITHPDDFQQDSVFS
RLLAGELTSVTAQKRYRHKQGDWIWTEVTVSLIHDADGRAISDLAIVLDI
SDLKQANAALQASEARFRTIFEQAAAGINQIDASGRFTEANQYYCDLLGY
SRAELLTLTFVDVLHPEVLAQYWSENNFILSGEIEFLEYEKRLRHKNGDW
IWVKSNISVLRDQAGELAGNLEVVVDIRDRKQAELALHASEDRFRAIFEQ
AAAGINQIDVSGRFTEANQYYCNLLGYSRAELLTLTFVDVIHPEDLAKHW
SEVDRIVRGEIDFLDYERRERHKNGDWIWIKSNISVLRDGAGQVVGNLAV
VVDIRDRKQAELALQESQARFQLLSAASPAVIYTVIETAQGINRFDYISP
AAEEIHEIPVDTLLQNGMLISEQMHPEDREHYAATYAASLQALAPFTCEW
RIITPSGQTKWLRASSCPEQRPDGDIAWHGIALDISTRKQAELESQTLQT
ALVEAQRIAHIGNWAFDLASQKITWSLELFRMFGLDPAQDEPSYPDYLQL
IHPDDRLLLQQAIDRAVTAGTPYSIDYQAQLPDGSTRYHEGRGEVERDCS
GQITRLLGTCLDITDRKRVEQIILQQARQEALLREIGQRIRQSLDLQTIF
DTACQEIRSCLNADRVGIFKFDPDSGYDDGEFIAEACVGGLPSVLTIPVQ
DHCFGDNYATLYAQGHYCVIDDIYSANMADCYIDLLAQFQVRATLVMPLF
CGDVLWGLLCIHQCNAPRQWQQANIDLGQQLANQLAIAIQQAILYEQLQS
ELQERQRAETKISQQLQQQTALGMIWQQIRQSLDLQDILAIVTQQVQVVF
QC
DRVIVFQLFADGRSQIVEEEVLGSLPALRTMHWEDEVWSQDILALYWQG
QPRIVPDVMDDIWTDCLVEYAQAGQIKSKIVAPILQQGHTATGNRWQDPN
HPHKLWGVLVVHACH
ERRTWKAEDAQLLQQIANQLAIAIRQAHLFEQLQ
QELIQRQQAQQQLVERNQELAIANQDLSRATRLKDEFLANMSHELRTPLN
VILGFAQVLNSDLSLQPQHQDYIRIMHRSGDHLLHLINDILDLSKIEANR
ITLEPESIDLFSLLHDLQAMFQERATDKELQFTLALPPDLPQYIVADPNK
LRQVLINLLNNAIKFTQQGQVILSVRLQGAEADQQFHLSSSITSSDTPPT
PSLCFQVIDTGVGIPSEEIDIIFDAFTQARAGKSTLGSTGLGLAISRSLV
KLMGGELTVNSAPDQGSTFQFAIPLHLARGEDVTSEGSLGTVIGLAPGQS
PYRILVVDDQPDNRQLLVTVFSQIGLEVQEAASGADAIAANQQWHPHLIW
MDLRMPDMDGCEATRQIRAQAQELDSENRPEDPVIIAFTAQASMDERTRA
LESGCDDFVSKPIQLNLILSKMADYLDLRYEYAQTVTPAPGAQSATATAI
TLDAQSLRIMPLEWIAALHKAALHCDDQAASSLVQEIPTSQSVLVEGLNR
LIYDYKFESIAQLTSPLLLE cya56DRAFT2_02270
(Bold and underlined region = SEQ ID NO: 10)
(SEQ ID NO: 38)

MLFPPDRLDEEPQILARLMRGERVEHFETVRISKEGKSIEVSATISLLKN
AAGEVVGVSKILRDISDRKQAEKSLQESQQFIQTVIDTVPLPLFWKDRSS
VFLGCNQQFVRILGAPSSKEVVGKTDFDLLPTEEEASAFQADDRGVMESG
QAKLGIEEMLTFANGEQRWLETHKAPLRDWSGNVIGMVGTFQDVTDRKQA
ELELQKNTERLVFALKSGAKEFEMQLQQTTDRLSLALNSGAIGYWEWDIQ
QNILVWDDRMYELYGYLKENYSHLPYEIWANAVHPDDRDLTETLLQQAVL
GKTEYDCEFRIIHPDHSIHFIKAYGTLNRDASGNPLSIIGINFDITDRKQ
AEQIILQQANRETLLRGITQRIRQYLDLSIIFDTACQEIQQLLQSDRVGI
FKFYPESNFDDGEFVAESVVNGFSSAMEVHIHDHCFGEGYAAEYAQGRMQ

VVNDIDNAGLMDCHRDVLAQFQVRANLAIPLLCGNNLWGLLSIHQCAHTR

QWQEDEINLIQQIANQLAIAIQQASLYEQLQEELLIRQQSQSKIAQQLRE

QQTLATITNKIRESLSIKEILAVVTQQVIDVLSGDRAIIFQLFDNGNSQI

VEESVHSNFLNLKALNWDNEVWSQEILDCYWQGKPRIVPDVMNDIWTECL

VEYSLKGQIKSKIVAPILLESHISENHRWVATDGYKKLWGVLVVYACAEQ

REWQDSEAQLLQQVANQLAIAIQQASIYEESQQEIAERKQAEQQLTETNQ

QLARATRLKDEFLANMSHELRTPLNSILGMNEALQEEVFGGINERQLKAL

QTIESSSRHLLALINDILDVAKIESGQVTLELTATDIDSLCKSSLAFIKQ

QALTKRIQLIPRIPKHLPKIMLDERRIRQVLINLLNNAVKFTLEGGTITL

EVSQVQLESSTTNPTPLKYLKIAVIDTGIGISAENIQKLFQPFIQIDSAL

NRQYNGTGLGLALVKRLVEIHGGTVELTSELGVGSCFAINLPINIVSPAI

EEQTEQDLSGQSQIGQSQTEGLISPLILLAEDNEANIATFSSYLEAMGYR

ILSATDGQQAIDLAKAEHPDLILMDIQMPVMDGLEAIKQIRLDPNLADIP

IIALTALAMEGDRERCLAVGANEYLSKPIKLKALADTIRNILKNRN

Ga0039498_104087
(Bold and underlined region = SEQ ID NO: 11)
(SEQ ID NO: 39)

VVESSDDAIITKTIEGIITSWNPAAERLFGYSEAEAIGQPISMLFPPDRL

DEEPQIFARLMRGERVEHFETVRISKEGKSIEVSATISLLKNAAGEVVGV

SKILRDISDRKQAEKSLQESQQFIQTVIDTVPLPLFWKDRSSVFLGCNQQ

FVRILGAPSSKEVVGKTDFDLLPTEEEASAFQADDRGVMESGQAKLGIEE

MLTFANGEQRWLETHKAPLRDWSGNVIGMVGTFQDVTDRKQAELELQKNT

ERLVFALKSGAIGWWEWDLQSDIAVWDDRVYELYGVSNQTNPQPTYEIWK

NALHPHDAEAIEAINRKIAAGQIDEYDTEFRVVHPDGSIHFLKAYGMLKR

DADGKPQSITGINFDVSDRKEFEVQLQQTTDRLSLALKSGAIGCWEWDIQ

QDFLVWDDRMYELYGYLKENYSHLPYEIWANAVHPDDRNATETLLQKAIL

GQAEYDYEFRVIHPDRSVHFIKAYGKVKQDSQGNAESMIGINFDISDRKQ

AEQIILQQANRETLLRAITQRIRQSLDLSIIFDTACQEIQQLLQSDRVGI

FKFYPESNFDDGEFVAESVVDGFTSAMEVHIHDHCFGEGYAAAYAQGRIQ

VLNDIDNAGLMDCHRDVLAEFQVRANLVIPLLCGNNLWGLVCIHQCAHTR

QWQEHEINLIQQIANQLAIAIQQASLYEQLQEELLIRQQSQSKIAQQLRE

QQTLATITNKIRESLSIKEILAVVTQQVKDMLSGDRAIIFQLFDNGNSQI

VEESVHSNFLNLKALNWDNEVWSQEILDCYWQGKPRIVPDVMNDIWTECL

VEYSLKGQIKSKIVAPILLESHISENHRWVATDGYKKLWGVLVVHACAEQ

REWQDSEAQLLQQIANQLAIAIQQANLYEQSQQEIAERKQAEQQLTETNQ

QLARATRLKDEFLANMSHELRTPLNSILGMNEALQEEVFGGINERQLKAL

QTIESSSRHLLALINDILDVAKIESGQVTLELTATDLDSLCQSSLAFIKQ

QALAKRIKLIPRIPKHLPEIMLDERRIRQVLINLLNNAVKFTLEGGTITL

EVSQVQRESSTTNPTPLNYLKIAVIDTGIGISAENIQKLFQPFIQIDSAL

NRQYNGTGLGLALVKRLVEIHGGTVELTSELGVGSCFAINLPINVGFPAI

EEQTEQDLSGQSQIGQSQTEGLISPLILLAEDNEANIVTFSSYLEAKGYR

ILLANDGQQAIDLAKAEHPDLILMDIQMPVMDGLEAIKQIRLDPNLADIP

IIALTALVMEGDHERCLAVGANEYLSKPIKLKQLATIIQQILVRT

Ga0039499_10213
(Bold and underlined region = SEQ ID NO: 22)
(SEQ ID NO: 40)

VVESSDDAIITKTIEGIITSWNPAAERLFGYSEAEAIGQPISMLFPPDRL

DEEPQIFARLMRGERVEHFETVRISKEGKSIEVSATISLLKNAAGEVVGV

SKILRDISDRKQAEKSLQESQQFIQTVIDTVPLPLFWKDRSSVFLGCNQQ

FVRILGAPSSKEVVGKTDFDLLPTEEEASAFQADDRGVMESGQAKLGIEE

MLTFANGEQRWLETHKAPLRDWSGNVIGMVGTFQDVTDRKQAELELQKNT

ERLVFALKSGAIGWWEWDLQSDIAVWDDRVYELYGVSNQTNPQPTYEIWK

NALHPHDAEAIEAINRKIAAGQIDEYDTEFRVVHPDGSIHFLKAYGMLKR

DADGKPQSITGINFDVSDRKEFEVQLQQTTDRLSLALKSGAIGCWEWDIQ

QDFLVWDDRMYELYGYLKENYSHLPYEIWANAVHPDDRNATETLLQKAIL

GQAEYDYEFRVIHPDRSVHFIKAYGKVKQDSQGNAESMIGINFDISDRKQ

AEQIILQQANRETLLRAITQRIRQSLDLSIIFDTACQEIQQLLQSDRVGI

FKFYPESNFDDGEFVAESVVDGFTSAMEVHIHDHCFGEGYAAAYAQGRIQ

VLNDIDNAGLMDCHRDVLAEFQVRANLVIPLLCGNNLWGLVCIHQCAHTR

QWQEHEINLIQQIANQLAIAIQQASLYEQLQEELLIRQQSQSKIAQQLRE

QQTLATITNKIRESLSIKEILAVVTQQVKDMLSGDRAIIFQLFDNGNSQI

VEESVHSNFLNLKALNWDNEVWSQEILDCYWQGKPRIVPDVMNDIWTECL

VEYSLKGQIKSKIVAPILLESHISENHRWVATDGYKKLWGVLVVHACAEQ

REWQDSEAQLLQQIANQLAIAIQQANLYEQSQQEIAERKQAEQQLTETNQ

QLARATRLKDEFLANMSHELRTPLNSILGMNEALQEEVFGGINERQLKAL

QTIESSSRHLLALINDILDVAKIESGQVTLELTATDIDSLCKSSLAFIKQ

QALTKRIQLIPRIPKHLPKIMLDERRIRQVLINLLNNAVKFTLEGGTITL

EVSQVQLESSTTNPTPLKYLKIAVIDTGIGISAENIQKLFQPFIQIDSAL

NRQYNGTGLGLALVKRLVEIHGGTVELTSELGVGSCFAINLPINIVSPAI

EEQTEQDLSGQSQIGQSQTEGLISPLILLAEDNEANIATFSSYLEAKGYR

ILSATDGQQAIDLVKAEHPDLILMDIQMPVMDGLEAIKQIRLDPNLADIP

IIALTALAMEGDHERCLAVGANEYLSKPIKLKALADTIRNILKNRN

Cal6303_3693
(Bold and underlined region = SEQ ID NO: 15)
(SEQ ID NO: 41)

MFNNTTVLTTSELKSAIVRDPLIVKPDMTLIDAIAQMSGVRTLCETTQTI

DGQLDNLYLEARASCVLIVEEGKLLGIFTERDVVRLSAQQYSFENLKIRE

VMTHPVISLRESDFTDLFFPVNLLQQHHIRHIPILDQQDQVVGLLTNESL

RQSSRPVDLLRLRLVYEVMTKEVICGAPDSSMLAIAQLMAKHRVSSIIIV

QPDNSETESLQIPVGIITERDIVQFQALGLNLKTCLAKVVMSTPIFAVKP

NDSLWLVQQLMEQRLIHRLAVTGEQGELLGIVTQTSLLKALNPLEIYKLA

EVLEKKVVKLEAEKIALLETRTVELEQQIEARTFVIKAKAERERLVLEIA

TQIRSSLSLQTILDTTVAEVRQLLGCDRVNIWQFDANWQTITVAESTDSP

MSLLGKRVIDTCFQDDYAKIYRQGRICVMRDIYKAKISDYHRDMLIRLQT

-continued

RAKILVPLFCGEQLWGLLNVTESQHPRNWEAEEIELLEALSVQLAIALQQ

ATNHQKLQEELHERQRIELILQKLVTGTATVTGEDFFPALVRHIAEALNV

RYAVVTEIVDNKLHTLGFWANGALKPSMSYCAVDNACEYSLRDGEFYCQS

KVQELFPEDLNLAAMEADSYVGIALKDDLGNAIGNLCILDTQPLTEAQRI

EAIAILQVFAARATAELQRQTANNALHRLNQNLEQRVEERTEQLQAREAK

IAQQLRLQKTLGVIIQKIRESLDISEILVTVTHQVKELLQSDRVIVFRLL

GDGRSQIVQEAVSNEFPVLKDRQWENEVWSQEILPGYWQGKPRIVPDVMN

DIWTECLVEYSREGKIQSKIVAPILQDLYSGERDLTVERGGLLPLREKHR

WVAPYLTNKLWGVLVVHACEEKRVWKDSEAELLQQIANQLAIAIQQASLF

EQLQQELAERQQAEAKLTDSNQQLAVSNQQLARVTRLKDEFLANMSHELR

TPLNAILGMTEGLQEQVFGVVNEQQLKALQLVERSGLHLLELINDILDVA

KIEAGQIELDYAPTSVAHLCESSLVFIKQQALQKRIQLEIKLQINLPDLF

VDERRIRQVLINLLNNAVKFTPERGCITLEVTQITLNISDADSPEQYFLR

FAVRDTGIGISPENIKNLFQPFVQIDSALNRQYTGTGLGLALVKRIIELH

GGLVGLTSELGVGSCFTIDLPFAPNHTSPSVIAAGDQPVATSELDPSSPN

EVWLTPLILLAEDNEANISTVSSYLKAKGYRIVLAQNGQEAIDVAKTHH

PDLILMDIQMPGMDGLEAMRQIRLDPNLAEIPIVALTALAMTGDRDRCLT

AGANDYLSKPIKLKQLANTIQQLTNAVKDNK fdiDRAFT29700
(Bold and underlined region = SEQ ID NO: 12)
(SEQ ID NO: 42)

MFKHTTALTSSELKSAIVRNPLIVGLDTLVIDAIALMSGVRAVCDANKLD

ELDIDARSSCVLVVDNHSLLGIFTEKDVVRLCAQQRPLENLAIREVMIHP

VIALHESDLTDVFFAVNLLQQYHIRHLPILDEQDLVVGLLTNETLRQSSR

AINLLRLRLAFEVMSREVICAAPDSSILAIAQLMTAHRVSSVMIVQPGGS

EAAPVKIPVGILTERDIVQFHALGLNLETCCAHMVMSTPIFAVKPEDSLL

VVQQIMEQRLIRRLAVTGEQGELLGILTQSSLLQALNPLELYKLAEVLEK

KVVQLETEKVQLLEARTAELEQQVEARTTALTKTKAEQAQLVSDIAMQIRS

SLSLQTILETTVQQVRQFLGCDRVIILRFEEDGPAAVVAESTNSSLSLMG

RWIKDGCFQKNYRENYCQGQIRVVKDIYTTQMTNCHRQMLISLQIRAKIL

IPLLCNGELWGLLNVSESDKAREWQQSEVELLQALSVHLEIALQQATIHQ

QLQEQLRDRQRAEMTLQKLVTGTAAVTGDDFFPALVSHIAEALNVCCALV

NELVGDKLYSLGFWENGALQPAISYHIAQTPCEHSLRDGEFYCQSQLQTI

FPDNLALQTMQADSYLGIALKDNLGNTIGNLCILDRQPLSQTKYTEAIAI

LQVFAARAAAELQRIAANDALHRLNQDLEARVEQRTEELQAREVELHKTS

ERLALSLKSGGIGCWEWDILQNTILWDERMSELYGVTPQSDSCIVYDTWT

KKLHPDDRTQTETLLQQAVLGQAEYNTEFRVVHPDGSIYFIKAYGVVVRD

EQGSPQKMIGVHFDISDRKRAEIALQSSELRFRRIFDSNVVGMLFADFKG

DITDANDRFLQMVGYTREELNAGALSWKAITPSEYVFADVGALKHLSQYG

AMNPWEKEYYRKDGSKIPVLLGVAMLPGSDYQTICVVVDISEQKAALQER

QQAEMQLQQQARHKQLLWNITQTIRQSLDIEVIINAAVTEIRQVLGVDRV

ALYRFRADWSGEFVAESVAANWVKLVGSQVKKVWEDTYLQETQGGRFQNY

-continued

ETLVVADIDQAGLQPCHIELLQQFQAKAYVITPIFVNESLWGLFAMYHNH

RPHSWTTWEIELLRQIANQLAIAIQQASLYEKNQSELLVRQQAEARIALQ

LRRQQTLGAIIEQIRKSLDLNEILATVTQQVKDLMHCDRVIVFRLFADGR

SKIAEEAVSSEFVSLKNRHWGNEIWSQEILDFYWQGKPRIVPDVMNDLWT

HCLVEYSQEGQIQSKIVAPILQEVRDQNHRWVSPWATNKLWGILVVHACQ

ERRVWKNSEAQILQQIANQLAIAIQQASLFEQLQQELAERQQAEAKLTEI

NQQLAFSNEELARATRLKDEFLANMSHELRTPLNAILGMTEGLQDEVFGS

INQQQLKALDTIERSGSHLLELINDILDVAKIEAGQIKLDYTSISVANLC

QSSLAFIKQQALQKRIQLETKIPQNLPHLLVDERRIRQVLINLLNNAVKF

TPEGGRITLEVNQLSPDTTNNSLRQHFLQIAVKDTGIGIAPENINKLFKP

FIQIDSALNRQYAGTGLGLALVKRIVELHGGRVGLSSELGVGSCFTIELP

YTPVFPVVEDTQPDVTPEFVSSNLDHAGPLILLAEDNEANISTVSSYLKA

KGYRILLANNGKEAIELATTQYPNLILMDIQMPLMDGLEAIKLIRLDPNL

VNTPIVALTALAMNGDRDRCIAAGANDYLSKPVKLKQLATTIQQLLST

Osc7112_5903
(Bold and underlined region = SEQ ID NO: 14)
(SEQ ID NO: 43)

MFMRTTALTPIELRTAIVREPLVVSPDTTVMDAIAQMSGVRSLCNTPRTA

DGQLDDLHLEARSSCVLVVENEQLVGVLTERDVVRLSAQQRCLENVAMRE

VMAHPVVTLRESAFTDLFLAINLLREHHIRHLPILDELDRLVGLVTHESL

RQTSRPIDLLRLRTVAEVMTREVICAAPDSSLLTIVQLMAEHRVSSVMIV

HPGGISTEPLQIPVGILTERDIVQFQALGLNLETCLAQAVMSTPIFAVRS

DDSLWTVQQIVEQRSIRRLAVTGELGELLGIVTQTSLLQALSPLELYKLV

QKWEEKVVRLEAEKVALLANRNVELEQQVAARTAALKAKADREQLLNTIA

EQIRSSLNLSDILHTTVQEIHSLLGCDRVIIYQFQSELSGTVIAEAITDT

GRSVLYREARDPCMSPEWLEPYRQGRIRVINDIYDAEMTQCHQEMLVGFD

IRAKLMVPIVIEQQLRGLTIASYRAAPHSWTTDEIELLRQVSLQVAIALG

QAAIQQKLQNELVKRQRIEATLIESEQRYAALAAAAPVGIFRTDAEGLCT

YVNDRYFQIGGLRPGGTIGQGWQQGIHPDDRDLVIAQWEQFIQGNDSFEL

EYRFQRPDGTVTWVYGQCVAELDANGNRSGYIGTITDISDRKRTEVRLQE

SEERYASLVAAVPVGIFRADALGKCIYVNHWWCQISGLTPKTAVGEGWKQ

GLHPDDRDWVMAECEQSLQRNRSFQLEYRLQRPDGAVAWVYGQSVPELDA

DGQVVGYVGTTTDISDRKQAEQKLQQLNQQLETKVAERTQELWQVNSLQR

AILDCADYSIISTDPTGIIQTFNAAAERMLGYSAREIIGKATPLLIHDAN

EVIDRASSLSAELGQNIPPTFEVFVAKARQAPVSEEEWSYIRKDGSRFPV

SLSISTLKDVNQQIIGFLGIAKDISDRKRAELELQKLSDRLALSLKSGAI

GCWDFDLVQNTIFWDERMYELYGVTKQSDSPLPYDIWANRLHPEDRTATE

TLLQQAVLGQANFETEFRVLHPDGSLHFIKTFGVLVRDARGNPQSMIGVN

LDISRRKQAELQRQQLIQELSAFKQALDQSAIVVITDREGVISYVNDRFC

AVSGYSRDRLIGQTHRIVNSGYHPPAFFQDLWDTINSSQIWRGEICNRAK

NGSLYWVATTIVPFLDEQGRPFQYLAIRFDITDRKLAEATLQQENTFRQQ

IVENMVQGLCVFHQFEEFPFVSFTVWNQQMQTITGYTLEEINRLGWYQTL

-continued

YPNLEDREQAIANCRQMQPIAVEREIQRQDGQRRTISISTSVLSGDDGHL
YSLALIQDITDRQQTERENRLLKERLEFLLASSPAMIYSCKPYGDYDATF
MSKNIEAILGYKAEEFLSESGFWANHIHPEDAPRVFAHISDLFEHNTHQH
EYRFLHRDGHYVWLRDELRLLRDEAGKPIEIVGYFADISDVKQTEETLKI
QLAAIEAAIDGIAIIQGDTYLYLNQAHLELFGYERPEEVSGKSWKLLYSQ
QELERFEREVFPVLGRDRAWQGEAIALRKDGSTFAEGLSLTLTDDGLLIC
VCRDISDRKQIEAELAESEAKFRRLVEGVNDLIWSCEPDGILTYVSPQFK
TMFGWEEGAWIGKSFIYLVHPDDRPLVVTGYRKNIKFGKKSSDYEFRHRH
RDGNYVWVRSSATPVMNAEGELISIQGILSDISDRKQAELARESSEIRFR
RVFESSVSGMMFADFQGNITDANDRFLQMVGYTREELNAGMIHWDAMTPP
EYLPADFLAFERLRQDGEIESLEKEYYRKDGSRISVLLGAALLPGSEDQT
ICVLVDISDRKQAQKALQESQQFLQTVLDTIPLSVFWKNRESVFLGCNQQ
FATTLGLQSTSESIGKRDLDICQEEVEANEYCAMDRRLMETGEAILGIEE
TLTLPNGKPIFIETHKAPLRDCSGNVIGLVGTFQDITDRKEAELRLQQQA
KQERLLGAITKRMRSSLHLDEILNSTVEEIHQILQSDRTLVYRVFPEGTG
TAIAESVSPNRLKLLDILFPEEVFPEENYERYIEGRVYALNDSEDANESI
VPCLVEFLADIQVRAKLVVPIIQNQSLWGLLIVHQCDRPRQWQEWEINLL
KQIANQLAIAIQQSYLYEQVQSELAIRKQTEKAIALQLQRQRTLGEIAQQ
IRESLDINEILATVTQQVKEILQGDRIVVFRLFGDGRSQIVEEAVSSEFP
ALKDHHWEDELWSPEILNRYWQGKPRIVPDVMTDIWTDCLVEYATVCQVQ
SKIVAPILQEVRSSESHRWVAPGQTKKLWGVLVVHACREQRVWQESEAQL
LQQIANQLAIAIQQASLFKQLQQELTERQQAQQQLTERNEQLAVSNEELA
RATRLKDEFLANMSHELRTPLNAILGMSEGLQEQVFGIINEEQIKALQTI
ERSSSHLLELINDILDVAKIESGQMELDCTPVSINHLCQSSLAFIKQQAL
QKRIQLEIKVPLNLPDLLIDERRMRQVLINLLNNAVKFTPNGGRITLEVS
SQQRRADPDSADSPPHFLVKETLRISVIDTGIGIAPEHINKLFQPFIQID
GALNRQYTGTGLGLALVKRIVELHGGQVLLTSTVGVGSCFTIDLPCTGCA
PSSVDVESQTEPRIEPSGPEQQGGSPLILLAEDNEANISTVSSYLRAKGY
RILLAKDGEEAVALAKSENPNLILMDIQMPGMDGLEAMQQIRCDPNLVDL
PIVALTALAMTGDRDRCLAAGANDYLTKPVKLKQLASTIQQLLAK

Mvag_PCC9802_DRAFT2_00054240

(SEQ ID NO: 44)

MFMRTTALTPIELRTAIVREPLVVSPDTTVMDAIAQMSGVRSLCNTTRTA
DGQLDDLHLEARSSCVLVVENEQLVGVLTERDVVRLSAQQRSLENLVLRE
VMAHPVVTLRESAFTDLFFAINLLQQHHIRHLPILDDLDRLVGLVTHESL
RQTSRPIDLLRLRMVAEVMTREVICAAPDSSLLAIAQLMAENRVSSVVIV
HPGGISTEPLQIPVGILTERDIVQFQTLGLNLETCLAQAVMSTPIFAVRP
DDSLWTVQEIVEQRSIRRLAVTGELGELLGIVTQTSLLQALNPLELYKLV
QKWEEKVVRLEAEKVALLANRNVELEQQVEARTAALKAKADREQLLNTIA
EQIRSSLNLSDILQTTVQEIHSLLGCDRVIIYQFRSDFSGTVIAEAITDT
GRSVLHREAHDPCMSPEWLEPYRQGRIRIINDIYGEPMTQCHQEMLVGFD
IRAKLMVPIVIEEQLRGLMIASYRASAHSWTTDEIELLRQVSLQVAIALG

-continued

QAMIQQKLQNELVKRQRIEATLIESEQRYAALAAAAPVGIFRTDATGLCT
YVNDRYFQISGLTPGATIGHGWQQGVHPDDRDWVMVEWKQFIQGNRSFEL
EYRFQCPDGTVTWVYGQCVAELDANGHRSGYIGTITDISARKRTEVCLQE
SEERYATLVAAAPVGIFRADAVGNCIYVNDRWCQISGLTPKTAVGEGWQQ
GLHPDDRDCVIAEWEQSVQRNRPFQLEYRFQRPDGGVTSVYGQSVAERDA
DGQVVGYVGTTTDITDRKQAEQKLQQLNQQLETKVAERTQELWQVNSLQR
AILDCADYSIISSDPSGIIQTLNAAGERMLGYSAQEIIGQATPALIHDAN
EVIDRAASLSAELGQNIPPGFEVFVAKARQGLVSEEEWSYIRKDGSRFPV
SLSITALKDVHQQIIGFLGIAKDISDRKRAEAELQKLSERLALSLKSGAI
ASWEWNLGQNTILGDERMYELFAVTKPSDACQVYDFWANRLHPDDRIPTE
TLLHQAVLGQAEYDTEYRIVHPDGSLHFIKAYGVVVRDAQSNPQSMIGVN
FDISDRKQAELQRQQLIQELSAFKQALDQSAIVVITDREGVISYVNDRFC
VVSGYSRDRLIGQTHRLVNSGYHPPAFFQDLWRTINSSQIWRGEICNLAK
NGSLYWVATTIVPFLDEQGRPFQYLAIGFDITDRKLAEATLQQENTFRQQ
IVENMAEGLCVFHQVEEFPFVRFTVWNQQMQAITGYTLEEINRLGWYQTL
YPNLEDREQAIANCRQMQPIAVEREIQRQDGQRRTISISTSVLSGDDGHL
YALALIQDITHRQQTERENRLLKERLEFLLASSPAMIYSCKPYGDYELTF
MSKNMSAILGYKPEEFLSESGFWANHLHPEDAPRVFADLSALFEYNTHQH
EYRFLHHDGHYVWLRDELRVVRDEEGCPTEIIGYFADISDVKQTEETLKI
QLAAIEAAIDGIAIMQGDTYLYLNQAHLELFGYEHPQELLGKTWQLLYSP
EELERFEREVFPVLGRDRAWQGEAIGTRKDGSTFAEGLSLTLTENGLLIC
VCRDISDRKQIEAELAESEAKFRRLVEGANDLIWSCEPDGILTYVSPQFK
TMFGWDESAWIGKSFIYLVHPDDRSLVVTDYRENIKSGKKSSDYEFRHRH
RDGNYVWVRSSATPVINAEGELISIQGILSDISDRKEAEIARESSEIRFR
RVFESSVSGMIFADFQGNIIDANDRFLQMVGYTREELDAGLIHWDAMTPP
EYFPADVLAMERVMQDGAIEPWEKEYYRKDGSRISVLIGVALLPDSDDQT
ICVLVDISERKQAQKALQESQQFLQTVLDTIPLAVFWKNRESVFLGCNQQ
FAQTLGLPSTTESIGKKDLDICQEEVEANEYCAMDRRLMETGEAILGIEE
TLTLPNGKLIFIETHKAPLRDCSDNVIGLVGTFQDITDRKEAEQKLQQQA
KQERLLGAITKRMRSSLNLDEILNSTVEEIHQLLQSDRTLVYRVFPEGTG
AAIAESVSPNRLKLLDILFPEEVFPEDTYERYIQGRVYALNDSEDENESI
VPCLVEFLADIEVRAKLVVPIIQNQTLWGLLIVHQCDRPRQWQDWEINLL
KQIANQLAIAIQQSYLYEQVQSELAIRKQTENVIALQLQRQRTLGAIAQQ
IRESLDINQILAAVTQQVKEILQG
DRIIVFRLFGDGRSQIVEEAVSSEFPALKDHHWEDERWSQEILNRYWQG
KPRIVPNVMTDIWTDCLVEYASVGQVQSKIVAPILQEVRSSESHRWIAPG
QTKKLWGVLVVH
ACREQRVWQESEAQL
LQQIANQLAIAIQQASLFKQLQQELTERQQAQQQLTERNQQLGASNEELA
RATRLKDEFLANMSHELRTPLNAILGMSEGLQEQVFGIVNEQQIKALQTI

-continued

ERSSSHLLELINDILDVAKIESGQMELDCTPVSINHLCQSSLAFIKQQAL
QKRIQLEIQMPLNLPDLLIDERRMRQVLINLLNNAVKFTPNGGRITLEVS
RQQRPADPDSADSPPHFLVKETLRIAVIDTGIGIAPEHINKLFQPFIQID
GALNRQYTGTGLGLALVKRIVELHGGQVGLTSTVGVGSCFTIDLPCTACA
PSSVYLESQTEPRIEPSQPEEGGSPLILLAEDNEANITTISSYLRAKGYR
ILLAKNGEEAIALAKSENPNLILMDIQMPGMDGLEAMQRIRSDPNLVDLP
IIALTALAMTGDRDRCLAAGANDYLTKPVKLKQLASTIQQLLASK

Cyan7425_1390
(Bold and underlined region = SEQ ID NO: 17)
(SEQ ID NO: 45)

MPTQKVLESAIVSNPLIVLPETTVIDAIAQMSRAQITGSALSITATNEVH
QPAHSSCVLIVADCQLIGIFTAADVLRLIVQQRLQEGLLIREVMTHPVIT
LPGVAFTDLSVAINLLQQHRIRHLPLVDSANYPVGLLTYETLLATQNTVL
LEAATLEPELQVAARSTARKLEVEWEKLVAEVASKIRSSLSLSTILNTTV
EQVRQVLGCERVNIWQFETDSQIAVVAESTDFSISLIGEQVIDNCFQRGK
AERYRQGSIRVVSDIYTTEMSDCHRQLLTRLRTRAKILVPLICGRTLWGF
LNASESNQRRDWQPAEIELLQTLSLHLSIALQQATTHQRLQKELLARKQV
EACLRDREQRYGSLISTAPVGFFWTDAEGECIYANDRWCEIAGLSLEAAE
GQGWQAAIHPEDRERVRAEWQQAIQESRPFQLEYRFQRPDGAVIWVYGQV
VAEKNDMGAIGGYVGTITDIHARKQAEQQLHNLIAGTAAATGQDFFPVLV
QHIAQALNVPYVLVTEKIGGDRLCTLAYWANGELKPTLSLPIANTPCSHV
LQDGKFYCASQIQQQFANTLEGIELGAESYLGIALRDSQGEAIGTLCIVD
HQPIQEPQRLENLLVAFAARAAAELERERATQTLAQLNRELETKVAERTA
ALKASEERWQLVLKGANDGIWDWDLTTNRVFFSERWKNMRGLNQEQVSDR
LEEWSRSIHPDDYNCVMANLEAHLAGQTEFFEQEYRVRCQDGSYIWVLAR
GQALRDSSGQVVRMAGSEIDITARKQAEQENLRLKERLQFLLSVNPAVIF
TSEPGEDYAITFISDNVQTLMGYTPGDFITHPRFWADRIYPEDAPRIFAG
LSRLFEQGYHTHEYRFLYQDGFYHWVRNELRLFCDPAGHPLEIVGYCADI
SDLKQVEMELAESEAQFRCMVEGVNDLIWSVNDQNRFTYLSPQFATLFGW
EGREWIGHFARELIHPDDHPKLADYTQQVMEGRSLDNLEFRHRHQDGHFV
WVRSSATPLISSTGNVIGAQGILSDITTLKQAEMALQQSENRFRRVFSSN
VVGMMFTDFSGAIFDANDRFLAMVGYSRAELQAGELNWVTLTPLEYVQWD
IQAMLHLEKYGSIEPWEKEYYRADGSRIAVLIGVALLSETGSSCVCVVMD
ISDRKHAEQTIQQQIQKETLLRELTQRIRQSLDLQTIFTTACQEIRQVLQ
ADRVGIFQFYPTSNHNDGEFVAESVVEGLPSVLATPLHDHCFGEQYAPLY
VQGRYVAMEDISQLDPCHTDLLNQFQVKANLVIPLISGNDLWGLLCIHQC
RSTRRWQATEIDLSQQLATQLAIAFQQAVLYKQTQLELQERQLAETTIAQ
QLRQQKNLGTIIQHIRESLDLQQILATVTQQVKEALQGDRVIVFQLFPNG
KSRIVEEAVSSGLTVLKAGHWEDEVWPQEILPYYWQGQPRIVADVMDDRW
TDCLVGYSKQGEIVSKIVAPILQDIHTFEENPWANPSKRHQLWGVLVIHA
CRQPRVWKAEEAQLLQQIANQLAIAIQQANLFEQLQQELTERQQTQQQLT
ERNQQLAESNQKLAHATRLKDEFLANMSHELRTPLNAILGMTEGLTDVIF

-continued

GSINTQQKKALQTIDRSAHHLLELINDILDVAKIESGQIELNCAATSVLL
LCQSSLSFIKQQALRKNIHLEVQIPPHVPDVWVDERRIRQVLINLLNNAV
KFTPEGGSVTLSVQRQLIVQDPPPLQGITKVRVHRTPIEQQLGIQLQTSQ
FEVHNYLRIAVTDTGIGIPSHYLHKLFQPFVQIDSALNRQYTGTGLGLAL
VKRIVELHGGEVGVTSTEGAGSCFTIDLPCVSGSSSSSSPFLAESSPAHL
SDPANPPCILLAEDNEANISTISSYLKAKGYRVLVAKNGQEAIDLGQAAQ
PDLILMDIQMPGVDGLSAIQQLRQAPSSAHLPIIALTALAMNGDRDRCLA
AGANEYLSKPVKLSQLVILIQQLLTQS

Cyan7822_4053
(Bold and underlined region = SEQ ID NO: 5)
(SEQ ID NO: 46)

MIIPFPQLTPAIVRNPLVLSPDTKVLEAITSLINQRSQPVKSNCAVVVEN
GQIVGIVTKGDILVALAQSQTLDFLTISQVMSSPVVMLRESEFTGLESAI
NLFQTHSIDHLPIIDSENHLVGLLTSDSLSAVIQSYIMKDQKIAEKKTTL
QLENSFQAAILDEINHISSPKQEQRKLQESELNYTSLAEIAPIGIFRTDT
QGYCVYVNPRWCEIAGLTSEEAKGKGWEQVLHPDDDDEVSAQWYRSVEEN
RLFQLEYRFKRPNGEIRYVYGQSVALRDINQQIIGYLGTITDITEQKKTE
YRLKEALRLAKLGNWELDVQNNIGYWSEEVFHIFGREPQPFSPSFDGFLE
LVHPDDRSKVVASYTQHLEKRIPHEVVHRVPMPDGRIKVVVERCETAYDA
EGKPIHSLGTVQDITEYYKQETILKKLLAGTSNTLTQEFFSALVRHIAEA
LEVSYVIIAELIDERLHTFAFWGDEQLQKNIDVAICQTPCEYVIKDGFFY
CSHSIQEQFPQNTHLAQMQAESYLGIVLTDKNSHPIGILCVLDVKPMDRE
TAEMIQQILQIFAGRASAELERKRSDEALQQLKATLEAQVEERTQQLQES
QRFIQQITDQSPSILYLYDLQEQRNIYINQEVSRILGYSPTEIQEMGNLI
ISRLIHPQDLSRFNRYLEQLKQAQDHEILGVEYRFQDIKGQWRWFSGRDA
VFSRDSQGRVKQVIGVAQDITERKQAEQTLYLQAQQEKLLREINQRIRQS
LDLQTIFDTACQEILLLLQVDRVGIFRFDPESHYDDGEFIAEAMVAGLPS
AIAIHVHDHCFGEKFSSLYAQGKFLAVDDINNSELMDCHREILSQFQIKA
HLVLPLLCEEQLWGLLCVHQCYDTRHWKEAEIKLLQQITHQLTIAIQQAS
LYEQIRQKLRQQQAIAAIVQQVRQSLNIEEILNTITQDVRALFDCDRVII
FRLYSDGGSRIIEESVSTEFLPLKYCHWDDETWSQDILNLYWQGQPRIVP
DVMNDIYTECLHEYSREGQIQSKIVAPILLDLKEKENHRWVASTNSHKLW
GILVVHACREKRVWQNSEAQLLQQIANQLAIAIQQASLFEQLQVEIEDKQ
QKNAELDRATRLKDEFLANMSHELRTPLNAILGMTEGLQDEIFGQINERQ
RKSLKIIEQAGNHLLELINDILDVSKIESGQLELHCTSTEIIPLCQSSLA
FVKQQAVKKRIQLDFNISSNILMLTLDERRIRQVIINLLNNAVKFTPEGG
KVGLEVVQIGENTVRFAVKDTGIGIAAENIPKLFQPFMQIDSALNRQYTG
TGLGLALVKRLVDLHGGEVSVTSELGVGSCFSVDLPLMESCSTDNFFDFQ
TPLTPEVEANSVNLKNAPLILLAEDNETNITTISNYLKAKKYKLILAKNG
KEAISLAQSQQPDLILMDICLPGINGLEAIQQIRQLPDLKDIPIIAVTAL
ALTGDRERCLEAGANEYLSKPLKLKELVALIQSLLE

-continued

Spi9445_1327
(Bold and underlined region = SEQ ID NO: 19)
(SEQ ID NO: 47)

MQSHSFSSIDVTEAICPRPHVISPTATVLEAIALMSGLSAPEVAPPDPQD
PHSTDLSPLAPLWKGGKEGGEEGGGISSCVLVVVERDSDETQGQRVVGIL
TERDIVRLSAQQQDIRELSVGEAMTQPVLTLRPSELTDIFSLLQFLEQHH
LRHVPIVDEQERLMGLISHETLRNLARPVDLLRLRSVQEVMTQTVLTASP
DASLLEIAQLLAENRLSSVILTRPLAGGDLGEYPVGIVTERDVVQFQALG
GNFGEILAEEVMSSPLFTLRPDADLWTAQQAMEKRRIRRVVVTGEGGELL
GIVTQTSLLRSFNPLELYRLAEVLEQKVARLEAERVTLLERRTQELEQQV
QERTQTIEAQAERVRLLLDIATSLRNSLDLGTILQTAVDEVRRVLECDRV
MIYQLEEGLRGEIIAESMISGGRSVLHREANDPCVTPEWLESYRQGRVRV
VRDIYEESLSLCHQEMLLSFEIRAKLMVPIVLEEHLWGLMIASYRDQPRD
WQTWEVELLQALSLQLAIALQQAGQHQQLQNEIRERQQAEQDLAALNAQL
EARVAQRTAELESREARYHALMEGASDAILLATPQGYIIEANAAAEELFG
YSRSELTQLHYSQLCPPEELQPVTQVWQSLVNPQQRVLWDGFILHAEGHS
IPIALSGTMIEVGDSIIFQGIFRDISARQQAEAALAKLSQRLSIALSSAA
LGCWEWDIAQNCLTWDKRMYALYGVESRVPPDDPSTVTVAYEVWSKGVHP
EDRQRTETLLQQALLGEAEYNTEFRVVHPDGSLHYIRAYGVVLRDAAGHP
QSMIGVNLDVTDTHEAQRELQASETRFRQVFDSNVVGMMFTNFVGEITEA
NDRFLAMLGYSRDDLHAGRLNWADLTPPEYQQQDVEAIYHLLTYNSIDPF
EKVYLHRDGHPVAVLLGVAMVCPAEGTCVCVVVDISDRKQAEIALQESQL
RLELALESSNTGLWDWNMQTGELWFNKQWKTMLGYGEDELENQLREWESR
VHPDDLPQTYQEVEQHIKGQTDVYRNEHRLRGKDGSYHWVLAQGRIVERD
GVGNPLRFIGTHTDISDRKNNELERQKLLQELSSFKFALDQSAIVVTTNL
KGQILYINDRFESISGYSQPEILGKTPQILNSKYHPPGFFAHLWTTILNG
QVWRNEICNRAKNGQIYWVDATIIPFLNPQGQPTQFLSIQFDITSRKQVE
LDLASSNSLLSTITHAQAQFITAANRLTIFEGLLESLLELTHSEYGFIGE
VLFQGDGTAHMEENFLKIRGVPYLQTHSITNIAWDAATEQFYQNNYEKGM
EFTNLKTLFGAVILTGKPVIANQAPTDPRRGGIPKGHPPLEAFLGIPFFK
GPELIGMVGIANRPGGYNEGIIARLGPFLTTCSNLIEGYRMDRHRQKAEA
MIAQQLRQRTVLGQIVQQIRESLNLQEILAITTQRVREILQG**DRVIVFRF
CDLGRTCIFEEAVAEDLPSLKYMNWEDEQWSSEILQFYWQGQPRIVPDVM
NDPLTPCLLDYSRQGQIQSKIVAPILQEIHNGERGNGEIDPWTDPESGNK
LWGLLVIH**ACHEKRIWQESEAELLQQIANQLAIAIRQSRLFEQLQEELTE
RQQTQIQLTQRNEELIRATRLKDEFLANMSHELRTPLNAILGMTEGLQDG
VFGSVNEGQRKALSTIERSGSHLLALINDILDLAKIESGQVELECAPTAI
ASLCQSSITFVKQQALKKHLHLSVNLPVNLPDIVLDERRIRQVLINLLNN
AVKFTPEGGRVTLEVTLPTPEQNSLPHLRFSVIDTGIGITPENLKKLFQP
FIQIDSALNRQYQGTGLGLAVTKRIVELHGGQVGVSSEEGKGSCFMIDLP
YQASVVFAPQTNSESHFDPHDLATQSPGKSSPLLLLAEDNEANISTISSY
LMAKGYRIEVAKNGQEAIHQAVALSPDLILMDVQMPGMDGLEAMKRMREI

-continued

PELATTPIIALTALAMDSDRDRCLQAGADEYLSKPVKLKQLTLTIQGLLK
S

Sta7437_1656
(Bold and underlined region = SEQ ID NO: 4)
(SEQ ID NO: 48)

MPLALSQIFHRLIANVPLRWVLTIPFVLPTIGAVAIVGYLSYRDGQEAVE
DLGHQLVAETNERVKQELETYLQTPVLINRLNVDAVARGQLDLQNIVALE
AVLFARLQQFERVSAVLFASPQGTFRLVDRLPDLYLVVADPPRPEQILIY
SLNSDGSRKELVRTNEGLDVRRDNPWYRRAVRTGKPGWSPIAQYGSLNFL
TLDASQPVYDRTTKSLLGVFAVHIRLDYLSEFLHHLDISRSGRVIIMDRN
GALIATSTEEQPYKFLAGTGYQRQFEQINIDESQDNLTRSLGKYLRKRPE
ILKSLERTRLLDFRYNGELQLVQIAPFQDQYGLNWQIVTVIPKSHFLKDI
QENKRTTALLCLLTLGVALALGLVAADKLTASFARLSRVSRELAAGNLAR
RLPTDSSIYELNGLAQTFNQMADQLQQSFDRIQIALEESEEKFATVFRTS
PDPMAIASLAEGRILEVNDSHVDFFGYSRAETIGRTVLVLNLWSNLDERE
KFRALLHQQGSVRNLEAQLRTKSGEVRTVLVSAEVQTLEGQDCTIIVLRD
ISERKQAQAALQESETRFRQLAETVREGFFVYETKSDHYSYVNPAYAAIM
GTPAQLFYQGMFHWLNNIHPDDCDHIEAGLLREHQGENFDEEYRFIRPNG
EIRWLRSKAFPLRDETKTIVRIVGTVEDITERKQLEQSLRSQAEEERLIT
TITQNIRQSLDLKKILATTVIEVQQTLNA**ERVLIFRMNPDGSGQVIEEAV
VPKYPVTDQMRWEDEHFPEDCYEYYRQGIPRIVPDVATDEWAKCLVEFMQ
EVGVKSKVVAPIVQVYEKSSTNAKVWGLLIVH**ACSHYRQWQESEVDFLQR
IGNQLAIAINQANLYQQLQAELAERQQTEEAFRESEELFRRAFDDAPIGI
ALVSPTGQFLKANTYYCNLLEYSEEELLTLTFQNITHPTDLEADFEVFRQ
MMAGEIRSYHLEKRYITKQGIVIPVLLNAASIRDQDDRPLYCVGQIQDIR
DRLKVERMKDEFISVVSHELRTPLTSIRGALGILGSGVFDNRPEKAKHML
QIAINNSDRLVRLVDDILSLERLESGKVQLVMEQCQVAELMQQAIDSLQA
LAERADLTLSVTPISATLWAAPDAIIQTLTNLLSNAIKFSSPGDTVWLKA
EIGSGEWATANGQQFSDTQTPYILFTVKDRGRGIPEDKLEIIFEQFQQVD
VSDSRQKGGTGLGLSICKRIVQQHGGRIWVESSLGEGSTFYFTLPIKEEN
D

MicvaDRAFT_3059
(Bold and underlined region = SEQ ID NO: 16)
(SEQ ID NO: 49)

MFMRTTALTPIELRTAIVREPLVVSPDTTVMDAIAQMSGVRSLCNTTRTA
DGQLDDLHLEARSSCVLVVENEQLVGVLTERDVVRLSAQQRSLENLVLRE
VMAHPVVTLRESAFTDLFFAINLLQQHHIRHLPILDDLDRLVGLVTHESL
RQTSRPIDLLRLRMVAEVMTREVICAAPDSSLLAIAQLMAENRVSSVVIV
HPGGISTEPLQIPVGILTERDIVQFQTLGLNLETCLAQAVMSTPIFAVRP
DDSLWTVQEIVEQRSIRRLAVTGELGELLGIVTQTSLLQALNPLELYKLV
QKWEEKVVRLEAEKVALLANRNVELEQQVEARTAALKAKADREQLLNTIA
EQIRSSLNLSDILQTTVQEIHSLLGCDRVIIYQFRSDFSGTVIAEAITDT
GRSVLHREAHDPCMSPEWLEPYRQGRIRIINDIYGEPMTQCHQEMLVGFD

-continued

IRAKLMVPIVIEEQLRGLMIASYRASAHSWTTDEIELLRQVSLQVAIALG
QAMIQQKLQNELVKRQRIEATLIESEQRYAALAAAAPVGIFRTDATGLCT
YVNDRYFQISGLTPGATIGHGWQQGVHPDDRDWVMVEWKQFIQGNRSFEL
EYRFQCPDGTVTWVYGQCVAELDANGHRSGYIGTITDISARKRTEVCLQE
SEERYATLVAAAPVGIFRADAVGNCIYVNDRWCQISGLTPKTAVGEGWQQ
GLHPDDRDCVIAEWEQSVQRNRPFQLEYRFQRPDGGVTSVYGQSVAERDA
DGQVVGYVGTTTDITDRKQAEQKLQQLNQQLETKVAERTQELWQVNSLQR
AILDCADYSIISSDPSGIIQTLNAAGERMLGYSAQEIIGQATPALIHDAN
EVIDRAASLSAELGQNIPPGFEVFVAKARQGLVSEEEWSYIRKDGSRFPV
SLSITALKDVHQQIIGFLGIAKDISDRKRAEAELQKLSERLALSLKSGAI
ASWEWNLGQNTILGDERMYELFAVTKPSDACQVYDFWANRLHPDDRIPTE
TLLHQAVLGQAEYDTEYRIVHPDGSLHFIKAYGVVVRDAQSNPQSMIGVN
FDISDRKQAELQRQQLIQELSAFKQALDQSAIVVITDREGVISYVNDRFC
VVSGYSRDRLIGQTHRLVNSGYHPPAFFQDLWRTINSSQIWRGEICNLAK
NGSLYWVATTIVPFLDEQGRPFQYLAIGFDITDRKLAEATLQQENTFRQQ
IVENMAEGLCVFHQVEEFPFVRFTVWNQQMQAITGYTLEEINRLGWYQTL
YPNLEDREQAIANCRQMQPIAVEREIQRQDGQRRTISISTSVLSGDDGHL
YALALIQDITHRQQTERENRLLKERLEFLLASSPAMIYSCKPYGDYELTF
MSKNMSAILGYKPEEFLSESGFWANHLHPEDAPRVFADLSALFEYNTHQH
EYRFLHHDGHYVWLRDELRVVRDEEGCPTEIIGYFADISDVKQTEETLKI
QLAAIEAAIDGIAIMQGDTYLYLNQAHLELFGYEHPQELLGKTWQLLYSP
EELERFEREVFPVLGRDRAWQGEAIGTRKDGSTFAEGLSLTLTENGLLIC
VCRDISDRKQIEAELAESEAKFRRLVEGANDLIWSCEPDGILTYVSPQFK
TMFGWDESAWIGKSFIYLVHPDDRSLVVTDYRENIKSGKKSSDYEFRHRH
RDGNYVWVRSSATPVINAEGELISIQGILSDISDRKEAEIARESSEIRFR
RVFESSVSGMIFADFQGNIIDANDRFLQMVGYTREELDAGLIHWDAMTPP
EYFPADVLAMERVMQDGAIEPWEKEYYRKDGSRISVLIGVALLPDSDDQT
ICVLVDISERKQAQKALQESQQFLQTVLDTIPLAVFWKNRESVFLGCNQQ
FAQTLGLPSTTESIGKKDLDICQEEVEANEYCAMDRRLMETGEAILGIEE
TLTLPNGKLIFIETHKAPLRDCSDNVIGLVGTFQDITDRKEAEQKLQQQA
KQERLLGAITKRMRSSLNLDEILNSTVEEIHQLLQSDRTLVYRVFPEGTG
AAIAESVSPNRLKLLDILFPEEVFPEDTYERYIQGRVYALNDSEDENESI
VPCLVEFLADIEVRAKLVVPIIQNQTLWGLLIVHQCDRPRQWQDWEINLL
KQIANQLAIAIQQSYLYEQVQSELAIRKQTENVIALQLQRQRTLGAIAQQ
IRESLDINQILAAVTQQVKEILQGDRIIVFRLFGDGRSQIVEEAVSSEFP
ALKDHHWEDERWSQEILNRYWQGKPRIVPNVMTDIWTDCLVEYASVGQVQ
SKIVAPILQEVRSSESHRWIAPGQTKKLWGVLVVHACREQRVWQESEAQL
LQQIANQLAIAIQQASLFKQLQQELTERQQAQQQLTERNQQLGASNEELA
RATRLKDEFLANMSHELRTPLNAILGMSEGLQEQVFGIVNEQQIKALQTI
ERSSSHLLELINDILDVAKIESGQMELDCTPVSINHLCQSSLAFIKQQAL
QKRIQLEIQMPLNLPDLLIDERRMRQVLINLLNNAVKFTPNGGRITLEVS

-continued

RQQRPADPDSADSPPHFLVKETLRIAVIDTGIGIAPEHINKLFQPFIQID
GALNRQYTGTGLGLALVKRIVELHGGQVGLTSTVGVGSCFTIDLPCTACA
PSSVYLESQTEPRIEPSQPEEGGALP

UYKDRAFT_01008 (WP_016871037;
bold and underlined region = SEQ ID NO: 24)
(SEQ ID NO: 50)
MSKSPSHLLAEAEKAQVLGKFTEAEEYYEQAIDTAKANGSLQTEALAYEL
AAKFYLERGRLRFAQNYIKEAHYAYTRLDARAKIKELETQYPQLRSELSA
ADSHTSTDLEAVIRANQAIASEIELERSLSVLMKILIENAQAQTGYLILP
CQTASTSTEKWAIAASGTIDIATNEQIIVLQSLAIADHLPASVIDYVIQT
LESVVVDDATREGNFINDTYIQQHQTKSILCVPLLHQEELLGIVYLENNI
TNGVFTKEQLKVIKLLSAQAAISLHNAKLYNQLRESEQQLRTREHRLNQI
LEAMPIGVTAHNTNGEFIYSNLKAQQLLGITAPLEVTTEQLLQVFQVYQA
GSDQLYPTDQLPIVRAFAGESVKIDDMELRQADKTVPLEVLTTPIFDETG
AVIYAITAFTDITERKQAQKLLAKYNQTLEAQIAERTEKLQQQHEILQTL
FDHMPVMLKLRDQTGQTVLINREYERVLGWSLREIRESDFLAECYPDLEQ
RQRVEEHIQAATGKWQDFKTRCRDDRYVDTTWANIRLSNGWTVGIGKDIS
DRKQLEAALQASKAKLKDILNSAQASIASFRVYPDGTWEPDYHSTGCETV
FGYTPQEFTPAVWSSRVPAEDLAAIIEQRSTAIPKGEALTVEYRFYHKNG
SLRWITETLTSRWDQVGGCWVVTMVAVDITAHKQAEQALQEAYRKLEEYS
TNQEAVNQELQRTLEDLQVLEEERQEQNHQLLIEQQRYRDLFNFAPDGYL
VTDAQGRILEANHAIATLLSVESGFLTGKLLVSFIPASARRAFRTQLNHL
SSLPDKQTWELSLQPRQGEPFPVEITVAPVRDAQKLIALRWLIRDITERK
QAETALRESEERFREIAENINQLFFVWSADSQQFLYISPGYEKIYGLTCE
SLYQNSRSWLEVVHPDDRPSVLQSLDQQYQGKHAQREYRIIKSDGTIRWM
FAEVFPIFDQTGNLLRYIGLTEDITERKRAEEALRQREQEFRALVENAPD
VISRVDREYRFCYINPRVELETGIPPAQWIGKTELEMGFPQTIVNPWHAA
LEHVFETKQEQIYEAEFPCPEGISYWLCRLVPELAEDGSVATVLSIARNI
TDRKRAEEALRESEQFLRSIYEGIAAGVCIVDVLEDGSFRYVGINPAHER
MSGLLSAEVAGKTPEQVFSPEDAQAVTARYRACIIARERITYEERLVFKG
KETWWITNLSPLQNENGQIYRLIGSCFNITRRKKLEQSLQLQAEQERLLI
TITQHIRQSLDLEQILRTTVVEVQRTLQTDRVLIFRLNQDGSGQIIEEAV
VPEYPMTYQMRWVDECFPDDCYEYYRQGNPRILPDVAKDENGACLVEFMQ
QIGVKSKVVAPIIQTLEDSSTRVWGLLIVHACSHYRQWQASEAEFLQQIS
NQLAIAIHQADLYYQLQIELAERKQMQLVLQERQAILRAIGDNLPKGFIF
QIVHVPDQGVYFSYISAGIEDLIGLKPEAIIQDANVLRNLIHEEDKPVRQ
KLGLKSLKTLCIFEMQMRFRSLRGNIIWLDVRSTPRRLRDGRTVWDGVGI
DITDIKQAEDALRRSEAHLAMAQKVAQIGSWEFDLQSQQINWSETTFHHW
GIEIDQGEPSFAELLVRVHPEDREILKQHIERAITQGIPYAFDLRIVLPD
GSIRYLDSRGEPLVNAQGQVIKLIGTSLDITARKQAEGALRESEERFRKA
FNAAPIGMALVSPQGQFLKVNHSLCEIAGYTEAEMLTLTLKDVIHTDDLE
ASLEAMQQMLANDIRLYQVEKRSLHKQGDVIHILLNVSLVKDQHRQPLYF -continued IVQIQDISDRYKVDRMKNEFISIVSHELRTPLTAIRGSLGILETGIFDHE
PEQAKEMLQIAFNNSDRLVRLVNDILDLERLESGKTQLVMETCEIADLVQ
QAIETVQAIAKEARVEISVMVANMQIWAAPDAIVQTLINLLSNAIKFSPV
GGTVWISTEVLNQEMEKWKDREIGRKISPHHPTTPSPHFPNSHILFAVKD
QGRGIPPEKLESIFGRFQQVDASDSRQKGGTGLGLSICKSIVDQHGGRIW
VESLLGEGSTFYFILPLKRGEA UYEDRAFT_06529 (WP_016878855;
bold and underlined region = SEQ ID NO: 25)
(SEQ ID NO: 51)

MPPDREKVGMGFDREEVSTNLQPQEALCARSESTKPKENILVVDDNPDDL
DFLIQILSKHGYQVQLVPSGKLALIAVESTLPDLILLDIMMPEMDGFEVC
SQLKASAQTKDIPIIFLSVLHKTFDKVKAFSLGAADYITKPFQPEEVLAR
VENQLRIQRLTKQLVEEIKERNIAQEQLKNKEKHYRRLFEGSVDGIVLTD
MQGRIIDCNASYQKMLGYSPEELKLLSFWDLTPIQWHCWEAEIVEQQIIE
RGYSDTYEKEYIRKDGTIFPVELTVYCQKNDCGQPEIMWANVRDISDASR
QAATRLRKQAQQALEQSIIKNRALLDAIPDMVFRCHVDGTYLEFKPAKDL
KPFVPPSKFLGKKIQKILPDQVAQKILQAQQQAILLGETQILEYQLPIDG
RLHDYEVRIVACGSHENILFVRDITERKLTEAALAKSEQKYRNLVETSQN
IIMSCDRQGAITFVNQAVKQIYGYDPKEMIGHPFTDFLPPEIAAKDLEVF
QQLLNGTPVNLYETTHRAKDGRLIHLLFNAIALFDEQGQVIGTTGTASDI
TARKQTEEELQQAYKKLEEYNAELQATNQELQCMLEELQFFELERQQQYH
QLIIEQKRYEDLFNFAPDGYLTTDATGIIQEANHAIAAYLSVDLKFLAGK
PLANFISEGDRRAFRTQLNQLLSLQQKQTWELKLQPINGEPFAVEMTVAP
VCGSSNQLISLRWLIRDITERKQAEAALRESEERFRQIAENIHQFFFVLS
ADSGEYLYLSPAYEKIWGQSCESLYQNPKSWLEFVHPDDRQLVLHSLYQK
NEGKRVQREYRIIRDDGTTRWIFAEVFPILAQSGELLRYVGLAEDITERK
STEESLRESEHFLRSIYEGIEAAVFIVDVLEDGRFRYVGINPANERMSGL
LSTEIAGRTPEQVLSPEDAQAVIDRYRTCVAARKPITYEESLVIQGKETW
WITNLAPLQSEDGQIYRLIGTSFNITVRKQLEHFLRSQAQQERLLGTITQ
HIRQSLNLEEILATTVIEVQQTLQADRALIFQLNQDGSGQIIQEAVIPDY
PVTNQMRWLDECFPDECYEYYCQGNARIVPDVAKDDWGACLVEFMQEVGV
KSKVVAPIVQSFEGSSNKVWGLLIVHACSHYRQWQASEVEFLQQLCNQLA
IAIHQANLYHQLQIELVERKHTEKALQAAQESLTIAIEAAQMGTWHLDIT
KDFASKRSLRHDQIFGYDTLQSEWGQKIARRHVVEEDREIFDAAFVRAME
TGKLDFEVRIQWPDGSIHWMAARGRFYFDDNGKPVYGGGVNFDITDRKQT
ELALRESEERFRRAFDDAAIGMAMVAIDGSFITVNRSLCEILGYSEAEFL
ALTFQDITHADDLHKALDYRQRLLVGETRTYQTQKRYIHKLGHEVWILLS
SSLVRERDGKPLYFINQYQDISDRQQISRMKNEFISIVSHELRTPLTAIR
GSLGILETGVLKDEPQQAKELLQIALKNSNRLMRLVNDILDLERLESGKV
RLIMQECEIGDLIKQATETVQAIADEANITLCATFPKIQIWAAPDAITQT

-continued

LINLLGNAIKFSPVGGSSVWLSAELFPDHVLFFVRDNGRGIPSDKLKTIFG
RFQQVDASDSRQKGGTGLGLAICKTIIRQHGGKIWVESVLGEGSTFYFTL
PFAQPDT

Fis9431DRAFT_3998 (WP_026722600;
bold and underlined region = SEQ ID NO: 26);
(SEQ ID NO: 52)

MITFLSHLIVEAEKAQVLGQVIATEEYYEQAIDAAKANNSLEQEASAYYE
AAKYYLERGRPRVAQNYIKEAHYAYKCLDATAKVKDLETKYPQLLFELSS
ANSNTCTRSTSFQFSSNASGEALELLEAVTRANVAISSEIELERLLRILM
KILIENTDAHTGYLILPASTNLENGEEWEIAASGTIDTEASEDALGKPVL
QISVQPLAIADHLPISVIDYIIHTLENVVVDDASCEGKFIHDSYIKEHQI
KSILCVPLLNQGQLIGIVYLENNLTQGVFTKKELNILNLLFVQAAISISH
AKIYKQLRESEKQLRAREKRINQILDAIPIGVTAHDPTGRFIYSNLKAQQ
LLGIKTPPEIKIEQLSEAFQVYRAGTDEFYPIEQLPLIRAFAGESVKSDD
MELRQVDKSIPLEVLTVPIFDGEGAVIYAIAAFKDITERKQAQKILADYN
YTLEAQIVARTEKLQQQNEILQALFDHIPVMLKIRDQADQTLLINQEYEH
TLGWTLEEMRDVDWLAKCYPDAEQRQQITEHIQAATGKWQDFRTRCHNGR
YIDTSWANIRLSTGQIIGIGQDISDRKELEKALQASQAKLNDILNSAGAS
IASFRVYPDRTWENEYHSLGCETVFGYSPEELTSELWLSRVPSQDLAAIT
EQAFAAIAQEQAITVEYRFYHKNCSLRWIAHTLTSRWDQAEGCWIVTMVG
VDISDRKQTEEELQQAYKQLEEYSADLEAINQELHLTLEHLQVLEEERRE
QHHRLMHEQQRYQELFNFAPDGYLLTDARGTIQEANCAITALLSIELGYL
IGKPLVSFIPASARRTFRTQLNHLSLLSDKQTWELSLRPRNGKPFPAEIT
VAPVRDGNKLIALRWLIRDITARKQAEIALRESEERFREIAENINQIFFV
WSANSEQFLYISPGYEKIYGMSCESLYQNPQSWLDLVHPDDRKSVWQSLN
EQSQGKPARREYRIIKSDGTIGWMFAEVFPIFDQTGKILRYIGLTEDITE
RKRAEEALLEREQFLRSIYDGTAAAIFIVDVLEDGSFRYVDINPAYEWMS
GLLSSEIVGKTPEQIFPLEEAQVISARFHNCATTGTRIPYEERLLIRDKE
TWWINVLTPIQREDGQIYRLIGSCFNITKRKKLEQSLRSQADQERLLITI
TQHIRQSLDLEQILATTVIEVQQMLQVDRALIFRLNEDGSGQVIKEAVVP
EYPVTEQMRWRDEPLPDYCYDFYRQGNPRIVPNVAIYDWASCLAEFLQQA
SVKSKIVAPIVQTLEDSSTRVWGLLIVHACSDYRQWEASEAEFLQQISNQ
LAIALHQANLYQQLQTELAERKQTEEALRQNQAHLAMAQKVSQIGSWEFD
LNSQKIRWSQITFHHWGLEPAKGEPSFTELLAKVHPQDREVLQQNVEQAI
AKGIPYTFDLRILWPDGSIRYLDSRAEPVFNAQGEVIHLIGTSLDITERK
QAEERLRESEERFRKAFDAAPIGVALVSPQGQFLKVNRSLCEIVGYTEAE
MLHLTMTEITHPDDLEADLEFIQKLLANEIRVYQVEKRYLHQRGDTIYIR
LNVSLVKDRHRKPLYFIAQIQDISDRYEVDRMKNEFISIVSHELRTPLTA
IRGSVGLLEEGVFDNEPEQAREMLQIACNHCDRLVRLLDEILDLERLESG
KVQLVMETCEIANLIQLAIGTVQTTANQARVEISVVIVPNMQISAEADSI
IRALTNLLSNAIKFSPAGGSTVWLSAELLTPEEDAGIEGQGGKEGQIAPAS
PVSPISPVSPISPMSPVSPVSPVSPMSPISPVSPISPVSPISPMSPMSPV

-continued

SPMSPVSPQSPQILFKIRDQGRGIPPDKLESIFERFQQVDVSDRRQKQGT

GLGLAICKNIVQQHGGHIWVESVLGEGSTFYFTLPITREEDC

PCC9339DRAFT_00524 (WP_017309337;
bold and underlined region = SEQ ID NO: 27)

(SEQ ID NO: 53)

MITFLSHLIVEADKARVLGQVIAAEEYYEQAIDGAKANASLEEEALAYEL

AAKYYLERGRPRFAQNYMKESYYAYRRLDATAKVKELETKYPRLLFELSS

ANSNTSTCFTSPKMSSISSEGALESLEAVIRANIAISSEIELERLLRVLI

KILIENADAQTGYLILPSPTNLENGEEWKIAASGIIDTEASDNTLGKPVF

KIGVQSLPIDDHLPTSIINYVIHTLENVVVDNASCEGKFIHDPYIQQHQT

KSILCTPLLNQDKLIGIVYLENNLTNGVFTKTQLNILQLLFTQAAISIHN

AKIFSQLRENEKQLSVREKRVNQILNVMPIAVTAHDTTGRYIYSNLKAQQ

LVGMKAPLEIKTEQLSEVFQVYQAGTDQLYPINKLPVVRTFAGESVKIND

MELRQDDKTIPLEVLTVPIFDETGAIIYAIAAFSDITERKQAQKLLADYN

QTLETQIAERTEKLQQQNEILQALFDHIPVMLKLRDQTDQTLVINREYER

VLGWTLDDLRDIDWLAKCYPDTEQRQQIREHIEAATGKWQDFRTRCQNGR

YVDTTWANIRLSTGQIIGIGKDISDRKQLEKALQASQAKLNDILNSAGAS

IASFRVYPDRSWDREYHSLGCENIFGYTPQELTPELWLSRVPSEDLTVIS

EQAFAAIAQEQATTLEYRFYHKNSSLRWIADTLTSRWDQAGGCWIVTMVG

VDITARKQAEMALQESEQFLRSIYEGTAAAIFIVDVLEDGRFRYVDINPA

HEWMSGLFSSEMAGKTPEQIFPPEDAQVINARFVACTTIGQRITYEERLE

IRGKETWWINVLTPIYTEDGQIYRLIGSCFNITRRKKLEHSLRSQADQEH

LLGTITQHIRQSLDLEQILATTVVEVQRTLQADRALIFRLNQDGSGQVIK

EAVVPEYPMTSQMRCTDECFPDDCYEYYRQGNARILPDVAKDEWSDCLVE

FMQQIGVKSKVVAPIIQTLEDSSTRVWGLLIVHACSNYRHWRASEAEFLQ

QISNQLAIALHQANLYNHLQTELAEHKQTEAALRQNQAHLAMAQKVSQIG

SWEFDVNSQNISCSQTTFHQWGIEPVKGEPSFSELLERVHPDDREVLQQK

VEQAITNRISYAFDLRIMRPDGSIRYLDSRAEPVLNAQGQVIQLIGTSLD

ITERKQAEEYLRESEERFRKAFDAAPIGVALVSPQGQFLMVNHSLCEIVG

YTEAEMLNLTMMEITHPDDLEADLELMQKLLANEIRVYQVEKRYLHNRGD

TIHTLLNVSLVRDQHREPLYFIAQIQDISDRYEVDRIKNEFISIVSHELR

TPLTAIRGAVGILETGVFDHEPEQAREMLQIAFNNSDRLVRLVNDILDLE

RLESGKIQLVTETCETANLVKQAIETVQAMANEAGVKIFVMVPNMQISAA

ADSIIQTLINLLSNAIKFSPAGGTVWLSAELVSPEEEGGMGGDGGGGGGG

GGGGDGGDGGDGGDGGQIAPISAKILFKVRDQGRGIPPEKLESIFGRFQQ

VDVSDRRQKRGTGLGLAICKNIVQQHGGCIWVESVLGEGSTFYFTLPITR

EEA

-continued

UYEDRAFT_00976 (WP_016873240;
bold and underlined region = SEQ ID NO: 28)

(SEQ ID NO: 54)

MIDSANSSQRLQKYFAKIPLWLLLVVPFVLQLLATVGVIGYLCYEAWQRS

THKVANQVMKEVGDRVQHYLSDYLETPQLINRLNANATDLNQIDINDPNS

LESHFLQQIQAFNSVSRIHFSNPQGGYISAGNDERGLSVAFTENFVRGTL

HVYGVDNQGKRTQQFVHQQNYDATKRPFYQAAAKASKPIWTPIYVYIPAS

TGLGIAASYPLYDQLNRLQGVLSTDLTLANINQFLSNLKIGTQGKVLILE

RSGLIVASSTSEKPFFISSNQRQTIRLKATESQEPLIRFTAQHLVSYFGD

LTKIKTPEQLQFEVKGKRLFLQVNPFTDRFGLDWLIVTVLPESDLIADLD

GNTQRMMLLSGFTLLLAIGTGILTACWIARPIRRLKKAAQAITKGQLNYP

IATGGIGEVAQLAQGFQVMANQLDSSFRALKASEQKFATLLSNVPIGISV

FDAKENPVLINKVGEEILGRGLVSDISFAQHSEVYQIYVAGTDQLYPTEQ

LPATRGLRGETALIDDMEIEVNGRRIPLEVHTIPVFDDDSNVIYAINAFR

DITQRRQAEKLWTDYEQELKCRVAEKTAALRQSEERFRLAVNHAPDVFVI

YDRDRRFLYVNEKARELTGWTLDHFIGYRDDDLFPPEVTAPYLPILQKTI

STKTLQIGECTIKLPEQKPSTFIVKYVPLLDEQGEIQQILGMTFDISDRK

QIEEILRQSEARLTMAQRVAQVGSWEFDLNSQKMTWSEETFYHWGFDSTP

EEPSYTELLKRVHPEDREILNYFFEQAIAQGIPYVLDLRIVRPDGSIRYL

DYRGEPLFNAQGQVIKLIGTSVDISDRKWTEEALRQSEALNRAIVNALPD

LIIRMHRDGTYLDVKPTTAFLTSASPLVVGLNVQAVLSPQVAQRRIAAIE

NALQTGEIQVYEFPFVIQGQSLWQEVRVMPLDVDEVLVVIRDLTERKKAE

EAVRLQAKREQLLRGITQRIRQSLDLEQILATTVNEVLQTLQSDRALIFR

LHGNGTGQVIQEAVRPEYPVTEQMLFPDECFPQECYEYYCQGQPRIVSDV

FAEDFSSCLVEFMQKIGVKSKIVAPIVQTTENSSTKVWGLLIVHACSQHR

QWQQSEADFLQQISNQLAIAIQQSQLYQQTRQQAQREQTLNRVVQAIRNS

LDLDTIFATTVSEVGLLLQVMRVNIMQYLPERGIWVSAADYVQDPSLGNT

VGFEIPDTSNPIATKIKQFEIVQIINDVASEEEIAQTYQGACLIVPLKVE

QQIWGSLTLVKDPPSAWQQFEVDLTIAVADQLAIAIQQANFYNQLQIELT

EHCQTEEALRRSEEQFRKAFDNAPIGMALVSLKGQFLKVNNSLCEILGYN

GEELLALTFADITHPDDLEPDLESRRQILAGEIRVYQAEKRYLHSSGNTI

HVLLKISLVRDQQRQPLYFIAQIQDISDRYKINRMKDEFVSIVSHELRTP

LTAIRGSLGILETGVLDHDPEQIKELLQIALNNSDRLMRLVNDILDLERL

ESGKVKLVMEACEVANLVKQATESVQAIADEANITLSVKFSNIQIWVAPD

AIVQTLINLLSNAIKFSPAGSTVWLSAEEGIGDREQVTGDRGQGIGDKEK

IFDNFSASSRSPCILFTVRDQGRGIPSDKLETIFERFQQVDVSDSRSKGG

TGLGLAICKSIVKQHGGKIWVESRVGEGSTFYFTLPITRK

What is claimed is:

1. A protein fusion construct comprising a far-red cyanobacteriochrome (CBCR) domain linked to a heterologous domain, wherein the far-red CBCR domain comprises a CBCR polypeptide, the CBCR polypeptide comprising (1) a GAF domain having an acidic motif, and (2) a tetrapyrrole chromophore; and wherein the far-red CBCR domain has at least one local absorbance maximum or local emission maximum at a wavelength from about 720 nm to about 760 nm.

2. The protein fusion construct of claim 1, wherein the acidic motif in the GAF domain comprises:

a conserved tryptophan residue; followed by two acidic amino acid residues, wherein at least one of the amino acid residues is an acidic amino acid residue; followed by a conserved glutamic acid residue; followed by a further amino acid residue; followed by an aromatic amino acid residue.

3. The protein fusion construct of claim 2, wherein the acidic motif in the GAF domain comprises an amino acid sequence set forth in SEQ ID NO: 1:

$$W\text{-}X^9\text{-}X^6\text{-}E\text{-}X^1\text{-}X^5 \quad (1)$$

wherein:

W is a tryptophan residue;

E is a glutamic acid residue;

$X^1$ is an independently selected amino acid residue;

$X^5$ is independently selected from the group consisting of a phenylalanine residue, a tyrosine residue, and a tryptophan residue;

$X^6$ is independently selected from the group consisting of an aspartic acid residue and an asparagine residue; and $X^9$ is independently selected from the group consisting of an aspartic acid residue, a glutamic acid residue, and a glutamine residue.

4. The protein fusion construct of claim 1, wherein the acidic motif in the GAF domain comprises:

a hydrophobic residue independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue; followed by a further amino acid residue; followed by a conserved aspartic acid residue; followed by a conserved glutamic acid residue; followed by a further amino acid residue; followed by a hydrophobic residue independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue; followed by a proline residue.

5. The protein fusion construct of claim 4, wherein the acidic motif in the GAF domain comprises an amino acid sequence set forth in SEQ ID NO: 2:

$$X2\text{-}X1\text{-}D\text{-}E\text{-}X1\text{-}X2\text{-}P \quad (2)$$

wherein:

each X2 is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

X1 is an independently selected amino acid residue;

D is an aspartic acid residue;

E is a glutamic acid residue; and

P is a proline residue.

6. The protein fusion construct of claim 1, wherein the CBCR polypeptide comprises an amino acid sequence as set forth in SEQ ID NO: 3:

$X^9$-R-$X^1$-$X^3$-$X^4$-F-$X^1$-$X^3$-$(X^1)_2$-$X^6$-G-$(X^1)_3$-$X^4$-$X^2$-E-E-$X^1$-V-$(X^1)_3$-$X^2$-$(X^1)_2$-$X^2$-$(X^1)_4$-W-$X^8$-$X^6$-E-$X^1$-$X^5$-$X^1$-$X^7$-$X^9$-$(X^2)_2$-$X^8$-$X^2$-Y-$X^1$-Q-G-$X^1$-P-R-I-V-$X^1$-$X^6$-V-$X^2$-$X^{10}$-$X^1$-D-$X^1$-$X^5$-$X^2$-$X^1$-C-L-$X^1$-E-$X^5$-$(X^1)_5$-$X^4$-$X^1$-S-K-$X^4$-V-A-P-I-$X^2$; (3)

wherein each A is an alanine residue, each C is a cysteine residue, each D is an aspartic acid residue, each E is a glutamic acid residue, each F is a phenylalanine residue, each G is a glycine residue, each I is an isoleucine residue, each K is a lysine residue, each L is a leucine residue, each P is a proline residue, each Q is a glutamine residue, each R is an arginine residue, each S is a serine residue, each V is a valine residue, each W is a tryptophan residue, and each Y is a tyrosine residue; and wherein:

each $X^1$ is an independently selected amino acid residue;

each $X^2$ is independently selected from the group consisting of an alanine residue, a cysteine residue, a valine residue, a threonine residue, a leucine residue, an isoleucine residue, a methionine residue, a phenylalanine residue, a tyrosine residue, and a tryptophan residue;

each $X^3$ is independently selected from the group consisting of a valine residue, a leucine residue, an isoleucine residue, and a methionine residue;

each $X^4$ is independently selected from the group consisting of a valine residue, an isoleucine residue, and a threonine residue;

each $X^5$ is independently selected from the group consisting of a phenylalanine residue, a tyrosine residue, and a tryptophan residue;

each $X^6$ is independently selected from the group consisting of an aspartic acid residue and an asparagine residue;

each $X^7$ is independently selected from the group consisting of a glutamic acid residue and a glutamine residue;

each $X^8$ is independently selected from the group consisting of an aspartic acid residue, an asparagine residue, a glutamic acid residue, and a glutamine residue;

each $X^9$ is independently selected from the group consisting of an aspartic acid residue and a glutamate residue; and $X^{10}$ is absent or $X^{10}$ is one or more independently selected amino acid residues.

7. The protein fusion construct of claim 6, wherein $X^{10}$ is absent.

8. The protein fusion construct of claim 1, wherein the tetrapyrrole chromophore is a bilin.

9. The protein fusion construct of claim 1, wherein the C-terminus and/or N-terminus of the CBCR polypeptide is linked to the heterologous domain.

10. The protein fusion construct of claim 1, wherein the heterologous domain comprises a heterologous oligopeptide or a heterologous polypeptide.

11. The protein fusion construct of claim 1, wherein the heterologous domain comprises a heterologous polypeptide selected from the group consisting of a signaling polypeptide, a structural polypeptide, a transport polypeptide, a targeting peptide, a hormone polypeptide, and a regulatory peptide.

12. The protein fusion construct of claim 1, wherein the heterologous domain comprises a streptavidin polypeptide.

* * * * *

SEQUENCE LISTING

<160> NUMBER OF SEQ ID NOS: 204

<210> SEQ ID NO 1

<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa = Asp or Glu
<220> FEATURE:
<221> NAME/KEY: VARIANT
<222> LOCATION: (3)..(3)
<223> OTHER INFORMATION: Xaa = Asp or Asn
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (6)..(6)
<223> OTHER INFORMATION: Xaa = Phe, Try, or Trp

<400> SEQUENCE: 1

Trp Xaa Xaa Glu Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (6)..(6)
<223> OTHER INFORMATION: Xaa = Ala, Cys, Val, Thr, Leu, Ile, Met, Phe, Try, or Trp

<400> SEQUENCE: 2

Xaa Xaa Asp Glu Xaa Xaa Pro Pro
1               5

<210> SEQ ID NO 3
<211> LENGTH: 85
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Asp or Glu
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: VARIANT
<222> LOCATION: (4)..(4)
<223> OTHER INFORMATION: Xaa = Val, Leu, Ile, or Met
<220> FEATURE:
<221> NAME/KEY: VARIANT
<222> LOCATION: (5)..(5)
<223> OTHER INFORMATION: Xaa = Val, Ile, orThr
<220> FEATURE:
<221> NAME/KEY: VARIANT
<222> LOCATION: (7)..(7)
<223> OTHER INFORMATION: Xaa = any amino acid
<220> FEATURE:
<221> NAME/KEY: VARIANT
<222> LOCATION: (8)..(8)
<223> OTHER INFORMATION: Xaa = Val, Leu, Ile, or Met
<220> FEATURE:
<221> NAME/KEY: VARIANT
<222> LOCATION: (9)..(10)
<223> OTHER INFORMATION: Xaa = any amino acid
<220> FEATURE:
<221> NAME/KEY: VARIANT
<222> LOCATION: (11)..(11)
<223> OTHER INFORMATION: Xaa = Asp or Asn
<220> FEATURE:
<221> NAME/KEY: VARIANT
<222> LOCATION: (13)..(15)
<223> OTHER INFORMATION: Xaa = any amino acid
<220> FEATURE:
<221> NAME/KEY: VARIANT
<222> LOCATION: (16)..(16)
<223> OTHER INFORMATION: Xaa = Val, Ile, orThr
<220> FEATURE:
<221> NAME/KEY: VARIANT
<222> LOCATION: (17)..(17)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (20)..(20)
<223> OTHER INFORMATION: Xaa = any amino acid
<220> FEATURE:
<221> NAME/KEY: VARIANT
<222> LOCATION: (22)..(24)
<223> OTHER INFORMATION: Xaa = any amino acid
<220> FEATURE:
<221> NAME/KEY: VARIANT
<222> LOCATION: (25)..(25)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (26)..(27)
<223> OTHER INFORMATION: Xaa = any amino acid
<220> FEATURE:
<221> NAME/KEY: VARIANT
<222> LOCATION: (28)..(28)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (29)..(32)
<223> OTHER INFORMATION: Xaa = any amino acid
<220> FEATURE:
<221> NAME/KEY: VARIANT
<222> LOCATION: (34)..(34)
<223> OTHER INFORMATION: Xaa =Asp, Asn, Glu, or Gln
<220> FEATURE:
<221> NAME/KEY: VARIANT
<222> LOCATION: (35)..(35)
<223> OTHER INFORMATION: Xaa = Asp or Asn
<220> FEATURE:
<221> NAME/KEY: VARIANT
<222> LOCATION: (37)..(37)
<223> OTHER INFORMATION: Xaa = any amino acid
<220> FEATURE:
<221> NAME/KEY: VARIANT
<222> LOCATION: (38)..(38)
<223> OTHER INFORMATION: Xaa = Phe, Try, or Trp
<220> FEATURE:
<221> NAME/KEY: VARIANT
<222> LOCATION: (39)..(39)
<223> OTHER INFORMATION: Xaa = any amino acid
<220> FEATURE:
<221> NAME/KEY: VARIANT
<222> LOCATION: (40)..(40)
<223> OTHER INFORMATION: Xaa = Glu or Gln
<220> FEATURE:
<221> NAME/KEY: VARIANT
<222> LOCATION: (41)..(41)
<223> OTHER INFORMATION: Xaa = Asp or Glu
<220> FEATURE:
<221> NAME/KEY: VARIANT
<222> LOCATION: (42)..(43)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (44)..(44)
<223> OTHER INFORMATION: Xaa =Asp, Asn, Glu, or Gln
<220> FEATURE:
<221> NAME/KEY: VARIANT
<222> LOCATION: (45)..(45)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (47)..(47)
<223> OTHER INFORMATION: Xaa = any amino acid
<220> FEATURE:
<221> NAME/KEY: VARIANT
<222> LOCATION: (50)..(50)
<223> OTHER INFORMATION: Xaa = any amino acid
<220> FEATURE:
<221> NAME/KEY: VARIANT
<222> LOCATION: (55)..(55)
<223> OTHER INFORMATION: Xaa = any amino acid
<220> FEATURE:
<221> NAME/KEY: VARIANT
<222> LOCATION: (56)..(56)
<223> OTHER INFORMATION: Xaa = Asp or Asn
<220> FEATURE:
<221> NAME/KEY: VARIANT
<222> LOCATION: (58)..(58)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (59)..(60)
<223> OTHER INFORMATION: Xaa = any amino acid
<220> FEATURE:
<221> NAME/KEY: VARIANT
<222> LOCATION: (62)..(62)
<223> OTHER INFORMATION: Xaa = any amino acid
<220> FEATURE:
<221> NAME/KEY: VARIANT
<222> LOCATION: (63)..(63)
<223> OTHER INFORMATION: Xaa = Phe, Try, or Trp
<220> FEATURE:
<221> NAME/KEY: VARIANT
<222> LOCATION: (64)..(64)
<223> OTHER INFORMATION: Xaa = Ala, Cys, Val, Thr, Leu, Ile, Met, Phe, Try, or Trp
<220> FEATURE:
<221> NAME/KEY: VARIANT
<222> LOCATION: (65)..(65)
<223> OTHER INFORMATION: Xaa = any amino acid
<220> FEATURE:
<221> NAME/KEY: VARIANT
<222> LOCATION: (68)..(68)
<223> OTHER INFORMATION: Xaa = any amino acid
<220> FEATURE:
<221> NAME/KEY: VARIANT
<222> LOCATION: (70)..(70)
<223> OTHER INFORMATION: Xaa = Phe, Try, or Trp
<220> FEATURE:
<221> NAME/KEY: VARIANT
<222> LOCATION: (71)..(75)
<223> OTHER INFORMATION: Xaa = any amino acid
<220> FEATURE:
<221> NAME/KEY: VARIANT
<222> LOCATION: (76)..(76)
<223> OTHER INFORMATION: Xaa = Val, Ile, orThr
<220> FEATURE:

<221> NAME/KEY: VARIANT
<222> LOCATION: (77)..(77)
<223> OTHER INFORMATION: Xaa = any amino acid
<220> FEATURE:
<221> NAME/KEY: VARIANT
<222> LOCATION: (80)..(80)
<223> OTHER INFORMATION: Xaa = Val, Ile, orThr
<220> FEATURE:
<221> NAME/KEY: VARIANT
<222> LOCATION: (85)..(85)
<223> OTHER INFORMATION: Xaa = Ala, Cys, Val, Thr, Leu, Ile, Met, Phe,
Try, or Trp

<400> SEQUENCE: 3

```
Xaa Arg Xaa Xaa Xaa Phe Xaa Xaa Xaa Xaa Xaa Gly Xaa Xaa Xaa Xaa
1               5                   10                  15

Xaa Glu Glu Xaa Val Xaa Xaa Xaa Xaa Xaa Xaa Xaa Xaa Xaa Xaa Xaa
            20                  25                  30

Trp Xaa Xaa Glu Xaa Xaa Xaa Xaa Xaa Xaa Xaa Xaa Xaa Tyr Xaa Gln
        35                  40                  45

Gly Xaa Pro Arg Ile Val Xaa Xaa Val Xaa Xaa Xaa Asp Xaa Xaa Xaa
    50                  55                  60

Xaa Cys Leu Xaa Glu Xaa Xaa Xaa Xaa Xaa Xaa Xaa Xaa Ser Lys Xaa
65                  70                  75                  80

Val Ala Pro Ile Xaa
                85
```

<210> SEQ ID NO 4
<211> LENGTH: 103
<212> TYPE: PRT
<213> ORGANISM: Unknown
<220> FEATURE:
<223> OTHER INFORMATION: Stanieria cyanosphaera PCC 7437

<400> SEQUENCE: 4

```
Glu Arg Val Leu Ile Phe Arg Met Asn Pro Asp Gly Ser Gly Gln Val
1               5                   10                  15

Ile Glu Glu Ala Val Val Pro Lys Tyr Pro Val Thr Asp Gln Met Arg
            20                  25                  30

Trp Glu Asp Glu His Phe Pro Glu Asp Cys Tyr Glu Tyr Tyr Arg Gln
        35                  40                  45

Gly Ile Pro Arg Ile Val Pro Asp Val Ala Thr Asp Glu Trp Ala Lys
    50                  55                  60

Cys Leu Val Glu Phe Met Gln Glu Val Gly Val Lys Ser Lys Val Val
65                  70                  75                  80

Ala Pro Ile Val Gln Val Tyr Glu Lys Ser Ser Thr Asn Ala Lys Val
                85                  90                  95

Trp Gly Leu Leu Ile Val His
            100
```

<210> SEQ ID NO 5
<211> LENGTH: 111
<212> TYPE: PRT
<213> ORGANISM: Unknown
<220> FEATURE:
<223> OTHER INFORMATION: Cyanothece sp. PCC 7822

<400> SEQUENCE: 5

```
Asp Arg Val Ile Ile Phe Arg Leu Tyr Ser Asp Gly Gly Ser Arg Ile
1               5                   10                  15

Ile Glu Glu Ser Val Ser Thr Glu Phe Leu Pro Leu Lys Tyr Cys His
            20                  25                  30
```

```
Trp Asp Asp Glu Thr Trp Ser Gln Asp Ile Leu Asn Leu Tyr Trp Gln
        35                  40                  45

Gly Gln Pro Arg Ile Val Pro Asp Val Met Asn Asp Ile Tyr Thr Glu
    50                  55                  60

Cys Leu His Glu Tyr Ser Arg Glu Gly Gln Ile Gln Ser Lys Ile Val
65                  70                  75                  80

Ala Pro Ile Leu Leu Asp Leu Lys Glu Lys Glu Asn His Arg Trp Val
                85                  90                  95

Ala Ser Thr Asn Ser His Lys Leu Trp Gly Ile Leu Val Val His
            100                 105                 110


<210> SEQ ID NO 6
<211> LENGTH: 111
<212> TYPE: PRT
<213> ORGANISM: Unknown
<220> FEATURE:
<223> OTHER INFORMATION: Anabaena cylindrica PCC 7122

<400> SEQUENCE: 6

Glu Arg Val Ile Ile Phe Arg Leu Phe Pro Asn Gly Arg Ser Gln Ile
1               5                   10                  15

Val Glu Glu Val Val Ser Ser Glu Tyr Ala Ala Leu Lys Asn Tyr His
            20                  25                  30

Trp Glu Asp Glu Lys Trp Ser Gln Glu Ile Leu Asp Cys Tyr Trp Gln
        35                  40                  45

Gly Lys Pro Arg Ile Val Pro Asp Val Ile Asn Asp Ile Trp Thr Ser
    50                  55                  60

Cys Leu Val Glu Tyr Thr Thr Gln Gly Asn Ile Gln Ser Lys Ile Val
65                  70                  75                  80

Ala Pro Ile Leu Gln Glu Leu Gly Glu Asn Glu Thr Gly Arg Trp Val
                85                  90                  95

Ser Ser Glu His Lys Gln Lys Leu Trp Gly Val Leu Val Val His
            100                 105                 110


<210> SEQ ID NO 7
<211> LENGTH: 111
<212> TYPE: PRT
<213> ORGANISM: Unknown
<220> FEATURE:
<223> OTHER INFORMATION: Anabaena cylindrica PCC 7122

<400> SEQUENCE: 7

Asp Arg Val Ile Val Phe Arg Leu Phe Ala Asp Gly Glu Ser Gln Ile
1               5                   10                  15

Val Glu Glu Ala Val Ser Gly Glu Leu Val Ser Leu Lys Asn Arg His
            20                  25                  30

Trp Asp Asn Glu Val Trp Ser Gln Glu Ile Leu Asp Tyr Tyr Trp Gln
        35                  40                  45

Gly Gln Pro Arg Ile Val Thr Asp Val Met Glu Asp Ile Trp Thr Asp
    50                  55                  60

Cys Leu Val Glu Tyr Ser Ile Glu Gly Gln Val Gln Ser Lys Ile Val
65                  70                  75                  80

Ala Pro Ile Leu Gln Glu Ala Gln Asp Gly Glu Lys Asn Arg Trp Val
                85                  90                  95

Ala Ser Gly Glu Asn Asn Lys Leu Trp Gly Val Leu Val Val His
            100                 105                 110
```

<210> SEQ ID NO 8
<211> LENGTH: 111
<212> TYPE: PRT
<213> ORGANISM: Nodosilinea nodulosa

<400> SEQUENCE: 8

```
Asp Arg Val Ile Val Phe Gln Val Ala Gln Asn Gly His Ser Cys Ile
1               5                   10                  15

Leu Glu Glu Ala Val Ala Pro Asp Leu Pro Gln Leu Lys Ala Met Gln
            20                  25                  30

Trp Asp Asp Glu Thr Trp Ser Gln Asp Ile Leu Glu His Tyr Trp Gln
        35                  40                  45

Gly Gln Pro Arg Ile Val Pro Asp Val Met Glu Asp His Trp Thr Asp
    50                  55                  60

Cys Leu Val Glu Tyr Ser Lys Ala Gly Gln Ile Gln Ser Lys Ile Val
65                  70                  75                  80

Ala Pro Ile Leu Gln Glu Leu Cys Asp Ile Glu Thr His Arg Trp Ala
                85                  90                  95

Ser Pro Glu Gly Ser Ser Lys Leu Trp Gly Val Leu Val Val His
            100                 105                 110
```

<210> SEQ ID NO 9
<211> LENGTH: 111
<212> TYPE: PRT
<213> ORGANISM: Unknown
<220> FEATURE:
<223> OTHER INFORMATION: Leptolyngbya sp. PCC 6406

<400> SEQUENCE: 9

```
Asp Arg Val Ile Val Phe Gln Val Tyr His Asp Gly His Ser Arg Ile
1               5                   10                  15

Val Glu Glu Ala Val Thr Pro Asp Leu Pro Ser Leu Lys Ala Met His
            20                  25                  30

Trp Glu Gly Glu Thr Trp Pro Leu Asp Ile Leu Glu His Tyr Trp Gln
        35                  40                  45

Gly Gln Pro Arg Ile Val Pro Asp Val Met Asp Asp Ile Trp Thr Asp
    50                  55                  60

Cys Leu Val Asp Tyr Ala Gln Ala Gly Gln Ile Gln Ser Lys Met Val
65                  70                  75                  80

Ala Pro Ile Leu Gln Glu Leu Arg Ser Val Glu Glu His Arg Trp Val
                85                  90                  95

Cys Pro Glu Gly Ser Asn Lys Leu Trp Gly Val Leu Val Val His
            100                 105                 110
```

<210> SEQ ID NO 10
<211> LENGTH: 111
<212> TYPE: PRT
<213> ORGANISM: Unknown
<220> FEATURE:
<223> OTHER INFORMATION: Planktothrix agardhii NIVA-CYA 56/3

<400> SEQUENCE: 10

```
Asp Arg Ala Ile Ile Phe Gln Leu Phe Asp Asn Gly Asn Ser Gln Ile
1               5                   10                  15

Val Glu Glu Ser Val His Ser Asn Phe Leu Asn Leu Lys Ala Leu Asn
            20                  25                  30

Trp Asp Asn Glu Val Trp Ser Gln Glu Ile Leu Asp Cys Tyr Trp Gln
        35                  40                  45

Gly Lys Pro Arg Ile Val Pro Asp Val Met Asn Asp Ile Trp Thr Glu
```

```
    50                  55                  60

Cys Leu Val Glu Tyr Ser Leu Lys Gly Gln Ile Lys Ser Lys Ile Val
65                  70                  75                  80

Ala Pro Ile Leu Leu Glu Ser His Ile Ser Glu Asn His Arg Trp Val
                85                  90                  95

Ala Thr Asp Gly Tyr Lys Lys Leu Trp Gly Val Leu Val Val Tyr
            100                 105                 110


<210> SEQ ID NO 11
<211> LENGTH: 111
<212> TYPE: PRT
<213> ORGANISM: Unknown
<220> FEATURE:
<223> OTHER INFORMATION: Tolypothrix sp. PCC 7601/1

<400> SEQUENCE: 11

Asp Arg Ala Ile Ile Phe Gln Leu Phe Asp Asn Gly Asn Ser Gln Ile
1               5                   10                  15

Val Glu Glu Ser Val His Ser Asn Phe Leu Asn Leu Lys Ala Leu Asn
            20                  25                  30

Trp Asp Asn Glu Val Trp Ser Gln Glu Ile Leu Asp Cys Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Leu Lys Gly Gln Ile Lys Ser Lys Ile Val
65                  70                  75                  80

Ala Pro Ile Leu Leu Glu Ser His Ile Ser Glu Asn His Arg Trp Val
                85                  90                  95

Ala Thr Asp Gly Tyr Lys Lys Leu Trp Gly Val Leu Val Val His
            100                 105                 110


<210> SEQ ID NO 12
<211> LENGTH: 110
<212> TYPE: PRT
<213> ORGANISM: Unknown
<220> FEATURE:
<223> OTHER INFORMATION: Synthetic Construct

<400> SEQUENCE: 12

Asp Arg Val Ile Val Phe Arg Leu Phe Ala Asp Gly Arg Ser Lys Ile
1               5                   10                  15

Ala Glu Glu Ala Val Ser Ser Glu Phe Val Ser Leu Lys Asn Arg His
            20                  25                  30

Trp Gly Asn Glu Ile Trp Ser Gln Glu Ile Leu Asp Phe Tyr Trp Gln
        35                  40                  45

Gly Lys Pro Arg Ile Val Pro Asp Val Met Asn Asp Leu Trp Thr His
    50                  55                  60

Cys Leu Val Glu Tyr Ser Gln Glu Gly Gln Ile Gln Ser Lys Ile Val
65                  70                  75                  80

Ala Pro Ile Leu Gln Glu Val Arg Asp Gln Asn His Arg Trp Val Ser
                85                  90                  95

Pro Trp Ala Thr Asn Lys Leu Trp Gly Ile Leu Val Val His
            100                 105                 110


<210> SEQ ID NO 13
<211> LENGTH: 111
<212> TYPE: PRT
<213> ORGANISM: Pseudanabaena biceps
```

<400> SEQUENCE: 13

```
Asp Arg Val Ile Val Phe Arg Leu Phe Ser Tyr Gly Asp Ser Gln Ile
1               5                   10                  15

Val Glu Glu Ala Val Ser Pro Glu Phe Thr Ser Leu Lys Ser Leu His
            20                  25                  30

Trp Glu Asn Glu Leu Trp Ser Pro Ala Ile Leu Asp Tyr Tyr Trp Gln
        35                  40                  45

Gly Lys Pro Arg Ile Val Pro Asp Val Met Val Asp Val Trp Thr Asp
    50                  55                  60

Cys Leu Ile Pro Tyr Ser Ile Glu Gly Gln Ile Lys Ser Lys Ile Val
65                  70                  75                  80

Ala Pro Ile Leu Gln Asp Leu Gly Asn Ile Glu Arg Ser Arg Trp Ile
                85                  90                  95

Ser Pro Leu Ala Asn Asn Lys Leu Trp Gly Val Leu Val Val His
            100                 105                 110
```

<210> SEQ ID NO 14
<211> LENGTH: 111
<212> TYPE: PRT
<213> ORGANISM: Unknown
<220> FEATURE:
<223> OTHER INFORMATION: Oscillatoria nigro-viridis PCC 7112

<400> SEQUENCE: 14

```
Asp Arg Ile Val Val Phe Arg Leu Phe Gly Asp Gly Arg Ser Gln Ile
1               5                   10                  15

Val Glu Glu Ala Val Ser Ser Glu Phe Pro Ala Leu Lys Asp His His
            20                  25                  30

Trp Glu Asp Glu Leu Trp Ser Pro Glu Ile Leu Asn Arg Tyr Trp Gln
        35                  40                  45

Gly Lys Pro Arg Ile Val Pro Asp Val Met Thr Asp Ile Trp Thr Asp
    50                  55                  60

Cys Leu Val Glu Tyr Ala Thr Val Cys Gln Val Gln Ser Lys Ile Val
65                  70                  75                  80

Ala Pro Ile Leu Gln Glu Val Arg Ser Ser Glu Ser His Arg Trp Val
                85                  90                  95

Ala Pro Gly Gln Thr Lys Lys Leu Trp Gly Val Leu Val Val His
            100                 105                 110
```

<210> SEQ ID NO 15
<211> LENGTH: 126
<212> TYPE: PRT
<213> ORGANISM: Unknown
<220> FEATURE:
<223> OTHER INFORMATION: Calothrix sp. PCC 6303

<400> SEQUENCE: 15

```
Asp Arg Val Ile Val Phe Arg Leu Leu Gly Asp Gly Arg Ser Gln Ile
1               5                   10                  15

Val Gln Glu Ala Val Ser Asn Glu Phe Pro Val Leu Lys Asp Arg Gln
            20                  25                  30

Trp Glu Asn Glu Val Trp Ser Gln Glu Ile Leu Asp Gly Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Arg Glu Gly Lys Ile Gln Ser Lys Ile Val
65                  70                  75                  80
```

-continued

```
Ala Pro Ile Leu Gln Asp Leu Tyr Ser Gly Glu Arg Asp Leu Thr Val
                85                  90                  95

Glu Arg Gly Gly Leu Leu Pro Leu Arg Glu Lys His Arg Trp Val Ala
            100                 105                 110

Pro Tyr Leu Thr Asn Lys Leu Trp Gly Val Leu Val Val His
        115                 120                 125
```

<210> SEQ ID NO 16
<211> LENGTH: 111
<212> TYPE: PRT
<213> ORGANISM: Microcoleus vaginatus

<400> SEQUENCE: 16

```
Asp Arg Ile Ile Val Phe Arg Leu Phe Gly Asp Gly Arg Ser Gln Ile
1               5                   10                  15

Val Glu Glu Ala Val Ser Ser Glu Phe Pro Ala Leu Lys Asp His His
            20                  25                  30

Trp Glu Asp Glu Arg Trp Ser Gln Glu Ile Leu Asn Arg Tyr Trp Gln
        35                  40                  45

Gly Lys Pro Arg Ile Val Pro Asn Val Met Thr Asp Ile Trp Thr Asp
    50                  55                  60

Cys Leu Val Glu Tyr Ala Ser Val Gly Gln Val Gln Ser Lys Ile Val
65                  70                  75                  80

Ala Pro Ile Leu Gln Glu Val Arg Ser Ser Glu Ser His Arg Trp Ile
                85                  90                  95

Ala Pro Gly Gln Thr Lys Lys Leu Trp Gly Val Leu Val Val His
            100                 105                 110
```

<210> SEQ ID NO 17
<211> LENGTH: 111
<212> TYPE: PRT
<213> ORGANISM: Unknown
<220> FEATURE:
<223> OTHER INFORMATION: Cyanothece sp. PCC 7425

<400> SEQUENCE: 17

```
Asp Arg Val Ile Val Phe Gln Leu Phe Pro Asn Gly Lys Ser Arg Ile
1               5                   10                  15

Val Glu Glu Ala Val Ser Ser Gly Leu Thr Val Leu Lys Ala Gly His
            20                  25                  30

Trp Glu Asp Glu Val Trp Pro Gln Glu Ile Leu Asp Tyr Tyr Trp Gln
        35                  40                  45

Gly Gln Pro Arg Ile Val Ala Asp Val Met Asp Asp Arg Trp Thr Asp
    50                  55                  60

Cys Leu Val Gly Tyr Ser Lys Gln Gly Glu Ile Val Ser Lys Ile Val
65                  70                  75                  80

Ala Pro Ile Leu Gln Asp Ile His Thr Phe Glu Glu Asn Pro Trp Ala
                85                  90                  95

Asn Pro Ser Lys Arg His Gln Leu Trp Gly Val Leu Val Ile His
            100                 105                 110
```

<210> SEQ ID NO 18
<211> LENGTH: 111
<212> TYPE: PRT
<213> ORGANISM: Nodosilinea nodulosa

<400> SEQUENCE: 18

```
Asp Arg Val Ile Ile Phe Gln Val His Ser Asp Gly His Ser Lys Ile
1               5                   10                  15
```

```
Val Glu Glu Ala Val Ser Glu Ser Leu Pro Thr Leu Lys Gly Met Arg
            20                  25                  30

Trp Glu Asp Glu Val Trp Ser Gln Asp Ile Leu Asp Val Tyr Trp Arg
        35                  40                  45

Gly Gln Pro Arg Ile Val Ala Asp Val Met Ala Asp Thr Trp Thr Asp
    50                  55                  60

Cys Leu Val Asp Tyr Ser Gln Ala Gly Gln Ile Gln Ser Lys Ile Val
65                  70                  75                  80

Ala Pro Ile Leu Gln Glu Ile Arg Thr Ser Glu Gly His Arg Trp Val
                85                  90                  95

Ala Pro Arg Ala Lys Asn Lys Ile Trp Gly Val Leu Val Val His
            100                 105                 110


<210> SEQ ID NO 19
<211> LENGTH: 116
<212> TYPE: PRT
<213> ORGANISM: Spirulina subsalsa

<400> SEQUENCE: 19

Asp Arg Val Ile Val Phe Arg Phe Cys Asp Leu Gly Arg Thr Cys Ile
1               5                   10                  15

Phe Glu Glu Ala Val Ala Glu Asp Leu Pro Ser Leu Lys Tyr Met Asn
            20                  25                  30

Trp Glu Asp Glu Gln Trp Ser Ser Glu Ile Leu Gln Phe Tyr Trp Gln
        35                  40                  45

Gly Gln Pro Arg Ile Val Pro Asp Val Met Asn Asp Pro Leu Thr Pro
    50                  55                  60

Cys Leu Leu Asp Tyr Ser Arg Gln Gly Gln Ile Gln Ser Lys Ile Val
65                  70                  75                  80

Ala Pro Ile Leu Gln Glu Ile His Asn Gly Glu Arg Gly Asn Gly Glu
                85                  90                  95

Ile Asp Pro Trp Thr Asp Pro Glu Ser Gly Asn Lys Leu Trp Gly Leu
            100                 105                 110

Leu Val Ile His
        115


<210> SEQ ID NO 20
<211> LENGTH: 110
<212> TYPE: PRT
<213> ORGANISM: Dolichospermum circinale

<400> SEQUENCE: 20

Glu Arg Val Ile Val Phe Arg Leu Phe Pro Asp Gly Lys Ser Gln Ile
1               5                   10                  15

Val Glu Glu Ser Val Ala Asn Gly Tyr Met Thr Phe Lys Asp Ser Tyr
            20                  25                  30

Trp Glu Asp Glu Lys Trp Ser Gln Asp Ile Leu Glu Tyr Tyr Trp Gln
        35                  40                  45

Gly Lys Pro Arg Ile Val Leu Asp Val Met Asp Asp Ile Trp Thr Asp
    50                  55                  60

Cys Leu Lys Ala Tyr Ser Arg Gln Gly Asn Ile Arg Ser Lys Ile Val
65                  70                  75                  80

Ala Pro Ile Leu Gln Asp Leu Val Glu Asn Glu Asn Gly Arg Trp Val
                85                  90                  95

Asn His Pro His Asn Lys Leu Trp Gly Val Leu Val Val His
            100                 105                 110
```

<210> SEQ ID NO 21
<211> LENGTH: 114
<212> TYPE: PRT
<213> ORGANISM: Unknown
<220> FEATURE:
<223> OTHER INFORMATION: Leptolyngbya sp. PCC 6406

<400> SEQUENCE: 21

```
Asp Arg Val Ile Val Phe Gln Leu Phe Ala Asp Gly Arg Ser Gln Ile
1               5                   10                  15

Val Glu Glu Glu Val Leu Gly Ser Leu Pro Ala Leu Arg Thr Met His
            20                  25                  30

Trp Glu Asp Glu Val Trp Ser Gln Asp Ile Leu Ala Leu Tyr Trp Gln
        35                  40                  45

Gly Gln Pro Arg Ile Val Pro Asp Val Met Asp Asp Ile Trp Thr Asp
    50                  55                  60

Cys Leu Val Glu Tyr Ala Gln Ala Gly Gln Ile Lys Ser Lys Ile Val
65                  70                  75                  80

Ala Pro Ile Leu Gln Gln Gly His Thr Ala Thr Gly Asn Arg Trp Gln
                85                  90                  95

Asp Pro Asn His Pro His Lys Leu Trp Gly Val Leu Val Val His Ala
            100                 105                 110

Cys His
```

<210> SEQ ID NO 22
<211> LENGTH: 111
<212> TYPE: PRT
<213> ORGANISM: Planktothrix prolifica

<400> SEQUENCE: 22

```
Asp Arg Ala Ile Ile Phe Gln Leu Phe Asp Asn Gly Asn Ser Gln Ile
1               5                   10                  15

Val Glu Glu Ser Val His Ser Asn Phe Leu Asn Leu Lys Ala Leu Asn
            20                  25                  30

Trp Asp Asn Glu Val Trp Ser Gln Glu Ile Leu Asp Cys Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Leu Lys Gly Gln Ile Lys Ser Lys Ile Val
65                  70                  75                  80

Ala Pro Ile Leu Leu Glu Ser His Ile Ser Glu Asn His Arg Trp Val
                85                  90                  95

Ala Thr Asp Gly Tyr Lys Lys Leu Trp Gly Val Leu Val Val His
            100                 105                 110
```

<210> SEQ ID NO 23
<211> LENGTH: 110
<212> TYPE: PRT
<213> ORGANISM: Anabaena circinalis

<400> SEQUENCE: 23

```
Glu Arg Val Ile Val Phe Arg Leu Phe Pro Asp Gly Lys Ser Gln Ile
1               5                   10                  15

Val Glu Glu Ala Val Ala Asn Gly Tyr Met Thr Phe Lys Asp Ser Tyr
            20                  25                  30

Trp Glu Asp Glu Lys Trp Ser Gln Asp Ile Leu Glu Tyr Tyr Trp Gln
        35                  40                  45
```

-continued

```
Gly Lys Pro Arg Ile Val Leu Asp Val Met Asp Asp Ile Trp Thr Asp
    50                  55                  60

Cys Leu Lys Ala Tyr Ser Arg Gln Gly Asn Ile Arg Ser Lys Ile Val
65                  70                  75                  80

Ala Pro Ile Leu Gln Asp Leu Val Glu Asn Glu Asn Gly Arg Trp Val
                85                  90                  95

Asn His Pro His Asn Lys Leu Trp Gly Val Leu Val Val His
            100                 105                 110


<210> SEQ ID NO 24
<211> LENGTH: 101
<212> TYPE: PRT
<213> ORGANISM: Fischerella thermalis

<400> SEQUENCE: 24

Asp Arg Val Leu Ile Phe Arg Leu Asn Gln Asp Gly Ser Gly Gln Ile
1               5                   10                  15

Ile Glu Glu Ala Val Val Pro Glu Tyr Pro Met Thr Tyr Gln Met Arg
            20                  25                  30

Trp Val Asp Glu Cys Phe Pro Asp Asp Cys Tyr Glu Tyr Tyr Arg Gln
        35                  40                  45

Gly Asn Pro Arg Ile Leu Pro Asp Val Ala Lys Asp Glu Trp Gly Ala
    50                  55                  60

Cys Leu Val Glu Phe Met Gln Gln Ile Gly Val Lys Ser Lys Val Val
65                  70                  75                  80

Ala Pro Ile Ile Gln Thr Leu Glu Asp Ser Ser Thr Arg Val Trp Gly
                85                  90                  95

Leu Leu Ile Val His
            100


<210> SEQ ID NO 25
<211> LENGTH: 101
<212> TYPE: PRT
<213> ORGANISM: Chlorogloeopsis fritschii

<400> SEQUENCE: 25

Asp Arg Ala Leu Ile Phe Gln Leu Asn Gln Asp Gly Ser Gly Gln Ile
1               5                   10                  15

Ile Gln Glu Ala Val Ile Pro Asp Tyr Pro Val Thr Asn Gln Met Arg
            20                  25                  30

Trp Leu Asp Glu Cys Phe Pro Asp Glu Cys Tyr Glu Tyr Tyr Cys Gln
        35                  40                  45

Gly Asn Ala Arg Ile Val Pro Asp Val Ala Lys Asp Asp Trp Gly Ala
    50                  55                  60

Cys Leu Val Glu Phe Met Gln Glu Val Gly Val Lys Ser Lys Val Val
65                  70                  75                  80

Ala Pro Ile Val Gln Ser Phe Glu Gly Ser Ser Asn Lys Val Trp Gly
                85                  90                  95

Leu Leu Ile Val His
            100


<210> SEQ ID NO 26
<211> LENGTH: 101
<212> TYPE: PRT
<213> ORGANISM: Unknown
<220> FEATURE:
<223> OTHER INFORMATION: Fischerella sp. PCC 9431
```

<400> SEQUENCE: 26

Asp Arg Ala Leu Ile Phe Arg Leu Asn Glu Asp Gly Ser Gly Gln Val
1 5 10 15

Ile Lys Glu Ala Val Val Pro Glu Tyr Pro Val Thr Glu Gln Met Arg
20 25 30

Trp Arg Asp Glu Pro Leu Pro Asp Tyr Cys Tyr Asp Phe Tyr Arg Gln
35 40 45

Gly Asn Pro Arg Ile Val Pro Asn Val Ala Ile Tyr Asp Trp Ala Ser
50 55 60

Cys Leu Ala Glu Phe Leu Gln Gln Ala Ser Val Lys Ser Lys Ile Val
65 70 75 80

Ala Pro Ile Val Gln Thr Leu Glu Asp Ser Ser Thr Arg Val Trp Gly
85 90 95

Leu Leu Ile Val His
100

<210> SEQ ID NO 27
<211> LENGTH: 101
<212> TYPE: PRT
<213> ORGANISM: Unknown
<220> FEATURE:
<223> OTHER INFORMATION: Fischerella sp. PCC 9339

<400> SEQUENCE: 27

Asp Arg Ala Leu Ile Phe Arg Leu Asn Gln Asp Gly Ser Gly Gln Val
1 5 10 15

Ile Lys Glu Ala Val Val Pro Glu Tyr Pro Met Thr Ser Gln Met Arg
20 25 30

Cys Thr Asp Glu Cys Phe Pro Asp Asp Cys Tyr Glu Tyr Tyr Arg Gln
35 40 45

Gly Asn Ala Arg Ile Leu Pro Asp Val Ala Lys Asp Glu Trp Ser Asp
50 55 60

Cys Leu Val Glu Phe Met Gln Gln Ile Gly Val Lys Ser Lys Val Val
65 70 75 80

Ala Pro Ile Ile Gln Thr Leu Glu Asp Ser Ser Thr Arg Val Trp Gly
85 90 95

Leu Leu Ile Val His
100

<210> SEQ ID NO 28
<211> LENGTH: 101
<212> TYPE: PRT
<213> ORGANISM: Chlorogloeopsis fritschii

<400> SEQUENCE: 28

Asp Arg Ala Leu Ile Phe Arg Leu His Gly Asn Gly Thr Gly Gln Val
1 5 10 15

Ile Gln Glu Ala Val Arg Pro Glu Tyr Pro Val Thr Glu Gln Met Leu
20 25 30

Phe Pro Asp Glu Cys Phe Pro Gln Glu Cys Tyr Glu Tyr Tyr Cys Gln
35 40 45

Gly Gln Pro Arg Ile Val Ser Asp Val Phe Ala Glu Asp Phe Ser Ser
50 55 60

Cys Leu Val Glu Phe Met Gln Lys Ile Gly Val Lys Ser Lys Ile Val
65 70 75 80

Ala Pro Ile Val Gln Thr Thr Glu Asn Ser Ser Thr Lys Val Trp Gly
85 90 95

```
Leu Leu Ile Val His
            100


<210> SEQ ID NO 29
<211> LENGTH: 1886
<212> TYPE: PRT
<213> ORGANISM: Unknown
<220> FEATURE:
<223> OTHER INFORMATION: Anabaena cylindrica PCC 7122

<400> SEQUENCE: 29

Met Phe Ser Arg Ser Val Ile Leu Thr Pro Ser Glu Leu Lys Ser Ala
1               5                   10                  15

Ile Ile Arg Asn Pro Leu Ile Val Lys Pro Glu Thr Thr Val Ile Asp
            20                  25                  30

Ala Ile Ala Met Leu Ala Ala Gly Ile Gly Gln Met Gly Gly Val Gly
        35                  40                  45

Ala Ile Ser Asn Thr Lys Ile Ile Asp Gly Gln Leu Asp Glu Leu His
    50                  55                  60

Leu Glu Thr Arg Pro Ser Cys Val Leu Val Met Glu Asp Gly Lys Leu
65                  70                  75                  80

Leu Gly Ile Phe Thr Glu Arg Asp Val Val Arg Leu Ile Ser Gln Gln
                85                  90                  95

His Ser Leu Glu Asn Leu Val Ile Gln Asp Val Met Thr Tyr Pro Val
            100                 105                 110

Val Thr Leu Tyr Glu Ser Ala Phe Ser Asp Leu Phe Ser Thr Ile Asn
        115                 120                 125

Leu Leu Gln Gln Tyr His Ile Arg His Ile Pro Ile Leu Asn Glu Gln
    130                 135                 140

Asp Cys Val Val Gly Leu Val Thr Asp Glu Ser Leu Arg Gln Ile Ser
145                 150                 155                 160

Asn Pro Ile Tyr Pro Leu Arg Ser Arg Leu Val Ser Ala Ala Met Thr
                165                 170                 175

Asn Glu Val Ile Cys Ala Ala Leu Asp Ser Ser Ile Arg Thr Ile Val
            180                 185                 190

Gln Leu Met Ala Lys Asn Cys Ile Ser Cys Val Ile Ile Val Gln Lys
        195                 200                 205

Arg Gly Ser Gln Ala Gln Pro Leu Gln Ile Pro Val Gly Ile Ile Thr
    210                 215                 220

Glu Gln Asp Ile Val Lys Phe Gln Val Leu Gly Leu Asn Leu Glu Thr
225                 230                 235                 240

Ser Gln Ala Glu Thr Val Met Ser Ala Pro Ile Phe Ser Val Lys Pro
                245                 250                 255

Asn Asp Ser Leu Glu Met Val Gln Gln Ile Met Glu Gln Gln Leu Ile
            260                 265                 270

Arg Lys Leu Ala Val Thr Asn Glu Glu Gly Asn Leu Leu Gly Ile Val
        275                 280                 285

Thr Gln Asn Ser Leu Leu Gln Thr Leu Asn Pro Leu Glu Leu Tyr Lys
    290                 295                 300

Leu Ala Glu Val Leu Glu Glu Lys Val Leu Arg Leu Glu Ala Glu Lys
305                 310                 315                 320

Ile Leu Leu Leu Glu Thr Arg Thr Val Glu Leu Glu Lys Glu Leu Ala
                325                 330                 335

Asp Gln Asn Ile Ala Leu Gln Thr Lys Thr Glu Gln Glu Lys Leu Val
            340                 345                 350
```

-continued

```
Ala Ile Ile Ala Thr Gln Ile Arg Ser Ser Leu Asn Leu Gln Thr Ile
        355                 360                 365

Leu Asp Thr Thr Val Glu Gln Ile Arg Gln Leu Leu Asn Cys Asp Arg
    370                 375                 380

Val Thr Ile Trp Gln Leu Glu Ala Asn Gly Lys Leu Ile Thr Val Ala
385                 390                 395                 400

Glu Ser Thr Gly Cys Thr Leu Ser Leu Leu Gly Gln Gln Ser Gln Asp
                405                 410                 415

Gln Cys Ile Ser Gln Gln Leu Val Glu Ile Tyr Gln Gln Gly Lys Ile
            420                 425                 430

Arg Ile Val Pro Asp Ile Tyr Thr Thr Glu Met Ser Asp Cys His Arg
        435                 440                 445

Asn Leu Leu Ile Ser Leu Asp Ile Arg Ala Lys Ile Leu Met Pro Leu
    450                 455                 460

Met Cys Gly Asp Glu Leu Trp Gly Phe Leu Asn Val Thr Glu Ser Gln
465                 470                 475                 480

His Pro Arg Gln Trp Gln Asp Ser Glu Ile Glu Leu Leu Lys Leu Leu
                485                 490                 495

Thr Val Gln Leu Ala Ile Ala Leu Gln Gln Ala Thr Thr His Gln Lys
            500                 505                 510

Leu Gln Glu Glu Leu Arg Glu Arg Gln Arg Ala Glu Ser Thr Leu Gln
        515                 520                 525

Lys Leu Val Thr Gly Thr Ala Ala Val Thr Gly Asp Asp Phe Phe Pro
    530                 535                 540

Ala Leu Val Gln His Ile Ala Glu Ala Leu Asp Val Ser Tyr Ala Ile
545                 550                 555                 560

Val Thr Glu Leu Val Gly Asp Gln Leu His Thr Leu Gly Phe Trp Ala
                565                 570                 575

Asn Gly Ser Leu Gln Pro Ser Val Ser Tyr Tyr Ala Ala His Thr Pro
            580                 585                 590

Cys Lys Tyr Ala Leu Arg Asp Gly Gln Phe Tyr Cys Lys Ser Gly Ile
        595                 600                 605

Gln Glu Ala Phe Ala Asn Asp Phe Asp Leu Val Met Met Arg Ala Asp
    610                 615                 620

Ser Tyr Leu Gly Ile Ala Leu Lys Asp Asp Leu Gly Asn Ala Ile Gly
625                 630                 635                 640

Asn Leu Cys Ile Leu Asp Val Gln Pro Leu His Asn Ser Gln Leu Lys
                645                 650                 655

Glu Ala Arg Asp Ile Leu Gln Val Phe Ala Ala Arg Ala Ala Ala Glu
            660                 665                 670

Leu Gln Arg Lys Ile Ala Lys Asp Ala Leu Ile Ser Leu Asn His Asn
        675                 680                 685

Leu Glu Leu Arg Ile Glu Gln Arg Thr Thr Lys Leu Gln Ala Arg Glu
    690                 695                 700

Ala Gln Leu Arg Asp Leu Phe Asp Asn Ala Thr Asp Leu Ile Gln Ser
705                 710                 715                 720

Ile Ser Leu Asn Gly Arg Ile Leu Phe Val Asn Lys Ser Trp Lys Glu
                725                 730                 735

Ala Leu Gly Tyr Asp Asp Thr Asp Leu Glu Lys Leu Ser Ile Phe Gln
            740                 745                 750

Val Ile His Pro Asp Glu Leu Val His Cys Gln Thr Val Met Ala Ser
        755                 760                 765
```

-continued

```
Leu Ala Ser Gly Asn Pro Ser Met Ser Met Glu Thr Arg Phe Leu Thr
    770                 775                 780

Lys Asp Gly Arg Glu Ile Ile Val Glu Gly Asn Val Asn Cys Gln Phe
785                 790                 795                 800

Ala Lys Gly Lys Pro Ile Ala Thr Arg Gly Val Phe Arg Asp Ile Thr
                805                 810                 815

Gln Arg Lys Gln Ala Glu Leu Ala Leu Glu Glu Ala Gln Gln Phe Leu
            820                 825                 830

Tyr Thr Val Leu Asp Thr Phe Pro Leu Phe Ile Phe Trp Lys Asn Arg
        835                 840                 845

Glu Ser Val Tyr Leu Gly Cys Asn Gln Asn Phe Ala Ile Ser Gly Gly
    850                 855                 860

Phe Ala Ser Pro Ala Glu Val Ile Gly Lys Thr Asp Asp Asp Phe Pro
865                 870                 875                 880

Trp Arg Asn Gly Glu Ala Asp Ile Tyr Arg Ala Asp Asp Arg Gln Val
                885                 890                 895

Ile Glu Ser Gly Ile Ala Lys Leu Gly Ile Ile Glu Thr Gln Gln Gln
            900                 905                 910

Thr Asn Gly Ser Thr Ile Trp Leu Glu Thr Asn Lys Leu Pro Leu Arg
        915                 920                 925

Asn Leu Lys Gly Glu Val Ile Gly Ile Leu Gly Thr Tyr Gln Asp Ile
    930                 935                 940

Thr Glu Arg Lys Gln Ala Glu Asn Ala Leu Gln Asn Ser Glu Leu Arg
945                 950                 955                 960

Phe Arg Arg Met Phe Asp Ser Ser Val Val Gly Met Ile Phe Ala Asp
                965                 970                 975

Phe Gln Gly Arg Ile Leu Asp Thr Asn Asp Arg Phe Leu Gln Met Leu
            980                 985                 990

Gly Tyr Thr Arg Asp Asp Phe Asn  Ala Gly Ala Ile Asn  Trp Leu Ala
        995                 1000                1005

Ile Thr  Pro Ser Glu Tyr Ile  Pro Thr Asp Phe Ala  Ala Ile Asp
    1010                 1015                 1020

His Leu  Met Lys Tyr Gly Glu  Ile Asp Pro Trp Glu  Lys Ala Tyr
    1025                 1030                 1035

Tyr Arg  Gln Asp Gly Ser Arg  Ile Pro Val Leu Ile  Gly Ala Ala
    1040                 1045                 1050

Ile Leu  Pro Glu Ser Lys Asp  Gln Thr Ile Cys Val  Val Val Asp
    1055                 1060                 1065

Ile Ser  Glu Gln Lys Ala Ala  Leu Arg Glu Arg Gln  Glu Ala Glu
    1070                 1075                 1080

Leu Ser  Leu Gln Gln Glu Ala  Met Tyr Lys Gln Leu  Leu Leu Thr
    1085                 1090                 1095

Leu Ser  Gln Ala Ile Arg Glu  Ser Leu Glu Ile Glu  Val Ile Leu
    1100                 1105                 1110

Asn Thr  Ser Val Asn Glu Ala  Arg Ser Leu Leu Val  Val Asp Arg
    1115                 1120                 1125

Val Ala  Val Tyr Arg Phe Gln  Pro Asp Trp Ser Gly  Glu Phe Ile
    1130                 1135                 1140

Thr Glu  Ala Val Val Pro Gly  Trp Val Lys Leu Ala  Ala Glu Ser
    1145                 1150                 1155

Asp Val  Lys Lys Val Trp Gln  Asp Thr Tyr Leu Gln  Glu Thr Gln
    1160                 1165                 1170

Gly Gly  Arg Phe Arg Asn Tyr  Glu Thr Leu Ile Val  Arg Asp Ile
```

-continued

```
    1175                1180                1185

Tyr Gln  Ala Gly Leu Gln Pro  Cys His Ile Glu Leu  Leu Glu Gln
    1190                1195                1200

Phe Gln  Ala Arg Ala Tyr Val  Ile Thr Pro Ile Phe  Val Gly Glu
    1205                1210                1215

Ser Leu  Trp Gly Leu Leu Gly  Met Tyr Gln Asn Asp  Gln Pro Tyr
    1220                1225                1230

Trp Trp  Thr Thr Gly Glu Ile  Glu Leu Leu Gln Gln  Ile Ala Ser
    1235                1240                1245

Gln Leu  Ala Ile Ala Ile Tyr  Gln Ala Asn Leu Tyr  Gln Gln Val
    1250                1255                1260

Gln Ala  Glu Leu Ile Ile Arg  Gln Lys Ala Glu Leu  Ala Ile Ser
    1265                1270                1275

His Gln  Leu Gln Gln Gln Arg  Thr Leu Gly Lys Ile  Val Gln Lys
    1280                1285                1290

Ile Arg  Asp Ser Leu Asp Ile  Lys Asp Ile Leu Ala  Thr Val Thr
    1295                1300                1305

Gln Glu  Ile Lys Asn Ser Leu  Asn Cys Asp Arg Val  Ile Val Phe
    1310                1315                1320

Arg Leu  Phe Ala Asp Gly Glu  Ser Gln Ile Val Glu  Glu Ala Val
    1325                1330                1335

Ser Gly  Glu Leu Val Ser Leu  Lys Asn Arg His Trp  Asp Asn Glu
    1340                1345                1350

Val Trp  Ser Gln Glu Ile Leu  Asp Tyr Tyr Trp Gln  Gly Gln Pro
    1355                1360                1365

Arg Ile  Val Thr Asp Val Met  Glu Asp Ile Trp Thr  Asp Cys Leu
    1370                1375                1380

Val Glu  Tyr Ser Ile Glu Gly  Gln Val Gln Ser Lys  Ile Val Ala
    1385                1390                1395

Pro Ile  Leu Gln Glu Ala Gln  Asp Gly Glu Lys Asn  Arg Trp Val
    1400                1405                1410

Ala Ser  Gly Glu Asn Asn Lys  Leu Trp Gly Val Leu  Val Val His
    1415                1420                1425

Ala Cys  Ser Glu Lys Arg Ile  Trp Lys Asp Cys Glu  Ala Gln Leu
    1430                1435                1440

Leu Gln  Gln Ile Ala Asn Gln  Leu Ala Ile Ala Ile  Gln Gln Ala
    1445                1450                1455

Asn Leu  Phe Glu Lys Leu Gln  Gln Glu Leu Thr Glu  Arg Gln Lys
    1460                1465                1470

Thr Glu  Ile Lys Leu Thr His  Ser Asn Gln Gln Leu  Ala Ile Ser
    1475                1480                1485

Asn Glu  Glu Leu Ala Arg Ala  Thr Arg Leu Lys Asp  Glu Phe Leu
    1490                1495                1500

Ala Asn  Met Ser His Glu Leu  Arg Thr Pro Leu Asn  Ala Ile Leu
    1505                1510                1515

Gly Met  Thr Glu Ala Leu Gln  Glu Gln Val Phe Gly  Gly Ile Asn
    1520                1525                1530

Glu Arg  Gln Leu Lys Ala Leu  Lys Thr Val Glu Asn  Ser Gly Asn
    1535                1540                1545

His Leu  Leu Glu Leu Ile Asn  Asp Ile Leu Asp Leu  Ala Lys Ile
    1550                1555                1560

Glu Ala  Gly Gln Ile Asn Leu  Asn Cys Thr Ser Ile  Ser Val Ser
    1565                1570                1575
```

```
His Leu  Cys Gln Ser Ser Leu  Ala Phe Ile Lys Gln  Gln Ala Leu
    1580                 1585                 1590

Lys Lys  Arg Ile Lys Leu Asn  Ile Lys Leu Pro Gln  Asn Leu Pro
    1595                 1600                 1605

Asp Leu  Phe Val Asp Glu Arg  Arg Ile Arg Gln Val  Leu Ile Asn
    1610                 1615                 1620

Leu Leu  Asn Asn Gly Val Lys  Phe Thr Pro Gln Gly  Gly Ser Ile
    1625                 1630                 1635

Thr Leu  Glu Val Thr Gln Phe  His Pro Asp Met Glu  Asn Ala Asp
    1640                 1645                 1650

Phe Phe  Pro Gln Gly Phe Leu  Arg Ile Thr Val Ile  Asp Thr Gly
    1655                 1660                 1665

Ile Gly  Ile Ser Pro Glu Asn  Ile Asn Arg Leu Phe  His Pro Phe
    1670                 1675                 1680

Ile Gln  Ile Asp Ser Ser Leu  Ser Arg Gln Tyr Asn  Gly Thr Gly
    1685                 1690                 1695

Leu Gly  Leu Ala Leu Val Lys  Gln Ile Val Glu Leu  His Gly Gly
    1700                 1705                 1710

Gln Val  Gly Leu Thr Ser Glu  Leu Gly Val Gly Ser  Cys Phe Met
    1715                 1720                 1725

Ile Asp  Leu Pro Cys Ser Pro  Leu Leu Ser Glu Ile  Thr Thr Asp
    1730                 1735                 1740

Asp Gln  Ser Ala Ser Thr Ser  Glu Leu Asp Phe Leu  Thr Ala Glu
    1745                 1750                 1755

Glu Ala  Glu Ser Gln Ala Pro  Leu Ile Leu Leu Ala  Glu Asp Asn
    1760                 1765                 1770

Glu Ala  Asn Ile Ile Thr Phe  Ser Ser Tyr Leu Glu  Ala Lys Gly
    1775                 1780                 1785

Tyr Gln  Ile Ile Leu Ala Arg  Asp Gly His Glu Ala  Val Asn Leu
    1790                 1795                 1800

Ala Lys  Thr His Gln Pro Asn  Leu Ile Leu Met Asp  Ile Gln Met
    1805                 1810                 1815

Pro Gly  Met Asp Gly Leu Glu  Ala Met Thr Gln Ile  Arg Leu Asp
    1820                 1825                 1830

Pro Lys  Leu Ile Asn Ile Pro  Ile Ile Ala Leu Thr  Ala Leu Ala
    1835                 1840                 1845

Met Thr  Gly Asp Arg Glu Arg  Cys Leu Glu Ala Gly  Ala Asn Asp
    1850                 1855                 1860

Tyr Leu  Thr Lys Pro Val Met  Leu Lys Gln Leu Ala  Thr Thr Ile
    1865                 1870                 1875

Gln Gln  Leu Leu Asn Lys Asp  Gly
    1880                 1885
```

<210> SEQ ID NO 30
<211> LENGTH: 1276
<212> TYPE: PRT
<213> ORGANISM: Unknown
<220> FEATURE:
<223> OTHER INFORMATION: Anabaena cylindrica PCC 7122

<400> SEQUENCE: 30

```
Met Phe Val Pro Ala Lys Ala His Thr Gln Ala Glu Leu Arg Leu Ala
1               5                   10                  15

Ile Val Arg Asp Pro Leu Leu Val Thr Pro Glu Thr Thr Val Val Glu
            20                  25                  30
```

```
Ala Ile Ala Gln Met Ser Gly Val Arg Ser Val Cys Ser Val Ser Gln
        35                  40                  45

Asn Thr Asp Ser Lys Gln Glu Ser Leu Leu Ala Glu Ala Arg Ser Ser
    50                  55                  60

Cys Val Val Val Val Glu Asn Asn Gln Pro Ile Gly Ile Phe Thr Glu
65                  70                  75                  80

Arg Asp Val Val Arg Leu Ser Ala Gln Arg Arg Lys Leu Asn Asn Leu
                85                  90                  95

Ala Ile Arg Asp Val Met Ala Tyr Pro Leu Val Thr Leu Tyr Glu Ser
            100                 105                 110

Glu Phe Thr Asp Leu Phe Phe Ala Ile Asn Leu Leu Gln His His Lys
        115                 120                 125

Ile Arg His Leu Pro Val Ile Asp Glu Gln Asn Gln Leu Val Gly Leu
    130                 135                 140

Leu Thr His Glu Ser Leu Arg Gln Lys Ser Arg Pro Val Asp Leu Leu
145                 150                 155                 160

Arg Leu Arg Leu Val Ser Glu Val Met Thr Thr Lys Val Ile Cys Ala
                165                 170                 175

Ala Pro His Ile Ser Ile Leu Met Ile Ala Arg Leu Met Ala Glu Asn
            180                 185                 190

Arg Ile Ser Ser Val Val Ile Val Gln Thr Gln Ala Ser Leu Ile Ile
        195                 200                 205

Pro Ile Gly Ile Val Thr Glu Arg Asp Ile Val Gln Phe Gln Ala Leu
    210                 215                 220

Asp Leu Asn Phe Glu Thr Cys Leu Ala Glu Ala Val Met Ser Thr Pro
225                 230                 235                 240

Ile Phe Cys Val Asn Ala Asp Glu Ser Leu Trp Asn Val Gln Gln Ile
                245                 250                 255

Met Glu Gln Arg Leu Ile Gln Arg Leu Ala Val Thr Gly Thr Asn Gly
            260                 265                 270

Glu Leu Leu Gly Ile Val Thr Gln Ser Ser Ile Leu Gln Val Leu Asn
        275                 280                 285

Pro Leu Glu Leu Tyr Lys Leu Thr Glu Leu Leu Glu Lys Lys Val Ser
    290                 295                 300

Gln Leu Glu Ala Glu Lys Ile Glu Leu Leu Glu Asn Arg Thr Val Glu
305                 310                 315                 320

Leu Glu Glu Glu Val Gly Glu Arg Thr Ile Ala Leu Arg Lys Lys Ile
                325                 330                 335

Val Arg Glu Gln Leu Ile Thr Lys Ile Ala Ala Gln Ile Arg Ser Ser
            340                 345                 350

Leu Asn Leu Gln Asp Ile Leu Asn Thr Thr Val Ala Glu Met Arg Ser
        355                 360                 365

Leu Leu Gln Cys Asp Arg Val Ile Ile Tyr Gln Phe Arg Pro Asp Phe
    370                 375                 380

Ser Gly Thr Val Ile Ala Glu Ser Ile Val Ala Asn Gly Val Ser Ile
385                 390                 395                 400

Leu His Asp Glu Pro Gln Asp Pro Cys Ile Thr Pro Glu Trp Leu Glu
                405                 410                 415

Pro Tyr Arg Gln Gly Gln Ile Arg Val Ile Asn Asp Ile His Ser Glu
            420                 425                 430

Ser Met Ser Asp Cys Tyr Gln Asp Met Leu Ile Glu Leu Asp Ile Arg
        435                 440                 445
```

-continued

```
Ala Lys Leu Met Val Pro Ile Val Ile Ala Glu Gln Leu Trp Gly Leu
    450                 455                 460

Ile Leu Thr Ser Tyr Arg Asp Gln Ser His Asn Trp Glu Leu Glu Glu
465                 470                 475                 480

Ile Glu Leu Val Arg Gln Leu Ser Ile Gln Leu Ser Val Ala Ile Gln
                485                 490                 495

Gln Ala Gln Thr His Gln Gln Leu Tyr Gln Leu Asn Gln Glu Leu Glu
            500                 505                 510

Asn Gln Ile Gln Glu Arg Thr Lys Ala Leu Gln Ala Ser Glu Ala Lys
        515                 520                 525

Tyr Arg Asn Leu Val Glu Ala Ala Thr His Val Thr Trp Leu Cys Asn
    530                 535                 540

Thr Lys Gly Glu Leu Ile Tyr Leu Ser Pro Gln Phe Gln Glu Leu Phe
545                 550                 555                 560

Gly Trp Glu Val Glu Lys Phe Tyr Gly Gln Ser Phe Ile Ser Leu Ile
                565                 570                 575

His Pro Asp Asp Arg Pro Tyr Met Ile Ser Thr Ser Glu Glu Leu Gly
            580                 585                 590

Lys Ser Asp Lys Asn Leu Val Ser Ala Glu Phe Arg His Leu His Gln
        595                 600                 605

Asn Gly Ser Tyr Ile Trp Val Glu Ser Lys Ala Ser Asn Leu Lys Asp
    610                 615                 620

Ala Ser Gly Val Ile Ile Gly Cys Gln Gly Val Leu Leu Asp Ile Ser
625                 630                 635                 640

Asp Arg Lys Gln Ala Glu Lys Ile Ile Lys Gln Gln Ala Glu Arg Glu
                645                 650                 655

His Leu Leu Tyr Gln Thr Thr Gln Arg Ile Arg Gln Ser Leu Asp Leu
            660                 665                 670

Ala Thr Ile Phe Asn Thr Ala Thr Gln Glu Ile Arg Gln Phe Met Asn
        675                 680                 685

Ala Asp Arg Val Val Ile Phe Gln Leu Asp Pro Val Ser Asn Phe Asn
    690                 695                 700

Asp Ser Lys Phe Val Ser Glu Ser Val Val Glu Gly Phe Thr Ser Ala
705                 710                 715                 720

Leu Ala Thr Lys Ile Asn Asn Lys Cys Phe Gly Glu Gln Tyr Ala Ala
                725                 730                 735

His Tyr Gln Gln Gly Arg Ile Gln Val Val Asp Asp Leu Asp Asn Ala
            740                 745                 750

Gly Leu Thr Asp Cys His Arg Asp Val Leu Ala Gln Phe Gln Val Arg
        755                 760                 765

Ala Asn Leu Val Val Pro Leu Leu Gln Gly Glu Asn Leu Trp Gly Leu
    770                 775                 780

Leu Cys Ile His Gln Cys Ser Val Pro Arg His Trp Gln Glu Phe Glu
785                 790                 795                 800

Val Glu Leu Val Gln Gln Ile Ala His Gln Leu Ala Ile Ala Ile Gln
                805                 810                 815

Gln Ser Ile Leu Tyr Glu Gln Val Gln Ser Glu Leu Ile Ile Arg Lys
            820                 825                 830

Gln Ala Glu Asp Ala Ile Ser Leu Gln Leu Gln Arg Gln Lys Ile Ile
        835                 840                 845

Gln Asp Ile Thr Gln Gln Ile Arg Ser Thr Leu Asn Val Asn His Ile
    850                 855                 860

Leu Ala Thr Val Thr Gln Gln Val Lys Glu Leu Met Gln Val Glu Arg
```

-continued

```
865                 870                 875                 880

Val Ile Ile Phe Arg Leu Phe Pro Asn Gly Arg Ser Gln Ile Val Glu
                885                 890                 895

Glu Val Val Ser Ser Glu Tyr Ala Ala Leu Lys Asn Tyr His Trp Glu
            900                 905                 910

Asp Glu Lys Trp Ser Gln Glu Ile Leu Asp Cys Tyr Trp Gln Gly Lys
        915                 920                 925

Pro Arg Ile Val Pro Asp Val Ile Asn Asp Ile Trp Thr Ser Cys Leu
    930                 935                 940

Val Glu Tyr Thr Thr Gln Gly Asn Ile Gln Ser Lys Ile Val Ala Pro
945                 950                 955                 960

Ile Leu Gln Glu Leu Gly Glu Asn Glu Thr Gly Arg Trp Val Ser Ser
                965                 970                 975

Glu His Lys Gln Lys Leu Trp Gly Val Leu Val Val His Ala Cys Ser
            980                 985                 990

Thr Lys Arg Val Trp Glu Glu Asp  Glu Ala Gln Leu Leu  Gln Gln Ile
        995                 1000                1005

Ala Asn  Gln Leu Ala Ile Ala  Ile Gln Gln Ala Ala  Leu Phe Glu
    1010                1015                1020

Gln Leu  Gln Leu Ser Leu Val  Gln Glu Lys Glu Val  Ser Lys Met
    1025                1030                1035

Arg Ser  Arg Phe Ile Thr Met  Ala Ser His Glu Phe  Arg Thr Pro
    1040                1045                1050

Leu Ala  Ile Ile Ala Ser Ser  Thr Gly Ile Leu Gln  Lys Phe Arg
    1055                1060                1065

Glu Arg  Leu Ser Ala Glu Lys  Gln Gln Glu His Leu  Gly Thr Ile
    1070                1075                1080

Gln Lys  Thr Ile Lys His Ile  Ile Gln Leu Leu Asp  Asp Val Leu
    1085                1090                1095

Met Ile  Asn Arg Thr Glu Ala  Glu Lys Met Glu Phe  Lys Pro Glu
    1100                1105                1110

Ala Ser  Asp Ile Ile Ala Phe  Cys His Gln Ile Thr  Gln Gln Ile
    1115                1120                1125

Glu Ala  Thr Ser Asn Lys His  Val Ile Glu Phe Ser  Phe Thr Ala
    1130                1135                1140

Ser Lys  Pro Ile Leu Asp Asn  Ser Phe Ile Val Gln  Leu Asp Lys
    1145                1150                1155

Lys Ile  Leu Gln Gln Ile Leu  Ala Asn Ile Leu Thr  Asn Ala Ile
    1160                1165                1170

Lys Tyr  Ser Pro Gln Thr Ser  Leu Ile Lys Phe Asp  Leu Thr Ile
    1175                1180                1185

Glu Asp  Asp Lys Leu Ile Phe  Lys Ile Lys Asp Ser  Gly Ile Gly
    1190                1195                1200

Ile Pro  Glu Glu Tyr Lys Ile  Asn Leu Phe Ala Pro  Phe His Arg
    1205                1210                1215

Ala Ser  Asn Val Gly Thr Ile  Ser Gly Thr Gly Leu  Gly Leu Ser
    1220                1225                1230

Ile Val  Lys Lys Cys Val Asp  Leu His Lys Gly Glu  Ile Ser Phe
    1235                1240                1245

Asp Ser  Lys Leu Gly Gln Gly  Thr Thr Phe Thr Ile  Ile Ile Pro
    1250                1255                1260

Tyr Ser  Arg Ile Gln Glu Ser  Gly Val Arg Ser Gln  Glu
    1265                1270                1275
```

<210> SEQ ID NO 31
<211> LENGTH: 1573
<212> TYPE: PRT
<213> ORGANISM: Anabaena circinalis

<400> SEQUENCE: 31

Met Leu Ile Pro Val Asn Ala Ile Ser Ala Thr Glu Leu Lys Ser Ala
1               5                   10                  15

Ile Thr Tyr Asn Pro Leu Leu Ala Thr Ala Asp Thr Thr Val Arg Glu
            20                  25                  30

Ala Val Val Gln Met Ser Gly Ile Ser Ala Asn Thr Leu Trp Leu Asn
        35                  40                  45

Val Pro Ala Val Cys Tyr Ile Pro Gln Thr Ala Asn Asn Tyr Leu Glu
    50                  55                  60

His Leu Gln Ile Gln Ala Cys Cys Ser Cys Val Leu Ile Val Glu Asn
65                  70                  75                  80

Asn Arg Pro Val Gly Ile Phe Arg Gln Glu Asp Val Val Lys Ile Ser
                85                  90                  95

Thr Gln Lys Pro Asn Leu Glu Asp Leu Ala Leu Arg Asp Val Met Thr
            100                 105                 110

His Pro Val Ile Thr Leu Glu Glu Ser Lys Phe Thr Asp Leu Phe Ser
        115                 120                 125

Ala Leu Asn Leu Leu Gln His His Arg Ile Arg His Leu Pro Leu Val
    130                 135                 140

Asp Glu Glu Asn Gln Leu Val Gly Leu Leu Thr Tyr Glu Ser Leu Arg
145                 150                 155                 160

Gln Ile Leu Arg Pro Val Asp Leu Leu Arg Leu Arg Leu Val His Glu
                165                 170                 175

Val Met Thr Thr Asn Val Leu Cys Ala Pro Ala Asn Val Ser Ile Leu
            180                 185                 190

Glu Ile Ala Arg Leu Met Ala Glu Asn Gln Val Ser Ser Val Met Ile
        195                 200                 205

Val Glu Thr Gln Ala Ser Leu Thr Ile Pro Leu Gly Met Val Thr Glu
    210                 215                 220

His Asp Ile Val Gln Leu Lys Ala Leu Ser Val Asn Phe Asp Thr Cys
225                 230                 235                 240

Leu Ala Gln Thr Val Met Ser Thr Pro Val Phe Cys Val Thr Val Asp
                245                 250                 255

Glu Ser Leu Trp Asn Val Gln Gln Ile Met Glu Gln Arg Phe Ile Gln
            260                 265                 270

Leu Leu Ala Val Thr Gly Ser Lys Gly Glu Leu Leu Gly Ile Val Thr
        275                 280                 285

His Ser Ser Ile Leu Glu Ala Leu Asn Pro Trp Glu Leu Tyr Lys Leu
    290                 295                 300

Thr Ala Val Leu Gln Glu Lys Val Leu Gln Leu Glu Thr Glu Lys Ile
305                 310                 315                 320

Gln Leu Leu Glu Asn Arg Thr Leu Glu Leu Glu Lys Gln Ile Glu Glu
                325                 330                 335

Arg Thr Ile Lys Leu Arg Arg Lys Ala Glu Gln Glu Glu Leu Ile Asn
            340                 345                 350

Gln Ile Ala Thr Gln Ile His Ser Ser Leu Asp Leu Gln Glu Ile Leu
        355                 360                 365

Asn Asn Thr Val Val Gly Val Arg Ser Leu Leu Asn Cys Asp Arg Val

```
    370                 375                 380

Ile Val Tyr Gln Phe Ser Gly Asp Phe Arg Gly Gln Val Ile Ala Glu
385                 390                 395                 400

Ala Ile Ile Thr Gly Glu Ser Val Leu Asn Gln Glu Val His Asp Pro
                405                 410                 415

Cys Ile Ser Pro Glu Trp Leu Glu Leu Tyr Arg Gln Gly Gln Ile Arg
            420                 425                 430

Val Ile Asn Asp Ile Asn Thr Glu Ser Ile Thr Gln Cys His Gln Gln
        435                 440                 445

Met Leu Lys Asp Leu Asp Ile Arg Gly Lys Leu Leu Ser Pro Leu Ile
    450                 455                 460

Val Glu Asn Gln Leu Trp Gly Leu Met Leu Ala Ser Tyr Arg Asp Ile
465                 470                 475                 480

Pro His Asn Trp Glu Leu Glu Glu Ile Glu Leu Val Gln Gln Ile Ser
                485                 490                 495

Leu Arg Val Ala Ile Ala Ile Gln Gln Ala Asn Ile Tyr Gln Gln Thr
            500                 505                 510

Gln Ile Glu Ile His Gln Arg Gln Gln Ala Glu Glu Leu Ile Lys Gln
        515                 520                 525

Gln Leu Ala Glu Leu Lys Ile Trp Lys Asn Arg Tyr Glu Leu Ala Ser
    530                 535                 540

Thr Val Ser Gly Gln Ile Met Tyr Glu Tyr Asn Leu Leu Asn Asp Ala
545                 550                 555                 560

Pro Val Trp Pro Ala Asn Met Glu Glu Ile Leu Gly Tyr Ser Tyr Ser
                565                 570                 575

Glu Cys Pro Arg Asn Leu Ala Glu Phe Met Asp Ile Val His Pro Glu
            580                 585                 590

Asp Arg Asp Arg Leu Tyr Ser Leu Ile Gln Lys Lys Leu Ala His Lys
        595                 600                 605

Ser Pro Leu Ser Thr Glu Tyr Arg Leu Arg Arg Lys Asp Gly Asn Tyr
    610                 615                 620

Ile Trp Val Glu Asp Arg Asn Gln Val Val Leu Asp Asp Gln Gly Glu
625                 630                 635                 640

Ile Val Val Val Ile Gly Ala Ile Val Asp Ile Thr Val Arg Lys Asn
                645                 650                 655

Ser Glu Glu Lys Leu Ser Lys Leu Phe Gln Lys Ser Glu Lys Leu Gln
            660                 665                 670

Glu Arg Leu Ser Leu Val Leu Lys Gly Ser Asn Asp Ala Trp Trp Asp
        675                 680                 685

Trp Asp Leu Leu Glu Asp Thr Ile Tyr Tyr Ser Ala Arg Trp Phe Ser
    690                 695                 700

Leu Leu Gly Tyr Lys His Glu Glu Leu Tyr Leu Lys Ser Glu Ser Phe
705                 710                 715                 720

Trp Gln Asn Phe Met His Pro Glu Asp Ile Asp Pro Ile Arg Gly Asn
                725                 730                 735

Phe Asn Gln Ala Leu Asp Asp Lys Asn Ile Glu Phe Ile Glu Ser Lys
            740                 745                 750

Phe Arg Leu Arg His Lys Gln Glu Tyr Tyr Ile Phe Ile Asn Cys Arg
        755                 760                 765

Ser Tyr Ile Leu Arg Asp Glu Thr Gly Lys Ala Val Arg Val Ser Gly
    770                 775                 780

Ala Asn Thr Asp Ile Thr Gln Leu Val Gln Lys Glu Glu Glu Leu Gln
785                 790                 795                 800
```

```
Ala Thr Leu Asn Gln Leu Ser Gln Phe Asn Gln Lys Leu Glu Thr Arg
                805                 810                 815

Val Gln Lys Arg Thr Val Gln Leu Gln Asn Leu Ser Ser Arg Leu Glu
            820                 825                 830

Leu Ala Ile Lys Ala Ala Lys Ile Ala Ile Trp Glu Trp Asp Leu Asp
        835                 840                 845

Asn Asn His Thr Ile Trp Asp Lys Lys Met Tyr Glu Leu Tyr Gly Val
    850                 855                 860

Lys Pro Ser Glu Tyr Lys Asp Gly Met Glu Ile Leu Gln Thr Val Leu
865                 870                 875                 880

His Pro Glu Asp Ala Val Arg Val Asn Glu Ile Leu Gln His Lys Leu
                885                 890                 895

Lys Asp Gly Glu Glu Phe Glu Met Asp Phe Arg Ile Val Leu Pro Asp
            900                 905                 910

Gly Lys Ile Arg Val Leu Gln Ser Tyr Gly Ile Ile Lys Arg Asp Ser
        915                 920                 925

Gln Gly Lys Ala Glu Arg Val Ile Gly Val Asn Lys Asp Ile Thr Glu
    930                 935                 940

Trp Lys Gln Thr Glu Gln Lys Ile Lys Gln Gln Ala Glu Arg Glu Tyr
945                 950                 955                 960

Leu Leu Trp Glu Thr Thr Gln Arg Ile Arg Gln Ser Leu Asp Leu His
                965                 970                 975

Thr Ile Phe Asn Thr Ala Ala Ala Glu Ile Arg Gln Leu Met Asn Ala
            980                 985                 990

Asp Arg Val Gly Ile Phe Lys Phe  Asp Pro Asp Ser Asn  Phe Asn Tyr
        995                 1000                 1005

Gly Glu  Phe Val Ser Glu Ser  Val Val Pro Gly Phe  Ile Ser Ala
    1010                 1015                 1020

Leu Glu  Met Lys Val His Asp  Gln Cys Phe Gly Glu  Arg Phe Ser
    1025                 1030                 1035

Ser Asp  Tyr Ala Ala Gly Arg  Met Gln Ile Val Asp  Asp Ile Asp
    1040                 1045                 1050

Asn Ala  Gly Leu Ala Asp Cys  His Arg Asp Ile Leu  Ala Gln Phe
    1055                 1060                 1065

Gln Val  Arg Ala Asn Leu Val  Val Pro Leu Ile Gln  Gly Arg Ile
    1070                 1075                 1080

Leu Trp  Gly Leu Leu Cys Ile  His Gln Cys Ser Gln  Pro Arg His
    1085                 1090                 1095

Trp Glu  Asp Phe Glu Ile Glu  Leu Val Gln Gln Ile  Ala Asn Gln
    1100                 1105                 1110

Leu Ala  Ile Ala Ile Gln Gln  Ser Met Leu Tyr Glu  Gln Val Gln
    1115                 1120                 1125

Ser Glu  Leu Ile Ile Arg Lys  Gln Ala Glu Val Glu  Ile Tyr Leu
    1130                 1135                 1140

Gln Leu  Gln Arg Gln Arg Ala  Ile Gln Asp Ile Thr  Gln Glu Ile
    1145                 1150                 1155

Arg Ser  Ser Leu Asn Leu Asn  His Ile Leu Thr Thr  Ile Thr Ala
    1160                 1165                 1170

Lys Val  Gln Glu Leu Thr Lys  Ala Glu Arg Val Ile  Val Phe Arg
    1175                 1180                 1185

Leu Phe  Pro Asp Gly Lys Ser  Gln Ile Val Glu Glu  Ala Val Ala
    1190                 1195                 1200
```

-continued

```
Asn Gly  Tyr Met Thr Phe Lys  Asp Ser Tyr Trp Glu  Asp Glu Lys
    1205                 1210                 1215

Trp Ser  Gln Asp Ile Leu Glu  Tyr Tyr Trp Gln Gly  Lys Pro Arg
    1220                 1225                 1230

Ile Val  Leu Asp Val Met Asp  Asp Ile Trp Thr Asp  Cys Leu Lys
    1235                 1240                 1245

Ala Tyr  Ser Arg Gln Gly Asn  Ile Arg Ser Lys Ile  Val Ala Pro
    1250                 1255                 1260

Ile Leu  Gln Asp Leu Val Glu  Asn Glu Asn Gly Arg  Trp Val Asn
    1265                 1270                 1275

His Pro  His Asn Lys Leu Trp  Gly Val Leu Val Val  His Ala Cys
    1280                 1285                 1290

Gly Glu  Lys Arg Ile Trp Glu  Glu Ser Glu Ala Glu  Leu Leu Gln
    1295                 1300                 1305

Gln Ile  Ala Asn Gln Leu Ala  Ile Ala Ile Gln Gln  Ala Asp Leu
    1310                 1315                 1320

Phe Glu  Lys Leu Gln Lys Ser  Leu Lys Gln Glu Lys  Glu Ile Ser
    1325                 1330                 1335

Ala Met  Arg Ser Arg Phe Val  Ser Met Val Ser His  Glu Phe Arg
    1340                 1345                 1350

Thr Pro  Leu Ala Ile Ile Ser  Ser Ser Thr Gly Ile  Leu Gln Thr
    1355                 1360                 1365

Phe Gly  Asp Arg Leu Asn Ala  Glu Lys Lys Gln Gly  His Leu Glu
    1370                 1375                 1380

Thr Ile  Gln Lys Thr Ile Lys  Tyr Thr Val Gln Leu  Leu Asp Asp
    1385                 1390                 1395

Val Leu  Met Ile Asn Ser Val  Glu Thr Glu Lys Ile  Glu Phe Lys
    1400                 1405                 1410

Pro Glu  Thr Leu Asp Ile Ile  Asp Phe Cys Arg Arg  Leu Ile Arg
    1415                 1420                 1425

Glu Ile  Gln Gly Thr Ser Tyr  Ser His Val Ile Asp  Phe Ser Leu
    1430                 1435                 1440

Asn Ser  Thr Gln Leu Ile Leu  Asp His Thr Leu Phe  Ala Glu Phe
    1445                 1450                 1455

Asp Pro  Lys Ile Ile Arg Gln  Val Leu Thr Asn Leu  Leu Thr Asn
    1460                 1465                 1470

Ala Ile  Lys Tyr Ser Pro Gly  Ser Ser Thr Val Ser  Phe Ser Leu
    1475                 1480                 1485

Asn Ile  Thr Asp Lys Gln Ile  Val Phe Ile Val Gln  Asp Tyr Gly
    1490                 1495                 1500

Ile Gly  Ile Ser Glu Thr Asp  Gln Val Asn Leu Phe  Ala Ser Phe
    1505                 1510                 1515

Tyr Arg  Gly Ser Asn Val Gly  Asn Ile Ser Gly Thr  Gly Leu Gly
    1520                 1525                 1530

Leu Ala  Ile Val Lys Lys Cys  Val Asp Gln His Gln  Gly Lys Ile
    1535                 1540                 1545

Thr Leu  Glu Ser Lys Leu Asn  Gln Gly Thr Ile Phe  Lys Val Thr
    1550                 1555                 1560

Ile Pro  Arg Tyr Asn Leu Ile  Gly Asn Gly
    1565                 1570
```

<210> SEQ ID NO 32
<211> LENGTH: 1574
<212> TYPE: PRT

<213> ORGANISM: Dolichospermum circinale

<400> SEQUENCE: 32

```
Met Leu Ile Pro Val Asn Ala Ile Ser Ala Thr Glu Leu Lys Ser Ala
1               5                   10                  15

Ile Ile Tyr Asn Pro Leu Leu Ala Thr Ala Asp Thr Thr Val Arg Glu
            20                  25                  30

Ala Val Val Gln Met Ser Gly Ile Ala Ala Asn Pro Leu Trp Leu Thr
        35                  40                  45

Val Pro Ala Val Cys Ser Ile Pro His Ser Ala Asn Asn Tyr Leu Glu
    50                  55                  60

His Leu Gln Ile Gln Ala Cys Cys Ser Cys Val Leu Ile Val Glu Asn
65                  70                  75                  80

Asn Arg Pro Val Gly Ile Phe Thr Gln Gln Asp Val Val Glu Ile Ser
                85                  90                  95

Ala Gln Arg Pro Asn Leu Glu Asp Leu Ala Leu Arg Glu Val Met Thr
            100                 105                 110

His Pro Val Ile Thr Leu Gln Glu Ser Lys Phe Thr Asp Leu Phe Phe
        115                 120                 125

Thr Leu Asn Leu Leu Gln His His Arg Ile Arg His Leu Pro Leu Val
    130                 135                 140

Asp Glu Glu Asn Gln Leu Val Gly Leu Leu Thr Tyr Glu Ile Leu Arg
145                 150                 155                 160

Gln Ile Leu Arg Pro Val Asp Leu Leu Arg Leu Arg Leu Val His Glu
                165                 170                 175

Val Met Thr Thr Asn Val Leu Cys Ala Pro Ala Asn Val Ser Ile Leu
            180                 185                 190

Glu Ile Ala Arg Leu Met Thr Glu Asn Gln Val Ser Ser Val Met Ile
        195                 200                 205

Val Glu Thr Gln Ala Ser Leu Thr Ile Pro Leu Gly Met Val Thr Glu
    210                 215                 220

His Asp Ile Val Gln Leu Lys Ala Leu Ser Val Asn Phe Asp Thr Cys
225                 230                 235                 240

Leu Ala Gln Thr Val Met Ser Thr Pro Val Phe Cys Val Thr Val Asp
                245                 250                 255

Glu Ser Leu Trp Asn Val Gln Gln Ile Met Glu Gln Arg Phe Ile Gln
            260                 265                 270

Arg Leu Ala Val Thr Gly Ser Lys Gly Glu Leu Val Gly Ile Val Thr
        275                 280                 285

His Ser Ser Ile Leu Glu Ala Leu Asn Pro Trp Glu Leu Tyr Lys Leu
    290                 295                 300

Thr Ala Val Leu Gln Glu Lys Val Leu Gln Leu Glu Thr Glu Lys Ile
305                 310                 315                 320

Gln Leu Leu Gly Asn Arg Thr Leu Glu Leu Glu Lys Gln Ile Glu Glu
                325                 330                 335

Arg Thr Ile Lys Leu Arg Arg Lys Ala Glu Gln Glu Lys Leu Ile Asn
            340                 345                 350

Gln Ile Ala Thr Gln Ile Tyr Ser Ser Leu Asp Leu Gln Glu Ile Leu
        355                 360                 365

Asn Asn Thr Val Val Gly Val Arg Ser Leu Leu Asn Cys Asp Arg Val
    370                 375                 380

Ile Val Tyr Gln Phe Ser Gly Asp Phe Arg Gly Gln Val Ile Ala Glu
385                 390                 395                 400
```

-continued

```
Ala Ile Val Ala Gly Gly His Ser Val Leu His Gln Glu Val His Asp
                405                 410                 415

Pro Cys Ile Ser Pro Glu Trp Leu Glu Leu Tyr Arg Gln Gly Gln Ile
            420                 425                 430

Arg Val Ile Asn Asp Ile Asn Thr Glu Ser Ile Thr Gln Cys His Gln
        435                 440                 445

Gln Met Leu Lys Asp Leu Asp Ile Arg Gly Lys Leu Leu Ser Pro Leu
    450                 455                 460

Ile Val Glu Asn Gln Leu Trp Gly Leu Met Leu Ala Ser Tyr Arg Asp
465                 470                 475                 480

Ile Pro His Asn Trp Glu Leu Glu Glu Ile Glu Leu Val Gln Gln Ile
                485                 490                 495

Ser Leu Arg Val Ala Ile Ala Ile Gln Gln Ala Asn Ile Tyr Gln Gln
            500                 505                 510

Thr Gln Ile Glu Ile His Gln Arg Gln Gln Ala Glu Glu Leu Ile Lys
        515                 520                 525

Gln Gln Leu Ala Glu Leu Lys Ile Trp Lys Asn Arg Tyr Glu Leu Ala
    530                 535                 540

Ser Thr Ala Ser Gly Gln Ile Met Tyr Glu Tyr Asn Leu Leu Lys Asp
545                 550                 555                 560

Ala Pro Val Trp Ala Ala Asn Met Glu Glu Val Leu Gly Tyr Ser Tyr
                565                 570                 575

Ser Glu Cys Pro Arg Asn Leu Ala Glu Phe Met Asp Ile Val Tyr Pro
            580                 585                 590

Glu Asp Arg Asp Arg Leu Tyr Ser Leu Ile Gln Lys Asn Leu Ala Gln
        595                 600                 605

Lys Ser Pro Leu Ser Thr Glu Tyr Arg Leu Arg Arg Lys Asp Gly Asn
    610                 615                 620

Tyr Ile Trp Val Glu Asp Arg Asn Gln Val Val Leu Asp Asp Gln Gly
625                 630                 635                 640

Glu Ile Val Val Val Ile Gly Ala Ile Val Asp Ile Thr Val Arg Lys
                645                 650                 655

Asn Ser Glu Glu Lys Leu Ser Lys Leu Phe Gln Lys Ser Glu Lys Leu
            660                 665                 670

Gln Gln Arg Leu Ser Leu Val Leu Lys Gly Ser Asn Asp Ala Trp Trp
        675                 680                 685

Asp Trp Asp Ile Leu Asp Asp Thr Ile Tyr Tyr Ser Ala Arg Trp Phe
    690                 695                 700

Ser Leu Leu Gly Tyr Lys His Glu Glu Leu Tyr Leu Lys Ser Glu Ser
705                 710                 715                 720

Phe Trp Glu Asn Phe Met His Pro Glu Asp Ile Asp Pro Ile Arg Gly
                725                 730                 735

Asn Phe Asn Gln Ala Leu Asp Asp Lys Asn Ile Glu Phe Ile Glu Ser
            740                 745                 750

Lys Phe Arg Leu Arg His Lys Gln Glu Tyr Tyr Ile Phe Ile Asn Cys
        755                 760                 765

Arg Ser Tyr Ile Leu Arg Asp Glu Thr Gly Lys Ala Val Arg Val Ser
    770                 775                 780

Gly Ala Asn Thr Asp Ile Thr Gln Leu Val Arg Lys Glu Glu Glu Leu
785                 790                 795                 800

Gln Ala Thr Leu Asn Gln Leu Ser Gln Phe Asn Gln Lys Leu Glu Ala
                805                 810                 815

Arg Val Gln Lys Arg Thr Val Gln Leu Gln Asn Leu Ser Ser Arg Leu
```

```
            820                 825                 830

Glu Leu Ala Ile Lys Ala Ala Lys Ile Ala Ile Trp Glu Trp Asp Leu
        835                 840                 845

Asp Asn Asn His Thr Ile Trp Asp Lys Lys Met Tyr Glu Leu Tyr Gly
    850                 855                 860

Val Asn Pro Leu Glu Tyr Lys Asp Gly Met Glu Ile Leu Gln Thr Ala
865                 870                 875                 880

Leu His Pro Glu Asp Ala Val Arg Val Asn Glu Ile Leu Gln His Lys
                885                 890                 895

Leu Lys Asp Gly Glu Glu Phe Glu Met Asp Phe Arg Ile Val Leu Pro
            900                 905                 910

Asp Gly Lys Ile Arg Val Leu Gln Ser Tyr Gly Ile Ile Lys Arg Asp
        915                 920                 925

Ser Gln Gly Lys Ala Glu Arg Val Ile Gly Val Asn Arg Asp Ile Thr
    930                 935                 940

Glu Trp Lys Gln Ala Glu Gln Lys Ile Lys Gln Gln Ala Glu Arg Glu
945                 950                 955                 960

His Leu Leu Arg Glu Thr Thr Gln Arg Ile Arg Gln Ser Leu Asp Leu
                965                 970                 975

His Thr Ile Phe Asn Thr Ala Ala Ala Glu Ile Arg Gln Leu Met Asn
            980                 985                 990

Ala Asp Arg Val Gly Ile Phe Lys  Phe Asp Pro Val Ser  Asn Phe Asn
        995                 1000                1005

Tyr Gly  Glu Phe Val Ser Glu  Ser Val Val Pro Gly  Phe Ile Ser
    1010                1015                1020

Ala Leu  Glu Met Lys Val His  Asp Gln Cys Phe Gly  Glu Lys Phe
    1025                1030                1035

Ser Pro  Asp Tyr Ala Ala Gly  Arg Met Gln Ile Val  Asp Asp Ile
    1040                1045                1050

Asp Asn  Ala Gly Leu Ala Asp  Cys His Arg Asp Ile  Leu Ala Gln
    1055                1060                1065

Phe Gln  Val Lys Ala Asn Leu  Val Val Pro Leu Ile  Gln Gly Lys
    1070                1075                1080

Asn Leu  Trp Gly Leu Leu Cys  Ile His Gln Cys Ser  Gln Pro Arg
    1085                1090                1095

His Trp  Glu Asp Phe Glu Ile  Glu Leu Val Gln Gln  Ile Ala Asn
    1100                1105                1110

Gln Leu  Ala Ile Ala Ile Lys  Gln Ser Met Leu Tyr  Glu Gln Val
    1115                1120                1125

Gln Ser  Glu Leu Ile Ile Arg  Lys Gln Ala Glu Val  Glu Ile Tyr
    1130                1135                1140

Leu Gln  Leu Gln Arg Gln Arg  Ala Ile Gln Asp Ile  Thr Gln Glu
    1145                1150                1155

Ile Arg  Ser Ser Leu Asn Leu  Asn His Ile Leu Thr  Thr Ile Thr
    1160                1165                1170

Ala Lys  Val Gln Glu Leu Thr  Gln Ala Glu Arg Val  Ile Val Phe
    1175                1180                1185

Arg Leu  Phe Pro Asp Gly Lys  Ser Gln Ile Val Glu  Glu Ser Val
    1190                1195                1200

Ala Asn  Gly Tyr Met Thr Phe  Lys Asp Ser Tyr Trp  Glu Asp Glu
    1205                1210                1215

Lys Trp  Ser Gln Asp Ile Leu  Glu Tyr Tyr Trp Gln  Gly Lys Pro
    1220                1225                1230
```

Arg Ile Val Leu Asp Val Met Asp Asp Ile Trp Thr Asp Cys Leu
1235 1240 1245

Lys Ala Tyr Ser Arg Gln Gly Asn Ile Arg Ser Lys Ile Val Ala
1250 1255 1260

Pro Ile Leu Gln Asp Leu Val Glu Asn Glu Asn Gly Arg Trp Val
1265 1270 1275

Asn His Pro His Asn Lys Leu Trp Gly Val Leu Val Val His Ala
1280 1285 1290

Cys Gly Glu Lys Arg Ile Trp Glu Glu Ser Glu Ala Glu Leu Leu
1295 1300 1305

Gln Gln Ile Ala Asn Gln Leu Ala Ile Ala Ile Gln Gln Ala Asp
1310 1315 1320

Leu Phe Glu Lys Leu Gln Lys Ser Leu Lys Gln Glu Lys Glu Ile
1325 1330 1335

Ser Ala Met Arg Ser Arg Phe Val Ser Met Val Ser His Glu Phe
1340 1345 1350

Arg Thr Pro Leu Ala Ile Ile Ser Ser Ser Thr Gly Ile Leu Gln
1355 1360 1365

Thr Phe Gly Asp Arg Leu Asn Ala Glu Lys Lys Gln Gly His Leu
1370 1375 1380

Glu Thr Ile Gln Lys Thr Ile Lys Tyr Thr Val Gln Leu Leu Asp
1385 1390 1395

Asp Val Leu Met Ile Asn Ser Val Glu Thr Glu Lys Ile Glu Phe
1400 1405 1410

Lys Pro Glu Thr Leu Asp Ile Ile Asp Phe Cys Arg Arg Leu Ile
1415 1420 1425

Arg Glu Ile Gln Gly Thr Ser Tyr Ser His Val Ile Asp Phe Ser
1430 1435 1440

Leu Asn Ser Thr Gln Leu Ile Leu Asp His Thr Leu Phe Ala Glu
1445 1450 1455

Phe Asp Pro Lys Ile Ile Arg Gln Val Leu Thr Asn Leu Leu Thr
1460 1465 1470

Asn Ala Ile Lys Tyr Ser Pro Gly Ser Ser Thr Val Ser Phe Ser
1475 1480 1485

Leu Asn Ile Thr Asp Lys Gln Ile Val Phe Ile Val Gln Asp Tyr
1490 1495 1500

Gly Ile Gly Ile Ser Glu Thr Asp Gln Val Asn Leu Phe Ala Ser
1505 1510 1515

Phe Tyr Arg Gly Ser Asn Val Gly Asn Ile Ser Gly Thr Gly Leu
1520 1525 1530

Gly Leu Ala Ile Val Lys Lys Cys Val Asp Gln His Gln Gly Lys
1535 1540 1545

Ile Thr Leu Glu Ser Lys Leu Asn Gln Gly Thr Ile Phe Lys Val
1550 1555 1560

Thr Ile Pro Arg Tyr Asn Leu Ile Gly Asn Gly
1565 1570

<210> SEQ ID NO 33
<211> LENGTH: 1677
<212> TYPE: PRT
<213> ORGANISM: Pseudanabaena biceps

<400> SEQUENCE: 33

Met Ser Val Ala Lys Leu Asn Ala Ser Glu Leu Ser Ser Ala Ile Ile

-continued

```
1               5                   10                  15

Arg Pro Pro Val Val Val Ala Ala His Thr Thr Val Met Glu Ala Ile
            20                  25                  30

Ala Gln Met Leu Gly Gly Gly Phe Asp Thr Ser Val Gln Ser Ala Pro
        35                  40                  45

Asn Asp Arg His Asn Asp Arg His Asn Asp Cys Gln Glu Ser Thr Ser
    50                  55                  60

Ser Tyr Val Ile Ala Ile Ala Glu Asp Gly Arg Ala Ile Gly Ile Leu
65                  70                  75                  80

Thr Glu Arg Asp Val Met Arg Leu Ser Phe Gln Gln Ala Asp Phe Thr
                85                  90                  95

Arg Leu Gln Ile His Glu Val Met Thr Cys Pro Leu Val Thr Leu Tyr
            100                 105                 110

Glu Ala Asp Phe Cys Asp Ile Ser Leu Ala Val Gln Leu Phe Gln Gln
        115                 120                 125

His Ser Ile Arg His Leu Pro Ile Leu Asp Tyr Arg Asp Arg Pro Val
    130                 135                 140

Gly Ile Val Thr Ala Glu Ser Leu Gln His Phe Leu Gln Gln His Gln
145                 150                 155                 160

Gln Asn Ser Ala Ala Glu Leu Thr Ala Lys Asn Ile Ala Arg Glu Gln
                165                 170                 175

Leu Ile Ala Gln Ile Ala Asp His Ile Arg Leu Ser Phe Asn Leu Gln
            180                 185                 190

Glu Val Leu Asp Ser Cys Val Gln Glu Val Arg Asn Phe Leu Gln Cys
        195                 200                 205

Asp Arg Val Val Val Tyr Gln Phe Gln Ser Asp Trp Ser Gly Phe Ile
    210                 215                 220

Ile Ser Glu Ser Val Glu Ser Pro Phe Val Ile Ser Leu Gly Asn His
225                 230                 235                 240

Ile Gln Asp Ser Cys Phe Gln Ser Gln Ala Lys Gln Arg Tyr Asp His
                245                 250                 255

Asp Gln Pro Ile Ile Val Asn Asn Ile Tyr Asn Ala Gly Tyr Ala Pro
            260                 265                 270

Cys His Ile Glu Val Leu Glu Gln Tyr Gln Val Lys Ala Asn Ile Val
        275                 280                 285

Ile Pro Leu Gln Val Ser Gly Asn Leu Trp Gly Leu Leu Ile Gly His
    290                 295                 300

Gln Cys Arg Glu His Arg Asp Trp Gln Pro Glu Asp Ala Ser Leu Leu
305                 310                 315                 320

Arg Asn Ile Ala Ile His Leu Ala Ile Ala Ile Gln Gln Leu Tyr Ala
                325                 330                 335

Tyr Glu Gln Ala Gln Lys Glu Leu Thr Glu Arg Gln Arg Ser Glu Ala
            340                 345                 350

Leu Ile Gln Gln Gln Leu Ala Glu Leu Thr Glu Trp Tyr Tyr Arg Tyr
        355                 360                 365

Glu Ala Ala Glu Lys Ala Ser Gly Gln Met Leu Tyr Glu Tyr Asp Leu
    370                 375                 380

Ser Ser Lys Ser Leu Ile Trp Gly Ala Asn Ile Ala Arg Val Leu Gly
385                 390                 395                 400

Phe Thr Val Ser Glu Ser Pro Lys Asn Leu Ser Asp Leu Leu Ser Ala
                405                 410                 415

Ile His Pro Glu Asp Arg Asn His Phe Phe Gln Thr Ala Glu Ile Cys
            420                 425                 430
```

-continued

```
Arg Thr Asn Gln Thr Pro Phe Phe Cys Gln Tyr Arg Leu Lys His Gln
        435                 440                 445

Glu Gly Tyr Tyr Ile Trp Val Glu Asp Arg Asn Gln Trp Leu Phe Asp
    450                 455                 460

Asp Arg Gly Glu Ala Lys Arg Leu Ile Gly Met Ile Ala Asp Ile Ser
465                 470                 475                 480

Asp Arg Lys Asn Ala Glu Ile Asn Leu Lys Ile Ser Glu Ala His His
                485                 490                 495

Arg Ala Leu Ile Lys Ala Ile Pro Asp Leu Phe Met Arg Ile Asp Arg
            500                 505                 510

Ser Gly Ile Tyr Leu Glu Phe Val Cys Ile Pro Ser Gln His Arg Ile
        515                 520                 525

Ile Gly His Leu Leu Asp Met Asn Gly Val His Val Ser Glu Thr Ile
    530                 535                 540

Pro Pro Glu Leu Ala Gln Arg Arg Met Glu Tyr Ile Glu Leu Ala Leu
545                 550                 555                 560

Gln Thr Gln Ser Leu Gln Ile Tyr Glu Gln Asp Phe Ser Thr Pro Glu
                565                 570                 575

Ile Asp His Ile Glu Glu Val Arg Val Val Pro Tyr His Glu Asn Glu
            580                 585                 590

Val Leu Leu Leu Val Arg Asp Ile Ser Asp Arg Lys Lys Ala Glu Arg
        595                 600                 605

Glu Leu Lys His Thr Glu Lys Leu Phe Arg Glu Ala Gln Arg Ile Ala
    610                 615                 620

Lys Ile Gly Asn Trp Glu Leu Asn Leu Thr Asn Gln Val Leu Tyr Trp
625                 630                 635                 640

Ser Asp Glu Ile Phe Arg Ile Ser Glu Ile Asp Pro Gln Gln Phe Ser
                645                 650                 655

Ala Ser Tyr Glu Thr Phe Leu Asn Thr Val His Pro Glu Asp Arg Glu
            660                 665                 670

Met Val Asp Arg Ala Tyr Gln Gln Ser Val Ser Asp Arg Leu Pro Tyr
        675                 680                 685

Asn Ile Val His Arg Leu Leu Leu Pro Asp Gly Arg Ile Lys Tyr Ile
    690                 695                 700

Gln Asn Gln Gly Glu Thr Ile Tyr Ala Glu Asp Gly Ser Pro Lys Leu
705                 710                 715                 720

Ser Gln Gly Thr Ile Gln Asp Ile Thr Ser Leu Lys Gln Thr Glu Leu
                725                 730                 735

Glu Leu Glu Asn Leu Asn Asp Gln Leu Glu Ala Arg Met Leu Glu Arg
            740                 745                 750

Glu Thr Arg Tyr Trp Ala Leu Met Asn Gly Ala Ser Asp Ala Ile Met
        755                 760                 765

Leu Ala Asp Leu Gln Gly Asn Ile Leu Glu Val Asn Met Gln Ala Glu
    770                 775                 780

Gln Ile Leu Gly Tyr Ser Arg Ala Glu Leu Thr Ser Met His Phe Thr
785                 790                 795                 800

Gln Leu His Pro Glu Glu Glu Leu Thr Arg Thr Arg Asp Ala Phe Glu
                805                 810                 815

Ser Leu Thr His Gln Gln Lys Ile Gln Val Tyr Asp Ile Ile Phe Ile
            820                 825                 830

Thr Lys Asn Gly Gln Leu Ile Pro Phe Asp Val Ser Ala Ser Val Ile
        835                 840                 845
```

```
Asp Ile Gln Gly Glu Pro Ile Leu Gln Gly Ile Phe Arg Asp Ile Arg
    850                 855                 860

Asp Arg Lys Gln Ile Glu Ser Asp Leu Gln Glu Ser Arg Asp Arg Ser
865                 870                 875                 880

Gln Gln Lys Ala Ser Gln Glu Thr Ile Leu Arg Lys Ile Thr Gln Arg
                885                 890                 895

Ile Arg Gln Ser Leu Asn Leu Gln Val Ile Phe Asp Thr Ala Cys His
            900                 905                 910

Glu Ile Arg Gln Ile Leu Gln Ala Asp Arg Val Gly Ile Phe Gln Phe
        915                 920                 925

Asp Ala Asp Thr Asn Tyr Ser Asp Gly Glu Phe Val Ala Glu Ser Thr
    930                 935                 940

Val Glu Gly Phe Ser Ser Val Leu Ala Ile Arg Leu Gln Asp Tyr Cys
945                 950                 955                 960

Phe Gly Asp Ser Tyr Ser Phe Ser Tyr Ser Gln Gly Arg Cys Gln Ile
                965                 970                 975

Val Asp Asp Ile Tyr Gln Thr Asp Leu Glu Lys Cys His Thr Cys Ile
            980                 985                 990

Leu Glu Gln Phe Gln Val Arg Ala  Asn Leu Val Ile Pro  Leu Leu Cys
        995                 1000                 1005

Gly Glu  Ala Leu Trp Gly Leu  Leu Cys Ile His Gln  Cys Ser Ala
    1010                 1015                 1020

Pro Arg  His Trp Gln Asn Phe  Glu Ile Glu Leu Ser  Gln Gln Ile
    1025                 1030                 1035

Ala Asn  Gln Leu Gly Ile Ala  Ile Tyr Gln Ala Ser  Leu Tyr Gln
    1040                 1045                 1050

Gln Ala  Gln Ser Glu Leu Leu  Ile Arg Gln Lys Ala  Glu Val Ala
    1055                 1060                 1065

Ile Ser  Gln Gln Leu Arg Gln  Gln Gln Thr Ile Gly  Ala Ile Thr
    1070                 1075                 1080

Gln Lys  Ile Arg Glu Ser Leu  Asp Ile Asn Ala Ile  Leu Ser Thr
    1085                 1090                 1095

Val Thr  Arg Gln Val Lys Glu  Val Leu Asn Cys Asp  Arg Val Ile
    1100                 1105                 1110

Val Phe  Arg Leu Phe Ser Tyr  Gly Asp Ser Gln Ile  Val Glu Glu
    1115                 1120                 1125

Ala Val  Ser Pro Glu Phe Thr  Ser Leu Lys Ser Leu  His Trp Glu
    1130                 1135                 1140

Asn Glu  Leu Trp Ser Pro Ala  Ile Leu Asp Tyr Tyr  Trp Gln Gly
    1145                 1150                 1155

Lys Pro  Arg Ile Val Pro Asp  Val Met Val Asp Val  Trp Thr Asp
    1160                 1165                 1170

Cys Leu  Ile Pro Tyr Ser Ile  Glu Gly Gln Ile Lys  Ser Lys Ile
    1175                 1180                 1185

Val Ala  Pro Ile Leu Gln Asp  Leu Gly Asn Ile Glu  Arg Ser Arg
    1190                 1195                 1200

Trp Ile  Ser Pro Leu Ala Asn  Asn Lys Leu Trp Gly  Val Leu Val
    1205                 1210                 1215

Val His  Ala Cys Ala Glu Lys  Arg Val Trp Gln Asp  Ser Glu Ala
    1220                 1225                 1230

Gln Leu  Leu Gln Gln Ile Ala  Asn Gln Leu Ala Ile  Ala Ile Gln
    1235                 1240                 1245

Gln Ala  Ser Leu Phe Ala Gln  Val Gln Gln Glu Leu  Ser Asp Arg
```

```
    1250                1255                1260

Gln Gln  Ala Gln Gln Gln Leu  Thr Ala Thr Asn Arg  Lys Leu Ala
    1265                1270                1275

Leu Ser  Asn Gln Glu Leu Glu  Arg Ala Thr Arg Leu  Lys Asp Glu
    1280                1285                1290

Phe Leu  Ala Asn Met Ser His  Glu Leu Arg Thr Pro  Leu Asn Ala
    1295                1300                1305

Ile Leu  Gly Ile Thr Glu Gly  Leu Gln Glu Glu Val  Phe Gly Val
    1310                1315                1320

Leu Asn  Ala Lys Gln Lys Gln  Val Leu Leu Ala Val  Glu Arg Ser
    1325                1330                1335

Gly Asn  His Leu Leu Asp Leu  Ile Asn Asp Ile Leu  Asp Leu Ala
    1340                1345                1350

Lys Ile  Glu Ala Gly Lys Val  Thr Leu Asp Arg Ser  Leu Thr Asn
    1355                1360                1365

Ile Glu  Gln Leu Ser Gln Ser  Ser Leu Met Phe Val  Met Gln Gln
    1370                1375                1380

Ala Leu  Gln Lys Asn Ile Gln  Leu His Ile Gln Val  Glu Lys Ser
    1385                1390                1395

Leu Pro  Asp Leu Lys Ile Asp  Glu Arg Arg Ile Arg  Gln Val Leu
    1400                1405                1410

Ile Asn  Leu Leu Asn Asn Ala  Val Lys Phe Thr Leu  Glu Asn Gly
    1415                1420                1425

Arg Val  Val Leu Glu Val Thr  Leu His Lys Val Asn  Asp Ser Asn
    1430                1435                1440

Leu Gln  Asp Val Thr His Trp  Val Arg Phe Ala Val  Ile Asp Thr
    1445                1450                1455

Gly Ile  Gly Ile Thr Pro His  Ala Leu Gln Thr Leu  Phe Gln Pro
    1460                1465                1470

Phe Ile  Gln Val Asp Ser Ala  Leu Asn Arg Gln Tyr  Glu Gly Thr
    1475                1480                1485

Gly Leu  Gly Leu Ala Leu Val  Lys Arg Ile Val Glu  Met His Gly
    1490                1495                1500

Gly Gln  Val Lys Ala Thr Ser  Asp Phe Gly Val Gly  Ser Cys Phe
    1505                1510                1515

Thr Ile  Glu Leu Pro Tyr Asn  Glu Arg Asp Ser Ser  Leu Leu Leu
    1520                1525                1530

Lys His  Ser Asn Ser Phe Pro  Ser Asp Phe Val Pro  Glu Pro Asp
    1535                1540                1545

Ala Lys  Asp Ser Gln Leu Gly  His Pro Leu Ile Leu  Ile Ala Glu
    1550                1555                1560

Asp Asn  Glu Ala Asn Ile Ile  Thr Phe Ser Ser Tyr  Leu Ser Ala
    1565                1570                1575

Asn Gly  Tyr Arg Val Ile Val  Ala Lys Asp Gly Gln  Thr Ala Val
    1580                1585                1590

Asp Leu  Val Gln Ser Glu His  Pro Asp Leu Val Leu  Met Asp Ile
    1595                1600                1605

Gln Met  Pro Gly Met Asp Gly  Leu Lys Ala Ile Glu  Tyr Ile Arg
    1610                1615                1620

Gln His  Gln Leu Ser Asn Ala  Pro Ile Ile Ala Val  Thr Ala Leu
    1625                1630                1635

Ala Met  Val Gly Asp Arg Glu  Arg Cys Leu Ala Ala  Gly Ala Asn
    1640                1645                1650
```

Asp Tyr Leu Ser Lys Pro Val Lys Leu Lys Lys Leu Ala Glu Val
1655 1660 1665

Val Gln Gln Phe Leu His Pro Pro Cys
1670 1675

<210> SEQ ID NO 34
<211> LENGTH: 2237
<212> TYPE: PRT
<213> ORGANISM: Nodosilinea nodulosa

<400> SEQUENCE: 34

Met Ala Thr Pro Arg Pro Ala Asp Leu Thr Ala Ala Ile Ile Asp Lys
1 5 10 15

Pro Leu Thr Val Gln Pro Asp Val Ser Ala Gly Thr Ala Ile Ala Leu
20 25 30

Met Gly Gly Val Ser Thr Pro Gly Pro Thr Gly His Asp Pro Ala Gly
35 40 45

Glu Asp Gly Leu His Met Glu Ala Gly Ser Cys Val Val Val Val Glu
50 55 60

Gln Gly Arg Val Val Gly Leu Leu Thr Glu Arg Asp Val Val Arg Leu
65 70 75 80

Ser Ala Gln Gln Arg Ser Leu Asp Arg Leu Ser Val Ala Glu Val Met
85 90 95

Thr Gln Pro Val Ile Thr Arg Arg Leu Ser Asp Leu Thr Asp Leu Thr
100 105 110

Ser Thr Ile Glu Leu Leu Gln Gln His Arg Leu Arg His Leu Pro Leu
115 120 125

Val Asp Glu Gln Asp Cys Leu Val Gly Leu Val Thr His Asp Ser Leu
130 135 140

Trp Gln Ala Phe Ser Pro Leu Lys Tyr Cys Asn Leu Thr Glu Ala Leu
145 150 155 160

Glu Arg Lys Val Thr Arg Leu Glu Thr Glu Arg Leu Ala Leu Leu Glu
165 170 175

Asn Arg Ala Ala Glu Leu Glu Arg Gln Val Ala Glu Arg Thr Gln Met
180 185 190

Val Gln Val Gln Ala Glu Arg Asp Arg Leu Met Ala Gly Leu Ala Ala
195 200 205

Gln Ile Leu Ala Ser Leu Asp Val Gln Val Ile Leu Asp Thr Thr Val
210 215 220

Gln Gln Val Gln Gln Ile Leu Gly Cys Asp Arg Ala Ser Ile Trp Arg
225 230 235 240

Phe Glu Ala Asp Trp Thr Thr Val Val Val Ala Glu Ser Asn Asp Ala
245 250 255

Asp Arg Ser Leu Ile Gly Glu Arg Ile Ala Asp Lys Cys Phe Leu Glu
260 265 270

Thr Gln Val Glu Ala Tyr Arg Gln Gly Arg Ile Arg Val Val Ser Asp
275 280 285

Ile Asp Ala Ile Glu Met Ser Asp Cys His Arg Asn Met Leu Ile Arg
290 295 300

Leu Gln Thr Arg Ala Lys Ile Leu Val Pro Leu Leu Cys Gly Asp Glu
305 310 315 320

Leu Trp Gly Leu Leu Asn Val Thr Glu Met Gln Pro Arg Asp Trp Gln
325 330 335

Pro Ala Glu Val Glu Phe Val Arg Ser Leu Ser Ile Gln Leu Ala Ile

-continued

```
            340                 345                 350

Ala Leu Asn Gln Ala Ser Thr His Glu Gln Leu Arg Ser Glu Leu Gln
        355                 360                 365

Glu Arg Gln Gln Ala Glu Arg Gln Leu Arg Gln Ser Thr Glu Arg Leu
    370                 375                 380

Lys Lys Ala Gln Arg Ile Ala His Ile Gly Asn Trp Glu Leu Asp Leu
385                 390                 395                 400

Gln His Asn Thr Ser Tyr Trp Ser Lys Glu Val Phe Arg Ile Phe Glu
                405                 410                 415

Val Asp Ser Gln Gln Phe Ala Ala Ser Tyr Glu Ala Phe Leu Asp Leu
            420                 425                 430

Val His Pro Asp Asp Arg Thr Leu Ile Asp Thr Ala Tyr Ala Asn His
        435                 440                 445

Leu Arg Asp Arg Gln Pro Phe Ser Leu Val His Arg Leu Arg Leu Ala
    450                 455                 460

Asp Gly Arg Ile Lys Tyr Val Arg Glu Gln Cys Glu Thr Ile Tyr Ser
465                 470                 475                 480

Ala Asp Gly Thr Pro Arg Ile Ser Gln Gly Thr Val Gln Asp Ile Thr
                485                 490                 495

Pro Gln Gln Glu Ala Glu Ile Arg Arg Asp Arg Ala Glu Thr Thr Leu
            500                 505                 510

Arg Gln Leu Thr Glu Gly Thr Ala Ala Val Thr Gly Glu Ala Phe Phe
        515                 520                 525

Pro Ala Leu Val His His Ile Ser Glu Ala Leu Gly Val Arg Tyr Val
    530                 535                 540

Ser Ile Ser Gln Ala Met Pro Asp Gly Phe Gln Val Leu Ala Phe Phe
545                 550                 555                 560

Ala Asp Gly Glu Leu Ser Val Pro Leu Phe Leu Pro Tyr Asp Glu Leu
                565                 570                 575

Pro Cys Cys Phe Glu Ala Leu Gln Thr Gly Ser Cys Cys His Pro Thr
            580                 585                 590

Gly Val Gln Ala Leu Tyr Pro Asp Asn Ala Leu Phe Thr Asp Leu Gln
        595                 600                 605

Val Asp Ser Tyr Leu Gly Val Arg Leu Gln Asn Ala Ala Gly Asp Pro
    610                 615                 620

Ile Gly Asn Ile Cys Ile Leu His Asp Ala Pro Leu Ala Asp Leu Asp
625                 630                 635                 640

Trp Ala Lys Thr Leu Leu Thr Ile Phe Ala Ala Arg Ala Gly Ala Glu
                645                 650                 655

Leu Glu Arg Leu Met Thr Ala Gln Ala Leu Glu Gln Leu Asn Gly Glu
            660                 665                 670

Leu Glu Ser Arg Val Val Glu Arg Thr Ala Glu Leu Ala Glu Arg Glu
        675                 680                 685

Thr Leu Leu Gln Asp Phe Leu Asp Asn Ala Asn Asp Leu Ile Gln Met
    690                 695                 700

Val Asp Val Ser Thr Gly Arg Phe Glu Phe Val Asn Arg Ala Trp Gln
705                 710                 715                 720

Asn Val Leu Gly Tyr Thr Thr Ala Glu Val Ala Gln Leu Thr Cys Phe
                725                 730                 735

Asp Val Leu Ala Pro Asp Cys Leu Pro His Cys Gln Thr Val Phe Thr
            740                 745                 750

Gln Met Gln Ser Gly Ser Ile Thr His Val Glu Gln Met Glu Leu Thr
        755                 760                 765
```

```
Phe Ile Cys Lys Ser Gly Gln Arg Val Val Val Glu Gly Asn Val Asn
    770                 775                 780

Cys Arg Phe Ala Val Gly Ala Asp Gly Ser Gln Arg Pro Val Ser Thr
785                 790                 795                 800

Arg Gly Ile Phe Arg Asp Ile Thr Asp Arg Lys Thr Thr Glu Gln Glu
                805                 810                 815

Leu Gln Arg Arg Glu Ala Arg Tyr Arg Gly Leu Met Glu Gly Ala Ala
            820                 825                 830

Asp Ala Val Leu Leu Ile Asp Leu Glu Gly Asn Ile Leu Glu Ala Asn
        835                 840                 845

Gln Asn Ala Ala Ala Met Phe Gly Tyr Pro Leu Ala Glu Leu Ser Thr
    850                 855                 860

Leu His Phe Thr Gln Leu His Pro Ala Glu Thr Leu Pro Arg Ala Ala
865                 870                 875                 880

Ala Glu Phe Ala Glu Val Ala Gln Gly Gln Arg Thr Gln Val Leu Asp
                885                 890                 895

Met Pro Cys Cys Arg Arg Asp Gly Ser Val Val Pro Val Asp Ile Thr
            900                 905                 910

Ala Ser Val Ile Ser Thr Gly Glu Gly Arg Leu Val His Gly Ala Leu
        915                 920                 925

Arg Asp Ile Ser Asp Arg Lys Arg Tyr Glu Thr Ala Leu Gln Glu Ser
    930                 935                 940

Gln Gln Phe Leu Gln Thr Val Leu Asp Thr Val Pro Leu Ser Val Phe
945                 950                 955                 960

Trp Lys Asp Gln Asn Ser Arg Tyr Leu Gly Ala Asn Gln Arg Phe Leu
                965                 970                 975

Lys Asp Ala Ser Leu Gly Ser Val Ser Glu Leu Val Gly Lys Asp Asp
            980                 985                 990

Ser Ala Met Pro Trp Gly Val Thr  Glu Ala Asp Ala Tyr  Arg Ala Ala
        995                 1000                1005

Asp Arg  Val Val Met Asp Ser  Gly Glu Ala Lys Leu  Gly Ile Ile
    1010                 1015                1020

Glu Leu  Gln His Gln Gln Asp  Gly Ala Val Ile Trp  Leu Glu Thr
    1025                 1030                1035

Asn Lys  Leu Pro Leu Arg Asn  Leu Ala Gly Glu Val  Val Gly Ile
    1040                 1045                1050

Leu Gly  Thr Tyr Arg Asp Ile  Thr Glu Arg Lys Asn  Ala Glu Ile
    1055                 1060                1065

Ala Leu  Gln Arg Gln Leu Ala  Ala Ile Glu Ala Ala  Val Asn Gly
    1070                 1075                1080

Ile Ala  Ile Leu Glu Asn Glu  Arg Tyr Leu Tyr Phe  Asn Ser Ser
    1085                 1090                1095

His Ala  Lys Met Phe Gly Tyr  Glu Gln Ala Glu Glu  Leu Val Gly
    1100                 1105                1110

Gln Ser  Trp Arg Met Leu Tyr  Ser Pro Glu Gln Leu  Glu Arg Phe
    1115                 1120                1125

Asp Arg  Glu Ile Leu Pro Ile  Leu Ser Ala Glu Lys  Ser Trp Gln
    1130                 1135                1140

Gly Glu  Val Thr Ala Thr Arg  Lys Asp Gly Thr Thr  Phe Pro Glu
    1145                 1150                1155

Gln Leu  Ser Leu Thr Ile Ser  Thr Asp Asn Leu Leu  Ile Cys Val
    1160                 1165                1170
```

```
Cys Gln  Asp Ile Ser Glu Arg  Ala Arg Leu Asp Ala  Glu Arg Lys
    1175                 1180                 1185

Gln Ala  Glu Ala Ala Leu Arg  Glu Ser Glu Arg Arg  Tyr Ala Met
    1190                 1195                 1200

Leu Ala  Gln Ala Val Pro Val  Ala Ile Phe Arg Phe  Asp Leu Glu
    1205                 1210                 1215

Gly His  Cys Thr Tyr Val Asn  Glu Arg Trp Cys Glu  Met Thr Gly
    1220                 1225                 1230

Lys Pro  Ile Asp Phe Ala Leu  Asp Asp Arg Trp Leu  Glu Thr Ile
    1235                 1240                 1245

His Pro  Asp Asp Arg Glu Arg  Thr Gln Thr Val Ile  Gln Gln Trp
    1250                 1255                 1260

Leu Gln  Thr Gly Ala Val Ala  Pro Phe Gln Asn Glu  Ala Arg Ile
    1265                 1270                 1275

Leu Arg  Asp Asp Gly Ser Ile  Ile Trp Tyr Tyr Cys  Gln Met Leu
    1280                 1285                 1290

Leu Glu  Thr Asp Val Asn Gly  Ala Met Leu Gly Tyr  Val Gly Thr
    1295                 1300                 1305

Leu Thr  Asp Ile Ser Asp Arg  Lys Gln Ser Glu Glu  Ala Leu Gly
    1310                 1315                 1320

Glu Ser  Glu Glu Lys Phe Arg  Gln Leu Ala Glu Val  Val Asp Ala
    1325                 1330                 1335

Val Phe  Trp Ile Leu His Leu  Asn Arg Thr Asp Arg  Val Tyr Val
    1340                 1345                 1350

Ser Pro  Ala Tyr Glu Arg Ile  Trp Gly Arg Pro Cys  Thr Asp Leu
    1355                 1360                 1365

Tyr Ile  Thr Pro Asp Ala Trp  Ile Asp Arg Ile His  Ala Asp Asp
    1370                 1375                 1380

Arg Glu  Gln Val Leu Ala Ala  Ile Pro Lys Gln Leu  Glu Gly Thr
    1385                 1390                 1395

Phe Asp  Glu Glu Tyr Arg Ile  Val Arg Pro Asp Gly  Thr Gln Arg
    1400                 1405                 1410

Trp Ile  His Asp Arg Ala Phe  Pro Ile Arg Asn Ala  Gln Gly Gln
    1415                 1420                 1425

Val Tyr  Arg Leu Ala Gly Ile  Ala Glu Asp Ile Thr  Glu Arg Lys
    1430                 1435                 1440

Asn Ser  Glu Glu Ile Ile Cys  Gln Gln Ala Glu Arg  Glu Val Val
    1445                 1450                 1455

Leu Arg  Glu Ile Thr Gln His  Ile Arg Glu Ser Leu  Asp Leu Gln
    1460                 1465                 1470

Thr Ile  Phe Asn Thr Ala Cys  Asp Glu Ile Arg Ala  Phe Leu Arg
    1475                 1480                 1485

Ala Asp  Arg Val Gly Ile Phe  Lys Phe Tyr Pro Asp  Ser Gly Tyr
    1490                 1495                 1500

Asp Asp  Gly Glu Phe Val Ala  Glu Ser Val Val Asn  Gly Phe Ser
    1505                 1510                 1515

Ser Ala  Met Ala Ile Arg Ile  His Asp His Cys Phe  Gly Glu Asn
    1520                 1525                 1530

Tyr Ala  Asn Leu Tyr Ala Gln  Gly Arg Tyr Gln Val  Val Asp Asn
    1535                 1540                 1545

Ile Tyr  Ser Asn Gly Leu Thr  Pro Cys His Ser Asp  Ile Leu Ala
    1550                 1555                 1560

Gln Phe  Gln Val Gln Ala Asn  Leu Val Met Pro Leu  Leu Cys Asn
```

-continued

```
    1565                1570                1575

His Glu  Leu Trp Gly Leu Leu  Cys Ile His Gln Cys  Asp Ala Pro
    1580                1585                1590

Arg His  Trp Gln Gln Ser Glu  Ile Asn Leu Gly Gln  Gln Leu Ala
    1595                1600                1605

Asn Gln  Leu Ala Ile Ala Ile  Gln Gln Ala Ser Leu  Tyr Glu Gln
    1610                1615                1620

Val Gln  Thr Glu Leu Leu Glu  Arg Gln Gln Ala Glu  Ala Lys Ile
    1625                1630                1635

Ala Arg  Gln Leu Arg Gln Gln  Thr Ala Leu Glu Leu  Ile Leu Gln
    1640                1645                1650

Gln Ile  Arg Gln Ser Leu Asp  Leu Pro Glu Leu Leu  Ala Ile Ala
    1655                1660                1665

Thr Gln  Gln Val Gln Glu Leu  Leu Gln Ser Asp Arg  Val Ile Val
    1670                1675                1680

Phe Gln  Val Ala Gln Asn Gly  His Ser Cys Ile Leu  Glu Glu Ala
    1685                1690                1695

Val Ala  Pro Asp Leu Pro Gln  Leu Lys Ala Met Gln  Trp Asp Asp
    1700                1705                1710

Glu Thr  Trp Ser Gln Asp Ile  Leu Glu His Tyr Trp  Gln Gly Gln
    1715                1720                1725

Pro Arg  Ile Val Pro Asp Val  Met Glu Asp His Trp  Thr Asp Cys
    1730                1735                1740

Leu Val  Glu Tyr Ser Lys Ala  Gly Gln Ile Gln Ser  Lys Ile Val
    1745                1750                1755

Ala Pro  Ile Leu Gln Glu Leu  Cys Asp Ile Glu Thr  His Arg Trp
    1760                1765                1770

Ala Ser  Pro Glu Gly Ser Ser  Lys Leu Trp Gly Val  Leu Val Val
    1775                1780                1785

His Ala  Cys Arg Thr Arg Arg  Val Trp His Gln Gln  Glu Ala Gln
    1790                1795                1800

Leu Leu  Gln Gln Ile Ala Asn  Gln Leu Ala Ile Ala  Ile Gln Gln
    1805                1810                1815

Ala Asn  Leu Phe Glu Gln Leu  Gln Gln Glu Leu Gln  Glu Arg Gln
    1820                1825                1830

Gln Ala  Glu Ala Gln Leu Thr  Leu Thr Asn Gly Glu  Leu Met Arg
    1835                1840                1845

Ala Thr  Arg Leu Lys Asp Glu  Phe Leu Ala Asn Met  Ser His Glu
    1850                1855                1860

Leu Arg  Thr Pro Leu Asn Ala  Ile Leu Gly Met Thr  Glu Val Leu
    1865                1870                1875

Gln Asp  Asp Asp Val Phe Gly  Pro Val Asn Ala Gln  Gln Leu Lys
    1880                1885                1890

Ala Leu  Lys Thr Val Glu Arg  Ser Gly Thr His Leu  Leu Glu Leu
    1895                1900                1905

Ile Asn  Asp Val Leu Asp Val  Ala Lys Ile Glu Ala  Gly Gln Leu
    1910                1915                1920

Glu Leu  Asp Cys His Pro Thr  Ala Ile Ala Pro Leu  Cys Gln Ser
    1925                1930                1935

Ser Leu  Ala Phe Ile Lys Gln  Pro Ala Leu Lys Lys  Gly Leu Gln
    1940                1945                1950

Leu Ala  Val Lys Leu Pro Pro  Asn Leu Pro Glu Ile  Thr Leu Asp
    1955                1960                1965
```

Glu Arg Arg Ile Arg Gln Val Leu Ile Asn Leu Leu Ser Asn Ala
1970 1975 1980

Val Lys Phe Thr Leu Glu Gly Gly His Ile Thr Leu Asp Val Ser
1985 1990 1995

Leu Leu Pro Pro Thr Gln Ser His Pro Glu Leu Ser Tyr Leu Arg
2000 2005 2010

Phe Ala Val Thr Asp Thr Gly Ile Gly Ile Thr Pro Glu Asn Met
2015 2020 2025

Gln Arg Leu Phe Lys Pro Phe Val Gln Val Asp Ser Ser Leu Asn
2030 2035 2040

Arg Gln Tyr Gln Gly Thr Gly Leu Gly Leu Ala Leu Val Lys Arg
2045 2050 2055

Ile Val Glu Leu His Arg Gly Gln Val Gly Leu Thr Ser Asp Val
2060 2065 2070

Gly Val Gly Ser Cys Phe Thr Val Glu Leu Pro Tyr Gly Ala Gly
2075 2080 2085

Ile Pro Ala Pro Pro Val Pro Ala Pro Pro Ser Ala Ile Gly Pro
2090 2095 2100

Ala Thr Pro Leu Pro Lys Val Ala Ala Thr Pro Thr Thr Thr Pro
2105 2110 2115

Leu Ile Leu Leu Val Glu Asp Asn Glu Ala Asn Ile Ser Thr Leu
2120 2125 2130

Arg Ser Tyr Leu Gln Ala Lys Gly Cys Arg Val Glu Val Ala His
2135 2140 2145

Asn Gly Glu Glu Ala Ile Asp Trp Ala Gln His Lys Thr Pro Asp
2150 2155 2160

Leu Ile Leu Met Asp Ile Gln Met Pro Arg Met Asp Gly Leu Glu
2165 2170 2175

Ala Ile Gly His Leu Arg Arg Ile Pro Ser Leu Ala Asn Val Pro
2180 2185 2190

Val Ile Ala Leu Thr Ser Leu Ala Met Ala Gly Asp Arg Asp Arg
2195 2200 2205

Cys Ile Ala Ala Gly Ala Thr Asp Tyr Leu Thr Lys Pro Val Ser
2210 2215 2220

Leu Lys Gln Leu Asn Glu Arg Ile His Ala Leu Leu Thr Pro
2225 2230 2235

<210> SEQ ID NO 35
<211> LENGTH: 2034
<212> TYPE: PRT
<213> ORGANISM: Nodosilinea nodulosa

<400> SEQUENCE: 35

Met Arg Arg Phe Ser Trp Ser Arg His Leu Arg Gln Pro Phe Leu Leu
1 5 10 15

Trp Trp Leu Leu Leu Pro Leu Gly Leu Gln Thr Val Gly Thr Ala Val
20 25 30

Leu Ile Gly Val Leu Leu His Gly Asn Ala Ala Gln Pro Ala Val Glu
35 40 45

Ser Ala Asn Pro Leu Pro Ala Ala Asn Gly Tyr Leu Thr Pro Ala Ile
50 55 60

Ala Leu Trp Gly Ala Val Gln Val Leu Ala Val Gly Leu Gly Ala Ala
65 70 75 80

Ile Ala Arg Thr Val Ala Ala Pro Lys Arg Pro Gln Gly Gly Leu Pro

-continued

```
                85                  90                  95

Asn Ala Ser Ala Ser His Asp Cys Arg Met Ile Glu Ala Ala Leu Gln
            100                 105                 110

Ala Ser Glu Ala Arg Phe Gln Thr Leu Met Ala His Ile Pro Gly Met
        115                 120                 125

Val Tyr Arg Tyr Leu Pro Gly Ser Asp Gly Asp Gly Ala Phe Thr Tyr
    130                 135                 140

Val Ser Ala Gly Cys Tyr Glu Leu Phe Gly Leu Ser Pro Asn Gln Val
145                 150                 155                 160

Leu Gln Asn Ala Asn Ala Val Trp Gly Leu Ile His Pro Asp Asp Trp
                165                 170                 175

Pro Ser Leu Gln Ala Ser Val Ala Ser Ala Val Ala Arg Cys Ala Asp
            180                 185                 190

Trp His Trp Glu Gly Arg Phe Thr Thr Val Thr Gly Gln Pro Arg Trp
        195                 200                 205

Leu Gln Gly Arg Ala Arg Pro Gln Pro Thr Pro Ala Gly Ala Val Trp
    210                 215                 220

Asp Gly Leu Leu Ile Asp Ile Thr Ala Leu Lys Gln Thr Glu Thr Ala
225                 230                 235                 240

Leu Asn Gln Glu Ile Ser Tyr Arg Arg Ala Leu Leu Asn Ala Ser Ile
                245                 250                 255

Asp Gly Val Val Ile Val Asp Arg Glu Gly Asn Val Leu Glu Ala Asn
            260                 265                 270

His Ser Phe Thr Ala Met Leu Gly Tyr Thr Pro Ala Glu Ile Leu Ser
        275                 280                 285

Leu Asn Val Ala Asp Phe Asp Val Asp Leu Gly His Leu Lys Glu Asp
    290                 295                 300

Leu Lys Ser Glu Lys Thr Lys Leu Cys Leu Asp Arg Phe Glu Arg Leu
305                 310                 315                 320

His Arg Arg Lys Asp Gly Ser Thr Tyr Ala Val Glu Ile Ser Ala Asn
                325                 330                 335

Ala Val Asp Trp Asn Gly Gln Ala Val His Leu Cys Val Cys Arg Asp
            340                 345                 350

Ile Ser Asp Arg Val Arg Ala Glu Ala Ile Arg Arg Glu Ser Glu Ala
        355                 360                 365

Arg Tyr Leu Ser Ile Leu Glu Glu Gln Thr Glu Phe Ile Thr Arg Phe
    370                 375                 380

Gln Pro Asp Gly Lys Leu Ile Phe Val Asn Asn Ala Tyr Cys Arg Tyr
385                 390                 395                 400

Phe Ser Gln Ser Lys Ala Gln Leu Glu Gly Gln Asn Tyr Gln Pro Val
                405                 410                 415

Val Tyr Pro Ala Asp Gln Pro Ala Ile Asp Arg Cys Leu Ala Ser Leu
            420                 425                 430

Ser Pro Glu Thr Pro Ile Arg Thr Val Glu Asn Arg Val Tyr Val Arg
        435                 440                 445

Gly Glu Leu Arg Trp Thr Thr Trp Thr Asn Lys Ala Ile Tyr Asp Asp
    450                 455                 460

Cys Gly Asn Leu Ile Glu Leu Gln Ser Val Gly Gln Asp Ile His Asp
465                 470                 475                 480

Arg Lys Arg Ala Glu Leu Ala Leu Ala Glu Ser Glu Ala Arg Phe Gln
                485                 490                 495

Arg Leu Thr Ala Ala Ser Pro Ala Ile Ile Tyr Thr Val Ile Glu Ser
            500                 505                 510
```

```
Leu Gln Gly Ile Val Arg Phe Glu Tyr Leu Ser Pro Ala Ala Glu Glu
        515                 520                 525

Ile His Glu Ile Pro Ile Ala Thr Leu Met Gln Asn Gly Ala Leu Ile
    530                 535                 540

Ser Glu Gln Met His Pro Asp Asp Arg Glu Arg Tyr Leu Glu Ala Tyr
545                 550                 555                 560

Ala Ala Ser Leu Gln Ser Met Thr Thr Phe Ile Cys Glu Trp Arg Ile
                565                 570                 575

Ile Thr Pro Ser Gly Lys Thr Lys Trp Leu Lys Ala Asn Ser Arg Pro
            580                 585                 590

Glu Gln Arg Pro Ser Gly Glu Val Ala Trp His Gly Ile Thr Leu Asp
        595                 600                 605

Ile Thr Pro Arg Lys Gln Ala Glu Ala Ala Leu Gly Asn Leu Gln Ala
    610                 615                 620

Ala Leu Leu Glu Ala Gln Gln Val Ala His Ile Gly Asn Trp Glu Phe
625                 630                 635                 640

Asp Leu Ala Ser Gln Lys Ile Thr Trp Ser Pro Glu Leu Phe Arg Met
                645                 650                 655

Phe Gly Leu Asp Pro Ala Gln Gly Glu Pro Thr Tyr Ala Asp Tyr Leu
            660                 665                 670

Glu Leu Leu Gln Pro Asp Asp Arg Ile Leu Leu Gln Gln Ala Val Asp
        675                 680                 685

Arg Ala Ile Ala Glu Gly Thr Pro Tyr Arg Leu Asp Tyr Arg Val Leu
    690                 695                 700

Leu Pro Asp Gly Ser Leu Arg Tyr Gln Glu Gly Arg Gly Lys Val Glu
705                 710                 715                 720

Arg Asp Arg Thr Gly Gln Val Val Arg Leu Phe Gly Thr Ala Leu Asp
                725                 730                 735

Ile Thr Asp Arg Lys His Thr Glu Ile Ala Leu Gln Ala Ser Gln Leu
            740                 745                 750

Arg Leu Gln Leu Ala Ile Asn Ser Thr Gly Thr Gly Thr Trp Asp Trp
        755                 760                 765

Asn Met Gln Thr Asn Glu Val Leu Phe Asp Gln Lys Leu Trp Arg Ala
    770                 775                 780

Leu Leu Gly Tyr Gly Ala Asp Ala Ala Ile Asp Asn Ser Val Ala Glu
785                 790                 795                 800

Trp Glu Ser Arg Ile His Pro Lys Asp Lys Pro Gln Val Gln Ala Asp
                805                 810                 815

Ile Ala Arg His Ile Arg Gly Glu Thr Glu Ile Tyr Glu Asn Thr His
            820                 825                 830

Arg Leu Arg Cys His Asp Gly Thr Tyr Lys Trp Asn Leu Ala Gln Gly
        835                 840                 845

Lys Ile Ile Glu Arg Asp Asp Arg Gly Asn Pro Ile Arg Phe Val Gly
    850                 855                 860

Ile His Arg Asp Val Ser Glu Gln Val Leu Leu Asp Ala Gly Arg Arg
865                 870                 875                 880

Leu Ala Glu Glu Ala Leu Gln Ala Ser Glu Ala Arg Phe Arg Ala Ile
                885                 890                 895

Phe Glu Gln Ala Ala Val Gly Ile Asn Gln Ala Asp Ala Ser Gly Arg
            900                 905                 910

Phe Ile Gln Ala Asn Gln Tyr Phe Cys Gly Leu Leu Gly Tyr Thr Gln
        915                 920                 925
```

```
Ala Glu Leu Leu Arg Leu Thr Val Gln Asp Leu Thr His Pro Glu Asp
    930                 935                 940

Leu Glu Arg Asp Arg Leu Gln Ile Leu Arg Leu Phe Gln Gly Lys Gln
945                 950                 955                 960

Lys Gly Phe Thr Thr Ile Lys Arg Tyr Arg His Arg His Gly Ser Trp
                965                 970                 975

Ile Trp Thr Glu Val Thr Leu Ser Ala Ile Cys Asn Pro Ala Gly Glu
            980                 985                 990

Val Ile Ser Asp Leu Ala Ile Val  Val Asp Ile Arg Lys  Leu Arg Gln
        995                 1000                1005

Ala Asn  Ala Ala Leu Lys Ala  Ser Glu Ala Arg Leu  Arg Ala Ile
    1010                 1015                 1020

Phe Asp  Gln Ala Leu Ala Gly  Ile Asn Gln Ile Asp  Ser Gln Gly
    1025                 1030                 1035

Gln Phe  Thr Glu Ala Asn Gln  Tyr Phe Cys Asp Leu  Leu Gly Tyr
    1040                 1045                 1050

Ser Arg  Asp Glu Leu Leu Ala  Leu Lys Leu Glu Asp  Leu Ile His
    1055                 1060                 1065

Pro Asp  Asp Met Glu Arg Cys  Arg Glu Pro Val Asp  Arg Ile Leu
    1070                 1075                 1080

Arg Gly  Glu Ile Asp Asn Leu  Arg Leu Glu Arg Arg  Gln Arg His
    1085                 1090                 1095

Lys Asn  Gly Asp Trp Ile Trp  Thr Glu Ala Met Ile  Ser Leu Leu
    1100                 1105                 1110

Arg Asp  Glu Ala Gly Glu Val  Ile Gly Asn Leu Ala  Val Val Val
    1115                 1120                 1125

Asp Ile  Arg Glu Arg Ile Arg  Leu Glu Ala Asp Arg  Lys Arg Ala
    1130                 1135                 1140

Glu Gln  Thr Ile Arg Gln Gln  Ala Glu Arg Glu Thr  Met Leu Arg
    1145                 1150                 1155

Lys Leu  Thr Gln Ser Ile His  Arg Ser Leu Asp Leu  Gln Thr Ile
    1160                 1165                 1170

Phe Asp  Thr Ala Cys Arg Glu  Ile Arg Ala Cys Leu  Gln Ala Asp
    1175                 1180                 1185

Arg Val  Gly Ile Phe Lys Phe  Arg Pro Gly Ser Ser  Tyr Ser Thr
    1190                 1195                 1200

Gly Glu  Leu Val Ala Glu Ala  Met Val Asp Gly Val  Thr Pro Val
    1205                 1210                 1215

Leu Ala  Ile Pro Ile His Asp  His Cys Phe Gly Glu  Arg Arg Ala
    1220                 1225                 1230

Ala Phe  Tyr Ala Glu Gly His  Cys His Ile Ile Asp  Asp Ile Tyr
    1235                 1240                 1245

Ala Ser  Asp Leu Glu Asn Cys  Tyr Ile Asp Phe Leu  Ala Gln Leu
    1250                 1255                 1260

Gln Val  Arg Ala Asn Leu Val  Ile Pro Leu Leu Cys  Gly Arg Asp
    1265                 1270                 1275

Leu Trp  Gly Leu Leu Cys Ile  His Gln Cys Ala Gly  Pro Arg His
    1280                 1285                 1290

Trp Leu  Arg Ala Asp Ile Asp  Leu Gly Cys Gln Leu  Ala His Gln
    1295                 1300                 1305

Leu Ala  Leu Ala Ile Lys Gln  Ala Leu Phe Val Glu  Gln Ile Gln
    1310                 1315                 1320

Ser Glu  Leu Gln Val Arg Gln  Arg Ala Glu Ala Lys  Ile Ala His
```

```
    1325                1330                1335

Gln Leu  Arg Gln Gln Thr Ala  Leu Gly Met Ile Leu  Gln Gln Val
    1340                1345                1350

Arg Glu  Ser Leu Asp Leu Asp  Gln Ile Leu Ala Thr  Val Thr Gln
    1355                1360                1365

Asn Val  Gln Glu Ile Leu Gln  Ser Asp Arg Val Ile  Ile Phe Gln
    1370                1375                1380

Val His  Ser Asp Gly His Ser  Lys Ile Val Glu Glu  Ala Val Ser
    1385                1390                1395

Glu Ser  Leu Pro Thr Leu Lys  Gly Met Arg Trp Glu  Asp Glu Val
    1400                1405                1410

Trp Ser  Gln Asp Ile Leu Asp  Val Tyr Trp Arg Gly  Gln Pro Arg
    1415                1420                1425

Ile Val  Ala Asp Val Met Ala  Asp Thr Trp Thr Asp  Cys Leu Val
    1430                1435                1440

Asp Tyr  Ser Gln Ala Gly Gln  Ile Gln Ser Lys Ile  Val Ala Pro
    1445                1450                1455

Ile Leu  Gln Glu Ile Arg Thr  Ser Glu Gly His Arg  Trp Val Ala
    1460                1465                1470

Pro Arg  Ala Lys Asn Lys Ile  Trp Gly Val Leu Val  Val His Ala
    1475                1480                1485

Cys Arg  Gln Lys Arg Val Trp  Gln Asp Ser Glu Ala  Gln Leu Leu
    1490                1495                1500

Gln Gln  Ile Ala Asn Gln Leu  Ala Ile Ala Ile Gln  Gln Ser Thr
    1505                1510                1515

Leu Phe  Glu Gln Leu Gln Gln  Glu Leu Ser Asp Arg  Gln Leu Ala
    1520                1525                1530

Gln Gln  Gln Leu Thr Glu Ser  Asn Gln Glu Leu Ala  Val Ala Asn
    1535                1540                1545

Gln Ala  Leu Ser Arg Ala Thr  Arg Leu Lys Asp Glu  Phe Leu Ala
    1550                1555                1560

Asn Met  Ser His Glu Leu Arg  Thr Pro Leu Asn Val  Ile Leu Gly
    1565                1570                1575

Phe Ala  Gln Ile Leu Ser Ser  Asp Leu Ser Leu Gln  Ala Gln Gln
    1580                1585                1590

Gln Glu  Tyr Ile Arg Ile Met  His Arg Ser Gly Asp  His Leu Leu
    1595                1600                1605

His Leu  Ile Asn Asp Ile Leu  Asp Leu Ser Lys Ile  Glu Ala Asn
    1610                1615                1620

Arg Ile  Thr Leu Glu Pro Glu  Ser Ile Asp Leu Leu  Glu Leu Leu
    1625                1630                1635

His Asp  Leu Gln Gly Met Phe  Gln Glu Arg Ala Glu  Asp Lys Glu
    1640                1645                1650

Leu Arg  Phe Thr Leu Ala Leu  Ala Pro Asp Leu Pro  Gln Tyr Ile
    1655                1660                1665

Val Ala  Asp Pro Asn Lys Leu  Arg Gln Val Leu Ile  Asn Leu Leu
    1670                1675                1680

Gly Asn  Ala Ile Lys Phe Thr  Gln Glu Gly Ser Val  Ala Leu Arg
    1685                1690                1695

Val Ser  Leu Ala Leu Pro Glu  His Pro Glu Pro Gln  Pro Glu Pro
    1700                1705                1710

Pro Gln  Pro Tyr Leu Ser Phe  Ala Val Glu Asp Thr  Gly Thr Gly
    1715                1720                1725
```

Ile Ala Pro Ala Glu Leu Ala Ser Ile Phe Asp Ala Phe Thr Gln
1730 1735 1740

Ala Lys Ala Gly Lys Val Ser Leu Glu Gly Thr Gly Leu Gly Leu
1745 1750 1755

Ala Ile Ser Arg Ser Leu Val Gln Leu Met Gly Gly Ser Leu Thr
1760 1765 1770

Val Ser Ser Arg Leu Gly Gln Gly Ser Thr Phe Cys Phe Ser Leu
1775 1780 1785

Pro Cys His Arg Gly Arg Ala Glu Asp Val Ala Leu Thr Asn Tyr
1790 1795 1800

Pro Gly Ala Val Thr Gly Leu Ala Pro Ala Gln Pro Asn Tyr Arg
1805 1810 1815

Ile Leu Val Val Asp Asp Gln Pro Glu Asn Arg Gln Leu Leu Leu
1820 1825 1830

Ala Ala Phe Ser Gln Val Gly Leu Ala Val Arg Glu Ala Ala His
1835 1840 1845

Gly Ala Glu Ala Ile Ala Gln Trp Arg Gln Trp Gln Pro His Leu
1850 1855 1860

Ile Trp Met Asp Leu Arg Met Pro Thr Leu Asp Gly Cys Glu Ala
1865 1870 1875

Thr Arg Arg Ile Arg Ala Glu Ser Ala Ala Ile Ala Asn Gly Asp
1880 1885 1890

Arg Pro Ile Ile Ile Ala Leu Ser Ala Gln Ala Ser Asn Asp Glu
1895 1900 1905

Cys Ser Asn Ala Leu Ala Ala Gly Cys Asp Asp Phe Val Ser Lys
1910 1915 1920

Pro Val Lys Leu Asn Leu Leu Trp Thr Lys Met Ser Asp Tyr Leu
1925 1930 1935

Gly Leu Arg Tyr Val Tyr Ala Glu Thr Pro Thr Pro Ala Gly Leu
1940 1945 1950

Val Asn Pro Thr Ser Ala Lys Ala Ile Arg Ile Asp Thr Ser Asp
1955 1960 1965

Leu Gln Val Met Pro Pro Glu Trp Ile Gly Ala Leu His Gln Ala
1970 1975 1980

Ala Leu His Cys Asp Ser His Asp Thr Ala Gln Leu Ile Gln Gln
1985 1990 1995

Ile Pro Ala Glu His Gly Ala Leu Thr Thr Ser Leu Asn Arg Leu
2000 2005 2010

Leu Asp Gly Tyr Lys Phe Glu Val Ile Met Gln Leu Thr Gln Pro
2015 2020 2025

Tyr Leu Glu Ala Ala Pro
2030

<210> SEQ ID NO 36
<211> LENGTH: 2747
<212> TYPE: PRT
<213> ORGANISM: Unknown
<220> FEATURE:
<223> OTHER INFORMATION: Leptolyngbya sp. PCC 6406

<400> SEQUENCE: 36

Met Ile Arg Ala Met Lys Val Asp Leu Thr Ala Ala Ile Val Pro Ser
1 5 10 15

Pro Leu Thr Val Thr Pro Glu Thr Leu Val Gln Asp Ala Ile Ala Leu
20 25 30

```
Met Ser Ser Val Arg Thr Leu Cys Ser Thr Asp Arg Asn Pro Thr Ser
        35                  40                  45

Asn Asp Asn Leu His Leu Glu His Arg Ser Ser Cys Val Leu Val Val
    50                  55                  60

Val Glu Asn Asp Leu Val Ala Gly Ile Leu Thr Glu Arg Asp Val Val
65                  70                  75                  80

Arg Leu Ser Ala Gln Gln Gln Pro Leu Asp Gln Leu Leu Val Ala Glu
                85                  90                  95

Val Met Ala Gln Pro Val Ile Thr His Arg Gln Ser Asp Leu Thr Asp
            100                 105                 110

Leu Phe Ser Thr Ile His Leu Leu Lys His His His Ile Arg His Leu
        115                 120                 125

Pro Val Val Asp Asp Gln Asn Arg Leu Val Gly Leu Leu Thr His Glu
    130                 135                 140

Ser Leu Arg Gln Leu Thr Arg Pro Val Asp Leu Leu Arg Leu Arg Leu
145                 150                 155                 160

Val Gln Glu Val Met Thr Ala Asp Val Leu Cys Ala Ala Pro Asp Ser
                165                 170                 175

Ala Met Leu Glu Ile Ala Gln Leu Met Ala Asp Arg Arg Val Ser Ser
            180                 185                 190

Val Val Ile Thr Leu Pro Gly Gly Ser Thr Asp Ala Pro Phe Arg Arg
        195                 200                 205

Ala Val Gly Leu Leu Thr Glu Arg Asp Leu Val Gln Phe Gln Ala Leu
    210                 215                 220

Gly Leu Ser Leu Thr Thr Thr Thr Ala Gln Thr Val Met Ser Ser Pro
225                 230                 235                 240

Val Phe Ala Val Ala Pro Gln Asp Ser Leu Trp Thr Val Gln Gln Val
                245                 250                 255

Met Glu Gln His Arg Ile Arg Arg Val Ile Val Ala Gly Glu Gln Gly
            260                 265                 270

Glu Leu Leu Gly Ile Val Thr Gln Thr Ser Leu Leu Gln Ala Phe Asn
        275                 280                 285

Pro Ile Glu Leu Tyr Gln Leu Ala Glu Val Leu Glu Gln Lys Val Val
    290                 295                 300

His Leu Glu Thr Glu Arg Ile Ala Leu Leu Gln Ser Gln Ser Ala Glu
305                 310                 315                 320

Leu Glu Trp His Ile Thr Glu Ser Asn Gln Ala Ile Arg Met Gln Ala
                325                 330                 335

Glu Ile Asp Arg Leu Leu Gln Gly Phe Ala Leu Ala Thr Thr His Leu
            340                 345                 350

Met Thr Leu Gln Asp Gly His Glu Ser Val Gln Ala Ala Leu Asp Ala
        355                 360                 365

Leu Gly Ser Ala Leu Arg Val Asp Arg Ser Tyr Ile Phe Glu Asn His
    370                 375                 380

Pro His Pro Lys Thr Gly Glu Met Val Leu Ser Gln Arg Trp Glu Trp
385                 390                 395                 400

Val Ala Glu Gly Val Thr Arg Gln Ile Asp Asn Pro Glu Leu Gln Asn
                405                 410                 415

Ile Pro Val Asp Lys Val Leu Pro Asn Trp Tyr Gln Ser Leu Ser Gln
            420                 425                 430

Gly Gln Thr Val Gly Gly Leu Thr Lys Asp Phe Pro Glu Glu Glu Gln
        435                 440                 445
```

-continued

```
Ala His Leu Arg Pro Gln Gly Ile Val Ser Ile Leu Leu Val Pro Ile
    450                 455                 460

Phe Ile Glu Asp Tyr Phe Trp Gly Met Val Gly Phe Asp Asp Cys His
465                 470                 475                 480

Glu Glu Arg Val Trp Glu Asn Ser Thr Gln Ser Ala Leu Lys Ser Ile
                485                 490                 495

Ala Gly Thr Ile Gly Ser Ala Ile Ala Arg Arg Arg Ala Glu Ala Asn
            500                 505                 510

Ala Thr Leu Leu Ala Lys Arg Leu Gln Glu Ala Gln Arg Leu Ala His
        515                 520                 525

Val Gly Asn Trp Glu Gln Asp Leu Gln Arg His Thr Phe Tyr Trp Ser
    530                 535                 540

Glu Glu Val Phe Arg Ile Leu Glu Ile Asp Ala Gln Gln Ile Ser Ala
545                 550                 555                 560

Ser Tyr Glu Thr Phe Leu Gly Leu Val His Pro Asp Asp Leu Thr Leu
                565                 570                 575

Val Asp Glu Ala Tyr Ala Asn His Leu Arg Ser Arg Gln Pro Thr Ser
            580                 585                 590

Leu Val His Arg Leu Gln Met Pro Asp Gly Arg Ile Lys Tyr Met Gln
        595                 600                 605

Glu Trp Trp Glu Thr Thr Tyr Ser Ala Asp Gly Ala Pro Leu Ile Ser
    610                 615                 620

Arg Gly Thr Ala Gln Asp Ile Thr Gln Gln Gln Glu Ala Glu Leu Cys
625                 630                 635                 640

Arg Glu Arg Ala Glu Ala Ala Leu Arg Gln Val Ile Glu Gly Thr Ala
                645                 650                 655

Ala Val Thr Gly Glu Ala Phe Phe Pro Ala Leu Val Arg His Ile Ser
            660                 665                 670

Ala Ala Leu Gly Val Arg Tyr Val Ser Ile Asp Gln Ala Met Pro Glu
        675                 680                 685

Gly Phe Gln Val Leu Ala Phe Phe Ala Asp Gly Glu Leu Ser Pro Pro
    690                 695                 700

Leu Phe Leu Pro Tyr Asn Glu Leu Pro Cys Cys Phe Lys Ser Leu Gln
705                 710                 715                 720

Thr Gly Ser Cys Cys His Pro Ser Gly Val Gln Ala Leu Tyr Pro Gly
                725                 730                 735

Asn Ala Leu Phe His Asp Leu Gln Val Asp Ser Tyr Leu Gly Val Arg
            740                 745                 750

Leu Gln Asn Ala Ala Gly Asp Pro Ile Gly Asn Leu Cys Ile Leu His
        755                 760                 765

Asp Ala Pro Leu Ala Asp Pro Asp Trp Ala Gln Thr Leu Leu Ser Ile
    770                 775                 780

Phe Ala Ala Arg Ala Gly Ala Glu Leu Glu Arg Leu Met Thr Ala Gln
785                 790                 795                 800

Ala Leu Glu Gln Leu Asn Gly Glu Leu Glu Ser Arg Val Ala Glu Arg
                805                 810                 815

Thr Ala Ala Leu Ala Glu Arg Glu Ala Leu Leu Gln Asp Phe Leu Asp
            820                 825                 830

Asn Ala Asn Asp Leu Ile Gln Met Val Glu Ile Asp Thr Gly Arg Phe
        835                 840                 845

Glu Phe Val Asn Arg Ala Trp Gln Thr Val Leu Gly Tyr Thr Thr Asp
    850                 855                 860

Asp Val Ala Gln Leu Thr Cys Phe Asp Val Leu Ala Pro Asp Cys His
```

-continued

```
865                 870                 875                 880

Pro His Cys Gln Ala Ile Phe Ala Gln Met Gln Ser Gly Asp Ile Thr
                885                 890                 895

His Leu Asp Pro Met Glu Leu Thr Phe Val Gly Lys Ser Gly Gln Arg
            900                 905                 910

Val Val Val Glu Gly Asn Val Asn Cys Arg Phe Val Thr Glu Ala Asp
        915                 920                 925

Gly Arg Gln Arg Pro Val Ser Thr Arg Gly Ile Phe Arg Asp Ile Thr
    930                 935                 940

Ala Arg Lys Ala Ala Glu Leu Glu Leu Glu Arg Arg Glu Ala Arg Tyr
945                 950                 955                 960

Arg Ala Leu Met Glu Gly Ala Ser Asp Ala Ile Leu Leu Ala Asn Pro
                965                 970                 975

Glu Gly Tyr Leu Ile Glu Val Asn Pro Gln Ala Val Asp Leu Met Gly
            980                 985                 990

Tyr Glu His His Glu Leu Val Gly  Met His Phe Thr Gln  Leu His Pro
        995                 1000                1005

Pro Glu  Ala Leu Ser Thr Val  Ser Glu Ala Phe Gly  Ser Leu Ala
    1010                1015                1020

Gln Gly  Gly Arg Ile Glu Val  Leu Asn Phe Glu Ile  Leu Arg Gln
    1025                1030                1035

Asp Gly  Gln Arg Val Pro Val  Asp Ile Thr Gly Ser  Val Ile Glu
    1040                1045                1050

Val Gly  Glu Glu Thr Ile Ile  Gln Gly Ile Phe His  Asp Ile Arg
    1055                1060                1065

Glu Arg  Leu Gln Ala Glu Gln  Ala Leu Arg Asp Ser  Glu Ile Arg
    1070                1075                1080

Phe Arg  Arg Val Phe Glu Ser  Asn Val Val Gly Met  Ile Phe Ala
    1085                1090                1095

Asp Phe  Ser Gly His Ile Ser  Asp Ala Asn Asp Arg  Phe Leu Asp
    1100                1105                1110

Met Leu  Gly Tyr Ser Arg Gln  Glu Leu Glu Ser Gly  Cys Cys Leu
    1115                1120                1125

Asn Trp  Ala Asp Leu Thr Pro  Ser Glu Tyr Gln Ala  Gln Asp Glu
    1130                1135                1140

Ala Val  Ile Ala His Leu Gln  His His Glu Ala Ile  Thr Pro Trp
    1145                1150                1155

Glu Lys  Ala Tyr Arg His Lys  Asp Gly His Leu Val  Pro Val Leu
    1160                1165                1170

Ile Gly  Val Ala Val Leu Ser  Arg Glu Glu Gly Ser  Cys Val Gly
    1175                1180                1185

Val Val  Val Asp Ile Ser Asp  Arg Lys Arg Tyr Glu  Ile Ala Leu
    1190                1195                1200

Gln Glu  Ser Gln Gln Phe Leu  Gln Thr Ile Leu Asp  Thr Val Pro
    1205                1210                1215

Leu Ser  Val Phe Trp Lys Asp  Arg Thr Ser Lys Tyr  Leu Gly Ala
    1220                1225                1230

Asn Gln  Arg Phe Leu Gln Asp  Ala Asp Leu Ser Ser  Val Ser Glu
    1235                1240                1245

Leu Val  Gly Lys Thr Asp Leu  Asp Leu Pro Trp Gly  Ala Thr Glu
    1250                1255                1260

Ala Glu  Ala Tyr Arg Ala Asp  Asp Arg Ala Val Ile  Asp Ser Gly
    1265                1270                1275
```

Glu Ala Lys Leu Gly Ile Val Glu Thr Leu His Gln Lys Asp Gly
1280 1285 1290

Ala Glu Ile Trp Leu Glu Thr Asn Lys Leu Pro Leu Arg Asn Leu
1295 1300 1305

Ala Gly Asp Val Ile Gly Ile Leu Gly Thr Tyr Gln Asp Ile Thr
1310 1315 1320

Glu Arg Arg Asn Ala Asp Ile Ala Leu Gln Arg Gln Leu Val Val
1325 1330 1335

Ile Glu Ala Ala Ile Asn Gly Ile Ala Ile Leu Gln Asn Glu Arg
1340 1345 1350

Tyr Leu Tyr Leu Asn Ser Ser His Val Glu Leu Phe Gly Tyr Gln
1355 1360 1365

Ser Pro Gln Glu Leu Ile Gly Gln Ser Trp Arg Val Leu Tyr Ser
1370 1375 1380

Pro Glu Glu Leu Glu Arg Phe Asp Gln Glu Ile Trp Pro Ala Leu
1385 1390 1395

Tyr Glu Gln Met Ser Trp Arg Gly Glu Val Met Ala Thr Arg Lys
1400 1405 1410

Asp Gly Thr Thr Phe Pro Glu His Leu Ser Leu Thr Leu Ser Pro
1415 1420 1425

Asp Asn Leu Leu Ile Cys Val Cys Glu Asp Ile Ser Asp Arg Lys
1430 1435 1440

Gln Thr Glu Ala Ala Leu Lys Glu Ser Glu Gln Arg Tyr Ala Met
1445 1450 1455

Leu Ala Gln Ala Ala Pro Val Ala Ile Phe Arg Phe Asp Leu Gln
1460 1465 1470

Gly Gln Cys Thr Tyr Val Asn Glu Arg Trp Ser Glu Met Thr Gly
1475 1480 1485

Lys Pro Ile Ala Ser Ala Met Gly Asp Arg Trp Leu Glu Thr Ile
1490 1495 1500

His Pro Asp Asp Arg Glu Arg Ser Gln Thr Glu Thr Gln Gln Trp
1505 1510 1515

Leu Gln Ser Gly Thr Val Thr Met Phe Gln Asn Glu Ala Arg Ile
1520 1525 1530

Leu Arg Asp Asp Gly Ser Ile Val Trp Tyr Tyr Cys Gln Val Leu
1535 1540 1545

Val Glu Thr Asp Ala Asn Gly Thr Gln Thr Gly Tyr Val Gly Thr
1550 1555 1560

Leu Thr Asp Ile Ser Asp Arg Met Lys Ala Glu Gln Ala Leu Arg
1565 1570 1575

Asp Ser Glu Ile Arg Phe Arg Arg Val Phe Glu Ser Asn Val Val
1580 1585 1590

Gly Met Leu Phe Ala Asp Leu Ser Gly His Val Thr Asp Ala Asn
1595 1600 1605

Asp Arg Phe Leu Asp Leu Ile Gly Tyr Ser Arg Ala Asp Leu Glu
1610 1615 1620

Ala His Arg Ile Asn Trp Ala Gln Ile Thr Pro Pro Glu Tyr Val
1625 1630 1635

Glu Ala Asp Gln Arg Ala Ile Asp Gln Leu Gln Arg Tyr Gly Glu
1640 1645 1650

Ile Leu Pro Trp Glu Lys Glu Tyr Leu Arg Pro Asp Gly Arg Arg
1655 1660 1665

```
Val Ala Val Leu Ile Ser Val Ala Leu Leu Ser Ala Ile Asp Gly
    1670                1675                1680

Arg Cys Val Cys Val Val Val Asp Ile Ser Asp Arg Lys Arg Tyr
    1685                1690                1695

Glu Thr Ala Leu Gln Asp Ser Gln Gln Leu Leu Gln Thr Val Leu
    1700                1705                1710

Asp Thr Val Pro Leu Ser Val Phe Trp Lys Asp Arg Gln Ser Val
    1715                1720                1725

Ile Leu Gly Cys Asn Gln Pro Phe Ala Ser Ala Ser Gly Phe Ala
    1730                1735                1740

Glu Val Ala Asp Val Leu Gly Lys Asn Asn Phe Asp Leu Gly Phe
    1745                1750                1755

Thr Gln Ala Glu Ala Glu Ser Tyr Thr Ala Asp Asp Tyr Glu Val
    1760                1765                1770

Met Thr Ser Gly Ile Ala Lys Leu Gly Ile Glu Glu Thr Val Thr
    1775                1780                1785

Pro Ala Gly Ser Gln Gln Arg Trp Ile Glu Thr Asn Lys Leu Pro
    1790                1795                1800

Leu Arg Asp Gly Ala Gly Asn Ala Ile Gly Ile Val Gly Thr Phe
    1805                1810                1815

Gln Asp Ile Thr Asp Arg Lys Gln Ala Glu Glu Ala Leu Arg Glu
    1820                1825                1830

Ser Glu Glu Lys Phe Arg Gln Leu Ala Glu Val Val Asp Ala Val
    1835                1840                1845

Phe Trp Ile Leu His Leu Asn Arg Thr Asp Arg Val Tyr Val Ser
    1850                1855                1860

Pro Ala Tyr Glu Arg Ile Trp Gly Arg Pro Cys Thr Glu Leu Tyr
    1865                1870                1875

Val Thr Pro Asp Ala Trp Val Glu Met Ile His Ala Asp Asp Arg
    1880                1885                1890

Glu Gln Val Leu Ala Ala Ile Pro Lys Gln Ile Gln Gly Thr Phe
    1895                1900                1905

Asp Glu Glu Tyr Arg Ile Ile Arg Pro Asp Gly Thr Gln Arg Trp
    1910                1915                1920

Ile His Asp Arg Ala Phe Pro Ile Arg Asn Ala Gln Gly Glu Ile
    1925                1930                1935

Tyr Arg Leu Ala Gly Ile Ala Glu Asp Ile Thr Glu Arg Lys Arg
    1940                1945                1950

Ser Glu Glu Val Ile Arg Gln Gln Ala Ala Arg Glu Thr Val Leu
    1955                1960                1965

Arg Glu Ile Ser Gln Arg Ile Arg Glu Ser Leu Asp Leu Gln Thr
    1970                1975                1980

Ile Phe Asp Thr Ala Cys Glu Glu Ile Arg Thr Cys Leu Gln Ala
    1985                1990                1995

Asp Arg Val Gly Ile Phe Lys Phe Tyr Pro Asn Thr Gly Tyr Asp
    2000                2005                2010

Asp Gly Glu Phe Val Ala Glu Ser Val Val Asn Gly Leu Ser Ser
    2015                2020                2025

Val Val Ala Ile Arg Val His Asp His Cys Phe Gly Glu Asn Tyr
    2030                2035                2040

Ser Thr Leu Tyr Ala Gln Gly Arg Tyr Gln Val Val Asp Asp Ile
    2045                2050                2055

Tyr His Pro Gly Leu Thr Ser Tyr His Ala Asp Ile Leu Ala Gln
```

```
    2060                2065                2070

Phe Gln  Val Arg Ala Asn Leu  Val Met Pro Leu Leu  Cys Asn His
    2075                2080                2085

Glu Leu  Trp Gly Leu Leu Cys  Ile His Gln Cys Asp  Gly Pro Arg
    2090                2095                2100

His Trp  His Gln Ser Glu Val  Asp Leu Gly Gln Gln  Leu Ala Asn
    2105                2110                2115

Gln Leu  Ala Ile Ala Ile Gln  Gln Ala Ile Leu Tyr  Glu Gln Leu
    2120                2125                2130

Gln Ala  Glu Leu Gln Glu Arg  Gln Arg Ala Glu Ser  Thr Ile Thr
    2135                2140                2145

Gln Gln  Leu Arg Gln Gln Thr  Ala Leu Glu Leu Ile  Leu Gln Gln
    2150                2155                2160

Ile Arg  Lys Ser Leu Asp Leu  Pro Glu Ile Leu Ala  Ile Ala Thr
    2165                2170                2175

Gln Gln  Val Gln Glu Leu Leu  His Ser Asp Arg Val  Ile Val Phe
    2180                2185                2190

Gln Val  Tyr His Asp Gly His  Ser Arg Ile Val Glu  Glu Ala Val
    2195                2200                2205

Thr Pro  Asp Leu Pro Ser Leu  Lys Ala Met His Trp  Glu Gly Glu
    2210                2215                2220

Thr Trp  Pro Leu Asp Ile Leu  Glu His Tyr Trp Gln  Gly Gln Pro
    2225                2230                2235

Arg Ile  Val Pro Asp Val Met  Asp Asp Ile Trp Thr  Asp Cys Leu
    2240                2245                2250

Val Asp  Tyr Ala Gln Ala Gly  Gln Ile Gln Ser Lys  Met Val Ala
    2255                2260                2265

Pro Ile  Leu Gln Glu Leu Arg  Ser Val Glu Glu His  Arg Trp Val
    2270                2275                2280

Cys Pro  Glu Gly Ser Asn Lys  Leu Trp Gly Val Leu  Val Val His
    2285                2290                2295

Ala Cys  Gln Thr Gln Arg Val  Trp Gln Ala Asp Glu  Ala Gln Leu
    2300                2305                2310

Leu Gln  Gln Ile Ala Asn Gln  Leu Ala Ile Ala Ile  Gln Gln Ser
    2315                2320                2325

Asn Leu  Phe Glu Gln Leu Gln  Gln Glu Leu Thr Glu  Arg Gln Gln
    2330                2335                2340

Ala Gln  His Gln Leu Thr Glu  Arg Asn Glu Glu Leu  Ile Arg Ala
    2345                2350                2355

Thr Arg  Leu Lys Asp Glu Phe  Leu Ala Asn Met Ser  His Glu Leu
    2360                2365                2370

Arg Thr  Pro Leu Asn Thr Ile  Leu Gly Met Thr Glu  Ser Leu Gln
    2375                2380                2385

Glu Glu  Asp Val Phe Gly Pro  Val Asn Pro Gln Gln  Leu Lys Ala
    2390                2395                2400

Leu Lys  Ser Val Glu Arg Ser  Gly Leu His Leu Leu  Glu Leu Ile
    2405                2410                2415

Asn Asp  Val Leu Asn Val Ala  Lys Ile Glu Ala Gly  Gln Met Glu
    2420                2425                2430

Leu Asp  Tyr Thr Ser Thr Glu  Ile Ala Leu Leu Cys  Arg Ser Ser
    2435                2440                2445

Leu Thr  Phe Val Lys Gln Pro  Ala Phe Lys Lys Arg  Ile Gln Leu
    2450                2455                2460
```

Thr Val Asn Met Pro Pro Asp Leu Pro Glu Ile Thr Leu Asp Glu
2465 2470 2475

Arg Arg Ile Arg Gln Val Leu Ile Asn Leu Leu Asn Asn Ala Val
2480 2485 2490

Lys Phe Thr Pro Glu Gly Gly His Ile Thr Leu Asp Val Thr Pro
2495 2500 2505

Leu Thr Pro Ser Pro Pro Ser Lys Glu Pro Leu Tyr Leu Arg Phe
2510 2515 2520

Ala Val Thr Asp Thr Gly Ile Gly Ile Thr Pro Glu Asp Gln Gln
2525 2530 2535

Arg Leu Phe Gln Pro Phe Val Gln Val Asp Ser Ala Leu Asn Arg
2540 2545 2550

Gln Tyr Gln Gly Thr Gly Leu Gly Leu Ala Leu Val Lys Arg Ile
2555 2560 2565

Val Glu Leu His Gly Gly Gln Val Gly Leu Thr Ser Ala Val Gly
2570 2575 2580

Val Gly Ser Cys Phe Thr Phe Asp Leu Pro Tyr Gly Val Glu Ile
2585 2590 2595

Ala Leu Leu Pro Thr Pro Leu Gly Pro Gln Pro Asp Leu Ser Ala
2600 2605 2610

Thr Thr Pro Leu Gln Thr Glu Ala Ala Ile Pro Glu Ser Lys Ala
2615 2620 2625

Leu Ile Leu Leu Ala Glu Asp Asn Glu Ala Ser Ile Ser Thr Met
2630 2635 2640

Val Ser Tyr Leu Glu Ala Lys Gly Tyr Arg Val Ala Ile Ala Asn
2645 2650 2655

Asn Gly Gln Ala Ala Ile Glu Lys Ala Gln Arg Leu Arg Pro Asp
2660 2665 2670

Leu Ile Leu Met Asp Ile Gln Met Pro Gly Met Asp Gly Leu Glu
2675 2680 2685

Ala Ile Ser His Ile Arg Arg Asp Pro Asn Leu Ala Asp Ile Pro
2690 2695 2700

Val Ile Ala Leu Thr Ala Leu Ala Met Ser Gly Asp Arg Asp Arg
2705 2710 2715

Cys Leu Thr Ala Gly Ala Thr Asp Tyr Leu Ser Lys Pro Val Arg
2720 2725 2730

Met Lys Gln Leu Val Lys Arg Ile Gln Thr Leu Leu Asn Pro
2735 2740 2745

<210> SEQ ID NO 37
<211> LENGTH: 2320
<212> TYPE: PRT
<213> ORGANISM: Unknown
<220> FEATURE:
<223> OTHER INFORMATION: Leptolyngbya sp. PCC 6406

<400> SEQUENCE: 37

Met Arg Gln Phe Ser Asp Leu Asn Arg Pro Leu Gly Pro Ile Ser Leu
1 5 10 15

Gln Val Leu Phe Arg Val Ser Leu Gly Leu Gln Thr Val Gly Thr Met
20 25 30

Ala Leu Val Gly Tyr Leu Leu Tyr Gly Leu Leu Gly Tyr Gly Gly Gly
35 40 45

Val Gly Ala Gly Leu Pro Pro Leu Leu Ser Pro Leu Gly Gly Ser Val
50 55 60

-continued

```
Pro Leu Ala Ile Ala Leu Ile Ile Leu Ile Cys Gly Thr Trp Gly Val
65                  70                  75                  80

Thr Ile Val Leu Gly Phe Phe Thr Ser Arg Gln Ile Thr Gln Gly Ile
                85                  90                  95

Asp Gln Val Ile Gln Ala Ser Gln Thr Leu Ala Ala Gly Gln Met Pro
            100                 105                 110

Pro Pro Leu Pro Arg Gly Ser Met Ile Gly Asp Leu Asp Arg Leu Ala
        115                 120                 125

Gln Ser Phe Gln Gln Met Ala Thr Ala Val Asp Leu Tyr Gln Val Gln
    130                 135                 140

Thr Gln Asp Asn Leu Ala Ala Leu Glu Glu Lys Phe Thr Leu Leu Phe
145                 150                 155                 160

His Tyr Ser Pro Ile Pro Thr Trp Ile Ala Thr Leu Glu Glu Gly Arg
                165                 170                 175

Cys Leu Leu Val Asn Asp Ser Phe Cys Gln Leu Met Gly Tyr Ala Gln
            180                 185                 190

Ala Glu Ile Ile Gly Gln Thr Cys Arg Gln Leu Gln Phe Trp Asp Asn
        195                 200                 205

Leu Val Asp Tyr Gln Asn Phe Arg His Gly Leu Thr Thr Gln Gly Gln
    210                 215                 220

Val Arg Asp Phe Glu Cys Val Phe Arg Thr Gln Ser Gly Gly Thr Lys
225                 230                 235                 240

Thr Leu Leu Leu Thr Ala Gln Val Ser Cys Leu Glu Gly Gln Asp Cys
                245                 250                 255

Ile Leu Gly Ile Ala His Asp Ile Ser Asp Arg Lys Gln Ala Glu Leu
            260                 265                 270

Ala Leu Arg Asp Ser Glu Met Arg Leu Gln Ala Leu Leu Ala Asn Thr
        275                 280                 285

Pro Gly Met Ile Tyr Arg Tyr Leu Pro Ile Asp Asp Gly Gly Gly Thr
    290                 295                 300

Phe Leu Glu Val Ser Ala Gly Ala Tyr Glu Leu Leu Gly Leu Glu Pro
305                 310                 315                 320

Glu Gln Val Arg Gln Asp Val Ser Thr Val Trp Ala Leu Ile His Pro
                325                 330                 335

Glu Asp Val Leu Thr Leu Gln Asp Ser Val Glu Ile Ala Val Arg Asp
            340                 345                 350

Cys Thr Asp Trp His Trp Glu Gly Arg Leu Thr Thr Pro Ser Gly Glu
        355                 360                 365

Leu Lys Trp Leu Arg Gly Tyr Ser Arg Pro Tyr Val Thr Pro Ala Gly
    370                 375                 380

Ile Val Trp Asp Gly Leu Phe Thr Asp Ile Thr Ala Leu Lys Gln Thr
385                 390                 395                 400

Glu Ile Ser Leu His Gln Glu Val Ser Arg Arg Arg Ser Leu Phe Glu
                405                 410                 415

Thr Ser Ile Asp Gly Ile Val Ile Val Asp Arg Ala Gly Asn Val Leu
            420                 425                 430

Glu Ser Asn Ala Arg Phe Ala Asn Met Leu Gly Tyr Ser Leu Glu Glu
        435                 440                 445

Val Lys Thr Leu Asn Leu Val Asp Phe Asp Val Asn Leu Ser Ser Val
    450                 455                 460

Glu Ile Glu Gly Lys Ile Asp Lys Asp Glu Leu Cys Leu Asp His Phe
465                 470                 475                 480
```

```
Glu Ser Arg His Arg Arg Lys Asp Gly Ser Ile Tyr Ala Val Glu Ile
                485                 490                 495

Ser Ala Asn Thr Ile Asn Trp Gly Asp Gln Ser Val Ser Leu Cys Ile
            500                 505                 510

Cys Arg Asp Ile Thr Glu Arg Lys Arg Asn Glu Leu Ala Leu Gln Thr
        515                 520                 525

Ser Gln Leu Arg Leu Glu Leu Ala Leu Asp Ser Ser Gly Thr Gly Thr
    530                 535                 540

Trp Asp Trp Asn Met Glu Thr Asn Glu Val Phe Phe Ser Glu Lys Ser
545                 550                 555                 560

Trp Arg Ala Met Val Gly Tyr Gly Ala Asp Asp Arg Phe Gly Asn Thr
                565                 570                 575

Ile Thr Glu Trp Glu Ser Arg Ile His Pro Glu Asp Lys Ala Gln Leu
            580                 585                 590

Glu Val Asp Ile Ala Lys His Leu Arg Gly Glu Thr Glu Thr Tyr Glu
        595                 600                 605

Ser Val His Arg Ile Arg Cys Gln Asp Gly Thr Tyr Lys Trp Asn Leu
    610                 615                 620

Ala Gln Gly Lys Val Ile Glu Trp Asp Gln Ala Gly Asn Pro Val Arg
625                 630                 635                 640

Phe Ile Gly Leu Tyr Arg Asp Ile Ser Asp Arg Lys Gln Thr Glu Ile
                645                 650                 655

Ala Leu Ser Asn Leu Arg Ser Gln Leu Glu Arg Ala Gln Glu Ile Ala
            660                 665                 670

His Leu Gly His Trp Ser Phe Asp Leu Asp Thr Gln Lys Leu Thr Trp
        675                 680                 685

Ser Asp Glu Val Phe Arg Ile Phe Asp Met Thr Thr Asp Gln Asp Glu
    690                 695                 700

Pro Thr Phe Arg Glu His Leu Glu Gln Ile His Pro Asp Asp Gln Ser
705                 710                 715                 720

Ser Trp Leu Glu Arg Val Ala Glu Ala Asn Gln Gly Ile Pro Gln Asn
                725                 730                 735

Phe Cys Phe Arg Ile Leu Arg Pro Thr Gly Glu Val Arg Tyr Val Asn
            740                 745                 750

Ser Tyr Leu Glu Leu Glu Tyr Glu Gly Glu Gln Ile Val Arg Met Phe
        755                 760                 765

Gly Val Val Met Asp Ile Thr Glu Gln Lys Gln Asn Glu Leu Ala Leu
    770                 775                 780

Gln Ala Ser Glu Ala Arg Phe Arg Ala Ile Phe Glu Gln Ala Ala Val
785                 790                 795                 800

Gly Ile Asn Gln Ala Asp Val Ser Gly Gln Phe Ile Glu Ala Asn Gln
                805                 810                 815

Tyr Phe Cys Asp Leu Leu Gly Tyr Thr Arg Asp Glu Leu Leu Ala Leu
            820                 825                 830

Thr Phe Gln Ala Ile Thr His Pro Asp Asp Phe Gln Gln Asp Ser Val
        835                 840                 845

Phe Ser Arg Leu Leu Ala Gly Glu Leu Thr Ser Val Thr Ala Gln Lys
    850                 855                 860

Arg Tyr Arg His Lys Gln Gly Asp Trp Ile Trp Thr Glu Val Thr Val
865                 870                 875                 880

Ser Leu Ile His Asp Ala Asp Gly Arg Ala Ile Ser Asp Leu Ala Ile
                885                 890                 895

Val Leu Asp Ile Ser Asp Leu Lys Gln Ala Asn Ala Ala Leu Gln Ala
```

```
            900                 905                 910

Ser Glu Ala Arg Phe Arg Thr Ile Phe Glu Gln Ala Ala Ala Gly Ile
        915                 920                 925

Asn Gln Ile Asp Ala Ser Gly Arg Phe Thr Glu Ala Asn Gln Tyr Tyr
    930                 935                 940

Cys Asp Leu Leu Gly Tyr Ser Arg Ala Glu Leu Leu Thr Leu Thr Phe
945                 950                 955                 960

Val Asp Val Leu His Pro Glu Val Leu Ala Gln Tyr Trp Ser Glu Asn
                965                 970                 975

Asn Phe Ile Leu Ser Gly Glu Ile Glu Phe Leu Glu Tyr Glu Lys Arg
            980                 985                 990

Leu Arg His Lys Asn Gly Asp Trp  Ile Trp Val Lys Ser  Asn Ile Ser
        995                 1000                1005

Val Leu  Arg Asp Gln Ala Gly  Glu Leu Ala Gly Asn  Leu Glu Val
    1010                 1015                 1020

Val Val  Asp Ile Arg Asp Arg  Lys Gln Ala Glu Leu  Ala Leu His
    1025                 1030                 1035

Ala Ser  Glu Asp Arg Phe Arg  Ala Ile Phe Glu Gln  Ala Ala Ala
    1040                 1045                 1050

Gly Ile  Asn Gln Ile Asp Val  Ser Gly Arg Phe Thr  Glu Ala Asn
    1055                 1060                 1065

Gln Tyr  Tyr Cys Asn Leu Leu  Gly Tyr Ser Arg Ala  Glu Leu Leu
    1070                 1075                 1080

Thr Leu  Thr Phe Val Asp Val  Ile His Pro Glu Asp  Leu Ala Lys
    1085                 1090                 1095

His Trp  Ser Glu Val Asp Arg  Ile Val Arg Gly Glu  Ile Asp Phe
    1100                 1105                 1110

Leu Asp  Tyr Glu Arg Arg Glu  Arg His Lys Asn Gly  Asp Trp Ile
    1115                 1120                 1125

Trp Ile  Lys Ser Asn Ile Ser  Val Leu Arg Asp Gly  Ala Gly Gln
    1130                 1135                 1140

Val Val  Gly Asn Leu Ala Val  Val Val Asp Ile Arg  Asp Arg Lys
    1145                 1150                 1155

Gln Ala  Glu Leu Ala Leu Gln  Glu Ser Gln Ala Arg  Phe Gln Leu
    1160                 1165                 1170

Leu Ser  Ala Ala Ser Pro Ala  Val Ile Tyr Thr Val  Ile Glu Thr
    1175                 1180                 1185

Ala Gln  Gly Ile Asn Arg Phe  Asp Tyr Ile Ser Pro  Ala Ala Glu
    1190                 1195                 1200

Glu Ile  His Glu Ile Pro Val  Asp Thr Leu Leu Gln  Asn Gly Met
    1205                 1210                 1215

Leu Ile  Ser Glu Gln Met His  Pro Glu Asp Arg Glu  His Tyr Ala
    1220                 1225                 1230

Ala Thr  Tyr Ala Ala Ser Leu  Gln Ala Leu Ala Pro  Phe Thr Cys
    1235                 1240                 1245

Glu Trp  Arg Ile Ile Thr Pro  Ser Gly Gln Thr Lys  Trp Leu Arg
    1250                 1255                 1260

Ala Ser  Ser Cys Pro Glu Gln  Arg Pro Asp Gly Asp  Ile Ala Trp
    1265                 1270                 1275

His Gly  Ile Ala Leu Asp Ile  Ser Thr Arg Lys Gln  Ala Glu Leu
    1280                 1285                 1290

Glu Ser  Gln Thr Leu Gln Thr  Ala Leu Val Glu Ala  Gln Arg Ile
    1295                 1300                 1305
```

Ala His Ile Gly Asn Trp Ala Phe Asp Leu Ala Ser Gln Lys Ile
1310 1315 1320

Thr Trp Ser Leu Glu Leu Phe Arg Met Phe Gly Leu Asp Pro Ala
1325 1330 1335

Gln Asp Glu Pro Ser Tyr Pro Asp Tyr Leu Gln Leu Ile His Pro
1340 1345 1350

Asp Asp Arg Leu Leu Leu Gln Gln Ala Ile Asp Arg Ala Val Thr
1355 1360 1365

Ala Gly Thr Pro Tyr Ser Ile Asp Tyr Gln Ala Gln Leu Pro Asp
1370 1375 1380

Gly Ser Thr Arg Tyr His Glu Gly Arg Gly Glu Val Glu Arg Asp
1385 1390 1395

Cys Ser Gly Gln Ile Thr Arg Leu Leu Gly Thr Cys Leu Asp Ile
1400 1405 1410

Thr Asp Arg Lys Arg Val Glu Gln Ile Ile Leu Gln Gln Ala Arg
1415 1420 1425

Gln Glu Ala Leu Leu Arg Glu Ile Gly Gln Arg Ile Arg Gln Ser
1430 1435 1440

Leu Asp Leu Gln Thr Ile Phe Asp Thr Ala Cys Gln Glu Ile Arg
1445 1450 1455

Ser Cys Leu Asn Ala Asp Arg Val Gly Ile Phe Lys Phe Asp Pro
1460 1465 1470

Asp Ser Gly Tyr Asp Asp Gly Glu Phe Ile Ala Glu Ala Cys Val
1475 1480 1485

Gly Gly Leu Pro Ser Val Leu Thr Ile Pro Val Gln Asp His Cys
1490 1495 1500

Phe Gly Asp Asn Tyr Ala Thr Leu Tyr Ala Gln Gly His Tyr Cys
1505 1510 1515

Val Ile Asp Asp Ile Tyr Ser Ala Asn Met Ala Asp Cys Tyr Ile
1520 1525 1530

Asp Leu Leu Ala Gln Phe Gln Val Arg Ala Thr Leu Val Met Pro
1535 1540 1545

Leu Phe Cys Gly Asp Val Leu Trp Gly Leu Leu Cys Ile His Gln
1550 1555 1560

Cys Asn Ala Pro Arg Gln Trp Gln Gln Ala Asn Ile Asp Leu Gly
1565 1570 1575

Gln Gln Leu Ala Asn Gln Leu Ala Ile Ala Ile Gln Gln Ala Ile
1580 1585 1590

Leu Tyr Glu Gln Leu Gln Ser Glu Leu Gln Glu Arg Gln Arg Ala
1595 1600 1605

Glu Thr Lys Ile Ser Gln Gln Leu Gln Gln Gln Thr Ala Leu Gly
1610 1615 1620

Met Ile Trp Gln Gln Ile Arg Gln Ser Leu Asp Leu Gln Asp Ile
1625 1630 1635

Leu Ala Ile Val Thr Gln Gln Val Gln Val Val Phe Gln Cys Asp
1640 1645 1650

Arg Val Ile Val Phe Gln Leu Phe Ala Asp Gly Arg Ser Gln Ile
1655 1660 1665

Val Glu Glu Glu Val Leu Gly Ser Leu Pro Ala Leu Arg Thr Met
1670 1675 1680

His Trp Glu Asp Glu Val Trp Ser Gln Asp Ile Leu Ala Leu Tyr
1685 1690 1695

```
Trp Gln  Gly Gln Pro Arg Ile  Val Pro Asp Val Met  Asp Asp Ile
    1700                 1705                 1710

Trp Thr  Asp Cys Leu Val Glu  Tyr Ala Gln Ala Gly  Gln Ile Lys
    1715                 1720                 1725

Ser Lys  Ile Val Ala Pro Ile  Leu Gln Gln Gly His  Thr Ala Thr
    1730                 1735                 1740

Gly Asn  Arg Trp Gln Asp Pro  Asn His Pro His Lys  Leu Trp Gly
    1745                 1750                 1755

Val Leu  Val Val His Ala Cys  His Glu Arg Arg Thr  Trp Lys Ala
    1760                 1765                 1770

Glu Asp  Ala Gln Leu Leu Gln  Gln Ile Ala Asn Gln  Leu Ala Ile
    1775                 1780                 1785

Ala Ile  Arg Gln Ala His Leu  Phe Glu Gln Leu Gln  Gln Glu Leu
    1790                 1795                 1800

Ile Gln  Arg Gln Gln Ala Gln  Gln Gln Leu Val Glu  Arg Asn Gln
    1805                 1810                 1815

Glu Leu  Ala Ile Ala Asn Gln  Asp Leu Ser Arg Ala  Thr Arg Leu
    1820                 1825                 1830

Lys Asp  Glu Phe Leu Ala Asn  Met Ser His Glu Leu  Arg Thr Pro
    1835                 1840                 1845

Leu Asn  Val Ile Leu Gly Phe  Ala Gln Val Leu Asn  Ser Asp Leu
    1850                 1855                 1860

Ser Leu  Gln Pro Gln His Gln  Asp Tyr Ile Arg Ile  Met His Arg
    1865                 1870                 1875

Ser Gly  Asp His Leu Leu His  Leu Ile Asn Asp Ile  Leu Asp Leu
    1880                 1885                 1890

Ser Lys  Ile Glu Ala Asn Arg  Ile Thr Leu Glu Pro  Glu Ser Ile
    1895                 1900                 1905

Asp Leu  Phe Ser Leu Leu His  Asp Leu Gln Ala Met  Phe Gln Glu
    1910                 1915                 1920

Arg Ala  Thr Asp Lys Glu Leu  Gln Phe Thr Leu Ala  Leu Pro Pro
    1925                 1930                 1935

Asp Leu  Pro Gln Tyr Ile Val  Ala Asp Pro Asn Lys  Leu Arg Gln
    1940                 1945                 1950

Val Leu  Ile Asn Leu Leu Asn  Asn Ala Ile Lys Phe  Thr Gln Gln
    1955                 1960                 1965

Gly Gln  Val Ile Leu Ser Val  Arg Leu Gln Gly Ala  Glu Ala Asp
    1970                 1975                 1980

Gln Gln  Phe His Leu Ser Ser  Ser Ile Thr Ser Ser  Asp Thr Pro
    1985                 1990                 1995

Pro Thr  Pro Ser Leu Cys Phe  Gln Val Ile Asp Thr  Gly Val Gly
    2000                 2005                 2010

Ile Pro  Ser Glu Glu Ile Asp  Ile Ile Phe Asp Ala  Phe Thr Gln
    2015                 2020                 2025

Ala Arg  Ala Gly Lys Ser Thr  Leu Gly Ser Thr Gly  Leu Gly Leu
    2030                 2035                 2040

Ala Ile  Ser Arg Ser Leu Val  Lys Leu Met Gly Gly  Glu Leu Thr
    2045                 2050                 2055

Val Asn  Ser Ala Pro Asp Gln  Gly Ser Thr Phe Gln  Phe Ala Ile
    2060                 2065                 2070

Pro Leu  His Leu Ala Arg Gly  Glu Asp Val Thr Ser  Glu Gly Ser
    2075                 2080                 2085

Leu Gly  Thr Val Ile Gly Leu  Ala Pro Gly Gln Ser  Pro Tyr Arg
```

-continued 2090 2095 2100

Ile Leu Val Val Asp Asp Gln Pro Asp Asn Arg Gln Leu Leu Val
2105 2110 2115

Thr Val Phe Ser Gln Ile Gly Leu Glu Val Gln Glu Ala Ala Ser
2120 2125 2130

Gly Ala Asp Ala Ile Ala Ala Asn Gln Gln Trp His Pro His Leu
2135 2140 2145

Ile Trp Met Asp Leu Arg Met Pro Asp Met Asp Gly Cys Glu Ala
2150 2155 2160

Thr Arg Gln Ile Arg Ala Gln Ala Gln Glu Leu Asp Ser Glu Asn
2165 2170 2175

Arg Pro Glu Asp Pro Val Ile Ile Ala Phe Thr Ala Gln Ala Ser
2180 2185 2190

Met Asp Glu Arg Thr Arg Ala Leu Glu Ser Gly Cys Asp Asp Phe
2195 2200 2205

Val Ser Lys Pro Ile Gln Leu Asn Leu Ile Leu Ser Lys Met Ala
2210 2215 2220

Asp Tyr Leu Asp Leu Arg Tyr Glu Tyr Ala Gln Thr Val Thr Pro
2225 2230 2235

Ala Pro Gly Ala Gln Ser Ala Thr Ala Thr Ala Ile Thr Leu Asp
2240 2245 2250

Ala Gln Ser Leu Arg Ile Met Pro Leu Glu Trp Ile Ala Ala Leu
2255 2260 2265

His Lys Ala Ala Leu His Cys Asp Asp Gln Ala Ala Ser Ser Leu
2270 2275 2280

Val Gln Glu Ile Pro Thr Ser Gln Ser Val Leu Val Glu Gly Leu
2285 2290 2295

Asn Arg Leu Ile Tyr Asp Tyr Lys Phe Glu Ser Ile Ala Gln Leu
2300 2305 2310

Thr Ser Pro Leu Leu Leu Glu
2315 2320

<210> SEQ ID NO 38
<211> LENGTH: 1146
<212> TYPE: PRT
<213> ORGANISM: Planktothrix agardhii

<400> SEQUENCE: 38

Met Leu Phe Pro Pro Asp Arg Leu Asp Glu Glu Pro Gln Ile Leu Ala
1 5 10 15

Arg Leu Met Arg Gly Glu Arg Val Glu His Phe Glu Thr Val Arg Ile
20 25 30

Ser Lys Glu Gly Lys Ser Ile Glu Val Ser Ala Thr Ile Ser Leu Leu
35 40 45

Lys Asn Ala Ala Gly Glu Val Val Gly Val Ser Lys Ile Leu Arg Asp
50 55 60

Ile Ser Asp Arg Lys Gln Ala Glu Lys Ser Leu Gln Glu Ser Gln Gln
65 70 75 80

Phe Ile Gln Thr Val Ile Asp Thr Val Pro Leu Pro Leu Phe Trp Lys
85 90 95

Asp Arg Ser Ser Val Phe Leu Gly Cys Asn Gln Gln Phe Val Arg Ile
100 105 110

Leu Gly Ala Pro Ser Ser Lys Glu Val Val Gly Lys Thr Asp Phe Asp
115 120 125

```
Leu Leu Pro Thr Glu Glu Glu Ala Ser Ala Phe Gln Ala Asp Asp Arg
    130                 135                 140

Gly Val Met Glu Ser Gly Gln Ala Lys Leu Gly Ile Glu Glu Met Leu
145                 150                 155                 160

Thr Phe Ala Asn Gly Glu Gln Arg Trp Leu Glu Thr His Lys Ala Pro
                165                 170                 175

Leu Arg Asp Trp Ser Gly Asn Val Ile Gly Met Val Gly Thr Phe Gln
            180                 185                 190

Asp Val Thr Asp Arg Lys Gln Ala Glu Leu Glu Leu Gln Lys Asn Thr
        195                 200                 205

Glu Arg Leu Val Phe Ala Leu Lys Ser Gly Ala Lys Glu Phe Glu Met
    210                 215                 220

Gln Leu Gln Gln Thr Thr Asp Arg Leu Ser Leu Ala Leu Asn Ser Gly
225                 230                 235                 240

Ala Ile Gly Tyr Trp Glu Trp Asp Ile Gln Gln Asn Ile Leu Val Trp
                245                 250                 255

Asp Asp Arg Met Tyr Glu Leu Tyr Gly Tyr Leu Lys Glu Asn Tyr Ser
            260                 265                 270

His Leu Pro Tyr Glu Ile Trp Ala Asn Ala Val His Pro Asp Asp Arg
        275                 280                 285

Asp Leu Thr Glu Thr Leu Leu Gln Gln Ala Val Leu Gly Lys Thr Glu
    290                 295                 300

Tyr Asp Cys Glu Phe Arg Ile Ile His Pro Asp His Ser Ile His Phe
305                 310                 315                 320

Ile Lys Ala Tyr Gly Thr Leu Asn Arg Asp Ala Ser Gly Asn Pro Leu
                325                 330                 335

Ser Ile Ile Gly Ile Asn Phe Asp Ile Thr Asp Arg Lys Gln Ala Glu
            340                 345                 350

Gln Ile Ile Leu Gln Gln Ala Asn Arg Glu Thr Leu Leu Arg Gly Ile
        355                 360                 365

Thr Gln Arg Ile Arg Gln Tyr Leu Asp Leu Ser Ile Ile Phe Asp Thr
    370                 375                 380

Ala Cys Gln Glu Ile Gln Gln Leu Leu Gln Ser Asp Arg Val Gly Ile
385                 390                 395                 400

Phe Lys Phe Tyr Pro Glu Ser Asn Phe Asp Asp Gly Glu Phe Val Ala
                405                 410                 415

Glu Ser Val Val Asn Gly Phe Ser Ser Ala Met Glu Val His Ile His
            420                 425                 430

Asp His Cys Phe Gly Glu Gly Tyr Ala Ala Glu Tyr Ala Gln Gly Arg
        435                 440                 445

Met Gln Val Val Asn Asp Ile Asp Asn Ala Gly Leu Met Asp Cys His
    450                 455                 460

Arg Asp Val Leu Ala Gln Phe Gln Val Arg Ala Asn Leu Ala Ile Pro
465                 470                 475                 480

Leu Leu Cys Gly Asn Asn Leu Trp Gly Leu Leu Ser Ile His Gln Cys
                485                 490                 495

Ala His Thr Arg Gln Trp Gln Glu Asp Glu Ile Asn Leu Ile Gln Gln
            500                 505                 510

Ile Ala Asn Gln Leu Ala Ile Ala Ile Gln Gln Ala Ser Leu Tyr Glu
        515                 520                 525

Gln Leu Gln Glu Glu Leu Leu Ile Arg Gln Gln Ser Gln Ser Lys Ile
    530                 535                 540

Ala Gln Gln Leu Arg Glu Gln Gln Thr Leu Ala Thr Ile Thr Asn Lys
```

```
545                 550                 555                 560

Ile Arg Glu Ser Leu Ser Ile Lys Glu Ile Leu Ala Val Val Thr Gln
                565                 570                 575

Gln Val Ile Asp Val Leu Ser Gly Asp Arg Ala Ile Ile Phe Gln Leu
            580                 585                 590

Phe Asp Asn Gly Asn Ser Gln Ile Val Glu Glu Ser Val His Ser Asn
        595                 600                 605

Phe Leu Asn Leu Lys Ala Leu Asn Trp Asp Asn Glu Val Trp Ser Gln
    610                 615                 620

Glu Ile Leu Asp Cys Tyr Trp Gln Gly Lys Pro Arg Ile Val Pro Asp
625                 630                 635                 640

Val Met Asn Asp Ile Trp Thr Glu Cys Leu Val Glu Tyr Ser Leu Lys
                645                 650                 655

Gly Gln Ile Lys Ser Lys Ile Val Ala Pro Ile Leu Leu Glu Ser His
            660                 665                 670

Ile Ser Glu Asn His Arg Trp Val Ala Thr Asp Gly Tyr Lys Lys Leu
        675                 680                 685

Trp Gly Val Leu Val Val Tyr Ala Cys Ala Glu Gln Arg Glu Trp Gln
    690                 695                 700

Asp Ser Glu Ala Gln Leu Leu Gln Gln Val Ala Asn Gln Leu Ala Ile
705                 710                 715                 720

Ala Ile Gln Gln Ala Ser Ile Tyr Glu Glu Ser Gln Gln Glu Ile Ala
                725                 730                 735

Glu Arg Lys Gln Ala Glu Gln Gln Leu Thr Glu Thr Asn Gln Gln Leu
            740                 745                 750

Ala Arg Ala Thr Arg Leu Lys Asp Glu Phe Leu Ala Asn Met Ser His
        755                 760                 765

Glu Leu Arg Thr Pro Leu Asn Ser Ile Leu Gly Met Asn Glu Ala Leu
    770                 775                 780

Gln Glu Glu Val Phe Gly Gly Ile Asn Glu Arg Gln Leu Lys Ala Leu
785                 790                 795                 800

Gln Thr Ile Glu Ser Ser Ser Arg His Leu Leu Ala Leu Ile Asn Asp
                805                 810                 815

Ile Leu Asp Val Ala Lys Ile Glu Ser Gly Gln Val Thr Leu Glu Leu
            820                 825                 830

Thr Ala Thr Asp Ile Asp Ser Leu Cys Lys Ser Ser Leu Ala Phe Ile
        835                 840                 845

Lys Gln Gln Ala Leu Thr Lys Arg Ile Gln Leu Ile Pro Arg Ile Pro
    850                 855                 860

Lys His Leu Pro Lys Ile Met Leu Asp Glu Arg Arg Ile Arg Gln Val
865                 870                 875                 880

Leu Ile Asn Leu Leu Asn Asn Ala Val Lys Phe Thr Leu Glu Gly Gly
                885                 890                 895

Thr Ile Thr Leu Glu Val Ser Gln Val Gln Leu Glu Ser Ser Thr Thr
            900                 905                 910

Asn Pro Thr Pro Leu Lys Tyr Leu Lys Ile Ala Val Ile Asp Thr Gly
        915                 920                 925

Ile Gly Ile Ser Ala Glu Asn Ile Gln Lys Leu Phe Gln Pro Phe Ile
    930                 935                 940

Gln Ile Asp Ser Ala Leu Asn Arg Gln Tyr Asn Gly Thr Gly Leu Gly
945                 950                 955                 960

Leu Ala Leu Val Lys Arg Leu Val Glu Ile His Gly Gly Thr Val Glu
                965                 970                 975
```

Leu Thr Ser Glu Leu Gly Val Gly Ser Cys Phe Ala Ile Asn Leu Pro
980 985 990

Ile Asn Ile Val Ser Pro Ala Ile Glu Glu Gln Thr Glu Gln Asp Leu
995 1000 1005

Ser Gly Gln Ser Gln Ile Gly Gln Ser Gln Thr Glu Gly Leu Ile
1010 1015 1020

Ser Pro Leu Ile Leu Leu Ala Glu Asp Asn Glu Ala Asn Ile Ala
1025 1030 1035

Thr Phe Ser Ser Tyr Leu Glu Ala Met Gly Tyr Arg Ile Leu Ser
1040 1045 1050

Ala Thr Asp Gly Gln Gln Ala Ile Asp Leu Ala Lys Ala Glu His
1055 1060 1065

Pro Asp Leu Ile Leu Met Asp Ile Gln Met Pro Val Met Asp Gly
1070 1075 1080

Leu Glu Ala Ile Lys Gln Ile Arg Leu Asp Pro Asn Leu Ala Asp
1085 1090 1095

Ile Pro Ile Ile Ala Leu Thr Ala Leu Ala Met Glu Gly Asp Arg
1100 1105 1110

Glu Arg Cys Leu Ala Val Gly Ala Asn Glu Tyr Leu Ser Lys Pro
1115 1120 1125

Ile Lys Leu Lys Ala Leu Ala Asp Thr Ile Arg Asn Ile Leu Lys
1130 1135 1140

Asn Arg Asn
1145

<210> SEQ ID NO 39
<211> LENGTH: 1295
<212> TYPE: PRT
<213> ORGANISM: Planktothrix rubescens

<400> SEQUENCE: 39

Val Val Glu Ser Ser Asp Asp Ala Ile Ile Thr Lys Thr Ile Glu Gly
1 5 10 15

Ile Ile Thr Ser Trp Asn Pro Ala Ala Glu Arg Leu Phe Gly Tyr Ser
20 25 30

Glu Ala Glu Ala Ile Gly Gln Pro Ile Ser Met Leu Phe Pro Pro Asp
35 40 45

Arg Leu Asp Glu Glu Pro Gln Ile Phe Ala Arg Leu Met Arg Gly Glu
50 55 60

Arg Val Glu His Phe Glu Thr Val Arg Ile Ser Lys Glu Gly Lys Ser
65 70 75 80

Ile Glu Val Ser Ala Thr Ile Ser Leu Leu Lys Asn Ala Ala Gly Glu
85 90 95

Val Val Gly Val Ser Lys Ile Leu Arg Asp Ile Ser Asp Arg Lys Gln
100 105 110

Ala Glu Lys Ser Leu Gln Glu Ser Gln Gln Phe Ile Gln Thr Val Ile
115 120 125

Asp Thr Val Pro Leu Pro Leu Phe Trp Lys Asp Arg Ser Ser Val Phe
130 135 140

Leu Gly Cys Asn Gln Gln Phe Val Arg Ile Leu Gly Ala Pro Ser Ser
145 150 155 160

Lys Glu Val Val Gly Lys Thr Asp Phe Asp Leu Leu Pro Thr Glu Glu
165 170 175

Glu Ala Ser Ala Phe Gln Ala Asp Asp Arg Gly Val Met Glu Ser Gly

```
            180                 185                 190

Gln Ala Lys Leu Gly Ile Glu Glu Met Leu Thr Phe Ala Asn Gly Glu
        195                 200                 205

Gln Arg Trp Leu Glu Thr His Lys Ala Pro Leu Arg Asp Trp Ser Gly
    210                 215                 220

Asn Val Ile Gly Met Val Gly Thr Phe Gln Asp Val Thr Asp Arg Lys
225                 230                 235                 240

Gln Ala Glu Leu Glu Leu Gln Lys Asn Thr Glu Arg Leu Val Phe Ala
                245                 250                 255

Leu Lys Ser Gly Ala Ile Gly Trp Trp Glu Trp Asp Leu Gln Ser Asp
            260                 265                 270

Ile Ala Val Trp Asp Asp Arg Val Tyr Glu Leu Tyr Gly Val Ser Asn
        275                 280                 285

Gln Thr Asn Pro Gln Pro Thr Tyr Glu Ile Trp Lys Asn Ala Leu His
    290                 295                 300

Pro His Asp Ala Glu Ala Ile Glu Ala Ile Asn Arg Lys Ile Ala Ala
305                 310                 315                 320

Gly Gln Ile Asp Glu Tyr Asp Thr Glu Phe Arg Val Val His Pro Asp
                325                 330                 335

Gly Ser Ile His Phe Leu Lys Ala Tyr Gly Met Leu Lys Arg Asp Ala
            340                 345                 350

Asp Gly Lys Pro Gln Ser Ile Thr Gly Ile Asn Phe Asp Val Ser Asp
        355                 360                 365

Arg Lys Glu Phe Glu Val Gln Leu Gln Gln Thr Thr Asp Arg Leu Ser
    370                 375                 380

Leu Ala Leu Lys Ser Gly Ala Ile Gly Cys Trp Glu Trp Asp Ile Gln
385                 390                 395                 400

Gln Asp Phe Leu Val Trp Asp Asp Arg Met Tyr Glu Leu Tyr Gly Tyr
                405                 410                 415

Leu Lys Glu Asn Tyr Ser His Leu Pro Tyr Glu Ile Trp Ala Asn Ala
            420                 425                 430

Val His Pro Asp Asp Arg Asn Ala Thr Glu Thr Leu Leu Gln Lys Ala
        435                 440                 445

Ile Leu Gly Gln Ala Glu Tyr Asp Tyr Glu Phe Arg Val Ile His Pro
    450                 455                 460

Asp Arg Ser Val His Phe Ile Lys Ala Tyr Gly Lys Val Lys Gln Asp
465                 470                 475                 480

Ser Gln Gly Asn Ala Glu Ser Met Ile Gly Ile Asn Phe Asp Ile Ser
                485                 490                 495

Asp Arg Lys Gln Ala Glu Gln Ile Ile Leu Gln Gln Ala Asn Arg Glu
            500                 505                 510

Thr Leu Leu Arg Ala Ile Thr Gln Arg Ile Arg Gln Ser Leu Asp Leu
        515                 520                 525

Ser Ile Ile Phe Asp Thr Ala Cys Gln Glu Ile Gln Gln Leu Leu Gln
    530                 535                 540

Ser Asp Arg Val Gly Ile Phe Lys Phe Tyr Pro Glu Ser Asn Phe Asp
545                 550                 555                 560

Asp Gly Glu Phe Val Ala Glu Ser Val Val Asp Gly Phe Thr Ser Ala
                565                 570                 575

Met Glu Val His Ile His Asp His Cys Phe Gly Glu Gly Tyr Ala Ala
            580                 585                 590

Ala Tyr Ala Gln Gly Arg Ile Gln Val Leu Asn Asp Ile Asp Asn Ala
        595                 600                 605
```

-continued

```
Gly Leu Met Asp Cys His Arg Asp Val Leu Ala Glu Phe Gln Val Arg
    610                 615                 620

Ala Asn Leu Val Ile Pro Leu Leu Cys Gly Asn Asn Leu Trp Gly Leu
625                 630                 635                 640

Val Cys Ile His Gln Cys Ala His Thr Arg Gln Trp Gln Glu His Glu
                645                 650                 655

Ile Asn Leu Ile Gln Gln Ile Ala Asn Gln Leu Ala Ile Ala Ile Gln
            660                 665                 670

Gln Ala Ser Leu Tyr Glu Gln Leu Gln Glu Glu Leu Leu Ile Arg Gln
        675                 680                 685

Gln Ser Gln Ser Lys Ile Ala Gln Gln Leu Arg Glu Gln Gln Thr Leu
    690                 695                 700

Ala Thr Ile Thr Asn Lys Ile Arg Glu Ser Leu Ser Ile Lys Glu Ile
705                 710                 715                 720

Leu Ala Val Val Thr Gln Gln Val Lys Asp Met Leu Ser Gly Asp Arg
                725                 730                 735

Ala Ile Ile Phe Gln Leu Phe Asp Asn Gly Asn Ser Gln Ile Val Glu
            740                 745                 750

Glu Ser Val His Ser Asn Phe Leu Asn Leu Lys Ala Leu Asn Trp Asp
        755                 760                 765

Asn Glu Val Trp Ser Gln Glu Ile Leu Asp Cys Tyr Trp Gln Gly Lys
    770                 775                 780

Pro Arg Ile Val Pro Asp Val Met Asn Asp Ile Trp Thr Glu Cys Leu
785                 790                 795                 800

Val Glu Tyr Ser Leu Lys Gly Gln Ile Lys Ser Lys Ile Val Ala Pro
                805                 810                 815

Ile Leu Leu Glu Ser His Ile Ser Glu Asn His Arg Trp Val Ala Thr
            820                 825                 830

Asp Gly Tyr Lys Lys Leu Trp Gly Val Leu Val Val His Ala Cys Ala
        835                 840                 845

Glu Gln Arg Glu Trp Gln Asp Ser Glu Ala Gln Leu Leu Gln Gln Ile
    850                 855                 860

Ala Asn Gln Leu Ala Ile Ala Ile Gln Gln Ala Asn Leu Tyr Glu Gln
865                 870                 875                 880

Ser Gln Gln Glu Ile Ala Glu Arg Lys Gln Ala Glu Gln Gln Leu Thr
                885                 890                 895

Glu Thr Asn Gln Gln Leu Ala Arg Ala Thr Arg Leu Lys Asp Glu Phe
            900                 905                 910

Leu Ala Asn Met Ser His Glu Leu Arg Thr Pro Leu Asn Ser Ile Leu
        915                 920                 925

Gly Met Asn Glu Ala Leu Gln Glu Glu Val Phe Gly Gly Ile Asn Glu
    930                 935                 940

Arg Gln Leu Lys Ala Leu Gln Thr Ile Glu Ser Ser Ser Arg His Leu
945                 950                 955                 960

Leu Ala Leu Ile Asn Asp Ile Leu Asp Val Ala Lys Ile Glu Ser Gly
                965                 970                 975

Gln Val Thr Leu Glu Leu Thr Ala Thr Asp Leu Asp Ser Leu Cys Gln
            980                 985                 990

Ser Ser Leu Ala Phe Ile Lys Gln  Gln Ala Leu Ala Lys  Arg Ile Lys
        995                 1000                1005

Leu Ile  Pro Arg Ile Pro Lys  His Leu Pro Glu Ile  Met Leu Asp
    1010                1015                1020
```

```
Glu Arg  Arg Ile Arg Gln Val  Leu Ile Asn Leu Leu  Asn Asn Ala
    1025                 1030                 1035

Val Lys  Phe Thr Leu Glu Gly  Gly Thr Ile Thr Leu  Glu Val Ser
    1040                 1045                 1050

Gln Val  Gln Arg Glu Ser Ser  Thr Thr Asn Pro Thr  Pro Leu Asn
    1055                 1060                 1065

Tyr Leu  Lys Ile Ala Val Ile  Asp Thr Gly Ile Gly  Ile Ser Ala
    1070                 1075                 1080

Glu Asn  Ile Gln Lys Leu Phe  Gln Pro Phe Ile Gln  Ile Asp Ser
    1085                 1090                 1095

Ala Leu  Asn Arg Gln Tyr Asn  Gly Thr Gly Leu Gly  Leu Ala Leu
    1100                 1105                 1110

Val Lys  Arg Leu Val Glu Ile  His Gly Gly Thr Val  Glu Leu Thr
    1115                 1120                 1125

Ser Glu  Leu Gly Val Gly Ser  Cys Phe Ala Ile Asn  Leu Pro Ile
    1130                 1135                 1140

Asn Val  Gly Phe Pro Ala Ile  Glu Glu Gln Thr Glu  Gln Asp Leu
    1145                 1150                 1155

Ser Gly  Gln Ser Gln Ile Gly  Gln Ser Gln Thr Glu  Gly Leu Ile
    1160                 1165                 1170

Ser Pro  Leu Ile Leu Leu Ala  Glu Asp Asn Glu Ala  Asn Ile Val
    1175                 1180                 1185

Thr Phe  Ser Ser Tyr Leu Glu  Ala Lys Gly Tyr Arg  Ile Leu Leu
    1190                 1195                 1200

Ala Asn  Asp Gly Gln Gln Ala  Ile Asp Leu Ala Lys  Ala Glu His
    1205                 1210                 1215

Pro Asp  Leu Ile Leu Met Asp  Ile Gln Met Pro Val  Met Asp Gly
    1220                 1225                 1230

Leu Glu  Ala Ile Lys Gln Ile  Arg Leu Asp Pro Asn  Leu Ala Asp
    1235                 1240                 1245

Ile Pro  Ile Ile Ala Leu Thr  Ala Leu Val Met Glu  Gly Asp His
    1250                 1255                 1260

Glu Arg  Cys Leu Ala Val Gly  Ala Asn Glu Tyr Leu  Ser Lys Pro
    1265                 1270                 1275

Ile Lys  Leu Lys Gln Leu Ala  Thr Ile Ile Gln Gln  Ile Leu Val
    1280                 1285                 1290

Arg Thr
    1295
```

<210> SEQ ID NO 40
<211> LENGTH: 1296
<212> TYPE: PRT
<213> ORGANISM: Planktothrix prolifica

<400> SEQUENCE: 40

```
Val Val Glu Ser Ser Asp Asp Ala Ile Ile Thr Lys Thr Ile Glu Gly
1               5                   10                  15

Ile Ile Thr Ser Trp Asn Pro Ala Ala Glu Arg Leu Phe Gly Tyr Ser
            20                  25                  30

Glu Ala Glu Ala Ile Gly Gln Pro Ile Ser Met Leu Phe Pro Pro Asp
        35                  40                  45

Arg Leu Asp Glu Glu Pro Gln Ile Phe Ala Arg Leu Met Arg Gly Glu
    50                  55                  60

Arg Val Glu His Phe Glu Thr Val Arg Ile Ser Lys Glu Gly Lys Ser
65                  70                  75                  80
```

```
Ile Glu Val Ser Ala Thr Ile Ser Leu Leu Lys Asn Ala Ala Gly Glu
                85                  90                  95

Val Val Gly Val Ser Lys Ile Leu Arg Asp Ile Ser Asp Arg Lys Gln
            100                 105                 110

Ala Glu Lys Ser Leu Gln Glu Ser Gln Gln Phe Ile Gln Thr Val Ile
        115                 120                 125

Asp Thr Val Pro Leu Pro Leu Phe Trp Lys Asp Arg Ser Ser Val Phe
    130                 135                 140

Leu Gly Cys Asn Gln Gln Phe Val Arg Ile Leu Gly Ala Pro Ser Ser
145                 150                 155                 160

Lys Glu Val Val Gly Lys Thr Asp Phe Asp Leu Leu Pro Thr Glu Glu
                165                 170                 175

Glu Ala Ser Ala Phe Gln Ala Asp Asp Arg Gly Val Met Glu Ser Gly
            180                 185                 190

Gln Ala Lys Leu Gly Ile Glu Glu Met Leu Thr Phe Ala Asn Gly Glu
        195                 200                 205

Gln Arg Trp Leu Glu Thr His Lys Ala Pro Leu Arg Asp Trp Ser Gly
    210                 215                 220

Asn Val Ile Gly Met Val Gly Thr Phe Gln Asp Val Thr Asp Arg Lys
225                 230                 235                 240

Gln Ala Glu Leu Glu Leu Gln Lys Asn Thr Glu Arg Leu Val Phe Ala
                245                 250                 255

Leu Lys Ser Gly Ala Ile Gly Trp Trp Glu Trp Asp Leu Gln Ser Asp
            260                 265                 270

Ile Ala Val Trp Asp Asp Arg Val Tyr Glu Leu Tyr Gly Val Ser Asn
        275                 280                 285

Gln Thr Asn Pro Gln Pro Thr Tyr Glu Ile Trp Lys Asn Ala Leu His
    290                 295                 300

Pro His Asp Ala Glu Ala Ile Glu Ala Ile Asn Arg Lys Ile Ala Ala
305                 310                 315                 320

Gly Gln Ile Asp Glu Tyr Asp Thr Glu Phe Arg Val Val His Pro Asp
                325                 330                 335

Gly Ser Ile His Phe Leu Lys Ala Tyr Gly Met Leu Lys Arg Asp Ala
            340                 345                 350

Asp Gly Lys Pro Gln Ser Ile Thr Gly Ile Asn Phe Asp Val Ser Asp
        355                 360                 365

Arg Lys Glu Phe Glu Val Gln Leu Gln Gln Thr Thr Asp Arg Leu Ser
    370                 375                 380

Leu Ala Leu Lys Ser Gly Ala Ile Gly Cys Trp Glu Trp Asp Ile Gln
385                 390                 395                 400

Gln Asp Phe Leu Val Trp Asp Asp Arg Met Tyr Glu Leu Tyr Gly Tyr
                405                 410                 415

Leu Lys Glu Asn Tyr Ser His Leu Pro Tyr Glu Ile Trp Ala Asn Ala
            420                 425                 430

Val His Pro Asp Asp Arg Asn Ala Thr Glu Thr Leu Leu Gln Lys Ala
        435                 440                 445

Ile Leu Gly Gln Ala Glu Tyr Asp Tyr Glu Phe Arg Val Ile His Pro
    450                 455                 460

Asp Arg Ser Val His Phe Ile Lys Ala Tyr Gly Lys Val Lys Gln Asp
465                 470                 475                 480

Ser Gln Gly Asn Ala Glu Ser Met Ile Gly Ile Asn Phe Asp Ile Ser
                485                 490                 495
```

-continued

```
Asp Arg Lys Gln Ala Glu Gln Ile Ile Leu Gln Gln Ala Asn Arg Glu
            500                 505                 510

Thr Leu Leu Arg Ala Ile Thr Gln Arg Ile Arg Gln Ser Leu Asp Leu
        515                 520                 525

Ser Ile Ile Phe Asp Thr Ala Cys Gln Glu Ile Gln Gln Leu Leu Gln
    530                 535                 540

Ser Asp Arg Val Gly Ile Phe Lys Phe Tyr Pro Glu Ser Asn Phe Asp
545                 550                 555                 560

Asp Gly Glu Phe Val Ala Glu Ser Val Val Asp Gly Phe Thr Ser Ala
                565                 570                 575

Met Glu Val His Ile His Asp His Cys Phe Gly Glu Gly Tyr Ala Ala
            580                 585                 590

Ala Tyr Ala Gln Gly Arg Ile Gln Val Leu Asn Asp Ile Asp Asn Ala
        595                 600                 605

Gly Leu Met Asp Cys His Arg Asp Val Leu Ala Glu Phe Gln Val Arg
    610                 615                 620

Ala Asn Leu Val Ile Pro Leu Leu Cys Gly Asn Asn Leu Trp Gly Leu
625                 630                 635                 640

Val Cys Ile His Gln Cys Ala His Thr Arg Gln Trp Gln Glu His Glu
                645                 650                 655

Ile Asn Leu Ile Gln Gln Ile Ala Asn Gln Leu Ala Ile Ala Ile Gln
            660                 665                 670

Gln Ala Ser Leu Tyr Glu Gln Leu Gln Glu Glu Leu Leu Ile Arg Gln
        675                 680                 685

Gln Ser Gln Ser Lys Ile Ala Gln Gln Leu Arg Glu Gln Gln Thr Leu
    690                 695                 700

Ala Thr Ile Thr Asn Lys Ile Arg Glu Ser Leu Ser Ile Lys Glu Ile
705                 710                 715                 720

Leu Ala Val Val Thr Gln Gln Val Lys Asp Met Leu Ser Gly Asp Arg
                725                 730                 735

Ala Ile Ile Phe Gln Leu Phe Asp Asn Gly Asn Ser Gln Ile Val Glu
            740                 745                 750

Glu Ser Val His Ser Asn Phe Leu Asn Leu Lys Ala Leu Asn Trp Asp
        755                 760                 765

Asn Glu Val Trp Ser Gln Glu Ile Leu Asp Cys Tyr Trp Gln Gly Lys
    770                 775                 780

Pro Arg Ile Val Pro Asp Val Met Asn Asp Ile Trp Thr Glu Cys Leu
785                 790                 795                 800

Val Glu Tyr Ser Leu Lys Gly Gln Ile Lys Ser Lys Ile Val Ala Pro
                805                 810                 815

Ile Leu Leu Glu Ser His Ile Ser Glu Asn His Arg Trp Val Ala Thr
            820                 825                 830

Asp Gly Tyr Lys Lys Leu Trp Gly Val Leu Val Val His Ala Cys Ala
        835                 840                 845

Glu Gln Arg Glu Trp Gln Asp Ser Glu Ala Gln Leu Leu Gln Gln Ile
    850                 855                 860

Ala Asn Gln Leu Ala Ile Ala Ile Gln Gln Ala Asn Leu Tyr Glu Gln
865                 870                 875                 880

Ser Gln Gln Glu Ile Ala Glu Arg Lys Gln Ala Glu Gln Gln Leu Thr
                885                 890                 895

Glu Thr Asn Gln Gln Leu Ala Arg Ala Thr Arg Leu Lys Asp Glu Phe
            900                 905                 910

Leu Ala Asn Met Ser His Glu Leu Arg Thr Pro Leu Asn Ser Ile Leu
```

```
        915                 920                 925

Gly Met Asn Glu Ala Leu Gln Glu Glu Val Phe Gly Gly Ile Asn Glu
    930                 935                 940

Arg Gln Leu Lys Ala Leu Gln Thr Ile Glu Ser Ser Ser Arg His Leu
945                 950                 955                 960

Leu Ala Leu Ile Asn Asp Ile Leu Asp Val Ala Lys Ile Glu Ser Gly
                965                 970                 975

Gln Val Thr Leu Glu Leu Thr Ala Thr Asp Ile Asp Ser Leu Cys Lys
            980                 985                 990

Ser Ser Leu Ala Phe Ile Lys Gln  Gln Ala Leu Thr Lys  Arg Ile Gln
        995                 1000                 1005

Leu Ile  Pro Arg Ile Pro Lys  His Leu Pro Lys Ile  Met Leu Asp
    1010                 1015                 1020

Glu Arg  Arg Ile Arg Gln Val  Leu Ile Asn Leu Leu  Asn Asn Ala
    1025                 1030                 1035

Val Lys  Phe Thr Leu Glu Gly  Gly Thr Ile Thr Leu  Glu Val Ser
    1040                 1045                 1050

Gln Val  Gln Leu Glu Ser Ser  Thr Thr Asn Pro Thr  Pro Leu Lys
    1055                 1060                 1065

Tyr Leu  Lys Ile Ala Val Ile  Asp Thr Gly Ile Gly  Ile Ser Ala
    1070                 1075                 1080

Glu Asn  Ile Gln Lys Leu Phe  Gln Pro Phe Ile Gln  Ile Asp Ser
    1085                 1090                 1095

Ala Leu  Asn Arg Gln Tyr Asn  Gly Thr Gly Leu Gly  Leu Ala Leu
    1100                 1105                 1110

Val Lys  Arg Leu Val Glu Ile  His Gly Gly Thr Val  Glu Leu Thr
    1115                 1120                 1125

Ser Glu  Leu Gly Val Gly Ser  Cys Phe Ala Ile Asn  Leu Pro Ile
    1130                 1135                 1140

Asn Ile  Val Ser Pro Ala Ile  Glu Glu Gln Thr Glu  Gln Asp Leu
    1145                 1150                 1155

Ser Gly  Gln Ser Gln Ile Gly  Gln Ser Gln Thr Glu  Gly Leu Ile
    1160                 1165                 1170

Ser Pro  Leu Ile Leu Leu Ala  Glu Asp Asn Glu Ala  Asn Ile Ala
    1175                 1180                 1185

Thr Phe  Ser Ser Tyr Leu Glu  Ala Lys Gly Tyr Arg  Ile Leu Ser
    1190                 1195                 1200

Ala Thr  Asp Gly Gln Gln Ala  Ile Asp Leu Val Lys  Ala Glu His
    1205                 1210                 1215

Pro Asp  Leu Ile Leu Met Asp  Ile Gln Met Pro Val  Met Asp Gly
    1220                 1225                 1230

Leu Glu  Ala Ile Lys Gln Ile  Arg Leu Asp Pro Asn  Leu Ala Asp
    1235                 1240                 1245

Ile Pro  Ile Ile Ala Leu Thr  Ala Leu Ala Met Glu  Gly Asp His
    1250                 1255                 1260

Glu Arg  Cys Leu Ala Val Gly  Ala Asn Glu Tyr Leu  Ser Lys Pro
    1265                 1270                 1275

Ile Lys  Leu Lys Ala Leu Ala  Asp Thr Ile Arg Asn  Ile Leu Lys
    1280                 1285                 1290

Asn Arg  Asn
    1295

<210> SEQ ID NO 41
```

<211> LENGTH: 1331
<212> TYPE: PRT
<213> ORGANISM: Unknown
<220> FEATURE:
<223> OTHER INFORMATION: Calothrix sp. PCC 6303

<400> SEQUENCE: 41

Met Phe Asn Asn Thr Thr Val Leu Thr Thr Ser Glu Leu Lys Ser Ala
1               5                   10                  15

Ile Val Arg Asp Pro Leu Ile Val Lys Pro Asp Met Thr Leu Ile Asp
            20                  25                  30

Ala Ile Ala Gln Met Ser Gly Val Arg Thr Leu Cys Glu Thr Thr Gln
        35                  40                  45

Thr Ile Asp Gly Gln Leu Asp Asn Leu Tyr Leu Glu Ala Arg Ala Ser
    50                  55                  60

Cys Val Leu Ile Val Glu Glu Gly Lys Leu Leu Gly Ile Phe Thr Glu
65                  70                  75                  80

Arg Asp Val Val Arg Leu Ser Ala Gln Gln Tyr Ser Phe Glu Asn Leu
                85                  90                  95

Lys Ile Arg Glu Val Met Thr His Pro Val Ile Ser Leu Arg Glu Ser
            100                 105                 110

Asp Phe Thr Asp Leu Phe Phe Pro Val Asn Leu Leu Gln Gln His His
        115                 120                 125

Ile Arg His Ile Pro Ile Leu Asp Gln Gln Asp Gln Val Val Gly Leu
    130                 135                 140

Leu Thr Asn Glu Ser Leu Arg Gln Ser Ser Arg Pro Val Asp Leu Leu
145                 150                 155                 160

Arg Leu Arg Leu Val Tyr Glu Val Met Thr Lys Glu Val Ile Cys Gly
                165                 170                 175

Ala Pro Asp Ser Ser Met Leu Ala Ile Ala Gln Leu Met Ala Lys His
            180                 185                 190

Arg Val Ser Ser Ile Ile Ile Val Gln Pro Asp Asn Ser Glu Thr Glu
        195                 200                 205

Ser Leu Gln Ile Pro Val Gly Ile Ile Thr Glu Arg Asp Ile Val Gln
    210                 215                 220

Phe Gln Ala Leu Gly Leu Asn Leu Lys Thr Cys Leu Ala Lys Val Val
225                 230                 235                 240

Met Ser Thr Pro Ile Phe Ala Val Lys Pro Asn Asp Ser Leu Trp Leu
                245                 250                 255

Val Gln Gln Leu Met Glu Gln Arg Leu Ile His Arg Leu Ala Val Thr
            260                 265                 270

Gly Glu Gln Gly Glu Leu Leu Gly Ile Val Thr Gln Thr Ser Leu Leu
        275                 280                 285

Lys Ala Leu Asn Pro Leu Glu Ile Tyr Lys Leu Ala Glu Val Leu Glu
    290                 295                 300

Lys Lys Val Val Lys Leu Glu Ala Glu Lys Ile Ala Leu Leu Glu Thr
305                 310                 315                 320

Arg Thr Val Glu Leu Glu Gln Gln Ile Glu Ala Arg Thr Phe Val Ile
                325                 330                 335

Lys Ala Lys Ala Glu Arg Glu Arg Leu Val Leu Glu Ile Ala Thr Gln
            340                 345                 350

Ile Arg Ser Ser Leu Ser Leu Gln Thr Ile Leu Asp Thr Thr Val Ala
        355                 360                 365

Glu Val Arg Gln Leu Leu Gly Cys Asp Arg Val Asn Ile Trp Gln Phe
    370                 375                 380

-continued

```
Asp Ala Asn Trp Gln Thr Ile Thr Val Ala Glu Ser Thr Asp Ser Pro
385                 390                 395                 400

Met Ser Leu Leu Gly Lys Arg Val Ile Asp Thr Cys Phe Gln Asp Asp
                405                 410                 415

Tyr Ala Lys Ile Tyr Arg Gln Gly Arg Ile Cys Val Met Arg Asp Ile
            420                 425                 430

Tyr Lys Ala Lys Ile Ser Asp Tyr His Arg Asp Met Leu Ile Arg Leu
        435                 440                 445

Gln Thr Arg Ala Lys Ile Leu Val Pro Leu Phe Cys Gly Glu Gln Leu
    450                 455                 460

Trp Gly Leu Leu Asn Val Thr Glu Ser Gln His Pro Arg Asn Trp Glu
465                 470                 475                 480

Ala Glu Glu Ile Glu Leu Leu Glu Ala Leu Ser Val Gln Leu Ala Ile
                485                 490                 495

Ala Leu Gln Gln Ala Thr Asn His Gln Lys Leu Gln Glu Glu Leu His
            500                 505                 510

Glu Arg Gln Arg Ile Glu Leu Ile Leu Gln Lys Leu Val Thr Gly Thr
        515                 520                 525

Ala Thr Val Thr Gly Glu Asp Phe Phe Pro Ala Leu Val Arg His Ile
    530                 535                 540

Ala Glu Ala Leu Asn Val Arg Tyr Ala Val Val Thr Glu Ile Val Asp
545                 550                 555                 560

Asn Lys Leu His Thr Leu Gly Phe Trp Ala Asn Gly Ala Leu Lys Pro
                565                 570                 575

Ser Met Ser Tyr Cys Ala Val Asp Asn Ala Cys Glu Tyr Ser Leu Arg
            580                 585                 590

Asp Gly Glu Phe Tyr Cys Gln Ser Lys Val Gln Glu Leu Phe Pro Glu
        595                 600                 605

Asp Leu Asn Leu Ala Ala Met Glu Ala Asp Ser Tyr Val Gly Ile Ala
    610                 615                 620

Leu Lys Asp Asp Leu Gly Asn Ala Ile Gly Asn Leu Cys Ile Leu Asp
625                 630                 635                 640

Thr Gln Pro Leu Thr Glu Ala Gln Arg Ile Glu Ala Ile Ala Ile Leu
                645                 650                 655

Gln Val Phe Ala Ala Arg Ala Thr Ala Glu Leu Gln Arg Gln Thr Ala
            660                 665                 670

Asn Asn Ala Leu His Arg Leu Asn Gln Asn Leu Glu Gln Arg Val Glu
        675                 680                 685

Glu Arg Thr Glu Gln Leu Gln Ala Arg Glu Ala Lys Ile Ala Gln Gln
    690                 695                 700

Leu Arg Leu Gln Lys Thr Leu Gly Val Ile Ile Gln Lys Ile Arg Glu
705                 710                 715                 720

Ser Leu Asp Ile Ser Glu Ile Leu Val Thr Val Thr His Gln Val Lys
                725                 730                 735

Glu Leu Leu Gln Ser Asp Arg Val Ile Val Phe Arg Leu Leu Gly Asp
            740                 745                 750

Gly Arg Ser Gln Ile Val Gln Glu Ala Val Ser Asn Glu Phe Pro Val
        755                 760                 765

Leu Lys Asp Arg Gln Trp Glu Asn Glu Val Trp Ser Gln Glu Ile Leu
    770                 775                 780

Asp Gly Tyr Trp Gln Gly Lys Pro Arg Ile Val Pro Asp Val Met Asn
785                 790                 795                 800
```

-continued

```
Asp Ile Trp Thr Glu Cys Leu Val Glu Tyr Ser Arg Glu Gly Lys Ile
                805                 810                 815

Gln Ser Lys Ile Val Ala Pro Ile Leu Gln Asp Leu Tyr Ser Gly Glu
            820                 825                 830

Arg Asp Leu Thr Val Glu Arg Gly Gly Leu Leu Pro Leu Arg Glu Lys
        835                 840                 845

His Arg Trp Val Ala Pro Tyr Leu Thr Asn Lys Leu Trp Gly Val Leu
    850                 855                 860

Val Val His Ala Cys Glu Glu Lys Arg Val Trp Lys Asp Ser Glu Ala
865                 870                 875                 880

Glu Leu Leu Gln Gln Ile Ala Asn Gln Leu Ala Ile Ala Ile Gln Gln
                885                 890                 895

Ala Ser Leu Phe Glu Gln Leu Gln Gln Glu Leu Ala Glu Arg Gln Gln
            900                 905                 910

Ala Glu Ala Lys Leu Thr Asp Ser Asn Gln Gln Leu Ala Val Ser Asn
        915                 920                 925

Gln Gln Leu Ala Arg Val Thr Arg Leu Lys Asp Glu Phe Leu Ala Asn
    930                 935                 940

Met Ser His Glu Leu Arg Thr Pro Leu Asn Ala Ile Leu Gly Met Thr
945                 950                 955                 960

Glu Gly Leu Gln Glu Gln Val Phe Gly Val Val Asn Glu Gln Gln Leu
                965                 970                 975

Lys Ala Leu Gln Leu Val Glu Arg Ser Gly Leu His Leu Leu Glu Leu
            980                 985                 990

Ile Asn Asp Ile Leu Asp Val Ala  Lys Ile Glu Ala Gly  Gln Ile Glu
        995                 1000                1005

Leu Asp  Tyr Ala Pro Thr Ser  Val Ala His Leu Cys  Glu Ser Ser
    1010                1015                1020

Leu Val  Phe Ile Lys Gln Gln  Ala Leu Gln Lys Arg  Ile Gln Leu
    1025                1030                1035

Glu Ile  Lys Leu Gln Ile Asn  Leu Pro Asp Leu Phe  Val Asp Glu
    1040                1045                1050

Arg Arg  Ile Arg Gln Val Leu  Ile Asn Leu Leu Asn  Asn Ala Val
    1055                1060                1065

Lys Phe  Thr Pro Glu Arg Gly  Cys Ile Thr Leu Glu  Val Thr Gln
    1070                1075                1080

Ile Thr  Leu Asn Ile Ser Asp  Ala Asp Ser Pro Glu  Gln Tyr Phe
    1085                1090                1095

Leu Arg  Phe Ala Val Arg Asp  Thr Gly Ile Gly Ile  Ser Pro Glu
    1100                1105                1110

Asn Ile  Lys Asn Leu Phe Gln  Pro Phe Val Gln Ile  Asp Ser Ala
    1115                1120                1125

Leu Asn  Arg Gln Tyr Thr Gly  Thr Gly Leu Gly Leu  Ala Leu Val
    1130                1135                1140

Lys Arg  Ile Ile Glu Leu His  Gly Gly Leu Val Gly  Leu Thr Ser
    1145                1150                1155

Glu Leu  Gly Val Gly Ser Cys  Phe Thr Ile Asp Leu  Pro Phe Ala
    1160                1165                1170

Pro Asn  His Thr Ser Pro Ser  Val Ile Ala Ala Gly  Asp Gln Pro
    1175                1180                1185

Val Ala  Thr Ser Glu Leu Asp  Pro Ser Ser Pro Asn  Glu Val Val
    1190                1195                1200

Asn Leu  Thr Pro Leu Ile Leu  Leu Ala Glu Asp Asn  Glu Ala Asn
```

```
    1205                1210                1215

Ile Ser  Thr Val Ser Ser Tyr  Leu Lys Ala Lys Gly  Tyr Arg Ile
    1220                1225                1230

Val Leu  Ala Gln Asn Gly Gln  Glu Ala Ile Asp Val  Ala Lys Thr
    1235                1240                1245

His His  Pro Asp Leu Ile Leu  Met Asp Ile Gln Met  Pro Gly Met
    1250                1255                1260

Asp Gly  Leu Glu Ala Met Arg  Gln Ile Arg Leu Asp  Pro Asn Leu
    1265                1270                1275

Ala Glu  Ile Pro Ile Val Ala  Leu Thr Ala Leu Ala  Met Thr Gly
    1280                1285                1290

Asp Arg  Asp Arg Cys Leu Thr  Ala Gly Ala Asn Asp  Tyr Leu Ser
    1295                1300                1305

Lys Pro  Ile Lys Leu Lys Gln  Leu Ala Asn Thr Ile  Gln Gln Leu
    1310                1315                1320

Thr Asn  Ala Val Lys Asp Asn  Lys
    1325                1330
```

<210> SEQ ID NO 42
<211> LENGTH: 1748
<212> TYPE: PRT
<213> ORGANISM: Unknown
<220> FEATURE:
<223> OTHER INFORMATION: Tolypothrix sp. PCC 7601

<400> SEQUENCE: 42

```
Met Phe Lys His Thr Thr Ala Leu Thr Ser Ser Glu Leu Lys Ser Ala
1               5                   10                  15

Ile Val Arg Asn Pro Leu Ile Val Gly Leu Asp Thr Leu Val Ile Asp
            20                  25                  30

Ala Ile Ala Leu Met Ser Gly Val Arg Ala Val Cys Asp Ala Asn Lys
        35                  40                  45

Leu Asp Glu Leu Asp Ile Asp Ala Arg Ser Ser Cys Val Leu Val Val
    50                  55                  60

Asp Asn His Ser Leu Leu Gly Ile Phe Thr Glu Lys Asp Val Val Arg
65                  70                  75                  80

Leu Cys Ala Gln Gln Arg Pro Leu Glu Asn Leu Ala Ile Arg Glu Val
                85                  90                  95

Met Ile His Pro Val Ile Ala Leu His Glu Ser Asp Leu Thr Asp Val
            100                 105                 110

Phe Phe Ala Val Asn Leu Leu Gln Gln Tyr His Ile Arg His Leu Pro
        115                 120                 125

Ile Leu Asp Glu Gln Asp Leu Val Val Gly Leu Leu Thr Asn Glu Thr
    130                 135                 140

Leu Arg Gln Ser Ser Arg Ala Ile Asn Leu Leu Arg Leu Arg Leu Ala
145                 150                 155                 160

Phe Glu Val Met Ser Arg Glu Val Ile Cys Ala Ala Pro Asp Ser Ser
                165                 170                 175

Ile Leu Ala Ile Ala Gln Leu Met Thr Ala His Arg Val Ser Ser Val
            180                 185                 190

Met Ile Val Gln Pro Gly Gly Ser Glu Ala Ala Pro Val Lys Ile Pro
        195                 200                 205

Val Gly Ile Leu Thr Glu Arg Asp Ile Val Gln Phe His Ala Leu Gly
    210                 215                 220

Leu Asn Leu Glu Thr Cys Cys Ala His Met Val Met Ser Thr Pro Ile
```

-continued

```
225                 230                 235                 240

Phe Ala Val Lys Pro Glu Asp Ser Leu Leu Val Val Gln Gln Ile Met
                245                 250                 255

Glu Gln Arg Leu Ile Arg Arg Leu Ala Val Thr Gly Glu Gln Gly Glu
            260                 265                 270

Leu Leu Gly Ile Leu Thr Gln Ser Ser Leu Leu Gln Ala Leu Asn Pro
        275                 280                 285

Leu Glu Leu Tyr Lys Leu Ala Glu Val Leu Glu Lys Lys Val Val Gln
    290                 295                 300

Leu Glu Thr Glu Lys Val Gln Leu Leu Glu Ala Arg Thr Ala Glu Leu
305                 310                 315                 320

Glu Gln Gln Val Glu Ala Arg Thr Thr Ala Leu Lys Thr Lys Ala Glu
                325                 330                 335

Gln Ala Gln Leu Val Ser Asp Ile Ala Met Gln Ile Arg Ser Ser Leu
            340                 345                 350

Ser Leu Gln Thr Ile Leu Glu Thr Thr Val Gln Gln Val Arg Gln Phe
        355                 360                 365

Leu Gly Cys Asp Arg Val Ile Ile Leu Arg Phe Glu Glu Asp Gly Pro
    370                 375                 380

Ala Ala Val Val Ala Glu Ser Thr Asn Ser Ser Leu Ser Leu Met Gly
385                 390                 395                 400

Arg Trp Ile Lys Asp Gly Cys Phe Gln Lys Asn Tyr Arg Glu Asn Tyr
                405                 410                 415

Cys Gln Gly Gln Ile Arg Val Val Lys Asp Ile Tyr Thr Thr Gln Met
            420                 425                 430

Thr Asn Cys His Arg Gln Met Leu Ile Ser Leu Gln Ile Arg Ala Lys
        435                 440                 445

Ile Leu Ile Pro Leu Leu Cys Asn Gly Glu Leu Trp Gly Leu Leu Asn
    450                 455                 460

Val Ser Glu Ser Asp Lys Ala Arg Glu Trp Gln Gln Ser Glu Val Glu
465                 470                 475                 480

Leu Leu Gln Ala Leu Ser Val His Leu Glu Ile Ala Leu Gln Gln Ala
                485                 490                 495

Thr Ile His Gln Gln Leu Gln Glu Gln Leu Arg Asp Arg Gln Arg Ala
            500                 505                 510

Glu Met Thr Leu Gln Lys Leu Val Thr Gly Thr Ala Ala Val Thr Gly
        515                 520                 525

Asp Asp Phe Phe Pro Ala Leu Val Ser His Ile Ala Glu Ala Leu Asn
    530                 535                 540

Val Cys Cys Ala Leu Val Asn Glu Leu Val Gly Asp Lys Leu Tyr Ser
545                 550                 555                 560

Leu Gly Phe Trp Glu Asn Gly Ala Leu Gln Pro Ala Ile Ser Tyr His
                565                 570                 575

Ile Ala Gln Thr Pro Cys Glu His Ser Leu Arg Asp Gly Glu Phe Tyr
            580                 585                 590

Cys Gln Ser Gln Leu Gln Thr Ile Phe Pro Asp Asn Leu Ala Leu Gln
        595                 600                 605

Thr Met Gln Ala Asp Ser Tyr Leu Gly Ile Ala Leu Lys Asp Asn Leu
    610                 615                 620

Gly Asn Thr Ile Gly Asn Leu Cys Ile Leu Asp Arg Gln Pro Leu Ser
625                 630                 635                 640

Gln Thr Lys Tyr Thr Glu Ala Ile Ala Ile Leu Gln Val Phe Ala Ala
                645                 650                 655
```

Arg Ala Ala Ala Glu Leu Gln Arg Ile Ala Ala Asn Asp Ala Leu His
660 665 670

Arg Leu Asn Gln Asp Leu Glu Ala Arg Val Glu Gln Arg Thr Glu Glu
675 680 685

Leu Gln Ala Arg Glu Val Glu Leu His Lys Thr Ser Glu Arg Leu Ala
690 695 700

Leu Ser Leu Lys Ser Gly Gly Ile Gly Cys Trp Glu Trp Asp Ile Leu
705 710 715 720

Gln Asn Thr Ile Leu Trp Asp Glu Arg Met Ser Glu Leu Tyr Gly Val
725 730 735

Thr Pro Gln Ser Asp Ser Cys Ile Val Tyr Asp Thr Trp Thr Lys Lys
740 745 750

Leu His Pro Asp Asp Arg Thr Gln Thr Glu Thr Leu Leu Gln Gln Ala
755 760 765

Val Leu Gly Gln Ala Glu Tyr Asn Thr Glu Phe Arg Val Val His Pro
770 775 780

Asp Gly Ser Ile Tyr Phe Ile Lys Ala Tyr Gly Val Val Val Arg Asp
785 790 795 800

Glu Gln Gly Ser Pro Gln Lys Met Ile Gly Val His Phe Asp Ile Ser
805 810 815

Asp Arg Lys Arg Ala Glu Ile Ala Leu Gln Ser Ser Glu Leu Arg Phe
820 825 830

Arg Arg Ile Phe Asp Ser Asn Val Val Gly Met Leu Phe Ala Asp Phe
835 840 845

Lys Gly Asp Ile Thr Asp Ala Asn Asp Arg Phe Leu Gln Met Val Gly
850 855 860

Tyr Thr Arg Glu Glu Leu Asn Ala Gly Ala Leu Ser Trp Lys Ala Ile
865 870 875 880

Thr Pro Ser Glu Tyr Val Phe Ala Asp Val Gly Ala Leu Lys His Leu
885 890 895

Ser Gln Tyr Gly Ala Met Asn Pro Trp Glu Lys Glu Tyr Tyr Arg Lys
900 905 910

Asp Gly Ser Lys Ile Pro Val Leu Leu Gly Val Ala Met Leu Pro Gly
915 920 925

Ser Asp Tyr Gln Thr Ile Cys Val Val Val Asp Ile Ser Glu Gln Lys
930 935 940

Ala Ala Leu Gln Glu Arg Gln Gln Ala Glu Met Gln Leu Gln Gln Gln
945 950 955 960

Ala Arg His Lys Gln Leu Leu Trp Asn Ile Thr Gln Thr Ile Arg Gln
965 970 975

Ser Leu Asp Ile Glu Val Ile Ile Asn Ala Ala Val Thr Glu Ile Arg
980 985 990

Gln Val Leu Gly Val Asp Arg Val Ala Leu Tyr Arg Phe Arg Ala Asp
995 1000 1005

Trp Ser Gly Glu Phe Val Ala Glu Ser Val Ala Ala Asn Trp Val
1010 1015 1020

Lys Leu Val Gly Ser Gln Val Lys Lys Val Trp Glu Asp Thr Tyr
1025 1030 1035

Leu Gln Glu Thr Gln Gly Gly Arg Phe Gln Asn Tyr Glu Thr Leu
1040 1045 1050

Val Val Ala Asp Ile Asp Gln Ala Gly Leu Gln Pro Cys His Ile
1055 1060 1065

```
Glu Leu  Leu Gln Gln Phe Gln  Ala Lys Ala Tyr Val  Ile Thr Pro
    1070                 1075                 1080

Ile Phe  Val Asn Glu Ser Leu  Trp Gly Leu Phe Ala  Met Tyr His
    1085                 1090                 1095

Asn His  Arg Pro His Ser Trp  Thr Thr Trp Glu Ile  Glu Leu Leu
    1100                 1105                 1110

Arg Gln  Ile Ala Asn Gln Leu  Ala Ile Ala Ile Gln  Gln Ala Ser
    1115                 1120                 1125

Leu Tyr  Glu Lys Asn Gln Ser  Glu Leu Leu Val Arg  Gln Gln Ala
    1130                 1135                 1140

Glu Ala  Arg Ile Ala Leu Gln  Leu Arg Arg Gln Gln  Thr Leu Gly
    1145                 1150                 1155

Ala Ile  Ile Glu Gln Ile Arg  Lys Ser Leu Asp Leu  Asn Glu Ile
    1160                 1165                 1170

Leu Ala  Thr Val Thr Gln Gln  Val Lys Asp Leu Met  His Cys Asp
    1175                 1180                 1185

Arg Val  Ile Val Phe Arg Leu  Phe Ala Asp Gly Arg  Ser Lys Ile
    1190                 1195                 1200

Ala Glu  Glu Ala Val Ser Ser  Glu Phe Val Ser Leu  Lys Asn Arg
    1205                 1210                 1215

His Trp  Gly Asn Glu Ile Trp  Ser Gln Glu Ile Leu  Asp Phe Tyr
    1220                 1225                 1230

Trp Gln  Gly Lys Pro Arg Ile  Val Pro Asp Val Met  Asn Asp Leu
    1235                 1240                 1245

Trp Thr  His Cys Leu Val Glu  Tyr Ser Gln Glu Gly  Gln Ile Gln
    1250                 1255                 1260

Ser Lys  Ile Val Ala Pro Ile  Leu Gln Glu Val Arg  Asp Gln Asn
    1265                 1270                 1275

His Arg  Trp Val Ser Pro Trp  Ala Thr Asn Lys Leu  Trp Gly Ile
    1280                 1285                 1290

Leu Val  Val His Ala Cys Gln  Glu Arg Arg Val Trp  Lys Asn Ser
    1295                 1300                 1305

Glu Ala  Gln Ile Leu Gln Gln  Ile Ala Asn Gln Leu  Ala Ile Ala
    1310                 1315                 1320

Ile Gln  Gln Ala Ser Leu Phe  Glu Gln Leu Gln Gln  Glu Leu Ala
    1325                 1330                 1335

Glu Arg  Gln Gln Ala Glu Ala  Lys Leu Thr Glu Ile  Asn Gln Gln
    1340                 1345                 1350

Leu Ala  Phe Ser Asn Glu Glu  Leu Ala Arg Ala Thr  Arg Leu Lys
    1355                 1360                 1365

Asp Glu  Phe Leu Ala Asn Met  Ser His Glu Leu Arg  Thr Pro Leu
    1370                 1375                 1380

Asn Ala  Ile Leu Gly Met Thr  Glu Gly Leu Gln Asp  Glu Val Phe
    1385                 1390                 1395

Gly Ser  Ile Asn Gln Gln Gln  Leu Lys Ala Leu Asp  Thr Ile Glu
    1400                 1405                 1410

Arg Ser  Gly Ser His Leu Leu  Glu Leu Ile Asn Asp  Ile Leu Asp
    1415                 1420                 1425

Val Ala  Lys Ile Glu Ala Gly  Gln Ile Lys Leu Asp  Tyr Thr Ser
    1430                 1435                 1440

Ile Ser  Val Ala Asn Leu Cys  Gln Ser Ser Leu Ala  Phe Ile Lys
    1445                 1450                 1455

Gln Gln  Ala Leu Gln Lys Arg  Ile Gln Leu Glu Thr  Lys Ile Pro
```

```
    1460                1465                1470

Gln Asn  Leu Pro His Leu Leu  Val Asp Glu Arg Arg  Ile Arg Gln
    1475                1480                1485

Val Leu  Ile Asn Leu Leu Asn  Asn Ala Val Lys Phe  Thr Pro Glu
    1490                1495                1500

Gly Gly  Arg Ile Thr Leu Glu  Val Asn Gln Leu Ser  Pro Asp Thr
    1505                1510                1515

Thr Asn  Asn Ser Leu Arg Gln  His Phe Leu Gln Ile  Ala Val Lys
    1520                1525                1530

Asp Thr  Gly Ile Gly Ile Ala  Pro Glu Asn Ile Asn  Lys Leu Phe
    1535                1540                1545

Lys Pro  Phe Ile Gln Ile Asp  Ser Ala Leu Asn Arg  Gln Tyr Ala
    1550                1555                1560

Gly Thr  Gly Leu Gly Leu Ala  Leu Val Lys Arg Ile  Val Glu Leu
    1565                1570                1575

His Gly  Gly Arg Val Gly Leu  Ser Ser Glu Leu Gly  Val Gly Ser
    1580                1585                1590

Cys Phe  Thr Ile Glu Leu Pro  Tyr Thr Pro Val Phe  Pro Val Val
    1595                1600                1605

Glu Asp  Thr Gln Pro Asp Val  Thr Pro Glu Phe Val  Ser Ser Asn
    1610                1615                1620

Leu Asp  His Ala Gly Pro Leu  Ile Leu Leu Ala Glu  Asp Asn Glu
    1625                1630                1635

Ala Asn  Ile Ser Thr Val Ser  Ser Tyr Leu Lys Ala  Lys Gly Tyr
    1640                1645                1650

Arg Ile  Leu Leu Ala Asn Asn  Gly Lys Glu Ala Ile  Glu Leu Ala
    1655                1660                1665

Thr Thr  Gln Tyr Pro Asn Leu  Ile Leu Met Asp Ile  Gln Met Pro
    1670                1675                1680

Leu Met  Asp Gly Leu Glu Ala  Ile Lys Leu Ile Arg  Leu Asp Pro
    1685                1690                1695

Asn Leu  Val Asn Thr Pro Ile  Val Ala Leu Thr Ala  Leu Ala Met
    1700                1705                1710

Asn Gly  Asp Arg Asp Arg Cys  Ile Ala Ala Gly Ala  Asn Asp Tyr
    1715                1720                1725

Leu Ser  Lys Pro Val Lys Leu  Lys Gln Leu Ala Thr  Thr Ile Gln
    1730                1735                1740

Gln Leu  Leu Ser Thr
    1745
```

<210> SEQ ID NO 43
<211> LENGTH: 2745
<212> TYPE: PRT
<213> ORGANISM: Unknown
<220> FEATURE:
<223> OTHER INFORMATION: Oscillatoria nigro-viridis PCC 7112

<400> SEQUENCE: 43

```
Met Phe Met Arg Thr Thr Ala Leu Thr Pro Ile Glu Leu Arg Thr Ala
1               5                   10                  15

Ile Val Arg Glu Pro Leu Val Val Ser Pro Asp Thr Thr Val Met Asp
            20                  25                  30

Ala Ile Ala Gln Met Ser Gly Val Arg Ser Leu Cys Asn Thr Pro Arg
        35                  40                  45

Thr Ala Asp Gly Gln Leu Asp Asp Leu His Leu Glu Ala Arg Ser Ser
```

```
    50                  55                  60

Cys Val Leu Val Val Glu Asn Glu Gln Leu Val Gly Val Leu Thr Glu
65                  70                  75                  80

Arg Asp Val Val Arg Leu Ser Ala Gln Gln Arg Cys Leu Glu Asn Val
                85                  90                  95

Ala Met Arg Glu Val Met Ala His Pro Val Val Thr Leu Arg Glu Ser
            100                 105                 110

Ala Phe Thr Asp Leu Phe Leu Ala Ile Asn Leu Leu Arg Glu His His
        115                 120                 125

Ile Arg His Leu Pro Ile Leu Asp Glu Leu Asp Arg Leu Val Gly Leu
    130                 135                 140

Val Thr His Glu Ser Leu Arg Gln Thr Ser Arg Pro Ile Asp Leu Leu
145                 150                 155                 160

Arg Leu Arg Thr Val Ala Glu Val Met Thr Arg Glu Val Ile Cys Ala
                165                 170                 175

Ala Pro Asp Ser Ser Leu Leu Thr Ile Val Gln Leu Met Ala Glu His
            180                 185                 190

Arg Val Ser Ser Val Met Ile Val His Pro Gly Gly Ile Ser Thr Glu
        195                 200                 205

Pro Leu Gln Ile Pro Val Gly Ile Leu Thr Glu Arg Asp Ile Val Gln
    210                 215                 220

Phe Gln Ala Leu Gly Leu Asn Leu Glu Thr Cys Leu Ala Gln Ala Val
225                 230                 235                 240

Met Ser Thr Pro Ile Phe Ala Val Arg Ser Asp Asp Ser Leu Trp Thr
                245                 250                 255

Val Gln Gln Ile Val Glu Gln Arg Ser Ile Arg Arg Leu Ala Val Thr
            260                 265                 270

Gly Glu Leu Gly Glu Leu Leu Gly Ile Val Thr Gln Thr Ser Leu Leu
        275                 280                 285

Gln Ala Leu Ser Pro Leu Glu Leu Tyr Lys Leu Val Gln Lys Trp Glu
    290                 295                 300

Glu Lys Val Val Arg Leu Glu Ala Glu Lys Val Ala Leu Leu Ala Asn
305                 310                 315                 320

Arg Asn Val Glu Leu Glu Gln Gln Val Ala Ala Arg Thr Ala Ala Leu
                325                 330                 335

Lys Ala Lys Ala Asp Arg Glu Gln Leu Leu Asn Thr Ile Ala Glu Gln
            340                 345                 350

Ile Arg Ser Ser Leu Asn Leu Ser Asp Ile Leu His Thr Thr Val Gln
        355                 360                 365

Glu Ile His Ser Leu Leu Gly Cys Asp Arg Val Ile Ile Tyr Gln Phe
    370                 375                 380

Gln Ser Glu Leu Ser Gly Thr Val Ile Ala Glu Ala Ile Thr Asp Thr
385                 390                 395                 400

Gly Arg Ser Val Leu Tyr Arg Glu Ala Arg Asp Pro Cys Met Ser Pro
                405                 410                 415

Glu Trp Leu Glu Pro Tyr Arg Gln Gly Arg Ile Arg Val Ile Asn Asp
            420                 425                 430

Ile Tyr Asp Ala Glu Met Thr Gln Cys His Gln Glu Met Leu Val Gly
        435                 440                 445

Phe Asp Ile Arg Ala Lys Leu Met Val Pro Ile Val Ile Glu Gln Gln
    450                 455                 460

Leu Arg Gly Leu Thr Ile Ala Ser Tyr Arg Ala Ala Pro His Ser Trp
465                 470                 475                 480
```

```
Thr Thr Asp Glu Ile Glu Leu Leu Arg Gln Val Ser Leu Gln Val Ala
                485                 490                 495

Ile Ala Leu Gly Gln Ala Ala Ile Gln Gln Lys Leu Gln Asn Glu Leu
            500                 505                 510

Val Lys Arg Gln Arg Ile Glu Ala Thr Leu Ile Glu Ser Glu Gln Arg
        515                 520                 525

Tyr Ala Ala Leu Ala Ala Ala Ala Pro Val Gly Ile Phe Arg Thr Asp
    530                 535                 540

Ala Glu Gly Leu Cys Thr Tyr Val Asn Asp Arg Tyr Phe Gln Ile Gly
545                 550                 555                 560

Gly Leu Arg Pro Gly Gly Thr Ile Gly Gln Gly Trp Gln Gln Gly Ile
                565                 570                 575

His Pro Asp Asp Arg Asp Leu Val Ile Ala Gln Trp Glu Gln Phe Ile
            580                 585                 590

Gln Gly Asn Asp Ser Phe Glu Leu Glu Tyr Arg Phe Gln Arg Pro Asp
        595                 600                 605

Gly Thr Val Thr Trp Val Tyr Gly Gln Cys Val Ala Glu Leu Asp Ala
    610                 615                 620

Asn Gly Asn Arg Ser Gly Tyr Ile Gly Thr Ile Thr Asp Ile Ser Asp
625                 630                 635                 640

Arg Lys Arg Thr Glu Val Arg Leu Gln Glu Ser Glu Glu Arg Tyr Ala
                645                 650                 655

Ser Leu Val Ala Ala Val Pro Val Gly Ile Phe Arg Ala Asp Ala Leu
            660                 665                 670

Gly Lys Cys Ile Tyr Val Asn His Trp Trp Cys Gln Ile Ser Gly Leu
        675                 680                 685

Thr Pro Lys Thr Ala Val Gly Glu Gly Trp Lys Gln Gly Leu His Pro
    690                 695                 700

Asp Asp Arg Asp Trp Val Met Ala Glu Cys Glu Gln Ser Leu Gln Arg
705                 710                 715                 720

Asn Arg Ser Phe Gln Leu Glu Tyr Arg Leu Gln Arg Pro Asp Gly Ala
                725                 730                 735

Val Ala Trp Val Tyr Gly Gln Ser Val Pro Glu Leu Asp Ala Asp Gly
            740                 745                 750

Gln Val Val Gly Tyr Val Gly Thr Thr Thr Asp Ile Ser Asp Arg Lys
        755                 760                 765

Gln Ala Glu Gln Lys Leu Gln Gln Leu Asn Gln Gln Leu Glu Thr Lys
    770                 775                 780

Val Ala Glu Arg Thr Gln Glu Leu Trp Gln Val Asn Ser Leu Gln Arg
785                 790                 795                 800

Ala Ile Leu Asp Cys Ala Asp Tyr Ser Ile Ile Ser Thr Asp Pro Thr
                805                 810                 815

Gly Ile Ile Gln Thr Phe Asn Ala Ala Ala Glu Arg Met Leu Gly Tyr
            820                 825                 830

Ser Ala Arg Glu Ile Ile Gly Lys Ala Thr Pro Leu Leu Ile His Asp
        835                 840                 845

Ala Asn Glu Val Ile Asp Arg Ala Ser Ser Leu Ser Ala Glu Leu Gly
    850                 855                 860

Gln Asn Ile Pro Pro Thr Phe Glu Val Phe Val Ala Lys Ala Arg Gln
865                 870                 875                 880

Ala Pro Val Ser Glu Glu Glu Trp Ser Tyr Ile Arg Lys Asp Gly Ser
                885                 890                 895
```

-continued

```
Arg Phe Pro Val Ser Leu Ser Ile Ser Thr Leu Lys Asp Val Asn Gln
            900                 905                 910

Gln Ile Ile Gly Phe Leu Gly Ile Ala Lys Asp Ile Ser Asp Arg Lys
        915                 920                 925

Arg Ala Glu Leu Glu Leu Gln Lys Leu Ser Asp Arg Leu Ala Leu Ser
    930                 935                 940

Leu Lys Ser Gly Ala Ile Gly Cys Trp Asp Phe Asp Leu Val Gln Asn
945                 950                 955                 960

Thr Ile Phe Trp Asp Glu Arg Met Tyr Glu Leu Tyr Gly Val Thr Lys
                965                 970                 975

Gln Ser Asp Ser Pro Leu Pro Tyr Asp Ile Trp Ala Asn Arg Leu His
            980                 985                 990

Pro Glu Asp Arg Thr Ala Thr Glu  Thr Leu Leu Gln Gln  Ala Val Leu
        995                 1000                1005

Gly Gln  Ala Asn Phe Glu Thr  Glu Phe Arg Val Leu  His Pro Asp
    1010                 1015                1020

Gly Ser  Leu His Phe Ile Lys  Thr Phe Gly Val Leu  Val Arg Asp
    1025                 1030                1035

Ala Arg  Gly Asn Pro Gln Ser  Met Ile Gly Val Asn  Leu Asp Ile
    1040                 1045                1050

Ser Arg  Arg Lys Gln Ala Glu  Leu Gln Arg Gln Gln  Leu Ile Gln
    1055                 1060                1065

Glu Leu  Ser Ala Phe Lys Gln  Ala Leu Asp Gln Ser  Ala Ile Val
    1070                 1075                1080

Val Ile  Thr Asp Arg Glu Gly  Val Ile Ser Tyr Val  Asn Asp Arg
    1085                 1090                1095

Phe Cys  Ala Val Ser Gly Tyr  Ser Arg Asp Arg Leu  Ile Gly Gln
    1100                 1105                1110

Thr His  Arg Ile Val Asn Ser  Gly Tyr His Pro Pro  Ala Phe Phe
    1115                 1120                1125

Gln Asp  Leu Trp Asp Thr Ile  Asn Ser Ser Gln Ile  Trp Arg Gly
    1130                 1135                1140

Glu Ile  Cys Asn Arg Ala Lys  Asn Gly Ser Leu Tyr  Trp Val Ala
    1145                 1150                1155

Thr Thr  Ile Val Pro Phe Leu  Asp Glu Gln Gly Arg  Pro Phe Gln
    1160                 1165                1170

Tyr Leu  Ala Ile Arg Phe Asp  Ile Thr Asp Arg Lys  Leu Ala Glu
    1175                 1180                1185

Ala Thr  Leu Gln Gln Glu Asn  Thr Phe Arg Gln Gln  Ile Val Glu
    1190                 1195                1200

Asn Met  Val Gln Gly Leu Cys  Val Phe His Gln Phe  Glu Glu Phe
    1205                 1210                1215

Pro Phe  Val Ser Phe Thr Val  Trp Asn Gln Gln Met  Gln Thr Ile
    1220                 1225                1230

Thr Gly  Tyr Thr Leu Glu Glu  Ile Asn Arg Leu Gly  Trp Tyr Gln
    1235                 1240                1245

Thr Leu  Tyr Pro Asn Leu Glu  Asp Arg Glu Gln Ala  Ile Ala Asn
    1250                 1255                1260

Cys Arg  Gln Met Gln Pro Ile  Ala Val Glu Arg Glu  Ile Gln Arg
    1265                 1270                1275

Gln Asp  Gly Gln Arg Arg Thr  Ile Ser Ile Ser Thr  Ser Val Leu
    1280                 1285                1290

Ser Gly  Asp Asp Gly His Leu  Tyr Ser Leu Ala Leu  Ile Gln Asp
```

```
    1295                1300                1305

Ile Thr  Asp Arg Gln Gln Thr  Glu Arg Glu Asn Arg  Leu Leu Lys
    1310                1315                1320

Glu Arg  Leu Glu Phe Leu Leu  Ala Ser Ser Pro Ala  Met Ile Tyr
    1325                1330                1335

Ser Cys  Lys Pro Tyr Gly Asp  Tyr Asp Ala Thr Phe  Met Ser Lys
    1340                1345                1350

Asn Ile  Glu Ala Ile Leu Gly  Tyr Lys Ala Glu Glu  Phe Leu Ser
    1355                1360                1365

Glu Ser  Gly Phe Trp Ala Asn  His Ile His Pro Glu  Asp Ala Pro
    1370                1375                1380

Arg Val  Phe Ala His Ile Ser  Asp Leu Phe Glu His  Asn Thr His
    1385                1390                1395

Gln His  Glu Tyr Arg Phe Leu  His Arg Asp Gly His  Tyr Val Trp
    1400                1405                1410

Leu Arg  Asp Glu Leu Arg Leu  Leu Arg Asp Glu Ala  Gly Lys Pro
    1415                1420                1425

Ile Glu  Ile Val Gly Tyr Phe  Ala Asp Ile Ser Asp  Val Lys Gln
    1430                1435                1440

Thr Glu  Glu Thr Leu Lys Ile  Gln Leu Ala Ala Ile  Glu Ala Ala
    1445                1450                1455

Ile Asp  Gly Ile Ala Ile Ile  Gln Gly Asp Thr Tyr  Leu Tyr Leu
    1460                1465                1470

Asn Gln  Ala His Leu Glu Leu  Phe Gly Tyr Glu Arg  Pro Glu Glu
    1475                1480                1485

Val Ser  Gly Lys Ser Trp Lys  Leu Leu Tyr Ser Gln  Gln Glu Leu
    1490                1495                1500

Glu Arg  Phe Glu Arg Glu Val  Phe Pro Val Leu Gly  Arg Asp Arg
    1505                1510                1515

Ala Trp  Gln Gly Glu Ala Ile  Ala Leu Arg Lys Asp  Gly Ser Thr
    1520                1525                1530

Phe Ala  Glu Gly Leu Ser Leu  Thr Leu Thr Asp Asp  Gly Leu Leu
    1535                1540                1545

Ile Cys  Val Cys Arg Asp Ile  Ser Asp Arg Lys Gln  Ile Glu Ala
    1550                1555                1560

Glu Leu  Ala Glu Ser Glu Ala  Lys Phe Arg Arg Leu  Val Glu Gly
    1565                1570                1575

Val Asn  Asp Leu Ile Trp Ser  Cys Glu Pro Asp Gly  Ile Leu Thr
    1580                1585                1590

Tyr Val  Ser Pro Gln Phe Lys  Thr Met Phe Gly Trp  Glu Glu Gly
    1595                1600                1605

Ala Trp  Ile Gly Lys Ser Phe  Ile Tyr Leu Val His  Pro Asp Asp
    1610                1615                1620

Arg Pro  Leu Val Val Thr Gly  Tyr Arg Lys Asn Ile  Lys Phe Gly
    1625                1630                1635

Lys Lys  Ser Ser Asp Tyr Glu  Phe Arg His Arg His  Arg Asp Gly
    1640                1645                1650

Asn Tyr  Val Trp Val Arg Ser  Ser Ala Thr Pro Val  Met Asn Ala
    1655                1660                1665

Glu Gly  Glu Leu Ile Ser Ile  Gln Gly Ile Leu Ser  Asp Ile Ser
    1670                1675                1680

Asp Arg  Lys Gln Ala Glu Leu  Ala Arg Glu Ser Ser  Glu Ile Arg
    1685                1690                1695
```

Phe Arg Arg Val Phe Glu Ser Ser Val Ser Gly Met Met Phe Ala
1700 1705 1710

Asp Phe Gln Gly Asn Ile Thr Asp Ala Asn Asp Arg Phe Leu Gln
1715 1720 1725

Met Val Gly Tyr Thr Arg Glu Glu Leu Asn Ala Gly Met Ile His
1730 1735 1740

Trp Asp Ala Met Thr Pro Pro Glu Tyr Leu Pro Ala Asp Phe Leu
1745 1750 1755

Ala Phe Glu Arg Leu Arg Gln Asp Gly Glu Ile Glu Ser Leu Glu
1760 1765 1770

Lys Glu Tyr Tyr Arg Lys Asp Gly Ser Arg Ile Ser Val Leu Leu
1775 1780 1785

Gly Ala Ala Leu Leu Pro Gly Ser Glu Asp Gln Thr Ile Cys Val
1790 1795 1800

Leu Val Asp Ile Ser Asp Arg Lys Gln Ala Gln Lys Ala Leu Gln
1805 1810 1815

Glu Ser Gln Gln Phe Leu Gln Thr Val Leu Asp Thr Ile Pro Leu
1820 1825 1830

Ser Val Phe Trp Lys Asn Arg Glu Ser Val Phe Leu Gly Cys Asn
1835 1840 1845

Gln Gln Phe Ala Thr Thr Leu Gly Leu Gln Ser Thr Ser Glu Ser
1850 1855 1860

Ile Gly Lys Arg Asp Leu Asp Ile Cys Gln Glu Glu Val Glu Ala
1865 1870 1875

Asn Glu Tyr Cys Ala Met Asp Arg Arg Leu Met Glu Thr Gly Glu
1880 1885 1890

Ala Ile Leu Gly Ile Glu Glu Thr Leu Thr Leu Pro Asn Gly Lys
1895 1900 1905

Pro Ile Phe Ile Glu Thr His Lys Ala Pro Leu Arg Asp Cys Ser
1910 1915 1920

Gly Asn Val Ile Gly Leu Val Gly Thr Phe Gln Asp Ile Thr Asp
1925 1930 1935

Arg Lys Glu Ala Glu Leu Arg Leu Gln Gln Gln Ala Lys Gln Glu
1940 1945 1950

Arg Leu Leu Gly Ala Ile Thr Lys Arg Met Arg Ser Ser Leu His
1955 1960 1965

Leu Asp Glu Ile Leu Asn Ser Thr Val Glu Glu Ile His Gln Ile
1970 1975 1980

Leu Gln Ser Asp Arg Thr Leu Val Tyr Arg Val Phe Pro Glu Gly
1985 1990 1995

Thr Gly Thr Ala Ile Ala Glu Ser Val Ser Pro Asn Arg Leu Lys
2000 2005 2010

Leu Leu Asp Ile Leu Phe Pro Glu Glu Val Phe Pro Glu Glu Asn
2015 2020 2025

Tyr Glu Arg Tyr Ile Glu Gly Arg Val Tyr Ala Leu Asn Asp Ser
2030 2035 2040

Glu Asp Ala Asn Glu Ser Ile Val Pro Cys Leu Val Glu Phe Leu
2045 2050 2055

Ala Asp Ile Gln Val Arg Ala Lys Leu Val Val Pro Ile Ile Gln
2060 2065 2070

Asn Gln Ser Leu Trp Gly Leu Leu Ile Val His Gln Cys Asp Arg
2075 2080 2085

-continued

```
Pro Arg  Gln Trp Gln Glu Trp  Glu Ile Asn Leu Leu  Lys Gln Ile
    2090                 2095                 2100

Ala Asn  Gln Leu Ala Ile Ala  Ile Gln Gln Ser Tyr  Leu Tyr Glu
    2105                 2110                 2115

Gln Val  Gln Ser Glu Leu Ala  Ile Arg Lys Gln Thr  Glu Lys Ala
    2120                 2125                 2130

Ile Ala  Leu Gln Leu Gln Arg  Gln Arg Thr Leu Gly  Glu Ile Ala
    2135                 2140                 2145

Gln Gln  Ile Arg Glu Ser Leu  Asp Ile Asn Glu Ile  Leu Ala Thr
    2150                 2155                 2160

Val Thr  Gln Gln Val Lys Glu  Ile Leu Gln Gly Asp  Arg Ile Val
    2165                 2170                 2175

Val Phe  Arg Leu Phe Gly Asp  Gly Arg Ser Gln Ile  Val Glu Glu
    2180                 2185                 2190

Ala Val  Ser Ser Glu Phe Pro  Ala Leu Lys Asp His  His Trp Glu
    2195                 2200                 2205

Asp Glu  Leu Trp Ser Pro Glu  Ile Leu Asn Arg Tyr  Trp Gln Gly
    2210                 2215                 2220

Lys Pro  Arg Ile Val Pro Asp  Val Met Thr Asp Ile  Trp Thr Asp
    2225                 2230                 2235

Cys Leu  Val Glu Tyr Ala Thr  Val Cys Gln Val Gln  Ser Lys Ile
    2240                 2245                 2250

Val Ala  Pro Ile Leu Gln Glu  Val Arg Ser Ser Glu  Ser His Arg
    2255                 2260                 2265

Trp Val  Ala Pro Gly Gln Thr  Lys Lys Leu Trp Gly  Val Leu Val
    2270                 2275                 2280

Val His  Ala Cys Arg Glu Gln  Arg Val Trp Gln Glu  Ser Glu Ala
    2285                 2290                 2295

Gln Leu  Leu Gln Gln Ile Ala  Asn Gln Leu Ala Ile  Ala Ile Gln
    2300                 2305                 2310

Gln Ala  Ser Leu Phe Lys Gln  Leu Gln Gln Glu Leu  Thr Glu Arg
    2315                 2320                 2325

Gln Gln  Ala Gln Gln Gln Leu  Thr Glu Arg Asn Glu  Gln Leu Ala
    2330                 2335                 2340

Val Ser  Asn Glu Glu Leu Ala  Arg Ala Thr Arg Leu  Lys Asp Glu
    2345                 2350                 2355

Phe Leu  Ala Asn Met Ser His  Glu Leu Arg Thr Pro  Leu Asn Ala
    2360                 2365                 2370

Ile Leu  Gly Met Ser Glu Gly  Leu Gln Glu Gln Val  Phe Gly Ile
    2375                 2380                 2385

Ile Asn  Glu Glu Gln Ile Lys  Ala Leu Gln Thr Ile  Glu Arg Ser
    2390                 2395                 2400

Ser Ser  His Leu Leu Glu Leu  Ile Asn Asp Ile Leu  Asp Val Ala
    2405                 2410                 2415

Lys Ile  Glu Ser Gly Gln Met  Glu Leu Asp Cys Thr  Pro Val Ser
    2420                 2425                 2430

Ile Asn  His Leu Cys Gln Ser  Ser Leu Ala Phe Ile  Lys Gln Gln
    2435                 2440                 2445

Ala Leu  Gln Lys Arg Ile Gln  Leu Glu Ile Lys Val  Pro Leu Asn
    2450                 2455                 2460

Leu Pro  Asp Leu Leu Ile Asp  Glu Arg Arg Met Arg  Gln Val Leu
    2465                 2470                 2475

Ile Asn  Leu Leu Asn Asn Ala  Val Lys Phe Thr Pro  Asn Gly Gly
```

```
    2480                2485                2490

Arg Ile  Thr Leu Glu Val Ser  Ser Gln Gln Arg Arg  Ala Asp Pro
    2495                2500                2505

Asp Ser  Ala Asp Ser Pro Pro  His Phe Leu Val Lys  Glu Thr Leu
    2510                2515                2520

Arg Ile  Ser Val Ile Asp Thr  Gly Ile Gly Ile Ala  Pro Glu His
    2525                2530                2535

Ile Asn  Lys Leu Phe Gln Pro  Phe Ile Gln Ile Asp  Gly Ala Leu
    2540                2545                2550

Asn Arg  Gln Tyr Thr Gly Thr  Gly Leu Gly Leu Ala  Leu Val Lys
    2555                2560                2565

Arg Ile  Val Glu Leu His Gly  Gly Gln Val Leu Leu  Thr Ser Thr
    2570                2575                2580

Val Gly  Val Gly Ser Cys Phe  Thr Ile Asp Leu Pro  Cys Thr Gly
    2585                2590                2595

Cys Ala  Pro Ser Ser Val Asp  Val Glu Ser Gln Thr  Glu Pro Arg
    2600                2605                2610

Ile Glu  Pro Ser Gly Pro Glu  Gln Gln Gly Gly Ser  Pro Leu Ile
    2615                2620                2625

Leu Leu  Ala Glu Asp Asn Glu  Ala Asn Ile Ser Thr  Val Ser Ser
    2630                2635                2640

Tyr Leu  Arg Ala Lys Gly Tyr  Arg Ile Leu Leu Ala  Lys Asp Gly
    2645                2650                2655

Glu Glu  Ala Val Ala Leu Ala  Lys Ser Glu Asn Pro  Asn Leu Ile
    2660                2665                2670

Leu Met  Asp Ile Gln Met Pro  Gly Met Asp Gly Leu  Glu Ala Met
    2675                2680                2685

Gln Gln  Ile Arg Cys Asp Pro  Asn Leu Val Asp Leu  Pro Ile Val
    2690                2695                2700

Ala Leu  Thr Ala Leu Ala Met  Thr Gly Asp Arg Asp  Arg Cys Leu
    2705                2710                2715

Ala Ala  Gly Ala Asn Asp Tyr  Leu Thr Lys Pro Val  Lys Leu Lys
    2720                2725                2730

Gln Leu  Ala Ser Thr Ile Gln  Gln Leu Leu Ala Lys
    2735                2740                2745


<210> SEQ ID NO 44
<211> LENGTH: 2745
<212> TYPE: PRT
<213> ORGANISM: Microcoleus vaginatus

<400> SEQUENCE: 44

Met Phe Met Arg Thr Thr Ala Leu Thr Pro Ile Glu Leu Arg Thr Ala
1               5                   10                  15

Ile Val Arg Glu Pro Leu Val Val Ser Pro Asp Thr Thr Val Met Asp
            20                  25                  30

Ala Ile Ala Gln Met Ser Gly Val Arg Ser Leu Cys Asn Thr Thr Arg
        35                  40                  45

Thr Ala Asp Gly Gln Leu Asp Asp Leu His Leu Glu Ala Arg Ser Ser
    50                  55                  60

Cys Val Leu Val Val Glu Asn Glu Gln Leu Val Gly Val Leu Thr Glu
65                  70                  75                  80

Arg Asp Val Val Arg Leu Ser Ala Gln Gln Arg Ser Leu Glu Asn Leu
                85                  90                  95
```

-continued

```
Val Leu Arg Glu Val Met Ala His Pro Val Val Thr Leu Arg Glu Ser
            100                 105                 110

Ala Phe Thr Asp Leu Phe Phe Ala Ile Asn Leu Leu Gln Gln His His
        115                 120                 125

Ile Arg His Leu Pro Ile Leu Asp Asp Leu Asp Arg Leu Val Gly Leu
    130                 135                 140

Val Thr His Glu Ser Leu Arg Gln Thr Ser Arg Pro Ile Asp Leu Leu
145                 150                 155                 160

Arg Leu Arg Met Val Ala Glu Val Met Thr Arg Glu Val Ile Cys Ala
                165                 170                 175

Ala Pro Asp Ser Ser Leu Leu Ala Ile Ala Gln Leu Met Ala Glu Asn
            180                 185                 190

Arg Val Ser Ser Val Val Ile Val His Pro Gly Gly Ile Ser Thr Glu
        195                 200                 205

Pro Leu Gln Ile Pro Val Gly Ile Leu Thr Glu Arg Asp Ile Val Gln
    210                 215                 220

Phe Gln Thr Leu Gly Leu Asn Leu Glu Thr Cys Leu Ala Gln Ala Val
225                 230                 235                 240

Met Ser Thr Pro Ile Phe Ala Val Arg Pro Asp Asp Ser Leu Trp Thr
                245                 250                 255

Val Gln Glu Ile Val Glu Gln Arg Ser Ile Arg Arg Leu Ala Val Thr
            260                 265                 270

Gly Glu Leu Gly Glu Leu Leu Gly Ile Val Thr Gln Thr Ser Leu Leu
        275                 280                 285

Gln Ala Leu Asn Pro Leu Glu Leu Tyr Lys Leu Val Gln Lys Trp Glu
    290                 295                 300

Glu Lys Val Val Arg Leu Glu Ala Glu Lys Val Ala Leu Leu Ala Asn
305                 310                 315                 320

Arg Asn Val Glu Leu Glu Gln Gln Val Glu Ala Arg Thr Ala Ala Leu
                325                 330                 335

Lys Ala Lys Ala Asp Arg Glu Gln Leu Leu Asn Thr Ile Ala Glu Gln
            340                 345                 350

Ile Arg Ser Ser Leu Asn Leu Ser Asp Ile Leu Gln Thr Thr Val Gln
        355                 360                 365

Glu Ile His Ser Leu Leu Gly Cys Asp Arg Val Ile Ile Tyr Gln Phe
    370                 375                 380

Arg Ser Asp Phe Ser Gly Thr Val Ile Ala Glu Ala Ile Thr Asp Thr
385                 390                 395                 400

Gly Arg Ser Val Leu His Arg Glu Ala His Asp Pro Cys Met Ser Pro
                405                 410                 415

Glu Trp Leu Glu Pro Tyr Arg Gln Gly Arg Ile Arg Ile Ile Asn Asp
            420                 425                 430

Ile Tyr Gly Glu Pro Met Thr Gln Cys His Gln Glu Met Leu Val Gly
        435                 440                 445

Phe Asp Ile Arg Ala Lys Leu Met Val Pro Ile Val Ile Glu Glu Gln
    450                 455                 460

Leu Arg Gly Leu Met Ile Ala Ser Tyr Arg Ala Ser Ala His Ser Trp
465                 470                 475                 480

Thr Thr Asp Glu Ile Glu Leu Leu Arg Gln Val Ser Leu Gln Val Ala
                485                 490                 495

Ile Ala Leu Gly Gln Ala Met Ile Gln Gln Lys Leu Gln Asn Glu Leu
            500                 505                 510

Val Lys Arg Gln Arg Ile Glu Ala Thr Leu Ile Glu Ser Glu Gln Arg
```

```
        515                 520                 525

Tyr Ala Ala Leu Ala Ala Ala Ala Pro Val Gly Ile Phe Arg Thr Asp
    530                 535                 540

Ala Thr Gly Leu Cys Thr Tyr Val Asn Asp Arg Tyr Phe Gln Ile Ser
545                 550                 555                 560

Gly Leu Thr Pro Gly Ala Thr Ile Gly His Gly Trp Gln Gln Gly Val
                565                 570                 575

His Pro Asp Asp Arg Asp Trp Val Met Val Glu Trp Lys Gln Phe Ile
            580                 585                 590

Gln Gly Asn Arg Ser Phe Glu Leu Glu Tyr Arg Phe Gln Cys Pro Asp
        595                 600                 605

Gly Thr Val Thr Trp Val Tyr Gly Gln Cys Val Ala Glu Leu Asp Ala
    610                 615                 620

Asn Gly His Arg Ser Gly Tyr Ile Gly Thr Ile Thr Asp Ile Ser Ala
625                 630                 635                 640

Arg Lys Arg Thr Glu Val Cys Leu Gln Glu Ser Glu Glu Arg Tyr Ala
                645                 650                 655

Thr Leu Val Ala Ala Ala Pro Val Gly Ile Phe Arg Ala Asp Ala Val
            660                 665                 670

Gly Asn Cys Ile Tyr Val Asn Asp Arg Trp Cys Gln Ile Ser Gly Leu
        675                 680                 685

Thr Pro Lys Thr Ala Val Gly Glu Gly Trp Gln Gln Gly Leu His Pro
    690                 695                 700

Asp Asp Arg Asp Cys Val Ile Ala Glu Trp Glu Gln Ser Val Gln Arg
705                 710                 715                 720

Asn Arg Pro Phe Gln Leu Glu Tyr Arg Phe Gln Arg Pro Asp Gly Gly
                725                 730                 735

Val Thr Ser Val Tyr Gly Gln Ser Val Ala Glu Arg Asp Ala Asp Gly
            740                 745                 750

Gln Val Val Gly Tyr Val Gly Thr Thr Thr Asp Ile Thr Asp Arg Lys
        755                 760                 765

Gln Ala Glu Gln Lys Leu Gln Gln Leu Asn Gln Gln Leu Glu Thr Lys
    770                 775                 780

Val Ala Glu Arg Thr Gln Glu Leu Trp Gln Val Asn Ser Leu Gln Arg
785                 790                 795                 800

Ala Ile Leu Asp Cys Ala Asp Tyr Ser Ile Ile Ser Ser Asp Pro Ser
                805                 810                 815

Gly Ile Ile Gln Thr Leu Asn Ala Ala Gly Glu Arg Met Leu Gly Tyr
            820                 825                 830

Ser Ala Gln Glu Ile Ile Gly Gln Ala Thr Pro Ala Leu Ile His Asp
        835                 840                 845

Ala Asn Glu Val Ile Asp Arg Ala Ala Ser Leu Ser Ala Glu Leu Gly
    850                 855                 860

Gln Asn Ile Pro Pro Gly Phe Glu Val Phe Val Ala Lys Ala Arg Gln
865                 870                 875                 880

Gly Leu Val Ser Glu Glu Glu Trp Ser Tyr Ile Arg Lys Asp Gly Ser
                885                 890                 895

Arg Phe Pro Val Ser Leu Ser Ile Thr Ala Leu Lys Asp Val His Gln
            900                 905                 910

Gln Ile Ile Gly Phe Leu Gly Ile Ala Lys Asp Ile Ser Asp Arg Lys
        915                 920                 925

Arg Ala Glu Ala Glu Leu Gln Lys Leu Ser Glu Arg Leu Ala Leu Ser
    930                 935                 940
```

-continued

```
Leu Lys Ser Gly Ala Ile Ala Ser Trp Glu Trp Asn Leu Gly Gln Asn
945                 950                 955                 960

Thr Ile Leu Gly Asp Glu Arg Met Tyr Glu Leu Phe Ala Val Thr Lys
                965                 970                 975

Pro Ser Asp Ala Cys Gln Val Tyr Asp Phe Trp Ala Asn Arg Leu His
            980                 985                 990

Pro Asp Asp Arg Ile Pro Thr Glu  Thr Leu Leu His Gln  Ala Val Leu
        995                 1000                1005

Gly Gln  Ala Glu Tyr Asp Thr  Glu Tyr Arg Ile Val  His Pro Asp
    1010                 1015                 1020

Gly Ser  Leu His Phe Ile Lys  Ala Tyr Gly Val Val  Val Arg Asp
    1025                 1030                 1035

Ala Gln  Ser Asn Pro Gln Ser  Met Ile Gly Val Asn  Phe Asp Ile
    1040                 1045                 1050

Ser Asp  Arg Lys Gln Ala Glu  Leu Gln Arg Gln Gln  Leu Ile Gln
    1055                 1060                 1065

Glu Leu  Ser Ala Phe Lys Gln  Ala Leu Asp Gln Ser  Ala Ile Val
    1070                 1075                 1080

Val Ile  Thr Asp Arg Glu Gly  Val Ile Ser Tyr Val  Asn Asp Arg
    1085                 1090                 1095

Phe Cys  Val Val Ser Gly Tyr  Ser Arg Asp Arg Leu  Ile Gly Gln
    1100                 1105                 1110

Thr His  Arg Leu Val Asn Ser  Gly Tyr His Pro Pro  Ala Phe Phe
    1115                 1120                 1125

Gln Asp  Leu Trp Arg Thr Ile  Asn Ser Ser Gln Ile  Trp Arg Gly
    1130                 1135                 1140

Glu Ile  Cys Asn Leu Ala Lys  Asn Gly Ser Leu Tyr  Trp Val Ala
    1145                 1150                 1155

Thr Thr  Ile Val Pro Phe Leu  Asp Glu Gln Gly Arg  Pro Phe Gln
    1160                 1165                 1170

Tyr Leu  Ala Ile Gly Phe Asp  Ile Thr Asp Arg Lys  Leu Ala Glu
    1175                 1180                 1185

Ala Thr  Leu Gln Gln Glu Asn  Thr Phe Arg Gln Gln  Ile Val Glu
    1190                 1195                 1200

Asn Met  Ala Glu Gly Leu Cys  Val Phe His Gln Val  Glu Glu Phe
    1205                 1210                 1215

Pro Phe  Val Arg Phe Thr Val  Trp Asn Gln Gln Met  Gln Ala Ile
    1220                 1225                 1230

Thr Gly  Tyr Thr Leu Glu Glu  Ile Asn Arg Leu Gly  Trp Tyr Gln
    1235                 1240                 1245

Thr Leu  Tyr Pro Asn Leu Glu  Asp Arg Glu Gln Ala  Ile Ala Asn
    1250                 1255                 1260

Cys Arg  Gln Met Gln Pro Ile  Ala Val Glu Arg Glu  Ile Gln Arg
    1265                 1270                 1275

Gln Asp  Gly Gln Arg Arg Thr  Ile Ser Ile Ser Thr  Ser Val Leu
    1280                 1285                 1290

Ser Gly  Asp Asp Gly His Leu  Tyr Ala Leu Ala Leu  Ile Gln Asp
    1295                 1300                 1305

Ile Thr  His Arg Gln Gln Thr  Glu Arg Glu Asn Arg  Leu Leu Lys
    1310                 1315                 1320

Glu Arg  Leu Glu Phe Leu Leu  Ala Ser Ser Pro Ala  Met Ile Tyr
    1325                 1330                 1335
```

-continued

```
Ser Cys  Lys Pro Tyr Gly Asp  Tyr Glu Leu Thr Phe  Met Ser Lys
    1340                 1345                 1350

Asn Met  Ser Ala Ile Leu Gly  Tyr Lys Pro Glu Glu  Phe Leu Ser
    1355                 1360                 1365

Glu Ser  Gly Phe Trp Ala Asn  His Leu His Pro Glu  Asp Ala Pro
    1370                 1375                 1380

Arg Val  Phe Ala Asp Leu Ser  Ala Leu Phe Glu Tyr  Asn Thr His
    1385                 1390                 1395

Gln His  Glu Tyr Arg Phe Leu  His His Asp Gly His  Tyr Val Trp
    1400                 1405                 1410

Leu Arg  Asp Glu Leu Arg Val  Val Arg Asp Glu Glu  Gly Cys Pro
    1415                 1420                 1425

Thr Glu  Ile Ile Gly Tyr Phe  Ala Asp Ile Ser Asp  Val Lys Gln
    1430                 1435                 1440

Thr Glu  Glu Thr Leu Lys Ile  Gln Leu Ala Ala Ile  Glu Ala Ala
    1445                 1450                 1455

Ile Asp  Gly Ile Ala Ile Met  Gln Gly Asp Thr Tyr  Leu Tyr Leu
    1460                 1465                 1470

Asn Gln  Ala His Leu Glu Leu  Phe Gly Tyr Glu His  Pro Gln Glu
    1475                 1480                 1485

Leu Leu  Gly Lys Thr Trp Gln  Leu Leu Tyr Ser Pro  Glu Glu Leu
    1490                 1495                 1500

Glu Arg  Phe Glu Arg Glu Val  Phe Pro Val Leu Gly  Arg Asp Arg
    1505                 1510                 1515

Ala Trp  Gln Gly Glu Ala Ile  Gly Thr Arg Lys Asp  Gly Ser Thr
    1520                 1525                 1530

Phe Ala  Glu Gly Leu Ser Leu  Thr Leu Thr Glu Asn  Gly Leu Leu
    1535                 1540                 1545

Ile Cys  Val Cys Arg Asp Ile  Ser Asp Arg Lys Gln  Ile Glu Ala
    1550                 1555                 1560

Glu Leu  Ala Glu Ser Glu Ala  Lys Phe Arg Arg Leu  Val Glu Gly
    1565                 1570                 1575

Ala Asn  Asp Leu Ile Trp Ser  Cys Glu Pro Asp Gly  Ile Leu Thr
    1580                 1585                 1590

Tyr Val  Ser Pro Gln Phe Lys  Thr Met Phe Gly Trp  Asp Glu Ser
    1595                 1600                 1605

Ala Trp  Ile Gly Lys Ser Phe  Ile Tyr Leu Val His  Pro Asp Asp
    1610                 1615                 1620

Arg Ser  Leu Val Val Thr Asp  Tyr Arg Glu Asn Ile  Lys Ser Gly
    1625                 1630                 1635

Lys Lys  Ser Ser Asp Tyr Glu  Phe Arg His Arg His  Arg Asp Gly
    1640                 1645                 1650

Asn Tyr  Val Trp Val Arg Ser  Ser Ala Thr Pro Val  Ile Asn Ala
    1655                 1660                 1665

Glu Gly  Glu Leu Ile Ser Ile  Gln Gly Ile Leu Ser  Asp Ile Ser
    1670                 1675                 1680

Asp Arg  Lys Glu Ala Glu Ile  Ala Arg Glu Ser Ser  Glu Ile Arg
    1685                 1690                 1695

Phe Arg  Arg Val Phe Glu Ser  Ser Val Ser Gly Met  Ile Phe Ala
    1700                 1705                 1710

Asp Phe  Gln Gly Asn Ile Ile  Asp Ala Asn Asp Arg  Phe Leu Gln
    1715                 1720                 1725

Met Val  Gly Tyr Thr Arg Glu  Glu Leu Asp Ala Gly  Leu Ile His
```

```
    1730                1735                1740

Trp Asp  Ala Met Thr Pro Pro  Glu Tyr Phe Pro Ala  Asp Val Leu
    1745                1750                1755

Ala Met  Glu Arg Val Met Gln  Asp Gly Ala Ile Glu  Pro Trp Glu
    1760                1765                1770

Lys Glu  Tyr Tyr Arg Lys Asp  Gly Ser Arg Ile Ser  Val Leu Ile
    1775                1780                1785

Gly Val  Ala Leu Leu Pro Asp  Ser Asp Asp Gln Thr  Ile Cys Val
    1790                1795                1800

Leu Val  Asp Ile Ser Glu Arg  Lys Gln Ala Gln Lys  Ala Leu Gln
    1805                1810                1815

Glu Ser  Gln Gln Phe Leu Gln  Thr Val Leu Asp Thr  Ile Pro Leu
    1820                1825                1830

Ala Val  Phe Trp Lys Asn Arg  Glu Ser Val Phe Leu  Gly Cys Asn
    1835                1840                1845

Gln Gln  Phe Ala Gln Thr Leu  Gly Leu Pro Ser Thr  Thr Glu Ser
    1850                1855                1860

Ile Gly  Lys Lys Asp Leu Asp  Ile Cys Gln Glu Glu  Val Glu Ala
    1865                1870                1875

Asn Glu  Tyr Cys Ala Met Asp  Arg Arg Leu Met Glu  Thr Gly Glu
    1880                1885                1890

Ala Ile  Leu Gly Ile Glu Glu  Thr Leu Thr Leu Pro  Asn Gly Lys
    1895                1900                1905

Leu Ile  Phe Ile Glu Thr His  Lys Ala Pro Leu Arg  Asp Cys Ser
    1910                1915                1920

Asp Asn  Val Ile Gly Leu Val  Gly Thr Phe Gln Asp  Ile Thr Asp
    1925                1930                1935

Arg Lys  Glu Ala Glu Gln Lys  Leu Gln Gln Gln Ala  Lys Gln Glu
    1940                1945                1950

Arg Leu  Leu Gly Ala Ile Thr  Lys Arg Met Arg Ser  Ser Leu Asn
    1955                1960                1965

Leu Asp  Glu Ile Leu Asn Ser  Thr Val Glu Glu Ile  His Gln Leu
    1970                1975                1980

Leu Gln  Ser Asp Arg Thr Leu  Val Tyr Arg Val Phe  Pro Glu Gly
    1985                1990                1995

Thr Gly  Ala Ala Ile Ala Glu  Ser Val Ser Pro Asn  Arg Leu Lys
    2000                2005                2010

Leu Leu  Asp Ile Leu Phe Pro  Glu Glu Val Phe Pro  Glu Asp Thr
    2015                2020                2025

Tyr Glu  Arg Tyr Ile Gln Gly  Arg Val Tyr Ala Leu  Asn Asp Ser
    2030                2035                2040

Glu Asp  Glu Asn Glu Ser Ile  Val Pro Cys Leu Val  Glu Phe Leu
    2045                2050                2055

Ala Asp  Ile Glu Val Arg Ala  Lys Leu Val Val Pro  Ile Ile Gln
    2060                2065                2070

Asn Gln  Thr Leu Trp Gly Leu  Leu Ile Val His Gln  Cys Asp Arg
    2075                2080                2085

Pro Arg  Gln Trp Gln Asp Trp  Glu Ile Asn Leu Leu  Lys Gln Ile
    2090                2095                2100

Ala Asn  Gln Leu Ala Ile Ala  Ile Gln Gln Ser Tyr  Leu Tyr Glu
    2105                2110                2115

Gln Val  Gln Ser Glu Leu Ala  Ile Arg Lys Gln Thr  Glu Asn Val
    2120                2125                2130
```

Ile Ala Leu Gln Leu Gln Arg Gln Arg Thr Leu Gly Ala Ile Ala
2135 2140 2145

Gln Gln Ile Arg Glu Ser Leu Asp Ile Asn Gln Ile Leu Ala Ala
2150 2155 2160

Val Thr Gln Gln Val Lys Glu Ile Leu Gln Gly Asp Arg Ile Ile
2165 2170 2175

Val Phe Arg Leu Phe Gly Asp Gly Arg Ser Gln Ile Val Glu Glu
2180 2185 2190

Ala Val Ser Ser Glu Phe Pro Ala Leu Lys Asp His His Trp Glu
2195 2200 2205

Asp Glu Arg Trp Ser Gln Glu Ile Leu Asn Arg Tyr Trp Gln Gly
2210 2215 2220

Lys Pro Arg Ile Val Pro Asn Val Met Thr Asp Ile Trp Thr Asp
2225 2230 2235

Cys Leu Val Glu Tyr Ala Ser Val Gly Gln Val Gln Ser Lys Ile
2240 2245 2250

Val Ala Pro Ile Leu Gln Glu Val Arg Ser Ser Glu Ser His Arg
2255 2260 2265

Trp Ile Ala Pro Gly Gln Thr Lys Lys Leu Trp Gly Val Leu Val
2270 2275 2280

Val His Ala Cys Arg Glu Gln Arg Val Trp Gln Glu Ser Glu Ala
2285 2290 2295

Gln Leu Leu Gln Gln Ile Ala Asn Gln Leu Ala Ile Ala Ile Gln
2300 2305 2310

Gln Ala Ser Leu Phe Lys Gln Leu Gln Gln Glu Leu Thr Glu Arg
2315 2320 2325

Gln Gln Ala Gln Gln Gln Leu Thr Glu Arg Asn Gln Gln Leu Gly
2330 2335 2340

Ala Ser Asn Glu Glu Leu Ala Arg Ala Thr Arg Leu Lys Asp Glu
2345 2350 2355

Phe Leu Ala Asn Met Ser His Glu Leu Arg Thr Pro Leu Asn Ala
2360 2365 2370

Ile Leu Gly Met Ser Glu Gly Leu Gln Glu Gln Val Phe Gly Ile
2375 2380 2385

Val Asn Glu Gln Gln Ile Lys Ala Leu Gln Thr Ile Glu Arg Ser
2390 2395 2400

Ser Ser His Leu Leu Glu Leu Ile Asn Asp Ile Leu Asp Val Ala
2405 2410 2415

Lys Ile Glu Ser Gly Gln Met Glu Leu Asp Cys Thr Pro Val Ser
2420 2425 2430

Ile Asn His Leu Cys Gln Ser Ser Leu Ala Phe Ile Lys Gln Gln
2435 2440 2445

Ala Leu Gln Lys Arg Ile Gln Leu Glu Ile Gln Met Pro Leu Asn
2450 2455 2460

Leu Pro Asp Leu Leu Ile Asp Glu Arg Arg Met Arg Gln Val Leu
2465 2470 2475

Ile Asn Leu Leu Asn Asn Ala Val Lys Phe Thr Pro Asn Gly Gly
2480 2485 2490

Arg Ile Thr Leu Glu Val Ser Arg Gln Gln Arg Pro Ala Asp Pro
2495 2500 2505

Asp Ser Ala Asp Ser Pro Pro His Phe Leu Val Lys Glu Thr Leu
2510 2515 2520

```
Arg Ile  Ala Val Ile Asp Thr  Gly Ile Gly Ile Ala  Pro Glu His
    2525                 2530                 2535

Ile Asn  Lys Leu Phe Gln Pro  Phe Ile Gln Ile Asp  Gly Ala Leu
    2540                 2545                 2550

Asn Arg  Gln Tyr Thr Gly Thr  Gly Leu Gly Leu Ala  Leu Val Lys
    2555                 2560                 2565

Arg Ile  Val Glu Leu His Gly  Gly Gln Val Gly Leu  Thr Ser Thr
    2570                 2575                 2580

Val Gly  Val Gly Ser Cys Phe  Thr Ile Asp Leu Pro  Cys Thr Ala
    2585                 2590                 2595

Cys Ala  Pro Ser Ser Val Tyr  Leu Glu Ser Gln Thr  Glu Pro Arg
    2600                 2605                 2610

Ile Glu  Pro Ser Gln Pro Glu  Glu Gly Gly Ser Pro  Leu Ile Leu
    2615                 2620                 2625

Leu Ala  Glu Asp Asn Glu Ala  Asn Ile Thr Thr Ile  Ser Ser Tyr
    2630                 2635                 2640

Leu Arg  Ala Lys Gly Tyr Arg  Ile Leu Leu Ala Lys  Asn Gly Glu
    2645                 2650                 2655

Glu Ala  Ile Ala Leu Ala Lys  Ser Glu Asn Pro Asn  Leu Ile Leu
    2660                 2665                 2670

Met Asp  Ile Gln Met Pro Gly  Met Asp Gly Leu Glu  Ala Met Gln
    2675                 2680                 2685

Arg Ile  Arg Ser Asp Pro Asn  Leu Val Asp Leu Pro  Ile Ile Ala
    2690                 2695                 2700

Leu Thr  Ala Leu Ala Met Thr  Gly Asp Arg Asp Arg  Cys Leu Ala
    2705                 2710                 2715

Ala Gly  Ala Asn Asp Tyr Leu  Thr Lys Pro Val Lys  Leu Lys Gln
    2720                 2725                 2730

Leu Ala  Ser Thr Ile Gln Gln  Leu Leu Ala Ser Lys
    2735                 2740                 2745


<210> SEQ ID NO 45
<211> LENGTH: 1977
<212> TYPE: PRT
<213> ORGANISM: Unknown
<220> FEATURE:
<223> OTHER INFORMATION: Cyanothece sp. PCC 7425

<400> SEQUENCE: 45

Met Pro Thr Gln Lys Val Leu Glu Ser Ala Ile Val Ser Asn Pro Leu
1               5                   10                  15

Ile Val Leu Pro Glu Thr Thr Val Ile Asp Ala Ile Ala Gln Met Ser
            20                  25                  30

Arg Ala Gln Ile Thr Gly Ser Ala Leu Ser Ile Thr Ala Thr Asn Glu
        35                  40                  45

Val His Gln Pro Ala His Ser Ser Cys Val Leu Ile Val Ala Asp Cys
    50                  55                  60

Gln Leu Ile Gly Ile Phe Thr Ala Ala Asp Val Leu Arg Leu Ile Val
65                  70                  75                  80

Gln Gln Arg Leu Gln Glu Gly Leu Leu Ile Arg Glu Val Met Thr His
                85                  90                  95

Pro Val Ile Thr Leu Pro Gly Val Ala Phe Thr Asp Leu Ser Val Ala
            100                 105                 110

Ile Asn Leu Leu Gln Gln His Arg Ile Arg His Leu Pro Leu Val Asp
        115                 120                 125
```

-continued

```
Ser Ala Asn Tyr Pro Val Gly Leu Leu Thr Tyr Glu Thr Leu Leu Ala
    130                 135                 140

Thr Gln Asn Thr Val Leu Leu Glu Ala Ala Thr Leu Glu Pro Glu Leu
145                 150                 155                 160

Gln Val Ala Ala Arg Ser Thr Ala Arg Lys Leu Glu Val Glu Trp Glu
                165                 170                 175

Lys Leu Val Ala Glu Val Ala Ser Lys Ile Arg Ser Ser Leu Ser Leu
            180                 185                 190

Ser Thr Ile Leu Asn Thr Thr Val Glu Gln Val Arg Gln Val Leu Gly
        195                 200                 205

Cys Glu Arg Val Asn Ile Trp Gln Phe Glu Thr Asp Ser Gln Ile Ala
    210                 215                 220

Val Val Ala Glu Ser Thr Asp Phe Ser Ile Ser Leu Ile Gly Glu Gln
225                 230                 235                 240

Val Ile Asp Asn Cys Phe Gln Arg Gly Lys Ala Glu Arg Tyr Arg Gln
                245                 250                 255

Gly Ser Ile Arg Val Val Ser Asp Ile Tyr Thr Thr Glu Met Ser Asp
            260                 265                 270

Cys His Arg Gln Leu Leu Thr Arg Leu Arg Thr Arg Ala Lys Ile Leu
        275                 280                 285

Val Pro Leu Ile Cys Gly Arg Thr Leu Trp Gly Phe Leu Asn Ala Ser
    290                 295                 300

Glu Ser Asn Gln Arg Arg Asp Trp Gln Pro Ala Glu Ile Glu Leu Leu
305                 310                 315                 320

Gln Thr Leu Ser Leu His Leu Ser Ile Ala Leu Gln Gln Ala Thr Thr
                325                 330                 335

His Gln Arg Leu Gln Lys Glu Leu Leu Ala Arg Lys Gln Val Glu Ala
            340                 345                 350

Cys Leu Arg Asp Arg Glu Gln Arg Tyr Gly Ser Leu Ile Ser Thr Ala
        355                 360                 365

Pro Val Gly Phe Phe Trp Thr Asp Ala Glu Gly Glu Cys Ile Tyr Ala
    370                 375                 380

Asn Asp Arg Trp Cys Glu Ile Ala Gly Leu Ser Leu Glu Ala Ala Glu
385                 390                 395                 400

Gly Gln Gly Trp Gln Ala Ala Ile His Pro Glu Asp Arg Glu Arg Val
                405                 410                 415

Arg Ala Glu Trp Gln Gln Ala Ile Gln Glu Ser Arg Pro Phe Gln Leu
            420                 425                 430

Glu Tyr Arg Phe Gln Arg Pro Asp Gly Ala Val Ile Trp Val Tyr Gly
        435                 440                 445

Gln Val Val Ala Glu Lys Asn Asp Met Gly Ala Ile Gly Gly Tyr Val
    450                 455                 460

Gly Thr Ile Thr Asp Ile His Ala Arg Lys Gln Ala Glu Gln Gln Leu
465                 470                 475                 480

His Asn Leu Ile Ala Gly Thr Ala Ala Ala Thr Gly Gln Asp Phe Phe
                485                 490                 495

Pro Val Leu Val Gln His Ile Ala Gln Ala Leu Asn Val Pro Tyr Val
            500                 505                 510

Leu Val Thr Glu Lys Ile Gly Gly Asp Arg Leu Cys Thr Leu Ala Tyr
        515                 520                 525

Trp Ala Asn Gly Glu Leu Lys Pro Thr Leu Ser Leu Pro Ile Ala Asn
    530                 535                 540

Thr Pro Cys Ser His Val Leu Gln Asp Gly Lys Phe Tyr Cys Ala Ser
```

-continued

```
545                 550                 555                 560

Gln Ile Gln Gln Gln Phe Ala Asn Thr Leu Glu Gly Ile Glu Leu Gly
                565                 570                 575

Ala Glu Ser Tyr Leu Gly Ile Ala Leu Arg Asp Ser Gln Gly Glu Ala
            580                 585                 590

Ile Gly Thr Leu Cys Ile Val Asp His Gln Pro Ile Gln Glu Pro Gln
        595                 600                 605

Arg Leu Glu Asn Leu Leu Val Ala Phe Ala Ala Arg Ala Ala Ala Glu
    610                 615                 620

Leu Glu Arg Glu Arg Ala Thr Gln Thr Leu Ala Gln Leu Asn Arg Glu
625                 630                 635                 640

Leu Glu Thr Lys Val Ala Glu Arg Thr Ala Ala Leu Lys Ala Ser Glu
                645                 650                 655

Glu Arg Trp Gln Leu Val Leu Lys Gly Ala Asn Asp Gly Ile Trp Asp
            660                 665                 670

Trp Asp Leu Thr Thr Asn Arg Val Phe Phe Ser Glu Arg Trp Lys Asn
        675                 680                 685

Met Arg Gly Leu Asn Gln Glu Gln Val Ser Asp Arg Leu Glu Glu Trp
    690                 695                 700

Ser Arg Ser Ile His Pro Asp Asp Tyr Asn Cys Val Met Ala Asn Leu
705                 710                 715                 720

Glu Ala His Leu Ala Gly Gln Thr Glu Phe Phe Glu Gln Glu Tyr Arg
                725                 730                 735

Val Arg Cys Gln Asp Gly Ser Tyr Ile Trp Val Leu Ala Arg Gly Gln
            740                 745                 750

Ala Leu Arg Asp Ser Ser Gly Gln Val Val Arg Met Ala Gly Ser Glu
        755                 760                 765

Ile Asp Ile Thr Ala Arg Lys Gln Ala Glu Gln Glu Asn Leu Arg Leu
    770                 775                 780

Lys Glu Arg Leu Gln Phe Leu Leu Ser Val Asn Pro Ala Val Ile Phe
785                 790                 795                 800

Thr Ser Glu Pro Gly Glu Asp Tyr Ala Ile Thr Phe Ile Ser Asp Asn
                805                 810                 815

Val Gln Thr Leu Met Gly Tyr Thr Pro Gly Asp Phe Ile Thr His Pro
            820                 825                 830

Arg Phe Trp Ala Asp Arg Ile Tyr Pro Glu Asp Ala Pro Arg Ile Phe
        835                 840                 845

Ala Gly Leu Ser Arg Leu Phe Glu Gln Gly Tyr His Thr His Glu Tyr
    850                 855                 860

Arg Phe Leu Tyr Gln Asp Gly Phe Tyr His Trp Val Arg Asn Glu Leu
865                 870                 875                 880

Arg Leu Phe Cys Asp Pro Ala Gly His Pro Leu Glu Ile Val Gly Tyr
                885                 890                 895

Cys Ala Asp Ile Ser Asp Leu Lys Gln Val Glu Met Glu Leu Ala Glu
            900                 905                 910

Ser Glu Ala Gln Phe Arg Cys Met Val Glu Gly Val Asn Asp Leu Ile
        915                 920                 925

Trp Ser Val Asn Asp Gln Asn Arg Phe Thr Tyr Leu Ser Pro Gln Phe
    930                 935                 940

Ala Thr Leu Phe Gly Trp Glu Gly Arg Glu Trp Ile Gly His Phe Ala
945                 950                 955                 960

Arg Glu Leu Ile His Pro Asp Asp His Pro Lys Leu Ala Asp Tyr Thr
                965                 970                 975
```

-continued

```
Gln Gln Val Met Glu Gly Arg Ser Leu Asp Asn Leu Glu Phe Arg His
            980                 985                 990

Arg His Gln Asp Gly His Phe Val  Trp Val Arg Ser Ser  Ala Thr Pro
        995                 1000                1005

Leu Ile  Ser Ser Thr Gly Asn  Val Ile Gly Ala Gln  Gly Ile Leu
    1010                 1015                 1020

Ser Asp  Ile Thr Thr Leu Lys  Gln Ala Glu Met Ala  Leu Gln Gln
    1025                 1030                 1035

Ser Glu  Asn Arg Phe Arg Arg  Val Phe Ser Ser Asn  Val Val Gly
    1040                 1045                 1050

Met Met  Phe Thr Asp Phe Ser  Gly Ala Ile Phe Asp  Ala Asn Asp
    1055                 1060                 1065

Arg Phe  Leu Ala Met Val Gly  Tyr Ser Arg Ala Glu  Leu Gln Ala
    1070                 1075                 1080

Gly Glu  Leu Asn Trp Val Thr  Leu Thr Pro Leu Glu  Tyr Val Gln
    1085                 1090                 1095

Trp Asp  Ile Gln Ala Met Leu  His Leu Glu Lys Tyr  Gly Ser Ile
    1100                 1105                 1110

Glu Pro  Trp Glu Lys Glu Tyr  Tyr Arg Ala Asp Gly  Ser Arg Ile
    1115                 1120                 1125

Ala Val  Leu Ile Gly Val Ala  Leu Leu Ser Glu Thr  Gly Ser Ser
    1130                 1135                 1140

Cys Val  Cys Val Val Met Asp  Ile Ser Asp Arg Lys  His Ala Glu
    1145                 1150                 1155

Gln Thr  Ile Gln Gln Gln Ile  Gln Lys Glu Thr Leu  Leu Arg Glu
    1160                 1165                 1170

Leu Thr  Gln Arg Ile Arg Gln  Ser Leu Asp Leu Gln  Thr Ile Phe
    1175                 1180                 1185

Thr Thr  Ala Cys Gln Glu Ile  Arg Gln Val Leu Gln  Ala Asp Arg
    1190                 1195                 1200

Val Gly  Ile Phe Gln Phe Tyr  Pro Thr Ser Asn His  Asn Asp Gly
    1205                 1210                 1215

Glu Phe  Val Ala Glu Ser Val  Val Glu Gly Leu Pro  Ser Val Leu
    1220                 1225                 1230

Ala Thr  Pro Leu His Asp His  Cys Phe Gly Glu Gln  Tyr Ala Pro
    1235                 1240                 1245

Leu Tyr  Val Gln Gly Arg Tyr  Val Ala Met Glu Asp  Ile Ser Gln
    1250                 1255                 1260

Leu Asp  Pro Cys His Thr Asp  Leu Leu Asn Gln Phe  Gln Val Lys
    1265                 1270                 1275

Ala Asn  Leu Val Ile Pro Leu  Ile Ser Gly Asn Asp  Leu Trp Gly
    1280                 1285                 1290

Leu Leu  Cys Ile His Gln Cys  Arg Ser Thr Arg Arg  Trp Gln Ala
    1295                 1300                 1305

Thr Glu  Ile Asp Leu Ser Gln  Gln Leu Ala Thr Gln  Leu Ala Ile
    1310                 1315                 1320

Ala Phe  Gln Gln Ala Val Leu  Tyr Lys Gln Thr Gln  Leu Glu Leu
    1325                 1330                 1335

Gln Glu  Arg Gln Leu Ala Glu  Thr Thr Ile Ala Gln  Gln Leu Arg
    1340                 1345                 1350

Gln Gln  Lys Asn Leu Gly Thr  Ile Ile Gln His Ile  Arg Glu Ser
    1355                 1360                 1365
```

-continued

```
Leu Asp  Leu Gln Gln Ile Leu  Ala Thr Val Thr Gln  Gln Val Lys
    1370                 1375                 1380

Glu Ala  Leu Gln Gly Asp Arg  Val Ile Val Phe Gln  Leu Phe Pro
    1385                 1390                 1395

Asn Gly  Lys Ser Arg Ile Val  Glu Glu Ala Val Ser  Ser Gly Leu
    1400                 1405                 1410

Thr Val  Leu Lys Ala Gly His  Trp Glu Asp Glu Val  Trp Pro Gln
    1415                 1420                 1425

Glu Ile  Leu Asp Tyr Tyr Trp  Gln Gly Gln Pro Arg  Ile Val Ala
    1430                 1435                 1440

Asp Val  Met Asp Asp Arg Trp  Thr Asp Cys Leu Val  Gly Tyr Ser
    1445                 1450                 1455

Lys Gln  Gly Glu Ile Val Ser  Lys Ile Val Ala Pro  Ile Leu Gln
    1460                 1465                 1470

Asp Ile  His Thr Phe Glu Glu  Asn Pro Trp Ala Asn  Pro Ser Lys
    1475                 1480                 1485

Arg His  Gln Leu Trp Gly Val  Leu Val Ile His Ala  Cys Arg Gln
    1490                 1495                 1500

Pro Arg  Val Trp Lys Ala Glu  Glu Ala Gln Leu Leu  Gln Gln Ile
    1505                 1510                 1515

Ala Asn  Gln Leu Ala Ile Ala  Ile Gln Gln Ala Asn  Leu Phe Glu
    1520                 1525                 1530

Gln Leu  Gln Gln Glu Leu Thr  Glu Arg Gln Gln Thr  Gln Gln Gln
    1535                 1540                 1545

Leu Thr  Glu Arg Asn Gln Gln  Leu Ala Glu Ser Asn  Gln Lys Leu
    1550                 1555                 1560

Ala His  Ala Thr Arg Leu Lys  Asp Glu Phe Leu Ala  Asn Met Ser
    1565                 1570                 1575

His Glu  Leu Arg Thr Pro Leu  Asn Ala Ile Leu Gly  Met Thr Glu
    1580                 1585                 1590

Gly Leu  Thr Asp Val Ile Phe  Gly Ser Ile Asn Thr  Gln Gln Lys
    1595                 1600                 1605

Lys Ala  Leu Gln Thr Ile Asp  Arg Ser Ala His His  Leu Leu Glu
    1610                 1615                 1620

Leu Ile  Asn Asp Ile Leu Asp  Val Ala Lys Ile Glu  Ser Gly Gln
    1625                 1630                 1635

Ile Glu  Leu Asn Cys Ala Ala  Thr Ser Val Leu Leu  Leu Cys Gln
    1640                 1645                 1650

Ser Ser  Leu Ser Phe Ile Lys  Gln Gln Ala Leu Arg  Lys Asn Ile
    1655                 1660                 1665

His Leu  Glu Val Gln Ile Pro  Pro His Val Pro Asp  Val Trp Val
    1670                 1675                 1680

Asp Glu  Arg Arg Ile Arg Gln  Val Leu Ile Asn Leu  Leu Asn Asn
    1685                 1690                 1695

Ala Val  Lys Phe Thr Pro Glu  Gly Gly Ser Val Thr  Leu Ser Val
    1700                 1705                 1710

Gln Arg  Gln Leu Ile Val Gln  Asp Pro Pro Pro Leu  Gln Gly Ile
    1715                 1720                 1725

Thr Lys  Val Arg Val His Arg  Thr Pro Ile Glu Gln  Gln Leu Gly
    1730                 1735                 1740

Ile Gln  Leu Gln Thr Ser Gln  Phe Glu Val His Asn  Tyr Leu Arg
    1745                 1750                 1755

Ile Ala  Val Thr Asp Thr Gly  Ile Gly Ile Pro Ser  His Tyr Leu
```

```
    1760                1765                1770

His Lys  Leu Phe Gln Pro Phe  Val Gln Ile Asp Ser  Ala Leu Asn
    1775                1780                1785

Arg Gln  Tyr Thr Gly Thr Gly  Leu Gly Leu Ala Leu  Val Lys Arg
    1790                1795                1800

Ile Val  Glu Leu His Gly Gly  Glu Val Gly Val Thr  Ser Thr Glu
    1805                1810                1815

Gly Ala  Gly Ser Cys Phe Thr  Ile Asp Leu Pro Cys  Val Ser Gly
    1820                1825                1830

Ser Ser  Ser Ser Ser Ser Pro  Phe Leu Ala Glu Ser  Ser Pro Ala
    1835                1840                1845

His Leu  Ser Asp Pro Ala Asn  Pro Pro Cys Ile Leu  Leu Ala Glu
    1850                1855                1860

Asp Asn  Glu Ala Asn Ile Ser  Thr Ile Ser Ser Tyr  Leu Lys Ala
    1865                1870                1875

Lys Gly  Tyr Arg Val Leu Val  Ala Lys Asn Gly Gln  Glu Ala Ile
    1880                1885                1890

Asp Leu  Gly Gln Ala Ala Gln  Pro Asp Leu Ile Leu  Met Asp Ile
    1895                1900                1905

Gln Met  Pro Gly Val Asp Gly  Leu Ser Ala Ile Gln  Gln Leu Arg
    1910                1915                1920

Gln Ala  Pro Ser Ser Ala His  Leu Pro Ile Ile Ala  Leu Thr Ala
    1925                1930                1935

Leu Ala  Met Asn Gly Asp Arg  Asp Arg Cys Leu Ala  Ala Gly Ala
    1940                1945                1950

Asn Glu  Tyr Leu Ser Lys Pro  Val Lys Leu Ser Gln  Leu Val Ile
    1955                1960                1965

Leu Ile  Gln Gln Leu Leu Thr  Gln Ser
    1970                1975
```

<210> SEQ ID NO 46
<211> LENGTH: 1486
<212> TYPE: PRT
<213> ORGANISM: Unknown
<220> FEATURE:
<223> OTHER INFORMATION: Cyanothece sp. PCC 7822

<400> SEQUENCE: 46

```
Met Ile Ile Pro Phe Pro Gln Leu Thr Pro Ala Ile Val Arg Asn Pro
1               5                   10                  15

Leu Val Leu Ser Pro Asp Thr Lys Val Leu Glu Ala Ile Thr Ser Leu
            20                  25                  30

Ile Asn Gln Arg Ser Gln Pro Val Lys Ser Asn Cys Ala Val Val Val
        35                  40                  45

Glu Asn Gly Gln Ile Val Gly Ile Val Thr Lys Gly Asp Ile Leu Val
    50                  55                  60

Ala Leu Ala Gln Ser Gln Thr Leu Asp Phe Leu Thr Ile Ser Gln Val
65                  70                  75                  80

Met Ser Ser Pro Val Val Met Leu Arg Glu Ser Glu Phe Thr Gly Leu
                85                  90                  95

Glu Ser Ala Ile Asn Leu Phe Gln Thr His Ser Ile Asp His Leu Pro
            100                 105                 110

Ile Ile Asp Ser Glu Asn His Leu Val Gly Leu Leu Thr Ser Asp Ser
        115                 120                 125

Leu Ser Ala Val Ile Gln Ser Tyr Ile Met Lys Asp Gln Lys Ile Ala
```

```
    130                 135                 140

Glu Lys Lys Thr Thr Leu Gln Leu Glu Asn Ser Phe Gln Ala Ala Ile
145                 150                 155                 160

Leu Asp Glu Ile Asn His Ile Ser Ser Pro Lys Gln Glu Gln Arg Lys
                165                 170                 175

Leu Gln Glu Ser Glu Leu Asn Tyr Thr Ser Leu Ala Glu Ile Ala Pro
            180                 185                 190

Ile Gly Ile Phe Arg Thr Asp Thr Gln Gly Tyr Cys Val Tyr Val Asn
        195                 200                 205

Pro Arg Trp Cys Glu Ile Ala Gly Leu Thr Ser Glu Glu Ala Lys Gly
    210                 215                 220

Lys Gly Trp Glu Gln Val Leu His Pro Asp Asp Asp Asp Glu Val Ser
225                 230                 235                 240

Ala Gln Trp Tyr Arg Ser Val Glu Glu Asn Arg Leu Phe Gln Leu Glu
                245                 250                 255

Tyr Arg Phe Lys Arg Pro Asn Gly Glu Ile Arg Tyr Val Tyr Gly Gln
            260                 265                 270

Ser Val Ala Leu Arg Asp Ile Asn Gln Gln Ile Ile Gly Tyr Leu Gly
        275                 280                 285

Thr Ile Thr Asp Ile Thr Glu Gln Lys Lys Thr Glu Tyr Arg Leu Lys
    290                 295                 300

Glu Ala Leu Arg Leu Ala Lys Leu Gly Asn Trp Glu Leu Asp Val Gln
305                 310                 315                 320

Asn Asn Ile Gly Tyr Trp Ser Glu Glu Val Phe His Ile Phe Gly Arg
                325                 330                 335

Glu Pro Gln Pro Phe Ser Pro Ser Phe Asp Gly Phe Leu Glu Leu Val
            340                 345                 350

His Pro Asp Asp Arg Ser Lys Val Val Ala Ser Tyr Thr Gln His Leu
        355                 360                 365

Glu Lys Arg Ile Pro His Glu Val Val His Arg Val Pro Met Pro Asp
    370                 375                 380

Gly Arg Ile Lys Val Val Val Glu Arg Cys Glu Thr Ala Tyr Asp Ala
385                 390                 395                 400

Glu Gly Lys Pro Ile His Ser Leu Gly Thr Val Gln Asp Ile Thr Glu
                405                 410                 415

Tyr Tyr Lys Gln Glu Thr Ile Leu Lys Lys Leu Leu Ala Gly Thr Ser
            420                 425                 430

Asn Thr Leu Thr Gln Glu Phe Phe Ser Ala Leu Val Arg His Ile Ala
        435                 440                 445

Glu Ala Leu Glu Val Ser Tyr Val Ile Ile Ala Glu Leu Ile Asp Glu
    450                 455                 460

Arg Leu His Thr Phe Ala Phe Trp Gly Asp Glu Gln Leu Gln Lys Asn
465                 470                 475                 480

Ile Asp Val Ala Ile Cys Gln Thr Pro Cys Glu Tyr Val Ile Lys Asp
                485                 490                 495

Gly Phe Phe Tyr Cys Ser His Ser Ile Gln Glu Gln Phe Pro Gln Asn
            500                 505                 510

Thr His Leu Ala Gln Met Gln Ala Glu Ser Tyr Leu Gly Ile Val Leu
        515                 520                 525

Thr Asp Lys Asn Ser His Pro Ile Gly Ile Leu Cys Val Leu Asp Val
    530                 535                 540

Lys Pro Met Asp Arg Glu Thr Ala Glu Met Ile Gln Gln Ile Leu Gln
545                 550                 555                 560
```

```
Ile Phe Ala Gly Arg Ala Ser Ala Glu Leu Glu Arg Lys Arg Ser Asp
                565                 570                 575

Glu Ala Leu Gln Gln Leu Lys Ala Thr Leu Glu Ala Gln Val Glu Glu
            580                 585                 590

Arg Thr Gln Gln Leu Gln Glu Ser Gln Arg Phe Ile Gln Gln Ile Thr
        595                 600                 605

Asp Gln Ser Pro Ser Ile Leu Tyr Leu Tyr Asp Leu Gln Glu Gln Arg
    610                 615                 620

Asn Ile Tyr Ile Asn Gln Glu Val Ser Arg Ile Leu Gly Tyr Ser Pro
625                 630                 635                 640

Thr Glu Ile Gln Glu Met Gly Asn Leu Ile Ile Ser Arg Leu Ile His
                645                 650                 655

Pro Gln Asp Leu Ser Arg Phe Asn Arg Tyr Leu Glu Gln Leu Lys Gln
            660                 665                 670

Ala Gln Asp His Glu Ile Leu Gly Val Glu Tyr Arg Phe Gln Asp Ile
        675                 680                 685

Lys Gly Gln Trp Arg Trp Phe Ser Gly Arg Asp Ala Val Phe Ser Arg
    690                 695                 700

Asp Ser Gln Gly Arg Val Lys Gln Val Ile Gly Val Ala Gln Asp Ile
705                 710                 715                 720

Thr Glu Arg Lys Gln Ala Glu Gln Thr Leu Tyr Leu Gln Ala Gln Gln
                725                 730                 735

Glu Lys Leu Leu Arg Glu Ile Asn Gln Arg Ile Arg Gln Ser Leu Asp
            740                 745                 750

Leu Gln Thr Ile Phe Asp Thr Ala Cys Gln Glu Ile Leu Leu Leu Leu
        755                 760                 765

Gln Val Asp Arg Val Gly Ile Phe Arg Phe Asp Pro Glu Ser His Tyr
    770                 775                 780

Asp Asp Gly Glu Phe Ile Ala Glu Ala Met Val Ala Gly Leu Pro Ser
785                 790                 795                 800

Ala Ile Ala Ile His Val His Asp His Cys Phe Gly Glu Lys Phe Ser
                805                 810                 815

Ser Leu Tyr Ala Gln Gly Lys Phe Leu Ala Val Asp Asp Ile Asn Asn
            820                 825                 830

Ser Glu Leu Met Asp Cys His Arg Glu Ile Leu Ser Gln Phe Gln Ile
        835                 840                 845

Lys Ala His Leu Val Leu Pro Leu Leu Cys Glu Glu Gln Leu Trp Gly
    850                 855                 860

Leu Leu Cys Val His Gln Cys Tyr Asp Thr Arg His Trp Lys Glu Ala
865                 870                 875                 880

Glu Ile Lys Leu Leu Gln Gln Ile Thr His Gln Leu Thr Ile Ala Ile
                885                 890                 895

Gln Gln Ala Ser Leu Tyr Glu Gln Ile Arg Gln Lys Leu Arg Gln Gln
            900                 905                 910

Gln Ala Ile Ala Ala Ile Val Gln Gln Val Arg Gln Ser Leu Asn Ile
        915                 920                 925

Glu Glu Ile Leu Asn Thr Ile Thr Gln Asp Val Arg Ala Leu Phe Asp
    930                 935                 940

Cys Asp Arg Val Ile Ile Phe Arg Leu Tyr Ser Asp Gly Gly Ser Arg
945                 950                 955                 960

Ile Ile Glu Glu Ser Val Ser Thr Glu Phe Leu Pro Leu Lys Tyr Cys
                965                 970                 975
```

```
His Trp Asp Asp Glu Thr Trp Ser Gln Asp Ile Leu Asn Leu Tyr Trp
            980                 985                 990

Gln Gly Gln Pro Arg Ile Val Pro  Asp Val Met Asn Asp  Ile Tyr Thr
        995                 1000                 1005

Glu Cys  Leu His Glu Tyr Ser  Arg Glu Gly Gln Ile  Gln Ser Lys
    1010                 1015                 1020

Ile Val  Ala Pro Ile Leu Leu  Asp Leu Lys Glu Lys  Glu Asn His
    1025                 1030                 1035

Arg Trp  Val Ala Ser Thr Asn  Ser His Lys Leu Trp  Gly Ile Leu
    1040                 1045                 1050

Val Val  His Ala Cys Arg Glu  Lys Arg Val Trp Gln  Asn Ser Glu
    1055                 1060                 1065

Ala Gln  Leu Leu Gln Gln Ile  Ala Asn Gln Leu Ala  Ile Ala Ile
    1070                 1075                 1080

Gln Gln  Ala Ser Leu Phe Glu  Gln Leu Gln Val Glu  Ile Glu Asp
    1085                 1090                 1095

Lys Gln  Gln Lys Asn Ala Glu  Leu Asp Arg Ala Thr  Arg Leu Lys
    1100                 1105                 1110

Asp Glu  Phe Leu Ala Asn Met  Ser His Glu Leu Arg  Thr Pro Leu
    1115                 1120                 1125

Asn Ala  Ile Leu Gly Met Thr  Glu Gly Leu Gln Asp  Glu Ile Phe
    1130                 1135                 1140

Gly Gln  Ile Asn Glu Arg Gln  Arg Lys Ser Leu Lys  Ile Ile Glu
    1145                 1150                 1155

Gln Ala  Gly Asn His Leu Leu  Glu Leu Ile Asn Asp  Ile Leu Asp
    1160                 1165                 1170

Val Ser  Lys Ile Glu Ser Gly  Gln Leu Glu Leu His  Cys Thr Ser
    1175                 1180                 1185

Thr Glu  Ile Ile Pro Leu Cys  Gln Ser Ser Leu Ala  Phe Val Lys
    1190                 1195                 1200

Gln Gln  Ala Val Lys Lys Arg  Ile Gln Leu Asp Phe  Asn Ile Ser
    1205                 1210                 1215

Ser Asn  Ile Leu Met Leu Thr  Leu Asp Glu Arg Arg  Ile Arg Gln
    1220                 1225                 1230

Val Ile  Ile Asn Leu Leu Asn  Asn Ala Val Lys Phe  Thr Pro Glu
    1235                 1240                 1245

Gly Gly  Lys Val Gly Leu Glu  Val Val Gln Ile Gly  Glu Asn Thr
    1250                 1255                 1260

Val Arg  Phe Ala Val Lys Asp  Thr Gly Ile Gly Ile  Ala Ala Glu
    1265                 1270                 1275

Asn Ile  Pro Lys Leu Phe Gln  Pro Phe Met Gln Ile  Asp Ser Ala
    1280                 1285                 1290

Leu Asn  Arg Gln Tyr Thr Gly  Thr Gly Leu Gly Leu  Ala Leu Val
    1295                 1300                 1305

Lys Arg  Leu Val Asp Leu His  Gly Gly Glu Val Ser  Val Thr Ser
    1310                 1315                 1320

Glu Leu  Gly Val Gly Ser Cys  Phe Ser Val Asp Leu  Pro Leu Met
    1325                 1330                 1335

Glu Ser  Cys Ser Thr Asp Asn  Phe Phe Asp Phe Gln  Thr Pro Leu
    1340                 1345                 1350

Thr Pro  Glu Val Glu Ala Asn  Ser Val Asn Leu Lys  Asn Ala Pro
    1355                 1360                 1365

Leu Ile  Leu Leu Ala Glu Asp  Asn Glu Thr Asn Ile  Thr Thr Ile
```

```
    1370                1375                1380

Ser Asn  Tyr Leu Lys Ala Lys  Lys Tyr Lys Leu Ile  Leu Ala Lys
    1385                1390                1395

Asn Gly  Lys Glu Ala Ile Ser  Leu Ala Gln Ser Gln  Gln Pro Asp
    1400                1405                1410

Leu Ile  Leu Met Asp Ile Cys  Leu Pro Gly Ile Asn  Gly Leu Glu
    1415                1420                1425

Ala Ile  Gln Gln Ile Arg Gln  Leu Pro Asp Leu Lys  Asp Ile Pro
    1430                1435                1440

Ile Ile  Ala Val Thr Ala Leu  Ala Leu Thr Gly Asp  Arg Glu Arg
    1445                1450                1455

Cys Leu  Glu Ala Gly Ala Asn  Glu Tyr Leu Ser Lys  Pro Leu Lys
    1460                1465                1470

Leu Lys  Glu Leu Val Ala Leu  Ile Gln Ser Leu Leu  Glu
    1475                1480                1485


<210> SEQ ID NO 47
<211> LENGTH: 2001
<212> TYPE: PRT
<213> ORGANISM: Spirulina subsalsa

<400> SEQUENCE: 47

Met Gln Ser His Ser Phe Ser Ser Ile Asp Val Thr Glu Ala Ile Cys
1               5                   10                  15

Pro Arg Pro His Val Ile Ser Pro Thr Ala Thr Val Leu Glu Ala Ile
            20                  25                  30

Ala Leu Met Ser Gly Leu Ser Ala Pro Glu Val Ala Pro Pro Asp Pro
        35                  40                  45

Gln Asp Pro His Ser Thr Asp Leu Ser Pro Leu Ala Pro Leu Trp Lys
    50                  55                  60

Gly Gly Lys Glu Gly Gly Glu Glu Gly Gly Gly Ile Ser Ser Cys Val
65                  70                  75                  80

Leu Val Val Val Glu Arg Asp Ser Asp Glu Thr Gln Gly Gln Arg Val
                85                  90                  95

Val Gly Ile Leu Thr Glu Arg Asp Ile Val Arg Leu Ser Ala Gln Gln
            100                 105                 110

Gln Asp Ile Arg Glu Leu Ser Val Gly Glu Ala Met Thr Gln Pro Val
        115                 120                 125

Leu Thr Leu Arg Pro Ser Glu Leu Thr Asp Ile Phe Ser Leu Leu Gln
    130                 135                 140

Phe Leu Glu Gln His His Leu Arg His Val Pro Ile Val Asp Glu Gln
145                 150                 155                 160

Glu Arg Leu Met Gly Leu Ile Ser His Glu Thr Leu Arg Asn Leu Ala
                165                 170                 175

Arg Pro Val Asp Leu Leu Arg Leu Arg Ser Val Gln Glu Val Met Thr
            180                 185                 190

Gln Thr Val Leu Thr Ala Ser Pro Asp Ala Ser Leu Leu Glu Ile Ala
        195                 200                 205

Gln Leu Leu Ala Glu Asn Arg Leu Ser Ser Val Ile Leu Thr Arg Pro
    210                 215                 220

Leu Ala Gly Gly Asp Leu Gly Glu Tyr Pro Val Gly Ile Val Thr Glu
225                 230                 235                 240

Arg Asp Val Val Gln Phe Gln Ala Leu Gly Gly Asn Phe Gly Glu Ile
                245                 250                 255
```

-continued

```
Leu Ala Glu Glu Val Met Ser Ser Pro Leu Phe Thr Leu Arg Pro Asp
            260                 265                 270

Ala Asp Leu Trp Thr Ala Gln Gln Ala Met Glu Lys Arg Arg Ile Arg
        275                 280                 285

Arg Val Val Val Thr Gly Glu Gly Gly Glu Leu Leu Gly Ile Val Thr
    290                 295                 300

Gln Thr Ser Leu Leu Arg Ser Phe Asn Pro Leu Glu Leu Tyr Arg Leu
305                 310                 315                 320

Ala Glu Val Leu Glu Gln Lys Val Ala Arg Leu Glu Ala Glu Arg Val
                325                 330                 335

Thr Leu Leu Glu Arg Arg Thr Gln Glu Leu Glu Gln Gln Val Gln Glu
            340                 345                 350

Arg Thr Gln Thr Ile Glu Ala Gln Ala Glu Arg Val Arg Leu Leu Leu
        355                 360                 365

Asp Ile Ala Thr Ser Leu Arg Asn Ser Leu Asp Leu Gly Thr Ile Leu
    370                 375                 380

Gln Thr Ala Val Asp Glu Val Arg Arg Val Leu Glu Cys Asp Arg Val
385                 390                 395                 400

Met Ile Tyr Gln Leu Glu Glu Gly Leu Arg Gly Glu Ile Ile Ala Glu
                405                 410                 415

Ser Met Ile Ser Gly Gly Arg Ser Val Leu His Arg Glu Ala Asn Asp
            420                 425                 430

Pro Cys Val Thr Pro Glu Trp Leu Glu Ser Tyr Arg Gln Gly Arg Val
        435                 440                 445

Arg Val Val Arg Asp Ile Tyr Glu Glu Ser Leu Ser Leu Cys His Gln
    450                 455                 460

Glu Met Leu Leu Ser Phe Glu Ile Arg Ala Lys Leu Met Val Pro Ile
465                 470                 475                 480

Val Leu Glu Glu His Leu Trp Gly Leu Met Ile Ala Ser Tyr Arg Asp
                485                 490                 495

Gln Pro Arg Asp Trp Gln Thr Trp Glu Val Glu Leu Leu Gln Ala Leu
            500                 505                 510

Ser Leu Gln Leu Ala Ile Ala Leu Gln Gln Ala Gly Gln His Gln Gln
        515                 520                 525

Leu Gln Asn Glu Ile Arg Glu Arg Gln Gln Ala Glu Gln Asp Leu Ala
    530                 535                 540

Ala Leu Asn Ala Gln Leu Glu Ala Arg Val Ala Gln Arg Thr Ala Glu
545                 550                 555                 560

Leu Glu Ser Arg Glu Ala Arg Tyr His Ala Leu Met Glu Gly Ala Ser
                565                 570                 575

Asp Ala Ile Leu Leu Ala Thr Pro Gln Gly Tyr Ile Ile Glu Ala Asn
            580                 585                 590

Ala Ala Ala Glu Glu Leu Phe Gly Tyr Ser Arg Ser Glu Leu Thr Gln
        595                 600                 605

Leu His Tyr Ser Gln Leu Cys Pro Pro Glu Glu Leu Gln Pro Val Thr
    610                 615                 620

Gln Val Trp Gln Ser Leu Val Asn Pro Gln Gln Arg Val Leu Trp Asp
625                 630                 635                 640

Gly Phe Ile Leu His Ala Glu Gly His Ser Ile Pro Ile Ala Leu Ser
                645                 650                 655

Gly Thr Met Ile Glu Val Gly Asp Ser Ile Ile Phe Gln Gly Ile Phe
            660                 665                 670

Arg Asp Ile Ser Ala Arg Gln Gln Ala Glu Ala Ala Leu Ala Lys Leu
```

-continued

```
        675                 680                 685

Ser Gln Arg Leu Ser Ile Ala Leu Ser Ser Ala Ala Leu Gly Cys Trp
    690                 695                 700

Glu Trp Asp Ile Ala Gln Asn Cys Leu Thr Trp Asp Lys Arg Met Tyr
705                 710                 715                 720

Ala Leu Tyr Gly Val Glu Ser Arg Val Pro Pro Asp Asp Pro Ser Thr
                725                 730                 735

Val Thr Val Ala Tyr Glu Val Trp Ser Lys Gly Val His Pro Glu Asp
            740                 745                 750

Arg Gln Arg Thr Glu Thr Leu Leu Gln Gln Ala Leu Leu Gly Glu Ala
        755                 760                 765

Glu Tyr Asn Thr Glu Phe Arg Val Val His Pro Asp Gly Ser Leu His
    770                 775                 780

Tyr Ile Arg Ala Tyr Gly Val Val Leu Arg Asp Ala Ala Gly His Pro
785                 790                 795                 800

Gln Ser Met Ile Gly Val Asn Leu Asp Val Thr Asp Thr His Glu Ala
                805                 810                 815

Gln Arg Glu Leu Gln Ala Ser Glu Thr Arg Phe Arg Gln Val Phe Asp
            820                 825                 830

Ser Asn Val Val Gly Met Met Phe Thr Asn Phe Val Gly Glu Ile Thr
        835                 840                 845

Glu Ala Asn Asp Arg Phe Leu Ala Met Leu Gly Tyr Ser Arg Asp Asp
    850                 855                 860

Leu His Ala Gly Arg Leu Asn Trp Ala Asp Leu Thr Pro Pro Glu Tyr
865                 870                 875                 880

Gln Gln Gln Asp Val Glu Ala Ile Tyr His Leu Leu Thr Tyr Asn Ser
                885                 890                 895

Ile Asp Pro Phe Glu Lys Val Tyr Leu His Arg Asp Gly His Pro Val
            900                 905                 910

Ala Val Leu Leu Gly Val Ala Met Val Cys Pro Ala Glu Gly Thr Cys
        915                 920                 925

Val Cys Val Val Val Asp Ile Ser Asp Arg Lys Gln Ala Glu Ile Ala
    930                 935                 940

Leu Gln Glu Ser Gln Leu Arg Leu Glu Leu Ala Leu Glu Ser Ser Asn
945                 950                 955                 960

Thr Gly Leu Trp Asp Trp Asn Met Gln Thr Gly Glu Leu Trp Phe Asn
                965                 970                 975

Lys Gln Trp Lys Thr Met Leu Gly Tyr Gly Glu Asp Glu Leu Glu Asn
            980                 985                 990

Gln Leu Arg Glu Trp Glu Ser Arg  Val His Pro Asp Asp  Leu Pro Gln
        995                 1000                1005

Thr Tyr  Gln Glu Val Glu Gln  His Ile Lys Gly Gln  Thr Asp Val
    1010                 1015                 1020

Tyr Arg  Asn Glu His Arg Leu  Arg Gly Lys Asp Gly  Ser Tyr His
    1025                 1030                 1035

Trp Val  Leu Ala Gln Gly Arg  Ile Val Glu Arg Asp  Gly Val Gly
    1040                 1045                 1050

Asn Pro  Leu Arg Phe Ile Gly  Thr His Thr Asp Ile  Ser Asp Arg
    1055                 1060                 1065

Lys Asn  Asn Glu Leu Glu Arg  Gln Lys Leu Leu Gln  Glu Leu Ser
    1070                 1075                 1080

Ser Phe  Lys Phe Ala Leu Asp  Gln Ser Ala Ile Val  Val Thr Thr
    1085                 1090                 1095
```

```
Asn Leu  Lys Gly Gln Ile Leu  Tyr Ile Asn Asp Arg  Phe Glu Ser
    1100                 1105                 1110

Ile Ser  Gly Tyr Ser Gln Pro  Glu Ile Leu Gly Lys  Thr Pro Gln
    1115                 1120                 1125

Ile Leu  Asn Ser Lys Tyr His  Pro Pro Gly Phe Phe  Ala His Leu
    1130                 1135                 1140

Trp Thr  Thr Ile Leu Asn Gly  Gln Val Trp Arg Asn  Glu Ile Cys
    1145                 1150                 1155

Asn Arg  Ala Lys Asn Gly Gln  Ile Tyr Trp Val Asp  Ala Thr Ile
    1160                 1165                 1170

Ile Pro  Phe Leu Asn Pro Gln  Gly Gln Pro Thr Gln  Phe Leu Ser
    1175                 1180                 1185

Ile Gln  Phe Asp Ile Thr Ser  Arg Lys Gln Val Glu  Leu Asp Leu
    1190                 1195                 1200

Ala Ser  Ser Asn Ser Leu Leu  Ser Thr Ile Thr His  Ala Gln Ala
    1205                 1210                 1215

Gln Phe  Ile Thr Ala Ala Asn  Arg Leu Thr Ile Phe  Glu Gly Leu
    1220                 1225                 1230

Leu Glu  Ser Leu Leu Glu Leu  Thr His Ser Glu Tyr  Gly Phe Ile
    1235                 1240                 1245

Gly Glu  Val Leu Phe Gln Gly  Asp Gly Thr Ala His  Met Glu Glu
    1250                 1255                 1260

Asn Phe  Leu Lys Ile Arg Gly  Val Pro Tyr Leu Gln  Thr His Ser
    1265                 1270                 1275

Ile Thr  Asn Ile Ala Trp Asp  Ala Ala Thr Glu Gln  Phe Tyr Gln
    1280                 1285                 1290

Asn Asn  Tyr Glu Lys Gly Met  Glu Phe Thr Asn Leu  Lys Thr Leu
    1295                 1300                 1305

Phe Gly  Ala Val Ile Leu Thr  Gly Lys Pro Val Ile  Ala Asn Gln
    1310                 1315                 1320

Ala Pro  Thr Asp Pro Arg Arg  Gly Gly Ile Pro Lys  Gly His Pro
    1325                 1330                 1335

Pro Leu  Glu Ala Phe Leu Gly  Ile Pro Phe Phe Lys  Gly Pro Glu
    1340                 1345                 1350

Leu Ile  Gly Met Val Gly Ile  Ala Asn Arg Pro Gly  Gly Tyr Asn
    1355                 1360                 1365

Glu Gly  Ile Ile Ala Arg Leu  Gly Pro Phe Leu Thr  Thr Cys Ser
    1370                 1375                 1380

Asn Leu  Ile Glu Gly Tyr Arg  Met Asp Arg His Arg  Gln Lys Ala
    1385                 1390                 1395

Glu Ala  Met Ile Ala Gln Gln  Leu Arg Gln Arg Thr  Val Leu Gly
    1400                 1405                 1410

Gln Ile  Val Gln Gln Ile Arg  Glu Ser Leu Asn Leu  Gln Glu Ile
    1415                 1420                 1425

Leu Ala  Ile Thr Thr Gln Arg  Val Arg Glu Ile Leu  Gln Gly Asp
    1430                 1435                 1440

Arg Val  Ile Val Phe Arg Phe  Cys Asp Leu Gly Arg  Thr Cys Ile
    1445                 1450                 1455

Phe Glu  Glu Ala Val Ala Glu  Asp Leu Pro Ser Leu  Lys Tyr Met
    1460                 1465                 1470

Asn Trp  Glu Asp Glu Gln Trp  Ser Ser Glu Ile Leu  Gln Phe Tyr
    1475                 1480                 1485
```

```
Trp Gln  Gly Gln Pro Arg Ile  Val Pro Asp Val Met  Asn Asp Pro
    1490                 1495                 1500

Leu Thr  Pro Cys Leu Leu Asp  Tyr Ser Arg Gln Gly  Gln Ile Gln
    1505                 1510                 1515

Ser Lys  Ile Val Ala Pro Ile  Leu Gln Glu Ile His  Asn Gly Glu
    1520                 1525                 1530

Arg Gly  Asn Gly Glu Ile Asp  Pro Trp Thr Asp Pro  Glu Ser Gly
    1535                 1540                 1545

Asn Lys  Leu Trp Gly Leu Leu  Val Ile His Ala Cys  His Glu Lys
    1550                 1555                 1560

Arg Ile  Trp Gln Glu Ser Glu  Ala Glu Leu Leu Gln  Gln Ile Ala
    1565                 1570                 1575

Asn Gln  Leu Ala Ile Ala Ile  Arg Gln Ser Arg Leu  Phe Glu Gln
    1580                 1585                 1590

Leu Gln  Glu Glu Leu Thr Glu  Arg Gln Gln Thr Gln  Ile Gln Leu
    1595                 1600                 1605

Thr Gln  Arg Asn Glu Glu Leu  Ile Arg Ala Thr Arg  Leu Lys Asp
    1610                 1615                 1620

Glu Phe  Leu Ala Asn Met Ser  His Glu Leu Arg Thr  Pro Leu Asn
    1625                 1630                 1635

Ala Ile  Leu Gly Met Thr Glu  Gly Leu Gln Asp Gly  Val Phe Gly
    1640                 1645                 1650

Ser Val  Asn Glu Gly Gln Arg  Lys Ala Leu Ser Thr  Ile Glu Arg
    1655                 1660                 1665

Ser Gly  Ser His Leu Leu Ala  Leu Ile Asn Asp Ile  Leu Asp Leu
    1670                 1675                 1680

Ala Lys  Ile Glu Ser Gly Gln  Val Glu Leu Glu Cys  Ala Pro Thr
    1685                 1690                 1695

Ala Ile  Ala Ser Leu Cys Gln  Ser Ser Ile Thr Phe  Val Lys Gln
    1700                 1705                 1710

Gln Ala  Leu Lys Lys His Leu  His Leu Ser Val Asn  Leu Pro Val
    1715                 1720                 1725

Asn Leu  Pro Asp Ile Val Leu  Asp Glu Arg Arg Ile  Arg Gln Val
    1730                 1735                 1740

Leu Ile  Asn Leu Leu Asn Asn  Ala Val Lys Phe Thr  Pro Glu Gly
    1745                 1750                 1755

Gly Arg  Val Thr Leu Glu Val  Thr Leu Pro Thr Pro  Glu Gln Asn
    1760                 1765                 1770

Ser Leu  Pro His Leu Arg Phe  Ser Val Ile Asp Thr  Gly Ile Gly
    1775                 1780                 1785

Ile Thr  Pro Glu Asn Leu Lys  Lys Leu Phe Gln Pro  Phe Ile Gln
    1790                 1795                 1800

Ile Asp  Ser Ala Leu Asn Arg  Gln Tyr Gln Gly Thr  Gly Leu Gly
    1805                 1810                 1815

Leu Ala  Val Thr Lys Arg Ile  Val Glu Leu His Gly  Gly Gln Val
    1820                 1825                 1830

Gly Val  Ser Ser Glu Glu Gly  Lys Gly Ser Cys Phe  Met Ile Asp
    1835                 1840                 1845

Leu Pro  Tyr Gln Ala Ser Val  Val Phe Ala Pro Gln  Thr Asn Ser
    1850                 1855                 1860

Glu Ser  His Phe Asp Pro His  Asp Leu Ala Thr Gln  Ser Pro Gly
    1865                 1870                 1875

Lys Ser  Ser Pro Leu Leu Leu  Leu Ala Glu Asp Asn  Glu Ala Asn
```

```
    1880                1885                1890

Ile Ser  Thr Ile Ser Ser Tyr  Leu Met Ala Lys Gly  Tyr Arg Ile
    1895                1900                1905

Glu Val  Ala Lys Asn Gly Gln  Glu Ala Ile His Gln  Ala Val Ala
    1910                1915                1920

Leu Ser  Pro Asp Leu Ile Leu  Met Asp Val Gln Met  Pro Gly Met
    1925                1930                1935

Asp Gly  Leu Glu Ala Met Lys  Arg Met Arg Glu Ile  Pro Glu Leu
    1940                1945                1950

Ala Thr  Thr Pro Ile Ile Ala  Leu Thr Ala Leu Ala  Met Asp Ser
    1955                1960                1965

Asp Arg  Asp Arg Cys Leu Gln  Ala Gly Ala Asp Glu  Tyr Leu Ser
    1970                1975                1980

Lys Pro  Val Lys Leu Lys Gln  Leu Thr Leu Thr Ile  Gln Gly Leu
    1985                1990                1995

Leu Lys  Ser
    2000


<210> SEQ ID NO 48
<211> LENGTH: 1251
<212> TYPE: PRT
<213> ORGANISM: Unknown
<220> FEATURE:
<223> OTHER INFORMATION: Synthetic Construct

<400> SEQUENCE: 48

Met Pro Leu Ala Leu Ser Gln Ile Phe His Arg Leu Ile Ala Asn Val
1               5                   10                  15

Pro Leu Arg Trp Val Leu Thr Ile Pro Phe Val Leu Pro Thr Ile Gly
            20                  25                  30

Ala Val Ala Ile Val Gly Tyr Leu Ser Tyr Arg Asp Gly Gln Glu Ala
        35                  40                  45

Val Glu Asp Leu Gly His Gln Leu Val Ala Glu Thr Asn Glu Arg Val
    50                  55                  60

Lys Gln Glu Leu Glu Thr Tyr Leu Gln Thr Pro Val Leu Ile Asn Arg
65                  70                  75                  80

Leu Asn Val Asp Ala Val Ala Arg Gly Gln Leu Asp Leu Gln Asn Ile
                85                  90                  95

Val Ala Leu Glu Ala Val Leu Phe Ala Arg Leu Gln Gln Phe Glu Arg
            100                 105                 110

Val Ser Ala Val Leu Phe Ala Ser Pro Gln Gly Thr Phe Arg Leu Val
        115                 120                 125

Asp Arg Leu Pro Asp Leu Tyr Leu Val Val Ala Asp Pro Pro Arg Pro
    130                 135                 140

Glu Gln Ile Leu Ile Tyr Ser Leu Asn Ser Asp Gly Ser Arg Lys Glu
145                 150                 155                 160

Leu Val Arg Thr Asn Glu Gly Leu Asp Val Arg Arg Asp Asn Pro Trp
                165                 170                 175

Tyr Arg Arg Ala Val Arg Thr Gly Lys Pro Gly Trp Ser Pro Ile Ala
            180                 185                 190

Gln Tyr Gly Ser Leu Asn Phe Leu Thr Leu Asp Ala Ser Gln Pro Val
        195                 200                 205

Tyr Asp Arg Thr Thr Lys Ser Leu Leu Gly Val Phe Ala Val His Ile
    210                 215                 220

Arg Leu Asp Tyr Leu Ser Glu Phe Leu His His Leu Asp Ile Ser Arg
```

-continued

```
225                 230                 235                 240

Ser Gly Arg Val Ile Ile Met Asp Arg Asn Gly Ala Leu Ile Ala Thr
                245                 250                 255

Ser Thr Glu Glu Gln Pro Tyr Lys Phe Leu Ala Gly Thr Gly Tyr Gln
            260                 265                 270

Arg Gln Phe Glu Gln Ile Asn Ile Asp Glu Ser Gln Asp Asn Leu Thr
        275                 280                 285

Arg Ser Leu Gly Lys Tyr Leu Arg Lys Arg Pro Glu Ile Leu Lys Ser
    290                 295                 300

Leu Glu Arg Thr Arg Leu Leu Asp Phe Arg Tyr Asn Gly Glu Leu Gln
305                 310                 315                 320

Leu Val Gln Ile Ala Pro Phe Gln Asp Gln Tyr Gly Leu Asn Trp Gln
                325                 330                 335

Ile Val Thr Val Ile Pro Lys Ser His Phe Leu Lys Asp Ile Gln Glu
            340                 345                 350

Asn Lys Arg Thr Thr Ala Leu Leu Cys Leu Leu Thr Leu Gly Val Ala
        355                 360                 365

Leu Ala Leu Gly Leu Val Ala Ala Asp Lys Leu Thr Ala Ser Phe Ala
    370                 375                 380

Arg Leu Ser Arg Val Ser Arg Glu Leu Ala Ala Gly Asn Leu Ala Arg
385                 390                 395                 400

Arg Leu Pro Thr Asp Ser Ser Ile Tyr Glu Leu Asn Gly Leu Ala Gln
                405                 410                 415

Thr Phe Asn Gln Met Ala Asp Gln Leu Gln Gln Ser Phe Asp Arg Ile
            420                 425                 430

Gln Ile Ala Leu Glu Glu Ser Glu Glu Lys Phe Ala Thr Val Phe Arg
        435                 440                 445

Thr Ser Pro Asp Pro Met Ala Ile Ala Ser Leu Ala Glu Gly Arg Ile
    450                 455                 460

Leu Glu Val Asn Asp Ser His Val Asp Phe Phe Gly Tyr Ser Arg Ala
465                 470                 475                 480

Glu Thr Ile Gly Arg Thr Val Leu Val Leu Asn Leu Trp Ser Asn Leu
                485                 490                 495

Asp Glu Arg Glu Lys Phe Arg Ala Leu Leu His Gln Gln Gly Ser Val
            500                 505                 510

Arg Asn Leu Glu Ala Gln Leu Arg Thr Lys Ser Gly Glu Val Arg Thr
        515                 520                 525

Val Leu Val Ser Ala Glu Val Gln Thr Leu Glu Gly Gln Asp Cys Thr
    530                 535                 540

Ile Ile Val Leu Arg Asp Ile Ser Glu Arg Lys Gln Ala Gln Ala Ala
545                 550                 555                 560

Leu Gln Glu Ser Glu Thr Arg Phe Arg Gln Leu Ala Glu Thr Val Arg
                565                 570                 575

Glu Gly Phe Phe Val Tyr Glu Thr Lys Ser Asp His Tyr Ser Tyr Val
            580                 585                 590

Asn Pro Ala Tyr Ala Ala Ile Met Gly Thr Pro Ala Gln Leu Phe Tyr
        595                 600                 605

Gln Gly Met Phe His Trp Leu Asn Asn Ile His Pro Asp Asp Cys Asp
    610                 615                 620

His Ile Glu Ala Gly Leu Leu Arg Glu His Gln Gly Glu Asn Phe Asp
625                 630                 635                 640

Glu Glu Tyr Arg Phe Ile Arg Pro Asn Gly Glu Ile Arg Trp Leu Arg
                645                 650                 655
```

-continued

```
Ser Lys Ala Phe Pro Leu Arg Asp Glu Thr Lys Thr Ile Val Arg Ile
            660                 665                 670

Val Gly Thr Val Glu Asp Ile Thr Glu Arg Lys Gln Leu Glu Gln Ser
        675                 680                 685

Leu Arg Ser Gln Ala Glu Glu Glu Arg Leu Ile Thr Thr Ile Thr Gln
    690                 695                 700

Asn Ile Arg Gln Ser Leu Asp Leu Lys Lys Ile Leu Ala Thr Thr Val
705                 710                 715                 720

Ile Glu Val Gln Gln Thr Leu Asn Ala Glu Arg Val Leu Ile Phe Arg
                725                 730                 735

Met Asn Pro Asp Gly Ser Gly Gln Val Ile Glu Glu Ala Val Val Pro
            740                 745                 750

Lys Tyr Pro Val Thr Asp Gln Met Arg Trp Glu Asp Glu His Phe Pro
        755                 760                 765

Glu Asp Cys Tyr Glu Tyr Tyr Arg Gln Gly Ile Pro Arg Ile Val Pro
    770                 775                 780

Asp Val Ala Thr Asp Glu Trp Ala Lys Cys Leu Val Glu Phe Met Gln
785                 790                 795                 800

Glu Val Gly Val Lys Ser Lys Val Val Ala Pro Ile Val Gln Val Tyr
                805                 810                 815

Glu Lys Ser Ser Thr Asn Ala Lys Val Trp Gly Leu Leu Ile Val His
            820                 825                 830

Ala Cys Ser His Tyr Arg Gln Trp Gln Glu Ser Glu Val Asp Phe Leu
        835                 840                 845

Gln Arg Ile Gly Asn Gln Leu Ala Ile Ala Ile Asn Gln Ala Asn Leu
    850                 855                 860

Tyr Gln Gln Leu Gln Ala Glu Leu Ala Glu Arg Gln Gln Thr Glu Glu
865                 870                 875                 880

Ala Phe Arg Glu Ser Glu Glu Leu Phe Arg Arg Ala Phe Asp Asp Ala
                885                 890                 895

Pro Ile Gly Ile Ala Leu Val Ser Pro Thr Gly Gln Phe Leu Lys Ala
            900                 905                 910

Asn Thr Tyr Tyr Cys Asn Leu Leu Glu Tyr Ser Glu Glu Glu Leu Leu
        915                 920                 925

Thr Leu Thr Phe Gln Asn Ile Thr His Pro Thr Asp Leu Glu Ala Asp
    930                 935                 940

Phe Glu Val Phe Arg Gln Met Met Ala Gly Glu Ile Arg Ser Tyr His
945                 950                 955                 960

Leu Glu Lys Arg Tyr Ile Thr Lys Gln Gly Ile Val Ile Pro Val Leu
                965                 970                 975

Leu Asn Ala Ala Ser Ile Arg Asp Gln Asp Asp Arg Pro Leu Tyr Cys
            980                 985                 990

Val Gly Gln Ile Gln Asp Ile Arg  Asp Arg Leu Lys Val  Glu Arg Met
        995                 1000                1005

Lys Asp  Glu Phe Ile Ser Val  Val Ser His Glu Leu  Arg Thr Pro
    1010                1015                1020

Leu Thr  Ser Ile Arg Gly Ala  Leu Gly Ile Leu Gly  Ser Gly Val
    1025                1030                1035

Phe Asp  Asn Arg Pro Glu Lys  Ala Lys His Met Leu  Gln Ile Ala
    1040                1045                1050

Ile Asn  Asn Ser Asp Arg Leu  Val Arg Leu Val Asp  Asp Ile Leu
    1055                1060                1065
```

```
Ser Leu  Glu Arg Leu Glu Ser  Gly Lys Val Gln Leu  Val Met Glu
    1070                1075                1080

Gln Cys  Gln Val Ala Glu Leu  Met Gln Gln Ala Ile  Asp Ser Leu
    1085                1090                1095

Gln Ala  Leu Ala Glu Arg Ala  Asp Leu Thr Leu Ser  Val Thr Pro
    1100                1105                1110

Ile Ser  Ala Thr Leu Trp Ala  Ala Pro Asp Ala Ile  Ile Gln Thr
    1115                1120                1125

Leu Thr  Asn Leu Leu Ser Asn  Ala Ile Lys Phe Ser  Ser Pro Gly
    1130                1135                1140

Asp Thr  Val Trp Leu Lys Ala  Glu Ile Gly Ser Gly  Glu Trp Ala
    1145                1150                1155

Thr Ala  Asn Gly Gln Gln Phe  Ser Asp Thr Gln Thr  Pro Tyr Ile
    1160                1165                1170

Leu Phe  Thr Val Lys Asp Arg  Gly Arg Gly Ile Pro  Glu Asp Lys
    1175                1180                1185

Leu Glu  Ile Ile Phe Glu Gln  Phe Gln Gln Val Asp  Val Ser Asp
    1190                1195                1200

Ser Arg  Gln Lys Gly Gly Thr  Gly Leu Gly Leu Ser  Ile Cys Lys
    1205                1210                1215

Arg Ile  Val Gln Gln His Gly  Gly Arg Ile Trp Val  Glu Ser Ser
    1220                1225                1230

Leu Gly  Glu Gly Ser Thr Phe  Tyr Phe Thr Leu Pro  Ile Lys Glu
    1235                1240                1245

Glu Asn  Asp
    1250


<210> SEQ ID NO 49
<211> LENGTH: 2626
<212> TYPE: PRT
<213> ORGANISM: Microcoleus vaginatus

<400> SEQUENCE: 49

Met Phe Met Arg Thr Thr Ala Leu Thr Pro Ile Glu Leu Arg Thr Ala
1               5                   10                  15

Ile Val Arg Glu Pro Leu Val Val Ser Pro Asp Thr Thr Val Met Asp
            20                  25                  30

Ala Ile Ala Gln Met Ser Gly Val Arg Ser Leu Cys Asn Thr Thr Arg
        35                  40                  45

Thr Ala Asp Gly Gln Leu Asp Asp Leu His Leu Glu Ala Arg Ser Ser
    50                  55                  60

Cys Val Leu Val Val Glu Asn Glu Gln Leu Val Gly Val Leu Thr Glu
65                  70                  75                  80

Arg Asp Val Val Arg Leu Ser Ala Gln Gln Arg Ser Leu Glu Asn Leu
                85                  90                  95

Val Leu Arg Glu Val Met Ala His Pro Val Val Thr Leu Arg Glu Ser
            100                 105                 110

Ala Phe Thr Asp Leu Phe Phe Ala Ile Asn Leu Leu Gln Gln His His
        115                 120                 125

Ile Arg His Leu Pro Ile Leu Asp Asp Leu Asp Arg Leu Val Gly Leu
    130                 135                 140

Val Thr His Glu Ser Leu Arg Gln Thr Ser Arg Pro Ile Asp Leu Leu
145                 150                 155                 160

Arg Leu Arg Met Val Ala Glu Val Met Thr Arg Glu Val Ile Cys Ala
                165                 170                 175
```

-continued

```
Ala Pro Asp Ser Ser Leu Leu Ala Ile Ala Gln Leu Met Ala Glu Asn
            180                 185                 190

Arg Val Ser Ser Val Val Ile Val His Pro Gly Gly Ile Ser Thr Glu
        195                 200                 205

Pro Leu Gln Ile Pro Val Gly Ile Leu Thr Glu Arg Asp Ile Val Gln
    210                 215                 220

Phe Gln Thr Leu Gly Leu Asn Leu Glu Thr Cys Leu Ala Gln Ala Val
225                 230                 235                 240

Met Ser Thr Pro Ile Phe Ala Val Arg Pro Asp Asp Ser Leu Trp Thr
                245                 250                 255

Val Gln Glu Ile Val Glu Gln Arg Ser Ile Arg Arg Leu Ala Val Thr
            260                 265                 270

Gly Glu Leu Gly Glu Leu Leu Gly Ile Val Thr Gln Thr Ser Leu Leu
        275                 280                 285

Gln Ala Leu Asn Pro Leu Glu Leu Tyr Lys Leu Val Gln Lys Trp Glu
    290                 295                 300

Glu Lys Val Val Arg Leu Glu Ala Glu Lys Val Ala Leu Leu Ala Asn
305                 310                 315                 320

Arg Asn Val Glu Leu Glu Gln Gln Val Glu Ala Arg Thr Ala Ala Leu
                325                 330                 335

Lys Ala Lys Ala Asp Arg Glu Gln Leu Leu Asn Thr Ile Ala Glu Gln
            340                 345                 350

Ile Arg Ser Ser Leu Asn Leu Ser Asp Ile Leu Gln Thr Thr Val Gln
        355                 360                 365

Glu Ile His Ser Leu Leu Gly Cys Asp Arg Val Ile Ile Tyr Gln Phe
    370                 375                 380

Arg Ser Asp Phe Ser Gly Thr Val Ile Ala Glu Ala Ile Thr Asp Thr
385                 390                 395                 400

Gly Arg Ser Val Leu His Arg Glu Ala His Asp Pro Cys Met Ser Pro
                405                 410                 415

Glu Trp Leu Glu Pro Tyr Arg Gln Gly Arg Ile Arg Ile Ile Asn Asp
            420                 425                 430

Ile Tyr Gly Glu Pro Met Thr Gln Cys His Gln Glu Met Leu Val Gly
        435                 440                 445

Phe Asp Ile Arg Ala Lys Leu Met Val Pro Ile Val Ile Glu Glu Gln
    450                 455                 460

Leu Arg Gly Leu Met Ile Ala Ser Tyr Arg Ala Ser Ala His Ser Trp
465                 470                 475                 480

Thr Thr Asp Glu Ile Glu Leu Leu Arg Gln Val Ser Leu Gln Val Ala
                485                 490                 495

Ile Ala Leu Gly Gln Ala Met Ile Gln Gln Lys Leu Gln Asn Glu Leu
            500                 505                 510

Val Lys Arg Gln Arg Ile Glu Ala Thr Leu Ile Glu Ser Glu Gln Arg
        515                 520                 525

Tyr Ala Ala Leu Ala Ala Ala Ala Pro Val Gly Ile Phe Arg Thr Asp
    530                 535                 540

Ala Thr Gly Leu Cys Thr Tyr Val Asn Asp Arg Tyr Phe Gln Ile Ser
545                 550                 555                 560

Gly Leu Thr Pro Gly Ala Thr Ile Gly His Gly Trp Gln Gln Gly Val
                565                 570                 575

His Pro Asp Asp Arg Asp Trp Val Met Val Glu Trp Lys Gln Phe Ile
            580                 585                 590
```

```
Gln Gly Asn Arg Ser Phe Glu Leu Glu Tyr Arg Phe Gln Cys Pro Asp
        595                 600                 605

Gly Thr Val Thr Trp Val Tyr Gly Gln Cys Val Ala Glu Leu Asp Ala
    610                 615                 620

Asn Gly His Arg Ser Gly Tyr Ile Gly Thr Ile Thr Asp Ile Ser Ala
625                 630                 635                 640

Arg Lys Arg Thr Glu Val Cys Leu Gln Glu Ser Glu Glu Arg Tyr Ala
                645                 650                 655

Thr Leu Val Ala Ala Ala Pro Val Gly Ile Phe Arg Ala Asp Ala Val
            660                 665                 670

Gly Asn Cys Ile Tyr Val Asn Asp Arg Trp Cys Gln Ile Ser Gly Leu
        675                 680                 685

Thr Pro Lys Thr Ala Val Gly Glu Gly Trp Gln Gln Gly Leu His Pro
    690                 695                 700

Asp Asp Arg Asp Cys Val Ile Ala Glu Trp Glu Gln Ser Val Gln Arg
705                 710                 715                 720

Asn Arg Pro Phe Gln Leu Glu Tyr Arg Phe Gln Arg Pro Asp Gly Gly
                725                 730                 735

Val Thr Ser Val Tyr Gly Gln Ser Val Ala Glu Arg Asp Ala Asp Gly
            740                 745                 750

Gln Val Val Gly Tyr Val Gly Thr Thr Thr Asp Ile Thr Asp Arg Lys
        755                 760                 765

Gln Ala Glu Gln Lys Leu Gln Gln Leu Asn Gln Gln Leu Glu Thr Lys
    770                 775                 780

Val Ala Glu Arg Thr Gln Glu Leu Trp Gln Val Asn Ser Leu Gln Arg
785                 790                 795                 800

Ala Ile Leu Asp Cys Ala Asp Tyr Ser Ile Ile Ser Ser Asp Pro Ser
                805                 810                 815

Gly Ile Ile Gln Thr Leu Asn Ala Ala Gly Glu Arg Met Leu Gly Tyr
            820                 825                 830

Ser Ala Gln Glu Ile Ile Gly Gln Ala Thr Pro Ala Leu Ile His Asp
        835                 840                 845

Ala Asn Glu Val Ile Asp Arg Ala Ala Ser Leu Ser Ala Glu Leu Gly
    850                 855                 860

Gln Asn Ile Pro Pro Gly Phe Glu Val Phe Val Ala Lys Ala Arg Gln
865                 870                 875                 880

Gly Leu Val Ser Glu Glu Glu Trp Ser Tyr Ile Arg Lys Asp Gly Ser
                885                 890                 895

Arg Phe Pro Val Ser Leu Ser Ile Thr Ala Leu Lys Asp Val His Gln
            900                 905                 910

Gln Ile Ile Gly Phe Leu Gly Ile Ala Lys Asp Ile Ser Asp Arg Lys
        915                 920                 925

Arg Ala Glu Ala Glu Leu Gln Lys Leu Ser Glu Arg Leu Ala Leu Ser
    930                 935                 940

Leu Lys Ser Gly Ala Ile Ala Ser Trp Glu Trp Asn Leu Gly Gln Asn
945                 950                 955                 960

Thr Ile Leu Gly Asp Glu Arg Met Tyr Glu Leu Phe Ala Val Thr Lys
                965                 970                 975

Pro Ser Asp Ala Cys Gln Val Tyr Asp Phe Trp Ala Asn Arg Leu His
            980                 985                 990

Pro Asp Asp Arg Ile Pro Thr Glu  Thr Leu Leu His Gln  Ala Val Leu
        995                 1000                 1005

Gly Gln  Ala Glu Tyr Asp Thr  Glu Tyr Arg Ile Val  His Pro Asp
```

```
    1010                1015                1020

Gly Ser  Leu His Phe Ile Lys  Ala Tyr Gly Val Val  Val Arg Asp
    1025                1030                1035

Ala Gln  Ser Asn Pro Gln Ser  Met Ile Gly Val Asn  Phe Asp Ile
    1040                1045                1050

Ser Asp  Arg Lys Gln Ala Glu  Leu Gln Arg Gln Gln  Leu Ile Gln
    1055                1060                1065

Glu Leu  Ser Ala Phe Lys Gln  Ala Leu Asp Gln Ser  Ala Ile Val
    1070                1075                1080

Val Ile  Thr Asp Arg Glu Gly  Val Ile Ser Tyr Val  Asn Asp Arg
    1085                1090                1095

Phe Cys  Val Val Ser Gly Tyr  Ser Arg Asp Arg Leu  Ile Gly Gln
    1100                1105                1110

Thr His  Arg Leu Val Asn Ser  Gly Tyr His Pro Pro  Ala Phe Phe
    1115                1120                1125

Gln Asp  Leu Trp Arg Thr Ile  Asn Ser Ser Gln Ile  Trp Arg Gly
    1130                1135                1140

Glu Ile  Cys Asn Leu Ala Lys  Asn Gly Ser Leu Tyr  Trp Val Ala
    1145                1150                1155

Thr Thr  Ile Val Pro Phe Leu  Asp Glu Gln Gly Arg  Pro Phe Gln
    1160                1165                1170

Tyr Leu  Ala Ile Gly Phe Asp  Ile Thr Asp Arg Lys  Leu Ala Glu
    1175                1180                1185

Ala Thr  Leu Gln Gln Glu Asn  Thr Phe Arg Gln Gln  Ile Val Glu
    1190                1195                1200

Asn Met  Ala Glu Gly Leu Cys  Val Phe His Gln Val  Glu Glu Phe
    1205                1210                1215

Pro Phe  Val Arg Phe Thr Val  Trp Asn Gln Gln Met  Gln Ala Ile
    1220                1225                1230

Thr Gly  Tyr Thr Leu Glu Glu  Ile Asn Arg Leu Gly  Trp Tyr Gln
    1235                1240                1245

Thr Leu  Tyr Pro Asn Leu Glu  Asp Arg Glu Gln Ala  Ile Ala Asn
    1250                1255                1260

Cys Arg  Gln Met Gln Pro Ile  Ala Val Glu Arg Glu  Ile Gln Arg
    1265                1270                1275

Gln Asp  Gly Gln Arg Arg Thr  Ile Ser Ile Ser Thr  Ser Val Leu
    1280                1285                1290

Ser Gly  Asp Asp Gly His Leu  Tyr Ala Leu Ala Leu  Ile Gln Asp
    1295                1300                1305

Ile Thr  His Arg Gln Gln Thr  Glu Arg Glu Asn Arg  Leu Leu Lys
    1310                1315                1320

Glu Arg  Leu Glu Phe Leu Leu  Ala Ser Ser Pro Ala  Met Ile Tyr
    1325                1330                1335

Ser Cys  Lys Pro Tyr Gly Asp  Tyr Glu Leu Thr Phe  Met Ser Lys
    1340                1345                1350

Asn Met  Ser Ala Ile Leu Gly  Tyr Lys Pro Glu Glu  Phe Leu Ser
    1355                1360                1365

Glu Ser  Gly Phe Trp Ala Asn  His Leu His Pro Glu  Asp Ala Pro
    1370                1375                1380

Arg Val  Phe Ala Asp Leu Ser  Ala Leu Phe Glu Tyr  Asn Thr His
    1385                1390                1395

Gln His  Glu Tyr Arg Phe Leu  His His Asp Gly His  Tyr Val Trp
    1400                1405                1410
```

```
Leu Arg  Asp Glu Leu Arg Val  Val Arg Asp Glu Glu  Gly Cys Pro
    1415                 1420                 1425

Thr Glu  Ile Ile Gly Tyr Phe  Ala Asp Ile Ser Asp  Val Lys Gln
    1430                 1435                 1440

Thr Glu  Glu Thr Leu Lys Ile  Gln Leu Ala Ala Ile  Glu Ala Ala
    1445                 1450                 1455

Ile Asp  Gly Ile Ala Ile Met  Gln Gly Asp Thr Tyr  Leu Tyr Leu
    1460                 1465                 1470

Asn Gln  Ala His Leu Glu Leu  Phe Gly Tyr Glu His  Pro Gln Glu
    1475                 1480                 1485

Leu Leu  Gly Lys Thr Trp Gln  Leu Leu Tyr Ser Pro  Glu Glu Leu
    1490                 1495                 1500

Glu Arg  Phe Glu Arg Glu Val  Phe Pro Val Leu Gly  Arg Asp Arg
    1505                 1510                 1515

Ala Trp  Gln Gly Glu Ala Ile  Gly Thr Arg Lys Asp  Gly Ser Thr
    1520                 1525                 1530

Phe Ala  Glu Gly Leu Ser Leu  Thr Leu Thr Glu Asn  Gly Leu Leu
    1535                 1540                 1545

Ile Cys  Val Cys Arg Asp Ile  Ser Asp Arg Lys Gln  Ile Glu Ala
    1550                 1555                 1560

Glu Leu  Ala Glu Ser Glu Ala  Lys Phe Arg Arg Leu  Val Glu Gly
    1565                 1570                 1575

Ala Asn  Asp Leu Ile Trp Ser  Cys Glu Pro Asp Gly  Ile Leu Thr
    1580                 1585                 1590

Tyr Val  Ser Pro Gln Phe Lys  Thr Met Phe Gly Trp  Asp Glu Ser
    1595                 1600                 1605

Ala Trp  Ile Gly Lys Ser Phe  Ile Tyr Leu Val His  Pro Asp Asp
    1610                 1615                 1620

Arg Ser  Leu Val Val Thr Asp  Tyr Arg Glu Asn Ile  Lys Ser Gly
    1625                 1630                 1635

Lys Lys  Ser Ser Asp Tyr Glu  Phe Arg His Arg His  Arg Asp Gly
    1640                 1645                 1650

Asn Tyr  Val Trp Val Arg Ser  Ser Ala Thr Pro Val  Ile Asn Ala
    1655                 1660                 1665

Glu Gly  Glu Leu Ile Ser Ile  Gln Gly Ile Leu Ser  Asp Ile Ser
    1670                 1675                 1680

Asp Arg  Lys Glu Ala Glu Ile  Ala Arg Glu Ser Ser  Glu Ile Arg
    1685                 1690                 1695

Phe Arg  Arg Val Phe Glu Ser  Ser Val Ser Gly Met  Ile Phe Ala
    1700                 1705                 1710

Asp Phe  Gln Gly Asn Ile Ile  Asp Ala Asn Asp Arg  Phe Leu Gln
    1715                 1720                 1725

Met Val  Gly Tyr Thr Arg Glu  Glu Leu Asp Ala Gly  Leu Ile His
    1730                 1735                 1740

Trp Asp  Ala Met Thr Pro Pro  Glu Tyr Phe Pro Ala  Asp Val Leu
    1745                 1750                 1755

Ala Met  Glu Arg Val Met Gln  Asp Gly Ala Ile Glu  Pro Trp Glu
    1760                 1765                 1770

Lys Glu  Tyr Tyr Arg Lys Asp  Gly Ser Arg Ile Ser  Val Leu Ile
    1775                 1780                 1785

Gly Val  Ala Leu Leu Pro Asp  Ser Asp Asp Gln Thr  Ile Cys Val
    1790                 1795                 1800
```

Leu Val Asp Ile Ser Glu Arg Lys Gln Ala Gln Lys Ala Leu Gln
1805 1810 1815

Glu Ser Gln Gln Phe Leu Gln Thr Val Leu Asp Thr Ile Pro Leu
1820 1825 1830

Ala Val Phe Trp Lys Asn Arg Glu Ser Val Phe Leu Gly Cys Asn
1835 1840 1845

Gln Gln Phe Ala Gln Thr Leu Gly Leu Pro Ser Thr Thr Glu Ser
1850 1855 1860

Ile Gly Lys Lys Asp Leu Asp Ile Cys Gln Glu Glu Val Glu Ala
1865 1870 1875

Asn Glu Tyr Cys Ala Met Asp Arg Arg Leu Met Glu Thr Gly Glu
1880 1885 1890

Ala Ile Leu Gly Ile Glu Glu Thr Leu Thr Leu Pro Asn Gly Lys
1895 1900 1905

Leu Ile Phe Ile Glu Thr His Lys Ala Pro Leu Arg Asp Cys Ser
1910 1915 1920

Asp Asn Val Ile Gly Leu Val Gly Thr Phe Gln Asp Ile Thr Asp
1925 1930 1935

Arg Lys Glu Ala Glu Gln Lys Leu Gln Gln Gln Ala Lys Gln Glu
1940 1945 1950

Arg Leu Leu Gly Ala Ile Thr Lys Arg Met Arg Ser Ser Leu Asn
1955 1960 1965

Leu Asp Glu Ile Leu Asn Ser Thr Val Glu Glu Ile His Gln Leu
1970 1975 1980

Leu Gln Ser Asp Arg Thr Leu Val Tyr Arg Val Phe Pro Glu Gly
1985 1990 1995

Thr Gly Ala Ala Ile Ala Glu Ser Val Ser Pro Asn Arg Leu Lys
2000 2005 2010

Leu Leu Asp Ile Leu Phe Pro Glu Glu Val Phe Pro Glu Asp Thr
2015 2020 2025

Tyr Glu Arg Tyr Ile Gln Gly Arg Val Tyr Ala Leu Asn Asp Ser
2030 2035 2040

Glu Asp Glu Asn Glu Ser Ile Val Pro Cys Leu Val Glu Phe Leu
2045 2050 2055

Ala Asp Ile Glu Val Arg Ala Lys Leu Val Val Pro Ile Ile Gln
2060 2065 2070

Asn Gln Thr Leu Trp Gly Leu Leu Ile Val His Gln Cys Asp Arg
2075 2080 2085

Pro Arg Gln Trp Gln Asp Trp Glu Ile Asn Leu Leu Lys Gln Ile
2090 2095 2100

Ala Asn Gln Leu Ala Ile Ala Ile Gln Gln Ser Tyr Leu Tyr Glu
2105 2110 2115

Gln Val Gln Ser Glu Leu Ala Ile Arg Lys Gln Thr Glu Asn Val
2120 2125 2130

Ile Ala Leu Gln Leu Gln Arg Gln Arg Thr Leu Gly Ala Ile Ala
2135 2140 2145

Gln Gln Ile Arg Glu Ser Leu Asp Ile Asn Gln Ile Leu Ala Ala
2150 2155 2160

Val Thr Gln Gln Val Lys Glu Ile Leu Gln Gly Asp Arg Ile Ile
2165 2170 2175

Val Phe Arg Leu Phe Gly Asp Gly Arg Ser Gln Ile Val Glu Glu
2180 2185 2190

Ala Val Ser Ser Glu Phe Pro Ala Leu Lys Asp His His Trp Glu

```
    2195                2200                2205

Asp Glu  Arg Trp Ser Gln Glu  Ile Leu Asn Arg Tyr  Trp Gln Gly
    2210                2215                2220

Lys Pro  Arg Ile Val Pro Asn  Val Met Thr Asp Ile  Trp Thr Asp
    2225                2230                2235

Cys Leu  Val Glu Tyr Ala Ser  Val Gly Gln Val Gln  Ser Lys Ile
    2240                2245                2250

Val Ala  Pro Ile Leu Gln Glu  Val Arg Ser Ser Glu  Ser His Arg
    2255                2260                2265

Trp Ile  Ala Pro Gly Gln Thr  Lys Lys Leu Trp Gly  Val Leu Val
    2270                2275                2280

Val His  Ala Cys Arg Glu Gln  Arg Val Trp Gln Glu  Ser Glu Ala
    2285                2290                2295

Gln Leu  Leu Gln Gln Ile Ala  Asn Gln Leu Ala Ile  Ala Ile Gln
    2300                2305                2310

Gln Ala  Ser Leu Phe Lys Gln  Leu Gln Gln Glu Leu  Thr Glu Arg
    2315                2320                2325

Gln Gln  Ala Gln Gln Gln Leu  Thr Glu Arg Asn Gln  Gln Leu Gly
    2330                2335                2340

Ala Ser  Asn Glu Glu Leu Ala  Arg Ala Thr Arg Leu  Lys Asp Glu
    2345                2350                2355

Phe Leu  Ala Asn Met Ser His  Glu Leu Arg Thr Pro  Leu Asn Ala
    2360                2365                2370

Ile Leu  Gly Met Ser Glu Gly  Leu Gln Glu Gln Val  Phe Gly Ile
    2375                2380                2385

Val Asn  Glu Gln Gln Ile Lys  Ala Leu Gln Thr Ile  Glu Arg Ser
    2390                2395                2400

Ser Ser  His Leu Leu Glu Leu  Ile Asn Asp Ile Leu  Asp Val Ala
    2405                2410                2415

Lys Ile  Glu Ser Gly Gln Met  Glu Leu Asp Cys Thr  Pro Val Ser
    2420                2425                2430

Ile Asn  His Leu Cys Gln Ser  Ser Leu Ala Phe Ile  Lys Gln Gln
    2435                2440                2445

Ala Leu  Gln Lys Arg Ile Gln  Leu Glu Ile Gln Met  Pro Leu Asn
    2450                2455                2460

Leu Pro  Asp Leu Leu Ile Asp  Glu Arg Arg Met Arg  Gln Val Leu
    2465                2470                2475

Ile Asn  Leu Leu Asn Asn Ala  Val Lys Phe Thr Pro  Asn Gly Gly
    2480                2485                2490

Arg Ile  Thr Leu Glu Val Ser  Arg Gln Gln Arg Pro  Ala Asp Pro
    2495                2500                2505

Asp Ser  Ala Asp Ser Pro Pro  His Phe Leu Val Lys  Glu Thr Leu
    2510                2515                2520

Arg Ile  Ala Val Ile Asp Thr  Gly Ile Gly Ile Ala  Pro Glu His
    2525                2530                2535

Ile Asn  Lys Leu Phe Gln Pro  Phe Ile Gln Ile Asp  Gly Ala Leu
    2540                2545                2550

Asn Arg  Gln Tyr Thr Gly Thr  Gly Leu Gly Leu Ala  Leu Val Lys
    2555                2560                2565

Arg Ile  Val Glu Leu His Gly  Gly Gln Val Gly Leu  Thr Ser Thr
    2570                2575                2580

Val Gly  Val Gly Ser Cys Phe  Thr Ile Asp Leu Pro  Cys Thr Ala
    2585                2590                2595
```

```
Cys Ala  Pro Ser Ser Val Tyr  Leu Glu Ser Gln Thr  Glu Pro Arg
    2600                 2605                 2610

Ile Glu  Pro Ser Gln Pro Glu  Glu Gly Gly Ala Leu  Pro
    2615                 2620                 2625


<210> SEQ ID NO 50
<211> LENGTH: 2072
<212> TYPE: PRT
<213> ORGANISM: Fischerella thermalis

<400> SEQUENCE: 50

Met Ser Lys Ser Pro Ser His Leu Leu Ala Glu Ala Glu Lys Ala Gln
1               5                   10                  15

Val Leu Gly Lys Phe Thr Glu Ala Glu Glu Tyr Tyr Glu Gln Ala Ile
            20                  25                  30

Asp Thr Ala Lys Ala Asn Gly Ser Leu Gln Thr Glu Ala Leu Ala Tyr
        35                  40                  45

Glu Leu Ala Ala Lys Phe Tyr Leu Glu Arg Gly Arg Leu Arg Phe Ala
    50                  55                  60

Gln Asn Tyr Ile Lys Glu Ala His Tyr Ala Tyr Thr Arg Leu Asp Ala
65                  70                  75                  80

Arg Ala Lys Ile Lys Glu Leu Glu Thr Gln Tyr Pro Gln Leu Arg Ser
                85                  90                  95

Glu Leu Ser Ala Ala Asp Ser His Thr Ser Thr Asp Leu Glu Ala Val
            100                 105                 110

Ile Arg Ala Asn Gln Ala Ile Ala Ser Glu Ile Glu Leu Glu Arg Ser
        115                 120                 125

Leu Ser Val Leu Met Lys Ile Leu Ile Glu Asn Ala Gln Ala Gln Thr
    130                 135                 140

Gly Tyr Leu Ile Leu Pro Cys Gln Thr Ala Ser Thr Ser Thr Glu Lys
145                 150                 155                 160

Trp Ala Ile Ala Ala Ser Gly Thr Ile Asp Ile Ala Thr Asn Glu Gln
                165                 170                 175

Ile Ile Val Leu Gln Ser Leu Ala Ile Ala Asp His Leu Pro Ala Ser
            180                 185                 190

Val Ile Asp Tyr Val Ile Gln Thr Leu Glu Ser Val Val Val Asp Asp
        195                 200                 205

Ala Thr Arg Glu Gly Asn Phe Ile Asn Asp Thr Tyr Ile Gln Gln His
    210                 215                 220

Gln Thr Lys Ser Ile Leu Cys Val Pro Leu Leu His Gln Glu Glu Leu
225                 230                 235                 240

Leu Gly Ile Val Tyr Leu Glu Asn Asn Ile Thr Asn Gly Val Phe Thr
                245                 250                 255

Lys Glu Gln Leu Lys Val Ile Lys Leu Leu Ser Ala Gln Ala Ala Ile
            260                 265                 270

Ser Leu His Asn Ala Lys Leu Tyr Asn Gln Leu Arg Glu Ser Glu Gln
        275                 280                 285

Gln Leu Arg Thr Arg Glu His Arg Leu Asn Gln Ile Leu Glu Ala Met
    290                 295                 300

Pro Ile Gly Val Thr Ala His Asn Thr Asn Gly Glu Phe Ile Tyr Ser
305                 310                 315                 320

Asn Leu Lys Ala Gln Gln Leu Leu Gly Ile Thr Ala Pro Leu Glu Val
                325                 330                 335

Thr Thr Glu Gln Leu Leu Gln Val Phe Gln Val Tyr Gln Ala Gly Ser
```

-continued

```
            340                 345                 350

Asp Gln Leu Tyr Pro Thr Asp Gln Leu Pro Ile Val Arg Ala Phe Ala
        355                 360                 365

Gly Glu Ser Val Lys Ile Asp Asp Met Glu Leu Arg Gln Ala Asp Lys
    370                 375                 380

Thr Val Pro Leu Glu Val Leu Thr Thr Pro Ile Phe Asp Glu Thr Gly
385                 390                 395                 400

Ala Val Ile Tyr Ala Ile Thr Ala Phe Thr Asp Ile Thr Glu Arg Lys
                405                 410                 415

Gln Ala Gln Lys Leu Leu Ala Lys Tyr Asn Gln Thr Leu Glu Ala Gln
            420                 425                 430

Ile Ala Glu Arg Thr Glu Lys Leu Gln Gln Gln His Glu Ile Leu Gln
        435                 440                 445

Thr Leu Phe Asp His Met Pro Val Met Leu Lys Leu Arg Asp Gln Thr
    450                 455                 460

Gly Gln Thr Val Leu Ile Asn Arg Glu Tyr Glu Arg Val Leu Gly Trp
465                 470                 475                 480

Ser Leu Arg Glu Ile Arg Glu Ser Asp Phe Leu Ala Glu Cys Tyr Pro
                485                 490                 495

Asp Leu Glu Gln Arg Gln Arg Val Glu Glu His Ile Gln Ala Ala Thr
            500                 505                 510

Gly Lys Trp Gln Asp Phe Lys Thr Arg Cys Arg Asp Asp Arg Tyr Val
        515                 520                 525

Asp Thr Thr Trp Ala Asn Ile Arg Leu Ser Asn Gly Trp Thr Val Gly
    530                 535                 540

Ile Gly Lys Asp Ile Ser Asp Arg Lys Gln Leu Glu Ala Ala Leu Gln
545                 550                 555                 560

Ala Ser Lys Ala Lys Leu Lys Asp Ile Leu Asn Ser Ala Gln Ala Ser
                565                 570                 575

Ile Ala Ser Phe Arg Val Tyr Pro Asp Gly Thr Trp Glu Pro Asp Tyr
            580                 585                 590

His Ser Thr Gly Cys Glu Thr Val Phe Gly Tyr Thr Pro Gln Glu Phe
        595                 600                 605

Thr Pro Ala Val Trp Ser Ser Arg Val Pro Ala Glu Asp Leu Ala Ala
    610                 615                 620

Ile Ile Glu Gln Arg Ser Thr Ala Ile Pro Lys Gly Glu Ala Leu Thr
625                 630                 635                 640

Val Glu Tyr Arg Phe Tyr His Lys Asn Gly Ser Leu Arg Trp Ile Thr
                645                 650                 655

Glu Thr Leu Thr Ser Arg Trp Asp Gln Val Gly Gly Cys Trp Val Val
            660                 665                 670

Thr Met Val Ala Val Asp Ile Thr Ala His Lys Gln Ala Glu Gln Ala
        675                 680                 685

Leu Gln Glu Ala Tyr Arg Lys Leu Glu Glu Tyr Ser Thr Asn Gln Glu
    690                 695                 700

Ala Val Asn Gln Glu Leu Gln Arg Thr Leu Glu Asp Leu Gln Val Leu
705                 710                 715                 720

Glu Glu Glu Arg Gln Glu Gln Asn His Gln Leu Leu Ile Glu Gln Gln
                725                 730                 735

Arg Tyr Arg Asp Leu Phe Asn Phe Ala Pro Asp Gly Tyr Leu Val Thr
            740                 745                 750

Asp Ala Gln Gly Arg Ile Leu Glu Ala Asn His Ala Ile Ala Thr Leu
        755                 760                 765
```

```
Leu Ser Val Glu Ser Gly Phe Leu Thr Gly Lys Leu Leu Val Ser Phe
    770                 775                 780

Ile Pro Ala Ser Ala Arg Arg Ala Phe Arg Thr Gln Leu Asn His Leu
785                 790                 795                 800

Ser Ser Leu Pro Asp Lys Gln Thr Trp Glu Leu Ser Leu Gln Pro Arg
                805                 810                 815

Gln Gly Glu Pro Phe Pro Val Glu Ile Thr Val Ala Pro Val Arg Asp
            820                 825                 830

Ala Gln Lys Leu Ile Ala Leu Arg Trp Leu Ile Arg Asp Ile Thr Glu
        835                 840                 845

Arg Lys Gln Ala Glu Thr Ala Leu Arg Glu Ser Glu Glu Arg Phe Arg
    850                 855                 860

Glu Ile Ala Glu Asn Ile Asn Gln Leu Phe Phe Val Trp Ser Ala Asp
865                 870                 875                 880

Ser Gln Gln Phe Leu Tyr Ile Ser Pro Gly Tyr Glu Lys Ile Tyr Gly
                885                 890                 895

Leu Thr Cys Glu Ser Leu Tyr Gln Asn Ser Arg Ser Trp Leu Glu Val
            900                 905                 910

Val His Pro Asp Asp Arg Pro Ser Val Leu Gln Ser Leu Asp Gln Gln
        915                 920                 925

Tyr Gln Gly Lys His Ala Gln Arg Glu Tyr Arg Ile Ile Lys Ser Asp
    930                 935                 940

Gly Thr Ile Arg Trp Met Phe Ala Glu Val Phe Pro Ile Phe Asp Gln
945                 950                 955                 960

Thr Gly Asn Leu Leu Arg Tyr Ile Gly Leu Thr Glu Asp Ile Thr Glu
                965                 970                 975

Arg Lys Arg Ala Glu Glu Ala Leu Arg Gln Arg Glu Gln Glu Phe Arg
            980                 985                 990

Ala Leu Val Glu Asn Ala Pro Asp  Val Ile Ser Arg Val  Asp Arg Glu
        995                 1000                1005

Tyr Arg  Phe Cys Tyr Ile Asn  Pro Arg Val Glu Leu  Glu Thr Gly
    1010                1015                1020

Ile Pro  Pro Ala Gln Trp Ile  Gly Lys Thr Glu Leu  Glu Met Gly
    1025                1030                1035

Phe Pro  Gln Thr Ile Val Asn  Pro Trp His Ala Ala  Leu Glu His
    1040                1045                1050

Val Phe  Glu Thr Lys Gln Glu  Gln Ile Tyr Glu Ala  Glu Phe Pro
    1055                1060                1065

Cys Pro  Glu Gly Ile Ser Tyr  Trp Leu Cys Arg Leu  Val Pro Glu
    1070                1075                1080

Leu Ala  Glu Asp Gly Ser Val  Ala Thr Val Leu Ser  Ile Ala Arg
    1085                1090                1095

Asn Ile  Thr Asp Arg Lys Arg  Ala Glu Glu Ala Leu  Arg Glu Ser
    1100                1105                1110

Glu Gln  Phe Leu Arg Ser Ile  Tyr Glu Gly Ile Ala  Ala Gly Val
    1115                1120                1125

Cys Ile  Val Asp Val Leu Glu  Asp Gly Ser Phe Arg  Tyr Val Gly
    1130                1135                1140

Ile Asn  Pro Ala His Glu Arg  Met Ser Gly Leu Leu  Ser Ala Glu
    1145                1150                1155

Val Ala  Gly Lys Thr Pro Glu  Gln Val Phe Ser Pro  Glu Asp Ala
    1160                1165                1170
```

```
Gln Ala Val Thr Ala Arg Tyr Arg Ala Cys Ile Ile Ala Arg Glu
    1175                1180                1185

Arg Ile Thr Tyr Glu Glu Arg Leu Val Phe Lys Gly Lys Glu Thr
    1190                1195                1200

Trp Trp Ile Thr Asn Leu Ser Pro Leu Gln Asn Glu Asn Gly Gln
    1205                1210                1215

Ile Tyr Arg Leu Ile Gly Ser Cys Phe Asn Ile Thr Arg Arg Lys
    1220                1225                1230

Lys Leu Glu Gln Ser Leu Gln Leu Gln Ala Glu Gln Glu Arg Leu
    1235                1240                1245

Leu Ile Thr Ile Thr Gln His Ile Arg Gln Ser Leu Asp Leu Glu
    1250                1255                1260

Gln Ile Leu Arg Thr Thr Val Val Glu Val Gln Arg Thr Leu Gln
    1265                1270                1275

Thr Asp Arg Val Leu Ile Phe Arg Leu Asn Gln Asp Gly Ser Gly
    1280                1285                1290

Gln Ile Ile Glu Glu Ala Val Val Pro Glu Tyr Pro Met Thr Tyr
    1295                1300                1305

Gln Met Arg Trp Val Asp Glu Cys Phe Pro Asp Asp Cys Tyr Glu
    1310                1315                1320

Tyr Tyr Arg Gln Gly Asn Pro Arg Ile Leu Pro Asp Val Ala Lys
    1325                1330                1335

Asp Glu Trp Gly Ala Cys Leu Val Glu Phe Met Gln Gln Ile Gly
    1340                1345                1350

Val Lys Ser Lys Val Val Ala Pro Ile Ile Gln Thr Leu Glu Asp
    1355                1360                1365

Ser Ser Thr Arg Val Trp Gly Leu Leu Ile Val His Ala Cys Ser
    1370                1375                1380

His Tyr Arg Gln Trp Gln Ala Ser Glu Ala Glu Phe Leu Gln Gln
    1385                1390                1395

Ile Ser Asn Gln Leu Ala Ile Ala Ile His Gln Ala Asp Leu Tyr
    1400                1405                1410

Tyr Gln Leu Gln Ile Glu Leu Ala Glu Arg Lys Gln Met Gln Leu
    1415                1420                1425

Val Leu Gln Glu Arg Gln Ala Ile Leu Arg Ala Ile Gly Asp Asn
    1430                1435                1440

Leu Pro Lys Gly Phe Ile Phe Gln Ile Val His Val Pro Asp Gln
    1445                1450                1455

Gly Val Tyr Phe Ser Tyr Ile Ser Ala Gly Ile Glu Asp Leu Ile
    1460                1465                1470

Gly Leu Lys Pro Glu Ala Ile Ile Gln Asp Ala Asn Val Leu Arg
    1475                1480                1485

Asn Leu Ile His Glu Glu Asp Lys Pro Val Arg Gln Lys Leu Gly
    1490                1495                1500

Leu Lys Ser Leu Lys Thr Leu Cys Ile Phe Glu Met Gln Met Arg
    1505                1510                1515

Phe Arg Ser Leu Arg Gly Asn Ile Ile Trp Leu Asp Val Arg Ser
    1520                1525                1530

Thr Pro Arg Arg Leu Arg Asp Gly Arg Thr Val Trp Asp Gly Val
    1535                1540                1545

Gly Ile Asp Ile Thr Asp Ile Lys Gln Ala Glu Asp Ala Leu Arg
    1550                1555                1560

Arg Ser Glu Ala His Leu Ala Met Ala Gln Lys Val Ala Gln Ile
```

```
    1565                1570                1575

Gly Ser  Trp Glu Phe Asp Leu  Gln Ser Gln Gln Ile  Asn Trp Ser
    1580                1585                1590

Glu Thr  Thr Phe His His Trp  Gly Ile Glu Ile Asp  Gln Gly Glu
    1595                1600                1605

Pro Ser  Phe Ala Glu Leu Leu  Val Arg Val His Pro  Glu Asp Arg
    1610                1615                1620

Glu Ile  Leu Lys Gln His Ile  Glu Arg Ala Ile Thr  Gln Gly Ile
    1625                1630                1635

Pro Tyr  Ala Phe Asp Leu Arg  Ile Val Leu Pro Asp  Gly Ser Ile
    1640                1645                1650

Arg Tyr  Leu Asp Ser Arg Gly  Glu Pro Leu Val Asn  Ala Gln Gly
    1655                1660                1665

Gln Val  Ile Lys Leu Ile Gly  Thr Ser Leu Asp Ile  Thr Ala Arg
    1670                1675                1680

Lys Gln  Ala Glu Gly Ala Leu  Arg Glu Ser Glu Glu  Arg Phe Arg
    1685                1690                1695

Lys Ala  Phe Asn Ala Ala Pro  Ile Gly Met Ala Leu  Val Ser Pro
    1700                1705                1710

Gln Gly  Gln Phe Leu Lys Val  Asn His Ser Leu Cys  Glu Ile Ala
    1715                1720                1725

Gly Tyr  Thr Glu Ala Glu Met  Leu Thr Leu Thr Leu  Lys Asp Val
    1730                1735                1740

Ile His  Thr Asp Asp Leu Glu  Ala Ser Leu Glu Ala  Met Gln Gln
    1745                1750                1755

Met Leu  Ala Asn Asp Ile Arg  Leu Tyr Gln Val Glu  Lys Arg Ser
    1760                1765                1770

Leu His  Lys Gln Gly Asp Val  Ile His Ile Leu Leu  Asn Val Ser
    1775                1780                1785

Leu Val  Lys Asp Gln His Arg  Gln Pro Leu Tyr Phe  Ile Val Gln
    1790                1795                1800

Ile Gln  Asp Ile Ser Asp Arg  Tyr Lys Val Asp Arg  Met Lys Asn
    1805                1810                1815

Glu Phe  Ile Ser Ile Val Ser  His Glu Leu Arg Thr  Pro Leu Thr
    1820                1825                1830

Ala Ile  Arg Gly Ser Leu Gly  Ile Leu Glu Thr Gly  Ile Phe Asp
    1835                1840                1845

His Glu  Pro Glu Gln Ala Lys  Glu Met Leu Gln Ile  Ala Phe Asn
    1850                1855                1860

Asn Ser  Asp Arg Leu Val Arg  Leu Val Asn Asp Ile  Leu Asp Leu
    1865                1870                1875

Glu Arg  Leu Glu Ser Gly Lys  Thr Gln Leu Val Met  Glu Thr Cys
    1880                1885                1890

Glu Ile  Ala Asp Leu Val Gln  Gln Ala Ile Glu Thr  Val Gln Ala
    1895                1900                1905

Ile Ala  Lys Glu Ala Arg Val  Glu Ile Ser Val Met  Val Ala Asn
    1910                1915                1920

Met Gln  Ile Trp Ala Ala Pro  Asp Ala Ile Val Gln  Thr Leu Ile
    1925                1930                1935

Asn Leu  Leu Ser Asn Ala Ile  Lys Phe Ser Pro Val  Gly Gly Thr
    1940                1945                1950

Val Trp  Ile Ser Thr Glu Val  Leu Asn Gln Glu Met  Glu Lys Trp
    1955                1960                1965
```

```
Lys Asp  Arg Glu Ile Gly Arg  Lys Ile Ser Pro His  His Pro Thr
    1970                 1975                 1980

Thr Pro  Ser Pro His Phe Pro  Asn Ser His Ile Leu  Phe Ala Val
    1985                 1990                 1995

Lys Asp  Gln Gly Arg Gly Ile  Pro Pro Glu Lys Leu  Glu Ser Ile
    2000                 2005                 2010

Phe Gly  Arg Phe Gln Gln Val  Asp Ala Ser Asp Ser  Arg Gln Lys
    2015                 2020                 2025

Gly Gly  Thr Gly Leu Gly Leu  Ser Ile Cys Lys Ser  Ile Val Asp
    2030                 2035                 2040

Gln His  Gly Gly Arg Ile Trp  Val Glu Ser Leu Leu  Gly Glu Gly
    2045                 2050                 2055

Ser Thr  Phe Tyr Phe Ile Leu  Pro Leu Lys Arg Gly  Glu Ala
    2060                 2065                 2070


<210> SEQ ID NO 51
<211> LENGTH: 1657
<212> TYPE: PRT
<213> ORGANISM: Chlorogloeopsis fritschii

<400> SEQUENCE: 51

Met Pro Pro Asp Arg Glu Lys Val Gly Met Gly Phe Asp Arg Glu Glu
1               5                   10                  15

Val Ser Thr Asn Leu Gln Pro Gln Glu Ala Leu Cys Ala Arg Ser Glu
            20                  25                  30

Ser Thr Lys Pro Lys Glu Asn Ile Leu Val Val Asp Asp Asn Pro Asp
        35                  40                  45

Asp Leu Asp Phe Leu Ile Gln Ile Leu Ser Lys His Gly Tyr Gln Val
    50                  55                  60

Gln Leu Val Pro Ser Gly Lys Leu Ala Leu Ile Ala Val Glu Ser Thr
65                  70                  75                  80

Leu Pro Asp Leu Ile Leu Leu Asp Ile Met Met Pro Glu Met Asp Gly
                85                  90                  95

Phe Glu Val Cys Ser Gln Leu Lys Ala Ser Ala Gln Thr Lys Asp Ile
            100                 105                 110

Pro Ile Ile Phe Leu Ser Val Leu His Lys Thr Phe Asp Lys Val Lys
        115                 120                 125

Ala Phe Ser Leu Gly Ala Ala Asp Tyr Ile Thr Lys Pro Phe Gln Pro
    130                 135                 140

Glu Glu Val Leu Ala Arg Val Glu Asn Gln Leu Arg Ile Gln Arg Leu
145                 150                 155                 160

Thr Lys Gln Leu Val Glu Glu Ile Lys Glu Arg Asn Ile Ala Gln Glu
                165                 170                 175

Gln Leu Lys Asn Lys Glu Lys His Tyr Arg Arg Leu Phe Glu Gly Ser
            180                 185                 190

Val Asp Gly Ile Val Leu Thr Asp Met Gln Gly Arg Ile Ile Asp Cys
        195                 200                 205

Asn Ala Ser Tyr Gln Lys Met Leu Gly Tyr Ser Pro Glu Glu Leu Lys
    210                 215                 220

Leu Leu Ser Phe Trp Asp Leu Thr Pro Ile Gln Trp His Cys Trp Glu
225                 230                 235                 240

Ala Glu Ile Val Glu Gln Gln Ile Ile Glu Arg Gly Tyr Ser Asp Thr
                245                 250                 255

Tyr Glu Lys Glu Tyr Ile Arg Lys Asp Gly Thr Ile Phe Pro Val Glu
```

```
            260                 265                 270

Leu Thr Val Tyr Cys Gln Lys Asn Asp Cys Gly Gln Pro Glu Ile Met
        275                 280                 285

Trp Ala Asn Val Arg Asp Ile Ser Asp Ala Ser Arg Gln Ala Ala Thr
    290                 295                 300

Arg Leu Arg Lys Gln Ala Gln Gln Ala Leu Glu Gln Ser Ile Ile Lys
305                 310                 315                 320

Asn Arg Ala Leu Leu Asp Ala Ile Pro Asp Met Val Phe Arg Cys His
                325                 330                 335

Val Asp Gly Thr Tyr Leu Glu Phe Lys Pro Ala Lys Asp Leu Lys Pro
            340                 345                 350

Phe Val Pro Pro Ser Lys Phe Leu Gly Lys Lys Ile Gln Lys Ile Leu
        355                 360                 365

Pro Asp Gln Val Ala Gln Lys Ile Leu Gln Ala Gln Gln Gln Ala Ile
    370                 375                 380

Leu Leu Gly Glu Thr Gln Ile Leu Glu Tyr Gln Leu Pro Ile Asp Gly
385                 390                 395                 400

Arg Leu His Asp Tyr Glu Val Arg Ile Val Ala Cys Gly Ser His Glu
                405                 410                 415

Asn Ile Leu Phe Val Arg Asp Ile Thr Glu Arg Lys Leu Thr Glu Ala
            420                 425                 430

Ala Leu Ala Lys Ser Glu Gln Lys Tyr Arg Asn Leu Val Glu Thr Ser
        435                 440                 445

Gln Asn Ile Ile Met Ser Cys Asp Arg Gln Gly Ala Ile Thr Phe Val
    450                 455                 460

Asn Gln Ala Val Lys Gln Ile Tyr Gly Tyr Asp Pro Lys Glu Met Ile
465                 470                 475                 480

Gly His Pro Phe Thr Asp Phe Leu Pro Pro Glu Ile Ala Ala Lys Asp
                485                 490                 495

Leu Glu Val Phe Gln Gln Leu Leu Asn Gly Thr Pro Val Asn Leu Tyr
            500                 505                 510

Glu Thr Thr His Arg Ala Lys Asp Gly Arg Leu Ile His Leu Leu Phe
        515                 520                 525

Asn Ala Ile Ala Leu Phe Asp Glu Gln Gly Gln Val Ile Gly Thr Thr
    530                 535                 540

Gly Thr Ala Ser Asp Ile Thr Ala Arg Lys Gln Thr Glu Glu Glu Leu
545                 550                 555                 560

Gln Gln Ala Tyr Lys Lys Leu Glu Glu Tyr Asn Ala Glu Leu Gln Ala
                565                 570                 575

Thr Asn Gln Glu Leu Gln Cys Met Leu Glu Glu Leu Gln Phe Phe Glu
            580                 585                 590

Leu Glu Arg Gln Gln Gln Tyr His Gln Leu Ile Ile Glu Gln Lys Arg
        595                 600                 605

Tyr Glu Asp Leu Phe Asn Phe Ala Pro Asp Gly Tyr Leu Thr Thr Asp
    610                 615                 620

Ala Thr Gly Ile Ile Gln Glu Ala Asn His Ala Ile Ala Ala Tyr Leu
625                 630                 635                 640

Ser Val Asp Leu Lys Phe Leu Ala Gly Lys Pro Leu Ala Asn Phe Ile
                645                 650                 655

Ser Glu Gly Asp Arg Arg Ala Phe Arg Thr Gln Leu Asn Gln Leu Leu
            660                 665                 670

Ser Leu Gln Gln Lys Gln Thr Trp Glu Leu Lys Leu Gln Pro Ile Asn
        675                 680                 685
```

```
Gly Glu Pro Phe Ala Val Glu Met Thr Val Ala Pro Val Cys Gly Ser
    690                 695                 700

Ser Asn Gln Leu Ile Ser Leu Arg Trp Leu Ile Arg Asp Ile Thr Glu
705                 710                 715                 720

Arg Lys Gln Ala Glu Ala Ala Leu Arg Glu Ser Glu Glu Arg Phe Arg
                725                 730                 735

Gln Ile Ala Glu Asn Ile His Gln Phe Phe Phe Val Leu Ser Ala Asp
            740                 745                 750

Ser Gly Glu Tyr Leu Tyr Leu Ser Pro Ala Tyr Glu Lys Ile Trp Gly
        755                 760                 765

Gln Ser Cys Glu Ser Leu Tyr Gln Asn Pro Lys Ser Trp Leu Glu Phe
    770                 775                 780

Val His Pro Asp Asp Arg Gln Leu Val Leu His Ser Leu Tyr Gln Lys
785                 790                 795                 800

Asn Glu Gly Lys Arg Val Gln Arg Glu Tyr Arg Ile Ile Arg Asp Asp
                805                 810                 815

Gly Thr Thr Arg Trp Ile Phe Ala Glu Val Phe Pro Ile Leu Ala Gln
            820                 825                 830

Ser Gly Glu Leu Leu Arg Tyr Val Gly Leu Ala Glu Asp Ile Thr Glu
        835                 840                 845

Arg Lys Ser Thr Glu Glu Ser Leu Arg Glu Ser Glu His Phe Leu Arg
    850                 855                 860

Ser Ile Tyr Glu Gly Ile Glu Ala Ala Val Phe Ile Val Asp Val Leu
865                 870                 875                 880

Glu Asp Gly Arg Phe Arg Tyr Val Gly Ile Asn Pro Ala Asn Glu Arg
                885                 890                 895

Met Ser Gly Leu Leu Ser Thr Glu Ile Ala Gly Arg Thr Pro Glu Gln
            900                 905                 910

Val Leu Ser Pro Glu Asp Ala Gln Ala Val Ile Asp Arg Tyr Arg Thr
        915                 920                 925

Cys Val Ala Ala Arg Lys Pro Ile Thr Tyr Glu Glu Ser Leu Val Ile
    930                 935                 940

Gln Gly Lys Glu Thr Trp Trp Ile Thr Asn Leu Ala Pro Leu Gln Ser
945                 950                 955                 960

Glu Asp Gly Gln Ile Tyr Arg Leu Ile Gly Thr Ser Phe Asn Ile Thr
                965                 970                 975

Val Arg Lys Gln Leu Glu His Phe Leu Arg Ser Gln Ala Gln Gln Glu
            980                 985                 990

Arg Leu Leu Gly Thr Ile Thr Gln  His Ile Arg Gln Ser  Leu Asn Leu
        995                 1000                1005

Glu Glu  Ile Leu Ala Thr Thr  Val Ile Glu Val Gln  Gln Thr Leu
    1010                 1015                1020

Gln Ala  Asp Arg Ala Leu Ile  Phe Gln Leu Asn Gln  Asp Gly Ser
    1025                 1030                1035

Gly Gln  Ile Ile Gln Glu Ala  Val Ile Pro Asp Tyr  Pro Val Thr
    1040                 1045                1050

Asn Gln  Met Arg Trp Leu Asp  Glu Cys Phe Pro Asp  Glu Cys Tyr
    1055                 1060                1065

Glu Tyr  Tyr Cys Gln Gly Asn  Ala Arg Ile Val Pro  Asp Val Ala
    1070                 1075                1080

Lys Asp  Asp Trp Gly Ala Cys  Leu Val Glu Phe Met  Gln Glu Val
    1085                 1090                1095
```

-continued

```
Gly Val  Lys Ser Lys Val Val  Ala Pro Ile Val Gln  Ser Phe Glu
    1100                 1105                 1110

Gly Ser  Ser Asn Lys Val Trp  Gly Leu Leu Ile Val  His Ala Cys
    1115                 1120                 1125

Ser His  Tyr Arg Gln Trp Gln  Ala Ser Glu Val Glu  Phe Leu Gln
    1130                 1135                 1140

Gln Leu  Cys Asn Gln Leu Ala  Ile Ala Ile His Gln  Ala Asn Leu
    1145                 1150                 1155

Tyr His  Gln Leu Gln Ile Glu  Leu Val Glu Arg Lys  His Thr Glu
    1160                 1165                 1170

Lys Ala  Leu Gln Ala Ala Gln  Glu Ser Leu Thr Ile  Ala Ile Glu
    1175                 1180                 1185

Ala Ala  Gln Met Gly Thr Trp  His Leu Asp Ile Thr  Lys Asp Phe
    1190                 1195                 1200

Ala Ser  Lys Arg Ser Leu Arg  His Asp Gln Ile Phe  Gly Tyr Asp
    1205                 1210                 1215

Thr Leu  Gln Ser Glu Trp Gly  Gln Lys Ile Ala Arg  Arg His Val
    1220                 1225                 1230

Val Glu  Glu Asp Arg Glu Ile  Phe Asp Ala Ala Phe  Val Arg Ala
    1235                 1240                 1245

Met Glu  Thr Gly Lys Leu Asp  Phe Glu Val Arg Ile  Gln Trp Pro
    1250                 1255                 1260

Asp Gly  Ser Ile His Trp Met  Ala Ala Arg Gly Arg  Phe Tyr Phe
    1265                 1270                 1275

Asp Asp  Asn Gly Lys Pro Val  Tyr Gly Gly Gly Val  Asn Phe Asp
    1280                 1285                 1290

Ile Thr  Asp Arg Lys Gln Thr  Glu Leu Ala Leu Arg  Glu Ser Glu
    1295                 1300                 1305

Glu Arg  Phe Arg Arg Ala Phe  Asp Asp Ala Ala Ile  Gly Met Ala
    1310                 1315                 1320

Met Val  Ala Ile Asp Gly Ser  Phe Ile Thr Val Asn  Arg Ser Leu
    1325                 1330                 1335

Cys Glu  Ile Leu Gly Tyr Ser  Glu Ala Glu Phe Leu  Ala Leu Thr
    1340                 1345                 1350

Phe Gln  Asp Ile Thr His Ala  Asp Asp Leu His Lys  Ala Leu Asp
    1355                 1360                 1365

Tyr Arg  Gln Arg Leu Leu Val  Gly Glu Thr Arg Thr  Tyr Gln Thr
    1370                 1375                 1380

Gln Lys  Arg Tyr Ile His Lys  Leu Gly His Glu Val  Trp Ile Leu
    1385                 1390                 1395

Leu Ser  Ser Ser Leu Val Arg  Glu Arg Asp Gly Lys  Pro Leu Tyr
    1400                 1405                 1410

Phe Ile  Asn Gln Tyr Gln Asp  Ile Ser Asp Arg Gln  Gln Ile Ser
    1415                 1420                 1425

Arg Met  Lys Asn Glu Phe Ile  Ser Ile Val Ser His  Glu Leu Arg
    1430                 1435                 1440

Thr Pro  Leu Thr Ala Ile Arg  Gly Ser Leu Gly Ile  Leu Glu Thr
    1445                 1450                 1455

Gly Val  Leu Lys Asp Glu Pro  Gln Gln Ala Lys Glu  Leu Leu Gln
    1460                 1465                 1470

Ile Ala  Leu Lys Asn Ser Asn  Arg Leu Met Arg Leu  Val Asn Asp
    1475                 1480                 1485

Ile Leu  Asp Leu Glu Arg Leu  Glu Ser Gly Lys Val  Arg Leu Ile
```

```
    1490                1495                1500

Met Gln  Glu Cys Glu Ile Gly  Asp Leu Ile Lys Gln  Ala Thr Glu
    1505                1510                1515

Thr Val  Gln Ala Ile Ala Asp  Glu Ala Asn Ile Thr  Leu Cys Ala
    1520                1525                1530

Thr Phe  Pro Lys Ile Gln Ile  Trp Ala Ala Pro Asp  Ala Ile Thr
    1535                1540                1545

Gln Thr  Leu Ile Asn Leu Leu  Gly Asn Ala Ile Lys  Phe Ser Pro
    1550                1555                1560

Val Gly  Ser Ser Val Trp Leu  Ser Ala Glu Leu Phe  Pro Asp His
    1565                1570                1575

Val Leu  Phe Phe Val Arg Asp  Asn Gly Arg Gly Ile  Pro Ser Asp
    1580                1585                1590

Lys Leu  Lys Thr Ile Phe Gly  Arg Phe Gln Gln Val  Asp Ala Ser
    1595                1600                1605

Asp Ser  Arg Gln Lys Gly Gly  Thr Gly Leu Gly Leu  Ala Ile Cys
    1610                1615                1620

Lys Thr  Ile Ile Arg Gln His  Gly Gly Lys Ile Trp  Val Glu Ser
    1625                1630                1635

Val Leu  Gly Glu Gly Ser Thr  Phe Tyr Phe Thr Leu  Pro Phe Ala
    1640                1645                1650

Gln Pro  Asp Thr
    1655


<210> SEQ ID NO 52
<211> LENGTH: 1892
<212> TYPE: PRT
<213> ORGANISM: Unknown
<220> FEATURE:
<223> OTHER INFORMATION: Fischerella sp. PCC 9431

<400> SEQUENCE: 52

Met Ile Thr Phe Leu Ser His Leu Ile Val Glu Ala Glu Lys Ala Gln
1               5                   10                  15

Val Leu Gly Gln Val Ile Ala Thr Glu Glu Tyr Tyr Glu Gln Ala Ile
            20                  25                  30

Asp Ala Ala Lys Ala Asn Asn Ser Leu Glu Gln Glu Ala Ser Ala Tyr
        35                  40                  45

Tyr Glu Ala Ala Lys Tyr Tyr Leu Glu Arg Gly Arg Pro Arg Val Ala
    50                  55                  60

Gln Asn Tyr Ile Lys Glu Ala His Tyr Ala Tyr Lys Cys Leu Asp Ala
65                  70                  75                  80

Thr Ala Lys Val Lys Asp Leu Glu Thr Lys Tyr Pro Gln Leu Leu Phe
                85                  90                  95

Glu Leu Ser Ser Ala Asn Ser Asn Thr Cys Thr Arg Ser Thr Ser Phe
            100                 105                 110

Gln Phe Ser Ser Asn Ala Ser Gly Glu Ala Leu Glu Leu Leu Glu Ala
        115                 120                 125

Val Thr Arg Ala Asn Val Ala Ile Ser Ser Glu Ile Glu Leu Glu Arg
    130                 135                 140

Leu Leu Arg Ile Leu Met Lys Ile Leu Ile Glu Asn Thr Asp Ala His
145                 150                 155                 160

Thr Gly Tyr Leu Ile Leu Pro Ala Ser Thr Asn Leu Glu Asn Gly Glu
                165                 170                 175

Glu Trp Glu Ile Ala Ala Ser Gly Thr Ile Asp Thr Glu Ala Ser Glu
```

```
            180                 185                 190

Asp Ala Leu Gly Lys Pro Val Leu Gln Ile Ser Val Gln Pro Leu Ala
        195                 200                 205

Ile Ala Asp His Leu Pro Ile Ser Val Ile Asp Tyr Ile Ile His Thr
    210                 215                 220

Leu Glu Asn Val Val Val Asp Asp Ala Ser Cys Glu Gly Lys Phe Ile
225                 230                 235                 240

His Asp Ser Tyr Ile Lys Glu His Gln Ile Lys Ser Ile Leu Cys Val
                245                 250                 255

Pro Leu Leu Asn Gln Gly Gln Leu Ile Gly Ile Val Tyr Leu Glu Asn
            260                 265                 270

Asn Leu Thr Gln Gly Val Phe Thr Lys Lys Glu Leu Asn Ile Leu Asn
        275                 280                 285

Leu Leu Phe Val Gln Ala Ala Ile Ser Ile Ser His Ala Lys Ile Tyr
    290                 295                 300

Lys Gln Leu Arg Glu Ser Glu Lys Gln Leu Arg Ala Arg Glu Lys Arg
305                 310                 315                 320

Ile Asn Gln Ile Leu Asp Ala Ile Pro Ile Gly Val Thr Ala His Asp
                325                 330                 335

Pro Thr Gly Arg Phe Ile Tyr Ser Asn Leu Lys Ala Gln Gln Leu Leu
            340                 345                 350

Gly Ile Lys Thr Pro Pro Glu Ile Lys Ile Glu Gln Leu Ser Glu Ala
        355                 360                 365

Phe Gln Val Tyr Arg Ala Gly Thr Asp Glu Phe Tyr Pro Ile Glu Gln
    370                 375                 380

Leu Pro Leu Ile Arg Ala Phe Ala Gly Glu Ser Val Lys Ser Asp Asp
385                 390                 395                 400

Met Glu Leu Arg Gln Val Asp Lys Ser Ile Pro Leu Glu Val Leu Thr
                405                 410                 415

Val Pro Ile Phe Asp Gly Glu Gly Ala Val Ile Tyr Ala Ile Ala Ala
            420                 425                 430

Phe Lys Asp Ile Thr Glu Arg Lys Gln Ala Gln Lys Ile Leu Ala Asp
        435                 440                 445

Tyr Asn Tyr Thr Leu Glu Ala Gln Ile Val Ala Arg Thr Glu Lys Leu
    450                 455                 460

Gln Gln Gln Asn Glu Ile Leu Gln Ala Leu Phe Asp His Ile Pro Val
465                 470                 475                 480

Met Leu Lys Ile Arg Asp Gln Ala Asp Gln Thr Leu Leu Ile Asn Gln
                485                 490                 495

Glu Tyr Glu His Thr Leu Gly Trp Thr Leu Glu Glu Met Arg Asp Val
            500                 505                 510

Asp Trp Leu Ala Lys Cys Tyr Pro Asp Ala Glu Gln Arg Gln Gln Ile
        515                 520                 525

Thr Glu His Ile Gln Ala Ala Thr Gly Lys Trp Gln Asp Phe Arg Thr
    530                 535                 540

Arg Cys His Asn Gly Arg Tyr Ile Asp Thr Ser Trp Ala Asn Ile Arg
545                 550                 555                 560

Leu Ser Thr Gly Gln Ile Ile Gly Ile Gly Gln Asp Ile Ser Asp Arg
                565                 570                 575

Lys Glu Leu Glu Lys Ala Leu Gln Ala Ser Gln Ala Lys Leu Asn Asp
            580                 585                 590

Ile Leu Asn Ser Ala Gly Ala Ser Ile Ala Ser Phe Arg Val Tyr Pro
        595                 600                 605
```

```
Asp Arg Thr Trp Glu Asn Glu Tyr His Ser Leu Gly Cys Glu Thr Val
    610                 615                 620

Phe Gly Tyr Ser Pro Glu Glu Leu Thr Ser Glu Leu Trp Leu Ser Arg
625                 630                 635                 640

Val Pro Ser Gln Asp Leu Ala Ala Ile Thr Glu Gln Ala Phe Ala Ala
                645                 650                 655

Ile Ala Gln Glu Gln Ala Ile Thr Val Glu Tyr Arg Phe Tyr His Lys
            660                 665                 670

Asn Cys Ser Leu Arg Trp Ile Ala His Thr Leu Thr Ser Arg Trp Asp
        675                 680                 685

Gln Ala Glu Gly Cys Trp Ile Val Thr Met Val Gly Val Asp Ile Ser
    690                 695                 700

Asp Arg Lys Gln Thr Glu Glu Glu Leu Gln Gln Ala Tyr Lys Gln Leu
705                 710                 715                 720

Glu Glu Tyr Ser Ala Asp Leu Glu Ala Ile Asn Gln Glu Leu His Leu
                725                 730                 735

Thr Leu Glu His Leu Gln Val Leu Glu Glu Glu Arg Arg Glu Gln His
            740                 745                 750

His Arg Leu Met His Glu Gln Gln Arg Tyr Gln Glu Leu Phe Asn Phe
        755                 760                 765

Ala Pro Asp Gly Tyr Leu Leu Thr Asp Ala Arg Gly Thr Ile Gln Glu
    770                 775                 780

Ala Asn Cys Ala Ile Thr Ala Leu Leu Ser Ile Glu Leu Gly Tyr Leu
785                 790                 795                 800

Ile Gly Lys Pro Leu Val Ser Phe Ile Pro Ala Ser Ala Arg Arg Thr
                805                 810                 815

Phe Arg Thr Gln Leu Asn His Leu Ser Leu Leu Ser Asp Lys Gln Thr
            820                 825                 830

Trp Glu Leu Ser Leu Arg Pro Arg Asn Gly Lys Pro Phe Pro Ala Glu
        835                 840                 845

Ile Thr Val Ala Pro Val Arg Asp Gly Asn Lys Leu Ile Ala Leu Arg
    850                 855                 860

Trp Leu Ile Arg Asp Ile Thr Ala Arg Lys Gln Ala Glu Ile Ala Leu
865                 870                 875                 880

Arg Glu Ser Glu Glu Arg Phe Arg Glu Ile Ala Glu Asn Ile Asn Gln
                885                 890                 895

Ile Phe Phe Val Trp Ser Ala Asn Ser Glu Gln Phe Leu Tyr Ile Ser
            900                 905                 910

Pro Gly Tyr Glu Lys Ile Tyr Gly Met Ser Cys Glu Ser Leu Tyr Gln
        915                 920                 925

Asn Pro Gln Ser Trp Leu Asp Leu Val His Pro Asp Asp Arg Lys Ser
    930                 935                 940

Val Trp Gln Ser Leu Asn Glu Gln Ser Gln Gly Lys Pro Ala Arg Arg
945                 950                 955                 960

Glu Tyr Arg Ile Ile Lys Ser Asp Gly Thr Ile Gly Trp Met Phe Ala
                965                 970                 975

Glu Val Phe Pro Ile Phe Asp Gln Thr Gly Lys Ile Leu Arg Tyr Ile
            980                 985                 990

Gly Leu Thr Glu Asp Ile Thr Glu  Arg Lys Arg Ala Glu  Glu Ala Leu
        995                 1000                1005

Leu Glu  Arg Glu Gln Phe Leu  Arg Ser Ile Tyr Asp  Gly Thr Ala
    1010                1015                1020
```

```
Ala Ala  Ile Phe Ile Val Asp  Val Leu Glu Asp Gly  Ser Phe Arg
    1025                 1030                 1035

Tyr Val  Asp Ile Asn Pro Ala  Tyr Glu Trp Met Ser  Gly Leu Leu
    1040                 1045                 1050

Ser Ser  Glu Ile Val Gly Lys  Thr Pro Glu Gln Ile  Phe Pro Leu
    1055                 1060                 1065

Glu Glu  Ala Gln Val Ile Ser  Ala Arg Phe His Asn  Cys Ala Thr
    1070                 1075                 1080

Thr Gly  Thr Arg Ile Pro Tyr  Glu Glu Arg Leu Leu  Ile Arg Asp
    1085                 1090                 1095

Lys Glu  Thr Trp Trp Ile Asn  Val Leu Thr Pro Ile  Gln Arg Glu
    1100                 1105                 1110

Asp Gly  Gln Ile Tyr Arg Leu  Ile Gly Ser Cys Phe  Asn Ile Thr
    1115                 1120                 1125

Lys Arg  Lys Lys Leu Glu Gln  Ser Leu Arg Ser Gln  Ala Asp Gln
    1130                 1135                 1140

Glu Arg  Leu Leu Ile Thr Ile  Thr Gln His Ile Arg  Gln Ser Leu
    1145                 1150                 1155

Asp Leu  Glu Gln Ile Leu Ala  Thr Thr Val Ile Glu  Val Gln Gln
    1160                 1165                 1170

Met Leu  Gln Val Asp Arg Ala  Leu Ile Phe Arg Leu  Asn Glu Asp
    1175                 1180                 1185

Gly Ser  Gly Gln Val Ile Lys  Glu Ala Val Val Pro  Glu Tyr Pro
    1190                 1195                 1200

Val Thr  Glu Gln Met Arg Trp  Arg Asp Glu Pro Leu  Pro Asp Tyr
    1205                 1210                 1215

Cys Tyr  Asp Phe Tyr Arg Gln  Gly Asn Pro Arg Ile  Val Pro Asn
    1220                 1225                 1230

Val Ala  Ile Tyr Asp Trp Ala  Ser Cys Leu Ala Glu  Phe Leu Gln
    1235                 1240                 1245

Gln Ala  Ser Val Lys Ser Lys  Ile Val Ala Pro Ile  Val Gln Thr
    1250                 1255                 1260

Leu Glu  Asp Ser Ser Thr Arg  Val Trp Gly Leu Leu  Ile Val His
    1265                 1270                 1275

Ala Cys  Ser Asp Tyr Arg Gln  Trp Glu Ala Ser Glu  Ala Glu Phe
    1280                 1285                 1290

Leu Gln  Gln Ile Ser Asn Gln  Leu Ala Ile Ala Leu  His Gln Ala
    1295                 1300                 1305

Asn Leu  Tyr Gln Gln Leu Gln  Thr Glu Leu Ala Glu  Arg Lys Gln
    1310                 1315                 1320

Thr Glu  Glu Ala Leu Arg Gln  Asn Gln Ala His Leu  Ala Met Ala
    1325                 1330                 1335

Gln Lys  Val Ser Gln Ile Gly  Ser Trp Glu Phe Asp  Leu Asn Ser
    1340                 1345                 1350

Gln Lys  Ile Arg Trp Ser Gln  Ile Thr Phe His His  Trp Gly Leu
    1355                 1360                 1365

Glu Pro  Ala Lys Gly Glu Pro  Ser Phe Thr Glu Leu  Leu Ala Lys
    1370                 1375                 1380

Val His  Pro Gln Asp Arg Glu  Val Leu Gln Gln Asn  Val Glu Gln
    1385                 1390                 1395

Ala Ile  Ala Lys Gly Ile Pro  Tyr Thr Phe Asp Leu  Arg Ile Leu
    1400                 1405                 1410

Trp Pro  Asp Gly Ser Ile Arg  Tyr Leu Asp Ser Arg  Ala Glu Pro
```

```
    1415                1420                1425

Val Phe  Asn Ala Gln Gly Glu  Val Ile His Leu Ile  Gly Thr Ser
    1430                1435                1440

Leu Asp  Ile Thr Glu Arg Lys  Gln Ala Glu Glu Arg  Leu Arg Glu
    1445                1450                1455

Ser Glu  Glu Arg Phe Arg Lys  Ala Phe Asp Ala Ala  Pro Ile Gly
    1460                1465                1470

Val Ala  Leu Val Ser Pro Gln  Gly Gln Phe Leu Lys  Val Asn Arg
    1475                1480                1485

Ser Leu  Cys Glu Ile Val Gly  Tyr Thr Glu Ala Glu  Met Leu His
    1490                1495                1500

Leu Thr  Met Thr Glu Ile Thr  His Pro Asp Asp Leu  Glu Ala Asp
    1505                1510                1515

Leu Glu  Phe Ile Gln Lys Leu  Leu Ala Asn Glu Ile  Arg Val Tyr
    1520                1525                1530

Gln Val  Glu Lys Arg Tyr Leu  His Gln Arg Gly Asp  Thr Ile Tyr
    1535                1540                1545

Ile Arg  Leu Asn Val Ser Leu  Val Lys Asp Arg His  Arg Lys Pro
    1550                1555                1560

Leu Tyr  Phe Ile Ala Gln Ile  Gln Asp Ile Ser Asp  Arg Tyr Glu
    1565                1570                1575

Val Asp  Arg Met Lys Asn Glu  Phe Ile Ser Ile Val  Ser His Glu
    1580                1585                1590

Leu Arg  Thr Pro Leu Thr Ala  Ile Arg Gly Ser Val  Gly Leu Leu
    1595                1600                1605

Glu Glu  Gly Val Phe Asp Asn  Glu Pro Glu Gln Ala  Arg Glu Met
    1610                1615                1620

Leu Gln  Ile Ala Cys Asn His  Cys Asp Arg Leu Val  Arg Leu Leu
    1625                1630                1635

Asp Glu  Ile Leu Asp Leu Glu  Arg Leu Glu Ser Gly  Lys Val Gln
    1640                1645                1650

Leu Val  Met Glu Thr Cys Glu  Ile Ala Asn Leu Ile  Gln Leu Ala
    1655                1660                1665

Ile Gly  Thr Val Gln Thr Thr  Ala Asn Gln Ala Arg  Val Glu Ile
    1670                1675                1680

Ser Val  Val Ile Val Pro Asn  Met Gln Ile Ser Ala  Glu Ala Asp
    1685                1690                1695

Ser Ile  Ile Arg Ala Leu Thr  Asn Leu Leu Ser Asn  Ala Ile Lys
    1700                1705                1710

Phe Ser  Pro Ala Gly Ser Thr  Val Trp Leu Ser Ala  Glu Leu Leu
    1715                1720                1725

Thr Pro  Glu Glu Asp Ala Gly  Ile Glu Gly Gln Gly  Gly Lys Glu
    1730                1735                1740

Gly Gln  Ile Ala Pro Ala Ser  Pro Val Ser Pro Ile  Ser Pro Val
    1745                1750                1755

Ser Pro  Ile Ser Pro Met Ser  Pro Val Ser Pro Val  Ser Pro Val
    1760                1765                1770

Ser Pro  Met Ser Pro Ile Ser  Pro Val Ser Pro Ile  Ser Pro Val
    1775                1780                1785

Ser Pro  Ile Ser Pro Met Ser  Pro Met Ser Pro Val  Ser Pro Met
    1790                1795                1800

Ser Pro  Val Ser Pro Gln Ser  Pro Gln Ile Leu Phe  Lys Ile Arg
    1805                1810                1815
```

Asp Gln Gly Arg Gly Ile Pro Pro Asp Lys Leu Glu Ser Ile Phe
1820 1825 1830

Glu Arg Phe Gln Gln Val Asp Val Ser Asp Arg Arg Gln Lys Gln
1835 1840 1845

Gly Thr Gly Leu Gly Leu Ala Ile Cys Lys Asn Ile Val Gln Gln
1850 1855 1860

His Gly Gly His Ile Trp Val Glu Ser Val Leu Gly Glu Gly Ser
1865 1870 1875

Thr Phe Tyr Phe Thr Leu Pro Ile Thr Arg Glu Glu Asp Cys
1880 1885 1890

<210> SEQ ID NO 53
<211> LENGTH: 1553
<212> TYPE: PRT
<213> ORGANISM: Unknown
<220> FEATURE:
<223> OTHER INFORMATION: Fischerella sp. PCC 9339

<400> SEQUENCE: 53

Met Ile Thr Phe Leu Ser His Leu Ile Val Glu Ala Asp Lys Ala Arg
1 5 10 15

Val Leu Gly Gln Val Ile Ala Ala Glu Glu Tyr Tyr Glu Gln Ala Ile
20 25 30

Asp Gly Ala Lys Ala Asn Ala Ser Leu Glu Glu Glu Ala Leu Ala Tyr
35 40 45

Glu Leu Ala Ala Lys Tyr Tyr Leu Glu Arg Gly Arg Pro Arg Phe Ala
50 55 60

Gln Asn Tyr Met Lys Glu Ser Tyr Tyr Ala Tyr Arg Arg Leu Asp Ala
65 70 75 80

Thr Ala Lys Val Lys Glu Leu Glu Thr Lys Tyr Pro Arg Leu Leu Phe
85 90 95

Glu Leu Ser Ser Ala Asn Ser Asn Thr Ser Thr Cys Phe Thr Ser Pro
100 105 110

Lys Met Ser Ser Ile Ser Ser Glu Gly Ala Leu Glu Ser Leu Glu Ala
115 120 125

Val Ile Arg Ala Asn Ile Ala Ile Ser Ser Glu Ile Glu Leu Glu Arg
130 135 140

Leu Leu Arg Val Leu Ile Lys Ile Leu Ile Glu Asn Ala Asp Ala Gln
145 150 155 160

Thr Gly Tyr Leu Ile Leu Pro Ser Pro Thr Asn Leu Glu Asn Gly Glu
165 170 175

Glu Trp Lys Ile Ala Ala Ser Gly Ile Ile Asp Thr Glu Ala Ser Asp
180 185 190

Asn Thr Leu Gly Lys Pro Val Phe Lys Ile Gly Val Gln Ser Leu Pro
195 200 205

Ile Asp Asp His Leu Pro Thr Ser Ile Ile Asn Tyr Val Ile His Thr
210 215 220

Leu Glu Asn Val Val Val Asp Asn Ala Ser Cys Glu Gly Lys Phe Ile
225 230 235 240

His Asp Pro Tyr Ile Gln Gln His Gln Thr Lys Ser Ile Leu Cys Thr
245 250 255

Pro Leu Leu Asn Gln Asp Lys Leu Ile Gly Ile Val Tyr Leu Glu Asn
260 265 270

Asn Leu Thr Asn Gly Val Phe Thr Lys Thr Gln Leu Asn Ile Leu Gln
275 280 285

-continued

```
Leu Leu Phe Thr Gln Ala Ala Ile Ser Ile His Asn Ala Lys Ile Phe
    290                 295                 300

Ser Gln Leu Arg Glu Asn Glu Lys Gln Leu Ser Val Arg Glu Lys Arg
305                 310                 315                 320

Val Asn Gln Ile Leu Asn Val Met Pro Ile Ala Val Thr Ala His Asp
                325                 330                 335

Thr Thr Gly Arg Tyr Ile Tyr Ser Asn Leu Lys Ala Gln Gln Leu Val
            340                 345                 350

Gly Met Lys Ala Pro Leu Glu Ile Lys Thr Glu Gln Leu Ser Glu Val
        355                 360                 365

Phe Gln Val Tyr Gln Ala Gly Thr Asp Gln Leu Tyr Pro Ile Asn Lys
    370                 375                 380

Leu Pro Val Val Arg Thr Phe Ala Gly Glu Ser Val Lys Ile Asn Asp
385                 390                 395                 400

Met Glu Leu Arg Gln Asp Asp Lys Thr Ile Pro Leu Glu Val Leu Thr
                405                 410                 415

Val Pro Ile Phe Asp Glu Thr Gly Ala Ile Ile Tyr Ala Ile Ala Ala
            420                 425                 430

Phe Ser Asp Ile Thr Glu Arg Lys Gln Ala Gln Lys Leu Leu Ala Asp
        435                 440                 445

Tyr Asn Gln Thr Leu Glu Thr Gln Ile Ala Glu Arg Thr Glu Lys Leu
    450                 455                 460

Gln Gln Gln Asn Glu Ile Leu Gln Ala Leu Phe Asp His Ile Pro Val
465                 470                 475                 480

Met Leu Lys Leu Arg Asp Gln Thr Asp Gln Thr Leu Val Ile Asn Arg
                485                 490                 495

Glu Tyr Glu Arg Val Leu Gly Trp Thr Leu Asp Asp Leu Arg Asp Ile
            500                 505                 510

Asp Trp Leu Ala Lys Cys Tyr Pro Asp Thr Glu Gln Arg Gln Gln Ile
        515                 520                 525

Arg Glu His Ile Glu Ala Ala Thr Gly Lys Trp Gln Asp Phe Arg Thr
    530                 535                 540

Arg Cys Gln Asn Gly Arg Tyr Val Asp Thr Thr Trp Ala Asn Ile Arg
545                 550                 555                 560

Leu Ser Thr Gly Gln Ile Ile Gly Ile Gly Lys Asp Ile Ser Asp Arg
                565                 570                 575

Lys Gln Leu Glu Lys Ala Leu Gln Ala Ser Gln Ala Lys Leu Asn Asp
            580                 585                 590

Ile Leu Asn Ser Ala Gly Ala Ser Ile Ala Ser Phe Arg Val Tyr Pro
        595                 600                 605

Asp Arg Ser Trp Asp Arg Glu Tyr His Ser Leu Gly Cys Glu Asn Ile
    610                 615                 620

Phe Gly Tyr Thr Pro Gln Glu Leu Thr Pro Glu Leu Trp Leu Ser Arg
625                 630                 635                 640

Val Pro Ser Glu Asp Leu Thr Val Ile Ser Glu Gln Ala Phe Ala Ala
                645                 650                 655

Ile Ala Gln Glu Gln Ala Thr Thr Leu Glu Tyr Arg Phe Tyr His Lys
            660                 665                 670

Asn Ser Ser Leu Arg Trp Ile Ala Asp Thr Leu Thr Ser Arg Trp Asp
        675                 680                 685

Gln Ala Gly Gly Cys Trp Ile Val Thr Met Val Gly Val Asp Ile Thr
    690                 695                 700
```

-continued

```
Ala Arg Lys Gln Ala Glu Met Ala Leu Gln Glu Ser Glu Gln Phe Leu
705                 710                 715                 720

Arg Ser Ile Tyr Glu Gly Thr Ala Ala Ala Ile Phe Ile Val Asp Val
                725                 730                 735

Leu Glu Asp Gly Arg Phe Arg Tyr Val Asp Ile Asn Pro Ala His Glu
            740                 745                 750

Trp Met Ser Gly Leu Phe Ser Ser Glu Met Ala Gly Lys Thr Pro Glu
        755                 760                 765

Gln Ile Phe Pro Pro Glu Asp Ala Gln Val Ile Asn Ala Arg Phe Val
    770                 775                 780

Ala Cys Thr Thr Ile Gly Gln Arg Ile Thr Tyr Glu Glu Arg Leu Glu
785                 790                 795                 800

Ile Arg Gly Lys Glu Thr Trp Trp Ile Asn Val Leu Thr Pro Ile Tyr
                805                 810                 815

Thr Glu Asp Gly Gln Ile Tyr Arg Leu Ile Gly Ser Cys Phe Asn Ile
            820                 825                 830

Thr Arg Arg Lys Lys Leu Glu His Ser Leu Arg Ser Gln Ala Asp Gln
        835                 840                 845

Glu His Leu Leu Gly Thr Ile Thr Gln His Ile Arg Gln Ser Leu Asp
    850                 855                 860

Leu Glu Gln Ile Leu Ala Thr Thr Val Val Glu Val Gln Arg Thr Leu
865                 870                 875                 880

Gln Ala Asp Arg Ala Leu Ile Phe Arg Leu Asn Gln Asp Gly Ser Gly
                885                 890                 895

Gln Val Ile Lys Glu Ala Val Val Pro Glu Tyr Pro Met Thr Ser Gln
            900                 905                 910

Met Arg Cys Thr Asp Glu Cys Phe Pro Asp Asp Cys Tyr Glu Tyr Tyr
        915                 920                 925

Arg Gln Gly Asn Ala Arg Ile Leu Pro Asp Val Ala Lys Asp Glu Trp
    930                 935                 940

Ser Asp Cys Leu Val Glu Phe Met Gln Gln Ile Gly Val Lys Ser Lys
945                 950                 955                 960

Val Val Ala Pro Ile Ile Gln Thr Leu Glu Asp Ser Ser Thr Arg Val
                965                 970                 975

Trp Gly Leu Leu Ile Val His Ala Cys Ser Asn Tyr Arg His Trp Arg
            980                 985                 990

Ala Ser Glu Ala Glu Phe Leu Gln  Gln Ile Ser Asn Gln  Leu Ala Ile
        995                 1000                1005

Ala Leu  His Gln Ala Asn Leu  Tyr Asn His Leu Gln  Thr Glu Leu
    1010                1015                1020

Ala Glu  His Lys Gln Thr Glu  Ala Ala Leu Arg Gln  Asn Gln Ala
    1025                1030                1035

His Leu  Ala Met Ala Gln Lys  Val Ser Gln Ile Gly  Ser Trp Glu
    1040                1045                1050

Phe Asp  Val Asn Ser Gln Asn  Ile Ser Cys Ser Gln  Thr Thr Phe
    1055                1060                1065

His Gln  Trp Gly Ile Glu Pro  Val Lys Gly Glu Pro  Ser Phe Ser
    1070                1075                1080

Glu Leu  Leu Glu Arg Val His  Pro Asp Asp Arg Glu  Val Leu Gln
    1085                1090                1095

Gln Lys  Val Glu Gln Ala Ile  Thr Asn Arg Ile Ser  Tyr Ala Phe
    1100                1105                1110

Asp Leu  Arg Ile Met Arg Pro  Asp Gly Ser Ile Arg  Tyr Leu Asp
```

```
    1115                1120                1125

Ser Arg  Ala Glu Pro Val Leu  Asn Ala Gln Gly Gln  Val Ile Gln
    1130                1135                1140

Leu Ile  Gly Thr Ser Leu Asp  Ile Thr Glu Arg Lys  Gln Ala Glu
    1145                1150                1155

Glu Tyr  Leu Arg Glu Ser Glu  Glu Arg Phe Arg Lys  Ala Phe Asp
    1160                1165                1170

Ala Ala  Pro Ile Gly Val Ala  Leu Val Ser Pro Gln  Gly Gln Phe
    1175                1180                1185

Leu Met  Val Asn His Ser Leu  Cys Glu Ile Val Gly  Tyr Thr Glu
    1190                1195                1200

Ala Glu  Met Leu Asn Leu Thr  Met Met Glu Ile Thr  His Pro Asp
    1205                1210                1215

Asp Leu  Glu Ala Asp Leu Glu  Leu Met Gln Lys Leu  Leu Ala Asn
    1220                1225                1230

Glu Ile  Arg Val Tyr Gln Val  Glu Lys Arg Tyr Leu  His Asn Arg
    1235                1240                1245

Gly Asp  Thr Ile His Thr Leu  Leu Asn Val Ser Leu  Val Arg Asp
    1250                1255                1260

Gln His  Arg Glu Pro Leu Tyr  Phe Ile Ala Gln Ile  Gln Asp Ile
    1265                1270                1275

Ser Asp  Arg Tyr Glu Val Asp  Arg Ile Lys Asn Glu  Phe Ile Ser
    1280                1285                1290

Ile Val  Ser His Glu Leu Arg  Thr Pro Leu Thr Ala  Ile Arg Gly
    1295                1300                1305

Ala Val  Gly Ile Leu Glu Thr  Gly Val Phe Asp His  Glu Pro Glu
    1310                1315                1320

Gln Ala  Arg Glu Met Leu Gln  Ile Ala Phe Asn Asn  Ser Asp Arg
    1325                1330                1335

Leu Val  Arg Leu Val Asn Asp  Ile Leu Asp Leu Glu  Arg Leu Glu
    1340                1345                1350

Ser Gly  Lys Ile Gln Leu Val  Thr Glu Thr Cys Glu  Thr Ala Asn
    1355                1360                1365

Leu Val  Lys Gln Ala Ile Glu  Thr Val Gln Ala Met  Ala Asn Glu
    1370                1375                1380

Ala Gly  Val Lys Ile Phe Val  Met Val Pro Asn Met  Gln Ile Ser
    1385                1390                1395

Ala Ala  Ala Asp Ser Ile Ile  Gln Thr Leu Ile Asn  Leu Leu Ser
    1400                1405                1410

Asn Ala  Ile Lys Phe Ser Pro  Ala Gly Gly Thr Val  Trp Leu Ser
    1415                1420                1425

Ala Glu  Leu Val Ser Pro Glu  Glu Glu Gly Gly Met  Gly Gly Asp
    1430                1435                1440

Gly Gly  Gly Gly Gly Gly Gly  Gly Gly Gly Gly Asp  Gly Gly Asp
    1445                1450                1455

Gly Gly  Asp Gly Gly Asp Gly  Gly Gln Ile Ala Pro  Ile Ser Ala
    1460                1465                1470

Lys Ile  Leu Phe Lys Val Arg  Asp Gln Gly Arg Gly  Ile Pro Pro
    1475                1480                1485

Glu Lys  Leu Glu Ser Ile Phe  Gly Arg Phe Gln Gln  Val Asp Val
    1490                1495                1500

Ser Asp  Arg Arg Gln Lys Arg  Gly Thr Gly Leu Gly  Leu Ala Ile
    1505                1510                1515
```

Cys Lys Asn Ile Val Gln Gln His Gly Gly Cys Ile Trp Val Glu
1520 1525 1530

Ser Val Leu Gly Glu Gly Ser Thr Phe Tyr Phe Thr Leu Pro Ile
1535 1540 1545

Thr Arg Glu Glu Ala
1550

<210> SEQ ID NO 54
<211> LENGTH: 1690
<212> TYPE: PRT
<213> ORGANISM: Chlorogloeopsis fritschii

<400> SEQUENCE: 54

Met Ile Asp Ser Ala Asn Ser Ser Gln Arg Leu Gln Lys Tyr Phe Ala
1 5 10 15

Lys Ile Pro Leu Trp Leu Leu Leu Val Val Pro Phe Val Leu Gln Leu
20 25 30

Leu Ala Thr Val Gly Val Ile Gly Tyr Leu Cys Tyr Glu Ala Trp Gln
35 40 45

Arg Ser Thr His Lys Val Ala Asn Gln Val Met Lys Glu Val Gly Asp
50 55 60

Arg Val Gln His Tyr Leu Ser Asp Tyr Leu Glu Thr Pro Gln Leu Ile
65 70 75 80

Asn Arg Leu Asn Ala Asn Ala Thr Asp Leu Asn Gln Ile Asp Ile Asn
85 90 95

Asp Pro Asn Ser Leu Glu Ser His Phe Leu Gln Gln Ile Gln Ala Phe
100 105 110

Asn Ser Val Ser Arg Ile His Phe Ser Asn Pro Gln Gly Gly Tyr Ile
115 120 125

Ser Ala Gly Asn Asp Glu Arg Gly Leu Ser Val Ala Phe Thr Glu Asn
130 135 140

Phe Val Arg Gly Thr Leu His Val Tyr Gly Val Asp Asn Gln Gly Lys
145 150 155 160

Arg Thr Gln Gln Phe Val His Gln Gln Asn Tyr Asp Ala Thr Lys Arg
165 170 175

Pro Phe Tyr Gln Ala Ala Ala Lys Ala Ser Lys Pro Ile Trp Thr Pro
180 185 190

Ile Tyr Val Tyr Ile Pro Ala Ser Thr Gly Leu Gly Ile Ala Ala Ser
195 200 205

Tyr Pro Leu Tyr Asp Gln Leu Asn Arg Leu Gln Gly Val Leu Ser Thr
210 215 220

Asp Leu Thr Leu Ala Asn Ile Asn Gln Phe Leu Ser Asn Leu Lys Ile
225 230 235 240

Gly Thr Gln Gly Lys Val Leu Ile Leu Glu Arg Ser Gly Leu Ile Val
245 250 255

Ala Ser Ser Thr Ser Glu Lys Pro Phe Phe Ile Ser Ser Asn Gln Arg
260 265 270

Gln Thr Ile Arg Leu Lys Ala Thr Glu Ser Gln Glu Pro Leu Ile Arg
275 280 285

Phe Thr Ala Gln His Leu Val Ser Tyr Phe Gly Asp Leu Thr Lys Ile
290 295 300

Lys Thr Pro Glu Gln Leu Gln Phe Glu Val Lys Gly Lys Arg Leu Phe
305 310 315 320

Leu Gln Val Asn Pro Phe Thr Asp Arg Phe Gly Leu Asp Trp Leu Ile

-continued

```
                325                 330                 335

Val Thr Val Leu Pro Glu Ser Asp Leu Ile Ala Asp Leu Asp Gly Asn
            340                 345                 350

Thr Gln Arg Met Met Leu Leu Ser Gly Phe Thr Leu Leu Leu Ala Ile
        355                 360                 365

Gly Thr Gly Ile Leu Thr Ala Cys Trp Ile Ala Arg Pro Ile Arg Arg
    370                 375                 380

Leu Lys Lys Ala Ala Gln Ala Ile Thr Lys Gly Gln Leu Asn Tyr Pro
385                 390                 395                 400

Ile Ala Thr Gly Gly Ile Gly Glu Val Ala Gln Leu Ala Gln Gly Phe
                405                 410                 415

Gln Val Met Ala Asn Gln Leu Asp Ser Ser Phe Arg Ala Leu Lys Ala
            420                 425                 430

Ser Glu Gln Lys Phe Ala Thr Leu Leu Ser Asn Val Pro Ile Gly Ile
        435                 440                 445

Ser Val Phe Asp Ala Lys Glu Asn Pro Val Leu Ile Asn Lys Val Gly
    450                 455                 460

Glu Glu Ile Leu Gly Arg Gly Leu Val Ser Asp Ile Ser Phe Ala Gln
465                 470                 475                 480

His Ser Glu Val Tyr Gln Ile Tyr Val Ala Gly Thr Asp Gln Leu Tyr
                485                 490                 495

Pro Thr Glu Gln Leu Pro Ala Thr Arg Gly Leu Arg Gly Glu Thr Ala
            500                 505                 510

Leu Ile Asp Asp Met Glu Ile Glu Val Asn Gly Arg Arg Ile Pro Leu
        515                 520                 525

Glu Val His Thr Ile Pro Val Phe Asp Asp Asp Ser Asn Val Ile Tyr
    530                 535                 540

Ala Ile Asn Ala Phe Arg Asp Ile Thr Gln Arg Arg Gln Ala Glu Lys
545                 550                 555                 560

Leu Trp Thr Asp Tyr Glu Gln Glu Leu Lys Cys Arg Val Ala Glu Lys
                565                 570                 575

Thr Ala Ala Leu Arg Gln Ser Glu Glu Arg Phe Arg Leu Ala Val Asn
            580                 585                 590

His Ala Pro Asp Val Phe Val Ile Tyr Asp Arg Asp Arg Arg Phe Leu
        595                 600                 605

Tyr Val Asn Glu Lys Ala Arg Glu Leu Thr Gly Trp Thr Leu Asp His
    610                 615                 620

Phe Ile Gly Tyr Arg Asp Asp Asp Leu Phe Pro Pro Glu Val Thr Ala
625                 630                 635                 640

Pro Tyr Leu Pro Ile Leu Gln Lys Thr Ile Ser Thr Lys Thr Leu Gln
                645                 650                 655

Ile Gly Glu Cys Thr Ile Lys Leu Pro Glu Gln Lys Pro Ser Thr Phe
            660                 665                 670

Ile Val Lys Tyr Val Pro Leu Leu Asp Glu Gln Gly Glu Ile Gln Gln
        675                 680                 685

Ile Leu Gly Met Thr Phe Asp Ile Ser Asp Arg Lys Gln Ile Glu Glu
    690                 695                 700

Ile Leu Arg Gln Ser Glu Ala Arg Leu Thr Met Ala Gln Arg Val Ala
705                 710                 715                 720

Gln Val Gly Ser Trp Glu Phe Asp Leu Asn Ser Gln Lys Met Thr Trp
                725                 730                 735

Ser Glu Glu Thr Phe Tyr His Trp Gly Phe Asp Ser Thr Pro Glu Glu
            740                 745                 750
```

-continued

```
Pro Ser Tyr Thr Glu Leu Leu Lys Arg Val His Pro Glu Asp Arg Glu
        755                 760                 765

Ile Leu Asn Tyr Phe Phe Glu Gln Ala Ile Ala Gln Gly Ile Pro Tyr
    770                 775                 780

Val Leu Asp Leu Arg Ile Val Arg Pro Asp Gly Ser Ile Arg Tyr Leu
785                 790                 795                 800

Asp Tyr Arg Gly Glu Pro Leu Phe Asn Ala Gln Gly Gln Val Ile Lys
                805                 810                 815

Leu Ile Gly Thr Ser Val Asp Ile Ser Asp Arg Lys Trp Thr Glu Glu
            820                 825                 830

Ala Leu Arg Gln Ser Glu Ala Leu Asn Arg Ala Ile Val Asn Ala Leu
        835                 840                 845

Pro Asp Leu Ile Ile Arg Met His Arg Asp Gly Thr Tyr Leu Asp Val
    850                 855                 860

Lys Pro Thr Thr Ala Phe Leu Thr Ser Ala Ser Pro Leu Val Val Gly
865                 870                 875                 880

Leu Asn Val Gln Ala Val Leu Ser Pro Gln Val Ala Gln Arg Arg Ile
                885                 890                 895

Ala Ala Ile Glu Asn Ala Leu Gln Thr Gly Glu Ile Gln Val Tyr Glu
            900                 905                 910

Phe Pro Phe Val Ile Gln Gly Gln Ser Leu Trp Gln Glu Val Arg Val
        915                 920                 925

Met Pro Leu Asp Val Asp Glu Val Leu Val Val Ile Arg Asp Leu Thr
    930                 935                 940

Glu Arg Lys Lys Ala Glu Glu Ala Val Arg Leu Gln Ala Lys Arg Glu
945                 950                 955                 960

Gln Leu Leu Arg Gly Ile Thr Gln Arg Ile Arg Gln Ser Leu Asp Leu
                965                 970                 975

Glu Gln Ile Leu Ala Thr Thr Val Asn Glu Val Leu Gln Thr Leu Gln
            980                 985                 990

Ser Asp Arg Ala Leu Ile Phe Arg  Leu His Gly Asn Gly  Thr Gly Gln
        995                 1000                 1005

Val Ile  Gln Glu Ala Val Arg  Pro Glu Tyr Pro Val  Thr Glu Gln
    1010                 1015                 1020

Met Leu  Phe Pro Asp Glu Cys  Phe Pro Gln Glu Cys  Tyr Glu Tyr
    1025                 1030                 1035

Tyr Cys  Gln Gly Gln Pro Arg  Ile Val Ser Asp Val  Phe Ala Glu
    1040                 1045                 1050

Asp Phe  Ser Ser Cys Leu Val  Glu Phe Met Gln Lys  Ile Gly Val
    1055                 1060                 1065

Lys Ser  Lys Ile Val Ala Pro  Ile Val Gln Thr Thr  Glu Asn Ser
    1070                 1075                 1080

Ser Thr  Lys Val Trp Gly Leu  Leu Ile Val His Ala  Cys Ser Gln
    1085                 1090                 1095

His Arg  Gln Trp Gln Gln Ser  Glu Ala Asp Phe Leu  Gln Gln Ile
    1100                 1105                 1110

Ser Asn  Gln Leu Ala Ile Ala  Ile Gln Gln Ser Gln  Leu Tyr Gln
    1115                 1120                 1125

Gln Thr  Arg Gln Gln Ala Gln  Arg Glu Gln Thr Leu  Asn Arg Val
    1130                 1135                 1140

Val Gln  Ala Ile Arg Asn Ser  Leu Asp Leu Asp Thr  Ile Phe Ala
    1145                 1150                 1155
```

-continued

```
Thr Thr  Val Ser Glu Val Gly  Leu Leu Leu Gln Val  Met Arg Val
    1160                 1165                 1170

Asn Ile  Met Gln Tyr Leu Pro  Glu Arg Gly Ile Trp  Val Ser Ala
    1175                 1180                 1185

Ala Asp  Tyr Val Gln Asp Pro  Ser Leu Gly Asn Thr  Val Gly Phe
    1190                 1195                 1200

Glu Ile  Pro Asp Thr Ser Asn  Pro Ile Ala Thr Lys  Ile Lys Gln
    1205                 1210                 1215

Phe Glu  Ile Val Gln Ile Ile  Asn Asp Val Ala Ser  Glu Glu Glu
    1220                 1225                 1230

Ile Ala  Gln Thr Tyr Gln Gly  Ala Cys Leu Ile Val  Pro Leu Lys
    1235                 1240                 1245

Val Glu  Gln Gln Ile Trp Gly  Ser Leu Thr Leu Val  Lys Asp Pro
    1250                 1255                 1260

Pro Ser  Ala Trp Gln Gln Phe  Glu Val Asp Leu Thr  Ile Ala Val
    1265                 1270                 1275

Ala Asp  Gln Leu Ala Ile Ala  Ile Gln Gln Ala Asn  Phe Tyr Asn
    1280                 1285                 1290

Gln Leu  Gln Ile Glu Leu Thr  Glu His Cys Gln Thr  Glu Glu Ala
    1295                 1300                 1305

Leu Arg  Arg Ser Glu Glu Gln  Phe Arg Lys Ala Phe  Asp Asn Ala
    1310                 1315                 1320

Pro Ile  Gly Met Ala Leu Val  Ser Leu Lys Gly Gln  Phe Leu Lys
    1325                 1330                 1335

Val Asn  Asn Ser Leu Cys Glu  Ile Leu Gly Tyr Asn  Gly Glu Glu
    1340                 1345                 1350

Leu Leu  Ala Leu Thr Phe Ala  Asp Ile Thr His Pro  Asp Asp Leu
    1355                 1360                 1365

Glu Pro  Asp Leu Glu Ser Arg  Arg Gln Ile Leu Ala  Gly Glu Ile
    1370                 1375                 1380

Arg Val  Tyr Gln Ala Glu Lys  Arg Tyr Leu His Ser  Ser Gly Asn
    1385                 1390                 1395

Thr Ile  His Val Leu Leu Lys  Ile Ser Leu Val Arg  Asp Gln Gln
    1400                 1405                 1410

Arg Gln  Pro Leu Tyr Phe Ile  Ala Gln Ile Gln Asp  Ile Ser Asp
    1415                 1420                 1425

Arg Tyr  Lys Ile Asn Arg Met  Lys Asp Glu Phe Val  Ser Ile Val
    1430                 1435                 1440

Ser His  Glu Leu Arg Thr Pro  Leu Thr Ala Ile Arg  Gly Ser Leu
    1445                 1450                 1455

Gly Ile  Leu Glu Thr Gly Val  Leu Asp His Asp Pro  Glu Gln Ile
    1460                 1465                 1470

Lys Glu  Leu Leu Gln Ile Ala  Leu Asn Asn Ser Asp  Arg Leu Met
    1475                 1480                 1485

Arg Leu  Val Asn Asp Ile Leu  Asp Leu Glu Arg Leu  Glu Ser Gly
    1490                 1495                 1500

Lys Val  Lys Leu Val Met Glu  Ala Cys Glu Val Ala  Asn Leu Val
    1505                 1510                 1515

Lys Gln  Ala Thr Glu Ser Val  Gln Ala Ile Ala Asp  Glu Ala Asn
    1520                 1525                 1530

Ile Thr  Leu Ser Val Lys Phe  Ser Asn Ile Gln Ile  Trp Val Ala
    1535                 1540                 1545

Pro Asp  Ala Ile Val Gln Thr  Leu Ile Asn Leu Leu  Ser Asn Ala
```

```
    1550                1555                1560

Ile Lys  Phe Ser Pro Ala Gly  Ser Thr Val Trp Leu  Ser Ala Glu
    1565                1570                1575

Glu Gly  Ile Gly Asp Arg Glu  Gln Val Thr Gly Asp  Arg Gly Gln
    1580                1585                1590

Gly Ile  Gly Asp Lys Glu Lys  Ile Phe Asp Asn Phe  Ser Ala Ser
    1595                1600                1605

Ser Arg  Ser Pro Cys Ile Leu  Phe Thr Val Arg Asp  Gln Gly Arg
    1610                1615                1620

Gly Ile  Pro Ser Asp Lys Leu  Glu Thr Ile Phe Glu  Arg Phe Gln
    1625                1630                1635

Gln Val  Asp Val Ser Asp Ser  Arg Ser Lys Gly Gly  Thr Gly Leu
    1640                1645                1650

Gly Leu  Ala Ile Cys Lys Ser  Ile Val Lys Gln His  Gly Gly Lys
    1655                1660                1665

Ile Trp  Val Glu Ser Arg Val  Gly Glu Gly Ser Thr  Phe Tyr Phe
    1670                1675                1680

Thr Leu  Pro Ile Thr Arg Lys
    1685                1690
```

<210> SEQ ID NO 55
<211> LENGTH: 95
<212> TYPE: PRT
<213> ORGANISM: Nostoc punctiforme

<400> SEQUENCE: 55

```
Asp Arg Val Met Ile Tyr Lys Phe His Ala Asp Gly Asn Gly Gln Val
1               5                   10                  15

Ile Ala Glu Ser Ile Tyr Asn Asn Arg Leu Pro Ser Leu Leu Gly Leu
            20                  25                  30

Asn Phe Pro Ala Asp Asp Ile Pro Leu Ser Ala Arg Glu Leu Phe Leu
        35                  40                  45

Lys Leu Arg Val Arg Ser Val Val Asn Val Asp Thr Gln Glu Ile Gly
    50                  55                  60

Gln Ile His Cys His Ile Glu Tyr Leu Thr Ala Met Gly Val Lys Ser
65                  70                  75                  80

Ser Val Val Ala Pro Ile Leu Leu Trp Gly Leu Leu Val Ser His
                85                  90                  95
```

<210> SEQ ID NO 56
<211> LENGTH: 95
<212> TYPE: PRT
<213> ORGANISM: Unknown
<220> FEATURE:
<223> OTHER INFORMATION: Leptolyngbya sp. JSC-1

<400> SEQUENCE: 56

```
Asp Arg Val Lys Ile Tyr Arg Phe His Gly Asp Gly Ser Gly Glu Val
1               5                   10                  15

Val Ala Glu Ala Ile Arg Asp Gln Arg Leu Pro Ser Leu Leu His His
            20                  25                  30

Asn Phe Pro Ala Gly Asp Ile Pro Arg Glu Ala Arg Glu Leu Phe Leu
        35                  40                  45

Ser Val Arg Gln Arg Ser Ile Val Asn Val Ser Thr Gln Gln Ile Gly
    50                  55                  60

Ile Ser Pro Cys His Val Glu Tyr Leu Thr Ala Met Gly Val Lys Ser
65                  70                  75                  80
```

```
Ser Leu Val Val Pro Ile Leu Leu Trp Gly Leu Leu Val Ser His
                85                  90                  95


<210> SEQ ID NO 57
<211> LENGTH: 92
<212> TYPE: PRT
<213> ORGANISM: Unknown
<220> FEATURE:
<223> OTHER INFORMATION: Anabaena cylindrica PCC 7122

<400> SEQUENCE: 57

Glu Arg Val Ile Ile Phe Arg Leu Phe Pro Asn Gly Arg Ser Gln Ile
1               5                   10                  15

Val Glu Glu Val Val Ser Ser Glu Tyr Ala Ala Leu Lys Asn Tyr His
            20                  25                  30

Trp Glu Asp Glu Lys Trp Ser Gln Glu Ile Leu Asp Cys Tyr Trp Gln
        35                  40                  45

Gly Lys Pro Arg Ile Val Pro Asp Val Ile Asn Asp Ile Trp Thr Ser
    50                  55                  60

Cys Leu Val Glu Tyr Thr Thr Gln Gly Asn Ile Gln Ser Lys Ile Val
65                  70                  75                  80

Ala Pro Ile Leu Leu Trp Gly Val Leu Val Val His
                85                  90


<210> SEQ ID NO 58
<211> LENGTH: 92
<212> TYPE: PRT
<213> ORGANISM: Unknown
<220> FEATURE:
<223> OTHER INFORMATION: Anabaena cylindrica PCC 7122

<400> SEQUENCE: 58

Asp Arg Val Ile Val Phe Arg Leu Phe Ala Asp Gly Glu Ser Gln Ile
1               5                   10                  15

Val Glu Glu Ala Val Ser Gly Glu Leu Val Ser Leu Lys Asn Arg His
            20                  25                  30

Trp Asp Asn Glu Val Trp Ser Gln Glu Ile Leu Asp Tyr Tyr Trp Gln
        35                  40                  45

Gly Gln Pro Arg Ile Val Thr Asp Val Met Glu Asp Ile Trp Thr Asp
    50                  55                  60

Cys Leu Val Glu Tyr Ser Ile Glu Gly Gln Val Gln Ser Lys Ile Val
65                  70                  75                  80

Ala Pro Ile Leu Leu Trp Gly Val Leu Val Val His
                85                  90


<210> SEQ ID NO 59
<211> LENGTH: 92
<212> TYPE: PRT
<213> ORGANISM: Unknown
<220> FEATURE:
<223> OTHER INFORMATION: Cyanothece sp. PCC 7822

<400> SEQUENCE: 59

Asp Arg Val Ile Ile Phe Arg Leu Tyr Ser Asp Gly Gly Ser Arg Ile
1               5                   10                  15

Ile Glu Glu Ser Val Ser Thr Glu Phe Leu Pro Leu Lys Tyr Cys His
            20                  25                  30

Trp Asp Asp Glu Thr Trp Ser Gln Asp Ile Leu Asn Leu Tyr Trp Gln
        35                  40                  45
```

```
Gly Gln Pro Arg Ile Val Pro Asp Val Met Asn Asp Ile Tyr Thr Glu
    50                  55                  60

Cys Leu His Glu Tyr Ser Arg Glu Gly Gln Ile Gln Ser Lys Ile Val
65                  70                  75                  80

Ala Pro Ile Leu Leu Trp Gly Ile Leu Val Val His
                85                  90


<210> SEQ ID NO 60
<211> LENGTH: 92
<212> TYPE: PRT
<213> ORGANISM: Nodosilinea nodulosa

<400> SEQUENCE: 60

Asp Arg Val Ile Val Phe Gln Val Ala Gln Asn Gly His Ser Cys Ile
1               5                   10                  15

Leu Glu Glu Ala Val Ala Pro Asp Leu Pro Gln Leu Lys Ala Met Gln
            20                  25                  30

Trp Asp Asp Glu Thr Trp Ser Gln Asp Ile Leu Glu His Tyr Trp Gln
        35                  40                  45

Gly Gln Pro Arg Ile Val Pro Asp Val Met Glu Asp His Trp Thr Asp
    50                  55                  60

Cys Leu Val Glu Tyr Ser Lys Ala Gly Gln Ile Gln Ser Lys Ile Val
65                  70                  75                  80

Ala Pro Ile Leu Leu Trp Gly Val Leu Val Val His
                85                  90


<210> SEQ ID NO 61
<211> LENGTH: 92
<212> TYPE: PRT
<213> ORGANISM: Unknown
<220> FEATURE:
<223> OTHER INFORMATION: Leptolyngbya sp. PCC 6406

<400> SEQUENCE: 61

Asp Arg Val Ile Val Phe Gln Val Tyr His Asp Gly His Ser Arg Ile
1               5                   10                  15

Val Glu Glu Ala Val Thr Pro Asp Leu Pro Ser Leu Lys Ala Met His
            20                  25                  30

Trp Glu Gly Glu Thr Trp Pro Leu Asp Ile Leu Glu His Tyr Trp Gln
        35                  40                  45

Gly Gln Pro Arg Ile Val Pro Asp Val Met Asp Asp Ile Trp Thr Asp
    50                  55                  60

Cys Leu Val Asp Tyr Ala Gln Ala Gly Gln Ile Gln Ser Lys Met Val
65                  70                  75                  80

Ala Pro Ile Leu Leu Trp Gly Val Leu Val Val His
                85                  90


<210> SEQ ID NO 62
<211> LENGTH: 92
<212> TYPE: PRT
<213> ORGANISM: Unknown
<220> FEATURE:
<223> OTHER INFORMATION: Planktothrix agardhii NIVA-CYA 56/3

<400> SEQUENCE: 62

Asp Arg Ala Ile Ile Phe Gln Leu Phe Asp Asn Gly Asn Ser Gln Ile
1               5                   10                  15

Val Glu Glu Ser Val His Ser Asn Phe Leu Asn Leu Lys Ala Leu Asn
            20                  25                  30
```

-continued

```
Trp Asp Asn Glu Val Trp Ser Gln Glu Ile Leu Asp Cys Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Leu Lys Gly Gln Ile Lys Ser Lys Ile Val
65                  70                  75                  80

Ala Pro Ile Leu Leu Trp Gly Val Leu Val Val Tyr
                85                  90


<210> SEQ ID NO 63
<211> LENGTH: 92
<212> TYPE: PRT
<213> ORGANISM: Unknown
<220> FEATURE:
<223> OTHER INFORMATION: Planktothrix rubescens NIVA-CYA 407

<400> SEQUENCE: 63

Asp Arg Ala Ile Ile Phe Gln Leu Phe Asp Asn Gly Asn Ser Gln Ile
1               5                   10                  15

Val Glu Glu Ser Val His Ser Asn Phe Leu Asn Leu Lys Ala Leu Asn
            20                  25                  30

Trp Asp Asn Glu Val Trp Ser Gln Glu Ile Leu Asp Cys Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Leu Lys Gly Gln Ile Lys Ser Lys Ile Val
65                  70                  75                  80

Ala Pro Ile Leu Leu Trp Gly Val Leu Val Val His
                85                  90


<210> SEQ ID NO 64
<211> LENGTH: 92
<212> TYPE: PRT
<213> ORGANISM: Unknown
<220> FEATURE:
<223> OTHER INFORMATION: Tolypothrix sp. PCC 7601

<400> SEQUENCE: 64

Asp Arg Val Ile Val Phe Arg Leu Phe Ala Asp Gly Arg Ser Lys Ile
1               5                   10                  15

Ala Glu Glu Ala Val Ser Ser Glu Phe Val Ser Leu Lys Asn Arg His
            20                  25                  30

Trp Gly Asn Glu Ile Trp Ser Gln Glu Ile Leu Asp Phe Tyr Trp Gln
        35                  40                  45

Gly Lys Pro Arg Ile Val Pro Asp Val Met Asn Asp Leu Trp Thr His
    50                  55                  60

Cys Leu Val Glu Tyr Ser Gln Glu Gly Gln Ile Gln Ser Lys Ile Val
65                  70                  75                  80

Ala Pro Ile Leu Leu Trp Gly Ile Leu Val Val His
                85                  90


<210> SEQ ID NO 65
<211> LENGTH: 92
<212> TYPE: PRT
<213> ORGANISM: Pseudanabaena biceps

<400> SEQUENCE: 65

Asp Arg Val Ile Val Phe Arg Leu Phe Ser Tyr Gly Asp Ser Gln Ile
1               5                   10                  15
```

```
Val Glu Glu Ala Val Ser Pro Glu Phe Thr Ser Leu Lys Ser Leu His
            20                  25                  30

Trp Glu Asn Glu Leu Trp Ser Pro Ala Ile Leu Asp Tyr Tyr Trp Gln
        35                  40                  45

Gly Lys Pro Arg Ile Val Pro Asp Val Met Val Asp Val Trp Thr Asp
    50                  55                  60

Cys Leu Ile Pro Tyr Ser Ile Glu Gly Gln Ile Lys Ser Lys Ile Val
65                  70                  75                  80

Ala Pro Ile Leu Leu Trp Gly Val Leu Val Val His
                85                  90
```

<210> SEQ ID NO 66
<211> LENGTH: 92
<212> TYPE: PRT
<213> ORGANISM: Oscillatoria nigro-viridis

<400> SEQUENCE: 66

```
Asp Arg Ile Val Val Phe Arg Leu Phe Gly Asp Gly Arg Ser Gln Ile
1               5                   10                  15

Val Glu Glu Ala Val Ser Ser Glu Phe Pro Ala Leu Lys Asp His His
            20                  25                  30

Trp Glu Asp Glu Leu Trp Ser Pro Glu Ile Leu Asn Arg Tyr Trp Gln
        35                  40                  45

Gly Lys Pro Arg Ile Val Pro Asp Val Met Thr Asp Ile Trp Thr Asp
    50                  55                  60

Cys Leu Val Glu Tyr Ala Thr Val Cys Gln Val Gln Ser Lys Ile Val
65                  70                  75                  80

Ala Pro Ile Leu Leu Trp Gly Val Leu Val Val His
                85                  90
```

<210> SEQ ID NO 67
<211> LENGTH: 92
<212> TYPE: PRT
<213> ORGANISM: Calothrix parietina

<400> SEQUENCE: 67

```
Asp Arg Val Ile Val Phe Arg Leu Leu Gly Asp Gly Arg Ser Gln Ile
1               5                   10                  15

Val Gln Glu Ala Val Ser Asn Glu Phe Pro Val Leu Lys Asp Arg Gln
            20                  25                  30

Trp Glu Asn Glu Val Trp Ser Gln Glu Ile Leu Asp Gly Tyr Trp Gln
        35                  40                  45

Gly Lys Pro Arg Ile Val Pro Asp Val Met Asn Asp Ile Trp Thr Glu
    50                  55                  60

Cys Leu Val Glu Tyr Ser Arg Glu Gly Lys Ile Gln Ser Lys Ile Val
65                  70                  75                  80

Ala Pro Ile Leu Leu Trp Gly Val Leu Val Val His
                85                  90
```

<210> SEQ ID NO 68
<211> LENGTH: 92
<212> TYPE: PRT
<213> ORGANISM: Microcoleus vaginatus

<400> SEQUENCE: 68

```
Asp Arg Ile Ile Val Phe Arg Leu Phe Gly Asp Gly Arg Ser Gln Ile
1               5                   10                  15

Val Glu Glu Ala Val Ser Ser Glu Phe Pro Ala Leu Lys Asp His His
```

```
            20                  25                  30

Trp Glu Asp Glu Arg Trp Ser Gln Glu Ile Leu Asn Arg Tyr Trp Gln
        35                  40                  45

Gly Lys Pro Arg Ile Val Pro Asn Val Met Thr Asp Ile Trp Thr Asp
    50                  55                  60

Cys Leu Val Glu Tyr Ala Ser Val Gly Gln Val Gln Ser Lys Ile Val
65                  70                  75                  80

Ala Pro Ile Leu Leu Trp Gly Val Leu Val Val His
                85                  90


<210> SEQ ID NO 69
<211> LENGTH: 92
<212> TYPE: PRT
<213> ORGANISM: Unknown
<220> FEATURE:
<223> OTHER INFORMATION: Cyanothece sp. PCC 7425

<400> SEQUENCE: 69

Asp Arg Val Ile Val Phe Gln Leu Phe Pro Asn Gly Lys Ser Arg Ile
1               5                   10                  15

Val Glu Glu Ala Val Ser Ser Gly Leu Thr Val Leu Lys Ala Gly His
            20                  25                  30

Trp Glu Asp Glu Val Trp Pro Gln Glu Ile Leu Asp Tyr Tyr Trp Gln
        35                  40                  45

Gly Gln Pro Arg Ile Val Ala Asp Val Met Asp Asp Arg Trp Thr Asp
    50                  55                  60

Cys Leu Val Gly Tyr Ser Lys Gln Gly Glu Ile Val Ser Lys Ile Val
65                  70                  75                  80

Ala Pro Ile Leu Leu Trp Gly Val Leu Val Ile His
                85                  90


<210> SEQ ID NO 70
<211> LENGTH: 92
<212> TYPE: PRT
<213> ORGANISM: Nodosilinea nodulosa

<400> SEQUENCE: 70

Asp Arg Val Ile Ile Phe Gln Val His Ser Asp Gly His Ser Lys Ile
1               5                   10                  15

Val Glu Glu Ala Val Ser Glu Ser Leu Pro Thr Leu Lys Gly Met Arg
            20                  25                  30

Trp Glu Asp Glu Val Trp Ser Gln Asp Ile Leu Asp Val Tyr Trp Arg
        35                  40                  45

Gly Gln Pro Arg Ile Val Ala Asp Val Met Ala Asp Thr Trp Thr Asp
    50                  55                  60

Cys Leu Val Asp Tyr Ser Gln Ala Gly Gln Ile Gln Ser Lys Ile Val
65                  70                  75                  80

Ala Pro Ile Leu Ile Trp Gly Val Leu Val Val His
                85                  90


<210> SEQ ID NO 71
<211> LENGTH: 92
<212> TYPE: PRT
<213> ORGANISM: Spirulina subsalsa

<400> SEQUENCE: 71

Asp Arg Val Ile Val Phe Arg Phe Cys Asp Leu Gly Arg Thr Cys Ile
1               5                   10                  15
```

```
Phe Glu Glu Ala Val Ala Glu Asp Leu Pro Ser Leu Lys Tyr Met Asn
            20                  25                  30

Trp Glu Asp Glu Gln Trp Ser Ser Glu Ile Leu Gln Phe Tyr Trp Gln
        35                  40                  45

Gly Gln Pro Arg Ile Val Pro Asp Val Met Asn Asp Pro Leu Thr Pro
    50                  55                  60

Cys Leu Leu Asp Tyr Ser Arg Gln Gly Gln Ile Gln Ser Lys Ile Val
65                  70                  75                  80

Ala Pro Ile Leu Leu Trp Gly Leu Leu Val Ile His
                85                  90


<210> SEQ ID NO 72
<211> LENGTH: 92
<212> TYPE: PRT
<213> ORGANISM: Dolichospermum circinale

<400> SEQUENCE: 72

Glu Arg Val Ile Val Phe Arg Leu Phe Pro Asp Gly Lys Ser Gln Ile
1               5                   10                  15

Val Glu Glu Ser Val Ala Asn Gly Tyr Met Thr Phe Lys Asp Ser Tyr
            20                  25                  30

Trp Glu Asp Glu Lys Trp Ser Gln Asp Ile Leu Glu Tyr Tyr Trp Gln
        35                  40                  45

Gly Lys Pro Arg Ile Val Leu Asp Val Met Asp Asp Ile Trp Thr Asp
    50                  55                  60

Cys Leu Lys Ala Tyr Ser Arg Gln Gly Asn Ile Arg Ser Lys Ile Val
65                  70                  75                  80

Ala Pro Ile Leu Leu Trp Gly Val Leu Val Val His
                85                  90


<210> SEQ ID NO 73
<211> LENGTH: 92
<212> TYPE: PRT
<213> ORGANISM: Unknown
<220> FEATURE:
<223> OTHER INFORMATION: Leptolyngbya sp. PCC 6406

<400> SEQUENCE: 73

Asp Arg Val Ile Val Phe Gln Leu Phe Ala Asp Gly Arg Ser Gln Ile
1               5                   10                  15

Val Glu Glu Glu Val Leu Gly Ser Leu Pro Ala Leu Arg Thr Met His
            20                  25                  30

Trp Glu Asp Glu Val Trp Ser Gln Asp Ile Leu Ala Leu Tyr Trp Gln
        35                  40                  45

Gly Gln Pro Arg Ile Val Pro Asp Val Met Asp Asp Ile Trp Thr Asp
    50                  55                  60

Cys Leu Val Glu Tyr Ala Gln Ala Gly Gln Ile Lys Ser Lys Ile Val
65                  70                  75                  80

Ala Pro Ile Leu Leu Trp Gly Val Leu Val Val His
                85                  90


<210> SEQ ID NO 74
<211> LENGTH: 92
<212> TYPE: PRT
<213> ORGANISM: Planktothrix prolifica

<400> SEQUENCE: 74

Asp Arg Ala Ile Ile Phe Gln Leu Phe Asp Asn Gly Asn Ser Gln Ile
1               5                   10                  15
```

Val Glu Glu Ser Val His Ser Asn Phe Leu Asn Leu Lys Ala Leu Asn
20 25 30

Trp Asp Asn Glu Val Trp Ser Gln Glu Ile Leu Asp Cys Tyr Trp Gln
35 40 45

Gly Lys Pro Arg Ile Val Pro Asp Val Met Asn Asp Ile Trp Thr Glu
50 55 60

Cys Leu Val Glu Tyr Ser Leu Lys Gly Gln Ile Lys Ser Lys Ile Val
65 70 75 80

Ala Pro Ile Leu Leu Trp Gly Val Leu Val Val His
85 90

<210> SEQ ID NO 75
<211> LENGTH: 92
<212> TYPE: PRT
<213> ORGANISM: Anabaena circinalis

<400> SEQUENCE: 75

Glu Arg Val Ile Val Phe Arg Leu Phe Pro Asp Gly Lys Ser Gln Ile
1 5 10 15

Val Glu Glu Ala Val Ala Asn Gly Tyr Met Thr Phe Lys Asp Ser Tyr
20 25 30

Trp Glu Asp Glu Lys Trp Ser Gln Asp Ile Leu Glu Tyr Tyr Trp Gln
35 40 45

Gly Lys Pro Arg Ile Val Leu Asp Val Met Asp Asp Ile Trp Thr Asp
50 55 60

Cys Leu Lys Ala Tyr Ser Arg Gln Gly Asn Ile Arg Ser Lys Ile Val
65 70 75 80

Ala Pro Ile Leu Leu Trp Gly Val Leu Val Val His
85 90

<210> SEQ ID NO 76
<211> LENGTH: 92
<212> TYPE: PRT
<213> ORGANISM: Unknown
<220> FEATURE:
<223> OTHER INFORMATION: Stanieria cyanosphaera PCC 7437

<400> SEQUENCE: 76

Glu Arg Val Leu Ile Phe Arg Met Asn Pro Asp Gly Ser Gly Gln Val
1 5 10 15

Ile Glu Glu Ala Val Val Pro Lys Tyr Pro Val Thr Asp Gln Met Arg
20 25 30

Trp Glu Asp Glu His Phe Pro Glu Asp Cys Tyr Glu Tyr Tyr Arg Gln
35 40 45

Gly Ile Pro Arg Ile Val Pro Asp Val Ala Thr Asp Glu Trp Ala Lys
50 55 60

Cys Leu Val Glu Phe Met Gln Glu Val Gly Val Lys Ser Lys Val Val
65 70 75 80

Ala Pro Ile Val Val Trp Gly Leu Leu Ile Val His
85 90

<210> SEQ ID NO 77
<211> LENGTH: 92
<212> TYPE: PRT
<213> ORGANISM: Fischerella thermalis

<400> SEQUENCE: 77

Asp Arg Val Leu Ile Phe Arg Leu Asn Gln Asp Gly Ser Gly Gln Ile

```
1               5                   10                  15

Ile Glu Glu Ala Val Val Pro Glu Tyr Pro Met Thr Tyr Gln Met Arg
            20                  25                  30

Trp Val Asp Glu Cys Phe Pro Asp Asp Cys Tyr Glu Tyr Tyr Arg Gln
        35                  40                  45

Gly Asn Pro Arg Ile Leu Pro Asp Val Ala Lys Asp Glu Trp Gly Ala
    50                  55                  60

Cys Leu Val Glu Phe Met Gln Gln Ile Gly Val Lys Ser Lys Val Val
65                  70                  75                  80

Ala Pro Ile Ile Val Trp Gly Leu Leu Ile Val His
                85                  90


<210> SEQ ID NO 78
<211> LENGTH: 92
<212> TYPE: PRT
<213> ORGANISM: Chlorogloeopsis fritschii

<400> SEQUENCE: 78

Asp Arg Ala Leu Ile Phe Gln Leu Asn Gln Asp Gly Ser Gly Gln Ile
1               5                   10                  15

Ile Gln Glu Ala Val Ile Pro Asp Tyr Pro Val Thr Asn Gln Met Arg
            20                  25                  30

Trp Leu Asp Glu Cys Phe Pro Asp Glu Cys Tyr Glu Tyr Tyr Cys Gln
        35                  40                  45

Gly Asn Ala Arg Ile Val Pro Asp Val Ala Lys Asp Asp Trp Gly Ala
    50                  55                  60

Cys Leu Val Glu Phe Met Gln Glu Val Gly Val Lys Ser Lys Val Val
65                  70                  75                  80

Ala Pro Ile Val Val Trp Gly Leu Leu Ile Val His
                85                  90


<210> SEQ ID NO 79
<211> LENGTH: 92
<212> TYPE: PRT
<213> ORGANISM: Unknown
<220> FEATURE:
<223> OTHER INFORMATION: Fischerella sp. PCC 9431

<400> SEQUENCE: 79

Asp Arg Ala Leu Ile Phe Arg Leu Asn Glu Asp Gly Ser Gly Gln Val
1               5                   10                  15

Ile Lys Glu Ala Val Val Pro Glu Tyr Pro Val Thr Glu Gln Met Arg
            20                  25                  30

Trp Arg Asp Glu Pro Leu Pro Asp Tyr Cys Tyr Asp Phe Tyr Arg Gln
        35                  40                  45

Gly Asn Pro Arg Ile Val Pro Asn Val Ala Ile Tyr Asp Trp Ala Ser
    50                  55                  60

Cys Leu Ala Glu Phe Leu Gln Gln Ala Ser Val Lys Ser Lys Ile Val
65                  70                  75                  80

Ala Pro Ile Val Val Trp Gly Leu Leu Ile Val His
                85                  90


<210> SEQ ID NO 80
<211> LENGTH: 92
<212> TYPE: PRT
<213> ORGANISM: Unknown
<220> FEATURE:
<223> OTHER INFORMATION: Fischerella sp. PCC 9339
```

<400> SEQUENCE: 80

Asp Arg Ala Leu Ile Phe Arg Leu Asn Gln Asp Gly Ser Gly Gln Val
1 5 10 15

Ile Lys Glu Ala Val Val Pro Glu Tyr Pro Met Thr Ser Gln Met Arg
20 25 30

Cys Thr Asp Glu Cys Phe Pro Asp Asp Cys Tyr Glu Tyr Tyr Arg Gln
35 40 45

Gly Asn Ala Arg Ile Leu Pro Asp Val Ala Lys Asp Glu Trp Ser Asp
50 55 60

Cys Leu Val Glu Phe Met Gln Gln Ile Gly Val Lys Ser Lys Val Val
65 70 75 80

Ala Pro Ile Ile Val Trp Gly Leu Leu Ile Val His
85 90

<210> SEQ ID NO 81
<211> LENGTH: 92
<212> TYPE: PRT
<213> ORGANISM: Chlorogloeopsis fritschii

<400> SEQUENCE: 81

Asp Arg Ala Leu Ile Phe Arg Leu His Gly Asn Gly Thr Gly Gln Val
1 5 10 15

Ile Gln Glu Ala Val Arg Pro Glu Tyr Pro Val Thr Glu Gln Met Leu
20 25 30

Phe Pro Asp Glu Cys Phe Pro Gln Glu Cys Tyr Glu Tyr Tyr Cys Gln
35 40 45

Gly Gln Pro Arg Ile Val Ser Asp Val Phe Ala Glu Asp Phe Ser Ser
50 55 60

Cys Leu Val Glu Phe Met Gln Lys Ile Gly Val Lys Ser Lys Ile Val
65 70 75 80

Ala Pro Ile Val Val Trp Gly Leu Leu Ile Val His
85 90

<210> SEQ ID NO 82
<211> LENGTH: 93
<212> TYPE: PRT
<213> ORGANISM: Unknown
<220> FEATURE:
<223> OTHER INFORMATION: “Synechococcus sp. PCC 7502 ”

<400> SEQUENCE: 82

Asp Arg Ile Ile Ile Phe Gln Leu Phe Pro Asn Gly Ala Ser Gln Val
1 5 10 15

Val Lys Glu Ile Val Lys Pro Pro Tyr Pro Ser Ile Ile Gly Met Asn
20 25 30

Trp Gln Asp Glu His Phe Ser His Glu Gly Phe Glu Tyr Tyr Ile Asn
35 40 45

Ser Asn Pro Arg Thr Val Asn Asp Val Phe Glu Asp Asn Val Phe Ala
50 55 60

Asp Cys Leu Lys Glu Phe Met Ser Gln Ala Gln Ile Lys Ser Lys Ile
65 70 75 80

Val Ala Pro Ile Ile Leu Trp Gly Leu Leu Ile Val His
85 90

<210> SEQ ID NO 83
<211> LENGTH: 92
<212> TYPE: PRT
<213> ORGANISM: Unknown

<220> FEATURE:
<223> OTHER INFORMATION: Nostoc sp. PCC 7524

<400> SEQUENCE: 83

```
Glu Arg Ala Leu Ile Phe Arg Leu Met Pro Asn Gly Ser Gly Val Val
1               5                   10                  15

Leu Glu Glu Ser Val Val Pro Asp Tyr Pro Ser Ile Lys Ser Arg Leu
            20                  25                  30

Trp Gln Asp Glu Cys Ser Pro His Glu Leu Tyr Gln Phe Tyr Arg Asp
        35                  40                  45

Gly Asn Val Arg Ile Val Thr Asp Thr Gln Asn Asp Leu Trp Gly Glu
    50                  55                  60

Cys Leu Ala Glu Phe Met Ala Glu Ala Gln Val Gln Ser Lys Ile Val
65                  70                  75                  80

Ala Pro Ile Ala Val Trp Gly Leu Ile Ser Ile His
                85                  90
```

<210> SEQ ID NO 84
<211> LENGTH: 92
<212> TYPE: PRT
<213> ORGANISM: Unknown
<220> FEATURE:
<223> OTHER INFORMATION: Chamaesiphon sp. PCC6605

<400> SEQUENCE: 84

```
Asp Arg Val Thr Ile Phe Arg Val Phe Pro Asp Arg His Ile Arg Val
1               5                   10                  15

Val Glu Glu Val Val Met Pro Ser Tyr Pro Ser Leu Leu Gln Arg Asn
            20                  25                  30

Trp Glu Asp Glu Cys Ile Ser Gln Ala Glu Phe Asp Phe Tyr Leu His
        35                  40                  45

Gly His Pro His Ile Val Asn Asp Val Leu Gln Asp Ala Trp Ser Glu
    50                  55                  60

Cys Leu Pro Glu Tyr Val Asp Thr Ile Gly Val Lys Ser Lys Ile Val
65                  70                  75                  80

Ala Pro Ile Leu Leu Trp Gly Leu Leu Ser Ile His
                85                  90
```

<210> SEQ ID NO 85
<211> LENGTH: 92
<212> TYPE: PRT
<213> ORGANISM: Unknown
<220> FEATURE:
<223> OTHER INFORMATION: Acaryochloris marina MBIC11017

<400> SEQUENCE: 85

```
Asp Arg Ala Leu Leu Phe Arg Leu Met Pro Gly Gly Gly Gly Ile Ile
1               5                   10                  15

Leu Glu Glu Ser Val Leu Pro Asn Tyr Pro Ala Met Glu Glu Leu Asp
            20                  25                  30

Gly Glu Asp Gln Asp Phe Pro Pro Glu Tyr Tyr Glu Phe Tyr Leu His
        35                  40                  45

Arg Gln Pro Arg Ile Val Leu Asp Val Asp Gln Asp Asp Trp Ser Gln
    50                  55                  60

Cys Leu Lys Gln Phe Trp Leu Pro Ala Gln Val Lys Ser Lys Ile Val
65                  70                  75                  80

Ala Pro Ile Val Leu Trp Gly Leu Leu Val Val His
                85                  90
```

<210> SEQ ID NO 86
<211> LENGTH: 92
<212> TYPE: PRT
<213> ORGANISM: Unknown
<220> FEATURE:
<223> OTHER INFORMATION: Leptolyngbya sp. JSC-1

<400> SEQUENCE: 86

```
Asp Arg Ala Leu Val Phe Arg Leu Tyr Ala Asn Gly Thr Gly Cys Val
1               5                   10                  15

Ile Lys Glu Ala Thr Leu Pro Gln Tyr Pro Val Thr Ala Glu Met Arg
            20                  25                  30

Phe Pro Glu Glu Gln Phe Pro Leu Glu Cys Arg Thr Leu Tyr Gln Arg
        35                  40                  45

Gly Gln Ala Arg Ala Ile Thr Asn Val Asp Asn Asp Ile Leu Ala Asp
    50                  55                  60

Cys Leu Val Lys Phe Met His Gln Ile Gln Val Lys Ser Lys Leu Val
65                  70                  75                  80

Val Pro Ile Val Val Trp Gly Leu Leu Ile Leu His
                85                  90
```

<210> SEQ ID NO 87
<211> LENGTH: 92
<212> TYPE: PRT
<213> ORGANISM: Unknown
<220> FEATURE:
<223> OTHER INFORMATION: Hapalosiphon welwitschii UH strain IC-52-3

<400> SEQUENCE: 87

```
Asp Arg Val Leu Val Tyr His Ile Leu Ile Asp Gly Thr Gly Lys Val
1               5                   10                  15

Ile Ala Glu Ala Leu Thr Pro Gly Tyr Glu Ser Ile Leu Glu Gln Ser
            20                  25                  30

Phe Ser Val Glu Cys Phe Pro Thr Glu Cys Tyr Leu Arg Tyr Ala Gln
        35                  40                  45

Gly Glu Ile Tyr Ala Leu Arg Asp His Glu Glu Arg Gln Gln Pro Ser
    50                  55                  60

Cys Leu Ile Gln Phe Met Ala Asp Met Gln Ile Arg Ala Lys Leu Val
65                  70                  75                  80

Ile Pro Ile Val Leu Trp Gly Leu Leu Ile Ala His
                85                  90
```

<210> SEQ ID NO 88
<211> LENGTH: 92
<212> TYPE: PRT
<213> ORGANISM: Unknown
<220> FEATURE:
<223> OTHER INFORMATION: Planktothrix agardhii NIVA-CYA 15

<400> SEQUENCE: 88

```
Asp Arg Val Leu Ile Tyr Arg Ile Phe Pro Asn Gly Ser Gly Lys Thr
1               5                   10                  15

Ile Thr Glu Ser Val Ile Phe Pro Asp Leu Ser Ile Leu Asp Gln Tyr
            20                  25                  30

Phe Thr Asp Glu Thr Phe Ser Ser Glu Cys Glu Arg Phe Tyr Glu Gln
        35                  40                  45

Arg Lys Val Lys Ala Ile Asp Asn Ile Glu Ala Ala Tyr Pro Ser Asp
    50                  55                  60

Cys Met Arg Ala Leu Met Gln Gln Leu Gln Val Lys Ser Lys Leu Ile
```

```
65                  70                  75                  80

Ile Pro Ile Phe Leu Trp Gly Leu Met Leu Ala His
                85                  90


<210> SEQ ID NO 89
<211> LENGTH: 92
<212> TYPE: PRT
<213> ORGANISM: Unknown
<220> FEATURE:
<223> OTHER INFORMATION: Synechocystis sp. PCC 6714

<400> SEQUENCE: 89

Asp Arg Val Leu Ile Tyr Arg Ile Gln Glu Asn Gly Leu Gly Thr Thr
1               5                   10                  15

Val Ala Glu Ser Val Thr Gly Gly His Pro Ser Val Met Ala Met Asp
            20                  25                  30

Leu Asp Pro Glu Ser Phe Pro Val Glu Cys Tyr Gln Arg Tyr Leu Asn
        35                  40                  45

Gly Tyr Ile Tyr Ala Ser Thr Glu Arg Leu Pro Asp Cys Ala Ala Thr
    50                  55                  60

Cys Ala Thr Asn Cys Phe Thr Val Ala Glu Ser Lys Ser Arg Ile Val
65                  70                  75                  80

Ala Pro Ile Val Leu Trp Gly Leu Leu Ile Val His
                85                  90


<210> SEQ ID NO 90
<211> LENGTH: 92
<212> TYPE: PRT
<213> ORGANISM: Unknown
<220> FEATURE:
<223> OTHER INFORMATION: Synechocystis sp. PCC6803

<400> SEQUENCE: 90

Asp Arg Val Leu Ile His His Ile Gln Glu Asp Gly Leu Gly Thr Thr
1               5                   10                  15

Ile Ala Glu Ser Val Val Asn Gly Gln Pro Ser Val Met Gln Met Asp
            20                  25                  30

Leu Ser Pro Glu Ser Phe Pro Pro Glu Cys Tyr Gln Arg Tyr Leu Asn
        35                  40                  45

Gly Tyr Ile Tyr Ala Ser Arg Asp Gln Leu Pro Asp Cys Ala Ile Asn
    50                  55                  60

Cys Ala Val Gln Cys Phe Thr Val Ala Glu Ser Gln Ser Arg Ile Val
65                  70                  75                  80

Ala Pro Ile Val Leu Trp Gly Leu Leu Ile Val His
                85                  90


<210> SEQ ID NO 91
<211> LENGTH: 92
<212> TYPE: PRT
<213> ORGANISM: Unknown
<220> FEATURE:
<223> OTHER INFORMATION: Coleofasciculus chthonoplastes PCC 7420

<400> SEQUENCE: 91

Asp Arg Val Leu Val Tyr Gln Leu Phe Glu Asp Asn Arg Gly Arg Val
1               5                   10                  15

Ile Ala Glu Gly Val Ala Ser Gly Phe Pro Gln Leu Leu Asn Ser Ile
            20                  25                  30

Phe Pro Ala Glu Ala Phe Pro Pro Thr Cys Tyr Gln Asn Tyr Val Gln
        35                  40                  45
```

```
Gly Lys Val Tyr Thr Leu Ala Asp Arg Asp Arg Glu Asp Val Leu Pro
    50                  55                  60

Cys Met Val Asp Phe Met Arg Glu Tyr Ala Ile Arg Ala Lys Leu Val
65                  70                  75                  80

Val Pro Ile Val Leu Trp Gly Leu Leu Ile Val His
                85                  90
```

<210> SEQ ID NO 92
<211> LENGTH: 92
<212> TYPE: PRT
<213> ORGANISM: Unknown
<220> FEATURE:
<223> OTHER INFORMATION: Pseudanabaena sp. PCC 6802

<400> SEQUENCE: 92

```
Asp Arg Val Leu Val Cys Lys Ile Ala Arg Ser Gly Thr Gly Leu Val
1               5                   10                  15

Val Ala Glu Ser Val Ser Asn Pro Trp Asn Ser Leu Leu Asn Thr Tyr
            20                  25                  30

Phe Ser Ala Glu Ala Ile Pro Pro Glu Cys Leu Gln Ser Tyr Leu Glu
        35                  40                  45

Gly His Ile Thr Tyr Ile Thr Asp Arg Lys Ser Asp Pro Ile Leu Pro
    50                  55                  60

Cys Met Ser Glu Leu Met Ala Lys Leu Gln Val Glu Ala Ile Leu Ala
65                  70                  75                  80

Val Pro Ile Ile Leu Trp Gly Leu Leu Ile Ala His
                85                  90
```

<210> SEQ ID NO 93
<211> LENGTH: 93
<212> TYPE: PRT
<213> ORGANISM: Unknown
<220> FEATURE:
<223> OTHER INFORMATION: Chroococcidiopsis thermalis PCC 7203

<400> SEQUENCE: 93

```
Asp Arg Val Val Ile Tyr Arg Leu Arg Ser Asp Gly Thr Gly Ser Ala
1               5                   10                  15

Val Ala Glu Ala Val Leu Pro Gly Trp Phe Ser Val Leu Gly Gln Gln
            20                  25                  30

Phe Ala Ala Glu Val Phe Pro Glu Asp Cys His Gln Leu Tyr Cys Gln
        35                  40                  45

Gly Arg Ile Arg Gly Ile Ala Asp Val Glu Arg Glu Glu Asn Ile Ala
    50                  55                  60

Pro Cys Leu Val Glu Phe Met Arg Gln Phe Gln Val Lys Ala Lys Leu
65                  70                  75                  80

Val Val Pro Ile Thr Leu Trp Gly Leu Leu Ile Ala His
                85                  90
```

<210> SEQ ID NO 94
<211> LENGTH: 92
<212> TYPE: PRT
<213> ORGANISM: Unknown
<220> FEATURE:
<223> OTHER INFORMATION: Synthetic Construct

<400> SEQUENCE: 94

```
Asp Arg Val Leu Val Tyr Arg Ile Tyr Asn Asp Tyr Thr Gly Cys Val
1               5                   10                  15
```

```
Ile Ser Glu Ala Val Ser Pro Gln Trp Ser Ser Leu Leu Glu Lys Thr
            20                  25                  30

Phe Ser Glu Glu Ile Phe Pro Ser Gln Cys His Ser His Tyr Ile Gln
        35                  40                  45

Gly Lys Ile Ala Ser Ile Ala Asn Ile Asn Lys Gly Asn Ile Leu Pro
    50                  55                  60

Cys Leu Val Glu Phe Leu Thr Gln Phe Lys Val Gln Ala Lys Leu Ala
65                  70                  75                  80

Val Pro Ile Ile Leu Trp Gly Leu Leu Val Val His
                85                  90


<210> SEQ ID NO 95
<211> LENGTH: 92
<212> TYPE: PRT
<213> ORGANISM: Unknown
<220> FEATURE:
<223> OTHER INFORMATION: Geitlerinema sp. PCC7105

<400> SEQUENCE: 95

Glu Arg Val Leu Ile Phe Arg Leu Leu Glu Asn Arg Leu Ala Arg Val
1               5                   10                  15

Val Ser Glu Ser Val Ala Glu Gly Tyr Pro Gln Ser Ala Gly Met Glu
            20                  25                  30

Phe Pro Asp Glu Glu Phe Pro Arg Asp Cys Tyr Asp Asn Tyr Cys Arg
        35                  40                  45

Gly Leu Pro Arg Ile Val Ser Asp Val Glu Thr Asp Arg Phe Ala Pro
    50                  55                  60

Cys Leu Val Asp Phe Met Lys Gln Met Gln Val Arg Ser Lys Val Val
65                  70                  75                  80

Val Pro Ile Leu Leu Trp Gly Leu Leu Ile Ala His
                85                  90


<210> SEQ ID NO 96
<211> LENGTH: 92
<212> TYPE: PRT
<213> ORGANISM: Mastigocladopsis repens

<400> SEQUENCE: 96

Asp Arg Val Val Val Tyr Gln Val Gln Leu Asp Gly Thr Gly Ile Thr
1               5                   10                  15

Val Ala Glu Ala Met Met Gly Glu Trp Thr Ser Ile Leu Asp Gln Val
            20                  25                  30

Phe Pro Glu Glu Thr Phe Pro Gln Gln Ser His Gln Gln Tyr Leu Lys
        35                  40                  45

Gly Arg Ile Tyr Thr Leu Thr Asp Arg Asp Gln Gly Lys Ile Val Pro
    50                  55                  60

Cys Leu Ala Glu Phe Leu Ala Glu Ile Gln Val Arg Ala Lys Leu Val
65                  70                  75                  80

Val Pro Ile Ile Leu Trp Gly Leu Leu Ile Val His
                85                  90


<210> SEQ ID NO 97
<211> LENGTH: 92
<212> TYPE: PRT
<213> ORGANISM: Unknown
<220> FEATURE:
<223> OTHER INFORMATION: Microcoleus sp. PCC 7113

<400> SEQUENCE: 97
```

-continued

Asp Arg Val Leu Val Tyr Arg Val Trp Ser Asn Gly Ala Gly Arg Val
1               5                   10                  15

Ile Ala Glu Ala Val Ala Pro Gly Cys Ile Lys Val Leu Asp Ile Pro
            20                  25                  30

Leu Pro Thr Glu Thr Phe Pro Glu Glu Tyr Arg Gln Arg Tyr Ala Glu
        35                  40                  45

Gly Arg Ile Tyr Thr Leu Thr Asp Leu Asp His Glu Glu Val Ser Pro
    50                  55                  60

Cys Leu Ala Asn Cys Leu Lys Gln Ile Gln Val Arg Ala Lys Val Val
65                  70                  75                  80

Val Pro Ile Ile Leu Trp Gly Leu Leu Ile Ala His
                85                  90

<210> SEQ ID NO 98
<211> LENGTH: 94
<212> TYPE: PRT
<213> ORGANISM: Microcoleus vaginatus

<400> SEQUENCE: 98

Asp Arg Thr Leu Val Tyr Arg Val Phe Pro Glu Gly Thr Gly Ala Ala
1               5                   10                  15

Ile Ala Glu Ser Val Ser Pro Asn Arg Leu Lys Leu Leu Asp Ile Leu
            20                  25                  30

Phe Pro Glu Glu Val Phe Pro Glu Asp Thr Tyr Glu Arg Tyr Ile Gln
        35                  40                  45

Gly Arg Val Tyr Ala Leu Asn Asp Ser Glu Asp Glu Asn Glu Ser Ile
    50                  55                  60

Val Pro Cys Leu Val Glu Phe Leu Ala Asp Ile Glu Val Arg Ala Lys
65                  70                  75                  80

Leu Val Val Pro Ile Ile Leu Trp Gly Leu Leu Ile Val His
                85                  90

<210> SEQ ID NO 99
<211> LENGTH: 92
<212> TYPE: PRT
<213> ORGANISM: Unknown
<220> FEATURE:
<223> OTHER INFORMATION: Anabaena cylindrica PCC 7122

<400> SEQUENCE: 99

Asp Arg Val Leu Ile Tyr Arg Ile Trp Glu Asp Gly Thr Gly Cys Ala
1               5                   10                  15

Ile Thr Glu Thr Val Ser Glu Asn Tyr Pro Cys Ile Leu Gly Glu Thr
            20                  25                  30

Phe Pro Glu Glu Val Phe Pro Arg Glu Tyr His His Ala Tyr Thr Gln
        35                  40                  45

Gly Lys Thr Arg Ala Val Thr Asn Ile Asp Gln Ser Asp Val Glu Ser
    50                  55                  60

Cys Leu Ala Asp Phe Val Lys Gln Phe Gly Val Lys Ala Lys Leu Val
65                  70                  75                  80

Val Pro Ile Leu Leu Trp Gly Leu Leu Ile Ala His
                85                  90

<210> SEQ ID NO 100
<211> LENGTH: 94
<212> TYPE: PRT
<213> ORGANISM: Unknown
<220> FEATURE:
<223> OTHER INFORMATION: Oscillatoria nigro-viridis PCC 7112

<400> SEQUENCE: 100

Asp Arg Thr Leu Val Tyr Arg Val Phe Pro Glu Gly Thr Gly Thr Ala
1               5                   10                  15

Ile Ala Glu Ser Val Ser Pro Asn Arg Leu Lys Leu Leu Asp Ile Leu
            20                  25                  30

Phe Pro Glu Glu Val Phe Pro Glu Glu Asn Tyr Glu Arg Tyr Ile Glu
        35                  40                  45

Gly Arg Val Tyr Ala Leu Asn Asp Ser Glu Asp Ala Asn Glu Ser Ile
    50                  55                  60

Val Pro Cys Leu Val Glu Phe Leu Ala Asp Ile Gln Val Arg Ala Lys
65                  70                  75                  80

Leu Val Val Pro Ile Ile Leu Trp Gly Leu Leu Ile Val His
                85                  90

<210> SEQ ID NO 101
<211> LENGTH: 92
<212> TYPE: PRT
<213> ORGANISM: Unknown
<220> FEATURE:
<223> OTHER INFORMATION: Pleurocapsa sp. PCC 7319

<400> SEQUENCE: 101

Asp Arg Val Leu Ile Tyr Arg Ile Arg Glu Asp Gly Thr Gly Ser Thr
1               5                   10                  15

Ile Thr Glu Thr Val Leu Ser Pro Tyr Pro Ala Ile Leu Gly Gln Thr
            20                  25                  30

Phe Pro Glu Glu Val Phe Pro Thr Glu Tyr His Gln Ala Tyr Ile Gln
        35                  40                  45

Gly Lys Ser Arg Thr Ile Thr Asn Ile Glu Gln Asp Asp Val Glu Glu
    50                  55                  60

Cys Leu Ala Asp Phe Val Lys Gln Phe Gly Val Gln Ala Lys Leu Val
65                  70                  75                  80

Val Pro Ile Ile Leu Trp Gly Leu Leu Ile Ala His
                85                  90

<210> SEQ ID NO 102
<211> LENGTH: 92
<212> TYPE: PRT
<213> ORGANISM: Unknown
<220> FEATURE:
<223> OTHER INFORMATION: Anabaena sp. PCC 7108

<400> SEQUENCE: 102

Asp Arg Val Leu Ile Tyr Arg Leu Trp Glu Asp Gly Thr Gly Ser Ala
1               5                   10                  15

Ile Thr Glu Thr Val Ser Pro Asp Tyr Pro Cys Ile Leu Gly Glu Thr
            20                  25                  30

Phe Pro Ala Glu Val Phe Pro Lys Glu Tyr His Gln Ala Tyr Thr Gln
        35                  40                  45

Gly Lys Thr Arg Ala Ile Thr Asp Ile Asn Gln Ser Asp Val Asp Ser
    50                  55                  60

Cys Leu Ala Glu Phe Val Lys Gln Phe Gly Val Lys Ala Lys Leu Val
65                  70                  75                  80

Val Pro Ile Leu Leu Trp Gly Leu Leu Ile Ala His
                85                  90

<210> SEQ ID NO 103

<211> LENGTH: 92
<212> TYPE: PRT
<213> ORGANISM: Unknown
<220> FEATURE:
<223> OTHER INFORMATION: Oscillatoria acuminata PCC 6304

<400> SEQUENCE: 103

```
Asp Arg Val Leu Val Tyr Arg Val Trp Ala Asp Gly Thr Gly Ser Ala
1               5                   10                  15

Ile Ala Glu Ala Val Lys Pro Gly Trp Leu Lys Val Leu Asn Arg Val
            20                  25                  30

Phe Pro Glu Glu Val Phe Pro Pro Glu Asn Tyr Gln Arg Tyr Ile Glu
        35                  40                  45

Gly Arg Ile Cys Ala Leu Val Asp Arg Asp Ser Gly Gln Thr Leu Pro
    50                  55                  60

Cys Leu Val Glu Phe Met Lys Ser Ile Glu Val Arg Ala Lys Leu Val
65                  70                  75                  80

Val Pro Ile Val Leu Trp Gly Leu Leu Ile Ala His
                85                  90
```

<210> SEQ ID NO 104
<211> LENGTH: 92
<212> TYPE: PRT
<213> ORGANISM: Unknown
<220> FEATURE:
<223> OTHER INFORMATION: Oscillatoria sp. PCC 6304

<400> SEQUENCE: 104

```
Asp Arg Leu Leu Ile Tyr Arg Val Asp Pro Asp Gly Thr Gly Ile Val
1               5                   10                  15

Val Thr His Ser Ser Asp Pro Leu Ala Pro Glu Ile Asn Gly Asn Thr
            20                  25                  30

Phe Pro Gln Glu Thr Phe Ser Gln Glu Glu Arg Asp Arg Tyr Ala Gln
        35                  40                  45

Gly Glu Ile Val Ala Ile Ala Asp Thr Glu Leu Val Lys His Leu Pro
    50                  55                  60

Cys Leu Ala Ala Leu Ile Lys Thr Leu Lys Ile Lys Ala Lys Leu Val
65                  70                  75                  80

Ile Pro Ile Leu Leu Trp Gly Leu Leu Ile Ala His
                85                  90
```

<210> SEQ ID NO 105
<211> LENGTH: 92
<212> TYPE: PRT
<213> ORGANISM: Nostoc punctiforme

<400> SEQUENCE: 105

```
Asp Arg Val Leu Ile Tyr Arg Leu Trp Glu Asp Gly Thr Gly Ser Ala
1               5                   10                  15

Ile Thr Glu Thr Val Leu Pro Glu Tyr Thr Lys Ile Leu Gly Glu Thr
            20                  25                  30

Phe Pro Glu Glu Val Phe Pro Arg Glu Tyr His Gln Ala Tyr Ser Leu
        35                  40                  45

Gly Lys Thr Arg Ala Ile Ala Asn Val Glu Gln Ala Asp Val Glu Ser
    50                  55                  60

Cys Leu Ala Asp Phe Val Lys Gln Phe Gly Val Lys Ala Lys Leu Val
65                  70                  75                  80

Val Pro Ile Leu Leu Trp Gly Leu Leu Ile Ala His
                85                  90
```

<210> SEQ ID NO 106
<211> LENGTH: 94
<212> TYPE: PRT
<213> ORGANISM: Unknown
<220> FEATURE:
<223> OTHER INFORMATION: Synechococcus sp. PCC 7336

<400> SEQUENCE: 106

```
Asp Arg Val Leu Ile Tyr Gln Val Phe Pro Asn Gly Thr Gly Arg Ile
1               5                   10                  15

Ile Ser Glu Ala Val Leu Pro Ile Tyr Pro Glu Thr Leu Gly Val Asp
            20                  25                  30

Phe Pro Glu Glu Val Phe Pro Thr Asp Tyr Gln Glu Leu Tyr Ser Gln
        35                  40                  45

Gly Arg Ile Gln Ser Ile Pro Asn Ile His Asp Pro His Leu Glu Ile
    50                  55                  60

Ala Glu Cys Leu Ile Asp Phe Leu Glu Ala Trp Lys Val Arg Ala Lys
65                  70                  75                  80

Leu Val Val Pro Ile Leu Leu Trp Gly Leu Leu Ile Ala His
                85                  90
```

<210> SEQ ID NO 107
<211> LENGTH: 94
<212> TYPE: PRT
<213> ORGANISM: Unknown
<220> FEATURE:
<223> OTHER INFORMATION: Pseudanabaena sp. PCC 6802

<400> SEQUENCE: 107

```
Asp Arg Val Leu Ile Tyr Arg Ile Leu Ser His Gly Val Gly Arg Thr
1               5                   10                  15

Ile Ala Glu Ser Val Leu Pro Glu Tyr Pro Ala Ile Leu Gly Met Ser
            20                  25                  30

Phe Pro Glu Glu Val Leu Pro Leu Glu Tyr Gln Glu Leu Tyr Arg Gln
        35                  40                  45

Gly Arg Met Arg Ala Ile Glu Asp Val Lys Ala Glu Asp Thr Gly Leu
    50                  55                  60

Thr Pro Cys Leu Leu Glu Phe Val Glu Gln Trp Cys Val Arg Ala Lys
65                  70                  75                  80

Leu Thr Thr Pro Ile Leu Leu Trp Gly Leu Leu Ile Ala His
                85                  90
```

<210> SEQ ID NO 108
<211> LENGTH: 92
<212> TYPE: PRT
<213> ORGANISM: Pseudanabaena biceps

<400> SEQUENCE: 108

```
Asp Arg Val Leu Ile Tyr Arg Leu Trp Ser Asp Gly Thr Gly Ser Ala
1               5                   10                  15

Ile His Glu Thr Val Leu Pro Pro Tyr Pro Ser Ile Leu Gly Gln Val
            20                  25                  30

Phe Pro Glu Glu Val Phe Pro Ala Pro Tyr His Arg Ala Tyr Ser Leu
        35                  40                  45

Gly Lys Ile Leu Thr Ile Ala Asn Val Glu Gln Cys Glu Met Glu Val
    50                  55                  60

Cys Leu Arg Asp Phe Val Lys Gln Phe Gly Val Arg Ala Lys Leu Val
65                  70                  75                  80
```

Val Pro Ile Ile Leu Trp Gly Ile Leu Ile Ala His
85 90

<210> SEQ ID NO 109
<211> LENGTH: 94
<212> TYPE: PRT
<213> ORGANISM: Unknown
<220> FEATURE:
<223> OTHER INFORMATION: Tolypothrix sp. PCC 7601

<400> SEQUENCE: 109

Asp Arg Val Leu Ile Tyr His Val Leu Pro Asp Gly Thr Gly Lys Thr
1 5 10 15

Ile Ser Glu Ser Val Leu Pro Asp Tyr Pro Thr Leu Met Asp Leu Glu
20 25 30

Phe Pro Gln Glu Val Phe Pro Gln Glu Tyr Gln Gln Leu Tyr Ala Gln
35 40 45

Gly Arg Val Arg Ala Ile Ala Asp Val His Asp Pro Thr Ala Gly Leu
50 55 60

Ala Glu Cys Leu Val Glu Phe Val Asp Gln Phe His Ile Lys Ala Lys
65 70 75 80

Leu Ile Val Pro Ile Val Leu Trp Gly Leu Leu Ile Ala His
85 90

<210> SEQ ID NO 110
<211> LENGTH: 94
<212> TYPE: PRT
<213> ORGANISM: Mastigocoleus testarum

<400> SEQUENCE: 110

Asp Arg Val Leu Ile Tyr Gln Val Phe Ala Asn Gly Thr Gly Lys Ser
1 5 10 15

Ile Ser Glu Ala Val Leu Pro Glu Tyr Pro Ala Val Leu Gly Val Val
20 25 30

Phe Pro Glu Glu Val Phe Pro Gln Glu Tyr Arg Glu Leu Tyr Gly Gly
35 40 45

Gly Arg Val Lys Ala Ile Ala Asp Ile His Ser Pro Asp Ala Gly Leu
50 55 60

Ala Glu Cys Leu Val Glu Phe Met Asp Glu Trp Thr Val Lys Ala Lys
65 70 75 80

Leu Val Val Pro Ile Leu Leu Trp Gly Leu Leu Ile Ala His
85 90

<210> SEQ ID NO 111
<211> LENGTH: 92
<212> TYPE: PRT
<213> ORGANISM: Unknown
<220> FEATURE:
<223> OTHER INFORMATION: Synechocystis sp. PCC6803

<400> SEQUENCE: 111

Asp Arg Val Leu Ile Tyr Arg Ile Trp Gln Asp Gly Thr Gly Ser Ala
1 5 10 15

Ile Thr Glu Ser Val Asn Ala Asn Tyr Pro Ser Ile Leu Gly Arg Thr
20 25 30

Phe Ser Asp Glu Val Phe Pro Val Glu Tyr His Gln Ala Tyr Thr Lys
35 40 45

Gly Lys Val Arg Ala Ile Asn Asp Ile Asp Gln Asp Asp Ile Glu Ile
50 55 60

```
Cys Leu Ala Asp Phe Val Lys Gln Phe Gly Val Lys Ser Lys Leu Val
65                  70                  75                  80

Val Pro Ile Leu Leu Trp Gly Leu Leu Ile Thr His
                85                  90


<210> SEQ ID NO 112
<211> LENGTH: 94
<212> TYPE: PRT
<213> ORGANISM: Unknown
<220> FEATURE:
<223> OTHER INFORMATION: Leptolyngbya sp. JSC-1

<400> SEQUENCE: 112

Asp Arg Val Leu Ile Tyr Gln Val Leu Pro Asp Gly Thr Gly Lys Pro
1               5                   10                  15

Ile Ser Glu Ala Val Leu Pro Ala Tyr Pro Glu Ile Leu Gly Met Glu
            20                  25                  30

Phe Pro Glu Glu Val Phe Pro Lys Glu Tyr Gln Gln Leu Tyr Ala Gln
        35                  40                  45

Gly Arg Val Arg Ala Ile Ala Asp Val Arg Asp Pro Ala Ala Gly Leu
    50                  55                  60

Ala Glu Cys Leu Val Glu Phe Ile Glu Gln Phe Asp Ile Arg Ala Lys
65                  70                  75                  80

Leu Ile Val Pro Ile Leu Leu Trp Gly Leu Leu Ile Ala His
                85                  90


<210> SEQ ID NO 113
<211> LENGTH: 94
<212> TYPE: PRT
<213> ORGANISM: Unknown
<220> FEATURE:
<223> OTHER INFORMATION: Stanieria cyanosphaera PCC 7437

<400> SEQUENCE: 113

Asp Arg Val Leu Ile Tyr Gln Val Leu Ala Asn Gly Thr Gly Lys Pro
1               5                   10                  15

Ile Ser Glu Ala Val Leu Pro Glu Tyr Ala Pro Ile Leu Gly Ile Glu
            20                  25                  30

Phe Pro Glu Glu Val Phe Pro Lys Asp Tyr Gln Glu Leu Tyr Ala Ala
        35                  40                  45

Gly Arg Val Gln Ala Ile Ala Asn Val His Asp Pro Gln Met Gly Leu
    50                  55                  60

Ala Glu Cys Leu Val Asp Phe Met Glu Glu Trp Lys Val Gln Ala Lys
65                  70                  75                  80

Leu Val Val Pro Ile Leu Leu Trp Gly Leu Leu Ile Ala His
                85                  90


<210> SEQ ID NO 114
<211> LENGTH: 94
<212> TYPE: PRT
<213> ORGANISM: Unknown
<220> FEATURE:
<223> OTHER INFORMATION: Crinalium sp. PCC 9333

<400> SEQUENCE: 114

Asp Arg Val Leu Ile Tyr Arg Val Leu Ser Asp Gly Ser Gly Cys Thr
1               5                   10                  15

Ile Thr Glu Ala Val Leu Pro Gly Leu Pro Val Leu Val Gly Ile Pro
            20                  25                  30
```

Phe Pro Glu Glu Val Phe Pro Val Glu Tyr Gln Glu Leu Tyr Lys Leu
35 40 45

Gly Lys Val Gln Ser Ile Glu Asn Val Glu Gln Ala Tyr Ser Glu Glu
50 55 60

Thr Pro Cys Leu Val Glu Phe Leu Arg Gln Phe Ala Val Lys Ala Lys
65 70 75 80

Leu Ile Val Pro Ile Val Leu Trp Gly Leu Leu Ile Ala His
85 90

<210> SEQ ID NO 115
<211> LENGTH: 92
<212> TYPE: PRT
<213> ORGANISM: Unknown
<220> FEATURE:
<223> OTHER INFORMATION: Crinalium sp. PCC 9333

<400> SEQUENCE: 115

Asp Arg Val Leu Val Tyr Arg Ile Leu Ala Asp Gly Thr Gly Ser Ala
1 5 10 15

Ile Ala Glu Ser Val Asn Pro Gln Trp Ser Ser Ile Leu Glu Lys Thr
20 25 30

Phe Pro Ser Glu Val Phe Pro Glu Glu Tyr Arg Glu Leu Tyr Ser Lys
35 40 45

Gly Arg Ile Arg Ala Ile Ser Asp Val Thr Asn Gly Glu Leu Ala Pro
50 55 60

Cys Leu Thr Asp Phe Val Gln Asn Phe Asn Val Lys Ala Lys Leu Val
65 70 75 80

Val Pro Ile Ile Leu Trp Gly Leu Leu Ile Ala His
85 90

<210> SEQ ID NO 116
<211> LENGTH: 92
<212> TYPE: PRT
<213> ORGANISM: Unknown
<220> FEATURE:
<223> OTHER INFORMATION: Crinalium sp. PCC 9333

<400> SEQUENCE: 116

Asp Arg Val Leu Leu Tyr Gln Ile Leu Pro Asn Gly Thr Gly Met Val
1 5 10 15

Val Thr Glu Ala Val Asn Ser Gly Trp Lys Pro Ile Leu Gly Gln Val
20 25 30

Phe Ser Pro Glu Val Phe Pro Glu Glu Tyr His Gln Gln Tyr Val Gln
35 40 45

Gly Arg Ile Ser Ala Thr Ala Asp Val Glu Asn Asp Glu Val Leu Pro
50 55 60

Cys Leu Ile Glu Phe Leu Gln Asn Leu Gln Val Lys Ala Lys Leu Val
65 70 75 80

Val Pro Ile Ile Leu Trp Gly Leu Leu Ile Ala His
85 90

<210> SEQ ID NO 117
<211> LENGTH: 93
<212> TYPE: PRT
<213> ORGANISM: Unknown
<220> FEATURE:
<223> OTHER INFORMATION: Cyanothece sp. PCC7425

<400> SEQUENCE: 117

Asp Arg Val Leu Ile Tyr Arg Leu Trp Pro Asn Gly Thr Gly Ser Gly

```
1               5                   10                  15

Val Ala Glu Ala Ala Leu Pro Gly Leu Pro Gln Ile Met Gly Tyr Thr
            20                  25                  30

Phe Pro Glu Glu Val Phe Pro Glu Ala Ala Arg Gln Leu Tyr Cys Arg
        35                  40                  45

Gly Gln Ile Arg Glu Leu Val Asp Val Glu Gln Asp Gln Gln Ile Ser
    50                  55                  60

Ala Cys Met Val Glu Phe Leu Gln Gln Phe Trp Val Lys Ala Lys Leu
65                  70                  75                  80

Val Val Pro Ile Leu Leu Trp Gly Leu Leu Ile Val His
                85                  90
```

```
<210> SEQ ID NO 118
<211> LENGTH: 94
<212> TYPE: PRT
<213> ORGANISM: Unknown
<220> FEATURE:
<223> OTHER INFORMATION: Microcoleus sp. PCC 7113

<400> SEQUENCE: 118

Asp Arg Val Leu Ile Tyr Arg Val Trp Pro Asp Gly Lys Gly Cys Thr
1               5                   10                  15

Val Thr Glu Ala Val Gln Pro Gly Trp Pro Ala Ile Leu Gly Met Ser
            20                  25                  30

Phe Ala Glu Glu Val Phe Pro Leu Lys Tyr Gln Glu Leu Tyr Arg Gln
        35                  40                  45

Gly Gln Val His Ala Ile Ala Asp Val Glu Gln Ala Tyr Ala Glu Met
    50                  55                  60

Thr Pro Cys Leu Leu Glu Phe Leu His Pro Trp Gly Val Lys Ala Lys
65                  70                  75                  80

Leu Val Val Pro Ile Leu Leu Trp Gly Leu Leu Ile Ala His
                85                  90
```

```
<210> SEQ ID NO 119
<211> LENGTH: 92
<212> TYPE: PRT
<213> ORGANISM: Unknown
<220> FEATURE:
<223> OTHER INFORMATION: Microcoleus sp. PCC 7113

<400> SEQUENCE: 119

Asp Arg Val Leu Ile Tyr Arg Leu Trp Pro Asp Gly Thr Gly Ser Gly
1               5                   10                  15

Val Thr Glu Ala Ile Val Pro Gly Trp Ser Thr Val Leu Gly Gln Val
            20                  25                  30

Phe Glu Ala Glu Val Phe Pro Gln Glu Tyr His Gln Leu Tyr Ala Ser
        35                  40                  45

Gly Arg Ile Leu Ala Ile Lys Asn Val Glu Asp Ala Glu Ile Ser Pro
    50                  55                  60

Cys Met Val Glu Phe Leu Gln Gln Phe Glu Val Lys Ser Lys Leu Val
65                  70                  75                  80

Val Pro Ile Leu Leu Trp Gly Leu Leu Val Ala His
                85                  90
```

```
<210> SEQ ID NO 120
<211> LENGTH: 91
<212> TYPE: PRT
<213> ORGANISM: Nostoc azolla
```

<400> SEQUENCE: 120

Asp Arg Val Leu Ile Tyr Arg Leu Trp Glu Asp Gly Thr Gly Ser Ala
1 5 10 15

Ile Thr Glu Thr Val Ser Pro Asp Tyr Pro Cys Ile Leu Gly Arg Ile
20 25 30

Phe Pro Ala Glu Val Phe Pro Arg Glu Tyr His His Ala Tyr Thr Gln
35 40 45

Gly Arg Thr Thr Ala Ile Thr Asn Val Glu Ser Asp Val Asn Ser Cys
50 55 60

Leu Ala Glu Phe Leu Asn Gln Phe Gly Val Lys Ala Lys Leu Val Val
65 70 75 80

Pro Ile Leu Leu Trp Gly Leu Leu Ile Ala His
85 90

<210> SEQ ID NO 121
<211> LENGTH: 92
<212> TYPE: PRT
<213> ORGANISM: Unknown
<220> FEATURE:
<223> OTHER INFORMATION: Lyngbya sp. PCC 8106

<400> SEQUENCE: 121

Asp Arg Ala Leu Ile Tyr Gln Leu Tyr Ala Asp Gly Thr Gly Lys Val
1 5 10 15

Ile Ala Glu Ala Val Asn Ser Asp Trp Thr Ala Ile Leu Asp Gln Thr
20 25 30

Phe Pro Thr Glu Thr Phe Pro Ala Glu Ile Tyr Glu Asp Tyr Leu Gln
35 40 45

Gly Lys Val Gly Ile Ile Ser Asn Val Asp Thr Glu Asn Ile Leu Pro
50 55 60

Cys Leu Val Glu Phe Val Gln Gln Phe Gln Val Lys Ser Lys Val Thr
65 70 75 80

Leu Gly Ile Ile Leu Trp Gly Leu Leu Ile Ile His
85 90

<210> SEQ ID NO 122
<211> LENGTH: 94
<212> TYPE: PRT
<213> ORGANISM: Unknown
<220> FEATURE:
<223> OTHER INFORMATION: Synechococcus sp. PCC 7335

<400> SEQUENCE: 122

Asp Arg Val Leu Ile Tyr Gln Val Leu Pro Asp Gly Thr Gly Lys Ala
1 5 10 15

Val Ser Glu Ala Val Gln Ala Pro Tyr Pro Ser Ile Ile Glu Ile Pro
20 25 30

Phe Pro Glu Glu Val Phe Pro Glu Asp Tyr Gln Ala Leu Tyr Ala Glu
35 40 45

Gly Arg Ile Arg Ala Val Thr Asp Val Arg Ser Pro Lys Ala Asn Ile
50 55 60

Ala Glu Cys Leu Val Glu Phe Leu Ala Gln Trp Asp Val Arg Ser Lys
65 70 75 80

Leu Ile Val Pro Ile Val Leu Trp Gly Leu Leu Ile Ala His
85 90

<210> SEQ ID NO 123
<211> LENGTH: 94

<212> TYPE: PRT
<213> ORGANISM: Unknown
<220> FEATURE:
<223> OTHER INFORMATION: Xenococcus sp. PCC 7305

<400> SEQUENCE: 123

Asp Arg Val Leu Ile Tyr Gln Val Phe Thr Asn Gly Thr Gly Met Pro
1 5 10 15

Ile Arg Glu Ala Val Leu Pro Glu Phe Lys Pro Ile Leu Gly Val Lys
20 25 30

Phe Pro Glu Glu Val Phe Pro Glu Asp Tyr Arg Gln Leu Tyr Ser Gln
35 40 45

Gly Arg Val Ile Ala Ile Ala Asp Val Arg Ser Thr Asp Ala Asn Leu
50 55 60

Ala Glu Cys Leu Ile Glu Phe Met Asp Glu Trp Gln Ile Lys Ser Lys
65 70 75 80

Leu Val Val Pro Ile Leu Leu Trp Gly Leu Leu Ile Ala His
85 90

<210> SEQ ID NO 124
<211> LENGTH: 92
<212> TYPE: PRT
<213> ORGANISM: Unknown
<220> FEATURE:
<223> OTHER INFORMATION: Crinalium epipsammum PCC 9333

<400> SEQUENCE: 124

Glu Arg Ala Leu Ile Tyr Arg Phe Gly Trp Asn Arg Cys Gly Thr Val
1 5 10 15

Val Gln Glu Ala Val Ile Gly Asp Tyr Pro Ser Leu Leu Gly Arg Ser
20 25 30

Phe Ser Ala Glu Val Leu Pro Lys Glu Tyr His Gln Met Tyr Ser Gln
35 40 45

Gly Arg Val Gly Ile Ile His Asn Leu Asp Gln Asp Gln Leu Ser Pro
50 55 60

Cys Met Val Glu Phe Met Gln Glu Phe Glu Ala Lys Ala Lys Leu Val
65 70 75 80

Val Pro Ile Arg Leu Trp Gly Leu Leu Val Val His
85 90

<210> SEQ ID NO 125
<211> LENGTH: 92
<212> TYPE: PRT
<213> ORGANISM: Unknown
<220> FEATURE:
<223> OTHER INFORMATION: Nostoc sp. PCC 7120

<400> SEQUENCE: 125

Asp Arg Val Val Val Tyr Gln Phe Ala Pro Asp Met Ser Gly Lys Ile
1 5 10 15

Val Ala Glu Ser Val Lys Pro Gly Trp Lys Ile Ala Leu Gly Ala Asp
20 25 30

Ile Gln Asp Asn Cys Phe Gln Ser Gly Ala Gly Ala Asp Tyr Arg Gln
35 40 45

Gly His Lys Arg Ala Ile Ala Asn Ile Tyr Thr Ala Glu Leu Thr Asp
50 55 60

Cys His Leu Arg Leu Leu Glu Gln Phe Gln Val Lys Ala Asn Leu Val
65 70 75 80

Val Pro Ile Leu Leu Trp Gly Leu Leu Ile Ala His

```
                85                  90


<210> SEQ ID NO 126
<211> LENGTH: 92
<212> TYPE: PRT
<213> ORGANISM: Nostoc punctiforme

<400> SEQUENCE: 126

Asp Arg Val Val Val Tyr Gln Phe Asp Ser Glu Met Ile Gly Thr Ile
1               5                   10                  15

Met Ala Glu Ser Val Glu Pro Gly Trp Arg Val Ser Leu Gly Val Glu
            20                  25                  30

Ile Tyr Asp Thr Cys Phe Gln Thr Gly Lys Gly Ala Glu Tyr Tyr Gln
        35                  40                  45

Val Asn Lys Arg Ala Ile Ala Asn Ile Tyr Glu Ala Gly Leu Thr Asp
    50                  55                  60

Cys His Ile Arg Leu Leu Glu Gln Phe Glu Val Lys Ala Asn Leu Val
65                  70                  75                  80

Val Pro Ile Leu Leu Trp Gly Leu Leu Ile Ala His
                85                  90


<210> SEQ ID NO 127
<211> LENGTH: 92
<212> TYPE: PRT
<213> ORGANISM: Thermosynech-ococcus elongatus

<400> SEQUENCE: 127

Asp Arg Val Ile Val Tyr Ala Phe Asp Asp Asn Tyr Val Gly Thr Val
1               5                   10                  15

Val Ala Glu Ser Val Ala Glu Gly Trp Pro Gln Ala Arg Asp Gln Val
            20                  25                  30

Ile Glu Asp Pro Cys Phe Arg Glu His Trp Val Glu Ala Tyr Arg Gln
        35                  40                  45

Gly Arg Ile Gln Ala Thr Thr Asp Ile Phe Lys Ala Gly Leu Thr Glu
    50                  55                  60

Cys His Leu Asn Gln Leu Arg Pro Leu Lys Val Arg Ala Asn Leu Val
65                  70                  75                  80

Val Pro Met Val Leu Phe Gly Leu Leu Ile Ala His
                85                  90


<210> SEQ ID NO 128
<211> LENGTH: 92
<212> TYPE: PRT
<213> ORGANISM: Nostoc punctiforme

<400> SEQUENCE: 128

Asp Arg Val Ala Val Tyr Arg Phe Asn Pro Asn Trp Thr Gly Glu Phe
1               5                   10                  15

Val Ala Glu Ser Val Ala His Thr Trp Val Lys Leu Val Gly Pro Asp
            20                  25                  30

Trp Glu Asp Thr His Leu Gln Glu Thr Gln Gly Gly Arg Tyr Ala Gln
        35                  40                  45

Gly Glu Asn Phe Val Val Asn Asp Ile Tyr Gln Val Gly His Ser Pro
    50                  55                  60

Cys His Ile Glu Ile Leu Glu Gln Phe Glu Val Lys Ala Tyr Val Ile
65                  70                  75                  80

Val Pro Val Phe Leu Trp Gly Leu Leu Ala Ala Tyr
                85                  90
```

<210> SEQ ID NO 129
<211> LENGTH: 92
<212> TYPE: PRT
<213> ORGANISM: Nostoc punctiforme

<400> SEQUENCE: 129

Asp Arg Val Thr Ile Tyr Arg Phe Arg Ala Asp Trp Ser Gly Glu Phe
1 5 10 15

Val Ala Glu Ser Leu Ala Gln Gly Trp Thr Pro Val Arg Glu Ile Val
20 25 30

Val Ala Asp Asp Tyr Leu Gln Glu Thr Gln Gly Arg Asn Phe Ala Asn
35 40 45

Gly Lys Ser Ile Val Ile Lys Asp Ile Tyr Ser Ala Asn Tyr Ser Ile
50 55 60

Cys His Ile Ala Leu Leu Glu Leu Met Gln Ala Arg Ala Tyr Met Ile
65 70 75 80

Val Pro Ile Phe Leu Trp Gly Leu Leu Ala Ala Tyr
85 90

<210> SEQ ID NO 130
<211> LENGTH: 92
<212> TYPE: PRT
<213> ORGANISM: Unknown
<220> FEATURE:
<223> OTHER INFORMATION: Oscillatoria acuminata PCC 6304

<400> SEQUENCE: 130

Asp Arg Val Gly Val Tyr Arg Phe Lys Pro Asp Trp Ser Gly Asn Phe
1 5 10 15

Val Gly Glu Ser Val Ser Pro Gly Trp Asn Pro Leu Met Gly Asn Leu
20 25 30

Ile Ala Asp Thr His Leu Gln Glu Thr Gln Gly Gly Arg Tyr Arg Glu
35 40 45

Asn Gln Ala Leu Ala Val Asn Asp Ile Tyr Asn Val Gly His Ala Gln
50 55 60

Cys His Ile Glu Leu Leu Glu Thr Phe Gln Ala Lys Ala Tyr Ile Ile
65 70 75 80

Val Pro Ile Leu Leu Trp Gly Leu Leu Ala Ala Tyr
85 90

<210> SEQ ID NO 131
<211> LENGTH: 84
<212> TYPE: PRT
<213> ORGANISM: Unknown
<220> FEATURE:
<223> OTHER INFORMATION: Leptolyngbya sp. JSC-1

<400> SEQUENCE: 131

Ile Leu Ile Lys Glu Ile His His Arg Val Lys Asn Asn Leu Gln Val
1 5 10 15

Ile Ser Cys Leu Asn Leu Asp Thr Ala Ile Pro Cys Gly Leu Leu Leu
20 25 30

Asn Glu Leu Ile Thr Asn Ala Ile Leu Ser Val His Asp Asn Gly Ile
35 40 45

Cys Met Ser Ala Asp Leu Gly Leu Lys Ile Ala Tyr Asp Leu Ala Leu
50 55 60

Gln Leu Gln Gly Thr Leu Thr Leu Glu Arg Thr Gln Gly Thr Arg Phe
65 70 75 80

Gln Leu Ile Phe

<210> SEQ ID NO 132
<211> LENGTH: 84
<212> TYPE: PRT
<213> ORGANISM: Unknown
<220> FEATURE:
<223> OTHER INFORMATION: Planktothrix agardhii NIVA-CYA 15

<400> SEQUENCE: 132

Val Leu Leu Arg Glu Ile His His Arg Val Lys Asn Asn Leu Tyr Val
1               5                   10                  15

Ile Ser Thr Leu Ser Leu Glu Ser Ala Ile Pro Cys Gly Leu Leu Ile
            20                  25                  30

Asn Glu Leu Val Thr Asn Ser Phe Leu Lys Ile Ser Asp Asn Gly Ile
        35                  40                  45

Gly Ile Pro Asn Asp Leu Gly Leu Arg Leu Val Ser Ile Leu Ala Asp
    50                  55                  60

Gln Leu Glu Ala Ser Leu Glu Val Asp Cys Ser Asn Gly Thr Ser Phe
65                  70                  75                  80

Thr Leu Ile Phe

<210> SEQ ID NO 133
<211> LENGTH: 84
<212> TYPE: PRT
<213> ORGANISM: Unknown
<220> FEATURE:
<223> OTHER INFORMATION: Oscillatoria acuminata PCC 6304

<400> SEQUENCE: 133

Leu Leu Leu Lys Glu Val His His Arg Val Lys Asn Asn Leu Gln Val
1               5                   10                  15

Ile Ser Ser Leu Asn Leu Asp Thr Ala Ile Pro Cys Gly Leu Leu Leu
            20                  25                  30

Asn Glu Leu Val Ser Asn Ser Leu Leu Ile Val Arg Asp Thr Gly Arg
        35                  40                  45

Gly Leu Pro Glu Gly Leu Gly Leu Arg Leu Val Arg Ala Leu Thr Arg
    50                  55                  60

Gln Leu Arg Gly Thr Leu Asp Ile Glu Asn Ser His Gly Ala Cys Phe
65                  70                  75                  80

Gln Ile Thr Phe

<210> SEQ ID NO 134
<211> LENGTH: 85
<212> TYPE: PRT
<213> ORGANISM: Unknown
<220> FEATURE:
<223> OTHER INFORMATION: Nostoc sp. PCC 7120

<400> SEQUENCE: 134

Val Leu Leu Lys Glu Val His His Arg Val Lys Asn Asn Leu Gln Ile
1               5                   10                  15

Val Ser Glu Leu Asn Leu Asp Gln Ala Ile Ala Cys Gly Leu Ile Ile
            20                  25                  30

Asn Glu Leu Ile Ser Asn Ser Leu Leu Thr Ile Lys Asp Asn Gly Ile
        35                  40                  45

Gly Leu Pro Asp Asn Leu Gly Leu Ser Leu Val His Asp Leu Val Thr
    50                  55                  60

```
Glu Gln Leu Glu Gly Thr Val Ser Ile Glu Arg Gln Pro Gly Thr Thr
65                  70                  75                  80

Phe Lys Ile Gln Phe
                85


<210> SEQ ID NO 135
<211> LENGTH: 88
<212> TYPE: PRT
<213> ORGANISM: Nostoc punctiforme

<400> SEQUENCE: 135

Val Leu Leu Lys Glu Val His His Arg Val Lys Asn Asn Leu Gln Ile
1               5                   10                  15

Val Ser Asn Leu Asn Val Asp Gln Ala Ile Ala Cys Gly Leu Val Ile
            20                  25                  30

Asn Glu Leu Val Ser Asn Ala Leu Met Thr Ile Gln Asp Asn Gly Ile
        35                  40                  45

Gly Leu Pro Ala Asn Leu Gly Leu Ser Leu Val Tyr Asp Leu Val Thr
    50                  55                  60

Glu Gln Leu Glu Gly Asn Ile Thr Leu Glu Arg Asn His Gly Thr Gly
65                  70                  75                  80

Phe Lys Ile Lys Phe Lys Gln Leu
                85


<210> SEQ ID NO 136
<211> LENGTH: 84
<212> TYPE: PRT
<213> ORGANISM: Unknown
<220> FEATURE:
<223> OTHER INFORMATION: Lyngbya sp. PCC 8106

<400> SEQUENCE: 136

Val Leu Leu Lys Glu Ile His His Arg Val Lys Asn Asn Leu Leu Val
1               5                   10                  15

Val Ala Phe Leu Asn Ile Glu Thr Ala His Pro Cys Gly Leu Ile Val
            20                  25                  30

Asn Glu Leu Val Ser Asn Val Phe Leu Thr Val Gln Asp Asn Gly Ile
        35                  40                  45

Gly Phe Ser Asp Asn Leu Gly Met Glu Leu Ile Cys Thr Leu Thr Thr
    50                  55                  60

Gln Leu Glu Gly His Ile Glu Leu Ile Arg Gly Glu Gly Thr Thr Phe
65                  70                  75                  80

Asn Val Thr Phe


<210> SEQ ID NO 137
<211> LENGTH: 84
<212> TYPE: PRT
<213> ORGANISM: Unknown
<220> FEATURE:
<223> OTHER INFORMATION: Crinalium sp. PCC 9333

<400> SEQUENCE: 137

Ile Leu Leu Lys Glu Ile His His Arg Val Lys Asn Asn Leu Leu Val
1               5                   10                  15

Val Ser Glu Leu Asn Ile Glu Thr Ala Asn Pro Gly Gly Leu Ile Val
            20                  25                  30

Asn Glu Leu Val Ser Asn Ala Phe Leu Ile Ile Lys Asp Asn Gly Ile
        35                  40                  45

Gly Phe Pro Pro Asn Leu Gly Leu Gln Leu Val Cys Thr Leu Thr Glu
```

```
    50                  55                  60

Gln Leu Glu Gly Glu Ile Asn Leu Thr Lys Glu Asp Gly Thr Ala Phe
65                  70                  75                  80

Asn Leu Thr Phe


<210> SEQ ID NO 138
<211> LENGTH: 84
<212> TYPE: PRT
<213> ORGANISM: Unknown
<220> FEATURE:
<223> OTHER INFORMATION: Synthetic Construct

<400> SEQUENCE: 138

Val Leu Leu Lys Glu Ile His His Arg Val Lys Asn Asn Leu Leu Val
1               5                   10                  15

Val Ser Gly Leu Asn Ile Glu Thr Ala Gln Pro Cys Gly Leu Ile Val
            20                  25                  30

Asn Glu Leu Val Ser Asn Thr Leu Leu Thr Val Arg Asp Asn Gly Ile
        35                  40                  45

Gly Phe Pro Ala Gly Leu Gly Met Glu Leu Val Cys Thr Leu Thr Glu
    50                  55                  60

Gln Ile Glu Gly Thr Ile Thr Leu Asn Gln Glu Asn Gly Thr Leu Phe
65                  70                  75                  80

Thr Leu Ser Phe


<210> SEQ ID NO 139
<211> LENGTH: 89
<212> TYPE: PRT
<213> ORGANISM: Nostoc punctiforme

<400> SEQUENCE: 139

Gln Leu Val Ala Gly Ile Ala His Glu Ile Asn Asn Pro Ile Ser Phe
1               5                   10                  15

Ile Tyr Pro Leu Val Cys Tyr Gly Ala Gln Met Asn Gln Val Phe Met
            20                  25                  30

Asn Ile Leu Asn Asn Ala Ile Ile Trp Ile Ala Asp Asn Gly Cys Gly
        35                  40                  45

Ile Pro Glu Ile Gly Thr Gly Leu Gly Leu Ser Ile Ser Tyr Gln Ile
    50                  55                  60

Ile Val Glu Lys His Gly Gly Asn Ile Lys Cys Val Ser Glu Pro Gly
65                  70                  75                  80

Lys Gly Cys Glu Phe Trp Ile Glu Ile
                85


<210> SEQ ID NO 140
<211> LENGTH: 89
<212> TYPE: PRT
<213> ORGANISM: Unknown
<220> FEATURE:
<223> OTHER INFORMATION: Microcoleus sp. PCC 7113

<400> SEQUENCE: 140

Gln Leu Val Ala Gly Ile Ala His Glu Ile Asn Asn Pro Val Asn Phe
1               5                   10                  15

Ile Tyr Lys Val Gln Cys Tyr Ala Gly Gln Leu Asn Gln Val Phe Met
            20                  25                  30

Asn Ile Leu Ala Asn Ala Ile Ile Leu Ile Ser Asp Asn Gly Pro Gly
        35                  40                  45
```

```
Met Thr Gln Glu Gly Thr Gly Leu Gly Leu Ser Ile Ser Tyr Gln Ile
    50                  55                  60

Val Val Glu Lys His Gly Gly Arg Leu Glu Cys Ile Ser Ala Pro Gly
65                  70                  75                  80

Gln Gly Thr Val Phe Leu Ile Ser Leu
                85


<210> SEQ ID NO 141
<211> LENGTH: 89
<212> TYPE: PRT
<213> ORGANISM: Nostoc punctiforme

<400> SEQUENCE: 141

Gln Leu Val Ala Gly Val Ala His Glu Ile Asn Asn Pro Val Asn Phe
1               5                   10                  15

Ile Tyr Leu Val Glu Cys Tyr Ala Gly Pro Leu Asn Gln Val Phe Met
            20                  25                  30

Asn Val Leu Ser Asn Ala Ile Ile Arg Ile Ala Asp Asn Gly Ser Gly
        35                  40                  45

Ile Pro Glu Ala Gly Thr Gly Leu Gly Leu Ser Ile Ser Tyr Gln Ile
    50                  55                  60

Val Val Asp Lys His Gly Gly Val Phe Lys Cys Asp Ser Gln Pro Gly
65                  70                  75                  80

Leu Gly Thr Glu Phe Trp Ile Glu Ile
                85


<210> SEQ ID NO 142
<211> LENGTH: 89
<212> TYPE: PRT
<213> ORGANISM: Unknown
<220> FEATURE:
<223> OTHER INFORMATION: llatoria acuminata PCC 6304

<400> SEQUENCE: 142

Gln Leu Val Ala Gly Val Ala His Glu Ile Asn Asn Pro Val Asn Phe
1               5                   10                  15

Ile Tyr Leu Val Asp Cys Tyr Ala Ala Gln Met Asn Gln Val Phe Met
            20                  25                  30

Asn Ile Leu Ser Asn Ala Ile Ile Arg Ile Cys Asp Asn Gly Pro Gly
        35                  40                  45

Ile Pro Asp Glu Gly Thr Gly Leu Gly Leu Ser Ile Ser Tyr Gln Ile
    50                  55                  60

Val Val Glu Lys His Gly Gly Ser Leu Thr Cys Leu Ser Gln Pro Gly
65                  70                  75                  80

Gln Gly Thr Glu Phe Arg Ile Glu Leu
                85


<210> SEQ ID NO 143
<211> LENGTH: 88
<212> TYPE: PRT
<213> ORGANISM: Unknown
<220> FEATURE:
<223> OTHER INFORMATION: danabaena sp. PCC 6802

<400> SEQUENCE: 143

Thr Leu Ala Ser Gly Ile Ala His Asp Leu Asn Asn Val Leu Ala Pro
1               5                   10                  15

Ile Leu Asp Val Tyr Gly Asp Ala Thr Gln Leu His Gln Val Leu Ile
            20                  25                  30
```

```
Asn Leu Val Val Asn Ala Arg Ile Ala Ile Ala Asp Thr Gly Val Gly
        35                  40                  45

Ile Pro Pro Asp Gly Thr Gly Leu Gly Leu Ser Thr Val Leu Gly Ile
    50                  55                  60

Val Lys Ser His Gly Gly Phe Ile Asn Val Leu Ser Gln Val Gly Gln
65                  70                  75                  80

Gly Thr Gln Phe Lys Leu Phe Leu
                85
```

<210> SEQ ID NO 144
<211> LENGTH: 88
<212> TYPE: PRT
<213> ORGANISM: Unknown
<220> FEATURE:
<223> OTHER INFORMATION: Cyanothece sp. PCC7425

<400> SEQUENCE: 144

```
Gln Phe Ala Tyr Ile Ala Ser His Asp Leu Gln Glu Pro Leu Arg Met
1               5                   10                  15

Val Thr Thr Ile His Ala Asp Pro Thr Gln Leu Thr Gln Leu Phe Gln
            20                  25                  30

Asn Leu Ile Ser Asn Ala Ile Phe Ser Ile Glu Asp Asn Gly Ile Gly
        35                  40                  45

Ile Asp Pro Gln Gly Thr Gly Ile Gly Leu Ala Val Cys Lys Lys Ile
    50                  55                  60

Ile Glu Arg His Arg Gly Arg Ile Trp Val Gln Ser Glu Leu Gly Gln
65                  70                  75                  80

Gly Ala Thr Phe Tyr Phe Thr Leu
                85
```

<210> SEQ ID NO 145
<211> LENGTH: 88
<212> TYPE: PRT
<213> ORGANISM: Unknown
<220> FEATURE:
<223> OTHER INFORMATION: Chroococcidiopsis thermalis PCC 7203

<400> SEQUENCE: 145

```
Gln Phe Ala Ser Ile Ala Ser His Asp Leu Gln Glu Pro Leu Arg Lys
1               5                   10                  15

Ile Gln Ser Ile His Ala Asp Pro Leu Gln Met Arg Gln Leu Leu Gln
            20                  25                  30

Asn Leu Ile Gly Asn Ala Leu Ile Thr Val Glu Asp Asn Gly Ile Gly
        35                  40                  45

Phe Asp Gln Lys Gly Thr Gly Ile Gly Leu Ala Ile Cys Arg Lys Ile
    50                  55                  60

Val Glu Arg His Gly Gly Ser Ile Ala Ala Glu Ser Lys Pro Ser Gln
65                  70                  75                  80

Gly Ala Lys Phe Ile Val Thr Leu
                85
```

<210> SEQ ID NO 146
<211> LENGTH: 88
<212> TYPE: PRT
<213> ORGANISM: Unknown
<220> FEATURE:
<223> OTHER INFORMATION: Crinalium sp. PCC 9333

<400> SEQUENCE: 146

```
Gln Phe Ala Tyr Ile Ala Ser His Asp Leu Gln Glu Pro Leu Arg Lys
```

```
1               5                   10                  15

Ile Gln Thr Ile Asp Ala Asp Pro Leu Gln Met Arg Gln Leu Ile Gln
            20                  25                  30

Asn Leu Ile Ser Asn Ala Leu Ile Val Val Glu Asp Asn Gly Ile Gly
        35                  40                  45

Phe Asp Glu Lys Gly Thr Gly Met Gly Leu Ala Ile Cys Arg Lys Ile
    50                  55                  60

Val Glu Gln His Asn Gly Ser Ile Thr Ala Lys Ser Gln Leu Gly His
65                  70                  75                  80

Gly Ala Lys Phe Ile Val Thr Leu
                85
```

<210> SEQ ID NO 147
<211> LENGTH: 88
<212> TYPE: PRT
<213> ORGANISM: Unknown
<220> FEATURE:
<223> OTHER INFORMATION: Microcoleus sp. PCC 7113

<400> SEQUENCE: 147

```
Glu Phe Ala Tyr Val Ala Ser His Asp Leu Gln Glu Pro Leu Arg Lys
1               5                   10                  15

Ile Gln Ile Leu Glu Ala Asp Pro Ile Gln Met Arg Gln Leu Leu Gln
            20                  25                  30

Asn Leu Ile Gly Asn Ala Leu Ile Phe Ile Glu Asp Asn Gly Ile Gly
        35                  40                  45

Phe Asp Glu Lys Gly Thr Gly Met Gly Leu Ala Ile Cys Arg Lys Ile
    50                  55                  60

Val Glu Arg His Asp Gly Thr Ile Thr Ala Gln Ser Ser Pro Asn Leu
65                  70                  75                  80

Gly Ala Thr Phe Ile Ile Thr Leu
                85
```

<210> SEQ ID NO 148
<211> LENGTH: 88
<212> TYPE: PRT
<213> ORGANISM: Unknown
<220> FEATURE:
<223> OTHER INFORMATION: Synechocystis sp. PCC6803

<400> SEQUENCE: 148

```
Arg Phe Phe Ser Met Ala Ser His Glu Phe Arg Thr Pro Leu Ser Thr
1               5                   10                  15

Ala Leu Lys Ala Leu Val Asp Glu Arg Leu Val Arg Ser Ile Leu Ser
            20                  25                  30

Asn Leu Leu Ser Asn Ala Ile Phe Glu Val Thr Asp Gln Gly Ile Gly
        35                  40                  45

Ile Ser Pro Glu Gly Thr Gly Leu Gly Leu Met Val Ala Lys Lys Cys
    50                  55                  60

Val Asp Leu His Ser Gly Ser Ile Leu Leu Lys Ser Ala Val Asp Gln
65                  70                  75                  80

Gly Thr Thr Val Thr Ile Cys Leu
                85
```

<210> SEQ ID NO 149
<211> LENGTH: 88
<212> TYPE: PRT
<213> ORGANISM: Nostoc punctiforme

<400> SEQUENCE: 149

Arg Phe Phe Ser Met Ala Ser His Glu Phe Arg Thr Pro Leu Ser Thr
1 5 10 15

Ala Leu Pro Ala Ser Val Asp Glu Arg Leu Leu Arg Ser Ile Leu Ser
20 25 30

Asn Leu Leu Leu Asn Ala Ile Leu Gln Val Lys Asp Arg Gly Ile Gly
35 40 45

Ile Pro Leu Ala Gly Thr Gly Leu Gly Leu Val Val Val Lys Lys Cys
50 55 60

Val Asp Leu His Gln Gly His Ile Asn Ile Thr Ser Glu Ile Gly Ile
65 70 75 80

Gly Thr Thr Cys Ala Ile Ala Leu
85

<210> SEQ ID NO 150
<211> LENGTH: 88
<212> TYPE: PRT
<213> ORGANISM: Pseudanabaena biceps

<400> SEQUENCE: 150

Arg Phe Phe Ser Met Ala Ser His Glu Phe Arg Thr Pro Leu Ser Thr
1 5 10 15

Ala Leu Asn Val Tyr Leu Asp Glu Lys Leu Trp Arg Ser Leu Leu Ala
20 25 30

Asn Leu Leu Ser Asn Ala Ile Leu Thr Val Ala Asp Arg Gly Ile Gly
35 40 45

Ile Pro Leu Glu Gly Thr Gly Leu Gly Leu Val Val Val Lys Lys Cys
50 55 60

Val Asp Leu His Gln Gly Thr Ile Glu Ile Lys Ser Glu Val Gly Leu
65 70 75 80

Gly Thr Ile Cys Arg Ile Ala Ile
85

<210> SEQ ID NO 151
<211> LENGTH: 88
<212> TYPE: PRT
<213> ORGANISM: Unknown
<220> FEATURE:
<223> OTHER INFORMATION: Pleurocapsa sp. PCC 7319

<400> SEQUENCE: 151

Arg Phe Phe Ser Met Ala Ser His Glu Phe Arg Thr Pro Leu Ser Thr
1 5 10 15

Val Leu Arg Ile Cys Leu Asp Glu Lys Leu Met Arg Ser Ile Met Ala
20 25 30

Asn Leu Leu Ser Asn Ala Ile Ile Gln Ile Thr Asp Asn Gly Ile Gly
35 40 45

Ile Ala Pro Asp Gly Thr Gly Leu Gly Leu Val Val Val Lys Lys Cys
50 55 60

Val Asp Leu His Asp Gly Gln Ile Asp Leu Phe Ser Gln Leu Asn Leu
65 70 75 80

Gly Thr Thr Val Lys Val Thr Leu
85

<210> SEQ ID NO 152
<211> LENGTH: 88
<212> TYPE: PRT
<213> ORGANISM: Nostoc azollae

<400> SEQUENCE: 152

Arg Phe Phe Ser Met Ala Ser His Glu Phe Arg Thr Pro Leu Ser Thr
1 5 10 15

Ala Leu Gln Ala Tyr Leu Asp Glu Lys Leu Leu Arg Ser Ile Leu Gly
20 25 30

Asn Leu Leu Ser Asn Ala Ile Ile Gln Ile Ser Asp His Gly Ile Gly
35 40 45

Ile Ser Thr Thr Gly Thr Gly Leu Gly Leu Val Val Val Lys Lys Cys
50 55 60

Val Asp Leu His Gly Gly His Leu Asn Ile Val Ser Glu Leu Gly His
65 70 75 80

Gly Thr Thr Val Thr Val Thr Leu
85

<210> SEQ ID NO 153
<211> LENGTH: 88
<212> TYPE: PRT
<213> ORGANISM: Unknown
<220> FEATURE:
<223> OTHER INFORMATION: Anabaena cylindrica PCC 7122

<400> SEQUENCE: 153

Arg Phe Phe Ser Met Ala Ser His Glu Phe Arg Thr Pro Leu Ser Val
1 5 10 15

Ala Leu Lys Ala Tyr Leu Asp Glu Lys Leu Leu Arg Ser Ile Leu Gly
20 25 30

Asn Leu Leu Ser Asn Ala Ile Ile Lys Ile Cys Asp Gln Gly Ile Gly
35 40 45

Ile Pro Thr Asn Gly Thr Gly Leu Gly Leu Met Val Val Lys Lys Cys
50 55 60

Ile Asp Leu His Gln Gly Ser Leu Ser Ile Ile Ser Ala Ser Gly His
65 70 75 80

Gly Thr Thr Val Thr Val Ile Leu
85

<210> SEQ ID NO 154
<211> LENGTH: 88
<212> TYPE: PRT
<213> ORGANISM: Unknown
<220> FEATURE:
<223> OTHER INFORMATION: Anabaena sp. PCC 7108

<400> SEQUENCE: 154

Arg Phe Phe Ser Met Ala Ser His Glu Phe Arg Thr Pro Leu Ser Val
1 5 10 15

Thr Leu Lys Ala Tyr Leu Asp Glu Lys Leu Leu Arg Ser Ile Leu Gly
20 25 30

Asn Leu Leu Ser Asn Ala Ile Ile Lys Ile Ser Asp Gln Gly Ile Gly
35 40 45

Ile Pro Val Thr Gly Thr Gly Leu Gly Leu Val Val Val Gln Lys Cys
50 55 60

Val Asp Leu His Gly Gly Ser Leu Lys Ile Val Ser Asp Ser Gly Asn
65 70 75 80

Gly Thr Thr Val Thr Val Ile Leu
85

<210> SEQ ID NO 155

<211> LENGTH: 88
<212> TYPE: PRT
<213> ORGANISM: Unknown
<220> FEATURE:
<223> OTHER INFORMATION: Synechocystis sp. PCC 6714

<400> SEQUENCE: 155

```
Arg Phe Ile Ser Thr Thr Ser His Glu Phe Arg Thr Pro Leu Ala Ile
1               5                   10                  15

Ile Ser Ile Val Ala Phe Asp Pro Lys Leu Leu Arg Arg Ile Leu Thr
            20                  25                  30

Asn Leu Leu Ser Asn Ala Ile Phe Ser Val Arg Asp Tyr Gly Ile Gly
        35                  40                  45

Ile Asp Ala Glu Gly Thr Gly Leu Gly Leu Ser Ile Val Lys Lys Ser
    50                  55                  60

Val Glu Leu His Gly Gly Ala Ile Ala Ile Thr Ser Glu Leu Gly Gln
65                  70                  75                  80

Gly Ser Cys Phe Glu Val Asp Leu
                85
```

<210> SEQ ID NO 156
<211> LENGTH: 88
<212> TYPE: PRT
<213> ORGANISM: Unknown
<220> FEATURE:
<223> OTHER INFORMATION: Synechocystis sp. PCC6803

<400> SEQUENCE: 156

```
Arg Phe Ile Ser Thr Thr Ser His Glu Phe Arg Thr Pro Leu Ala Ile
1               5                   10                  15

Ile Ser Ile Val Ala Phe Asp Pro Lys Leu Leu Arg Gln Ile Leu Thr
            20                  25                  30

Asn Leu Leu Gly Asn Ala Ile Phe Ser Val Gln Asp His Gly Ile Gly
        35                  40                  45

Ile Gly Pro Glu Gly Thr Gly Leu Gly Leu Pro Ile Val Lys Lys Cys
    50                  55                  60

Ala Glu Leu His Gly Gly Met Ile Thr Val Thr Ser Gln Leu Gly Gln
65                  70                  75                  80

Gly Ser Arg Phe Glu Val Glu Leu
                85
```

<210> SEQ ID NO 157
<211> LENGTH: 88
<212> TYPE: PRT
<213> ORGANISM: Unknown
<220> FEATURE:
<223> OTHER INFORMATION: Hapalosiphon welwitschii UH strain IC-52-3

<400> SEQUENCE: 157

```
Arg Phe Ile Ala Met Thr Ser His Glu Phe Arg Thr Pro Leu Ala Val
1               5                   10                  15

Ile Ala Thr Ala His Leu Asp Lys Lys Leu Leu Arg Gln Met Leu Ser
            20                  25                  30

Asn Leu Leu Ser Asn Ala Val Phe Leu Ile Thr Asp Gln Gly Ile Gly
        35                  40                  45

Ile Ser Lys Gln Gly Thr Gly Leu Gly Leu Thr Ile Val Lys Lys Cys
    50                  55                  60

Val Glu Leu Gln Gly Gly Lys Ile Ser Val Ala Ser Glu Ile Glu Ala
65                  70                  75                  80
```

Gly Thr Thr Phe Thr Val Glu Leu
85

<210> SEQ ID NO 158
<211> LENGTH: 88
<212> TYPE: PRT
<213> ORGANISM: Unknown
<220> FEATURE:
<223> OTHER INFORMATION: Anabaena cylindrica PCC 7122

<400> SEQUENCE: 158

Arg Phe Ile Thr Met Ala Ser His Glu Phe Arg Thr Pro Leu Ala Ile
1 5 10 15

Ile Ala Ile Val Gln Leu Asp Lys Lys Ile Leu Gln Gln Ile Leu Ala
20 25 30

Asn Ile Leu Thr Asn Ala Ile Phe Lys Ile Lys Asp Ser Gly Ile Gly
35 40 45

Ile Pro Glu Glu Gly Thr Gly Leu Gly Leu Ser Ile Val Lys Lys Cys
50 55 60

Val Asp Leu His Lys Gly Glu Ile Ser Phe Asp Ser Lys Leu Gly Gln
65 70 75 80

Gly Thr Thr Phe Thr Ile Ile Ile
85

<210> SEQ ID NO 159
<211> LENGTH: 88
<212> TYPE: PRT
<213> ORGANISM: Dolichospermum circinale

<400> SEQUENCE: 159

Arg Phe Val Ser Met Val Ser His Glu Phe Arg Thr Pro Leu Ala Ile
1 5 10 15

Ile Ser Phe Ala Glu Phe Asp Pro Lys Ile Ile Arg Gln Val Leu Thr
20 25 30

Asn Leu Leu Thr Asn Ala Ile Phe Ile Val Gln Asp Tyr Gly Ile Gly
35 40 45

Ile Ser Glu Thr Gly Thr Gly Leu Gly Leu Ala Ile Val Lys Lys Cys
50 55 60

Val Asp Gln His Gln Gly Lys Ile Thr Leu Glu Ser Lys Leu Asn Gln
65 70 75 80

Gly Thr Ile Phe Lys Val Thr Ile
85

<210> SEQ ID NO 160
<211> LENGTH: 88
<212> TYPE: PRT
<213> ORGANISM: Unknown
<220> FEATURE:
<223> OTHER INFORMATION: Anabaena circinalis AWQC310F

<400> SEQUENCE: 160

Arg Phe Val Ser Met Val Ser His Glu Phe Arg Thr Pro Leu Ala Ile
1 5 10 15

Ile Ser Phe Ala Glu Phe Asp Pro Lys Ile Ile Arg Gln Val Leu Thr
20 25 30

Asn Leu Leu Thr Asn Ala Ile Phe Ile Val Gln Asp Tyr Gly Ile Gly
35 40 45

Ile Ser Glu Thr Gly Thr Gly Leu Gly Leu Ala Ile Val Lys Lys Cys
50 55 60

```
Val Asp Gln His Gln Gly Lys Ile Thr Leu Glu Ser Lys Leu Asn Gln
65                  70                  75                  80

Gly Thr Ile Phe Lys Val Thr Ile
                85


<210> SEQ ID NO 161
<211> LENGTH: 88
<212> TYPE: PRT
<213> ORGANISM: Unknown
<220> FEATURE:
<223> OTHER INFORMATION: Crinalium epipsammum PCC 9333

<400> SEQUENCE: 161

Arg Phe Val Ser Thr Val Ser His Glu Phe Arg Thr Pro Leu Ser Thr
1               5                   10                  15

Ile Leu Phe Val Glu Phe Asp Asn Gln Leu Met Gly Gln Ile Ile Asn
            20                  25                  30

Asn Leu Leu Thr Asn Ala Val Leu Ser Ile Cys Asp Gln Gly Ile Gly
        35                  40                  45

Ile Pro His Ser Gly Asn Gly Leu Gly Leu Ser Ile Val Lys Lys Ala
    50                  55                  60

Ile Glu Leu His Gly Gly Asn Ile Ile Val Glu Ser Glu Val Gly Val
65                  70                  75                  80

Gly Thr Thr Phe Thr Val Cys Ile
                85


<210> SEQ ID NO 162
<211> LENGTH: 88
<212> TYPE: PRT
<213> ORGANISM: Unknown
<220> FEATURE:
<223> OTHER INFORMATION: Crinalium sp. PCC 9333

<400> SEQUENCE: 162

Arg Phe Val Thr Ile Ala Ser His Glu Phe Arg Thr Pro Leu Ala Ile
1               5                   10                  15

Ile Leu Asn Val Glu Ile Asp Glu Lys Leu Leu Arg Gln Met Leu Thr
            20                  25                  30

Asn Leu Leu Ser Asn Ala Val Phe Gln Ile Gln Asp Gln Gly Ile Gly
        35                  40                  45

Ile Pro Val Thr Gly Thr Gly Leu Gly Asn Thr Ile Ile Lys Asn Ala
    50                  55                  60

Val Glu Ala His Gly Gly Met Ile Thr Ile Glu Ser Glu Val Asp Val
65                  70                  75                  80

Gly Thr Thr Phe Thr Val Ser Leu
                85


<210> SEQ ID NO 163
<211> LENGTH: 88
<212> TYPE: PRT
<213> ORGANISM: Unknown
<220> FEATURE:
<223> OTHER INFORMATION: Geitlerinema sp. PCC7105

<400> SEQUENCE: 163

Glu Phe Val Ser Ile Val Ser His Glu Leu Arg Thr Pro Leu Thr Ser
1               5                   10                  15

Met Arg Lys Leu Trp Val Asp Gly Asp Arg Thr Ile Gln Val Leu Thr
            20                  25                  30

Asn Leu Ile Ser Asn Ala Ile Val Gln Val Cys Asp Arg Gly Arg Gly
```

35 40 45

Ile Pro Ser Asp Gly Thr Gly Leu Gly Leu Ala Ile Cys Arg Arg Leu
50 55 60

Val Leu Glu His Gly Gly Arg Ile Trp Ala Glu Asn Arg Pro Gly Gly
65 70 75 80

Gly Thr Arg Met Ser Val Val Leu
85

<210> SEQ ID NO 164
<211> LENGTH: 88
<212> TYPE: PRT
<213> ORGANISM: Unknown
<220> FEATURE:
<223> OTHER INFORMATION: Synechococcus sp. PCC 7336

<400> SEQUENCE: 164

Glu Phe Ile Thr Ile Val Ser His Glu Leu Arg Thr Pro Leu Thr Ser
1 5 10 15

Ile His Glu Ile Ser Val Asp Pro Asp Phe Met Ile Gln Ala Phe Thr
20 25 30

Asn Leu Leu Ser Asn Ala Ile Phe Glu Val Arg Asp Glu Gly Gln Gly
35 40 45

Ile Pro Ser Asp Gly Thr Gly Leu Gly Leu Ala Ile Cys Arg Lys Ile
50 55 60

Ile Glu Gln His Glu Gly Gln Ile Trp Val Glu Ser Ser Ile Gly Lys
65 70 75 80

Gly Ser Ser Phe Tyr Phe Ile Leu
85

<210> SEQ ID NO 165
<211> LENGTH: 88
<212> TYPE: PRT
<213> ORGANISM: Unknown
<220> FEATURE:
<223> OTHER INFORMATION: Synechococcus sp. PCC 7335

<400> SEQUENCE: 165

Glu Phe Ile Ala Val Val Ser His Glu Leu Arg Thr Pro Leu Thr Ser
1 5 10 15

Ile His Ser Ile Trp Ala Asp Pro Asp Tyr Ile Val Arg Ala Leu Thr
20 25 30

Asn Leu Leu Gly Asn Ala Ile Phe Cys Val Gln Asp Asn Gly Gln Gly
35 40 45

Ile Pro His Asn Gly Thr Gly Leu Gly Leu Thr Ile Cys Arg Lys Ile
50 55 60

Val Glu Gln His Gly Gly Lys Ile Trp Ala Glu Ser Gln Leu Gly Lys
65 70 75 80

Gly Ser Arg Phe Ser Phe Thr Val
85

<210> SEQ ID NO 166
<211> LENGTH: 88
<212> TYPE: PRT
<213> ORGANISM: Unknown
<220> FEATURE:
<223> OTHER INFORMATION: Tolypothrix sp. PCC 76012

<400> SEQUENCE: 166

Glu Phe Ile Ser Ile Ile Ser His Glu Leu Arg Thr Pro Leu Thr Ser
1 5 10 15

```
Leu His Ser Val Trp Ala Asp Ala Asp Tyr Ile Leu Gln Ala Leu Thr
            20                  25                  30

Asn Leu Leu Ser Asn Ala Ile Phe Arg Val Arg Asp Glu Gly Gln Gly
        35                  40                  45

Ile Pro Ala Asp Gly Thr Gly Leu Gly Leu Thr Ile Cys Arg Lys Ile
    50                  55                  60

Ile Glu Gln His Asn Gly Arg Ile Trp Ala Glu Ser Thr Pro Gly Cys
65                  70                  75                  80

Gly Ser Thr Phe Ala Phe Thr Leu
                85


<210> SEQ ID NO 167
<211> LENGTH: 88
<212> TYPE: PRT
<213> ORGANISM: Unknown
<220> FEATURE:
<223> OTHER INFORMATION: Leptolyngbya sp. JSC-1

<400> SEQUENCE: 167

Glu Phe Ile Ser Val Val Ser His Glu Leu Arg Thr Pro Leu Thr Ser
1               5                   10                  15

Leu His Leu Ile Trp Ala Asp Ser Asp Tyr Ile Val Gln Ala Leu Thr
            20                  25                  30

Asn Leu Leu Ser Asn Ala Ile Phe Gln Val Arg Asp Gln Gly Gln Gly
        35                  40                  45

Ile Pro Ala Asp Gly Thr Gly Leu Gly Leu Thr Ile Cys Arg Lys Ile
    50                  55                  60

Ile Glu Gln His Asp Gly Arg Ile Trp Ala Glu Ser Lys Leu Gly Glu
65                  70                  75                  80

Gly Ser Thr Phe Phe Phe Thr Val
                85


<210> SEQ ID NO 168
<211> LENGTH: 88
<212> TYPE: PRT
<213> ORGANISM: Unknown
<220> FEATURE:
<223> OTHER INFORMATION: Xenococcus sp. PCC 7305

<400> SEQUENCE: 168

Glu Phe Ile Ser Val Val Ser His Glu Leu Arg Thr Pro Leu Thr Ser
1               5                   10                  15

Ile His Ile Val Trp Ala Asp Arg Asp Tyr Ile Val Gln Ala Leu Thr
            20                  25                  30

Asn Leu Leu Ser Asn Ala Ile Phe Ala Val Gln Asp Gln Gly Gln Gly
        35                  40                  45

Ile Pro Glu Asp Gly Thr Gly Leu Gly Leu Ala Ile Cys Arg Gln Ile
    50                  55                  60

Val Glu Gly His Gly Gly Gln Ile Trp Val Glu Ser Cys Leu Asp Lys
65                  70                  75                  80

Gly Ser Thr Phe Tyr Phe Thr Leu
                85


<210> SEQ ID NO 169
<211> LENGTH: 88
<212> TYPE: PRT
<213> ORGANISM: Mastigocoleus testarum

<400> SEQUENCE: 169
```

```
Glu Phe Ile Ser Val Val Ser His Glu Leu Arg Thr Pro Leu Thr Ser
1               5                   10                  15

Ile His Val Val Trp Ala Asp Arg Asp Tyr Ile Val Gln Thr Leu Thr
            20                  25                  30

Asn Leu Leu Ser Asn Ala Ile Phe Glu Val Lys Asp Arg Gly Gln Gly
        35                  40                  45

Ile Pro Thr Ser Gly Thr Gly Leu Gly Leu Ala Ile Cys Arg Gln Ile
    50                  55                  60

Ile Glu Gly His Gly Gly Lys Ile Trp Ala Glu Ser Cys Leu Glu Glu
65                  70                  75                  80

Gly Ser Thr Phe Tyr Phe Thr Leu
                85


<210> SEQ ID NO 170
<211> LENGTH: 88
<212> TYPE: PRT
<213> ORGANISM: Unknown
<220> FEATURE:
<223> OTHER INFORMATION: Stanieria cyanosphaera PCC 7437

<400> SEQUENCE: 170

Glu Phe Ile Ser Val Val Ser His Glu Leu Arg Thr Pro Leu Thr Ser
1               5                   10                  15

Ile His Val Val Trp Ala Asp Arg Asp Tyr Ile Val Gln Thr Leu Thr
            20                  25                  30

Asn Leu Leu Ser Asn Ala Ile Phe Glu Val Lys Asp Gln Gly Gln Gly
        35                  40                  45

Ile Pro Ala Asn Gly Thr Gly Leu Gly Leu Ala Ile Cys Arg His Ile
    50                  55                  60

Ile Glu Glu His Gly Gly Lys Ile Trp Ala Glu Ser Ser Leu Gly Gly
65                  70                  75                  80

Gly Ser Thr Phe Tyr Phe Thr Leu
                85


<210> SEQ ID NO 171
<211> LENGTH: 88
<212> TYPE: PRT
<213> ORGANISM: Unknown
<220> FEATURE:
<223> OTHER INFORMATION: Leptolyngbya sp. JSC-1

<400> SEQUENCE: 171

Glu Phe Val Ser Ile Val Ser His Glu Leu Arg Thr Pro Leu Thr Ser
1               5                   10                  15

Ile Arg Thr Leu Trp Ala Asp Pro Asp Arg Ile Ile Gln Thr Phe Thr
            20                  25                  30

Asn Leu Leu Asn Asn Ala Ile Phe Arg Ile Lys Asp Gln Gly Val Gly
        35                  40                  45

Ile Pro Ala Asp Gly Thr Gly Leu Gly Leu Thr Ile Cys Arg Gly Ile
    50                  55                  60

Val Gln Gln His Gln Gly Gln Ile Trp Val Glu Ser Lys Leu Gly Glu
65                  70                  75                  80

Gly Ser Thr Phe Cys Phe Ser Leu
                85


<210> SEQ ID NO 172
<211> LENGTH: 88
<212> TYPE: PRT
```

<213> ORGANISM: Mastigocladopsis repens

<400> SEQUENCE: 172

Glu Phe Ile Ser Val Val Ser His Glu Leu Arg Thr Pro Leu Ala Ala
1 5 10 15

Ile His Gln Val Trp Ala Asp Pro Asp Arg Ile Ile Gln Thr Leu Val
20 25 30

Asn Leu Val Ser Asn Ala Ile Phe Lys Val Gln Asp Gln Gly Arg Gly
35 40 45

Ile Pro Tyr Asp Gly Thr Gly Leu Gly Leu Pro Ile Cys Arg Ser Ile
50 55 60

Val Glu Gln His Gly Gly Lys Ile Trp Ala Glu Ser Val Leu Gly Lys
65 70 75 80

Gly Ser Val Phe Tyr Phe Thr Leu
85

<210> SEQ ID NO 173
<211> LENGTH: 88
<212> TYPE: PRT
<213> ORGANISM: Unknown
<220> FEATURE:
<223> OTHER INFORMATION: Microcoleus sp. PCC 7113

<400> SEQUENCE: 173

Glu Phe Ile Ser Ile Val Ser His Glu Leu Arg Thr Pro Leu Ser Ser
1 5 10 15

Ile Arg Gln Val Trp Ala Asp Arg Asp Arg Ile Leu Gln Thr Leu Val
20 25 30

Asn Leu Val Ser Asn Ala Ile Phe Gln Val Lys Asp Gln Gly Arg Gly
35 40 45

Ile Pro Ala Asp Gly Thr Gly Leu Gly Leu Ala Ile Cys Lys Ser Ile
50 55 60

Val Gln Gln His Gly Gly Lys Ile Trp Val Glu Ser Val Val Gly Glu
65 70 75 80

Gly Ser Asn Phe Tyr Phe Thr Leu
85

<210> SEQ ID NO 174
<211> LENGTH: 88
<212> TYPE: PRT
<213> ORGANISM: Unknown
<220> FEATURE:
<223> OTHER INFORMATION: Stanieria cyanosphaera PCC 7437

<400> SEQUENCE: 174

Glu Phe Ile Ser Val Val Ser His Glu Leu Arg Thr Pro Leu Thr Ser
1 5 10 15

Ile Arg Thr Leu Trp Ala Ala Pro Asp Ala Ile Ile Gln Thr Leu Thr
20 25 30

Asn Leu Leu Ser Asn Ala Ile Phe Thr Val Lys Asp Arg Gly Arg Gly
35 40 45

Ile Pro Glu Asp Gly Thr Gly Leu Gly Leu Ser Ile Cys Lys Arg Ile
50 55 60

Val Gln Gln His Gly Gly Arg Ile Trp Val Glu Ser Ser Leu Gly Glu
65 70 75 80

Gly Ser Thr Phe Tyr Phe Thr Leu
85

<210> SEQ ID NO 175
<211> LENGTH: 88
<212> TYPE: PRT
<213> ORGANISM: Unknown
<220> FEATURE:
<223> OTHER INFORMATION: Fischerella sp. PCC 9431

<400> SEQUENCE: 175

```
Glu Phe Ile Ser Ile Val Ser His Glu Leu Arg Thr Pro Leu Thr Ala
1               5                   10                  15

Ile Arg Gln Ile Ser Ala Glu Ala Asp Ser Ile Ile Arg Ala Leu Thr
            20                  25                  30

Asn Leu Leu Ser Asn Ala Ile Phe Lys Ile Arg Asp Gln Gly Arg Gly
        35                  40                  45

Ile Pro Pro Asp Gly Thr Gly Leu Gly Leu Ala Ile Cys Lys Asn Ile
    50                  55                  60

Val Gln Gln His Gly Gly His Ile Trp Val Glu Ser Val Leu Gly Glu
65                  70                  75                  80

Gly Ser Thr Phe Tyr Phe Thr Leu
                85
```

<210> SEQ ID NO 176
<211> LENGTH: 88
<212> TYPE: PRT
<213> ORGANISM: Unknown
<220> FEATURE:
<223> OTHER INFORMATION: Fischerella sp. PCC 9339

<400> SEQUENCE: 176

```
Glu Phe Ile Ser Ile Val Ser His Glu Leu Arg Thr Pro Leu Thr Ala
1               5                   10                  15

Ile Arg Gln Ile Ser Ala Ala Ala Asp Ser Ile Ile Gln Thr Leu Ile
            20                  25                  30

Asn Leu Leu Ser Asn Ala Ile Phe Lys Val Arg Asp Gln Gly Arg Gly
        35                  40                  45

Ile Pro Pro Glu Gly Thr Gly Leu Gly Leu Ala Ile Cys Lys Asn Ile
    50                  55                  60

Val Gln Gln His Gly Gly Cys Ile Trp Val Glu Ser Val Leu Gly Glu
65                  70                  75                  80

Gly Ser Thr Phe Tyr Phe Thr Leu
                85
```

<210> SEQ ID NO 177
<211> LENGTH: 88
<212> TYPE: PRT
<213> ORGANISM: Fischerella thermalis

<400> SEQUENCE: 177

```
Glu Phe Ile Ser Ile Val Ser His Glu Leu Arg Thr Pro Leu Thr Ala
1               5                   10                  15

Ile Arg Gln Ile Trp Ala Ala Pro Asp Ala Ile Val Gln Thr Leu Ile
            20                  25                  30

Asn Leu Leu Ser Asn Ala Ile Phe Ala Val Lys Asp Gln Gly Arg Gly
        35                  40                  45

Ile Pro Pro Glu Gly Thr Gly Leu Gly Leu Ser Ile Cys Lys Ser Ile
    50                  55                  60

Val Asp Gln His Gly Gly Arg Ile Trp Val Glu Ser Leu Leu Gly Glu
65                  70                  75                  80

Gly Ser Thr Phe Tyr Phe Ile Leu
```

85

<210> SEQ ID NO 178
<211> LENGTH: 88
<212> TYPE: PRT
<213> ORGANISM: Unknown
<220> FEATURE:
<223> OTHER INFORMATION: Synechococcus sp. PCC 7502

<400> SEQUENCE: 178

Glu Phe Ile Ser Ile Val Ser His Glu Leu Arg Thr Pro Leu Thr Ala
1 5 10 15

Ile Arg Gln Ile Trp Ala Ala Pro Asp Ala Ile Val Gln Thr Leu Ile
20 25 30

Asn Leu Leu Ser Asn Ala Ile Phe Ala Val Lys Asp Gln Gly Arg Gly
35 40 45

Ile Pro Pro Glu Gly Thr Gly Leu Gly Leu Ser Ile Cys Lys Ser Ile
50 55 60

Val Asp Gln His Gly Gly Arg Ile Trp Val Glu Ser Leu Leu Gly Glu
65 70 75 80

Gly Ser Thr Phe Tyr Phe Ile Leu
85

<210> SEQ ID NO 179
<211> LENGTH: 88
<212> TYPE: PRT
<213> ORGANISM: Chlorogloeopsis fritschii

<400> SEQUENCE: 179

Glu Phe Val Ser Ile Val Ser His Glu Leu Arg Thr Pro Leu Thr Ala
1 5 10 15

Ile Arg Gln Ile Trp Val Ala Pro Asp Ala Ile Val Gln Thr Leu Ile
20 25 30

Asn Leu Leu Ser Asn Ala Ile Phe Thr Val Arg Asp Gln Gly Arg Gly
35 40 45

Ile Pro Ser Asp Gly Thr Gly Leu Gly Leu Ala Ile Cys Lys Ser Ile
50 55 60

Val Lys Gln His Gly Gly Lys Ile Trp Val Glu Ser Arg Val Gly Glu
65 70 75 80

Gly Ser Thr Phe Tyr Phe Thr Leu
85

<210> SEQ ID NO 180
<211> LENGTH: 88
<212> TYPE: PRT
<213> ORGANISM: Chlorogloeopsis fritschii

<400> SEQUENCE: 180

Glu Phe Ile Ser Ile Val Ser His Glu Leu Arg Thr Pro Leu Thr Ala
1 5 10 15

Ile Arg Gln Ile Trp Ala Ala Pro Asp Ala Ile Thr Gln Thr Leu Ile
20 25 30

Asn Leu Leu Gly Asn Ala Ile Phe Phe Val Arg Asp Asn Gly Arg Gly
35 40 45

Ile Pro Ser Asp Gly Thr Gly Leu Gly Leu Ala Ile Cys Lys Thr Ile
50 55 60

Ile Arg Gln His Gly Gly Lys Ile Trp Val Glu Ser Val Leu Gly Glu
65 70 75 80

Gly Ser Thr Phe Tyr Phe Thr Leu
                85

<210> SEQ ID NO 181
<211> LENGTH: 88
<212> TYPE: PRT
<213> ORGANISM: Unknown
<220> FEATURE:
<223> OTHER INFORMATION: Chamaesiphon sp. PCC6605

<400> SEQUENCE: 181

Glu Phe Leu Ala Ser Met Ser His Glu Leu Arg Thr Pro Leu Asn Ala
1               5                   10                  15

Ile Leu Asn Ile Arg Val Asp Asp Leu Arg Ile Arg Gln Val Leu Ile
            20                  25                  30

Asn Leu Leu Ser Asn Ala Val Leu Ser Ile Val Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Thr Val Thr Val Glu Ser Gln Val Asp Arg
65                  70                  75                  80

Gly Ser Cys Phe Arg Val Cys Leu
                85

<210> SEQ ID NO 182
<211> LENGTH: 88
<212> TYPE: PRT
<213> ORGANISM: Unknown
<220> FEATURE:
<223> OTHER INFORMATION: Nostoc sp. PCC 7524

<400> SEQUENCE: 182

Glu Phe Leu Ala Ser Met Ser His Glu Leu Arg Thr Pro Leu Asn Ala
1               5                   10                  15

Ile Leu Asp Ile Ala Val Asp Glu Arg Arg Met Arg Gln Val Leu Ile
            20                  25                  30

Asn Leu Leu Asn Asn Ala Val Phe Ala Val Ile Asp Thr Gly Ile Gly
        35                  40                  45

Ile Ala Pro Glu Gly Thr Gly Leu Gly Leu Ala Leu Val Arg Gln Ile
    50                  55                  60

Ala Glu Leu His Gly Gly Asn Val Thr Val Ser Ser Glu Val Gly Lys
65                  70                  75                  80

Gly Ser Cys Phe Thr Val Arg Leu
                85

<210> SEQ ID NO 183
<211> LENGTH: 88
<212> TYPE: PRT
<213> ORGANISM: Pseudanabaena biceps

<400> SEQUENCE: 183

Glu Phe Leu Ala Asn Met Ser His Glu Leu Arg Thr Pro Leu Asn Ala
1               5                   10                  15

Ile Leu Asp Leu Lys Ile Asp Glu Arg Arg Ile Arg Gln Val Leu Ile
            20                  25                  30

Asn Leu Leu Asn Asn Ala Val Phe Ala Val Ile Asp Thr Gly Ile Gly
        35                  40                  45

Ile Thr Pro His Gly Thr Gly Leu Gly Leu Ala Leu Val Lys Arg Ile
    50                  55                  60

```
Val Glu Met His Gly Gly Gln Val Lys Ala Thr Ser Asp Phe Gly Val
65                  70                  75                  80

Gly Ser Cys Phe Thr Ile Glu Leu
                85


<210> SEQ ID NO 184
<211> LENGTH: 88
<212> TYPE: PRT
<213> ORGANISM: Unknown
<220> FEATURE:
<223> OTHER INFORMATION: Oscillatoria sp. PCC 6304

<400> SEQUENCE: 184

Glu Phe Leu Ala Asn Met Ser His Glu Leu Arg Thr Pro Leu Asn Ala
1               5                   10                  15

Ile Leu Asp Val Trp Val Asp Glu Arg Arg Ile Arg Gln Val Leu Ile
            20                  25                  30

Asn Leu Leu Asn Asn Ala Val Ile Ala Val Thr Asp Thr Gly Ile Gly
        35                  40                  45

Ile Pro Ser His Gly Thr Gly Leu Gly Leu Ala Leu Val Lys Arg Ile
    50                  55                  60

Val Glu Leu His Gly Gly Glu Val Gly Val Thr Ser Thr Glu Gly Ala
65                  70                  75                  80

Gly Ser Cys Phe Thr Ile Asp Leu
                85


<210> SEQ ID NO 185
<211> LENGTH: 88
<212> TYPE: PRT
<213> ORGANISM: Unknown
<220> FEATURE:
<223> OTHER INFORMATION: Cy7822_4053g2

<400> SEQUENCE: 185

Glu Phe Leu Ala Asn Met Ser His Glu Leu Arg Thr Pro Leu Asn Ala
1               5                   10                  15

Ile Leu Met Leu Thr Leu Asp Glu Arg Arg Ile Arg Gln Val Ile Ile
            20                  25                  30

Asn Leu Leu Asn Asn Ala Val Phe Ala Val Lys Asp Thr Gly Ile Gly
        35                  40                  45

Ile Ala Ala Glu Gly Thr Gly Leu Gly Leu Ala Leu Val Lys Arg Leu
    50                  55                  60

Val Asp Leu His Gly Gly Glu Val Ser Val Thr Ser Glu Leu Gly Val
65                  70                  75                  80

Gly Ser Cys Phe Ser Val Asp Leu
                85


<210> SEQ ID NO 186
<211> LENGTH: 88
<212> TYPE: PRT
<213> ORGANISM: Unknown
<220> FEATURE:
<223> OTHER INFORMATION: Planktothrix agardhii NIVA-CYA 56/3

<400> SEQUENCE: 186

Glu Phe Leu Ala Asn Met Ser His Glu Leu Arg Thr Pro Leu Asn Ser
1               5                   10                  15

Ile Leu Lys Ile Met Leu Asp Glu Arg Arg Ile Arg Gln Val Leu Ile
            20                  25                  30

Asn Leu Leu Asn Asn Ala Val Ile Ala Val Ile Asp Thr Gly Ile Gly
```

```
        35                  40                  45

Ile Ser Ala Glu Gly Thr Gly Leu Gly Leu Ala Leu Val Lys Arg Leu
    50                  55                  60

Val Glu Ile His Gly Gly Thr Val Glu Leu Thr Ser Glu Leu Gly Val
65                  70                  75                  80

Gly Ser Cys Phe Ala Ile Asn Leu
                85


<210> SEQ ID NO 187
<211> LENGTH: 88
<212> TYPE: PRT
<213> ORGANISM: Unknown
<220> FEATURE:
<223> OTHER INFORMATION: Planktothrix prolifica NIVA-CYA 406

<400> SEQUENCE: 187

Glu Phe Leu Ala Asn Met Ser His Glu Leu Arg Thr Pro Leu Asn Ser
1               5                   10                  15

Ile Leu Lys Ile Met Leu Asp Glu Arg Arg Ile Arg Gln Val Leu Ile
            20                  25                  30

Asn Leu Leu Asn Asn Ala Val Ile Ala Val Ile Asp Thr Gly Ile Gly
        35                  40                  45

Ile Ser Ala Glu Gly Thr Gly Leu Gly Leu Ala Leu Val Lys Arg Leu
    50                  55                  60

Val Glu Ile His Gly Gly Thr Val Glu Leu Thr Ser Glu Leu Gly Val
65                  70                  75                  80

Gly Ser Cys Phe Ala Ile Asn Leu
                85


<210> SEQ ID NO 188
<211> LENGTH: 88
<212> TYPE: PRT
<213> ORGANISM: Unknown
<220> FEATURE:
<223> OTHER INFORMATION: Planktothrix rubescens NIVA-CYA 407

<400> SEQUENCE: 188

Glu Phe Leu Ala Asn Met Ser His Glu Leu Arg Thr Pro Leu Asn Ser
1               5                   10                  15

Ile Leu Glu Ile Met Leu Asp Glu Arg Arg Ile Arg Gln Val Leu Ile
            20                  25                  30

Asn Leu Leu Asn Asn Ala Val Ile Ala Val Ile Asp Thr Gly Ile Gly
        35                  40                  45

Ile Ser Ala Glu Gly Thr Gly Leu Gly Leu Ala Leu Val Lys Arg Leu
    50                  55                  60

Val Glu Ile His Gly Gly Thr Val Glu Leu Thr Ser Glu Leu Gly Val
65                  70                  75                  80

Gly Ser Cys Phe Ala Ile Asn Leu
                85


<210> SEQ ID NO 189
<211> LENGTH: 88
<212> TYPE: PRT
<213> ORGANISM: Spirulina subsalsa

<400> SEQUENCE: 189

Glu Phe Leu Ala Asn Met Ser His Glu Leu Arg Thr Pro Leu Asn Ala
1               5                   10                  15

Ile Leu Asp Ile Val Leu Asp Glu Arg Arg Ile Arg Gln Val Leu Ile
```

```
            20                  25                  30

Asn Leu Leu Asn Asn Ala Val Phe Ser Val Ile Asp Thr Gly Ile Gly
        35                  40                  45

Ile Thr Pro Glu Gly Thr Gly Leu Gly Leu Ala Val Thr Lys Arg Ile
    50                  55                  60

Val Glu Leu His Gly Gly Gln Val Gly Val Ser Ser Glu Glu Gly Lys
65                  70                  75                  80

Gly Ser Cys Phe Met Ile Asp Leu
                85


<210> SEQ ID NO 190
<211> LENGTH: 88
<212> TYPE: PRT
<213> ORGANISM: Nodosilinea nodulosa

<400> SEQUENCE: 190

Glu Phe Leu Ala Asn Met Ser His Glu Leu Arg Thr Pro Leu Asn Ala
1               5                   10                  15

Ile Leu Glu Ile Thr Leu Asp Glu Arg Arg Ile Arg Gln Val Leu Ile
            20                  25                  30

Asn Leu Leu Ser Asn Ala Val Phe Ala Val Thr Asp Thr Gly Ile Gly
        35                  40                  45

Ile Thr Pro Glu Gly Thr Gly Leu Gly Leu Ala Leu Val Lys Arg Ile
    50                  55                  60

Val Glu Leu His Arg Gly Gln Val Gly Leu Thr Ser Asp Val Gly Val
65                  70                  75                  80

Gly Ser Cys Phe Thr Val Glu Leu
                85


<210> SEQ ID NO 191
<211> LENGTH: 88
<212> TYPE: PRT
<213> ORGANISM: Unknown
<220> FEATURE:
<223> OTHER INFORMATION: Leptolyngbya PCC 6406

<400> SEQUENCE: 191

Glu Phe Leu Ala Asn Met Ser His Glu Leu Arg Thr Pro Leu Asn Thr
1               5                   10                  15

Ile Leu Glu Ile Thr Leu Asp Glu Arg Arg Ile Arg Gln Val Leu Ile
            20                  25                  30

Asn Leu Leu Asn Asn Ala Val Phe Ala Val Thr Asp Thr Gly Ile Gly
        35                  40                  45

Ile Thr Pro Glu Gly Thr Gly Leu Gly Leu Ala Leu Val Lys Arg Ile
    50                  55                  60

Val Glu Leu His Gly Gly Gln Val Gly Leu Thr Ser Ala Val Gly Val
65                  70                  75                  80

Gly Ser Cys Phe Thr Phe Asp Leu
                85


<210> SEQ ID NO 192
<211> LENGTH: 88
<212> TYPE: PRT
<213> ORGANISM: Unknown
<220> FEATURE:
<223> OTHER INFORMATION: Oscillatoria nigro-viridis PCC 7112

<400> SEQUENCE: 192

Glu Phe Leu Ala Asn Met Ser His Glu Leu Arg Thr Pro Leu Asn Ala
```

-continued

```
1               5                   10                  15

Ile Leu Asp Leu Leu Ile Asp Glu Arg Arg Met Arg Gln Val Leu Ile
            20                  25                  30

Asn Leu Leu Asn Asn Ala Val Ile Ser Val Ile Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Gln Val Leu Leu Thr Ser Thr Val Gly Val
65                  70                  75                  80

Gly Ser Cys Phe Thr Ile Asp Leu
                85


<210> SEQ ID NO 193
<211> LENGTH: 88
<212> TYPE: PRT
<213> ORGANISM: Unknown
<220> FEATURE:
<223> OTHER INFORMATION: Oscillatoria nigro-viridis PCC 7112

<400> SEQUENCE: 193

Glu Phe Leu Ala Asn Met Ser His Glu Leu Arg Thr Pro Leu Asn Ala
1               5                   10                  15

Ile Leu Asp Leu Leu Ile Asp Glu Arg Arg Met Arg Gln Val Leu Ile
            20                  25                  30

Asn Leu Leu Asn Asn Ala Val Ile Ser Val Ile Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Gln Val Leu Leu Thr Ser Thr Val Gly Val
65                  70                  75                  80

Gly Ser Cys Phe Thr Ile Asp Leu
                85


<210> SEQ ID NO 194
<211> LENGTH: 88
<212> TYPE: PRT
<213> ORGANISM: Microcoleus vaginatus

<400> SEQUENCE: 194

Glu Phe Leu Ala Asn Met Ser His Glu Leu Arg Thr Pro Leu Asn Ala
1               5                   10                  15

Ile Leu Asp Leu Leu Ile Asp Glu Arg Arg Met Arg Gln Val Leu Ile
            20                  25                  30

Asn Leu Leu Asn Asn Ala Val Ile Ala Val Ile Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Gln Val Gly Leu Thr Ser Thr Val Gly Val
65                  70                  75                  80

Gly Ser Cys Phe Thr Ile Asp Leu
                85


<210> SEQ ID NO 195
<211> LENGTH: 88
<212> TYPE: PRT
<213> ORGANISM: Microcoleus vaginatus

<400> SEQUENCE: 195
```

```
Glu Phe Leu Ala Asn Met Ser His Glu Leu Arg Thr Pro Leu Asn Ala
1               5                   10                  15

Ile Leu Asp Leu Leu Ile Asp Glu Arg Arg Met Arg Gln Val Leu Ile
            20                  25                  30

Asn Leu Leu Asn Asn Ala Val Ile Ala Val Ile Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Gln Val Gly Leu Thr Ser Thr Val Gly Val
65                  70                  75                  80

Gly Ser Cys Phe Thr Ile Asp Leu
                85


<210> SEQ ID NO 196
<211> LENGTH: 88
<212> TYPE: PRT
<213> ORGANISM: Unknown
<220> FEATURE:
<223> OTHER INFORMATION: Anabaena cylindrica PCC 7122

<400> SEQUENCE: 196

Glu Phe Leu Ala Asn Met Ser His Glu Leu Arg Thr Pro Leu Asn Ala
1               5                   10                  15

Ile Leu Asp Leu Phe Val Asp Glu Arg Arg Ile Arg Gln Val Leu Ile
            20                  25                  30

Asn Leu Leu Asn Asn Gly Val Ile Thr Val Ile Asp Thr Gly Ile Gly
        35                  40                  45

Ile Ser Pro Glu Gly Thr Gly Leu Gly Leu Ala Leu Val Lys Gln Ile
    50                  55                  60

Val Glu Leu His Gly Gly Gln Val Gly Leu Thr Ser Glu Leu Gly Val
65                  70                  75                  80

Gly Ser Cys Phe Met Ile Asp Leu
                85


<210> SEQ ID NO 197
<211> LENGTH: 88
<212> TYPE: PRT
<213> ORGANISM: Unknown
<220> FEATURE:
<223> OTHER INFORMATION: Calothrix parietina PCC 6303

<400> SEQUENCE: 197

Glu Phe Leu Ala Asn Met Ser His Glu Leu Arg Thr Pro Leu Asn Ala
1               5                   10                  15

Ile Leu Asp Leu Phe Val Asp Glu Arg Arg Ile Arg Gln Val Leu Ile
            20                  25                  30

Asn Leu Leu Asn Asn Ala Val Phe Ala Val Arg Asp Thr Gly Ile Gly
        35                  40                  45

Ile Ser Pro Glu Gly Thr Gly Leu Gly Leu Ala Leu Val Lys Arg Ile
    50                  55                  60

Ile Glu Leu His Gly Gly Leu Val Gly Leu Thr Ser Glu Leu Gly Val
65                  70                  75                  80

Gly Ser Cys Phe Thr Ile Asp Leu
                85


<210> SEQ ID NO 198
<211> LENGTH: 88
<212> TYPE: PRT
<213> ORGANISM: Unknown
```

<220> FEATURE:
<223> OTHER INFORMATION: Tolypothrix sp. PCC 7601

<400> SEQUENCE: 198

Glu Phe Leu Ala Asn Met Ser His Glu Leu Arg Thr Pro Leu Asn Ala
1               5                   10                  15

Ile Leu His Leu Leu Val Asp Glu Arg Arg Ile Arg Gln Val Leu Ile
            20                  25                  30

Asn Leu Leu Asn Asn Ala Val Ile Ala Val Lys Asp Thr Gly Ile Gly
        35                  40                  45

Ile Ala Pro Glu Gly Thr Gly Leu Gly Leu Ala Leu Val Lys Arg Ile
    50                  55                  60

Val Glu Leu His Gly Gly Arg Val Gly Leu Ser Ser Glu Leu Gly Val
65                  70                  75                  80

Gly Ser Cys Phe Thr Ile Glu Leu
                85

<210> SEQ ID NO 199
<211> LENGTH: 88
<212> TYPE: PRT
<213> ORGANISM: Unknown
<220> FEATURE:
<223> OTHER INFORMATION: Coleofasciculus chthonoplastes PCC 7420

<400> SEQUENCE: 199

Glu Phe Leu Ala Asn Met Ser His Glu Leu Arg Thr Pro Leu Asn Ala
1               5                   10                  15

Ile Leu Thr Ile Leu Gly Asp Glu Arg Arg Leu Gln Gln Val Leu Ile
            20                  25                  30

Asn Leu Leu Ser Asn Ala Val Ile Ser Val Ser Asp Thr Gly Ile Gly
        35                  40                  45

Ile Ala Lys Glu Gly Thr Gly Leu Gly Leu Ala Leu Val Arg Arg Ile
    50                  55                  60

Val Glu Leu His Gly Gly Trp Val Thr Val Glu Ser Glu Ile Gly Lys
65                  70                  75                  80

Gly Ser Cys Phe Thr Val Arg Leu
                85

<210> SEQ ID NO 200
<211> LENGTH: 88
<212> TYPE: PRT
<213> ORGANISM: Unknown
<220> FEATURE:
<223> OTHER INFORMATION: Pseudanabaena sp. PCC 6802

<400> SEQUENCE: 200

Glu Phe Leu Ala Asn Met Ser His Glu Leu Arg Thr Pro Leu Asn Ala
1               5                   10                  15

Ile Leu Pro Val Phe Met Asp Glu Arg Arg Met Arg Gln Val Leu Ile
            20                  25                  30

Asn Leu Leu Ser Asn Ala Val Phe Asn Val Ile Asp Thr Gly Ile Gly
        35                  40                  45

Ile Ala Ser Lys Gly Thr Gly Leu Gly Leu Ala Leu Val Arg Arg Ile
    50                  55                  60

Val Glu Met His Gly Gly Lys Val Ser Val Glu Ser Glu Val Gly Gln
65                  70                  75                  80

Gly Ser Lys Phe Gln Val Asn Ile
                85

<210> SEQ ID NO 201
<211> LENGTH: 88
<212> TYPE: PRT
<213> ORGANISM: Nodosilinea nodulosa

<400> SEQUENCE: 201

```
Glu Phe Leu Ala Asn Met Ser His Glu Leu Arg Thr Pro Leu Asn Val
1               5                   10                  15

Ile Leu Tyr Ile Val Ala Asp Pro Asn Lys Leu Arg Gln Val Leu Ile
            20                  25                  30

Asn Leu Leu Gly Asn Ala Ile Phe Ala Val Glu Asp Thr Gly Thr Gly
        35                  40                  45

Ile Ala Pro Ala Gly Thr Gly Leu Gly Leu Ala Ile Ser Arg Ser Leu
    50                  55                  60

Val Gln Leu Met Gly Gly Ser Leu Thr Val Ser Ser Arg Leu Gly Gln
65                  70                  75                  80

Gly Ser Thr Phe Cys Phe Ser Leu
                85
```

<210> SEQ ID NO 202
<211> LENGTH: 88
<212> TYPE: PRT
<213> ORGANISM: Unknown
<220> FEATURE:
<223> OTHER INFORMATION: Leptolyngbya sp. PCC 6406

<400> SEQUENCE: 202

```
Glu Phe Leu Ala Asn Met Ser His Glu Leu Arg Thr Pro Leu Asn Val
1               5                   10                  15

Ile Leu Tyr Ile Val Ala Asp Pro Asn Lys Leu Arg Gln Val Leu Ile
            20                  25                  30

Asn Leu Leu Asn Asn Ala Ile Phe Gln Val Ile Asp Thr Gly Val Gly
        35                  40                  45

Ile Pro Ser Glu Ser Thr Gly Leu Gly Leu Ala Ile Ser Arg Ser Leu
    50                  55                  60

Val Lys Leu Met Gly Gly Glu Leu Thr Val Asn Ser Ala Pro Asp Gln
65                  70                  75                  80

Gly Ser Thr Phe Gln Phe Ala Ile
                85
```

<210> SEQ ID NO 203
<211> LENGTH: 88
<212> TYPE: PRT
<213> ORGANISM: Unknown
<220> FEATURE:
<223> OTHER INFORMATION: Oscillatoria sp. PCC 6304

<400> SEQUENCE: 203

```
Glu Phe Leu Ala Asn Met Ser His Glu Leu Arg Thr Pro Leu Asn Ala
1               5                   10                  15

Ile Leu Met Ile Met Ser Asp Glu Ser Lys Leu Arg Gln Val Leu Ile
            20                  25                  30

Asn Ile Leu Gly Asn Ala Ile Ile Glu Ile Ala Asp Thr Gly Ser Gly
        35                  40                  45

Ile Ala Pro Glu Gly Thr Gly Leu Gly Leu Pro Ile Ser Arg Lys Phe
    50                  55                  60

Ile Gln Leu Met Gly Gly Asp Ile His Val Ser Ser Thr Val Gly Val
65                  70                  75                  80
```

-continued

```
Gly Thr Val Phe Ser Phe Glu Ile
                85


<210> SEQ ID NO 204
<211> LENGTH: 88
<212> TYPE: PRT
<213> ORGANISM: Unknown
<220> FEATURE:
<223> OTHER INFORMATION: Acaryochloris marina MBIC11017

<400> SEQUENCE: 204

Ile Phe Leu Ala Asn Met Ser His Glu Leu Arg Thr Pro Leu Asn Ala
1               5                   10                  15

Ile Leu Tyr Ile Arg Thr Asp Pro Gly Lys Leu Arg Gln Val Leu Met
            20                  25                  30

Asn Leu Leu Ser Asn Ala Ile Phe Thr Val Ser Asp Thr Gly Ser Gly
        35                  40                  45

Ile Ala Pro Glu Gly Thr Gly Leu Gly Leu Ala Ile Ser Arg Gln Phe
    50                  55                  60

Val Gln Ile Met Gly Gly Asn Leu Thr Ala His Ser Ile His Asn Gln
65                  70                  75                  80

Gly Thr Thr Leu Thr Phe Asn Ile
                85
```